(12) United States Patent
Hoffman et al.

(10) Patent No.: US 11,783,638 B2
(45) Date of Patent: Oct. 10, 2023

(54) MONITORING FITNESS USING A MOBILE DEVICE

(71) Applicant: NIKE, Inc., Beaverton, OR (US)

(72) Inventors: Michael T. Hoffman, Portland, OR (US); Kwamina Crankson, Portland, OR (US); Jason Nims, Portland, OR (US); Michael L. Orenstein, Portland, OR (US); Kristen Laina White, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 17/746,686

(22) Filed: May 17, 2022

(65) Prior Publication Data

US 2022/0277594 A1 Sep. 1, 2022

Related U.S. Application Data

(63) Continuation of application No. 16/736,894, filed on Jan. 8, 2020, now Pat. No. 11,468,711, which is a (Continued)

(51) Int. Cl.
*G06V 40/20* (2022.01)
*A61B 5/00* (2006.01)
(Continued)

(52) U.S. Cl.
CPC ............ *G06V 40/23* (2022.01); *A61B 5/0002* (2013.01); *A61B 5/1118* (2013.01); *G01C 21/20* (2013.01);
(Continued)

(58) Field of Classification Search
CPC ..... G06V 40/23; A61B 5/0002; A61B 5/1118; A61B 5/6807; A61B 5/6895; A61B 5/742;
(Continued)

(56) References Cited

U.S. PATENT DOCUMENTS

| | | |
|---|---|---|
| 4,860,763 A | 8/1989 | Schminke |
| 4,911,427 A | 3/1990 | Matsumoto et al. |

(Continued)

FOREIGN PATENT DOCUMENTS

| | | |
|---|---|---|
| CA | 2512601 A1 | 3/2002 |
| CN | 101367011 A | 2/2009 |

(Continued)

OTHER PUBLICATIONS

United States District Court Southern District of New York (Foley Square), Defendant's "Disclosure of Preliminary Invalidity Contentions", *NIKE, Inc. v. Lululemon Athletica Inc, et al.*, Case 1:22-cv-00082, filed Jul. 18, 2022, 1097 pages.

(Continued)

*Primary Examiner* — Pierre E Elisca
(74) *Attorney, Agent, or Firm* — Banner & Witcoff, Ltd.

(57) ABSTRACT

Athletic performance monitoring and tracking may provide multiple ways in which to track athletic movement and activity. Workouts may also be tagged with various parameters including mood, weather, terrain, athletic equipment, friends used and the like. Workout information may be shared to social messaging and networking outlets. Workout information shared may include map information including images of maps, interactive maps, links to maps, route information and the like and/or combinations thereof. Additionally or alternatively, an application may be configured to execute within a context of a social networking system to facilitate athletic activity data transfer and generation of workout entries in the social networking site.

25 Claims, 178 Drawing Sheets

Related U.S. Application Data continuation of application No. 14/475,134, filed on Sep. 2, 2014, now Pat. No. 10,572,721, which is a continuation-in-part of application No. 13/315,875, filed on Dec. 9, 2011, now Pat. No. 9,532,734, which is a continuation-in-part of application No. 13/205,895, filed on Aug. 9, 2011, now Pat. No. 9,248,340.

(60) Provisional application No. 61/371,842, filed on Aug. 9, 2010.

(51) Int. Cl.
| | |
|---|---|
| *A61B 5/11* | (2006.01) |
| *G01C 21/20* | (2006.01) |
| *G01C 22/00* | (2006.01) |
| *G06F 1/16* | (2006.01) |
| *G06Q 50/00* | (2012.01) |
| *G16H 20/40* | (2018.01) |
| *G16H 20/30* | (2018.01) |

(52) U.S. Cl.
CPC ......... *G01C 22/006* (2013.01); *G06F 1/1698* (2013.01); *G06Q 50/01* (2013.01); *G16H 20/30* (2018.01); *G16H 20/40* (2018.01); *A61B 5/6807* (2013.01); *A61B 5/6895* (2013.01); *A61B 5/742* (2013.01); *Y02A 90/10* (2018.01)

(58) Field of Classification Search
CPC ..... G01C 21/20; G01C 22/006; G06F 1/1698; G06Q 50/01; G16H 20/30; G16H 20/40; Y02A 90/10
USPC .......................................................... 700/91
See application file for complete search history.

(56) References Cited

U.S. PATENT DOCUMENTS

| | | |
|---|---|---|
| 5,527,239 A | 6/1996 | Abbondanza |
| 5,626,538 A | 5/1997 | Dalebout et al. |
| 5,667,459 A | 9/1997 | Su |
| 5,879,270 A | 3/1999 | Huish et al. |
| 5,888,172 A | 3/1999 | Andrus et al. |
| 6,009,138 A | 12/1999 | Slusky |
| 6,013,007 A | 1/2000 | Root et al. |
| 6,026,335 A | 2/2000 | Atlas |
| 6,077,193 A | 6/2000 | Buhler et al. |
| 6,122,960 A | 9/2000 | Hutchings et al. |
| 6,132,391 A | 10/2000 | Onar et al. |
| 6,157,372 A | 12/2000 | Blackburn et al. |
| 6,359,837 B1 | 3/2002 | Tsukamoto |
| 6,443,904 B2 | 9/2002 | Nissila |
| 6,458,060 B1 | 10/2002 | Watterson et al. |
| 6,463,385 B1 | 10/2002 | Fry |
| 6,513,532 B2 | 2/2003 | Mault et al. |
| 6,527,674 B1 | 3/2003 | Clem |
| 6,532,432 B1 | 3/2003 | Nagatsuma et al. |
| 6,539,336 B1 | 3/2003 | Vock et al. |
| 6,549,845 B2 | 4/2003 | Eakle, Jr. et al. |
| 6,585,622 B1 | 7/2003 | Shum et al. |
| 6,594,617 B2 | 7/2003 | Scherzinger |
| 6,601,016 B1 | 7/2003 | Brown et al. |
| 6,607,493 B2 | 8/2003 | Song |
| 6,648,798 B2 | 11/2003 | Yoo |
| 6,656,091 B1 | 12/2003 | Abelbeck et al. |
| 6,672,991 B2 | 1/2004 | O'Malley |
| 6,687,535 B2 | 2/2004 | Hautala et al. |
| 6,730,047 B2 | 5/2004 | Socci et al. |
| 6,736,759 B1 | 5/2004 | Stubbs et al. |
| 6,744,403 B2 | 6/2004 | Milnes et al. |
| 6,786,848 B2 | 9/2004 | Yamashita et al. |
| 6,796,927 B2 | 9/2004 | Toyama |
| 6,837,827 B1 | 1/2005 | Lee et al. |
| 6,856,934 B2 | 2/2005 | Vock et al. |
| 6,858,006 B2 | 2/2005 | MacCarter et al. |
| 6,868,338 B1 | 3/2005 | Elliott |
| 6,902,513 B1 | 6/2005 | McClure |
| 6,997,852 B2 | 2/2006 | Watterson et al. |
| 7,054,678 B2 | 5/2006 | Dardik et al. |
| 7,076,291 B2 | 7/2006 | Pulkkinen et al. |
| 7,097,588 B2 | 8/2006 | Watterson et al. |
| 7,162,392 B2 | 1/2007 | Vock et al. |
| 7,166,062 B1 | 1/2007 | Watterson et al. |
| 7,171,331 B2 | 1/2007 | Vock et al. |
| 7,251,454 B2 | 7/2007 | White |
| 7,398,151 B1 | 7/2008 | Burrell et al. |
| 7,467,060 B2 | 12/2008 | Kulach et al. |
| 7,480,512 B2 | 1/2009 | Graham et al. |
| 7,559,877 B2 | 7/2009 | Parks et al. |
| 7,670,263 B2 | 3/2010 | Ellis et al. |
| 7,699,753 B2 | 4/2010 | Daikeler et al. |
| 7,722,502 B2 | 5/2010 | Holkkola |
| 7,745,716 B1 | 6/2010 | Murphy |
| 7,771,320 B2 | 8/2010 | Riley et al. |
| 7,805,149 B2 | 9/2010 | Werner et al. |
| 7,810,392 B2 | 10/2010 | Kitagawa |
| 7,841,966 B2 | 11/2010 | Aaron et al. |
| 7,850,514 B2 | 12/2010 | Weber |
| 8,083,643 B2 | 12/2011 | Ng et al. |
| 8,109,858 B2 | 2/2012 | Redmann |
| 8,152,695 B2 | 4/2012 | Riley et al. |
| 8,177,260 B2 | 5/2012 | Trapper et al. |
| 8,212,136 B2 | 7/2012 | Shirai et al. |
| 8,253,586 B1 | 8/2012 | Matak |
| 8,346,524 B2 | 1/2013 | Turgiss et al. |
| 8,517,896 B2 | 8/2013 | Robinette et al. |
| 8,562,489 B2 | 10/2013 | Burton et al. |
| 8,568,277 B2 | 10/2013 | Johnson |
| 8,814,755 B2 | 8/2014 | Ellis et al. |
| 8,845,496 B2 | 9/2014 | Arrasvuori et al. |
| 9,390,229 B1 | 7/2016 | Kahn et al. |
| 9,504,414 B2 | 11/2016 | Coza et al. |
| 10,610,761 B1 | 4/2020 | Matak et al. |
| 2001/0041879 A1 | 11/2001 | Karami et al. |
| 2002/0022551 A1 | 2/2002 | Watterson et al. |
| 2002/0077219 A1 | 6/2002 | Cohen et al. |
| 2002/0160883 A1 | 10/2002 | Dugan |
| 2003/0065257 A1 | 4/2003 | Mault et al. |
| 2003/0065561 A1 | 4/2003 | Brown et al. |
| 2003/0134714 A1 | 7/2003 | Oishi et al. |
| 2003/0190062 A1 | 10/2003 | Noro et al. |
| 2005/0038679 A1 | 2/2005 | Short |
| 2005/0070809 A1 | 3/2005 | Acres |
| 2005/0234307 A1 | 10/2005 | Heinonen et al. |
| 2005/0250458 A1 | 11/2005 | Graham et al. |
| 2005/0272564 A1 | 12/2005 | Pyles et al. |
| 2006/0003872 A1 | 1/2006 | Chiles et al. |
| 2006/0107822 A1 | 5/2006 | Bowen |
| 2006/0111944 A1 | 5/2006 | Sirmans et al. |
| 2006/0189360 A1 | 8/2006 | White |
| 2006/0189440 A1 | 8/2006 | Gravagne |
| 2006/0255955 A1 | 11/2006 | O'Connor et al. |
| 2007/0032345 A1 | 2/2007 | Padmanabhan et al. |
| 2007/0049301 A1 | 3/2007 | Mock et al. |
| 2007/0239479 A1 | 10/2007 | Arrasvuori et al. |
| 2008/0009275 A1 | 1/2008 | Werner et al. |
| 2008/0086318 A1 | 4/2008 | Gilley et al. |
| 2008/0096726 A1 | 4/2008 | Riley et al. |
| 2008/0097633 A1 | 4/2008 | Jochelson et al. |
| 2008/0109158 A1 | 5/2008 | Huhtala et al. |
| 2008/0146302 A1 | 6/2008 | Olsen et al. |
| 2008/0188354 A1 | 8/2008 | Pauws et al. |
| 2008/0200312 A1 | 8/2008 | Tagliabue |
| 2008/0207401 A1 | 8/2008 | Harding et al. |
| 2008/0254946 A1 | 10/2008 | Pauws et al. |
| 2008/0287198 A1 | 11/2008 | Callery et al. |
| 2009/0044687 A1 | 2/2009 | Sorber |
| 2009/0047645 A1 | 2/2009 | Dibenedetto et al. |
| 2009/0048070 A1 | 2/2009 | Vincent et al. |
| 2009/0049979 A1 | 2/2009 | Naik et al. |
| 2009/0082677 A1 | 3/2009 | Shih et al. |
| 2009/0144369 A1 | 6/2009 | Brown |
| 2009/0144639 A1 | 6/2009 | Nims et al. |

(56) References Cited

U.S. PATENT DOCUMENTS

| | | | |
|---|---|---|---|
| 2009/0150178 A1 | 6/2009 | Sutton et al. | |
| 2009/0189982 A1 | 7/2009 | Tawiah | |
| 2009/0195350 A1 | 8/2009 | Tsern et al. | |
| 2010/0009643 A1 | 1/2010 | Haartsen | |
| 2010/0048358 A1 | 2/2010 | Tchao et al. | |
| 2010/0073329 A1 | 3/2010 | Raman et al. | |
| 2010/0088023 A1 | 4/2010 | Werner | |
| 2010/0127926 A1 | 5/2010 | Wang | |
| 2010/0137748 A1 | 6/2010 | Sone et al. | |
| 2010/0222179 A1 | 9/2010 | Temple et al. | |
| 2010/0273610 A1 | 10/2010 | Johnson | |
| 2010/0292600 A1 | 11/2010 | DiBenedetto et al. | |
| 2011/0054646 A1 | 3/2011 | Hernandez et al. | |
| 2011/0087970 A1 | 4/2011 | Swink et al. | |
| 2011/0098156 A1 | 4/2011 | Ng et al. | |
| 2011/0161085 A1 | 6/2011 | Boda et al. | |
| 2011/0172909 A1 | 7/2011 | Kahn et al. | |
| 2012/0015778 A1 | 1/2012 | Lee et al. | |
| 2012/0015779 A1 | 1/2012 | Powch et al. | |
| 2012/0041767 A1 | 2/2012 | Hoffman et al. | |
| 2012/0078396 A1 | 3/2012 | Case, Jr. et al. | |
| 2012/0239173 A1 | 9/2012 | Laikari et al. | |
| 2012/0245716 A1 | 9/2012 | Srinivasan et al. | |
| 2012/0283855 A1 | 11/2012 | Hoffman et al. | |
| 2012/0323346 A1 | 12/2012 | Ashby et al. | |
| 2014/0240122 A1 | 8/2014 | Roberts et al. | |
| 2014/0281956 A1 | 9/2014 | Anderson et al. | |
| 2015/0142143 A1* | 5/2015 | Cobbett | A61B 5/681 700/91 |
| 2015/0324751 A1 | 11/2015 | Orenstein et al. | |
| 2017/0259116 A1* | 9/2017 | Mestas | G16H 20/30 |
| 2017/0266494 A1* | 9/2017 | Crankson | A63B 24/0062 |
| 2017/0266531 A1* | 9/2017 | Elford | A63B 24/0062 |
| 2018/0093131 A1* | 4/2018 | Barnes | G06Q 30/0255 |
| 2021/0001178 A1* | 1/2021 | Crankson | A63B 24/0021 |
| 2021/0128976 A1* | 5/2021 | Barnes | A63B 24/0062 |

FOREIGN PATENT DOCUMENTS

| | | |
|---|---|---|
| CN | 101367013 A | 2/2009 |
| CN | 201259672 Y | 6/2009 |
| CN | 101485559 A | 7/2009 |
| CN | 101583403 A | 11/2009 |
| CN | 101711915 A | 5/2010 |
| CN | 101713660 A | 5/2010 |
| CN | 101738596 A | 6/2010 |
| CN | 101755406 A | 6/2010 |
| CN | 101970066 A | 2/2011 |
| CN | 102063574 A | 5/2011 |
| CN | 102449560 A | 5/2012 |
| CN | 102770188 A | 11/2012 |
| CN | 103154954 A | 6/2013 |
| CN | 103182175 A | 7/2013 |
| CN | 103752006 A | 4/2014 |
| DE | 102008049380 A1 | 4/2010 |
| EP | 0956819 A1 | 11/1999 |
| EP | 2324762 A1 | 5/2011 |
| EP | 2770454 A1 | 8/2014 |
| JP | H0938051 A | 2/1997 |
| JP | 2002507734 A | 3/2002 |
| JP | 2002539535 A | 11/2002 |
| JP | 2003141260 A | 5/2003 |
| JP | 2003315085 A | 11/2003 |
| JP | 2004015606 A | 1/2004 |
| JP | 2004110628 A | 4/2004 |
| JP | 2006229549 A | 8/2006 |
| JP | 2007292505 A | 11/2007 |
| JP | 2008312047 A | 12/2008 |
| JP | 2010075715 A | 4/2010 |
| JP | 2010079068 A | 4/2010 |
| JP | 2010088886 A | 4/2010 |
| JP | 2010517725 A | 5/2010 |
| JP | 2010136864 A | 6/2010 |
| JP | 2010246109 A | 10/2010 |
| JP | 2010253303 A | 11/2010 |
| JP | 2011517966 A | 6/2011 |
| JP | 2011518360 A | 6/2011 |
| JP | 2013543156 | 11/2013 |
| JP | 2014044623 A | 3/2014 |
| JP | 2014134903 A | 7/2014 |
| KR | 20070112189 A | 11/2007 |
| KR | 20130045382 A | 5/2013 |
| TW | 201027419 A | 7/2010 |
| WO | 9949279 A1 | 9/1999 |
| WO | 2001041879 A1 | 6/2001 |
| WO | 2001045014 A1 | 6/2001 |
| WO | 2002035997 A1 | 5/2002 |
| WO | 2002055959 A1 | 7/2002 |
| WO | 2002067449 A2 | 8/2002 |
| WO | 2002101408 A1 | 12/2002 |
| WO | 2004015606 A1 | 2/2004 |
| WO | 2006111687 A1 | 10/2006 |
| WO | 2008046443 A1 | 4/2008 |
| WO | 2008060043 A1 | 5/2008 |
| WO | 2009094323 A1 | 7/2009 |
| WO | 2009108887 A2 | 9/2009 |
| WO | 2009129402 A1 | 10/2009 |
| WO | 2009146250 A1 | 12/2009 |
| WO | 2010126825 A1 | 11/2010 |
| WO | 2011028383 A1 | 3/2011 |
| WO | 2011072111 A2 | 6/2011 |
| WO | 2011143670 A1 | 11/2011 |

OTHER PUBLICATIONS

United States District Court Southern District of New York (Foley Square), Defendant's "Amended Exhibits", (Exhs. D-1, E-1, E-2, E-3, E-4, E-5, E-6) *Nike, Inc.* v. *Lululemon Athletica Inc. et al.*, Case 1:22-cv-00082, filed Jul. 26, 2022, 183 pages.

David R. Bassett, Jr., Validity and Reliability Issues in Objective Monitoring of Physical Activity, Research Quarterly for Exercise and Sport, vol. 71, No. 2, pp. 30-36 (2000) ("Bassett"), 7 pages.

Chris Hall, Nokia Sports Tracker, Pocket-lint (Jul. 25, 2008), https://www.pocket-lint.com/phones/reviews/nokia/70414-nokia-sports-tracker-mobile-application ("Hall"), 11 pages.

Jozsef Hajdu, Provided Services of Social Networks for Sport, TKK T-110.5190 Seminar on Internetworking (Apr. 28-29, 2008), http://www.cse.tkk.fi/en/publications/B/1/papers/Hajdu_final.pdf ("Hajdu"), 8 pages.

Zee, Breaking: Goodbye Twitter? Facebook adds @mentions to status updates (Sep. 10, 2009, 9:16 PM), https://thenextweb.com/news/breaking-facebook-adds-mentions-status-updates?amp=1 ("Zee"), 6 pages.

Robert Anderson (@rsa), Twitter (Nov. 2, 2006, 11:58 PM), https://twitter.com/rsa/status/55281?lang=en ("Anderson"), 3 pages.

Scott Tousignant (@TheFitB), Twitter (Nov. 27, 2008, 12:27 PM), https://twitter.com/TheFitB/status/1026679285 ("Tousignant"), 1 page.

Internet webpage wii.nintendo.com/controller.jsp, dated Nov. 30, 2006 and retrieved from the Internet Archive ("Nintendo webpage").

Jun. 13, 2013—(WO) ISR & WO—App. No. PCT/US2012/068202.

Dec. 9, 2015—(EP) ESR—App No. 15183562.6.

United States District Court Southern District of New York (Foley Square), "Complaint (w/o exhibits)", *NIKE, Inc.* v. *Lululemon Athletica Inc. et al.*, Case 1:22-cv-00082, filed Jan. 5, 2022, 29 pages.

United States District Court Southern District of New York (Foley Square), "Answer", *NIKE, Inc.* v. *Lululemon Athletica Inc. et al.*, Case 1:22-cv-00082, filed Jan. 14, 2022, 15 pages.

United States District Court Southern District of New York (Foley Square), "Docket", *NIKE, Inc.* v. *Lululemon Athletica Inc. et al.*, Case 1:22-cv-00082, printed Jul. 26, 2022, 8 pages.

Nov. 9, 2022—Petition (w/Exh. 1001 (U.S. Pat. No. 10,232,220)) for Inter Partes Review of U.S. Pat. No. 10,232,220, Case No. IPR2023-00180, U.S. Patent Office, Before the Patent Trial and Appeal Board, 295 pages.

Declaration and Curriculum Vitae of Dr. Henry H. Houh, Nov. 9, 2022, 84 pages (Ex. 1003, IPR Pet.).

(56) References Cited

OTHER PUBLICATIONS

Declaration of Nathaniel E. Frank-White, Aug. 29, 2022, 27 pages (Ex. 1006, IPR Pet.).

Martha Fry (@MarthaFry), Twitter (Jan. 5, 2009, 3:34 PM), https://twitter.com/MarthaFry/status/1098244147, 2 pages (Ex. 1007, IPR Pet.).

Scott Tousignant (@TheFitB), Twitter (Nov. 27, 2008, 9:27AM), https://twitter.com/TheFitB/status/1026679285, 2 pages (Ex. 1008, IPR Pet.).

David Marcus (@davidmarcus), Twitter (Jul. 9, 2009, 6:56PM), https://twitter.com/davidmarcus/status/2560866346, 2 pages (Ex. 1009, IPR Pet.).

Martha Fry (@MarthaFry), Twitter (Jul. 11, 2009, 5:11AM), https://twitter.com/MarthaFry/status/2582964533, 2 pages (Ex. 1010, IPR Pet.).

Mark Prasatik (@mprasatik), Twitter (Jul. 18, 2009, 5:11AM), https://twitter.com/mprasatik/status/2705395365, 2 pages (Ex. 1011, IPR Pet.).

"Printout of Wayback Machine General Information, Internet Archive (Oct. 3, 2022), https://help.archive.org/help/wayback-machine-general-information/, 6 pages (Ex. 1012, IPR Pet.)."

"Claire Cain Miller, Popularity or Income? Two Sites Fight It Out, The New York Times (Oct. 20, 2008), https://www.nytimes.com/2008/10/21/technology/start-ups/21twitter.html, 4 pages (Ex. 1013, IPR Pet.)."

Apr. 27, 2009—Application as filed, U.S. Appl. No. 61/172,990 (Ex. 1014, IPR Pet.).

Jun. 2, 2009—Application as filed, U.S. Appl. No. 61/183,172 (Ex. 1015, IPR Pet.).

U.S. Appl. No. 17/738,813, filed May 6, 2022, Michael T. Hoffman et al.

U.S. Appl. No. 17/738,855, filed May 6, 2022, Michael T. Hoffman et al.

U.S. Appl. No. 17/746,651, filed May 17, 2022, Michael T. Hoffman et al.

U.S. Appl. No. 16/736,894, filed Jan. 8, 2020, Michael T. Hoffman et al.

Jun. 2, 2023 (EP) Communication with European Search Report—App EP22201477, 9 pages.

* cited by examiner

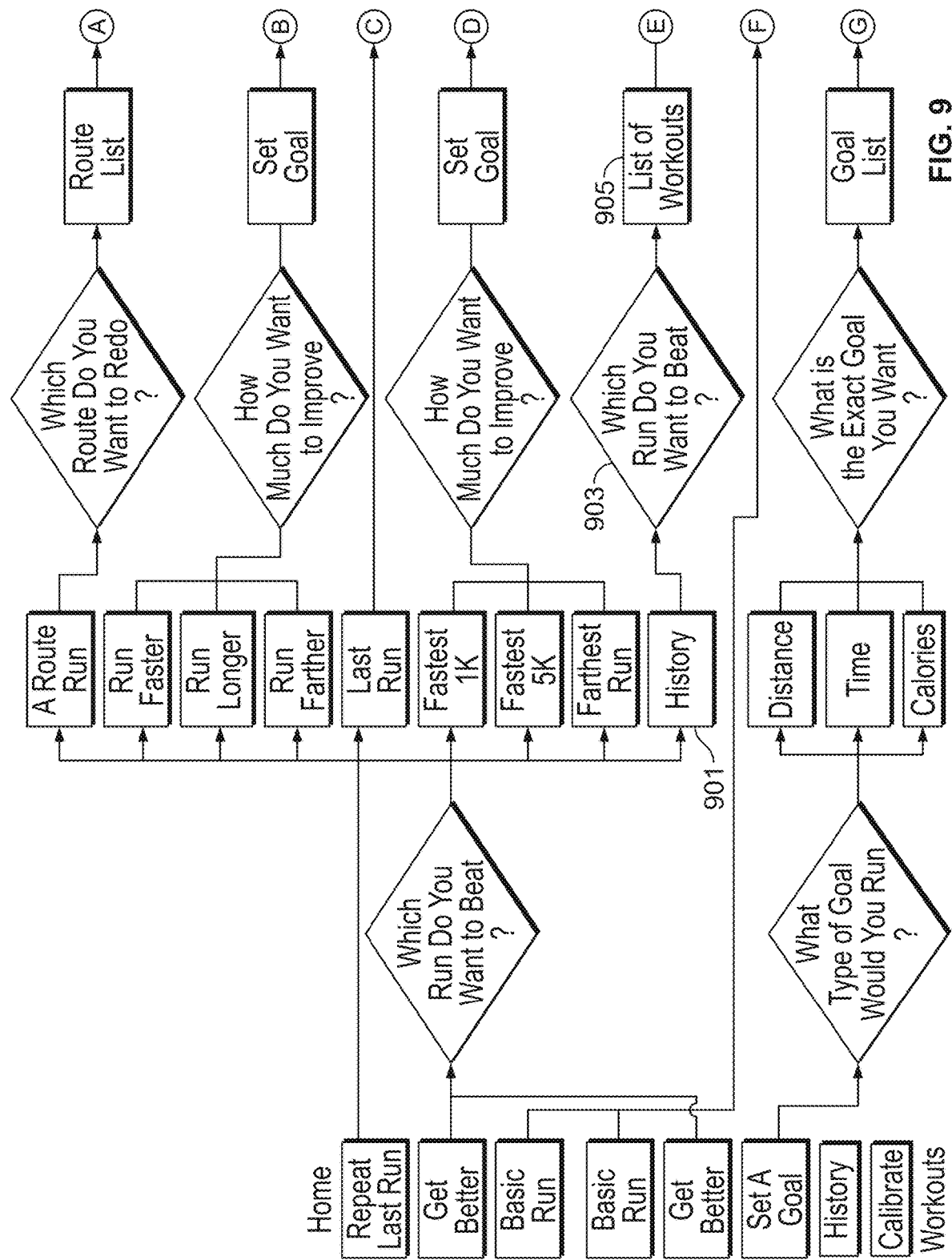

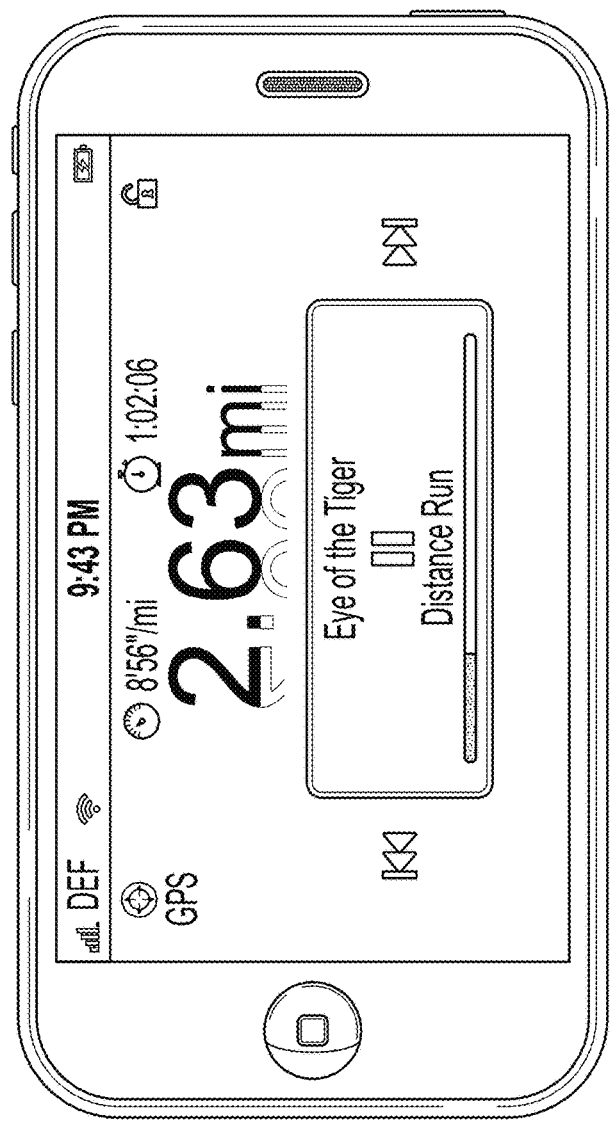
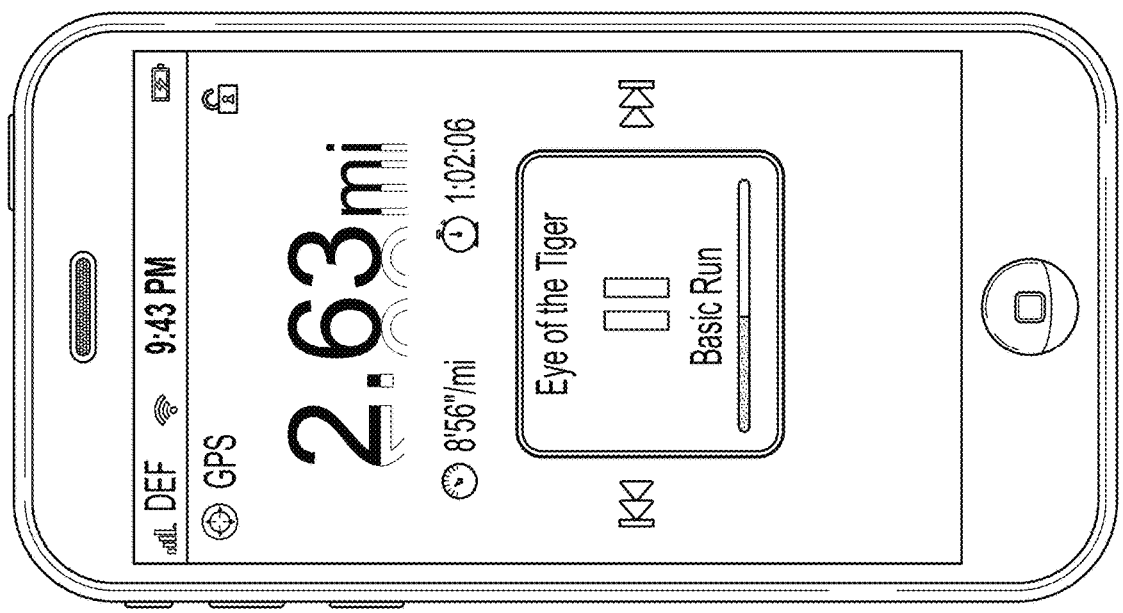
FIG. 23B
FIG. 23A

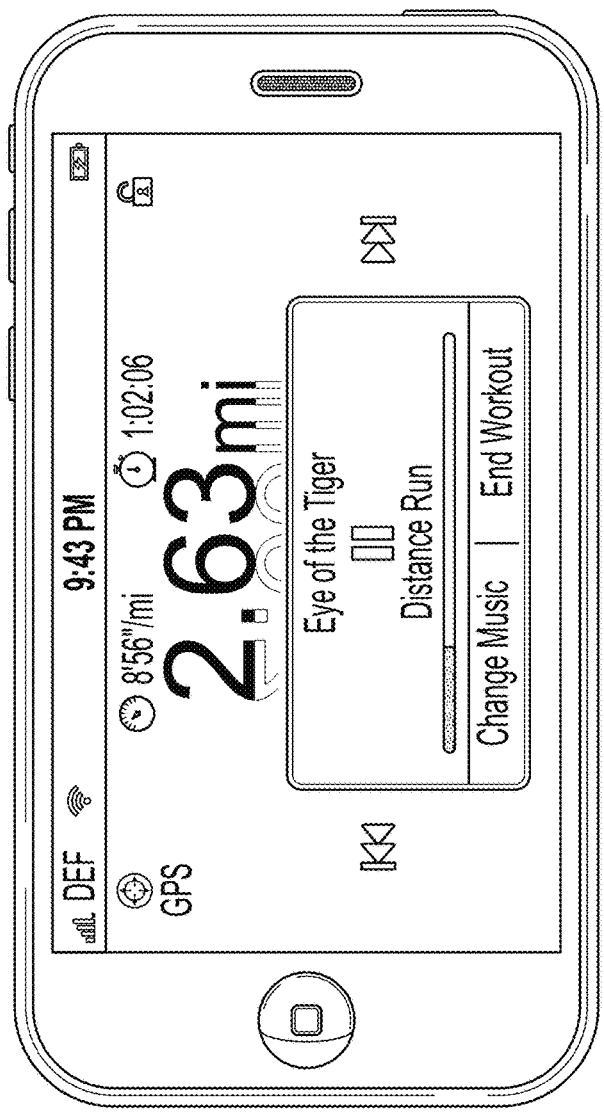
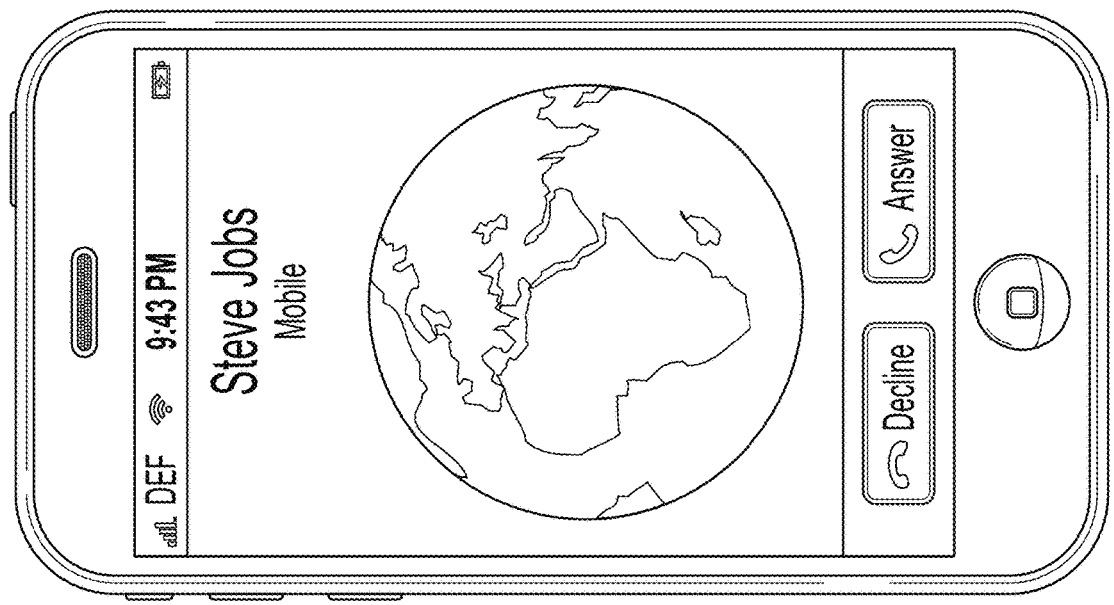
FIG. 27B
FIG. 27A

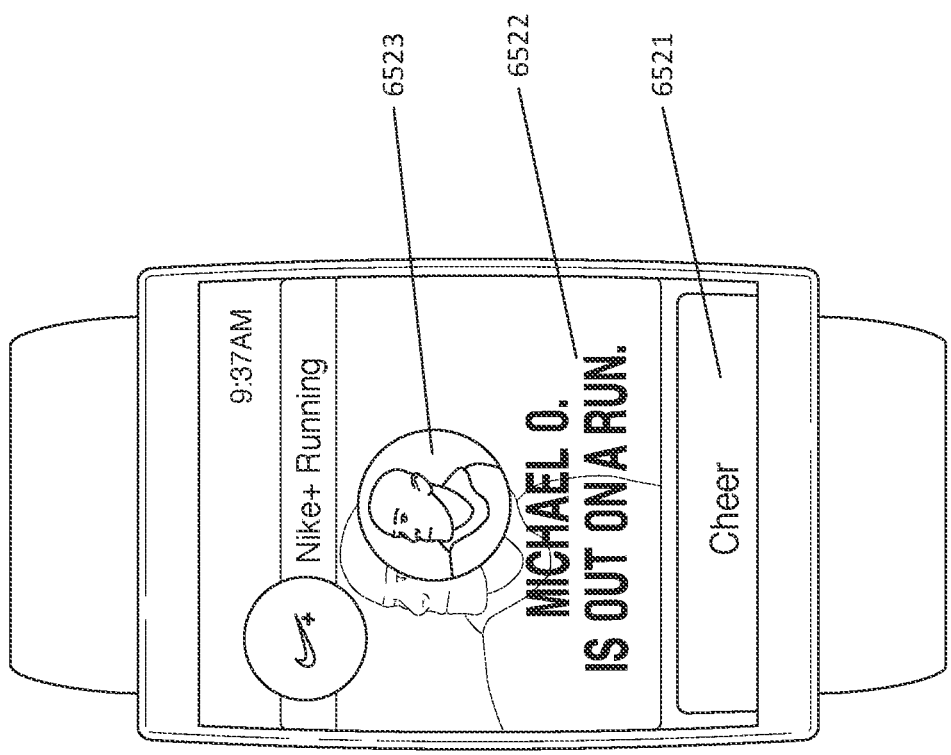
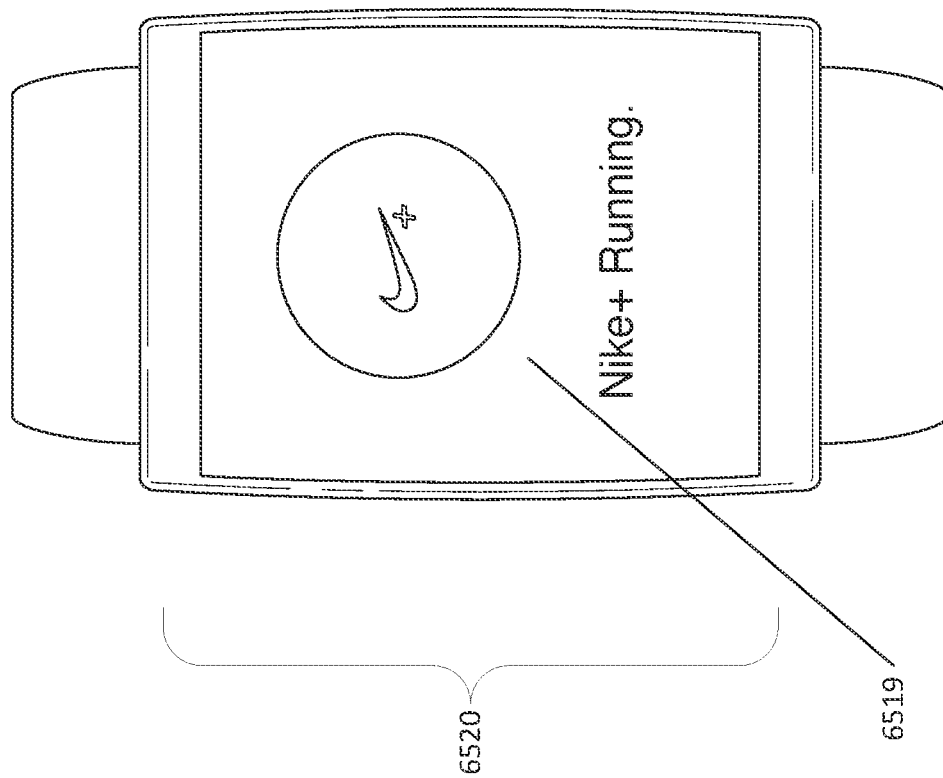
FIG. 65E

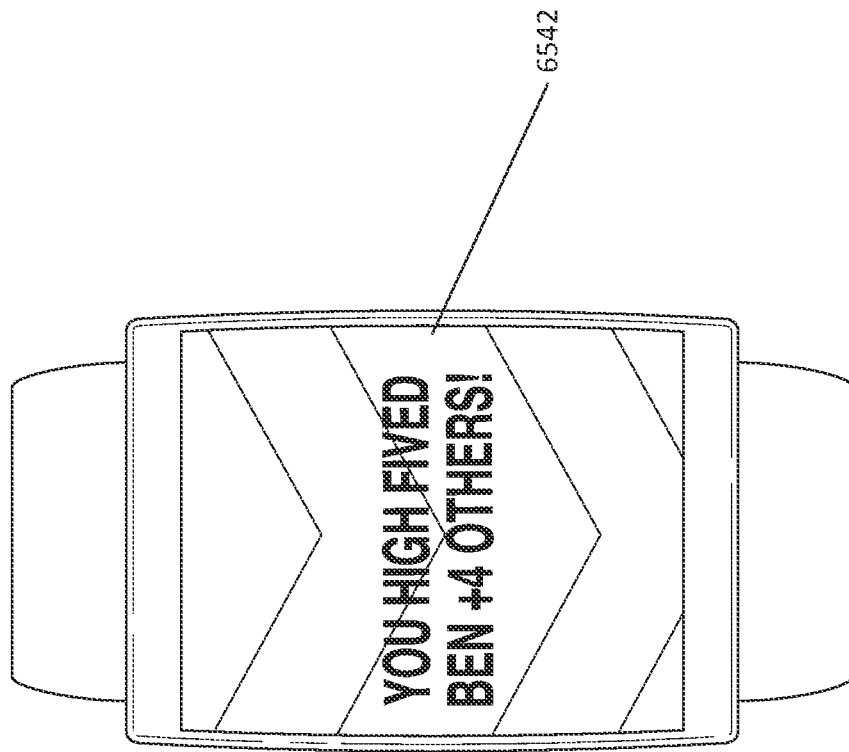
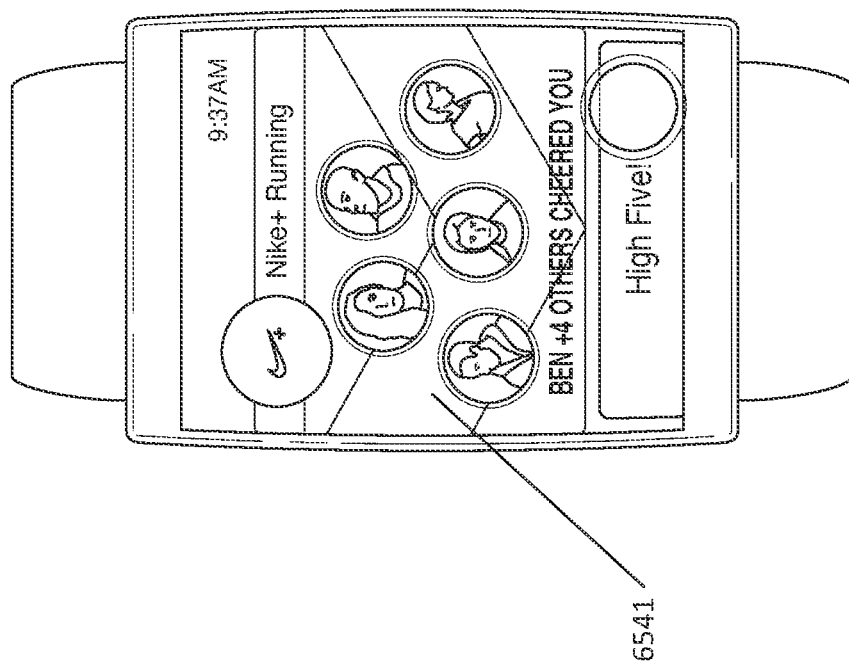
FIG. 65G

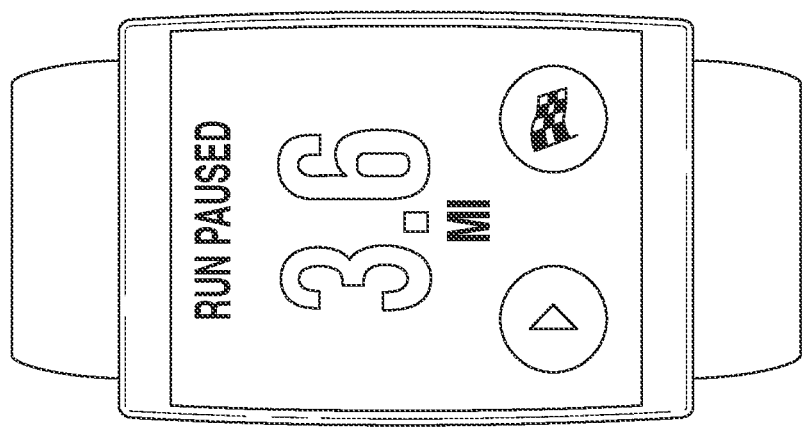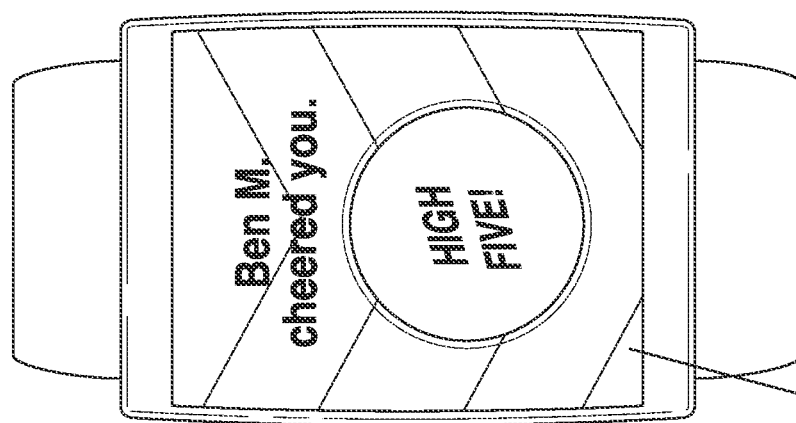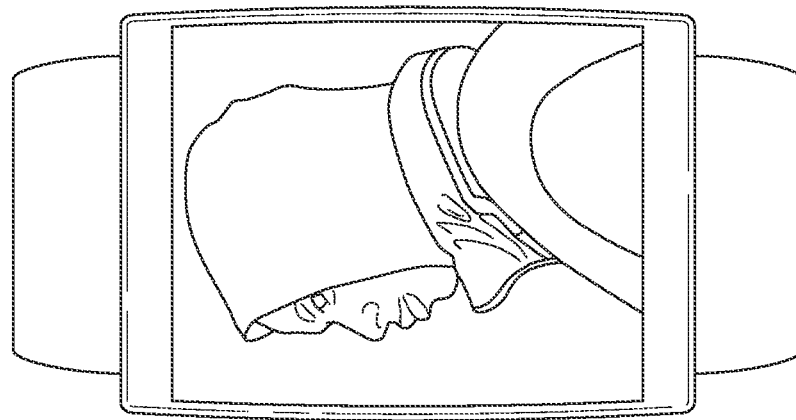
FIG. 65H

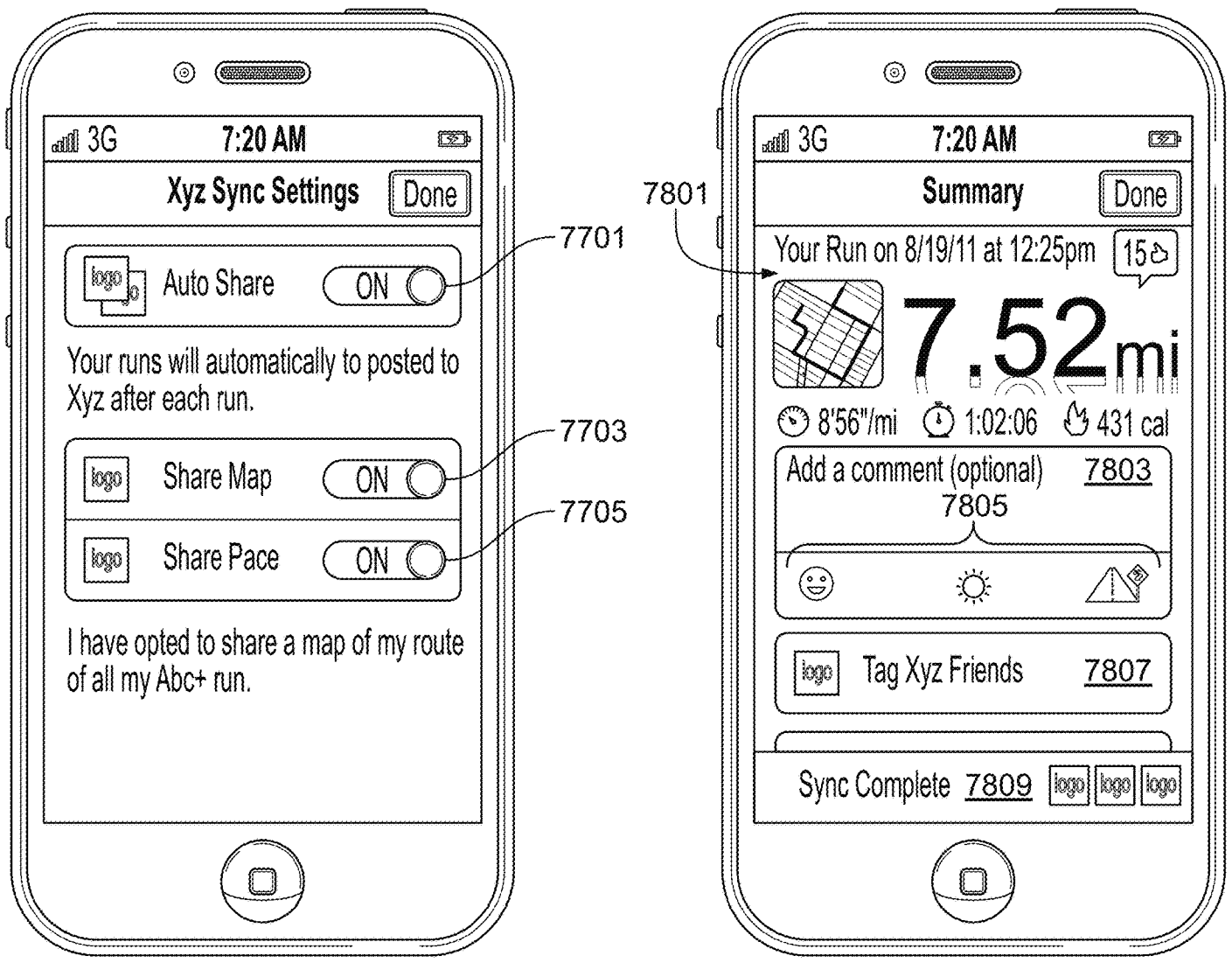

FIG. 80

MONITORING FITNESS USING A MOBILE DEVICE

CROSS-REFERENCE TO RELATED APPLICATIONS

This application is a continuation of U.S. patent application Ser. No. 16/736,894, which is a continuation of U.S. patent application Ser. No. 14/475,134, entitled "Monitoring Fitness Using a Mobile Device," and filed Sep. 2, 2014, now U.S. patent Ser. No. 10/572,721, which is a continuation-in-part of U.S. patent application Ser. No. 13/315,875, now U.S. Pat. No. 9,532,734, entitled "Monitoring Fitness Using A Mobile Device," and filed on Dec. 9, 2011, which is a continuation-in-part of U.S. patent application Ser. No. 13/205,895, now U.S. Pat. No. 9,248,340, entitled "Monitoring Fitness Using A Mobile Device," and filed on Aug. 9, 2011, which claims the benefit of priority from U.S. Provisional Application No. 61/371,842, entitled "Monitoring Fitness Using A Mobile Device," and filed Aug. 9, 2010. The contents of the above-noted applications are incorporated herein, by reference, in their entirety.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling. Additionally, oftentimes, individuals might not be as motivated to exercise because of the extra effort that may be required in recording and tracking workout results. For example, an individual may be required to manually enter workout information such as a number of miles run, a route run, an average heart rate and the like, into a database in order to track his or her progress. In another example, individuals may need to use special fitness-dedicated devices to automatically track workout results. In some instances, different types of fitness equipment may be required depending on if the individual is working out indoors or outdoors, on a treadmill or running an outdoor route and the like.

Motivation may also result from achieving progress in an individual's fitness level. However, progress often involves increasing or otherwise altering a workout regimen. For example, individuals may start running faster or for longer periods of time to increase endurance. In some cases, individuals might repeat the same workout, thus failing to challenge themselves to improve on previous performances. Without being prompted to perform a more strenuous workout, an individual might not see results as quickly or at all and thus become unmotivated.

BRIEF SUMMARY

According to one or more aspects, a user may record and track athletic activity using a mobile device having multiple types of location determination systems such as a global positioning system (GPS) and an accelerometer or other types of devices (e.g., pedometer) not dependent on remote systems. By using both a GPS device and an accelerometer, the mobile device may record workout data for both indoor (e.g., stationary) workouts and outdoor workouts. The mobile device may switch from using one device to the other device depending on the conditions. For example, if a GPS signal is lost, the accelerometer may be activated and used as back-up to provide workout related data. Once a GPS signal is reacquired, the system may begin recording the GPS data once again. The system may automatically switch between the two sensors (or use both) depending on signal availability and/or strength, detected movement, location (indoors vs. outdoors), user preferences (e.g., preferred types of workout data, preferred accuracy) and the like.

According to another aspect, the systems and methods described herein may provide challenges or suggestions for improvement workouts. For example, the system may offer options to a user to improve on a previous run or other athletic activity. The user may select from a list of suggested improvement runs or create a customized run based on a previously recorded run or workout. In a particular example, the system may suggest improvement runs that increase a pace, a distance, calories burned or an amount of time run by 5%. In another example, the system may analyze an athlete's trend over a predefined time period such as a week, a month, 6 months or the like and identify an average amount of progress per week or day. The system may then suggest an improvement workout that incorporates the determined average amount of progress. Other activity improvement algorithms may be used to generate a suggested workout to help an athlete improve one or more athletic activity metrics.

According to yet another aspect, a user may synchronize data to and view data from an athletic activity monitoring service provider. The user may download data to a mobile fitness monitoring device to track historical runs and his or her progress over a specified period of time. Additionally or alternatively, some data may be stored locally in the user's mobile device and supplemented with data from a remote network site (e.g., the athletic activity monitoring service provider). Further, data recorded by the mobile device (e.g., GPS data or accelerometer data) may be synchronized with the remote network site to alleviate storage requirements of the mobile device. Additionally, synchronization with the remote network site may allow the user to view athletic activity information from other locations and devices. Further, the workout information may be shared through one or more social outlets. In one example, an application or applet may be configured to interface with, facilitate and receive athletic activity data from an athletic activity monitoring and tracking system, site and/or device. The application may execute on or within a context of a network site such as a social network site or system. Additionally or alternatively, a user may configure permissions and options for sharing workout information. For example, a user may select what types of information are to be shared through a social networking site. Sharing option may further include specification of conditions under which various types of information are to be shared.

According to another aspect, runs completed using a location determination device may be stored with route information. Route information includes the path taken by the user during the workout. The route may be displayed against a map to allow the user to view various information and statistics about the run. For example, distance markers, pace markers and elevation markers may be displayed. Additionally, indicators may be provided for identifying fastest and slowest pace, highest and lowest heart rate, highest and lowest elevation and the like. Color and other visual elements of the route may be used to indicate various types of athletic information including pace, heart rate, type of music being played, temperature (ambient or body), and the like. The route display may be customizable according to user preferences. Users may further create routes from scratch or based on a previously recorded GPS route/run.

Maps may also be shared in one or more arrangements. For example, a map of a user's run or walk or other activity may be transmitted to a community site, a social network, another user's device, an e-mail address, a text or multimedia message destination and the like. In addition or alternatively to an image of the map, the map information may include an interactive map that users may modify or navigate to view surrounding areas, information about the user's route and performance and the like. In some examples, other users may download the map and use the route for their own activity. The map or route information may be formatted in such a manner that it is usable by an athletic activity monitoring application upon download. Maps and map information uploaded to a server, community site or social network may further be used to aggregate activity data for a user. For example, all map and route information may be collected into a summary of the user's runs or workouts including total distance, average distance, total time, average time, average pace, top X (e.g., 1, 2, 5, 10, 15, etc.) workout locations and the like. Additionally or alternatively, users may tag friends within the map or for a specific route or more generally in a workout to identify other users who ran the same route, ran at the same time, would be interested in the route, should be notified of the workout or route and the like and/or combinations thereof. Sharing of map and route information may be toggled on or off as desired. According to still another aspect, coaching may be provided to the user to aid in improvement and the achievement of goals. In one example, coaching may include instructional commentary to identify particular actions that the user may take to achieve or exceed a particular goal. Coaching may include voice or video overlays of celebrities such as athletes, movie stars, singers, musicians and the like. Coaching may also take into account automatically determined, location-specific parameters such as weather and terrain and may further evaluate performances by other users performed at the same or a similar location.

According to yet another aspect, a mobile athletic activity monitoring device may further offer comments, suggestions and words of encouragement to the user pre-, mid- and post-run or athletic workout. For example, if a user reaches a predefined distance during a run, the device may generate and render text, audio and/or video messages to the user. In one or more arrangements, celebrity messages may be included as a congratulatory or motivational message. In another example, congratulatory or motivational messages may be provided based on a set trigger such as reaching a certain distance or achieving a specified pace. In one arrangement, a user may be provided with certain sound, visual or haptic feedback upon receiving a threshold number of messages from friends (e.g., through a social networking site such as TWITTER or FACEBOOK).

Still further, a user may tag or otherwise associate various parameters and notes with a workout session. The tags, notes and/or parameters, in some instances, may be automatically detected. For example, weather, terrain, incline, elevation, body temperature and the like may be automatically registered as a parameter or tagged parameter of a workout session based on information that is determined through devices such as a GPS receiver, heart rate monitor, gyroscopes, accelerometers, thermometers and the like. In some examples, athletic equipment used during a workout may be tagged. This information may then be used to monitor wear on the athletic equipment, recommend new, supplemental and/or replacement equipment, determine what equipment provides better results and the like.

According to still another aspect, methods and systems for automatically identifying and matching a user with other challenge participants may be provided. For example, the system may receive a request to initiate a run and to challenge one or more other users to the run from a first user. The system may allow the user to select and invite particular users to be challenged or, alternatively or additionally, automatically identify such other users. In one example, attributes of the first user may be determined and compared to the attributes of other users. The system might only identify challenges that are currently online. The identified users may then be invited to participate in the challenge. If a user accepts the challenge, the participants may compete in the challenge, at the conclusion of which, a winner may be declared. Rewards, accolades and other recognition may be provided to the winner. Additionally or alternatively, the system may automatically suggest a schedule for a further challenge between the two participants to encourage improvement and athletic activity.

These and other features of the present disclosure will become apparent from the following detailed description.

BRIEF DESCRIPTION OF THE DRAWINGS

FIGS. 23A and 23B illustrate example in-run interfaces displaying workout information without a power song option according to one or more aspects described herein.

FIGS. 27A-27H illustrate additional or alternative user interfaces that may be displayed while a user is conducting a run according to one or more aspects described herein.

FIGS. 65E-65H illustrate example device interfaces according to one or more aspects described herein.

FIGS. 66A-66K illustrate example interfaces that may include workout reviews according to one or more aspects described herein.

FIG. 77 illustrates an example sharing permissions configuration interface.

FIGS. 78A-78C illustrate example workout summary interfaces through which a user may configure activity information sharing options.

FIG. 80 illustrates an example social networking page including a workout entry.

DETAILED DESCRIPTION

Athletic Activity Overview

Figure 1:
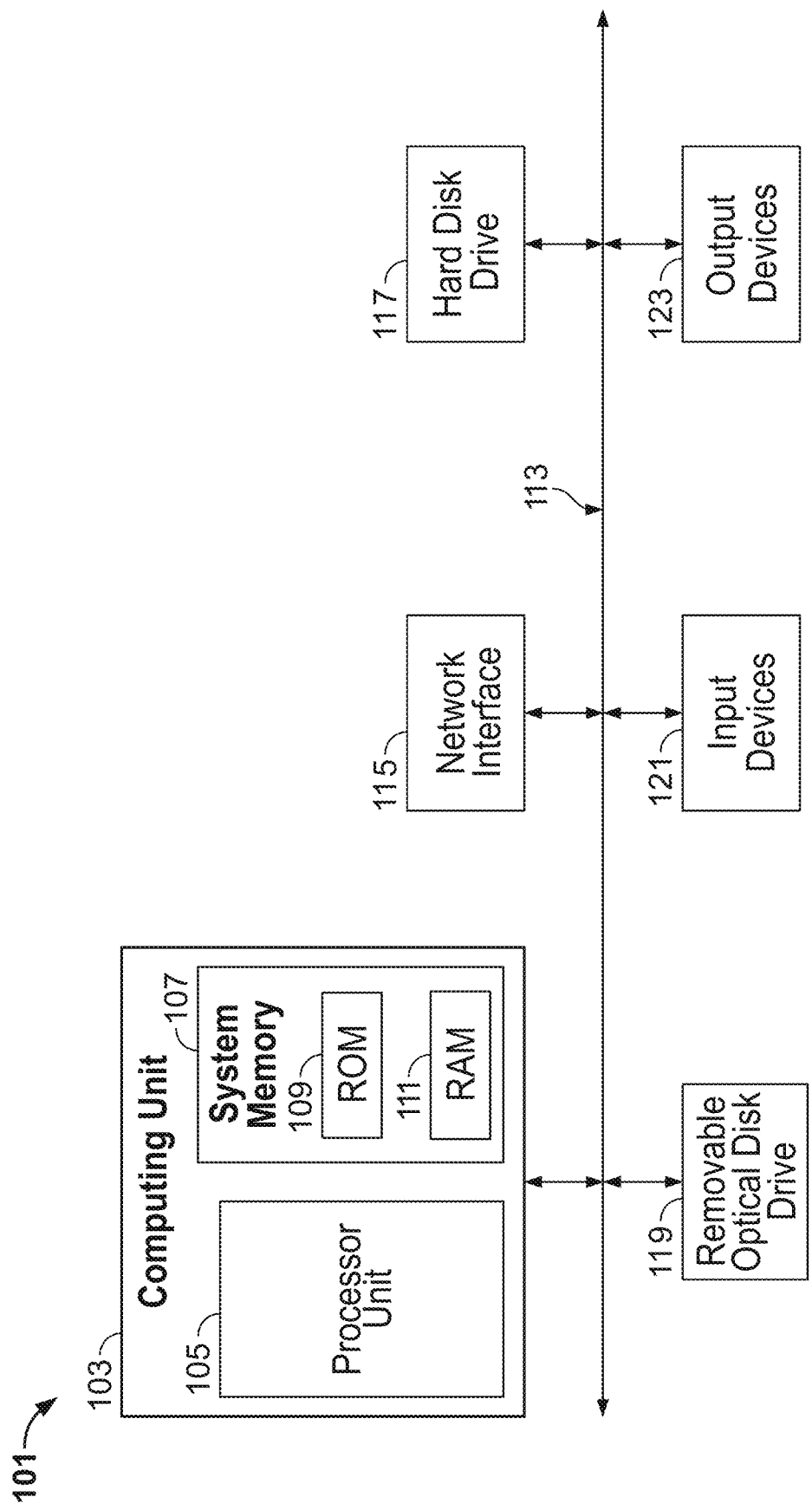
FIG. 1 illustrates a computing device that may be used to implement various examples of the invention.

Aspects of the disclosure relate to the measurement, collection, display and management of athletic and non-athletic information. As will be appreciated by those of ordinary skill in the art, athletic information must first be obtained from an individual person. With various implementations of the invention, one or more different athletic information monitoring devices may be used to measure and record athletic data corresponding to athletic activity performed by a person and convert that information into a form of currency. Typically, an athletic information monitoring device will incorporate a sensor or multiple sensors for measuring parameters relating to the person being monitored, and a computing device for processing the parameters measured by the sensor(s).

Once an athletic information monitoring device has recorded athletic information for a person's athletic activity, the person may then transfer the recorded athletic information to one or more separate devices, in order to view the recorded athletic data. A user may, for example, download the recorded athletic information from an athletic information monitoring device to a separate collection device. The collection device may, in turn, transfer the athletic information collected from the athletic information monitoring device to a separate display configuration device, where the athletic information can be organized and configured for subsequent viewing with, e.g., still another device. As will be discussed in more detail below, various implementations of the invention will allow a person to record, collect and display athletic information using a group of computing devices communicating over a network, such as the Internet.

For example, some aspects described herein allow a person to measure and record athletic information using a special-purpose computing device. The user can then transfer the recorded athletic information to a local computing device, such as a personal desktop or laptop computer. More particularly, a user can download recorded athletic information from the athletic information monitoring device to a collection software tool on a local computer that acts as a "client" in a computer network. The collection software tool will then transfer the downloaded athletic information through the network to a remote "server" computer. A display configuration software tool on the remote server computer will then save the transferred athletic information. Later, a person can use the client computer or another local computer to retrieve the stored athletic information from the server computer. In response to a display request from a local computer, the display configuration software tool will configure the requested athletic information for display on the local computer, and then transmit the configured athletic information to the local computer for display.

Computing Device

Various examples of the invention may be implemented using electronic circuitry configured to perform one or more functions. For example, with some embodiments of the invention, the athletic information monitoring device, the collection device, the display device or any combination thereof may be implemented using one or more application-specific integrated circuits (ASICs). More typically, however, components of various examples of the invention will be implemented using a programmable computing device executing firmware or software instructions, or by some combination of purpose-specific electronic circuitry and firmware or software instructions executing on a programmable computing device.

Accordingly, FIG. 1 shows one illustrative example of a computer 101 that can be used to implement various embodiments of the invention. As seen in this figure, the computer 101 has a computing unit 103. The computing unit 103 typically includes a processing unit 105 and a system memory 107. The processing unit 105 may be any type of processing device for executing software instructions, but will conventionally be a microprocessor device. The system memory 107 may include both a read-only memory (ROM) 109 and a random access memory (RAM) 111. As will be appreciated by those of ordinary skill in the art, both the read-only memory (ROM) 109 and the random access memory (RAM) 111 may store software instructions for execution by the processing unit 105.

The processing unit 105 and the system memory 107 are connected, either directly or indirectly, through a bus 113 or alternate communication structure to one or more peripheral devices. For example, the processing unit 105 or the system memory 107 may be directly or indirectly connected to additional memory storage, such as the hard disk drive 115, the removable magnetic disk drive 117, the optical disk drive 119, and the flash memory card 121. The processing unit 105 and the system memory 107 also may be directly or indirectly connected to one or more input devices 123 and one or more output devices 125. The input devices 123 may include, for example, a keyboard, touch screen, a remote control pad, a pointing device (such as a mouse, touchpad, stylus, trackball, or joystick), a scanner, a camera or a microphone. The output devices 125 may include, for example, a monitor display, haptic feedback device, television, printer, stereo, or speakers.

Still further, the computing unit 103 will be directly or indirectly connected to one or more network interfaces 127 for communicating with a network. This type of network interface 127, also sometimes referred to as a network adapter or network interface card (NIC), translates data and control signals from the computing unit 103 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 127 may employ any suitable connection agent for connecting to a network, including, for example, a wireless transceiver, a power line adapter, a modem, or an Ethernet connection.

It should be appreciated that, in addition to the input, output and storage peripheral devices specifically listed above, the computing device may be connected to a variety of other peripheral devices, including some that may perform input, output and storage functions, or some combination thereof. For example, the computer 101 may be connected to a digital music player, such as an IPOD® brand digital music player available from Apple, Inc. of Cupertino, Calif. As known in the art, this type of digital music player can serve as both an output device for a computer (e.g., outputting music from a sound file or pictures from an image file) and a storage device. In addition, this type of digital music play also can serve as an input device for inputting recorded athletic information, as will be discussed in more detail below.

In addition to a digital music player, the computer 101 may be connected to or otherwise include one or more other peripheral devices, such as a telephone. The telephone may be, for example, a wireless "smart phone." In one example, the communication device may be an IPHONE® brand portable communication device, available from Apple, Inc. of Cupertino, Calif. As known in the art, this type of telephone communicates through a wireless network using radio frequency transmissions. In addition to simple communication functionality, a "smart phone" may also provide a user with one or more data management functions, such as sending, receiving and viewing electronic messages (e.g., electronic mail messages, SMS text messages, etc.), recording or playing back sound files, recording or playing back image files (e.g., still picture or moving video image files), viewing and editing files with text (e.g., Microsoft Word or Excel files, or Adobe Acrobat files), etc. Because of the data management capability of this type of telephone, a user may connect the telephone with the computer 101 so that their data maintained may be synchronized.

Of course, still other peripheral devices may be included with our otherwise connected to a computer 101 of the type illustrated in FIG. 1, as is well known in the art. In some cases, a peripheral device may be permanently or semi-permanently connected to the computing unit 103. For example, with many computers, the computing unit 103, the hard disk drive 117, the removable optical disk drive 119 and a display are semi-permanently encased in a single housing. Still other peripheral devices may be removably connected to the computer 101, however. The computer 101 may include, for example, one or more communication ports through which a peripheral device can be connected to the computing unit 103 (either directly or indirectly through the bus 113). These communication ports may thus include a parallel bus port or a serial bus port, such as a serial bus port using the Universal Serial Bus (USB) standard or the IEEE 1394 High Speed Serial Bus standard (e.g., a Firewire port). Alternately or additionally, the computer 101 may include a wireless data "port," such as a Bluetooth interface, a Wi-Fi interface, an infrared data port, or the like.

It should be appreciated that a computing device employed according various examples of the invention may include more components than the computer 101 illustrated in FIG. 1, fewer components than the computer 101, or a different combination of components than the computer 101. Some implementations of the invention, for example, may employ one or more computing devices that are intended to have a very specific functionality, such as a digital music player or server computer. These computing devices may thus omit unnecessary peripherals, such as the network interface 115, removable optical disk drive 119, printers, scanners, external hard drives, etc. Some implementations of the invention may alternately or additionally employ computing devices that are intended to be capable of a wide variety of functions, such as a desktop or laptop personal computer. These computing devices may have any combination of peripheral devices or additional components as desired.

Athletic Information Monitoring Device

Figure 2:
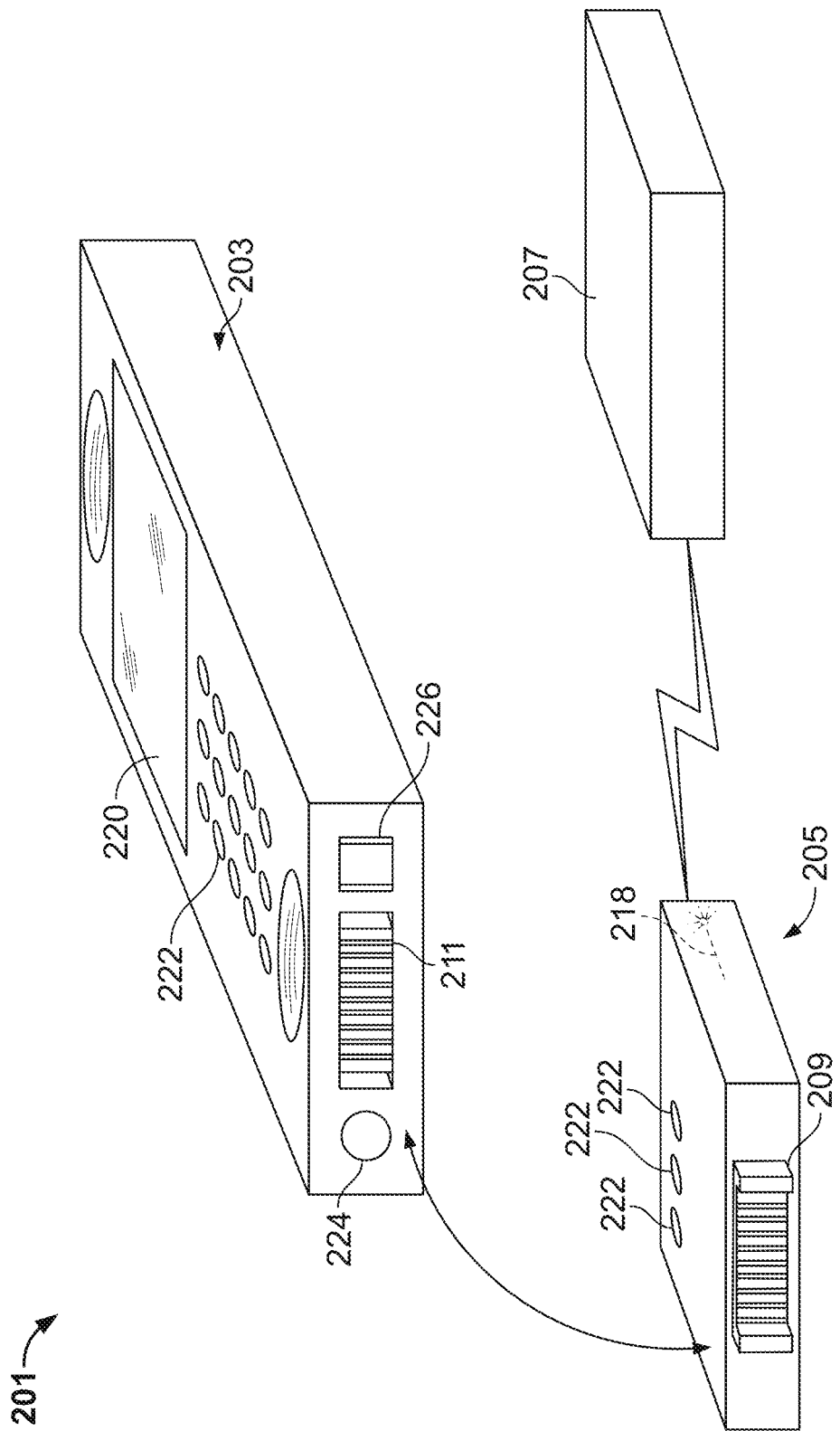
FIGS. 2 and 3 illustrate an example of an athletic information monitoring device that may be employed according to various examples of the invention.

FIG. 2 illustrates one example of an athletic information monitoring device 201 that may be employed according to various examples of the invention to measure athletic information corresponding a user's athletic activity. As shown in this figure, the athletic information monitoring device 201 includes a digital music player 203, an electronic interface device 205, and an athletic parameter measurement device 207. As will be described in more detail, the digital music player 203 is (releasably) connected to the electronic interface device 205, and the combination is worn or otherwise carried by the user while he or she is performing an athletic activity, such as running or walking. Additionally, digital music player 203 may include telecommunication components for making and receiving telephone communications, text messages, multimedia messages and the like. In one or more examples, digital music player 203 may correspond to a smartphone configured to execute computer applications, provide telecommunication capabilities, play audio, video, provide haptic feedback, access local and wide area networks and the like.

The athletic parameter measurement device 207 may be worn or carried by the user while he or she is performing an athletic activity, and measures one or more athletic parameters relating to the athletic performance being performed by the user. The athletic parameter measurement device 207 transmits signals to the electronic interface device 205 that correspond to the measured athletic parameter. The electronic interface device 205 receives the signals from the athletic parameter measurement device 207, and provides the received information to the digital music player 203. In one or more arrangements, electronic interface device 205 might not be included as part of the athletic monitoring system 201. Instead, the digital music player 203 may include a communication device configured to receive sensor data from one or more athletic measurement sensors and to transmit instructions thereto.

Figure 3:
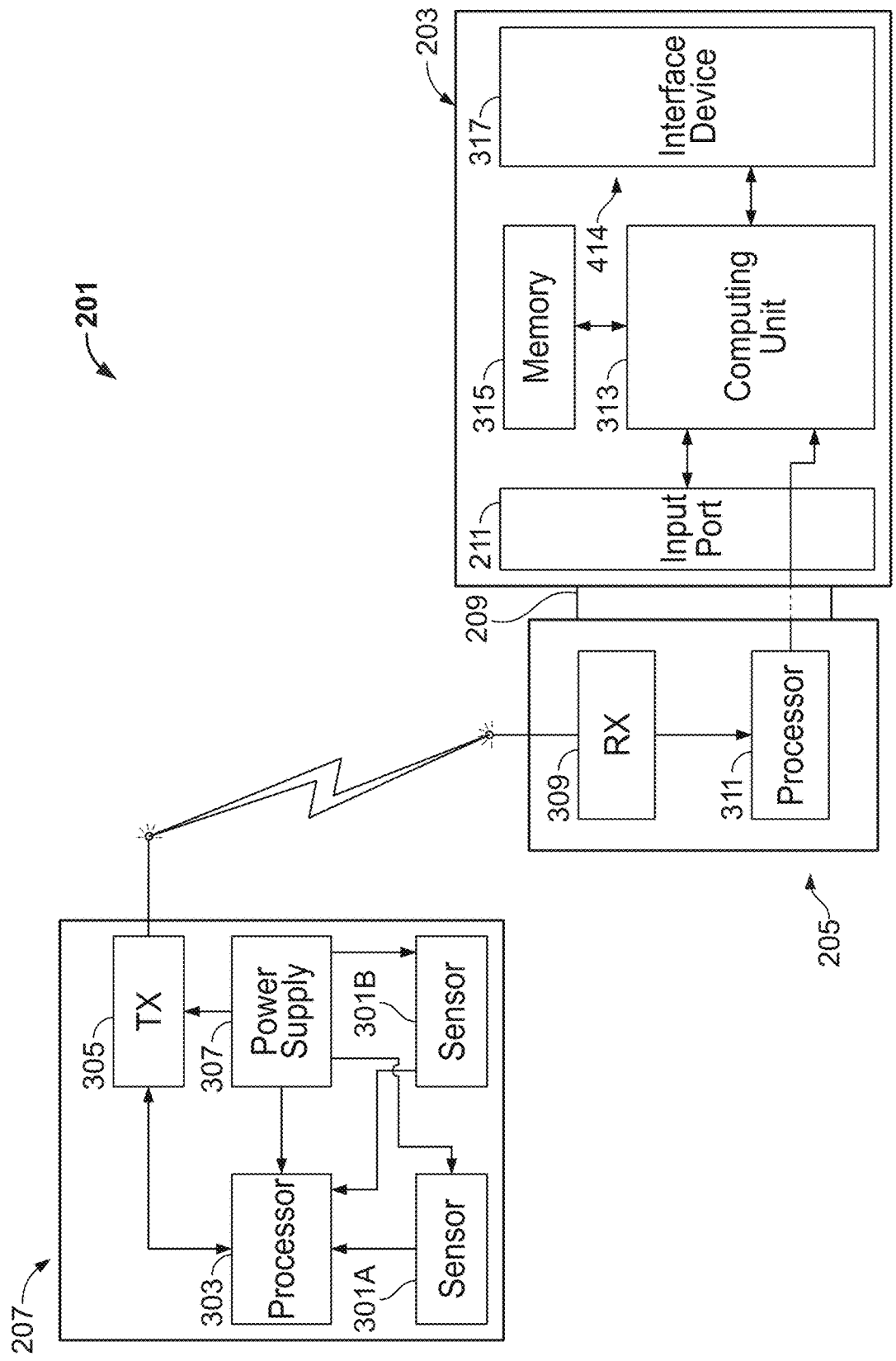
Figure 4:
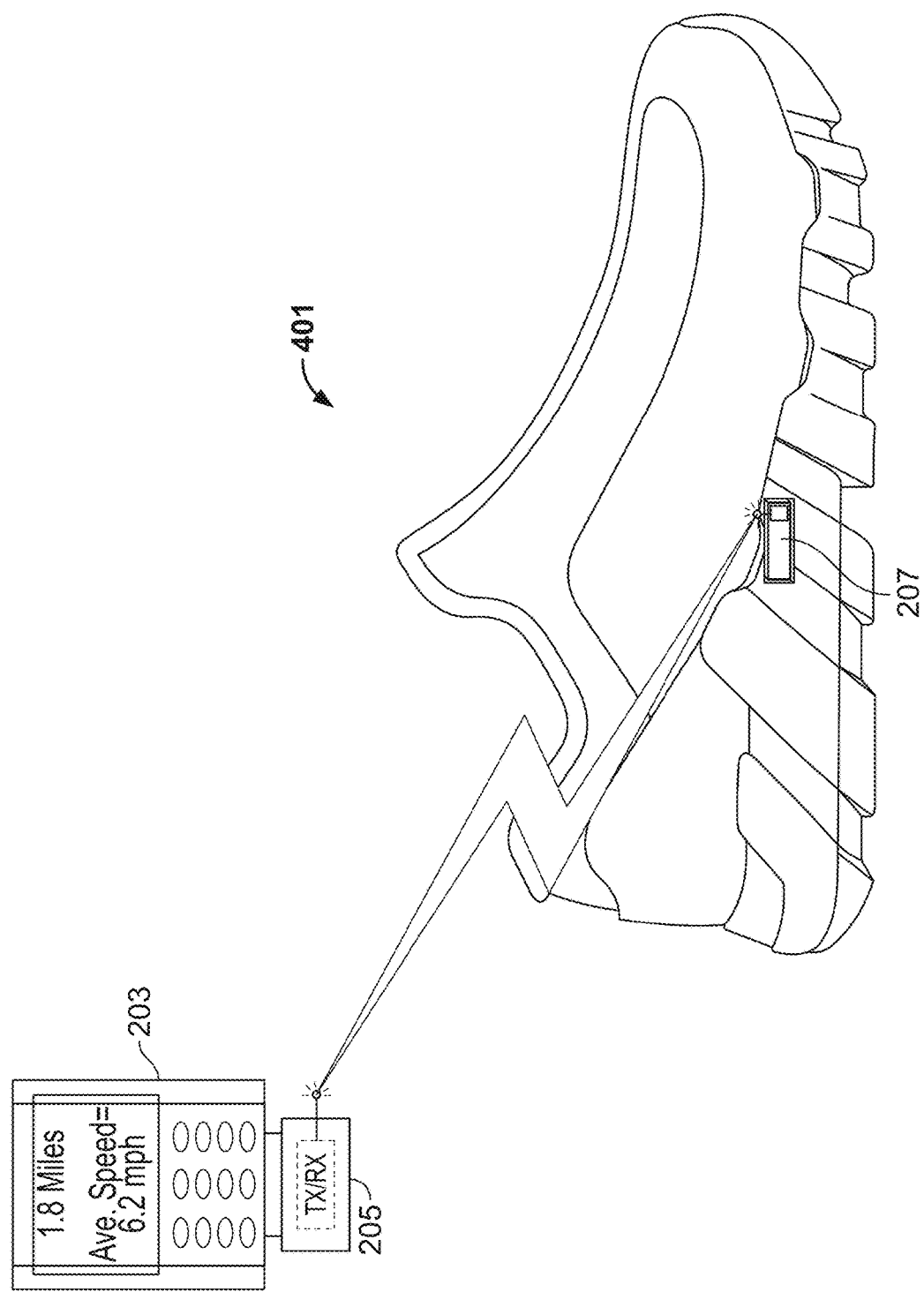
FIG. 4 illustrates one environment in which an athletic parameter measurement device according to various examples of the invention may be employed.

As shown in more detail in FIG. 3, the athletic parameter measurement device 207 includes one or more sensors 301 for measuring an athletic parameter associated with a person wearing or otherwise using the athletic parameter measurement device 207. With the illustrated implementations, for example, the sensors 301A and 301B may be accelerometers (such as piezoelectric accelerometers) for measuring the acceleration of the athletic parameter measurement device 207 in two orthogonal directions. The athletic parameter measurement device 207 is carried or otherwise worn by a user to measure the desired athletic parameter while the user exercises. For example, as shown in FIG. 4, the athletic parameter measurement device 207 may be located the sole of a user's shoe 401 while the user walks or runs. With this arrangement, the sensors 301 will produce electrical signals corresponding to the movement of the user's foot. As known in the art, these signals can then be used to generate athletic data representative of the athletic activity performed by the user. In other examples, athletic parameter measurement device 207 may be worn on a chest strap or on a user's wrist or may be incorporated within digital music player 203.

The athletic parameter measurement device 207 also includes a processor 303 for processing the electrical signals output by the sensors 301. With some implementations of the invention, the processor 303 may be a programmable microprocessor. For still other implementations of the invention, however, the processor 303 may be a purpose-specific circuit device, such as an ASIC. The processor 303 may perform any desired operation on the signals output from the sensors 301, such as curve smoothing, noise filtering, outlier removal, amplification, summation, integration, or the like. The processor 303 provides the processed signals to a transmitter 307. The athletic parameter measurement device 207 also includes a power supply 307, for providing power to the sensors 301, the processor 303, and the transmitter 305 as needed. The power supply 307 may be, for example, a battery.

The athletic parameter measurement device 207 transmits the processed signals to the electronic interface device 205, as seen in FIG. 4, or directly to the digital music player 203. Returning now to FIG. 3, the electronic interface device 205 includes a receiver 309 which receives the processed signals transmitted by the transmitter 305 in the athletic parameter measurement device 207. The receiver 309 relays the processed signals to a second processor 311, which processes the signals further Like the processor 303, the processor 311 may perform any desired operation on the processed signals, such as curve smoothing, noise filtering, outlier removal, amplification, summation, integration, or the like.

The processor 303 provides the processed signals to the digital music player 203. Referring back now to FIG. 2, in one arrangement, the electronic interface device 205 includes a connector system 209 that physically plugs into and connects with a conventional input port 211 provided on digital music player 203. The input port 211 into which the connector system 209 of the electronic interface device 205 connects may be any desired type of input port for transferring data, such as a parallel data port, a serial data port, an earphone or microphone jack, etc.) The connector system 209 may include any suitable connecting devices, such as wires, pins, electrical connectors, and the like, so as to make an electrical connection or other suitable connection with corresponding elements provided in the input port 211 of the digital music player 203 (e.g., to allow electronic and/or data communications between the interface device 205 and the electronic interface device 205). If necessary or desired, additional securing elements may be provided to securely connect the interface device 205 to the digital music player 203, such as straps, hooks, buckles, clips, clamps, clasps, retaining elements, mechanical connectors, and the like.

Returning now to FIG. 3, the processor 311 provides the processed signals to the computing unit 313. The computing unit 313 may initially store the processed signals in the memory 315. Further, with some implementations of the invention, the computing unit 313 may operate on the processed signals provided by the athletic information monitoring device 201 to generate a set of athletic data corresponding to the athletic activity performed by the user. For example, if the athletic information monitoring device 201 includes accelerometers for measuring the movement of the user's foot, the computing unit 313 may analyze the processed signals from the athletic information monitoring device 201 to generate a set of athletic data describing the user's speed at specific instances during the user's athletic activity and the total distance traveled by the user at each of those specific instances. Various techniques for determining a user's speed from accelerometer signals are described in, for example, U.S. Pat. No. 6,898,550 to Blackadar et al., entitled "Monitoring Activity Of A User In Locomotion On Foot," and issued on May 24, 2005, U.S. Pat. No. 6,882,955 to Ohlenbusch et al., entitled "Monitoring Activity Of A User In Locomotion On Foot," and issued on Apr. 19, 2005, U.S. Pat. No. 6,876,947 to Darley et al., entitled "Monitoring Activity Of A User In Locomotion On Foot," and issued on Apr. 5, 2005, U.S. Pat. No. 6,493,652 to Ohlenbusch et al., entitled "Monitoring Activity Of A User In Locomotion On Foot," and issued on Dec. 10, 2002, U.S. Pat. No. 6,298,314 to Blackadar et al., entitled "Detecting The Starting And Stopping Of Movement Of A Person On Foot," and issued on Oct. 2, 2001, U.S. Pat. No. 6,052,654 to Gaudet et al., entitled "Measuring Foot Contact Time And Foot Loft Time Of A Person In Locomotion," and issued on Apr. 18, 2000, U.S. Pat. No. 6,018,705 to Gaudet et al., entitled "Measuring Foot Contact Time And Foot Loft Time Of A Person In Locomotion," and issued on Jan. 25, 2000, each of which are incorporated entirely herein by reference.

The athletic data set may also include a time value associated with each speed value and/or each distance value. If the athletic information monitoring device 201 can be employed to collect athletic information from different users, then the athletic data computing unit 313 may additionally prompt the user to identify himself or herself in some way. This identification information may then be included with the athletic data set generated from the information provided by the athletic information monitoring device 201. Once the computing unit 313 has generated a set of athletic data from the information provided by the athletic information monitoring device 201, the computing unit 313 may store the athletic data set in the memory 315. As will be discussed in more detail below, when the digital music player 203 subsequently is connected to a computing device implementing an athletic information collection tool, the computing unit 313 will download the athletic data to a display configuration tool hosted on a remote computing device.

While wireless communication between the between the athletic parameter measurement device 207 and the interface device 205 is described for the embodiments illustrated in FIGS. 2-4, any desired manner of communicating between the athletic parameter measurement device 207 and the interface device 205 may be used without departing from the invention, including wired connections. Also, any desired way of placing data derived from the physical or physiological data from the athletic parameter measurement device 207 in the proper form or format for display on or output from electronic device 210 may be provided without departing from the invention. For example, if desired, the athletic parameter measurement device 207 may be specially designed and/or programmed for use with one or more specific electronic devices, e.g., pre-programmed and/or wired to operate with a specific device or devices and to provide output data in a form and format suitable for those devices. In this situation, the interface devices 205 may be marketed and sold to specifically target certain electronic devices, such as specific models of digital music players and even other electronic devices, such as telephones, watches, personal digital assistants, etc. As another alternative, if desired, the interface devices 205 may be programmed at a later time to operate with a wide variety of different electronic devices, e.g., by downloading display or device driver and/or format data for specific electronic devices from the Internet, from disk, or from another source, etc.

If desired, in accordance with at least some examples of this invention, the electronic interface device 205 may further include a display 220 and/or a user input system 222, such as one or more rotary input devices, switches, buttons (as shown in the illustrated example in FIG. 2), mouse or trackball elements, touch screens, or the like, or some combination thereof. The display 220 may be employed to show, for example, information relating to music being played by the digital music player 203, information relating to the athletic information signals being received by the digital music player 203, athletic data being generated by the digital music player 203 from the received athletic information signals, etc. The user input system 222 may be employed, for example: to control one or more aspects of the processing of the input data received via interface device 205, to control input data receipt (e.g., timing, types of information received, on-demand data requests, etc.), to control data output to or by the electronic device 203, to control the athletic parameter measurement device 207, etc. Alternatively or additionally, if desired, the input system on the digital music player 203 (e.g., buttons 222, a touch screen, a digitizer/stylus based input, a rotary input device, a trackball or roller ball, a mouse, etc.), may be used to provide user input data to the interface device 205 and/or to the athletic parameter measurement device 207. As still another example, if desired, a voice input system may be provided with the interface device 205 and/or the digital music player 203, e.g., to enable user input via voice commands. Any other desired type of user input system, for control of any system elements and/or for any purpose, may be provided without departing from the invention.

The digital music player 203 may include additional input and/or output elements, e.g., such as ports 224 and 226 shown in FIG. 2, e.g., for headphones (or other audio output), power supplies, wireless communications, infrared input, microphone input, or other devices. If desired, and if these ports 224 and/or 226 would be covered when the interface device 205 is attached to the electronic device 203, the interface device 205 may be equipped with similar external ports to ports 224 and/or 226, and internal circuitry may be provided in the interface device 205 to enable the user to plug the same additional devices into the interface device 205 as they might plug into the digital music player 203 and still take advantage of the same functions (e.g., to thereby allow the necessary data, signals, power, and/or information to pass through the interface device 205 to the user, to another output, and/or to the digital music player 203).

It should be appreciated that, while some specific embodiments of the invention described above relate to a digital music player 203, alternate examples of the invention may be implemented using any portable electronic device. For example, with some implementations of the invention, the athletic parameter measurement device 207 may be used in conjunction with a mobile telephone, a watch, a personal digital assistant, another type of music player (such as a compact disc or satellite radio music player), a portable computer, or any other desired electronic device. Still further, some implementations of the invention may alternately or additionally omit the use of the interface device 205. For example, the athletic parameter measurement device 207 may be configured to communicate using the Bluetooth wireless communication protocol, so that it can be employed with Bluetooth-capable mobile telephones, personal digital assistants, watches or personal computers. Of course, still other wireless or wired communication techniques could be employed while omitting the interface device 205.

It also should be appreciated that, while a specific example of an athletic parameter measurement device 207 has been described above for ease of understanding, any type of desired athletic parameter measurement device 207 can be employed with various embodiments of the invention. For example, with some implementations of the invention, the athletic parameter measurement device 207 may be a heart rate monitor, a blood oxygen monitor, a satellite positioning device (e.g., a Global Positioning Satellite (GPS) navigation device) or other location determination system, a device for measuring the electrical activity of the user (e.g., an EKG monitor), or any other device that measures one or more physical parameters of the user. Still further, the athletic parameter measurement device 207 may measure one or more operational parameters of some device being manipulated by the user, such as the speed and/or distance of a bicycle, the speed and/or work performed by a treadmill, rowing machine, elliptical machine, stationary bicycle, the speed and/or distance traveled by skis (water or snow), skates (roller or ice), or snowshoes or the like worn by the user, etc.

Also, while the athletic parameter measurement device 207 has been described as being separate for the digital music player 203 or other portable electronic device that receives the signals from the athletic parameter measurement device 207, with some implementations of the invention the athletic parameter measurement device 207 may be incorporated into the digital music player 203 or other portable electronic device. For example, some implementations of the invention may employ a music player, mobile telephone, watch or personal digital assistant that incorporates accelerometers, a satellite positioning device, or any other desired device for measuring athletic activity. Still further, it should be appreciated that various implementations of the invention may employ a plurality of athletic parameter measurement devices 207, incorporated into the digital music player 203 or other portable electronic device, separate from the digital music player 203 or other portable electronic device, or some combination thereof.

Athletic Collection and Display Tools

Figure 5:
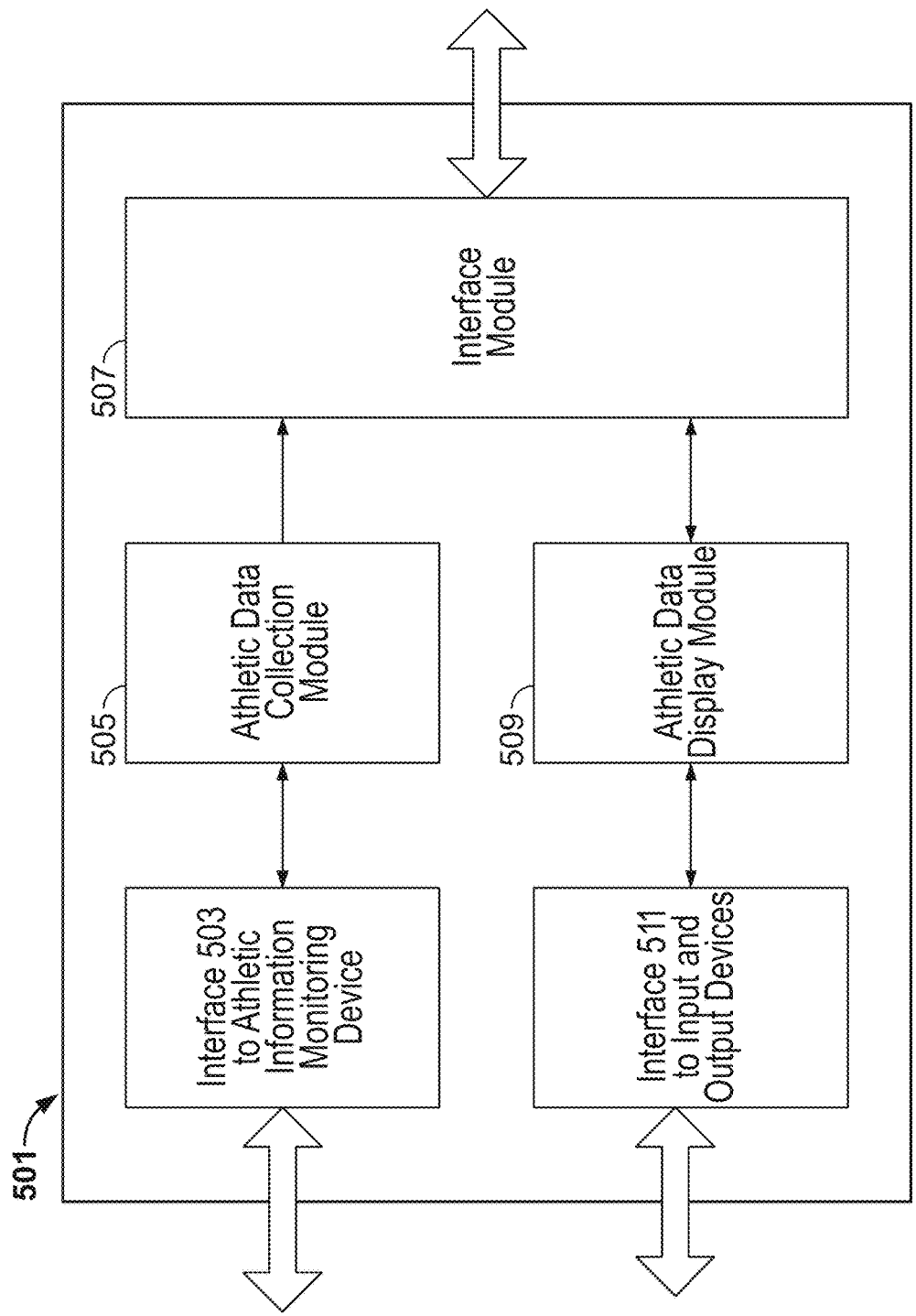
FIG. 5 illustrates an example of an athletic information collection and display device that may be employed to collect and/or display athletic data according to various implementations of the invention.

FIG. 5 illustrates an example of an athletic information collection and display device 501 that may be employed to collect and/or display athletic data according to various implementations of the invention. As will be discussed in more detail below, the athletic information collection and display device 501 may both collect and display athletic data. The athletic information collection and display device 501 may be implemented using any suitable variation of the computing device 101 previously described. In some situations, however, the information collection and display device 501 may be commercially implemented using a desktop or laptop personal computer using, e.g., a version of the Microsoft Windows operating system available from Microsoft Corporation of Redmond, Wash., a version of the Apple Macintosh operating system available for Apple Corporation of Cupertino, Calif., or a version of the Unix or Linux operating systems available from a plurality of vendors.

As shown FIG. 5, the athletic information collection and display device 501 includes an interface 503 for receiving data from the athletic information monitoring device 201. The interface 503 may be implemented using, e.g., electrical components, software components (such as application program interfaces (APIs)), or some combination thereof. The athletic information collection and display device 501 also has an athletic data collection module 505. With various examples of the invention, the athletic data collection module 505 may detect when the digital music player 203 or other portable electronic device storing one or more athletic data sets is connected to the athletic information collection and display device 501 through the interface 503, establish a communication session with the digital music player 203 or other portable electronic device to retrieve the athletic data set or sets. In some implementations of the invention, the athletic data collection module 505 may delete athletic data sets from the digital music player 203 or other portable electronic device after the athletic data sets have been retrieved.

With some examples of the invention, the athletic data collection module 505 may perform some further operations on the athletic data sets retrieved from the digital music player 203 or other portable electronic device. For example, if the athletic information monitoring device 201 can be employed to collect athletic information from different users, then the athletic data collection module 505 may additionally prompt the user to identify himself or herself (if this information was not previously obtained by the athletic information collection and display device 501). This identification information may then be included with the retrieved athletic data sets.

As previously noted, the athletic information collection and display device 501 typically will generate sets of athletic data from information measured by one or more athletic parameter measurement devices 207. With some embodiments of the invention, however, the athletic information collection and display device 501 may instead store the raw information provided by the athletic parameter measurement devices 207. With these embodiments, the athletic data collection module 505 may retrieve the raw information from the digital music player 203 or other portable electronic device, and then generate athletic data sets from the raw information itself. Of course, still other examples of the invention may divide functions relating to the generation of athletic data from the raw information measured by athletic parameter measurement devices 207 between the athletic data collection module 505 and the digital music player 203 or other portable electronic device as desired.

The athletic data collection module 505 may be implemented by, for example, software instructions executed by a computing unit 113 of a computing device 101. With some examples of the invention the athletic data collection module 505 may be implemented by a conventional software tool, such as a browser. Alternately, athletic data collection module 505 may be implemented by a purpose-specific software tool or by a conventional software tool enhanced to perform athletic data collection functions. For example, the athletic data collection module 505 may be implemented by a software tool that incorporates a conventional browser to perform a variety of functions. These functions may include, e.g., selecting, purchasing, and downloading music and video content in addition to collecting athletic data from a digital music player 203 or other portable electronic device.

Once the athletic data collection module 505 has collected the processed signals provided by the athletic information monitoring device 201, the athletic data collection module 505 transmits the athletic data set to an athletic data display configuration device 601 through an interface module 507. The athletic information collection and display device 501 may communicate with the athletic data display configuration device 601 through a conventional network, such as the Internet. With these configurations, the interface module 507 may be implemented using any conventional type of network interface, such as a network interface card. Of course, any type of desired hardware or software combination alternately may be used to allow the athletic data collection module 505 to send the collected athletic data to the athletic data display configuration device 601. With some implementations of the invention, the athletic data collection module 505 may automatically forward collected athletic data to the athletic data display configuration device 601. For example, the athletic data collection module 505 may attempt to forward collected athletic data to the athletic data display configuration device 601 immediately after collection, at a prescheduled interval, upon the detection of a network connection to the athletic data display configuration device 601, or some combination thereof. Alternately or additionally, the athletic data collection module 505 may prompt a user to specify when collected athletic data is sent to the athletic data display configuration device 601.

Figure 6:
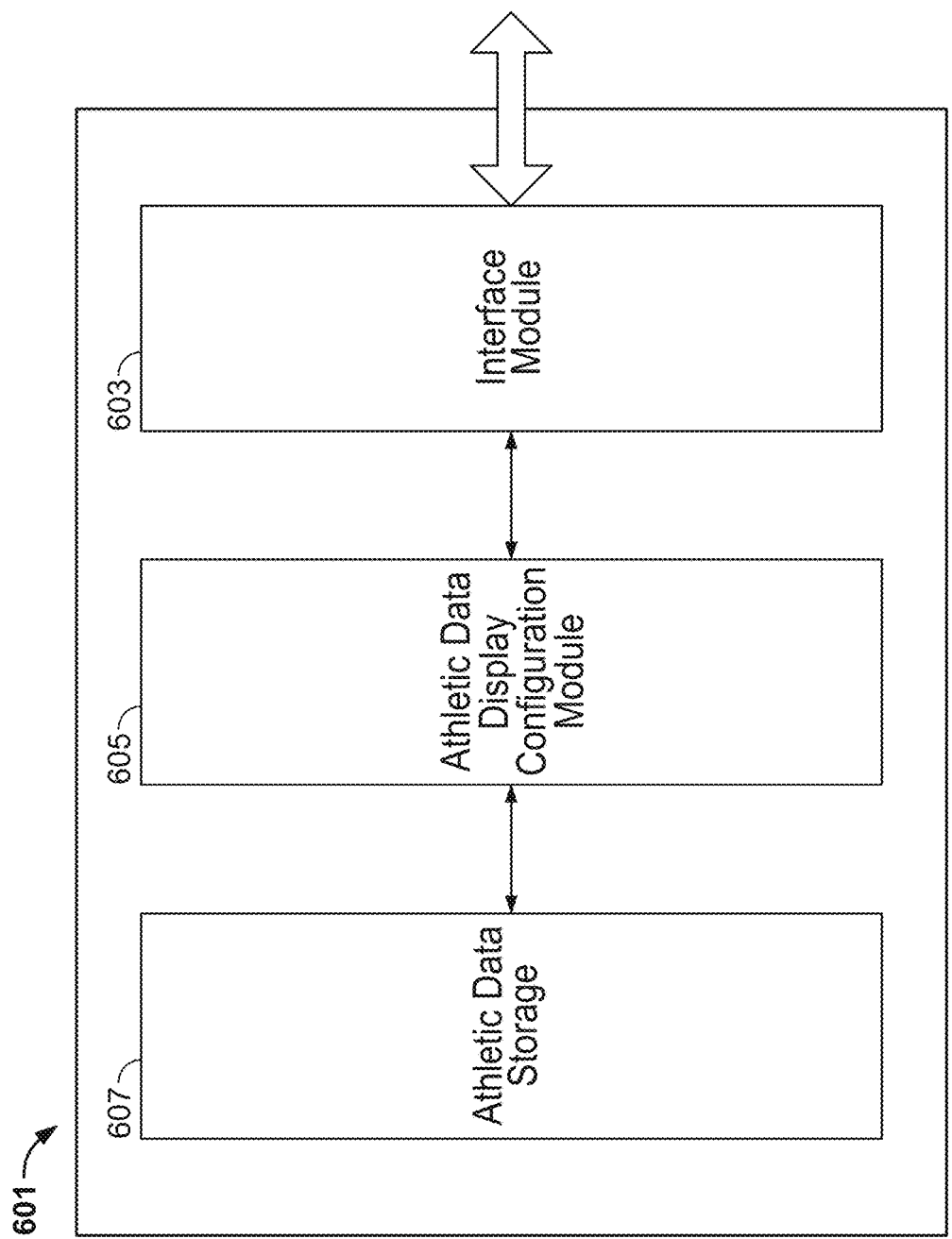
FIG. 6 illustrates an example of an athletic data display configuration device that may be employed according to various examples of the invention.

FIG. 6 illustrates an example of an athletic data display configuration device 601 that may be employed according to various examples of the invention. As seen in this figure, the athletic data display configuration device 601 includes an interface module 603 for communicating with the athletic information collection and display device 501. As previously noted, the athletic information collection and display device 501 may communicate with the athletic data display configuration device 601 through a conventional network, such as the Internet. With these configurations, the interface module 603 may be implemented using any conventional type of network interface, such as a network interface card. Of course, any type of desired hardware or software combination alternately may be used to allow the athletic data display configuration device 601 to communicate with the athletic information collection and display device 501.

The athletic data display configuration device 601 also includes an athletic data display configuration module 605, and an athletic data storage 607. When the interface 603 of the athletic data display configuration device 601 receives athletic data from the athletic information collection and display device 501, it provides the received athletic data to the athletic data display configuration module 605. The athletic data display configuration module 603 may then store the athletic data in the athletic data storage 607 for future use. As will be discussed in more detail below, the athletic data display configuration module 605 also will retrieve athletic data from the athletic data storage 607, and configure the retrieved athletic data for display through one or more user interfaces in a manner that is meaningful to a user.

Returning now to FIG. 5, when a user wishes to view information relating to his or her athletic activities (or the athletic activities of another, as will be discussed in more detail below), the user submits this request to the athletic information collection and display device 501. More particularly, the user can employ conventional input and output devices, such as a keyboard, mouse, display and the like. The display request is then provided to an athletic data display module 509 through a conventional interface input/output interface 511. As well known in the art, the interface input/output interface 511 may be implemented using any desired combination of hardware and software components, such as conventional application programming interfaces (APIs) used to detect and process input from input devices, and to send data to and otherwise control output devices.

With some examples of the invention, the athletic data display module 509 may be implemented using any conventional tool for receiving input to request and control the display of data, and then subsequently displaying the data in the manner requested. For example, the athletic data display module 509 may be implemented using a conventional browser program, such as Microsoft Internet Explorer, Mozilla Firefox, or Opera executing on a computing unit 113. With still other embodiments of the invention, the athletic data display module 509 may be implemented using a conventional browser program that has been enhanced by one or more display tools, such as an ActiveX plug-in, a Java script or a version of the Macromedia Flash Player or Adobe Flash Player, available from Adobe Systems Incorporated of San Jose, Calif. In still other embodiments of the invention, the athletic data display module 509 may be implemented by, for example, a purpose-specific software tool for displaying athletic data.

As will be discussed in more detail below, when a user activates the athletic data display module 509, he or she is provided with a user interface prompting the use to select what collected athletic data he or she wishes to view, the format in which the user wishes to view the collected athletic data, etc. This user interface may be generated by the athletic data display module 509, the athletic data display configuration module 605, or some combination thereof. When a user employs the provided user interface to submit a request to view athletic data, the athletic data display module 509 relays the request to the athletic data display configuration module 605. In response, the athletic data display configuration module 605 configures the requested athletic data for display by the athletic data display module 509. For example, as will be discussed in more detail below, a user may request to view the total distance run by a user for each day in a one week period. In response, the athletic data display configuration module 605 will retrieve the relevant distance data from the athletic data storage 607. It will then configure the retrieved distance data to be displayed through a desired image (e.g., a bar graph), and provide the configured athletic data to the athletic data display module 509 for display to the user.

It should be noted that, with some embodiments of the invention, the data display configuration functions may be divided between the athletic data display module 509 and the athletic data display configuration module 605. For example, if the athletic data display module 509 is implemented by a simple browser, then the athletic data display module 509 may serve as a "thin client" for the athletic data display configuration module 605. That is, all of the data display configuration functions may be performed by the athletic data display configuration module 605. The athletic data display module 509 will then only display the information provided to it. Alternately, if the athletic data display module 509 is implemented by a purpose-specific software tool, then most or all of the data display configuration functions may be performed by the athletic data display module 509. With these examples, the athletic data display configuration module 605 may be used only to store and retrieve athletic data from the athletic data storage 607.

Athletic Activity Monitoring Using a GPS-Enabled Mobile Device

As noted above, various software (e.g., athletic display module 509 of FIG. 5) and hardware (e.g., digital music player 203 of FIG. 2 and/or athletic information collection and display device 501 of FIG. 5) may be used to track athletic activity and provide such information to an individual. In one arrangement, the software and/or hardware may be included in a mobile device such as a mobile communication device or mobile computing device. Use of a mobile device for detecting, collecting, processing and display of athletic information may provide an athlete with athletic activity information in a variety of environments. For example, to view processed or collected athletic activity information, the athlete may use his or her mobile device instead of having to use a stationary computing system. Such mobile devices may include smartphones, mobile telephones, personal data assistants (PDAs), laptop computing devices, digital music players, tablet computers, wrist worn devices, and the like. Computer executable instructions in the form of a software application or applet may be stored in the mobile device, allowing the mobile device to perform various athletic activity tracking and monitoring functions. For example, the mobile device may offer feedback, challenges, suggestions, encouragement and other data in response to an individual's athletic performance. In one example, the computing device may challenge the individual to perform a more strenuous or more difficult workout than in a previous workout session in order to help the individual improve and achieve greater progress. By achieving more substantial progress, the individual may be more motivated to continue exercising on a regular basis. In another example, the mobile device may be configured to encourage and motivate the individual based on his or her performance and/or comments and encouragement received from other individuals.

Figure 7:
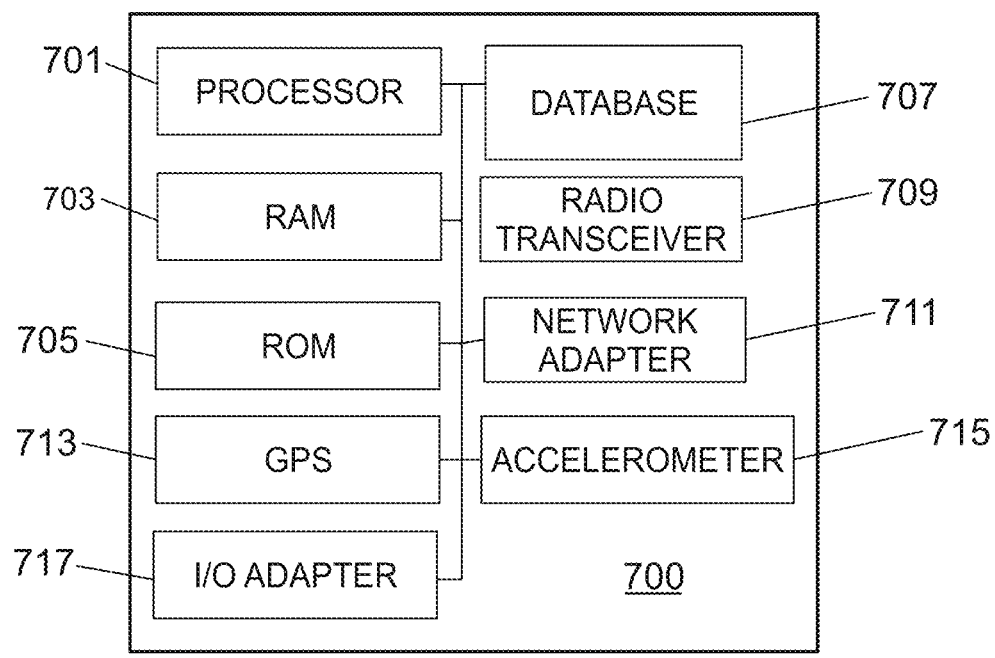
FIG. 7 illustrates an example mobile athletic activity monitoring device according to one or more aspects described herein.

FIG. 7 illustrates a block diagram of an example mobile device that may be used to track athletic activity information and provide various types of feedback to an individual. In a particular example, the mobile device may correspond to a digital music player such as digital music player 203 of FIG. 2. Mobile device 700 may include processor 701, RAM 703, ROM 705, database 707, radio transceiver 709, network adapter 711, global positioning system (GPS) device 713, accelerometer 715 and I/O adapter 717. Computer readable media such as RAM 703 and ROM 703 may be configured to store computer readable instructions that, when executed, cause an apparatus such as mobile device 700 to perform one or more functions described herein. Processor 701 may be configured to perform various calculations and execute instructions stored in RAM 703 and ROM 705. Database 707 may provide storage for data including user information, phone numbers, network addresses, e-mail addresses, software, images, documents and the like. I/O adapter 717 may be configured to facilitate the reception and output of data to one or more input or output devices including a touchscreen display, a speaker, audio jack, physical keyboard, microphone and the like.

The inclusion of GPS device 713 and accelerometer 715 in a single mobile device 700 allows device 700 to record athletic activity data in multiple workout settings. For example, if an individual is running on a treadmill, GPS device 713 would likely be unable to detect or provide significant exercise data since the individual generally remains stationary and a GPS satellite signal may be unavailable. As such, the mobile device may instead use the accelerometer to determine a number of steps the individual has taken, a speed/acceleration (e.g., pace) of the individual and the like. If, on the other hand, the individual is running outdoors such that the individual moves from one location to another, the GPS device 713 or recording of data therefrom (e.g., GPS device is always active, but recording is turned on and off) may be activated and used instead. In one or more arrangements, mobile device 700 may automatically detect whether GPS device 713 should be used or accelerometer 715 should be used (or whether data should be recorded from GPS device 713 or accelerometer 715). For example, if device 700 determines that the individual's location is not changing, accelerometer 715 or recording data therefrom may be activated and used (again, the device might always be active, but recording data from the device is turned on and off). In some arrangements, both GPS device 713 and accelerometer 715 may be used in conjunction with one another to provide additional data granularity and/or to enhance accuracy of the data. Other sensors may also be included in mobile device 700 including a heart rate monitoring device to provide additional types of activity data. Additionally, in some instances, location may be determined using cellular triangulation if GPS is unavailable.

In one or more arrangements, mobile device 700 may automatically switch between a GPS without accelerometer setting, an accelerometer without GPS setting or a combination GPS and accelerometer setting (and in some cases, a cellular triangulation with accelerometer mode). The switching and determination of which mode to use may depend on a variety of factors including detected movement, GPS signal strength and availability, user preferences, location and the like. For example, if a GPS signal is low (e.g., below 50% strength, below 30% strength, below 10% strength, etc.), mobile device 700 may operate (e.g., record data from) both GPS device 713 and accelerometer 715 so that the accelerometer 715 data may supplement any potentially missing or inaccurate GPS information. Alternatively or additionally, GPS data and accelerometer data may be averaged or otherwise combined to determine an amount of athletic activity performed by the user. In another example, mobile device 700 may use and record data from the GPS device 613 without using or recording data from accelerometer 715 when the signal strength is above a predetermined level (e.g., 50%, 70%, 90%, etc.). In yet another example, if mobile device 700 detects movement via accelerometer 715 but does not detect change in position using GPS device 713, mobile device 700 may use accelerometer 715 without GPS device 713 for that workout. Further, if the device 700 begins detecting a GPS signal, device 700 may switch to GPS mode or a combination GPS/accelerometer mode. In other instances, an accelerometer 715 may be used without GPS device 713 if no GPS signal is available and/or a location of the user is indoors. The user location may automatically be determined using GPS (e.g., location, signal strength) or based on manual input.

According to one or more arrangements, mobile device 700 may determine that a user is performing stationary athletic activity by detecting steps taken at a predefined pace, receiving user indication of a start of athletic activity, detecting elevation of heart rate (e.g., through a heart rate sensor) and the like. In one example, the mobile device 700 may detect steps being taken above a threshold pace using data from the accelerometer 715. Upon detecting the steps being taken, the mobile device 700 may determine whether GPS data from GPS device 713 is available and/or indicates a change in location. If not (e.g., no GPS signal or no change in location), the mobile device 700 may register that the user is performing a stationary athletic activity. The mobile device 700 may further confirm this determination with the user. Additionally or alternatively, mobile device 700 may also determine whether an elevated heart rate is detected.

In other examples, other sensors may be used in concert with a location determination system to provide alternative or additional activity information. For example, a heart rate sensor may be used to determine whether the user is performing athletic activity if a location determination system does not detect a change in a user's physical location (or a change above a predefined threshold distance or altitude). Additionally or alternatively, GPS device 713 and/or accelerometer 715 may be physically separate devices from mobile device 700. For example, accelerometer 715 may correspond to a wrist-worn or shoe-integrated sensor. GPS device 713, for instance, may be incorporated in a wrist-worn device. Mobile device 700 may communicate and receive data from each of these separate devices using various wireless or wired communication systems including BLUETOOTH, Wi-Fi, infrared and the like.

Mobile device 700 or other computing systems may offer a variety of functions and options for defining a workout. For example, the system may offer the user options of starting a run from scratch or improving on a previously completed run. The run may then customized and encouragement and/or status information may be provided to the individual during and after the run.

Defining a Run—Overview

Using an athletic activity monitoring device such as device 700 of FIG. 7, a user may register athletic activity sessions and record data therefrom. Registration of an athletic activity session may include defining the type of activity, a duration of the activity, audio, video or haptic feedback to be provided and the like. This information may be entered through one or more applications execution on device 700. Accordingly, the user may set-up an athletic activity session in a mobile environment and shortly before engaging in the activity session.

Figure 8:
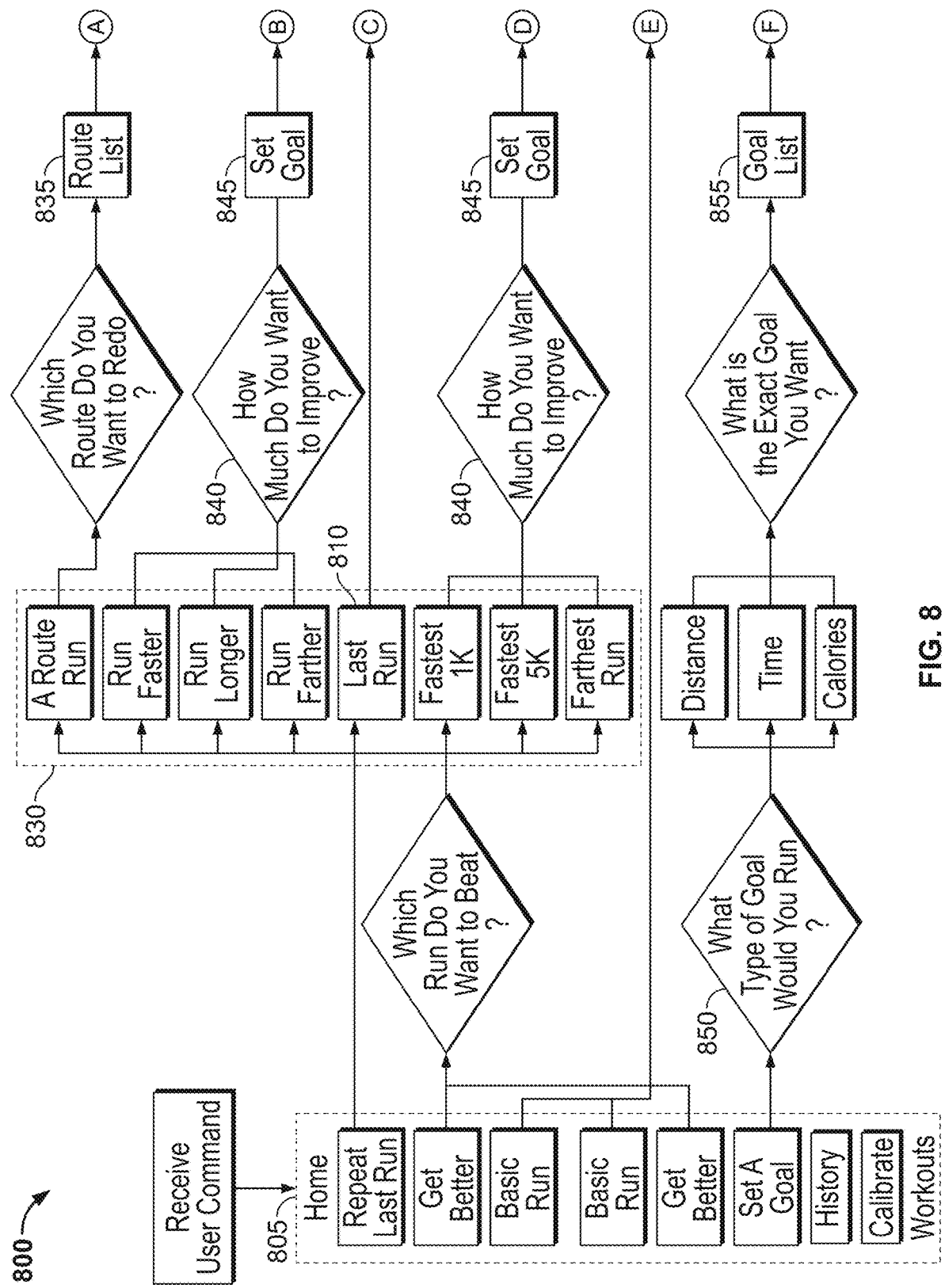
FIGS. 8 and 9 illustrate example methods for defining a workout according to one or more aspects described herein.
Figure 8:
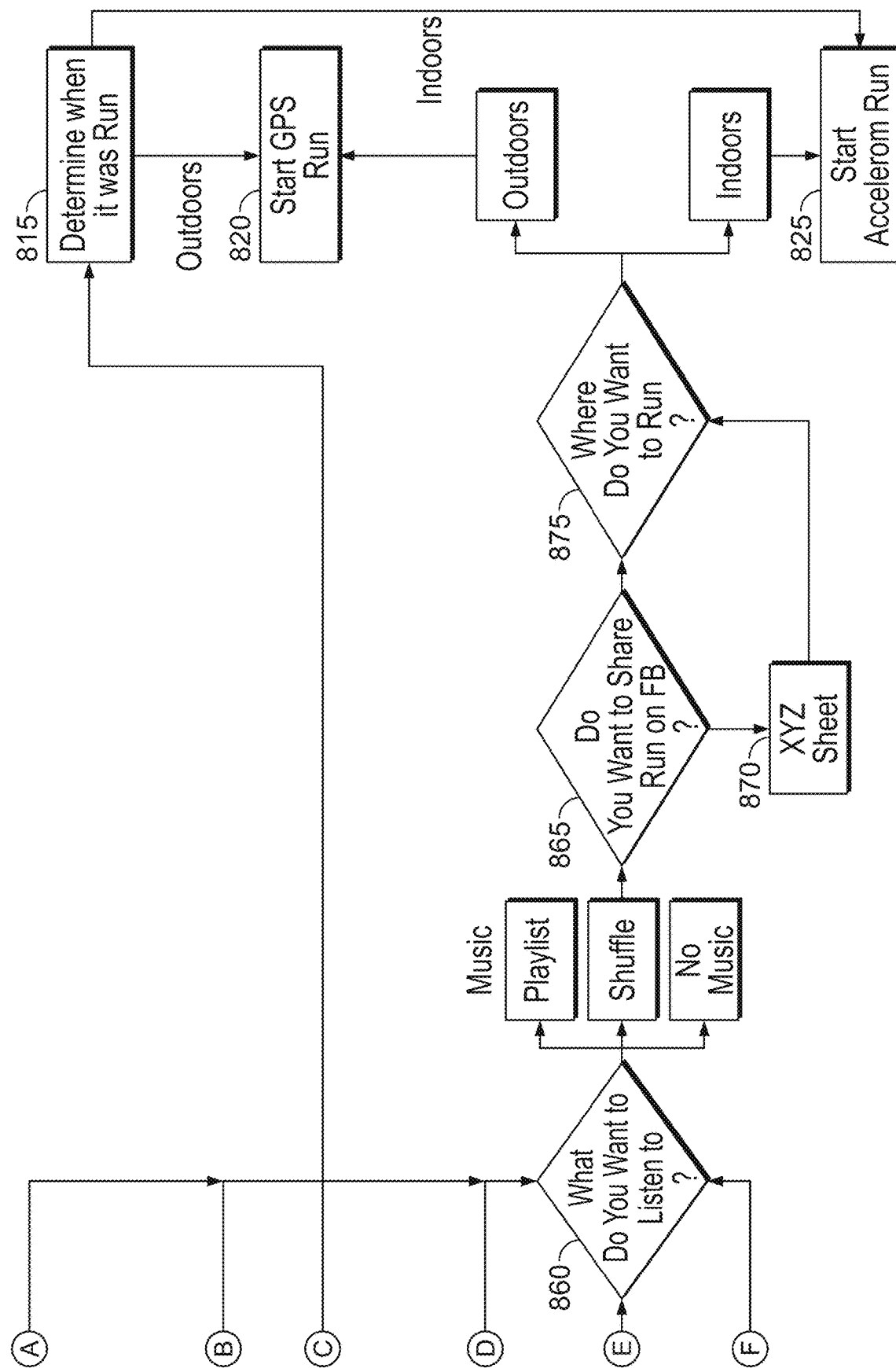

FIG. 8 is a flowchart illustrating an example process by which a user may define a run using a mobile device such as device 700 of FIG. 7 or other fitness monitoring device. In step 800, a system may receive user input corresponding to a command to initiate a workout. For example, the user input may comprise user selection of a workout option from a menu of applications or functions available on the system. In block 805, the system may subsequently offer the user multiple workout options in response to the command. For example, the system may provide options for repeating a last run, starting a basic run, improving on a past run, calibrating one or more sensing devices, viewing a workout history and/or setting a goal. The options may be categorized and displayed in separate sections or screens of a user interface. For example, a home screen may include a repeat last run option, a get better option and a basic run option while a workout screen may include the basic run option, the get better option, a goal setting option, a history option and a calibration option.

If the user chooses a repeat last run option, the user's most recent run may be retrieved from a database in step 810. This database may be local to the system or may be resident in a remote server. The system may then make a determination in step 815 as to where the run took place, e.g., outdoors or indoors, since the location of the run may determine what sensors are used in tracking the activity. For example, if the previous run occurred outdoors, the system may initiate a run to be tracked and monitored using a GPS device in block 820. On the other hand, if the run occurred indoors, the system may initiate a run to be tracked and monitored using an accelerometer system as shown in block 825. Initiation of the run may include activation of the relevant firmware, hardware and/or software, defining workout parameters (e.g., setting a calorie burning goal for indoors versus a distance goal for outdoors), generating a workout interface (e.g., a gym image for indoor runs and outdoor scenery for outdoor runs) and the like. As noted herein, in some arrangements, both accelerometer and GPS systems may be used to track various workout statistics if the workout allows for the use of GPS while only non-GPS devices may be used for indoor workouts. Using a device may include recording data from that device and instructing the device to communicate data at specified times (or continuously). Repeating a last run may also include using the same music playlist or other audio content as the previous run. Alternatively or additionally, the user may be provided with an option and opportunity to customize the audio content for the current run.

If the user chooses to improve his or her workout performance, the user may be presented a second set of options in block 830. The options may offer various methods of improvement including running a specific route, running faster, running longer, running farther, setting a personal best (time-wise) in the 1K or 5K, or setting a personal best in a distance run. If the user selects an option to complete a particular route, the user may be presented with a route list in block 835. The route list may include routes previously run and/or saved by the user, routes downloaded from a remote network site, routes run by friends or other acquaintances and the like. In some arrangements, the routes may be recommended to the user based on the user's past athletic performances including types of route previously run. For example, the user previously ran 3 miles on substantially flat terrain, the mobile device or another system may identify a similarly distanced route having a similar terrain. In some arrangements, the recommended routes may include routes seeking to challenge the user. For example, the recommendations may include 3.5 and 4 mile routes or routes that have a more significant hill profile to help the user improve.

If, on the other hand, the user selects one of the other options, the user may be asked to input a corresponding improvement amount in block 840. The system may subsequently set the goal for the workout based on the user input in block 845. The amount by which the user wants to improve his or her performance may be defined in terms of percentages or absolute values. For example, if the user wishes to run farther, the user may define the number of additional miles he wishes to run or a percentage increase in the number of miles. The total number of miles may then calculated based on a most recent run or based on a personal best depending on the type of improvement selected. In one example, if a user selects the option to run farther, the improvement goal may be defined based on the user's last run. If, however, the user selects the option to set a personal best in distance run, the improvement goal may be automatically, semi-automatically and/or manually defined based on a previous or current personal best in distance. For example, the system may automatically set the goal as a certain percentage (e.g., 5%) above the user's personal best in distance. Alternatively or additionally, the user may be given the option of selecting the workout from which he would like to improve from all previously recorded workouts.

If the user chooses a goal setting option from a workout menu, the user may be asked to select a type of goal he would like to set in block 850. The various types of goals may include distance, time and calories. Other types of goals may also be set such a pace, heart rate, percentage incline run and the like. In one or more arrangements, the user may select more than on goal type so set multiple goal parameters for the run. Upon selecting the type of goal, the system may display a list of goals to the user in block 855. The list of goals may include one or more predefined and/or automatically defined goals such as run a marathon, run for a specified time (e.g., 30 minutes) and/or burn a certain number of calories (e.g., 300 calories). The list of goals may also provide an option for the user to customize the goal. For example, if no predefined selection is available for running 10 miles, the user may set a customized goal for running 10 miles. In another example, if the user wishes to burn 500 calories, but the predefined calorie goals are in 200 calorie increments, the user may set a customized 500 calorie goal instead of being forced to choose either 400 or 600 calories.

Once a user has selected a workout type and/or defined a goal for the workout type, the system may prompt the user to select the type of music he or she wishes to listen to during the workout in block 860. The various selections may include a predefined playlist (user or system created), shuffle (e.g., random selection of songs or random order of songs) or no music. In block 865, the system may determine whether the user wishes to publish workout information on a social networking site such as FACEBOOK. Alternatively or additionally, the system may determine whether the user wishes to synchronize workout data to an athletic activity monitoring service. If so, the user may be prompted to enter various identification or login information so that the system may automatically access the user's account and synchronize or post information thereto. The user may also be prompted to enter publishing or synchronization options including whether the information is to be made available to the general public, a select group of friends or users, whether all data is to be synchronized or just a particular type of data (e.g., calories, distance run, route, etc.) and the like.

If the user does not wish to publish or synchronize the data or once the user has completed filling in the synchronization/publication information in block 870, the system may allow the user to define an environment in which the workout will take place in block 875. For example, the user may select either an outdoor or indoor workout. In some arrangements, the user may also select a particular location or type of equipment. For example, the user may indicate that he or she wishes to run on a treadmill or to use an elliptical machine. In accordance with the defined environment, the system may identify, select and initiate appropriate devices and sensors for detecting the results of the workout as described with respect to blocks 820 and 825. In some arrangements, the selection of a location or environment may also allow the device to more accurately calibrate its sensors and devices for that particular environment. Different sets of calibration data may be stored for different workouts, type of workouts and workout environments.

Other athletic activity session setting options may also be provided in the process. For example, the settings may allow an athlete to specify whether to post the performance information to a social networking site or a news feed, whether to synchronize or sending data to an athletic activity performance monitoring service and the like.

Figure 9:
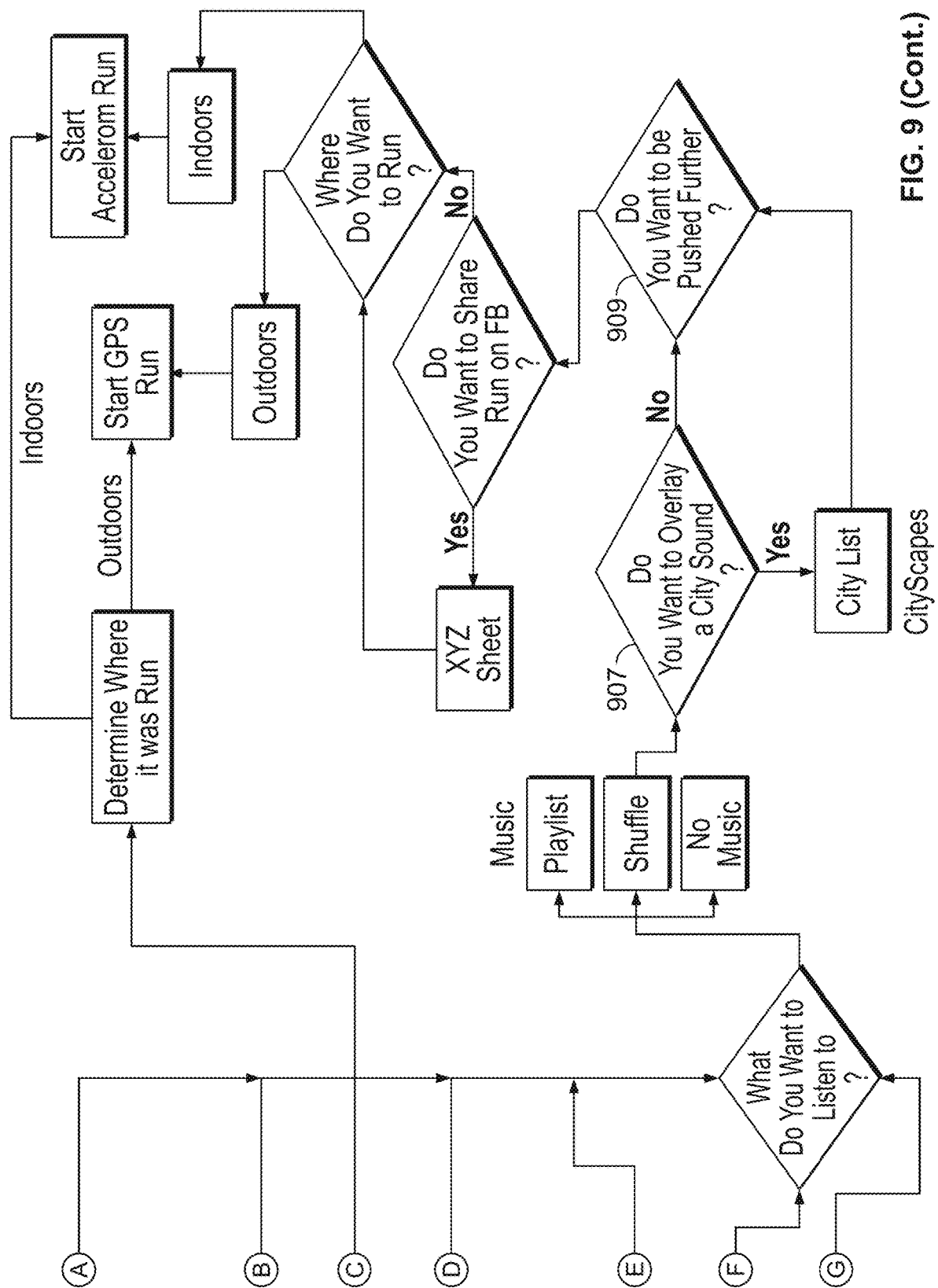

FIG. 9 illustrates another example process flow by which a user may define and initiate a workout. The process flow of FIG. 9 is similar to that described in FIG. 8, but includes additional options and features. For example, the process flow of FIG. 9 may include an improvement option that allows a user to select a past run on which to improve in blocks 901-905. The system may automatically select the workout parameter that the user is to improve or the user may select the parameter he or she would like to improve.

Alternatively, the user may select or be expected to improve upon multiple or all parameters (e.g., calories and distance) during the workout. Furthermore, the process flow may include an audio option in block 907 that allows a user to overlay various ambient noises and sounds such as city noises (e.g., cars honking/driving by, police sirens, children playing, etc.), country sounds (e.g., crickets, wind blowing, farm animal noises) and the like. The ambient noises and sounds may be presented to the user for selection in association with a list of cities, locations and/or environments. For example, the list may include cities such as New York, D.C., Boston, Los Angeles and Chicago and locations such as a bar, a club, a park, a beach and the like.

The process flow may include another option for allowing a user to choose whether he or she would like to receive prompts during the workout to further improve the individual's workout in block 909. For example, halfway through the workout, the system may automatically generate and display a prompt asking whether the individual would like to increase the run time by an additional 5 minutes or if the individual would like to burn 50 more calories. The improvement or additional amount may correspond to a percentage of the unmodified goal/workout, an amount that would increase the workout to beat a personal best in an athletic activity metric and the like. If the user does not wish to receive such prompts or notifications, the prompts may be deactivated for the workout. Alternatively, if the user selects the option to receive prompts, the user may also be allowed to define when the prompts are given and under what conditions. For example, the user may specify that prompts are only to be given during the last 30 minutes of a 1 hour run and only when the user's heart rate is below a certain amount. In another example, a user may ask that prompts be provided when the individual is on pace to exceed a distance goal and is running faster than an expected pace. Various other types of parameters and conditions may also be used to define triggers for prompts that seek to further improve the individual's workout performance.

According to one or more arrangements, the user may be provided with two types of improvement workout options. The first improvement workout option may be configured to provide improvement workout selections that are generated based on a standard amount of improvement (e.g., 5% improvement regardless of the individual) over a previous workout. A second improvement workout option may be configured to generate improvement workouts that are based on the user's attributes and/or past workout statistics. In one example, the amount of improvement incorporated into the improvement workouts for the second improvement workout option may be dynamically determined based on a user's previous trend. Alternatively or additionally, the amount of improvement set for the improvement workout in the second improvement workout option may consider the user's weight, height, gender and/or combinations thereof. For example, lower amount of improvement (e.g., a percentage improvement) may be set if the user's trend shows slower or more gradual progress over a specified time frame (e.g., a month) while a higher amount of improvement may be used to generate an improvement workout for a user if the user's trend shows faster progress over the specified time frame. Recommendations for improvement runs or workouts may also include a specific recommended route, recommended times of day or days of week for a workout. In one example, the recommendations may be based on weather forecasts specific to a location determined by a location determination system such as GPS.

Various types of user interfaces may be generated to allow a user to more easily set-up a workout session. For example, workout type selections and definitions, audio selections and the like may be graphically illustrated. A sequence of user interfaces may also be defined to more logically and efficiently guide a user through activity session set-up.

FIGS. 10A to 10G illustrates a sequence of user interfaces that may be generated and displayed when an individual begins a first run. A first run may be a new run for an individual who has no previously recorded workout history. When a user creates a first run, the user may initially be presented with a welcome interface 1000 of FIG. 10A. Interface 1000 may display user and workout information including a number of previous runs 1001 (e.g., 0 since the user does not have any previously recorded runs), average pace 1003, duration 1005 and calories burned 1007. Duration 1005 and calories burned 1007 measurements may be a total duration and total calories burned, respectively, across all runs performed or may be an average for each run. Interface 1000 may further display multiple options including an option to start a new run 1009 and an option to tour the features of the workout application 1011. Additionally or alternatively, interface 1000 may include options for accessing other aspects of the workout application including history option 1013 for display a list of previously recorded workouts and settings option 1015. Selection of settings option 1015 may cause a profile setup/edit interface to be displayed. In one arrangement, selecting new run option 1009 may also cause a profile setup/editing interface to be displayed if the user has no previous run history.

In one example, if no runs have been previously recorded, a history interface may be empty. FIG. 10G illustrates a history interface (e.g., display upon selecting history option 1013 of FIG. 10A) displaying a message 1051 that there are no saved runs. The interface may further include a run setup or initiation option 1053 to encourage the user to participate in a first run.

Figure 10B:
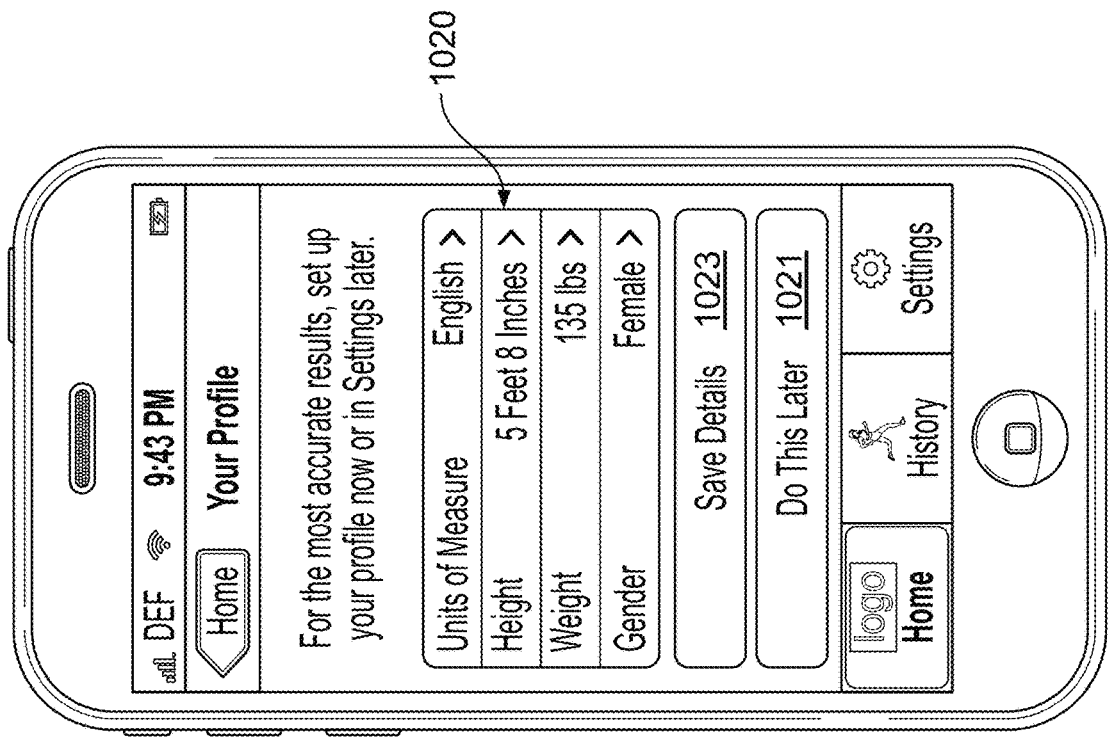
FIGS. 10A to 10G illustrate a sequence of user interfaces that may be generated and displayed when an individual begins a first run according to one or more aspects described herein.
Figure 10A:
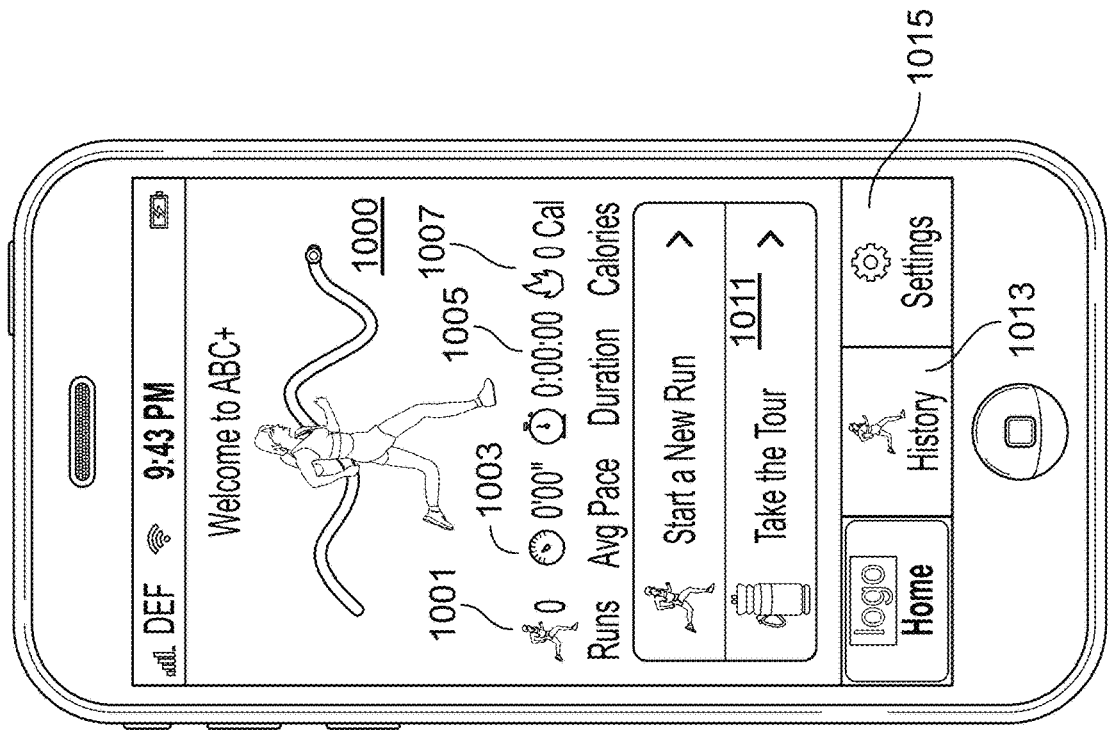
Figure 10D:
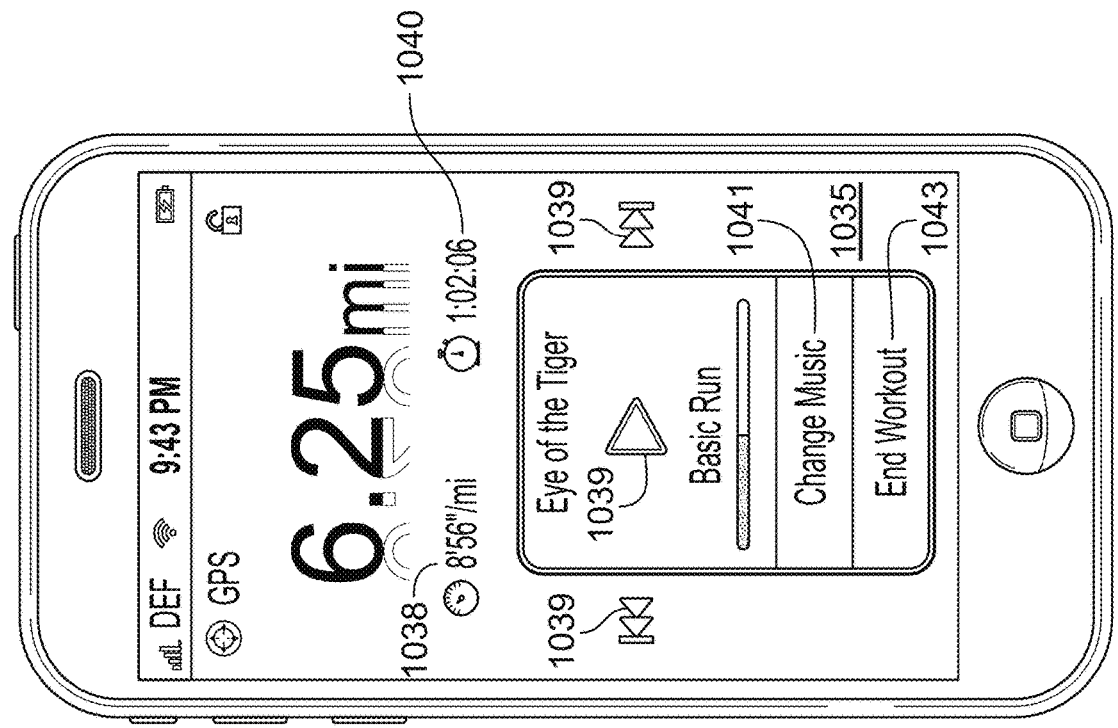

FIG. 10B illustrates a profile setup/editing interface 1020 through which a user may configure various workout and workout recordation parameters. For example, interface 1020 may allow the user to define the units of measure to use and to set the user's height, weight and gender. The profile setup/editing interface 1020 may be displayed upon the user selecting the option to start a new run session (as shown in FIG. 10A) and/or the user choosing settings options 1015 (FIG. 10A). Additional or alternative parameters may be changeable through interface 1020. The user may be provided with an option 1021 to skip a profile setup/editing function. If the user chooses to complete the profile setup, the user may save the profile information using option 1023. A user may navigate to other interfaces and screens such as home screen 1000 (FIG. 10A) by selecting home navigation option 1005.

Figure 10C:
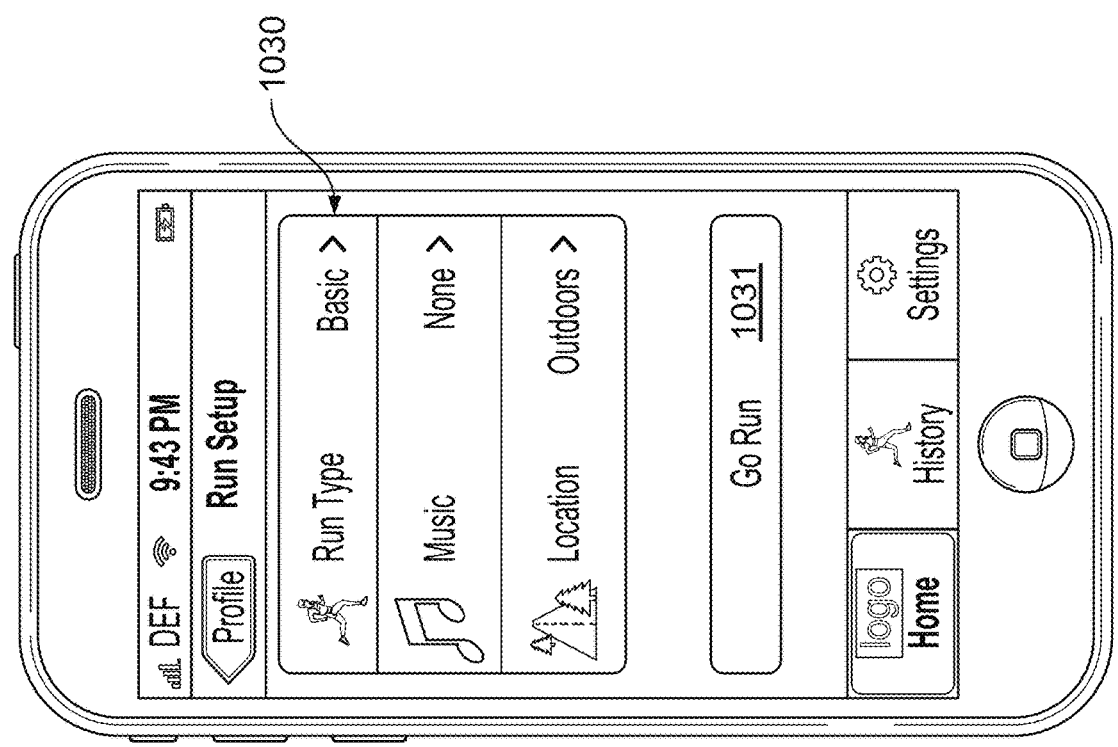
Figure 10F:
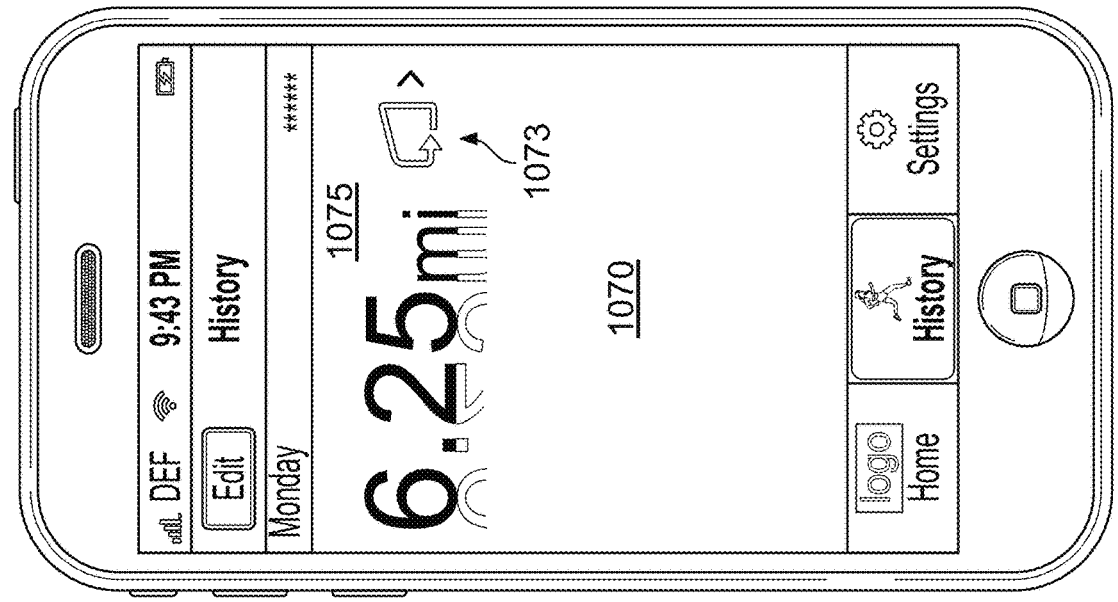

Once the user has completed setting up their profile or upon the user choosing to skip the profile definition menu, the user may be presented with a run setup interface 1030 as illustrated in FIG. 10C. Run setup interface 1030 may be configured to allow a user to define workout parameters for the new run. For example, the user may define the run type, the music that is to be played during the workout and the location, each of which are described in further detail herein. Once these parameters have been defined, the user may begin the run using option 1031.

FIG. 10D illustrates an in-run interface 1035 wherein a current distance run 1037 is displayed along with a pace 1038 and an amount of time spent in the workout 1040. The user may also be provided with options 1039 for controlling the playing of audio content, changing the audio content being played 1041 and ending the workout 1043.

Figure 10E:
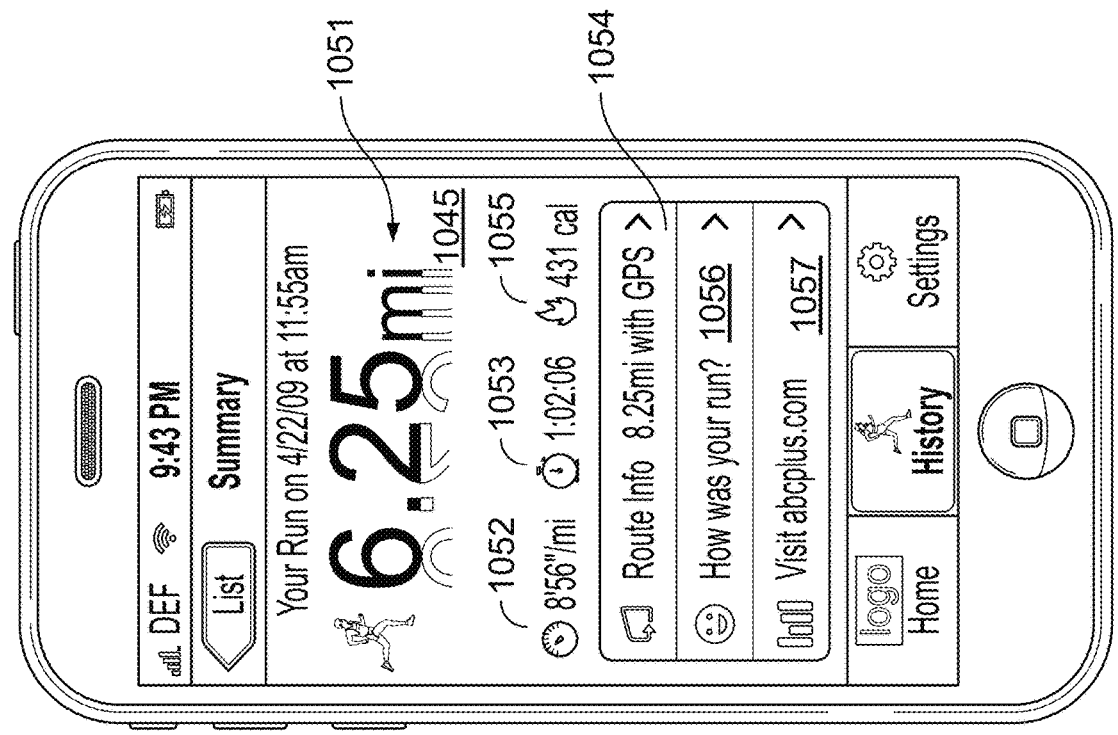
Figure 10G:
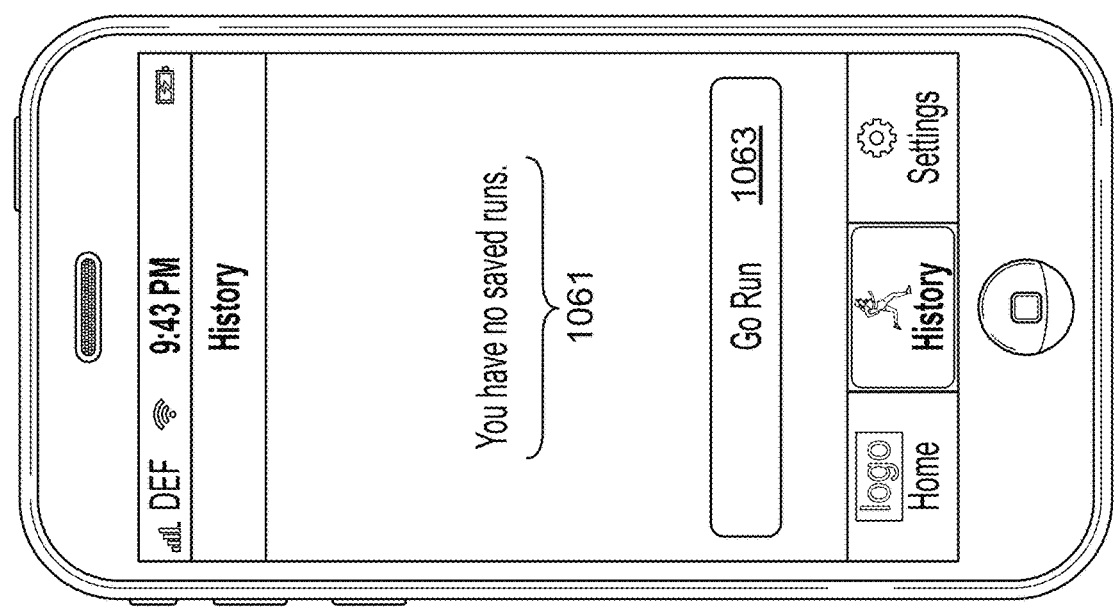

In FIG. 10E, interface 1045 displayed a workout summary upon completion or ending of the run. For example, summary interface 1045 includes a total distance run 1051, pace 1052, time spent running 1053 and calories burned 1055. Interface 1045 may further display option 1054 for displaying a route that the user run if the run was recorded using a GPS device. Other options may include an option 1056 to tag the run with the user's emotional or mental state (e.g., a mood) and an option 1057 to visit an athletic activity service provider site. Tagging may involve storing metadata, attribute or other type of information in association the one or more parameters or metrics of the activity data. Other or additional tags may also be used including a tag identifying athletic equipment (e.g., shoe) used during the workout and a tag specifying the weather during the workout. By tagging a workout with the athletic equipment used, a system may monitor the wear on the athletic equipment and recommend replacement upon reaching a threshold amount of wear or user (e.g., an amount of athletic activity performed using the athletic equipment). In one example, wear or amount of user/athletic activity performed may be measured by a distance run and the athletic equipment may include a shoe. In other examples, an amount of athletic activity performed may be determined based on calories burned and/or pace. Tagging athletic equipment might also provide insight (e.g., tracking) of how and where products are used, expected product life times, popularity (e.g., specific to different sports) and the like. Accordingly, an athletic activity monitoring service or product provider may use this information to better target, develop and/or improve products. Visiting the athletic activity service provider site may allow the user to view additional workout information that has been collected by the service provider for the user. This may allow the mobile device to minimize the amount of storage necessary in the mobile device, instead storing workout data in the service provider site.

Once the user has completed his or her first run, a history interface such as interface 1070 of FIG. 10F may include an entry 1075 corresponding to the first run. The workout entry 1075 may be identified in interface 1070 by one or more workout statistics such as a distance run. Additionally or alternatively, various icons or tags such as icon 1073 may be displayed in association with the entry 1075 to indicate that certain types of information are available for that entry 1075. For example, icon 1073 may indicate that a GPS route was recorded for the workout. Selection of entry 1075 may allow the user to view the recorded GPS route along with other details of the workout (e.g., calories burned, duration of the workout, user's mood after the workout).

Additionally or alternatively, a welcome or home interface such as interface 1000 of FIG. 10A may further include a feedback option providing the user with the ability to activate or deactivate feedback for his or her workout. Feedback may include audio, video or haptic feedback and may originate from other athletes, friends, celebrities, family, service providers (e.g., an athletic training and monitoring service) and the like. In some examples, the feedback may comprise audio, video or haptic content that is configured to be delivered during a workout upon the user achieving a certain goal or reaching a specified threshold. Feedback may also be provided post-workout if the user achieves a certain goal or reaches a threshold. In other examples, feedback may be provided based on other triggering events such as a number of comments received from others through social networking outlets such as FACEBOOK and TWIT- TER. The feedback option may also include various levels of granularity to allow a user to select sources of feedback that are desired and sources of feedback that are not desired during the workout. Additional feedback options may include whether audio being playing during the workout is to be paused during the feedback.

Feedback may be congratulatory, encouraging or motivating. For example, if the user accomplishes a certain goal, the feedback messages may be congratulatory. In some examples, if a user is not on track to meet a goal, the message may be motivating or encouraging. Feedback may also include suggestions for improvement. Accordingly, the type of message that is provided to the user may depend on a result or current status of a user's workout. The monitoring device or system may be configured to automatically select an appropriate type of message depending on the workout result or status.

In one or more examples, setting up a workout may include adding or defining desired coaching. Coaching may represent a type of feedback that is intended to be instructional, regimented and structured and to be provided prior to, during or after the workout and may be event-specific and/or user-specific. For example, coaching may provide instructions that are specific to a marathon if a user has selected a marathon as the type of workout event. In another example, coaching may provide specific instructions for interval training (e.g., run, slow to a first pace, accelerate to a second pace, cool down, warm up, etc.). The intervals may be defined based on user attributes including height, weight, gender, workout history and the like. Accordingly, the instructions may be cued time-wise or distance-wise based on the user-specific intervals or other event-specific actions to be taken. Appropriate coaching (e.g., instructions) may be selected upon a user defining a desired run, which may include selecting a desired run type, distance, pace and the like. Coaching may further include tips or advice provided to the user before a workout, during a workout and/or post-workout and may be provided audibly, visually and/or haptically. For example, instructions may be indicated through use of vibrations, visual indicators or audio tones or vocal instructions.

Coaching may also be specific to a particular location or time of day. For example, coaching may include recommendations for improving incline running if a given location has a more significant hill profile (e.g., San Francisco). In another example, coaching may recommend less strenuous workouts early in the day or later in the day depending on metabolic cycles, user preferences, meal times and the like. In still other examples, coaching may provide recommendations on how fast to run (e.g., a pace) for various types of terrain and/or during different types of weather conditions.

Figure 11A:
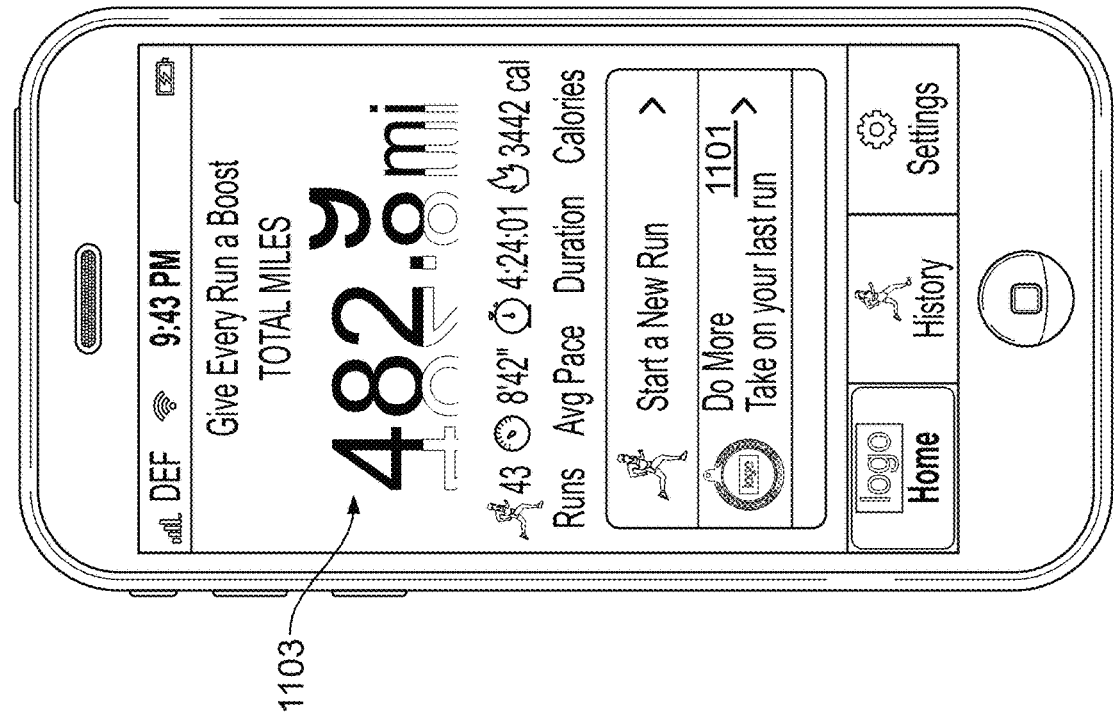
FIGS. 11A-11E illustrates a series of interfaces that may be generated and displayed after the user has completed and recorded a first run according to one or more aspects described herein.

Once a user has completed a first run, the application may provide different user interfaces reflecting the recorded workout history. For example, FIGS. 11A-11F illustrate a series of interfaces that may be generated and displayed after the user has completed and recorded a first run. FIG. 11A illustrates home interface 1100 that may be displayed for subsequent runs or workouts. Instead of displaying a tour option (e.g., 1011 of FIG. 10A), home interface 1100 may display option 1101 that allows a user to perform a workout that improves upon a previous workout. The previous workout may be chosen by a user or may be automatically selected. In one example, the selected previous workout may be the most recently recorded workout. Additionally, in contrast to a general image as displayed in interface 1000 of FIG. 10A, a total distance 1103 or other metric for all workouts recorded may be displayed in interface 1100.

Figure 11C:
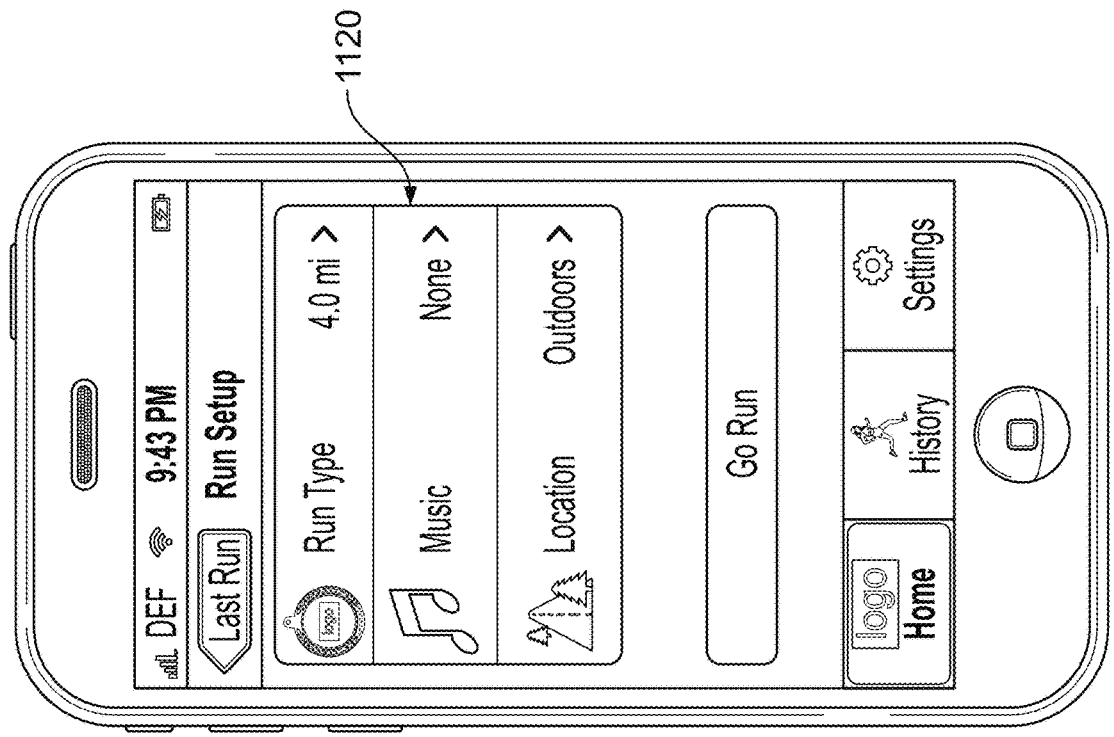
Figure 11B:
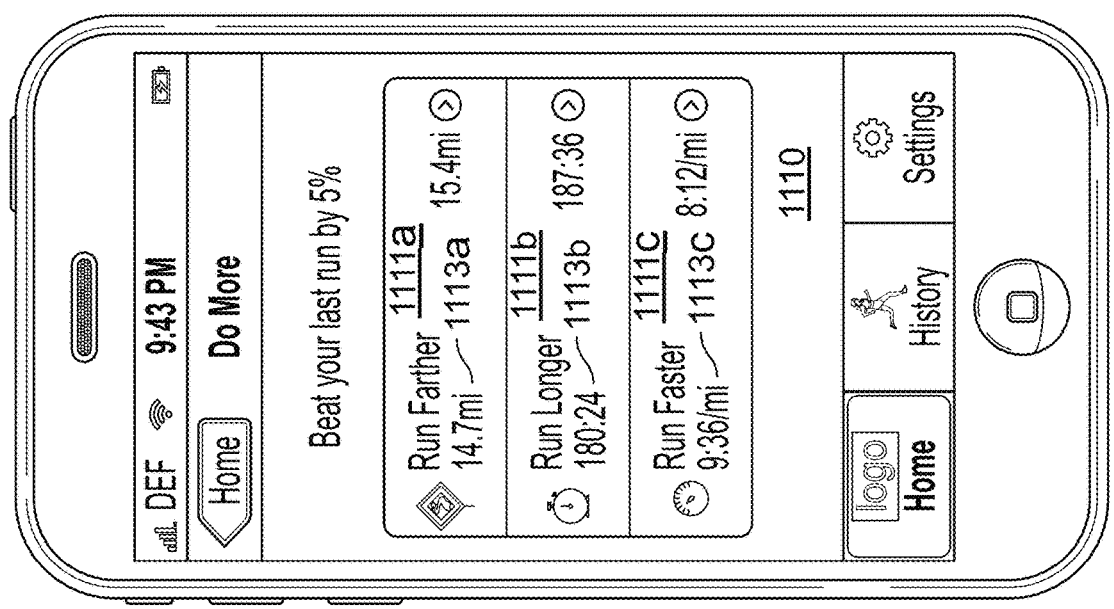

FIG. 11B illustrates interface 1110 that displays a variety of different workouts 1111 or workout types that may be selected by a user. Each of workouts 1111 may be generated by setting a goal that improves upon a previous workout by a predefined amount. For example, in interface 1110 workouts 1111 may be automatically generated by increasing one or more parameters of a previous workout by 5% or some other percentage or predefined amount. Accordingly, the user is able to challenge himself or herself to run farther, longer or faster. In one or more arrangements, the user may select the amount by which a previous workout's results are increased to define suggested workouts 1111. Each of suggested workouts 1111 may display the recorded metric for the previous workout 1113 along with the suggested or goal metric 1115 for the current workout. This allows the user to determine the amount of improvement that he or she would be achieving in choosing each of suggested workouts 1111.

As an alternative to selecting an improvement workout through interface 1120 of FIG. 11C, a user may choose to define a run that is not based on a previous workout. Similar to interface 1030 of FIG. 10C, interface 1120 may allow the user to define various parameters of the run including a run type, audio content to be played during the workout and a location.

In one or more arrangements, if a user completes an improvement run, a workout summary may include additional information. For example, summary interface 1130 of FIG. 11D includes a medal or other indicator/message 1131 congratulating the user for completing the improvement run. Audio icon 1133 may provide an indication that an audio message is available to the user. For example, the audio message may include words of encouragement (e.g., from a celebrity, a friend, or generic voice). Cheers or celebratory messages are described in further detail below. Upon selection of icon 1133, the message may be played. Indicator/message 1131 may also be displayed upon achieving other predefined goals such as performing 50 workouts, running 100 miles total (e.g., across all previous workouts), running 10 miles in 1 session, running 26.2 miles in one session, running for 30 minutes in a single session, running for 100 hours across all sessions and the like. Achievements, goals and rewards may be defined by the user, by an athletic training and/or monitoring service provider or by friends, family and acquaintances. For example, a friend may offer a user a coupon if the user runs 10 miles in 5 days.

Figure 11E:
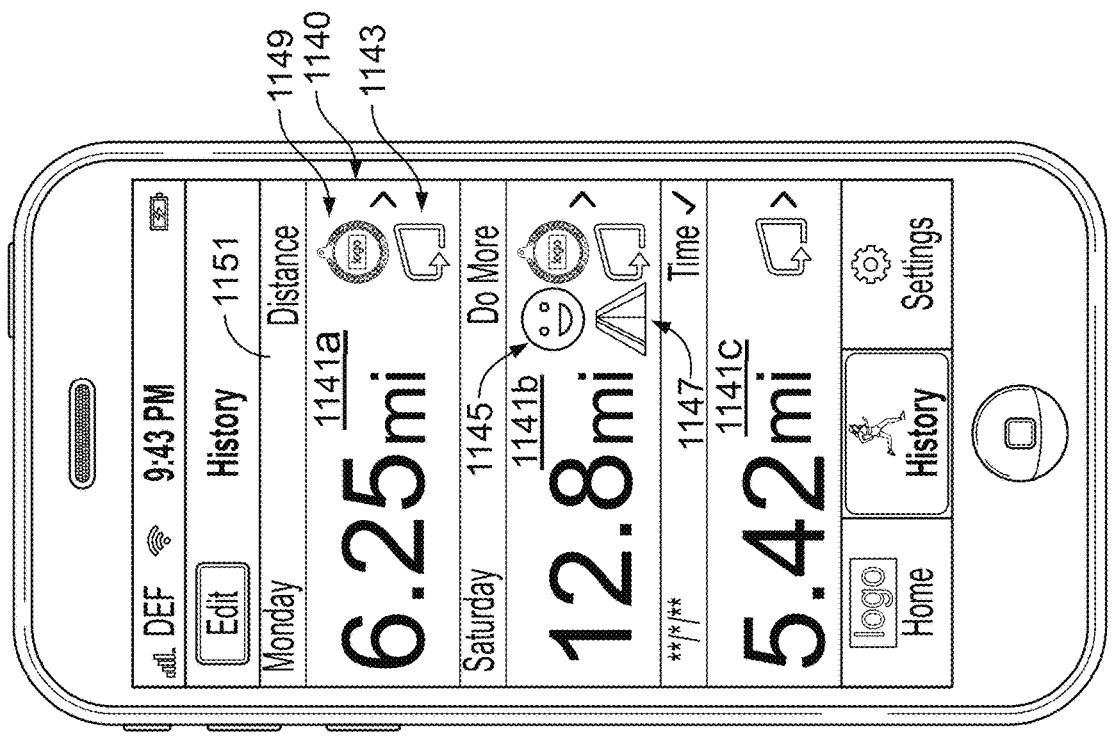
Figure 11D:
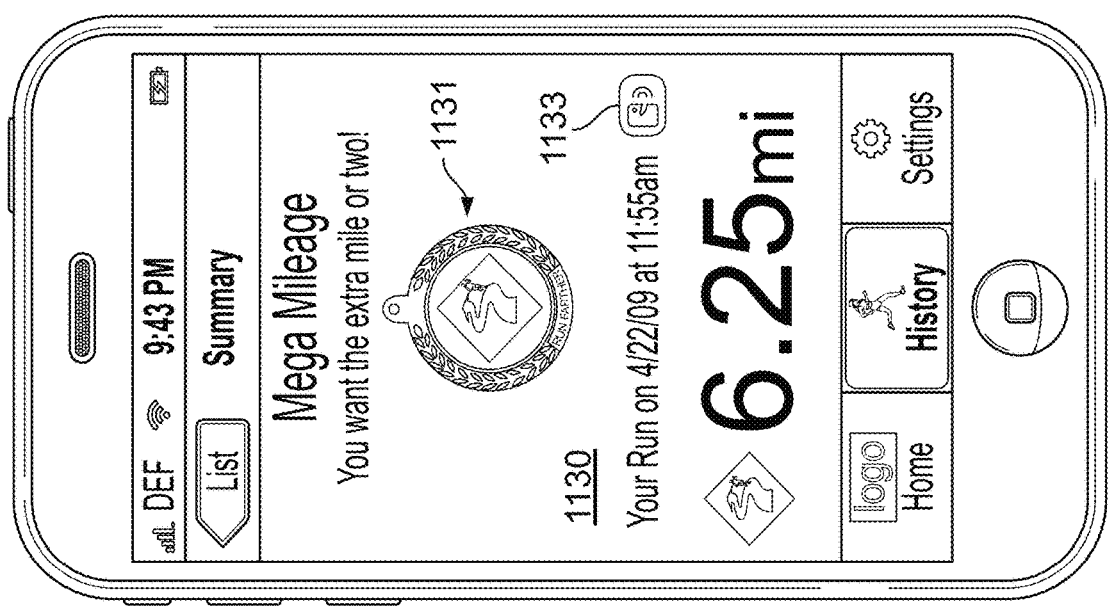

FIG. 11E illustrates another example history interface 1140 that includes a listing of multiple previously recorded workouts. Each entry 1141 in listing may be identified by a run type label 1151. For example, run type label 1151 may indicate that the run is a time run, an improvement run, a distance run and/or a basic run. In addition to a route indicator 1143, listing 1141 may include additional indicators for each entry that may indicate various attributes of the corresponding workout. For example, a face icon such as icon 1145 may indicate that mood information was tagged for the workout. Additionally, a road icon 1147 may indicate that the workout was performed outdoors while a medal icon 1149 may indicate that an achievement was completed during the workout. Other indicators may also be used, including an athletic equipment indicator to identify the type of athletic equipment used during the workout and a weather icon to specify the weather during the workout. History interface 1140 may display a list of all workouts stored on the device or, in some instances, only a predefined number of most recently recorded workouts.

Figure 12B:
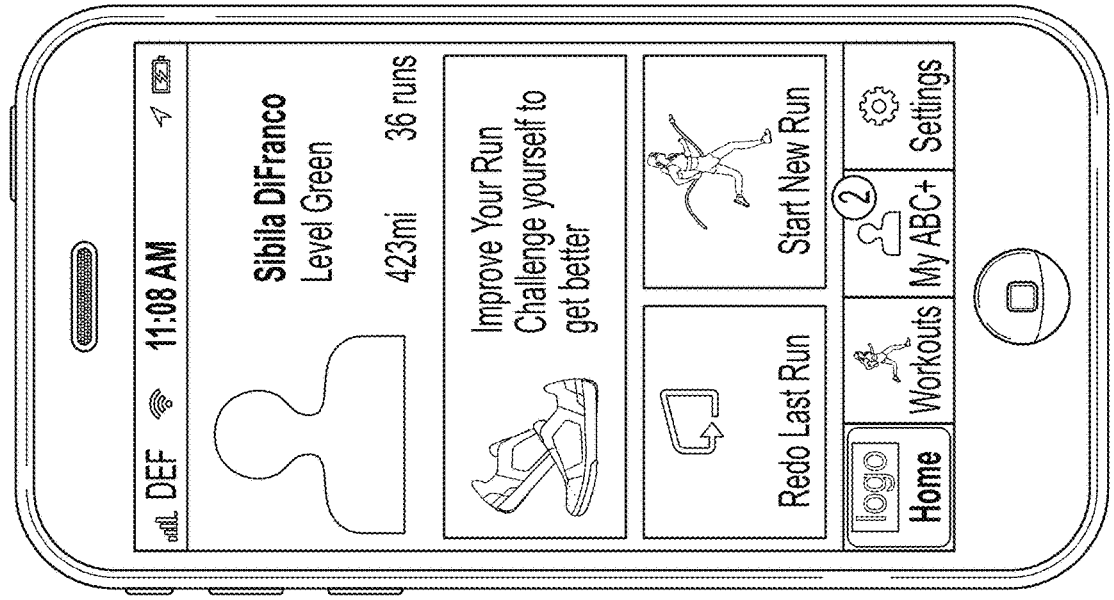
FIGS. 12A and 12B illustrate another example home screen interface that may be generated and displayed according to one or more aspects described herein.
Figure 12A:
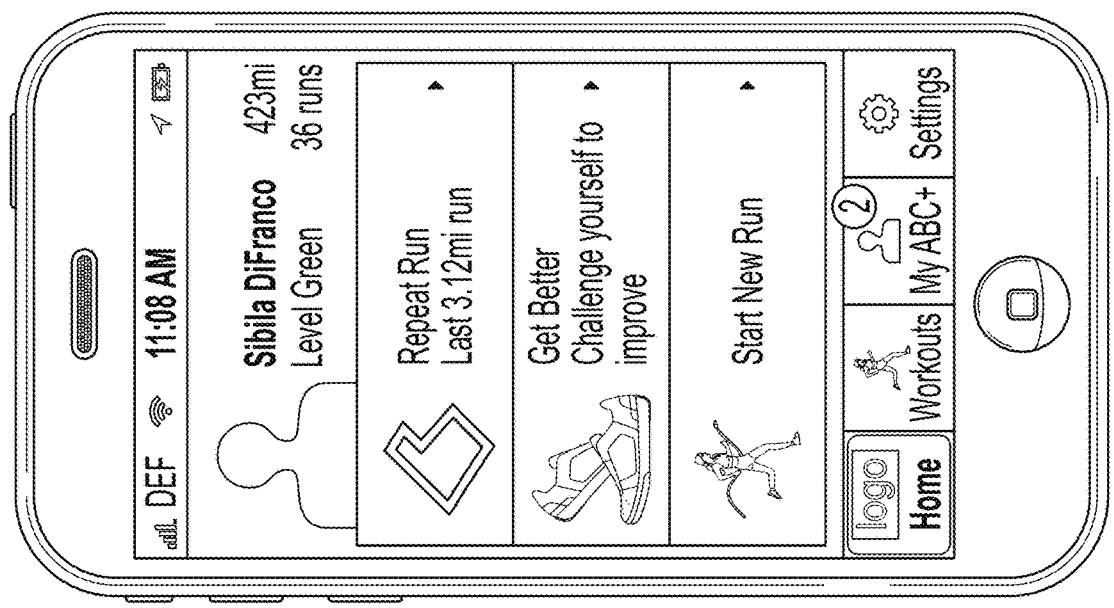

FIGS. 12A and 12B illustrate other example home screen interfaces that may be generated and displayed.

Messages provided to the user pre-run, in-run or post-run may be selected based on a user athletic activity level. Accordingly, if a user exhibits a high level of athletic activity over a predefined time frame (e.g., running at an average pace above a specified threshold or running an average distance above a certain threshold), the user may be classified in a first athletic activity level. If a user exhibits a mid-range level of activity (e.g., between two thresholds of average pace or average distance), the user may be classified in a second athletic activity level. If a user exhibits a low-range level of activity (e.g., below a specified threshold), the user may be classified in a third athletic activity level. Additional or alternatively activity levels may be defined as desired or needed. Messages, tips, information, coaching, advice and the like may then be selected based on the user's athletic activity level classification. For example, if a user is classified in the low-range level of activity, more instructional messages may be provided to the user. In addition, the device may be more specific in recommending products to the user.

If, on the other hand, the user is classified in the high-range level of activity, the user might not be provided such as many instructions or as substantial of instructions as the low activity level user. For example, a wear warning (e.g., without product recommendations) may be provided to the high activity level user while a wear warning with specific product recommendations and information explaining the dangers of worn products may be provided to a low activity level user. Mid-range activity level users may be provided with a level of information in between those provided to the high activity level and low activity level users. In one example, the wear warning with a product recommendation may be provided to the mid-range activity level user without the explanatory information.

Messages may also differ in tone, wording, expectations and the like depending on the user's activity level. For example, a high activity level user may receive messages that more strongly challenge the user to reach a specified goal or to exceed a set goal. For lower activity level users, the message may be more encouraging than challenging. For example, the message may provide words of encouragement even when the user is projected to fall short of the specified goal. In another example, the messages may identify a next activity level the user may reach and an amount of athletic activity required to reach that next level. Accordingly, such messages may be activity level and user specific. Other types of distinctions in messages may also be applied based on the varying levels of user activity.

Defining a Run—Run Type Selection

As illustrated in FIG. 10C, a run setup interface may allow the user to define the run type. For example, the user may wish to perform a distance run where the objective is reaching a certain distance, a time run where the goal is to run for a certain amount of time and/or a basic run where no objectives are set. If the user has completed and recorded at least a first run, the user may also be able to select an improvement run type in which the objective is to improve at least one metric from a previous workout. This latter option might only be available and displayed if a previous run has been completed and recorded.

Figure 13B:
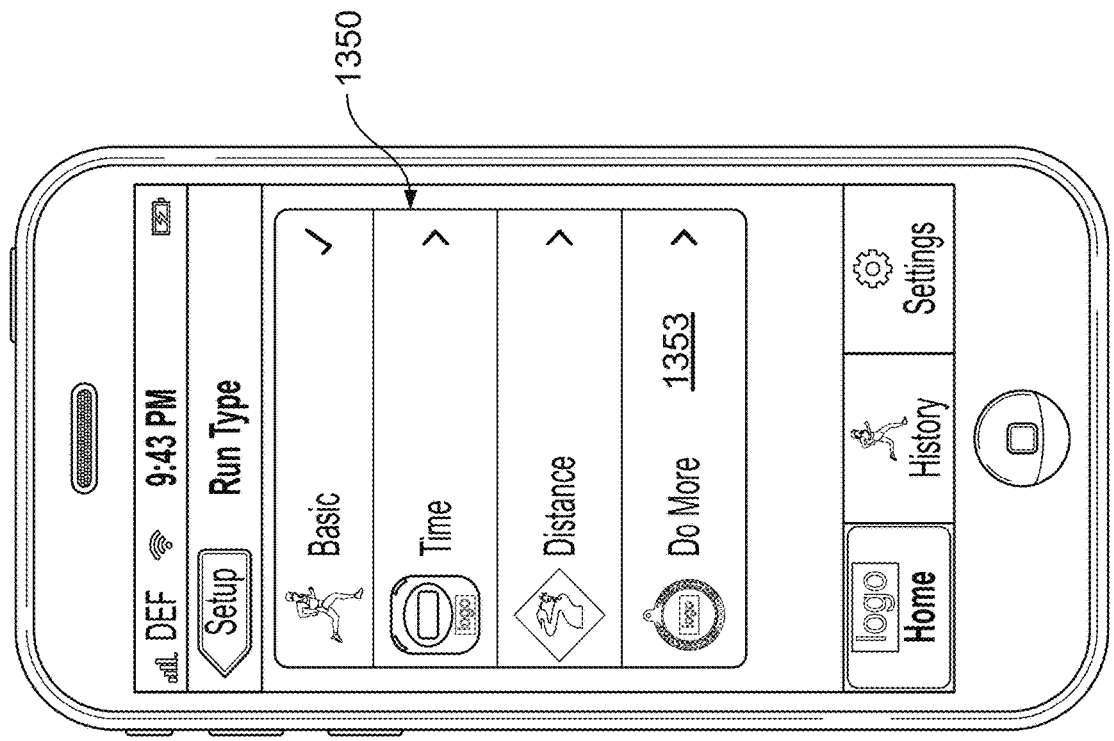
FIG. 13B illustrates an example run type selection interface that may be displayed when a user has a recorded run history according to one or more aspects described herein.
Figure 13A:
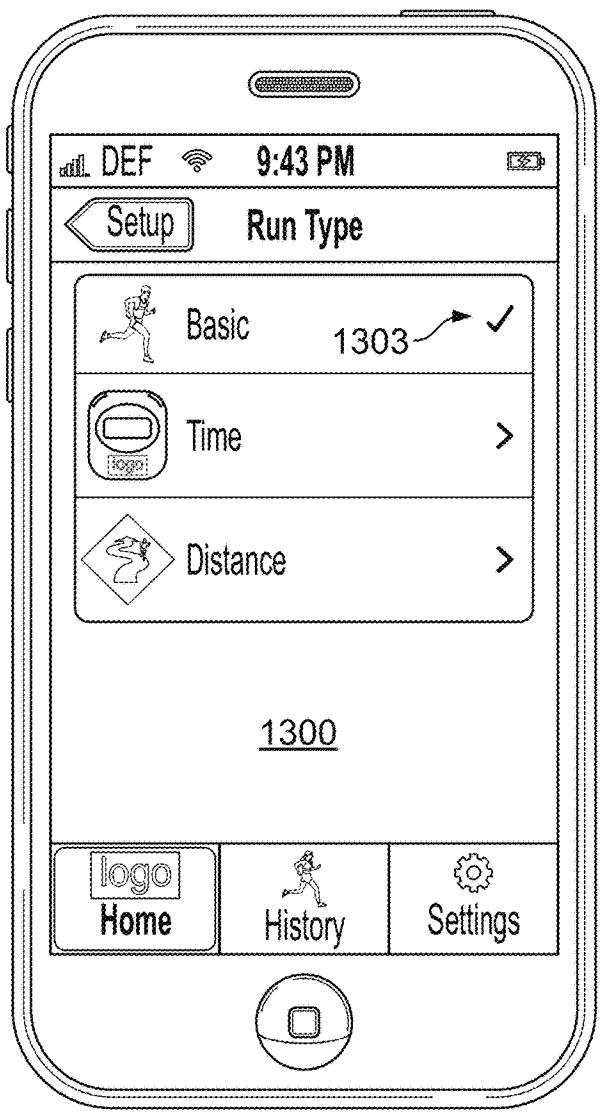
FIG. 13A illustrates an example run type selection interface for display when a user has no previous run history according to one or more aspects described herein.

FIGS. 13A and 13B illustrates a run type selection interface 1300 for display when a user has no previous run history and run type selection interface 1350 that may be displayed when the user has a recorded run history, respectively. Interfaces 1300 and 1350 may be similar except for the inclusion of a "Do More" or improvement run option 1353 in interface 1350 of FIG. 13B. A currently selected run type may be identified by an indicator such as check mark 1303.

Figure 14B:
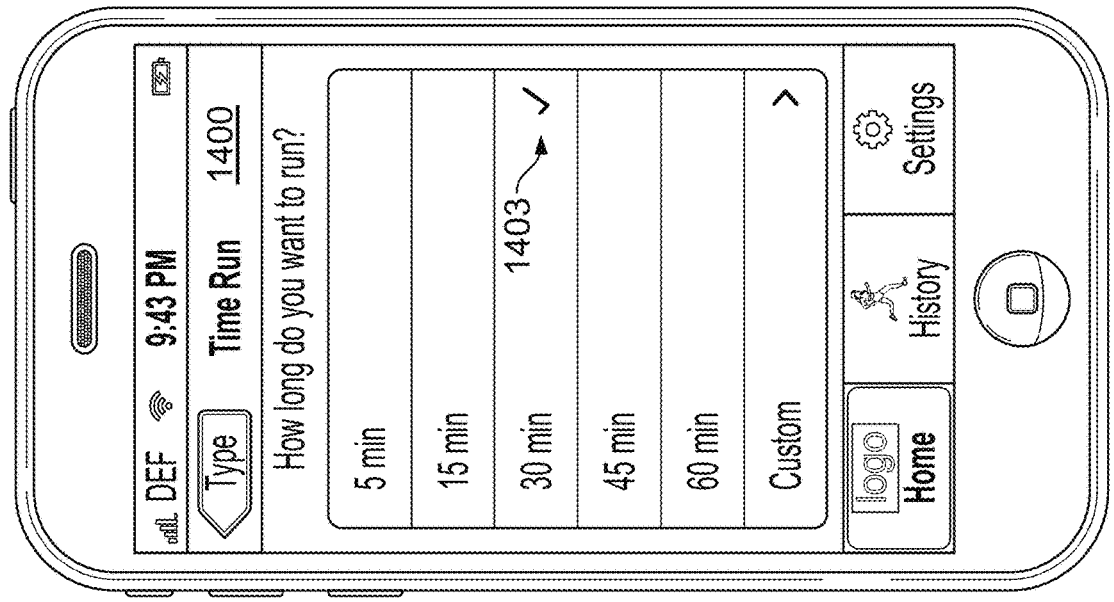
FIGS. 14A-14G illustrate a series of example user interfaces for defining a time run according to one or more aspects described herein.
Figure 14A:
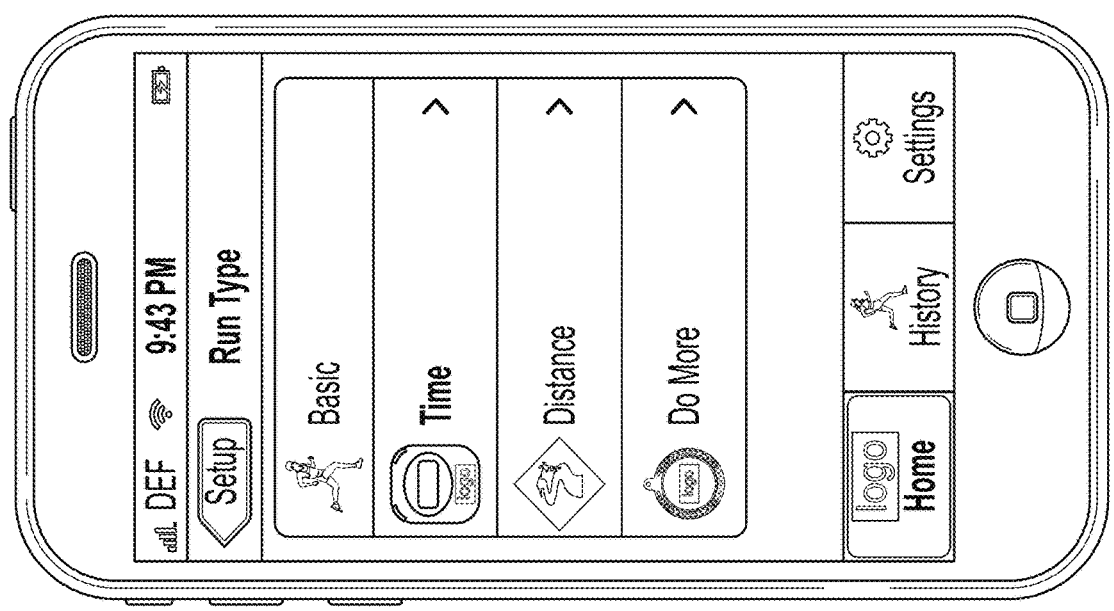
Figure 14D:
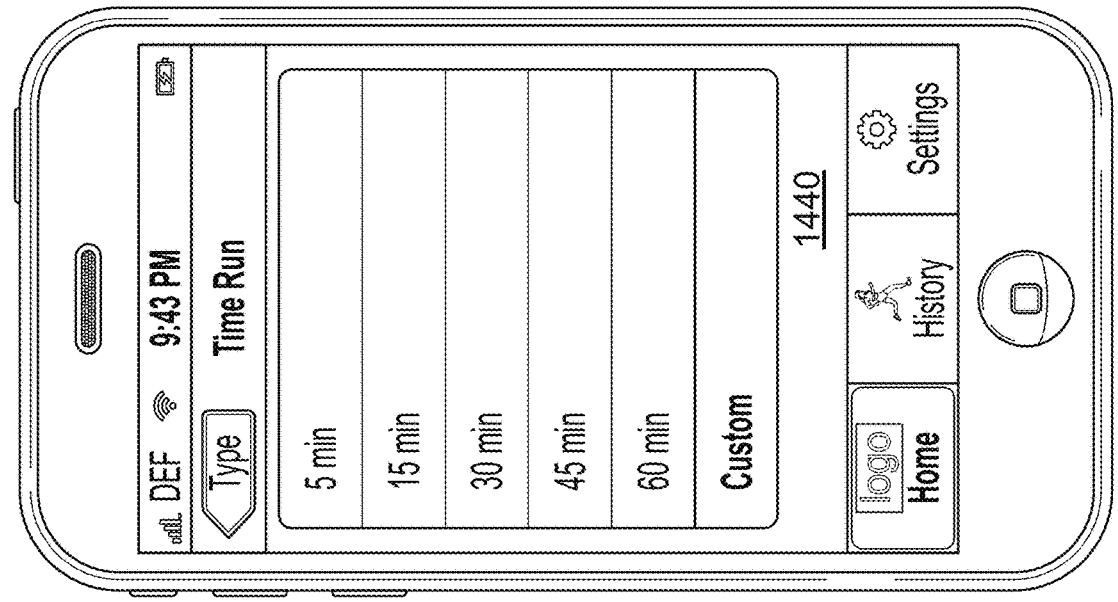
Figure 14C:
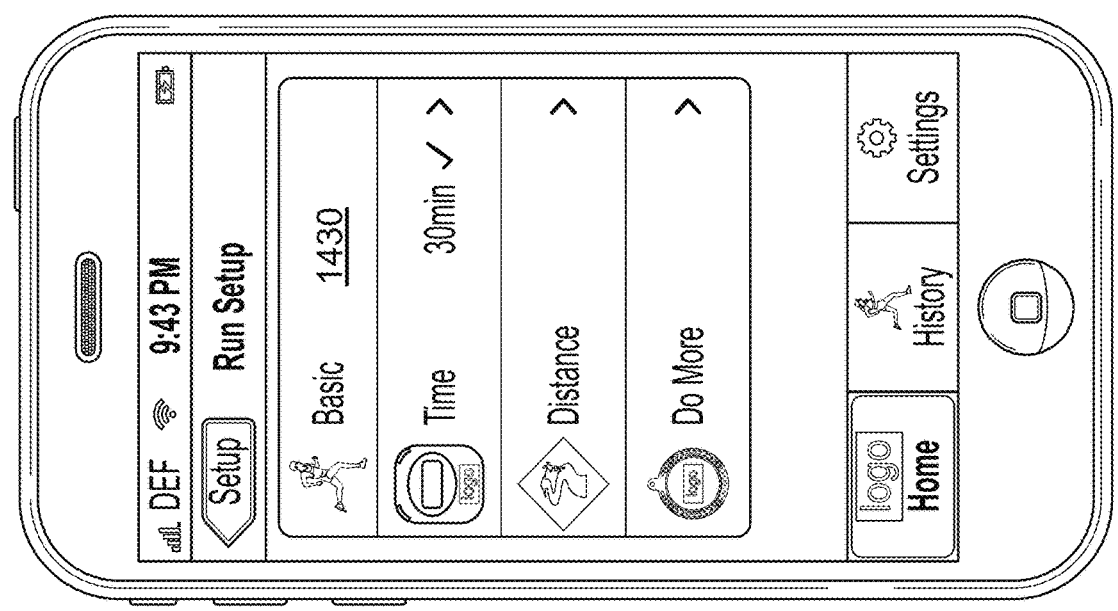
Figure 14F:
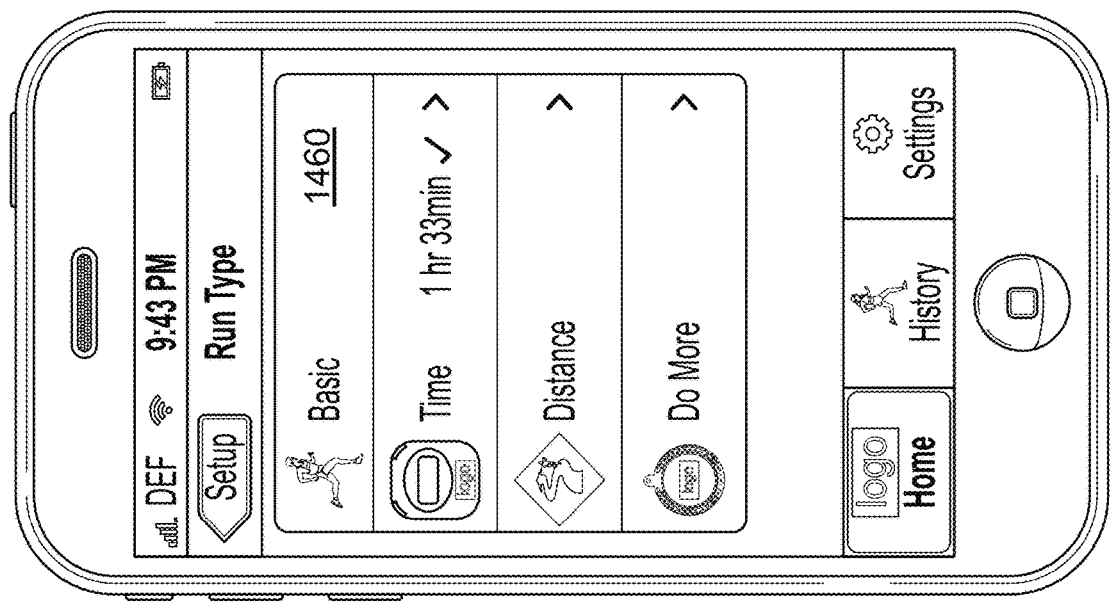

FIGS. 14A-14G illustrates a series of user interfaces for defining a time run. In FIG. 14A, a user has selected the time option. Accordingly, the time run type may be displayed differently than the other available run types. Subsequently, a user may be presented with time selection interface 1400 of FIG. 14B. Time selection interface 1400 may include multiple predefined times (e.g., 5 minutes, 15 minutes, 30 minutes, 45 minutes and 60 minutes) and a custom time option. A currently selected time (e.g., 30 minutes) may be identified by a selection mark 1403. Once the user has selected a time, the user may be returned to the run type selection interface where the selected run time is displayed in association with the time run type option. FIG. 14C illustrates run type interface 1430 that is displayed upon a user selecting a time run type and selecting a corresponding amount of time (e.g., through interface 1400 of FIG. 14B).

Figure 14E:
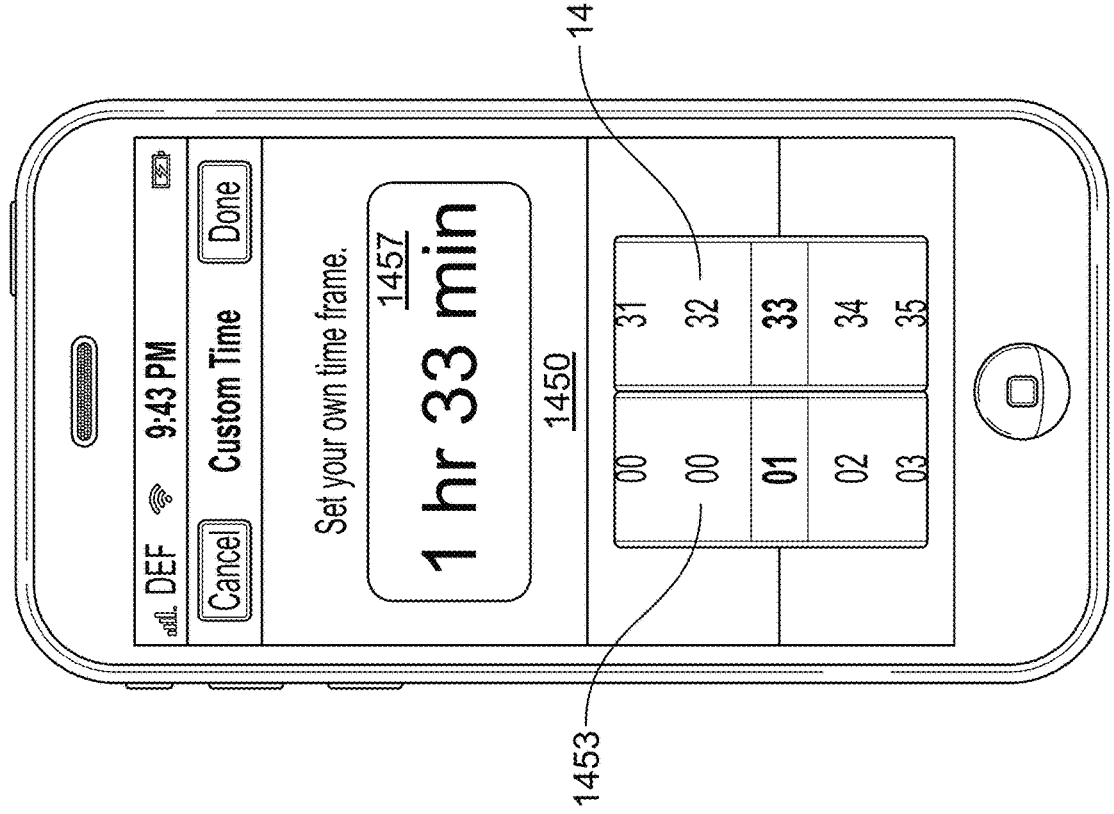
Figure 15A:
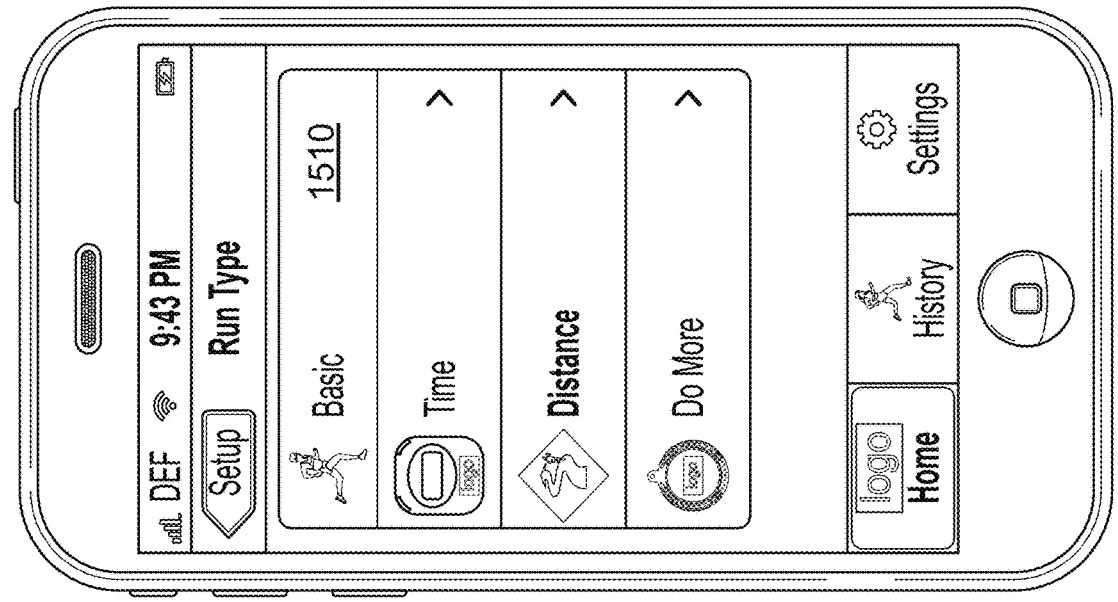
FIGS. 15A-15G illustrate a series of example user interfaces that may be displayed upon a user selecting a distance run type according to one or more aspects described herein.
Figure 14G:
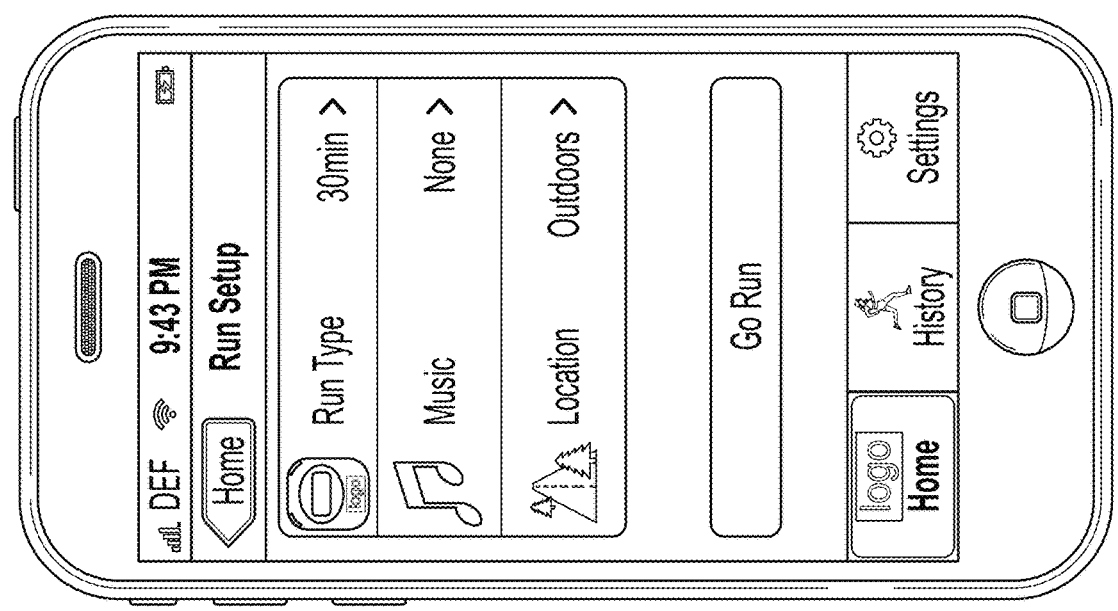

FIG. 14D illustrates interface 1440 in which a user selects a custom time option. In FIG. 14E, a user may be presented with an interface 1450 through which the user may manually define an amount of run time. For example, scroll wheels 1453 and 1455, may be provided to allow a user to define a number of hours and a number of minutes, respectively. The currently selected time may be displayed in portion 1457. As with FIG. 14C, FIG. 14F may display an interface such as interface 1460 in which the selected time may be displayed in association with the selected run type. In another example, FIG. 14G illustrates a run setup main menu indicating the run type as a 30 minute run. By identifying the run with the "30 min" tag, the application and device may indicate to the user that the currently defined run type is a time run and that the current time set is 30 minutes.

Figure 15C:
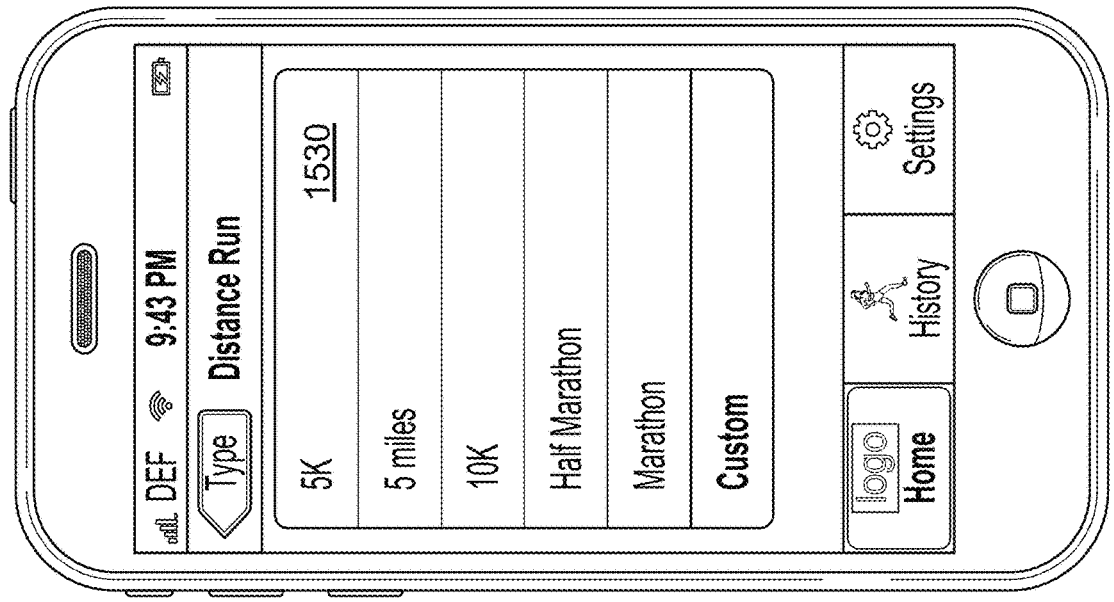
Figure 15B:
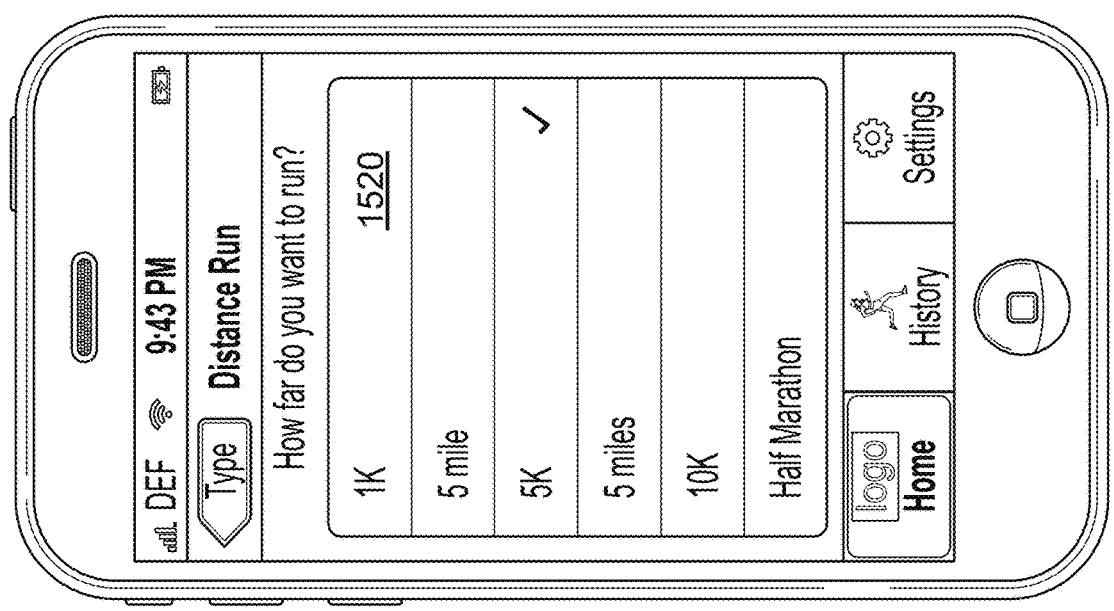
Figure 15E:
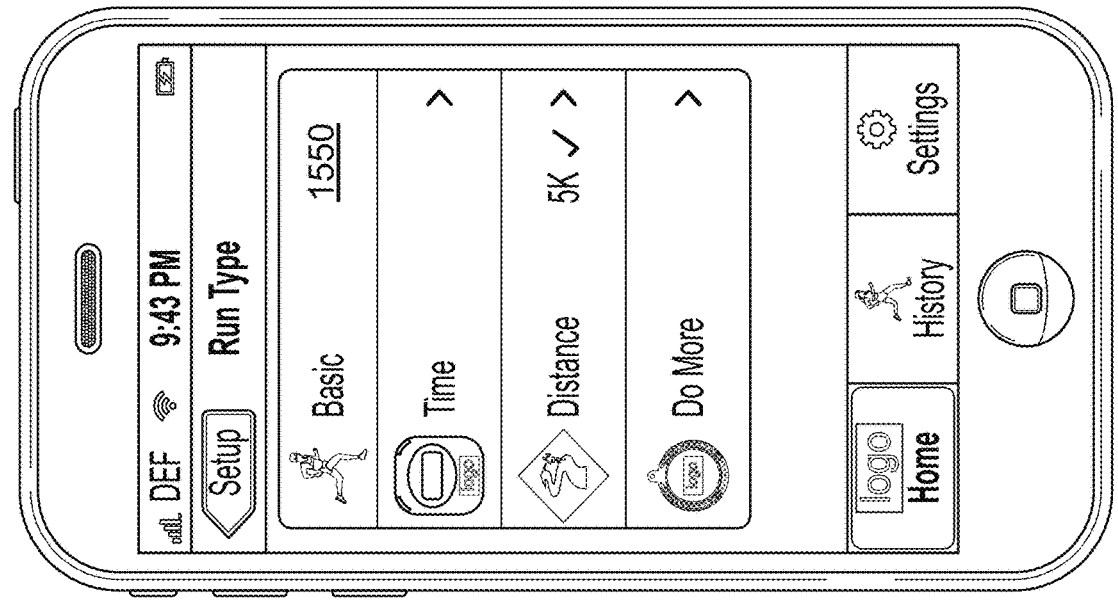
Figure 15D:
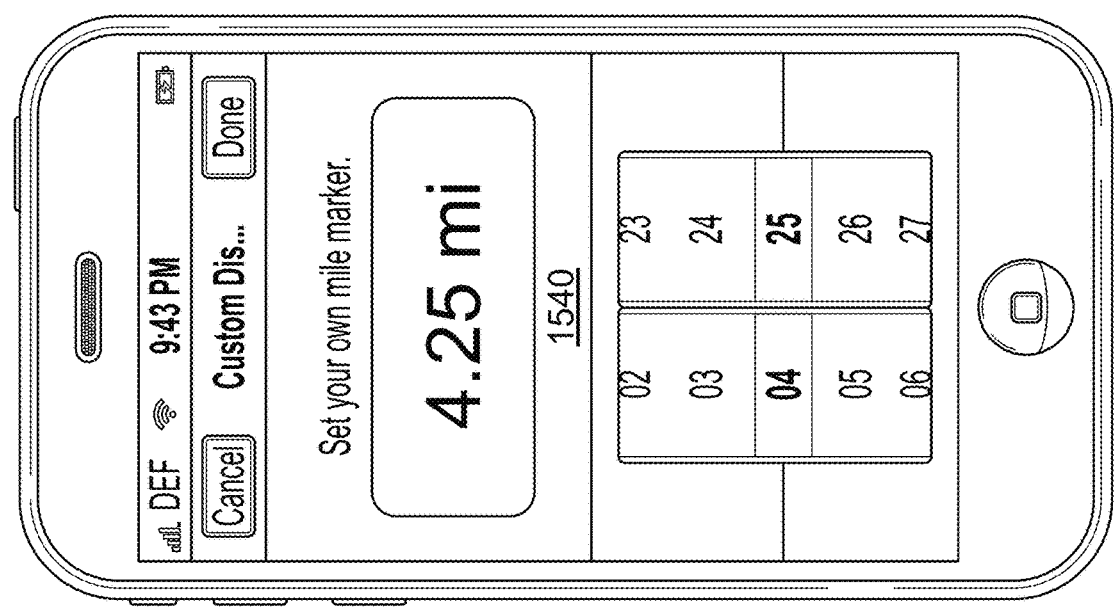
Figure 15G:
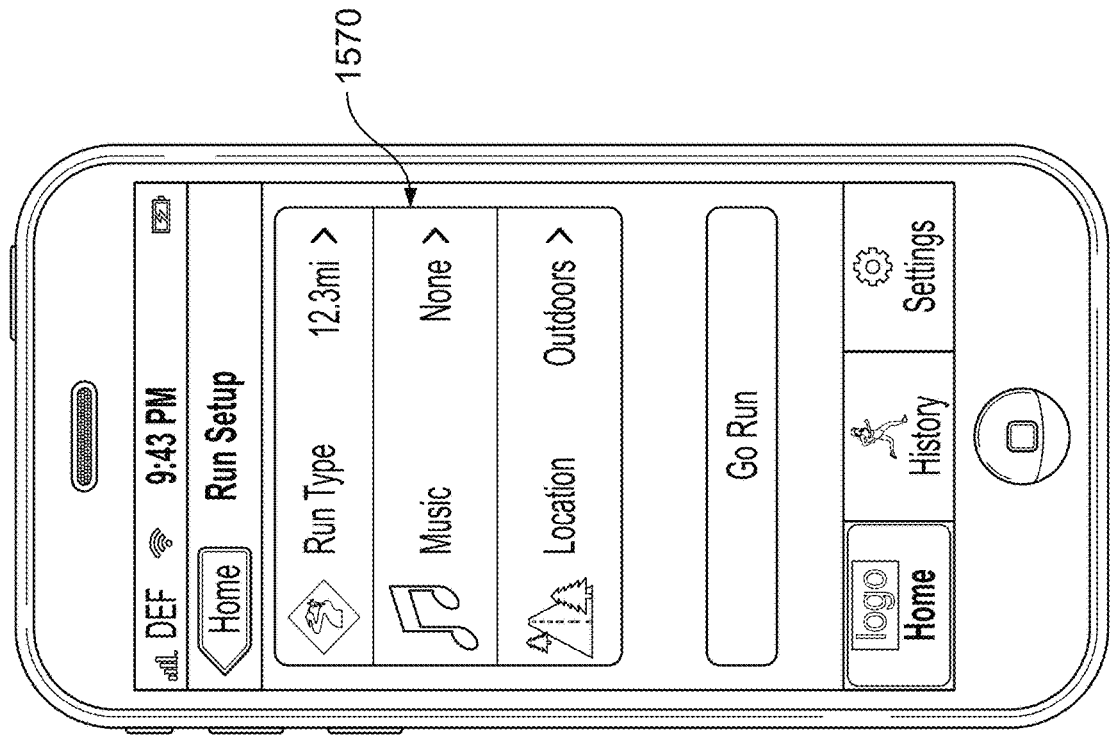
Figure 15F:
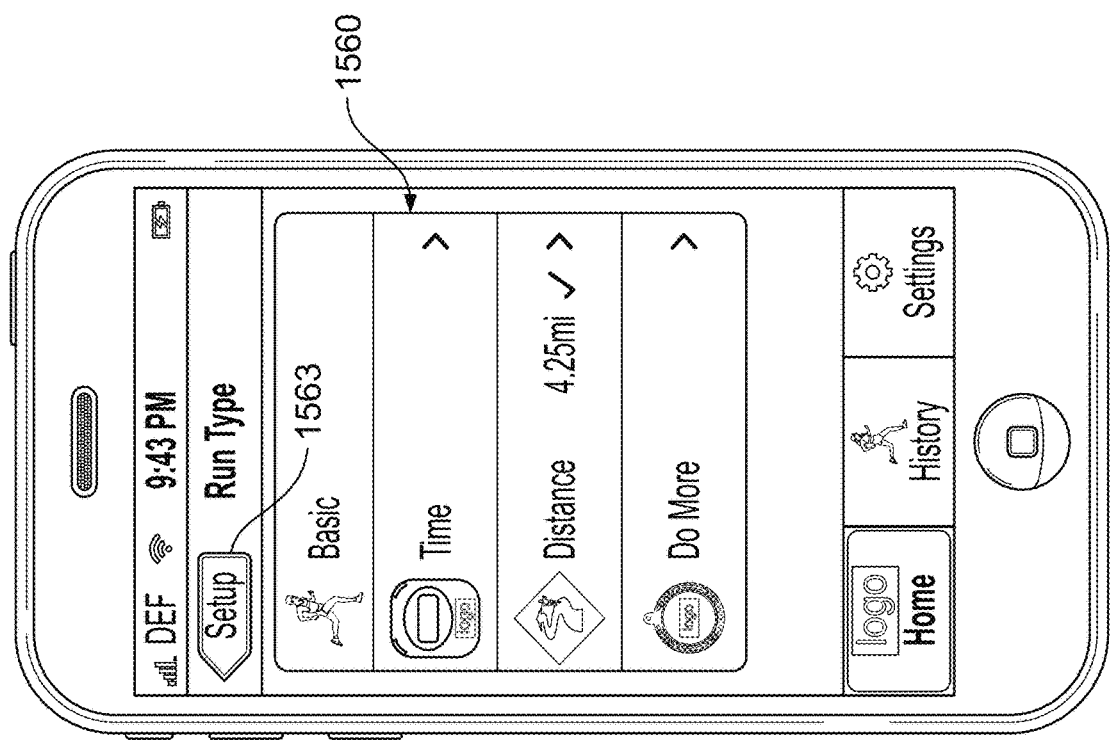

FIGS. 15A-15F illustrates a series of user interfaces that may be displayed upon a user selecting a distance run type. Similar to time selection, a user may select a distance option in interface 1510 of FIG. 15A and subsequently be presented with a list of run distance options in interface 1520 of FIG. 15B. For example, the list may include a 1K run, a 5 mile run, 5K run, a 10K run, a half marathon, a marathon and a custom distance. Selection of one of the predefined distances such as a 5K run may cause the 5K predefined distance to include a selection indicator. Alternatively, and as illustrated in FIGS. 15C and 15D, a user may select a custom distance in interface 1530 of FIG. 15C and subsequently manually define a custom distance in interface 1540 of FIG. 15D. Once the distance has been defined, the user may be returned to the run type selection interface in which the distance option is displayed with a selection indicator as illustrated in FIGS. 15E and 15F. The selected distance may also be displayed in association with the distance run type option. For example, in interface 1550 of FIG. 15E, "5K" may be displayed in the distance run type option to indicate that a 5K distance has been defined as the objective for the run. In another example, FIG. 15F illustrates an interface 1560 that displays a custom run distance such as 4.25 miles.

The user may confirm that the run type and run type settings are correct and return to a main setup interface using option 1563. Upon returning to the main run setup menu, the user may view the currently defined run parameters. For example, FIG. 15G illustrates interface 1570 that displays a distance of 12.3 miles with the run type parameter. The indication of mileage as opposed to time may signify that the run is a distance run rather than a time run.

Figure 16B:
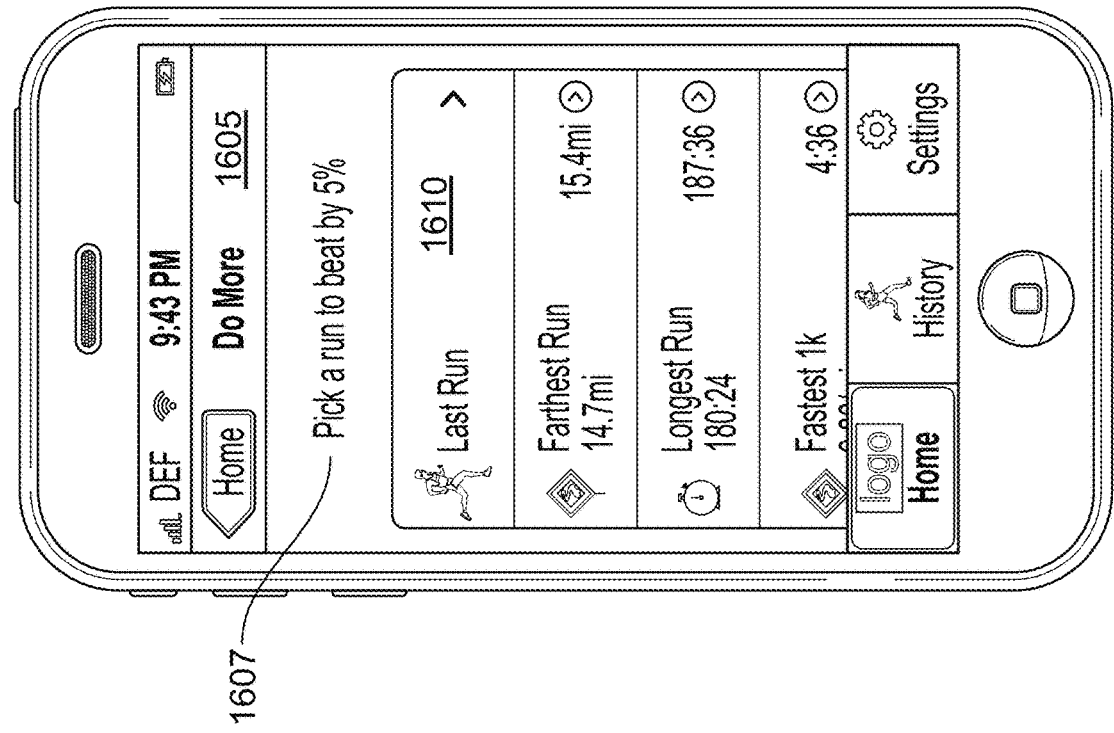
FIGS. 16A-16F illustrate a series of example user interfaces that may be generated and displayed upon a user selecting an improvement run type according to one or more aspects described herein.
Figure 16A:
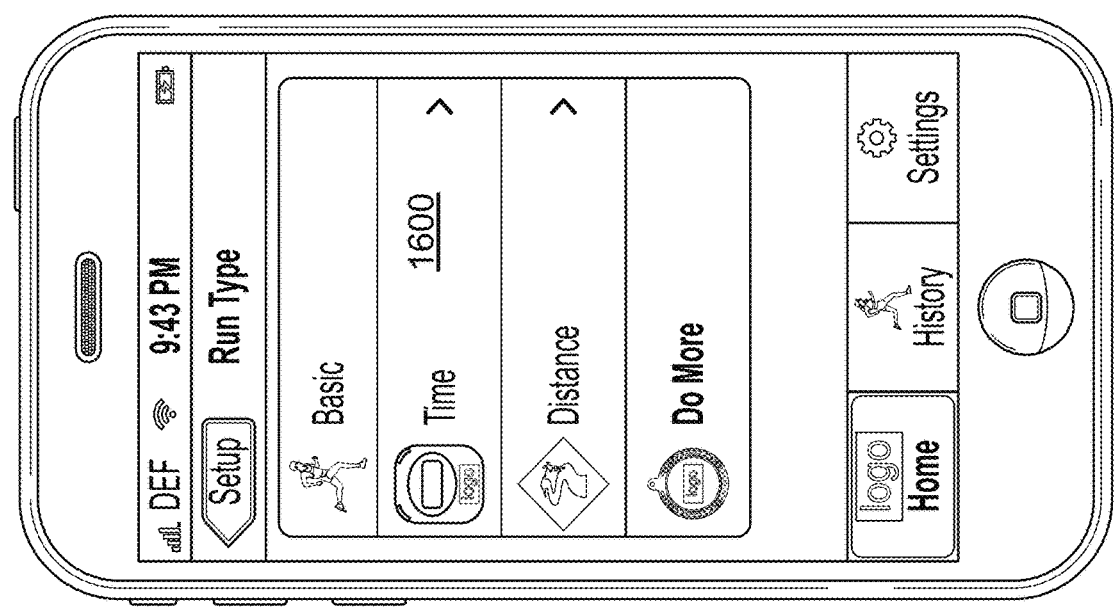
Figure 16D:
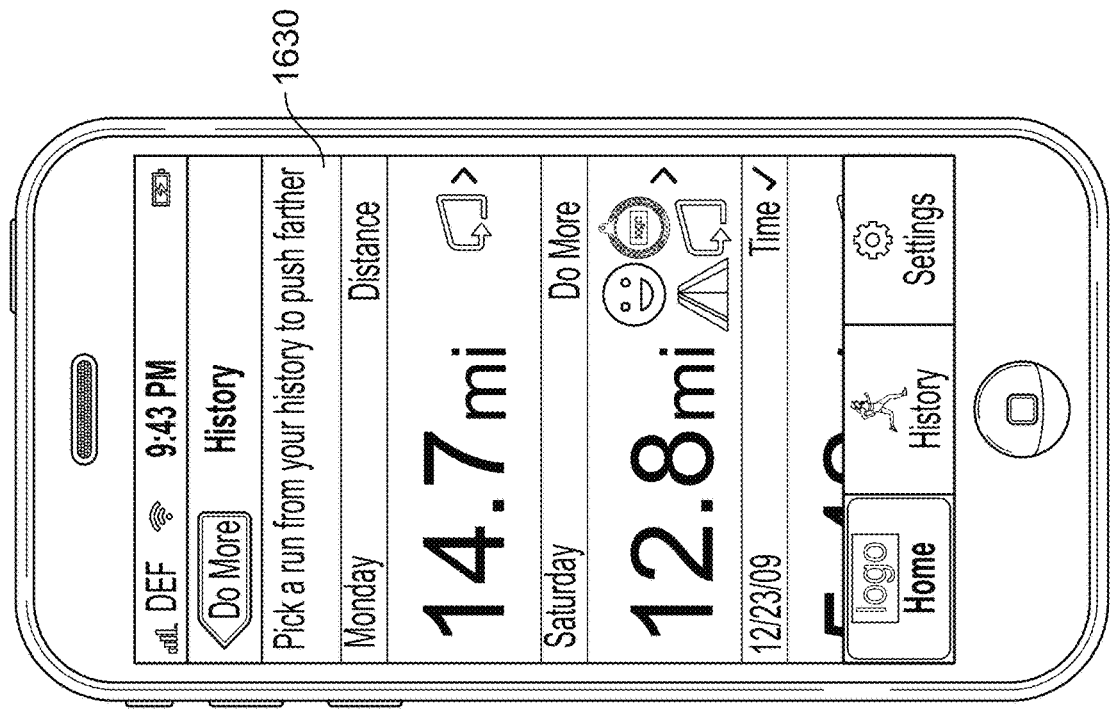
Figure 16C:
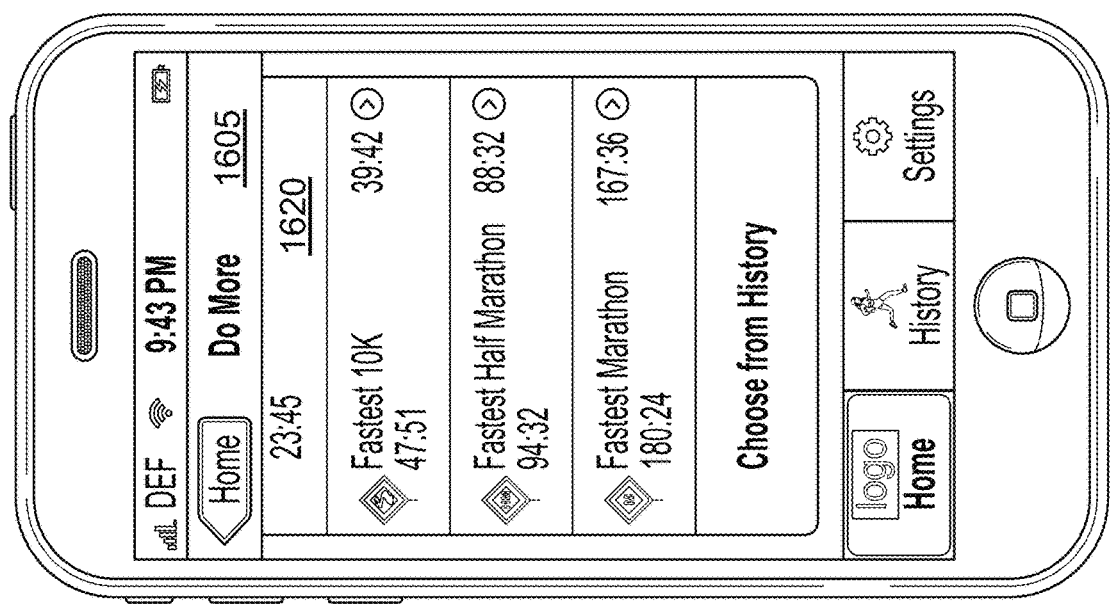

FIGS. 16A to 16F illustrates a series of user interfaces that may be generated and displayed upon a user selecting an improvement run type. As illustrated in FIG. 1600 of FIG. 16A, the "Do More" or improvement run type may be displayed in an alternate state (as compared to time, basic and distance run types) upon the user selecting the improvement run type. FIGS. 16B and 16C illustrate portions 1610 and 1620 of an improvement option listing and selection interface 1605. For example, in portion 1610, the user may select from a last run option (e.g., to beat one or more statistics of a previous run), a farthest run, a longest duration run and a fastest 1K run. Portion 1620 may include a fastest 10K run, a fastest half marathon, a fastest marathon and a history selection option. The objective of improvement run may be automatically defined to exceed a previous run (e.g., the longest run, the furthest run or the fastest 1K run) by a predefined amount. In one example, the objective may be to exceed the previous workout by 5%. The improvement amount may be indicated in portion 1607 of FIG. 16B. The improvement amount may be user defined, automatically set by the device or application, defined by an athletic activity monitoring service provider and the like.

If a history option is selected, e.g., from portion 1620 of FIG. 16C, the user may be presented with a listing of recorded runs. FIG. 16D illustrates a history interface 1630 displaying a list of recorded previous runs. The user may then select from one of the previously recorded run to improve. For example, the user may elect to improve upon a previous 14.7 mi run by 5%. Upon selecting the previously recorded 14.7 mile run, the user may be presented with interface 1640 of FIG. 16E in which the user may select a statistic or metric recorded in the 14.7 mile on which to improve. The system and application may automatically calculate the objectives with the improvement amounts added. For example, a user may select options to run farther, run for longer amounts of time and run at a faster pace.

Figure 16F:
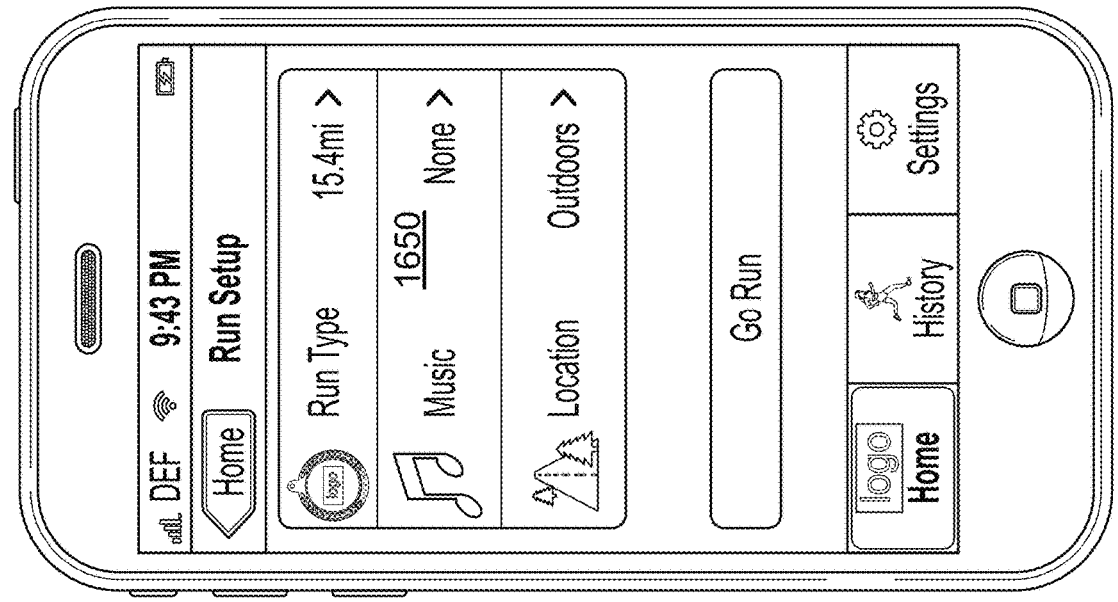
Figure 16E:
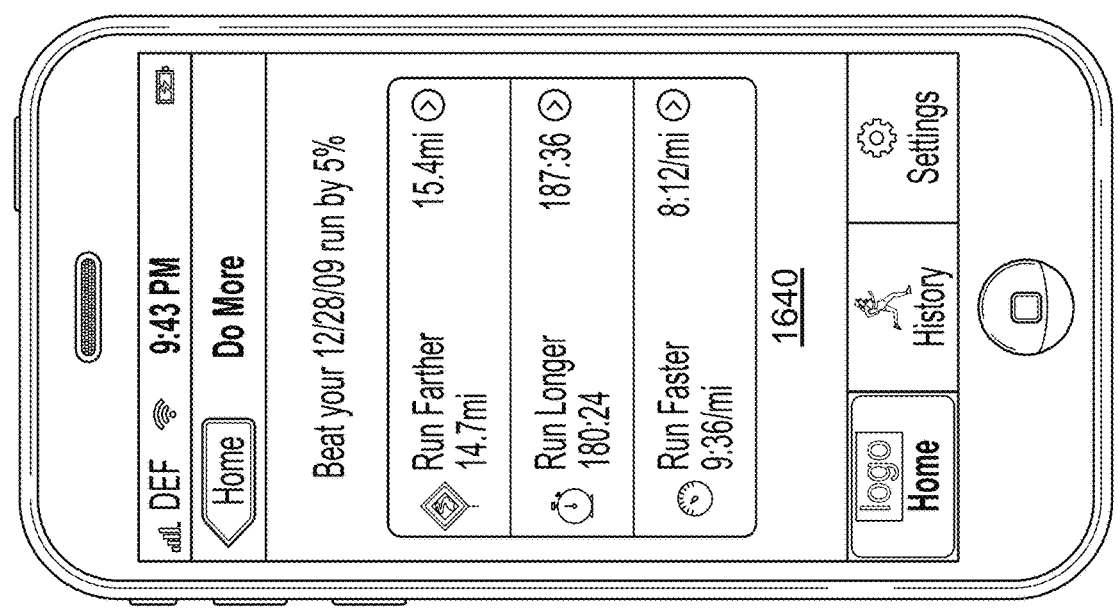
Figure 18A:
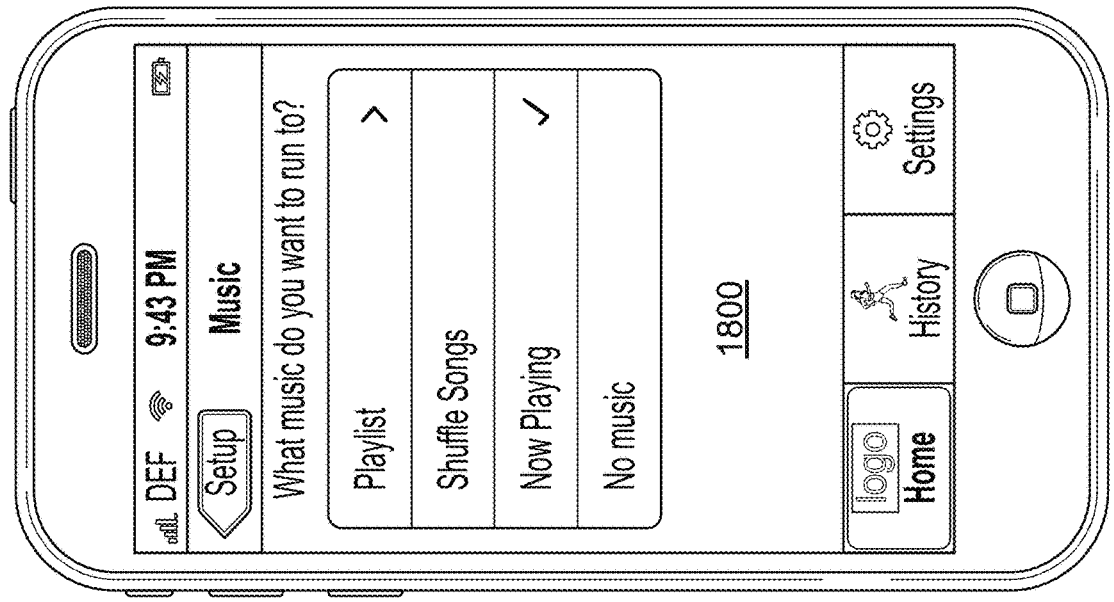
FIGS. 18A-18E illustrate a series of example audio content selection interfaces that may be generated and displayed upon selection of the audio content definition option according to one or more aspects described herein.

Once the desired improvement has been selected and defined, the user may be returned to a run setup menu such as interface 1650 of FIG. 16F in which the selected objective is displayed in association with the run type.

In one or more arrangements, once the desired type of run has been defined, the device may further generate coaching based on the defined run parameters. In one example, the coaching may advise the user to warm-up for a longer period of time if the intended run is a longer distance (e.g., 10 miles) than if the run was a shorter distance (e.g., 3 miles). Alternatively or additionally, different warm-up activities may be recommended depending on a desired pace or distance. The coaching may be provided as audio from an athlete or celebrity. In a particular example, a user may select a celebrity or well-known coach. Each coach may correspond to a different level of training difficulty and aggressiveness. For example, one coach may challenge the user to exceed his or her defined goal by 10% (e.g., by cuing the user to run faster than an average pace during the workout). Other coaches may challenge the user to exceed his or her defined goal by 30% (e.g., by cuing the user to run faster than an average pace more times and/or longer durations during the workout). Some coaches may correspond to different types of workouts. For example, a coach may prefer interval training while another coach may prefer short sprints to longer, slower runs.

Additionally, tips and advice provided to the user may further include a recommendation for athletic equipment, services and other products. For example, upon determining that the user is planning a new workout, the device may recommend purchasing a new pair of shoes if the user's current shoes are reaching a threshold wear state. The device may also recommend various types of apparel such as compression socks, leggings, t-shirts, shorts, pants and the like, windbreakers for windy areas, thermal underwear for colder locations, headbands or sweatbands in hotter climates and the like. According to one or more aspects, the product recommendations may be generated based on user descriptions of previous workouts. For example, if a user indicated that a workout was tiring, the device may recommend purchasing a sports drink prior to beginning the next workout. In another example, the weather or terrain specified in a previous workout or workouts may affect the type of product recommended. For example, one type of shoe may be recommended for road running while another type of shoe may be recommended for track running. In still another example, moisture wicking apparel may be recommended for warmer climates while thermal apparel may be recommended for colder climates.

Various other types of recommendations and recommendation factors may be used in conjunction with the aspects described herein. For example, recommended products may be digital or service-related. In particular, the device may recommend visiting a route mapping application or service upon completion of the run to allow the user to better visualize the various attributes of the run relative to a geographic map of the route. In another example, coaching or other types of tips and information may include location-specific advice. If the mobile device detects that the user is about to embark on a particular route, the device may provide advice regarding the various terrains along that route. In a particular example, the device may provide coaching (e.g., how fast to run, where to run slower or faster, how much energy to expend during certain portions of the route) depending on location-specific information or attributes including terrain, weather, inclines, elevations and the like. The location may be detected, as described herein, using GPS devices or by manually identifying a location using coordinates, zip codes, area codes, city names and/or combinations thereof. Other types of location information may include a number of users running in a particular area (region of country, world, particular route, city, state, zip code, area code, etc.). Location-specific information may also be provided during the workout as the user reaches or comes within a predefined amount of distance of a location.

Defining a Run—Training Audio & Environment Selection

Figure 17:
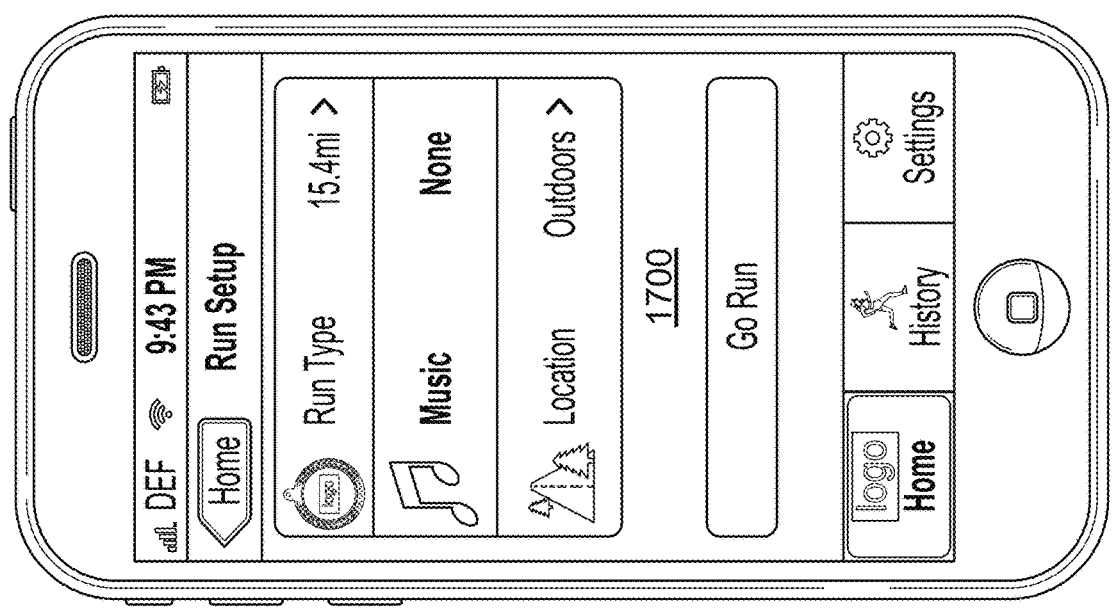
FIG. 17 illustrates an example interface through which a user may select a music definition option according to one or more aspects described herein.

In conjunction with selecting the run type, the user may also select audio content to be played during the workout. The user may also elect not to have any audio content playing during the workout. FIG. 17 illustrates a user selecting a music option from interface 1700. The music option may include a display of the current selected audio option. For example, if no audio content has been selected, the word "None" maybe displayed within the selection button. Alternatively, a selected playlist name or selection algorithm/parameter (e.g., random, category of music) may be displayed.

Figure 18C:
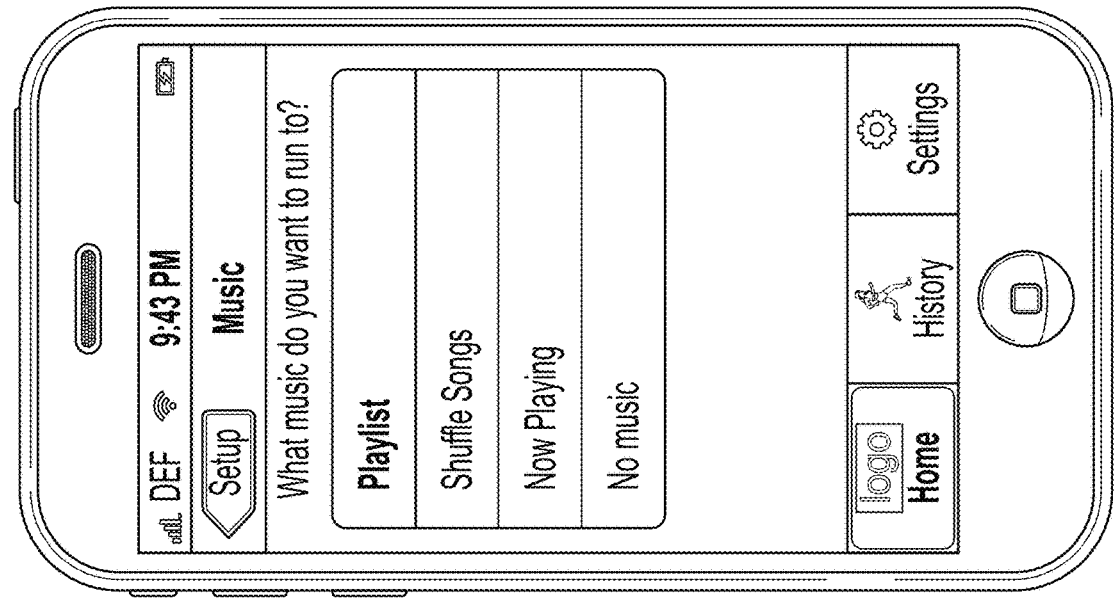
Figure 18B:
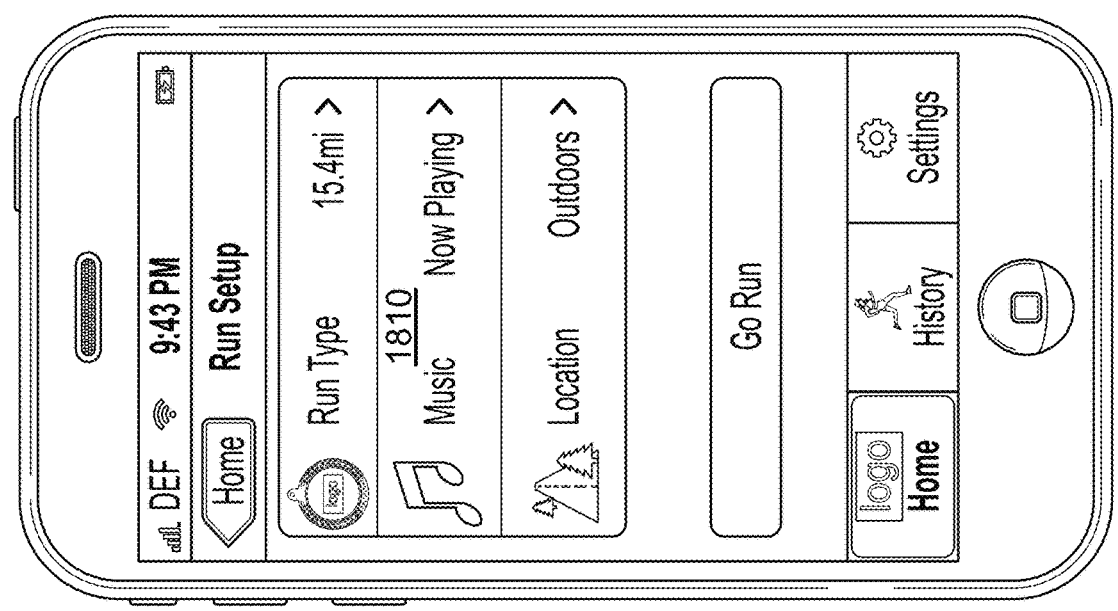

FIGS. 18A-18E illustrate a series of audio content selection interfaces that may be generated and displayed upon selection of the audio content definition option. For example, in FIG. 18A, interface 1800 may include a plurality of predefined audio content options including a playlist selection option, a shuffle option, a now playing option and a no music option. Shuffle option may allow a user to randomly select songs from all available songs. In some arrangements, the shuffle option may play the audio content in a random order as well (e.g., not necessarily in accordance with an order in which the audio content is stored or listed in a database of all available songs). Selection of now playing option may cause a current playlist or audio content category, artist, album or the like to be selected. If no audio is currently being played, the now playing option may select the most recently played or selected audio content. FIG. 18B illustrates run setup interface 1810 in which the user's selection of the now playing option is reflected in the music selection option.

Figure 18D:
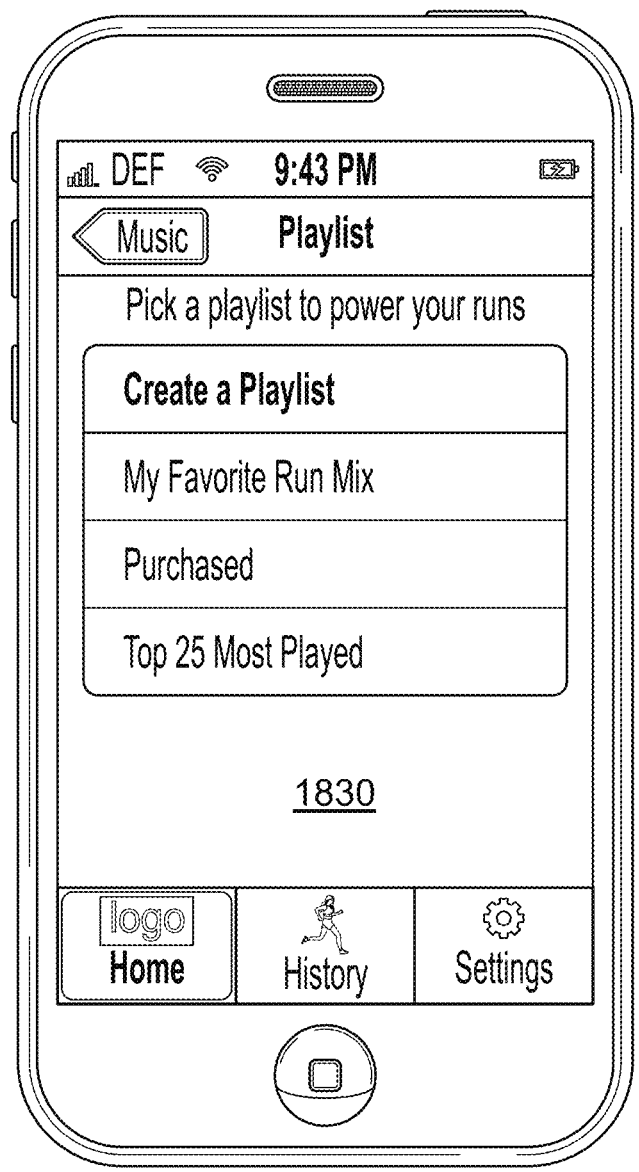

If, on the other hand, the user selects the playlist option (as illustrated in FIG. 18C), the user may be presented with a playlist selection interface. FIG. 18D illustrates an example playlist selection interface, i.e., interface 1830, in which the user may create a new playlist, select a favorite run mix playlist, a playlist comprising all purchased music and a playlist including the top 25 most played audio items. The favorite run mix playlist may be automatically generated by the device based the frequency that audio content or audio content playlist is played during workouts. Accordingly, the favorite run mix playlist may differ from the top 25 most played audio items as the top 25 most played may be determined based on a total frequency during workout and non-workout times while the favorite run mix playlist may be generated based only on audio content played during workouts.

Figure 18E:
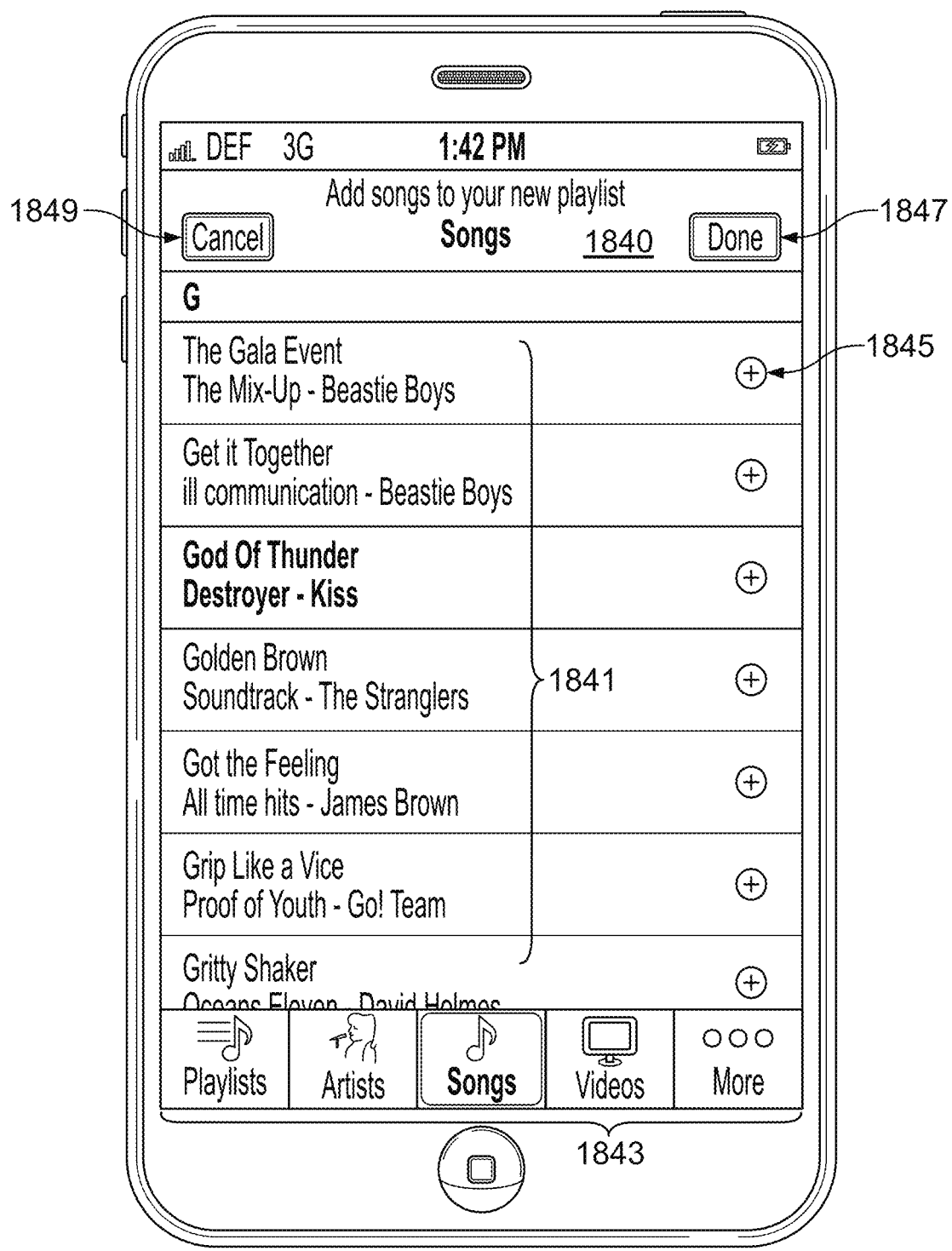

By selecting the playlist creation option, the user may be presented with an audio content list 1841 in a song selection interface 1840 of FIG. 18E. The user may be able to sort the list of audio content items using options 1843. For example, the user may sort or view the list by playlist membership, artist, songs and videos. The user may add audio content items to the list by select each desired item from the list. An add/remove indicator 1845 may change in appearance depending on if the corresponding audio content item is currently in the playlist being created. For example, if the audio content item is not in the playlist, indicator 1845 may be displayed as a plus symbol while if the audio content is in the playlist, indicator 1845 may be displayed as a minus symbol. Once the user has finished adding audio content to the playlist, the user may select option 1847 to continue the run setup. Alternatively, the user may cancel playlist creation by selection cancel option 1849. In one or more arrangements, audio content may be suggested or recommended to the user based on the user's previous workout performance during those audio content items. For example, if a user ran at an above average pace or ran an above average distance during a particular audio content item, the device may suggest that the audio content item be added to the playlist. The same process may be used to automatically generate a suggested playlist. For example, a playlist may be generated by selecting the 25, 30, 40, 50 or other number of songs during which the user exhibited the best workout performance (e.g., as defined by a particular statistic or metric such as calories burned, distance, pace and/or combination thereof).

According to one or more arrangement, the mobile device and workout monitoring application may select and/or suggest audio based on a duration of the workout. The duration of the workout may be user-defined or may be approximated/estimated based on previous workouts of the same length or type. For example, if a user has previously run 5 miles in 45 minutes, the mobile device or training application may approximate a duration for an upcoming 5 mile run workout. Once the duration has been determined, the mobile device or application may subsequently select one or more audio content items such as music, audio books, comedy shows, Internet radio or the like for the upcoming workout based on the expected duration. Accordingly, in the above examples, the mobile device may select to match the 45 minute duration of the run. In some configurations, the mobile device may add a predefined interval (e.g., 1 second, 2 seconds, 3 seconds, 5 seconds, 10 seconds, etc.) between each content selection. The interval may be factored into the overall duration of the audio content. Video content or a mixture of video and audio content may be selected in similar fashion.

A user may accept or reject the suggested playlist or may edit the playlist as desired. The playlist may be displayed with an indication of the total duration (with and/or without the inserted intervals between the content items). Accordingly, as the user is modifying the playlist, the duration may be updated in real-time. Additionally, the content duration may be displayed against a duration of the workout for easier visual comparison. For example, the workout duration may be displayed as a first bar while the content duration is displayed as a second bar overlapping the first bar. Other visual representations may be used (e.g., a pie chart).

Figure 19B:
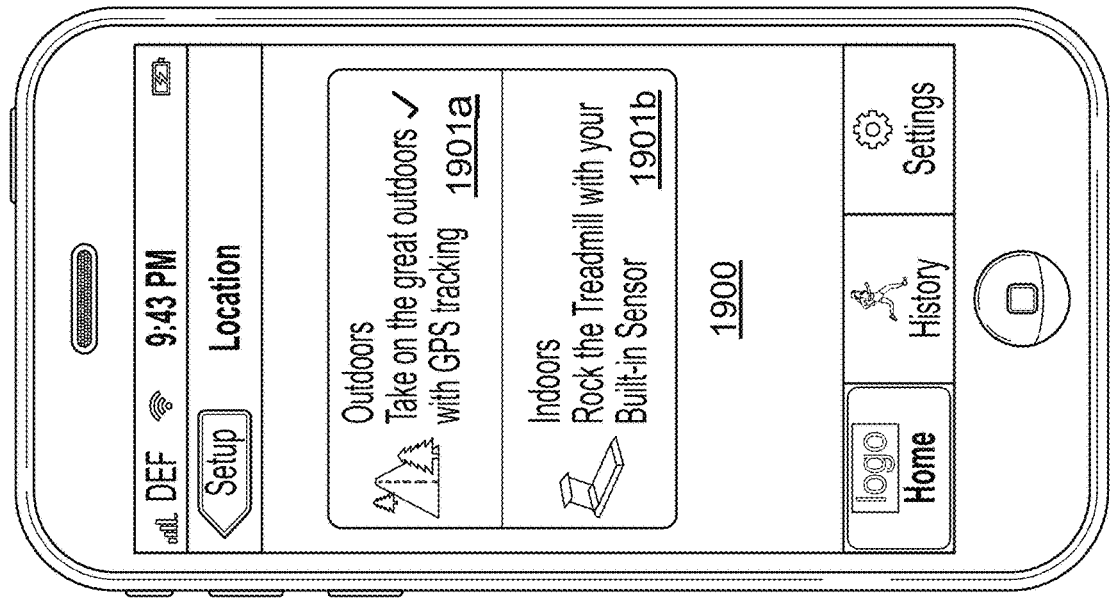
FIGS. 19A-19C illustrate a series of example location definition interfaces according to one or more aspects described herein.
Figure 19A:
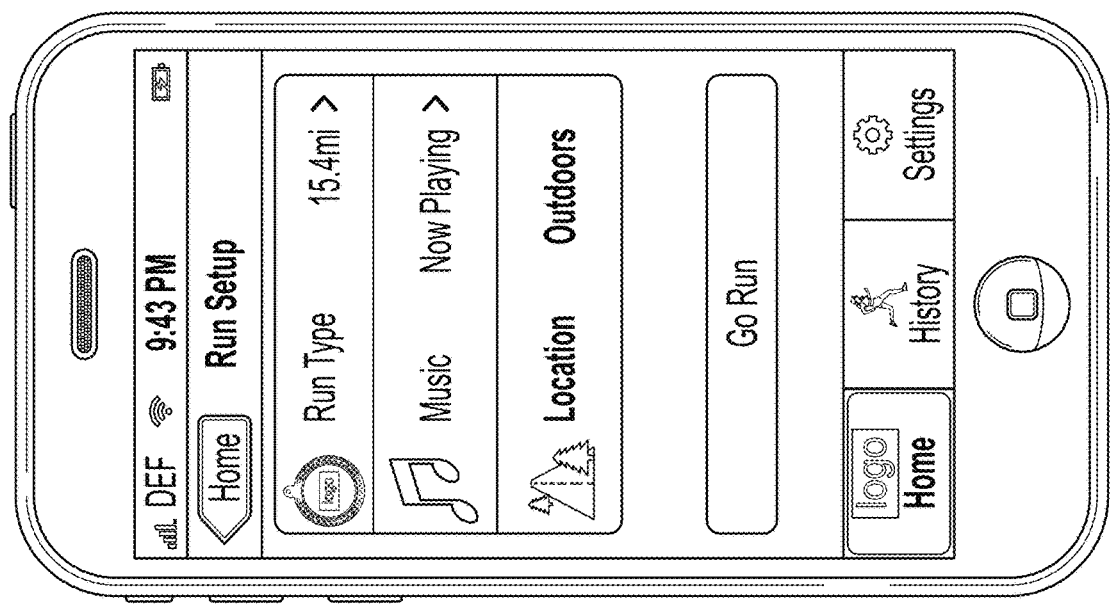
Figure 20A:
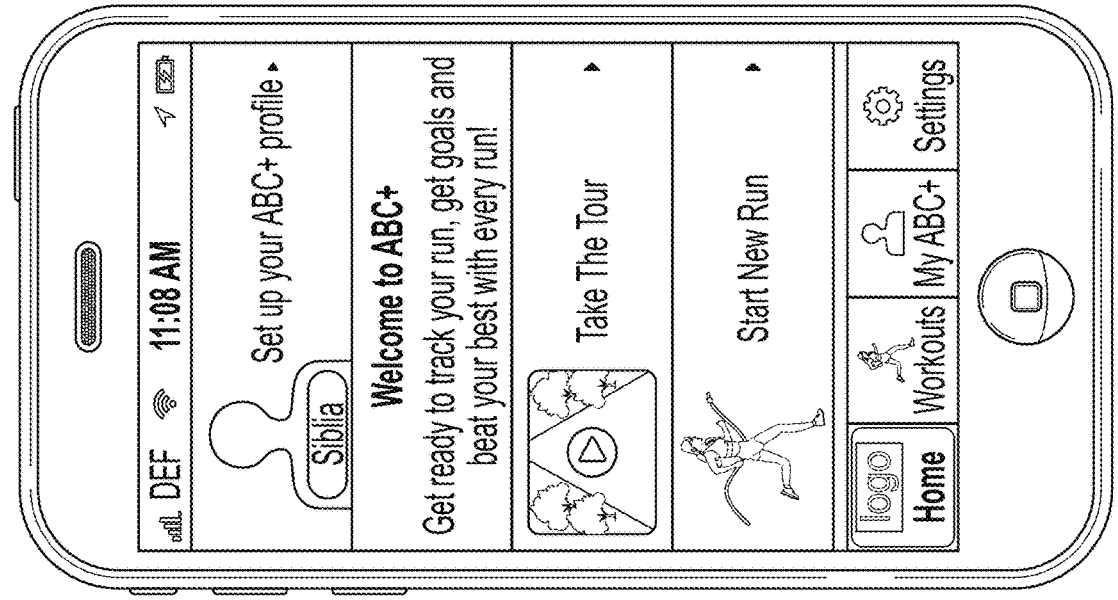
FIGS. 20A-20Z illustrate additional example interfaces that may be displayed for setting up a run according to one or more aspects described herein.
Figure 19C:
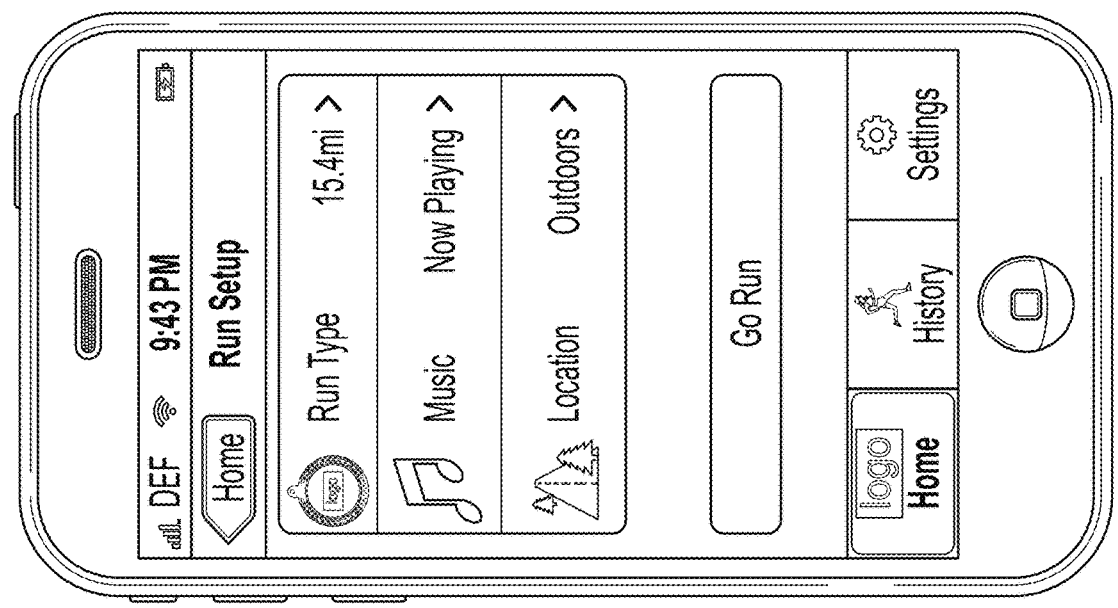

In addition to music selection and run type definition, the user may further define the location of the workout. FIGS. 19A-19C illustrate a series of location definition interfaces. Upon the user selecting a location setup option, the user may be presented with multiple available predefined locations 1901 in interface 1900 of FIG. 19B. Locations 1901 may include an outdoors environment and an indoor workout environment. Other locations and types of locations may be defined such as cities, landmarks and other categories of locations (e.g., parks). As noted herein, the selection of a particular location or location type may affect the types of sensors or devices that may be used for athletic activity monitoring. Additionally or alternatively, the algorithm used to measure athletic activity might also be affected by the selected location.

Figure 20C:
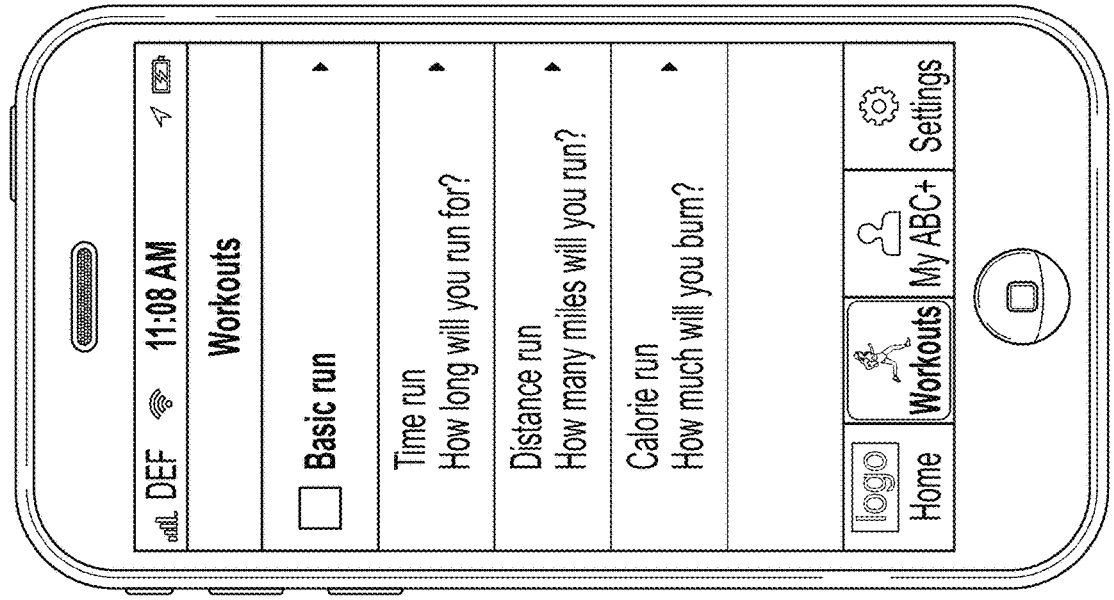
Figure 20B:
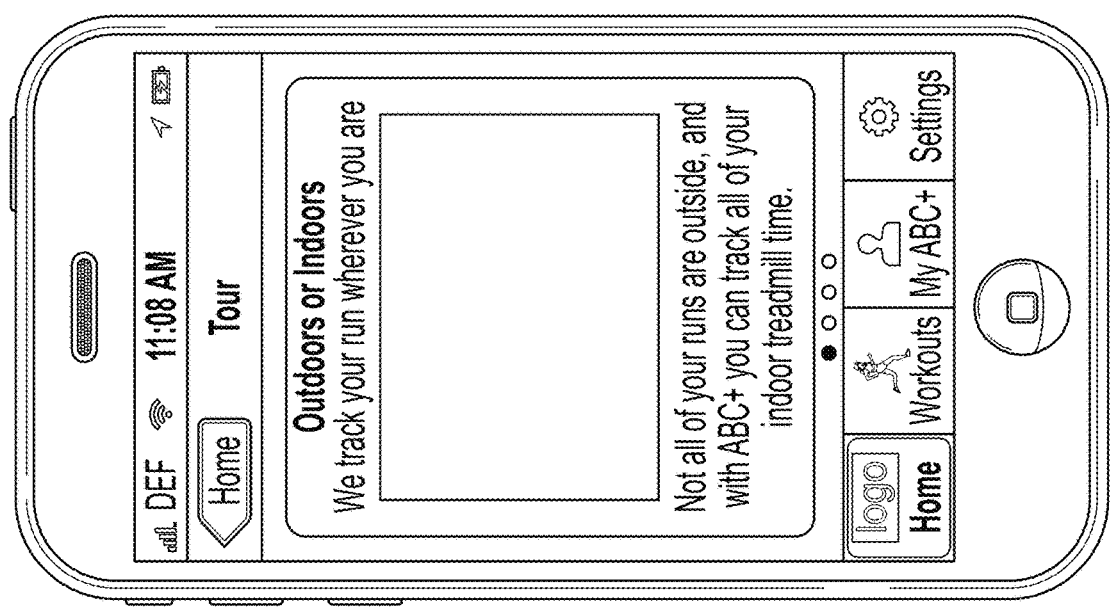
Figure 20E:
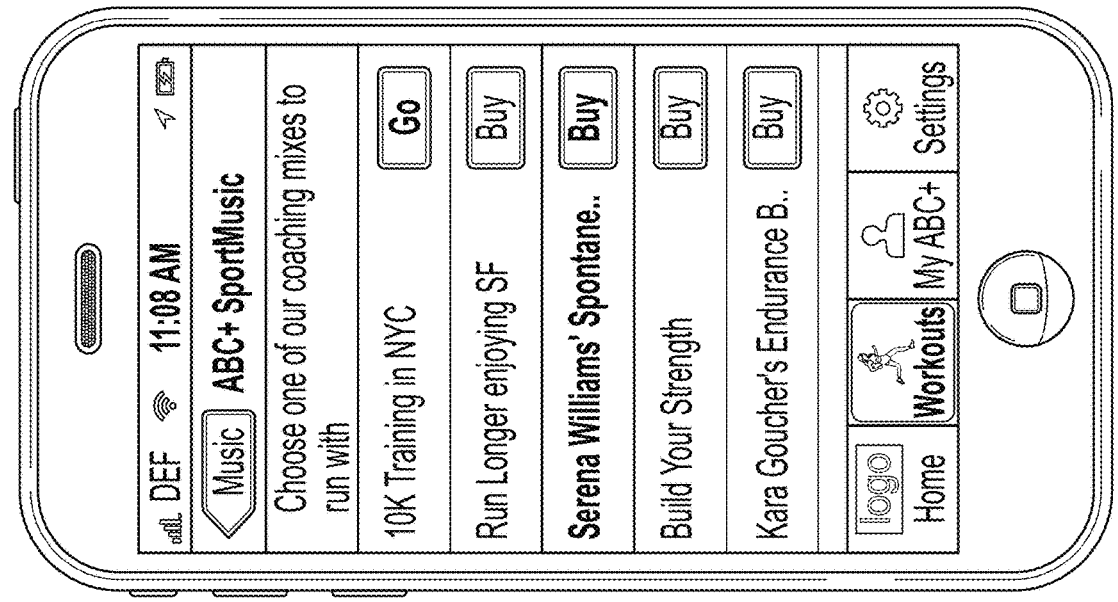
Figure 20D:
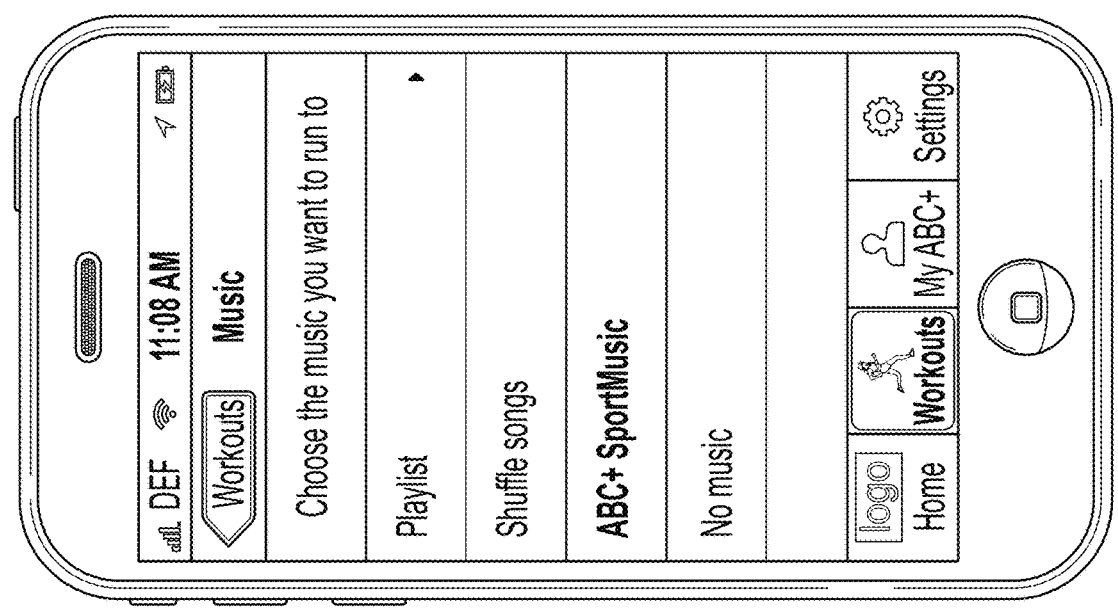
Figure 20F:
Figure 20H:
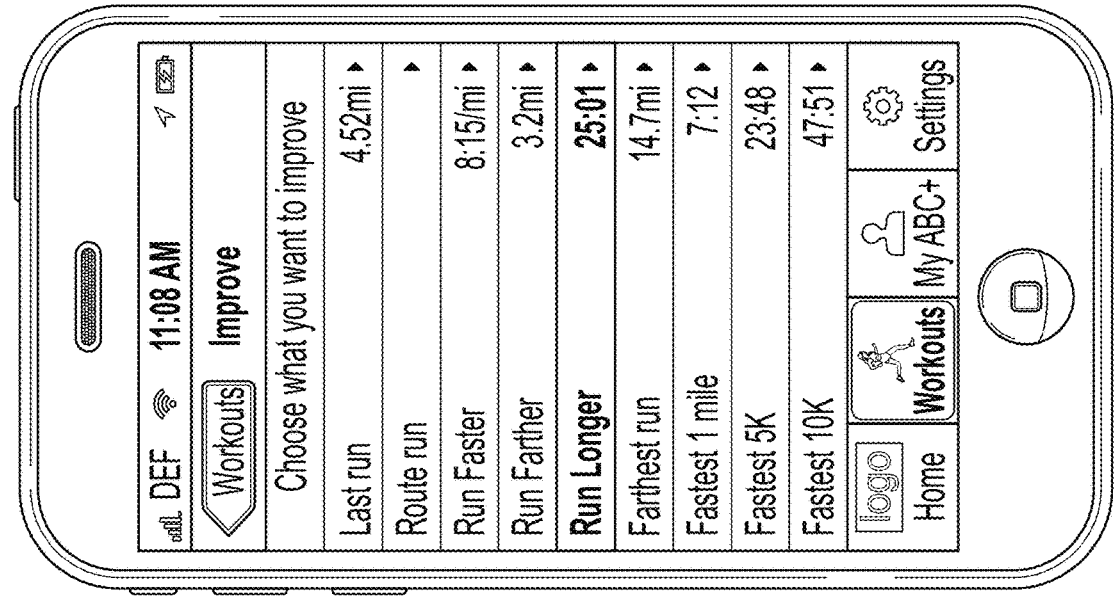
Figure 20G:
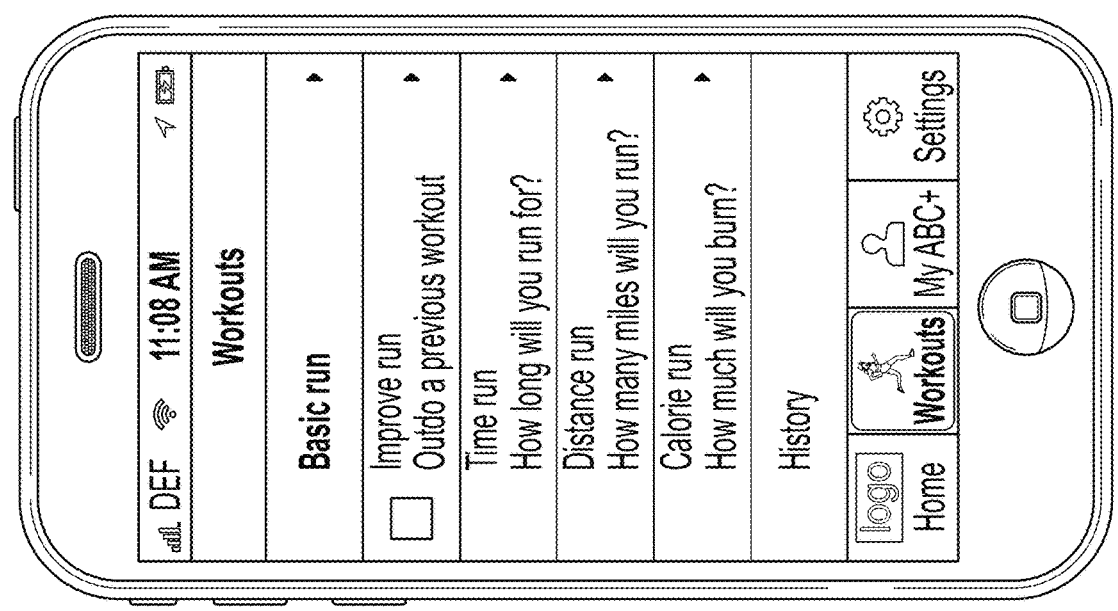
Figure 20J:
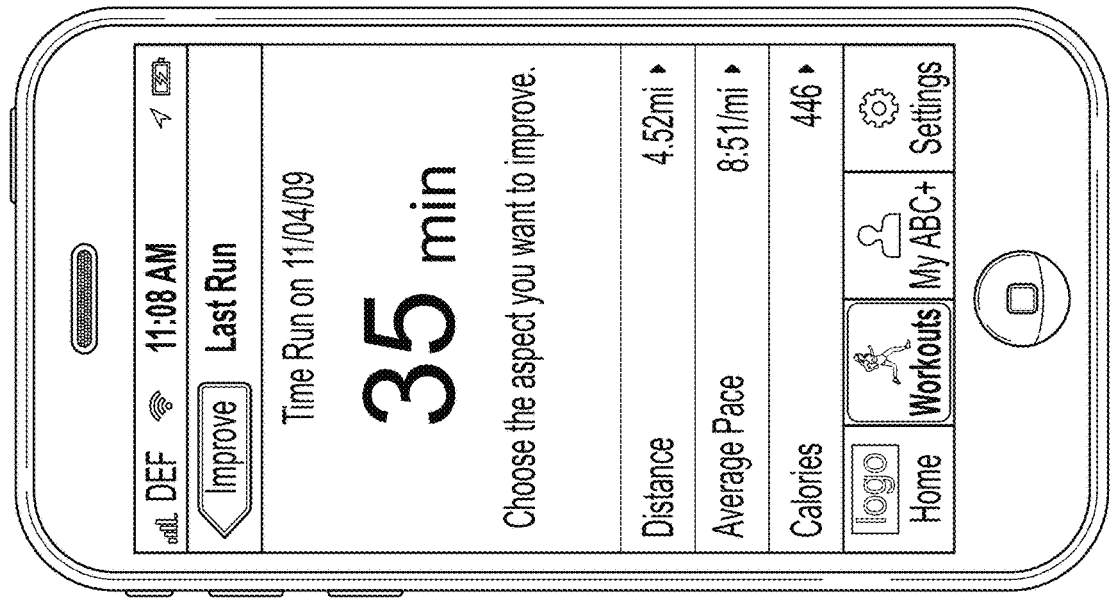
Figure 20I:
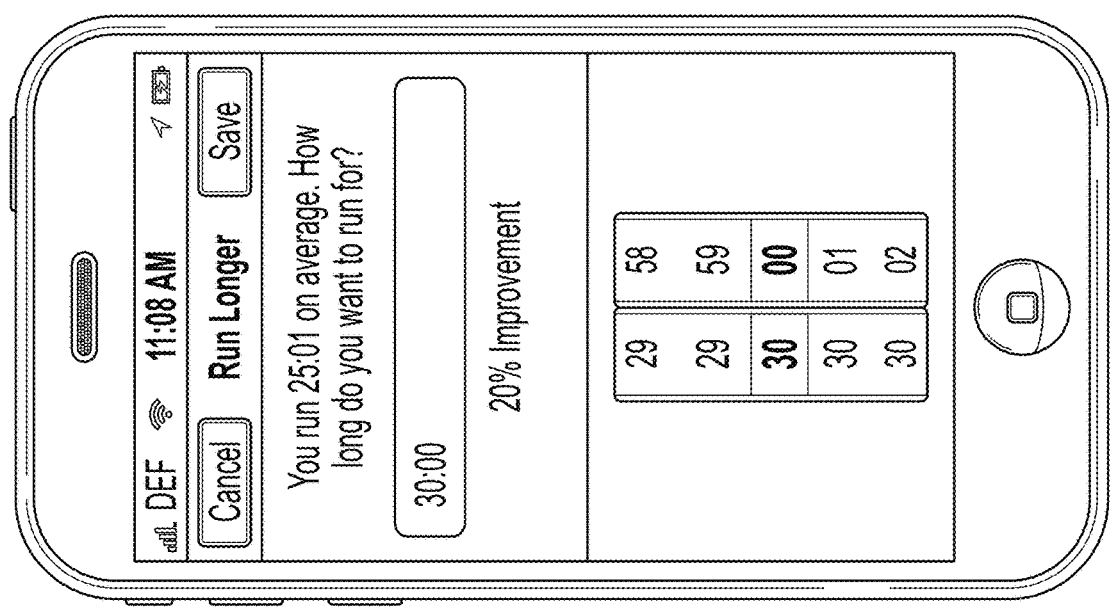
Figure 20L:
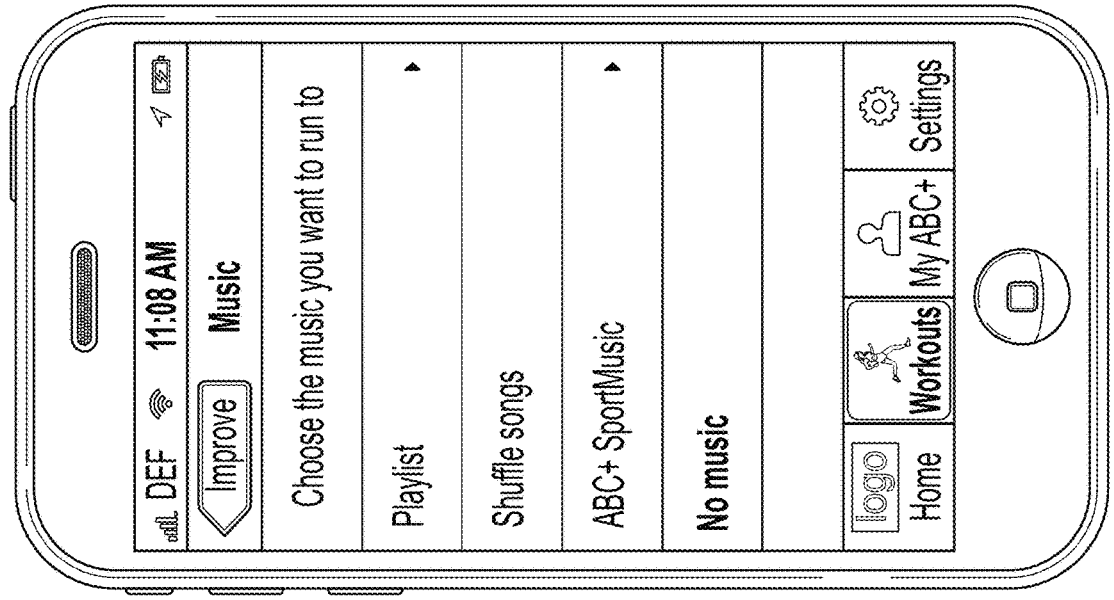
Figure 20K:
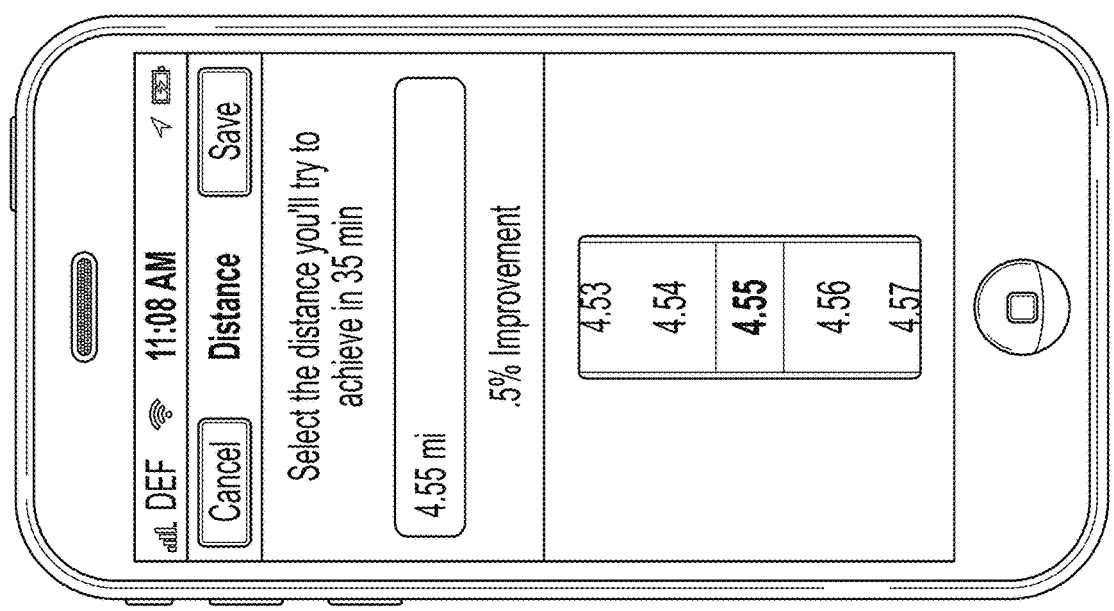
Figure 20N:
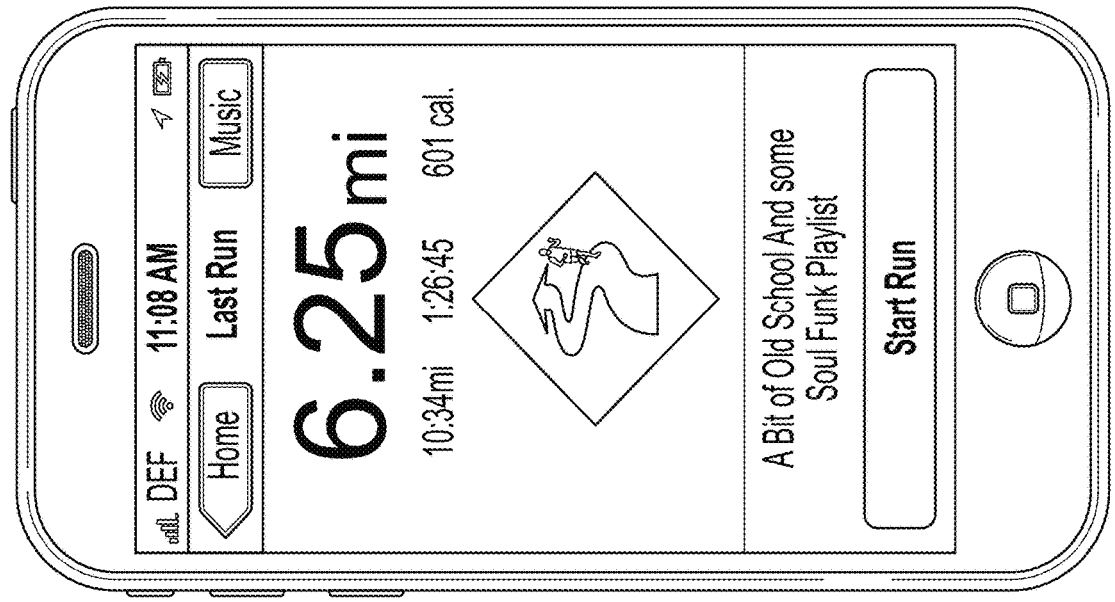
Figure 20M:
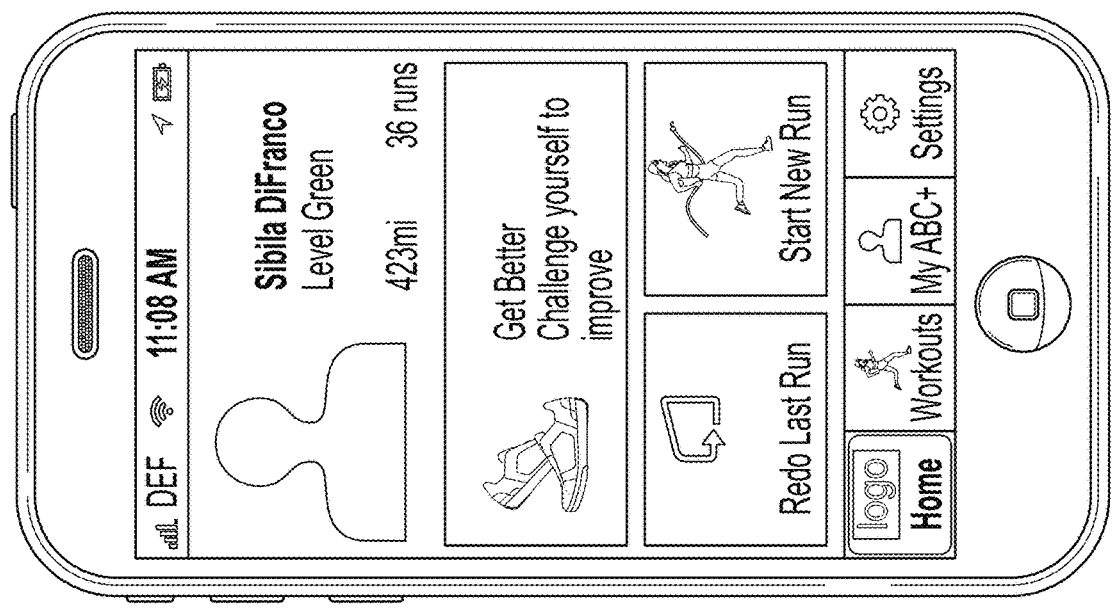
Figure 20P:
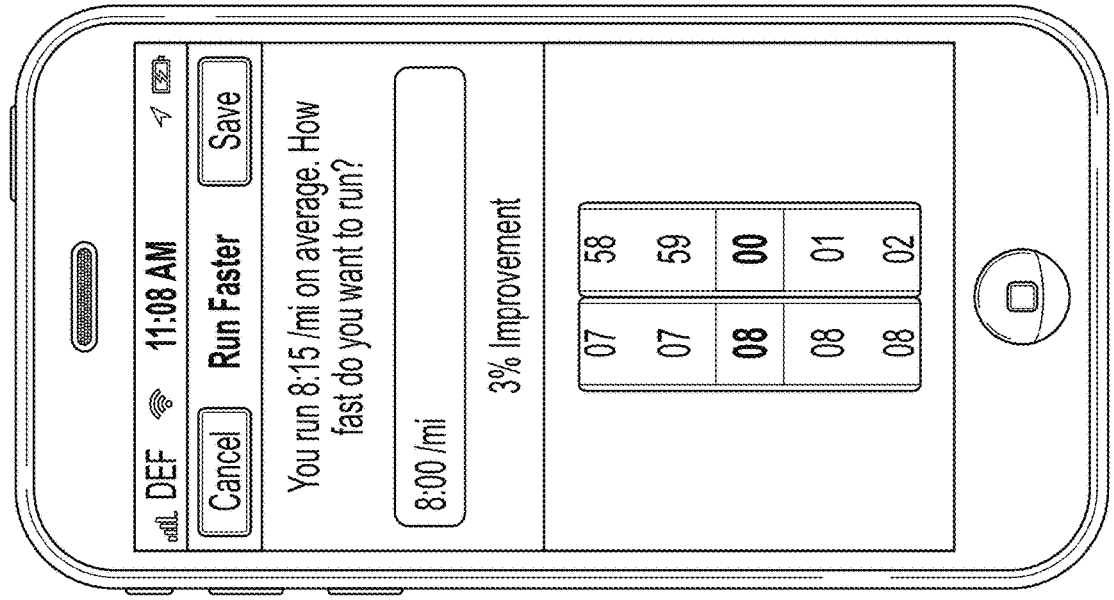
Figure 20O:
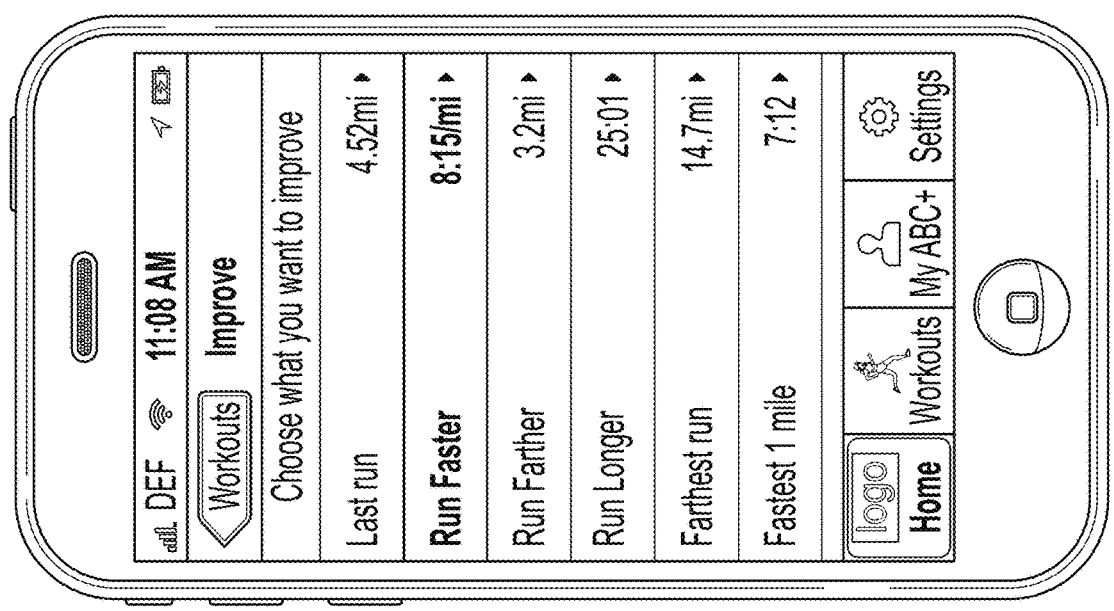
Figure 20R:
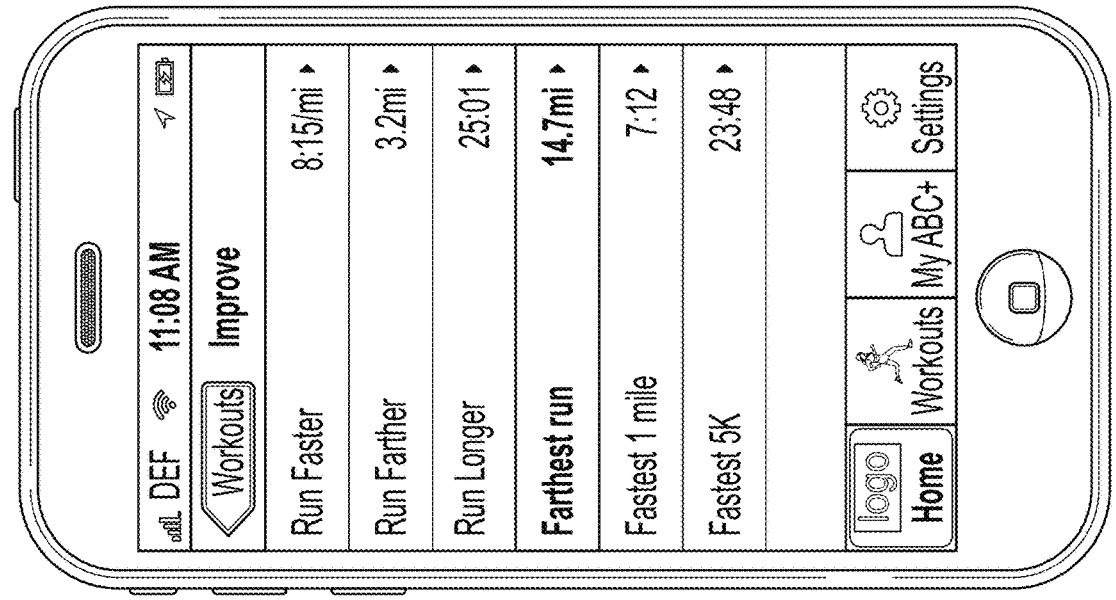
Figure 20Q:
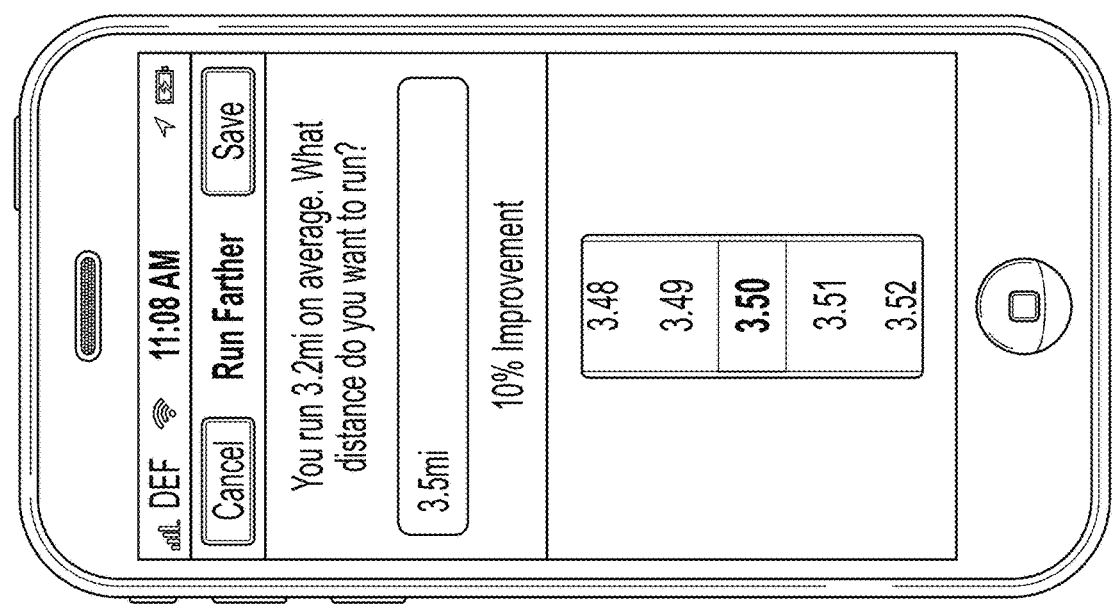
Figure 20T:
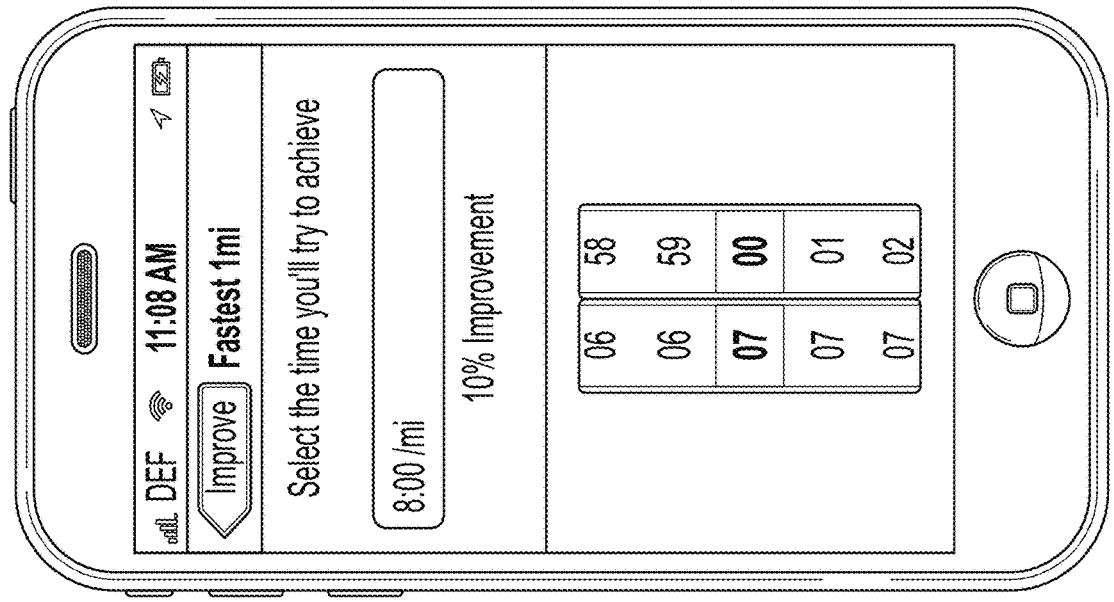
Figure 20S:
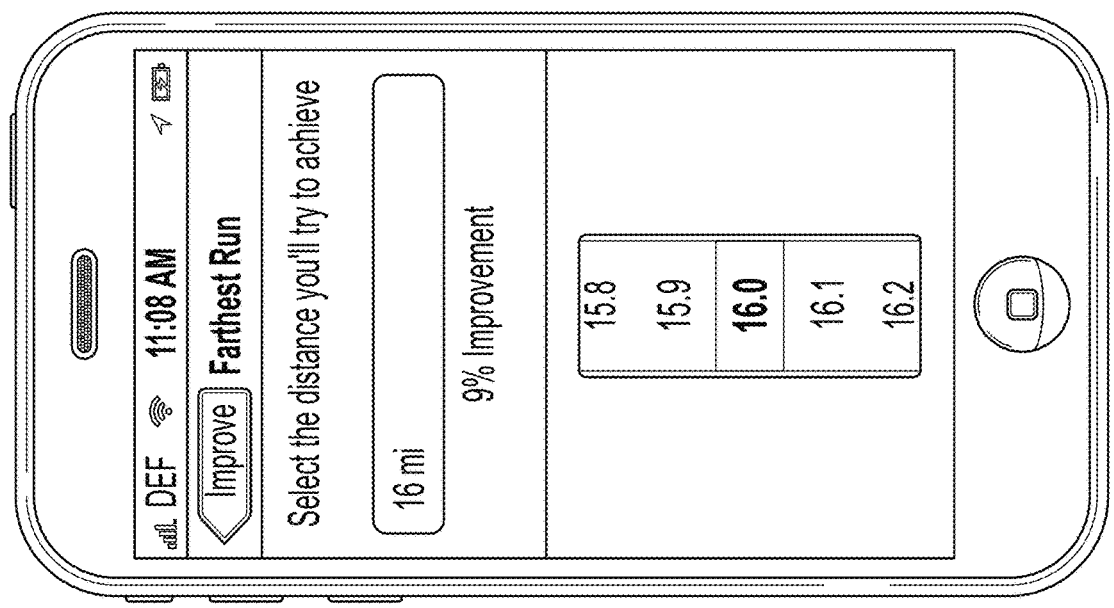
Figure 20V:
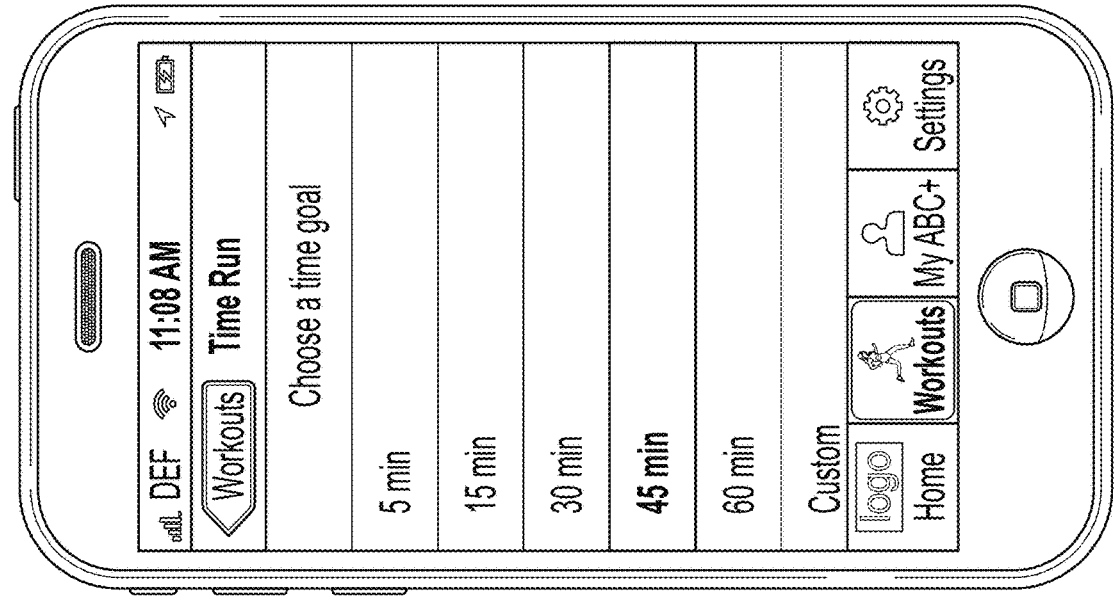
Figure 20U:
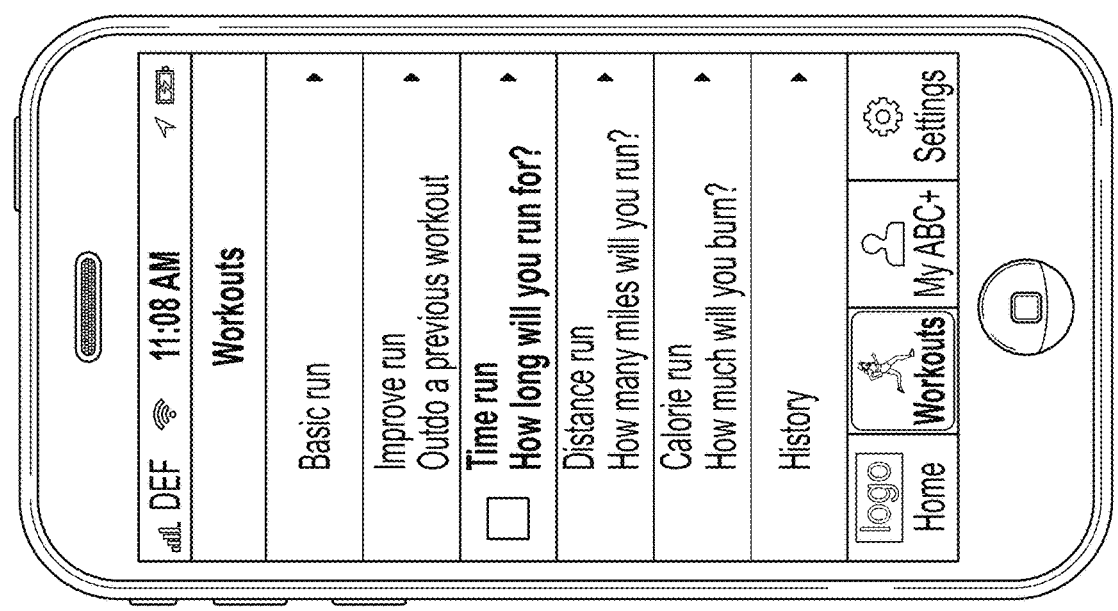

FIGS. 20A-20Z and FIGS. 21A-21D illustrate additional example interfaces that may be displayed for setting up a run. For example, FIG. 20N illustrates an interface that allows a user to repeat a previous run (e.g., with the same objectives, route, equipment, music). FIGS. 20P, 20Q, 20S and 20T illustrate example user interfaces through which a user may manually define an objective for an improvement run. The user may modify the pace the user wishes to achieve for the run. The interfaces may provide an indication of the amount of improvement reflected by the selected pace. For example, 8:00/mi may represent a 3% improvement over a fastest pace of 8:15/mi. In another example, 3.5 mi may represent a 10% improvement of a previous farthest run of 3.2 mi. In yet another example, the setting of a 16 mi goal may represent a 9% improvement over a previously farthest run of 14.7 mi.

Figure 20X:
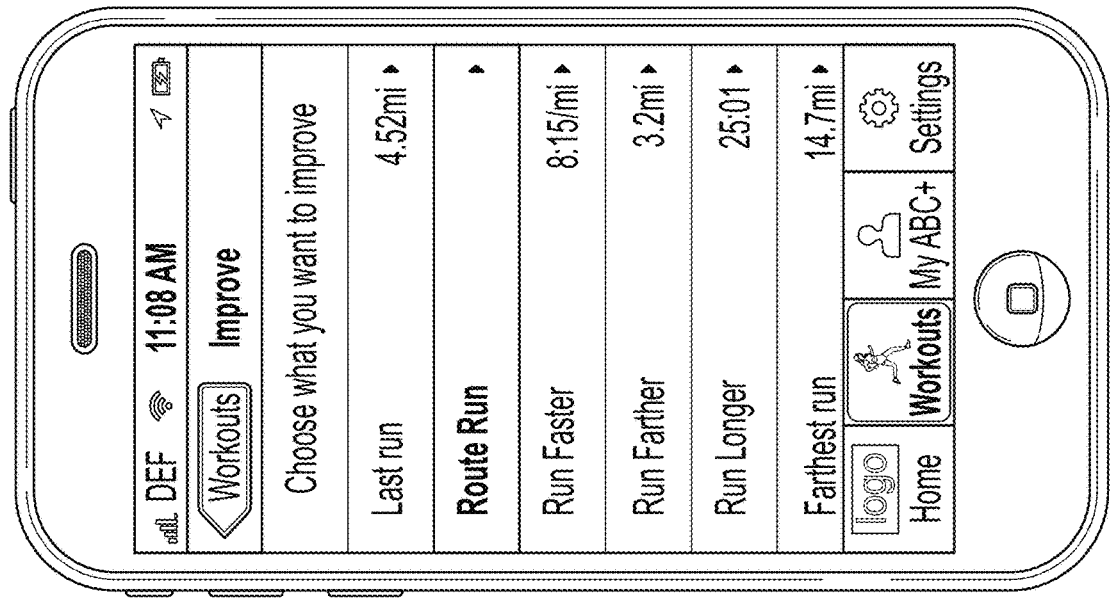
Figure 20W:
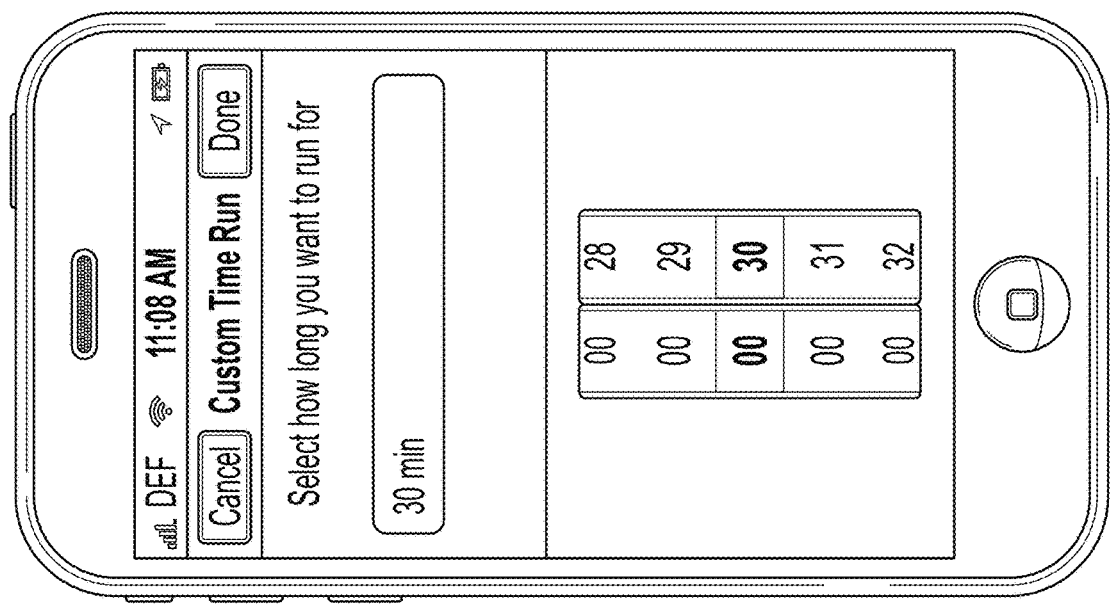
Figure 20Z:
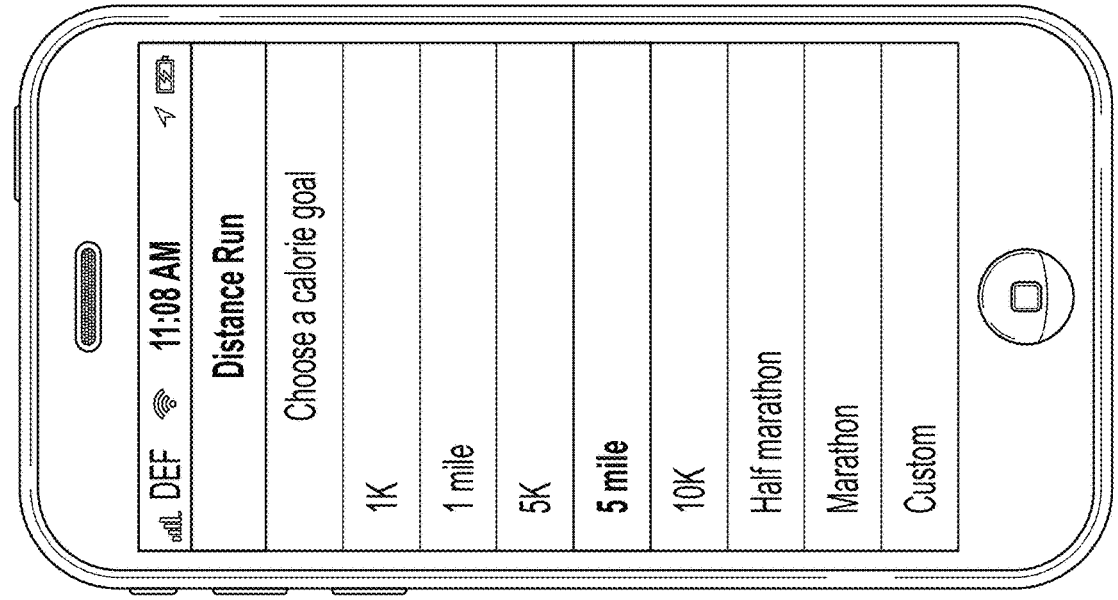
Figure 20Y:
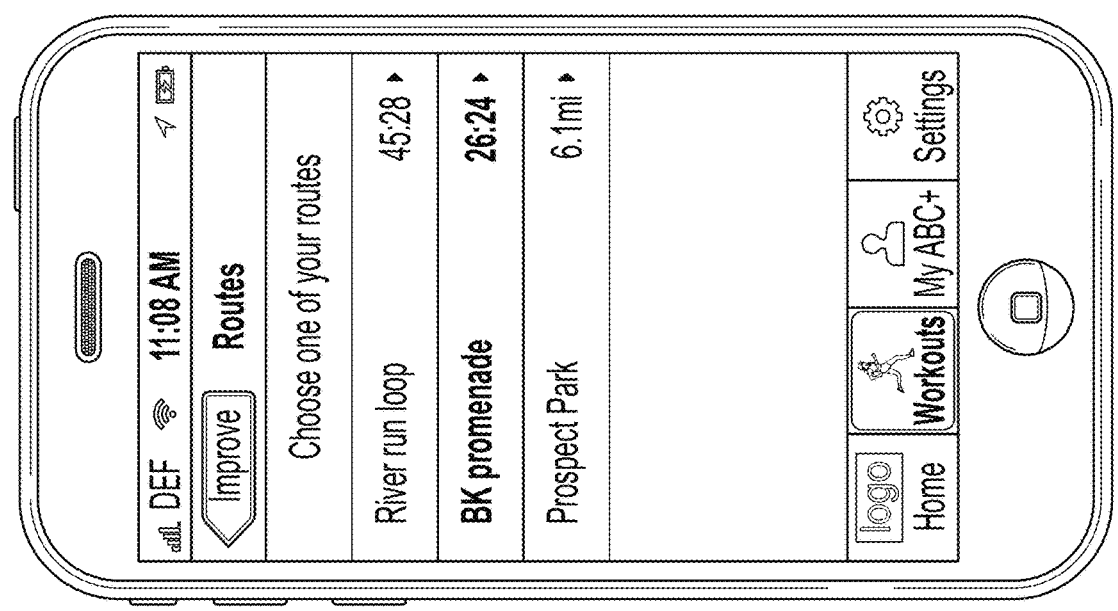
Figure 21B:
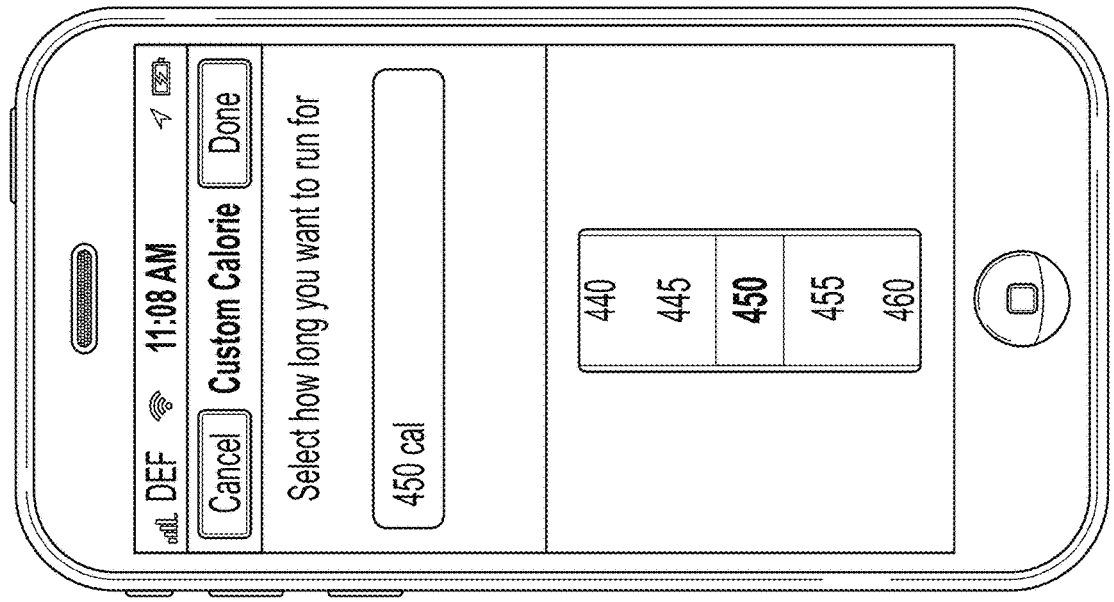
FIGS. 21A-21D illustrate additional example interfaces that may be displayed for setting up a run according to one or more aspects described herein.
Figure 21A:
Figure 21D:
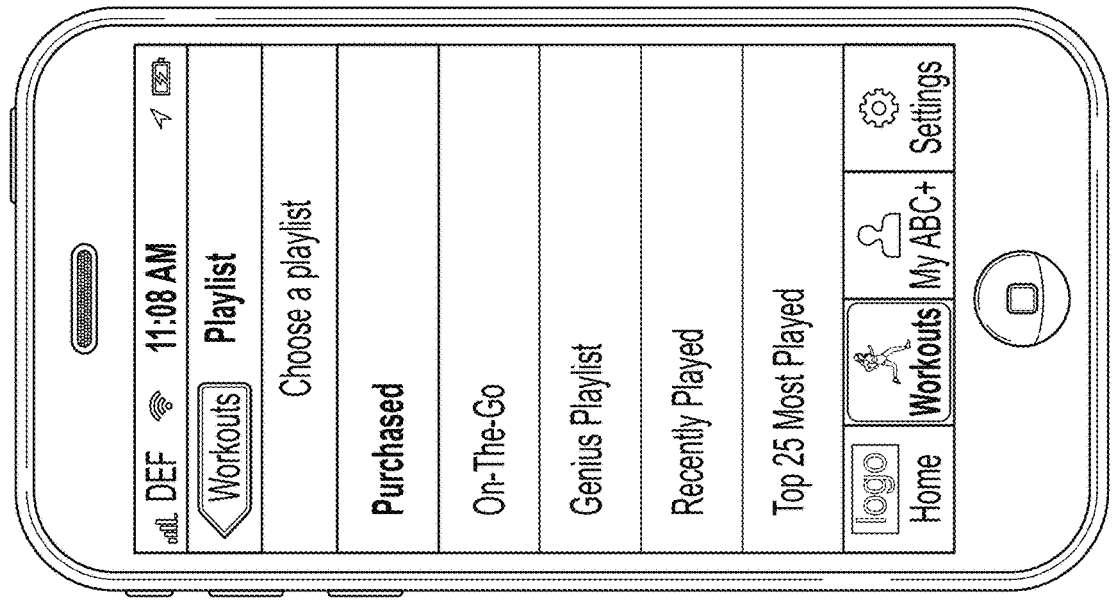
Figure 21C:
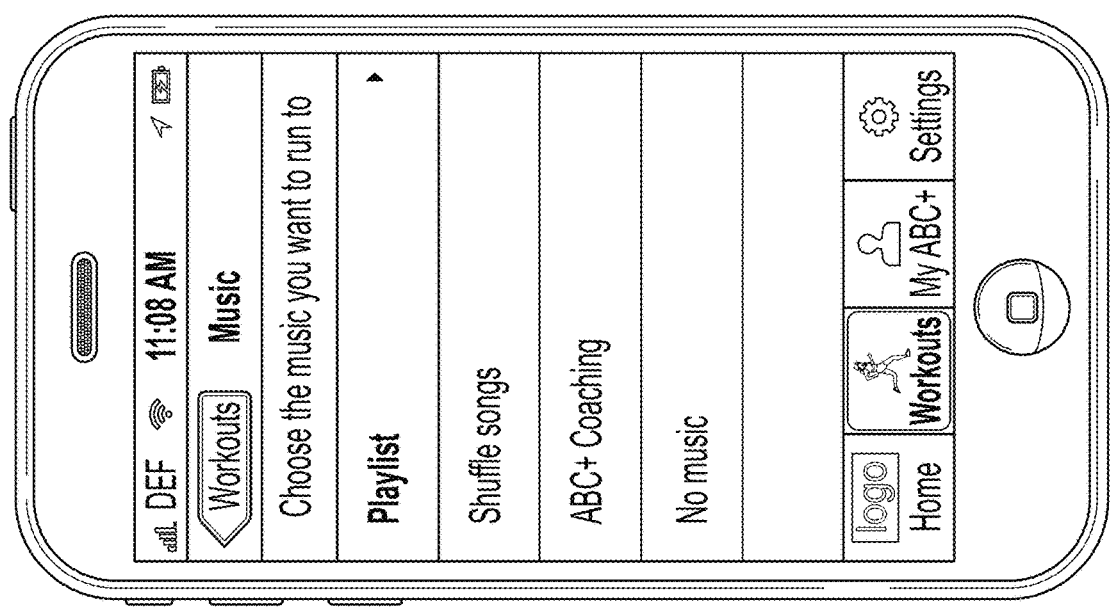

FIGS. 20X and 20Y illustrate interfaces that may be displayed upon a user selecting a route run. A route run may include runs for which a user wishes to select a specific route. The routes may be listed, as shown in FIG. 20Y, with corresponding route information such as a previous run time for the route or the distance of the route. The run time may correspond to fastest time achieved for the route or may be correspond to a most recent time achieved. Other route information may include identification of athletic equipment used for the route, an average, lowest and/or highest pace of the route, a number of users that have run the route and the like.

Mid-Run

Figure 22A:
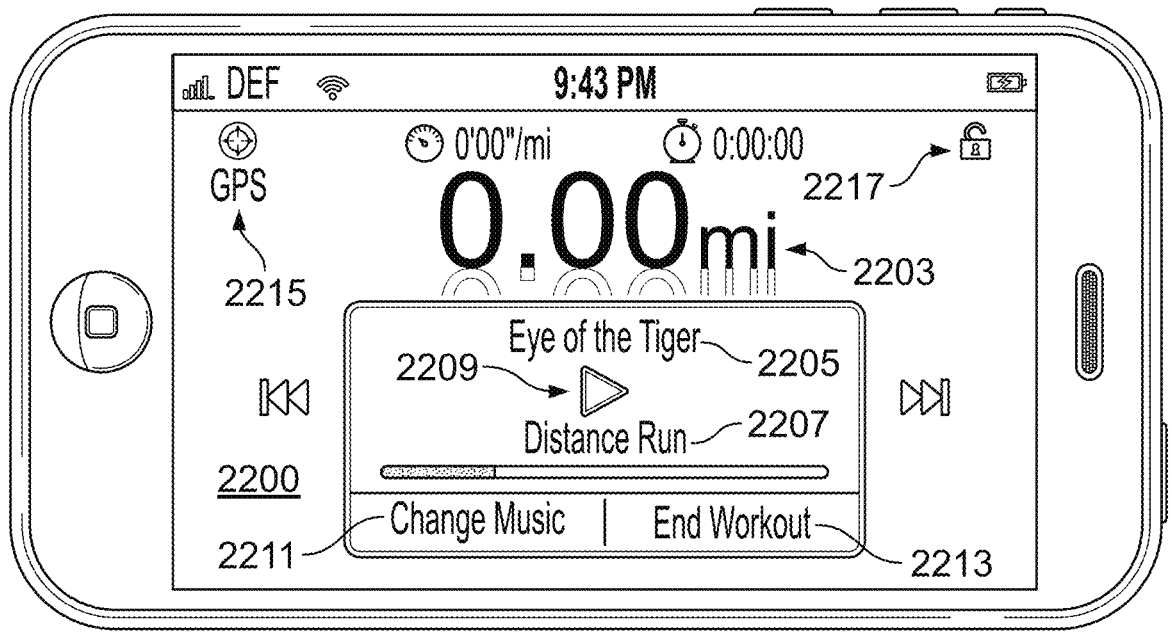
FIGS. 22A-22D illustrate various example interfaces that may be displayed to a user during a user's workout according to one or more aspects described herein.
Figure 22B:
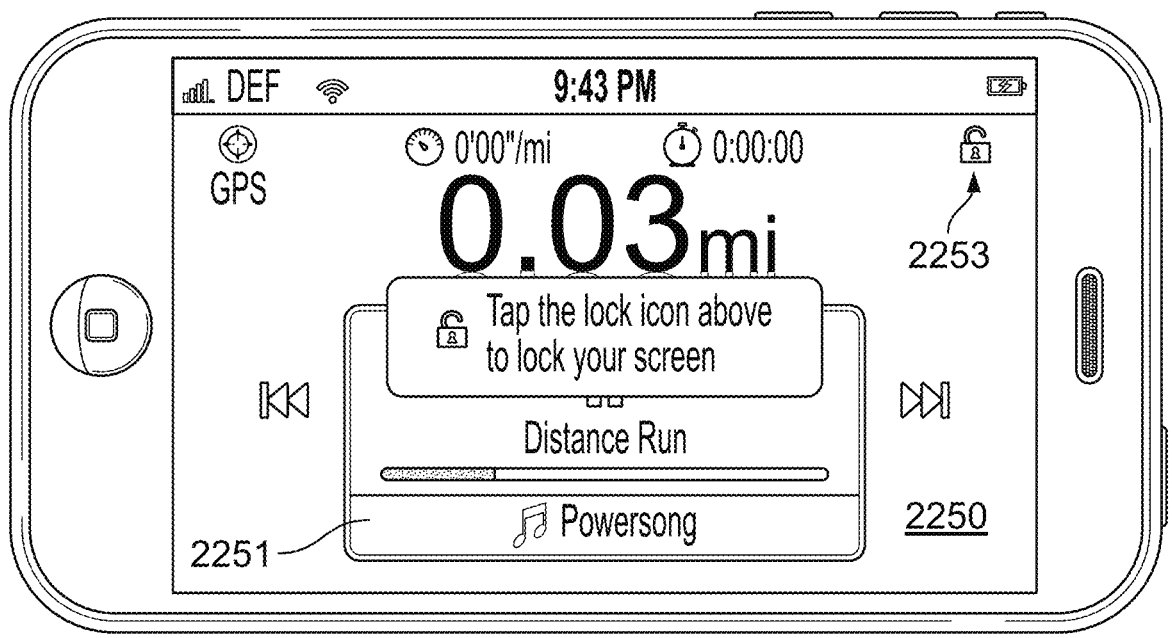
Figure 22D:
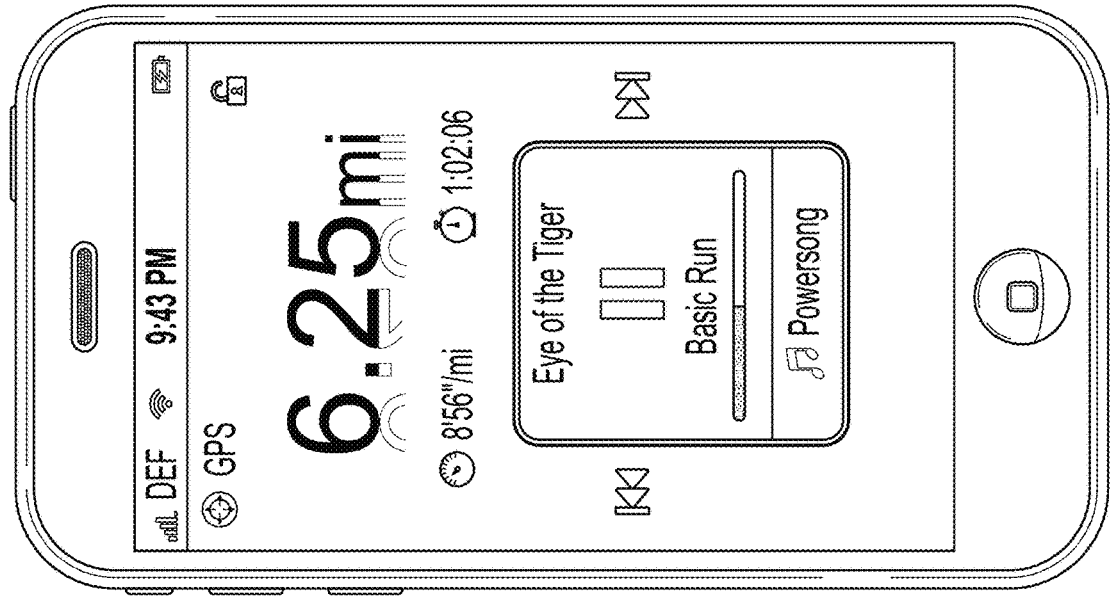
Figure 22C:
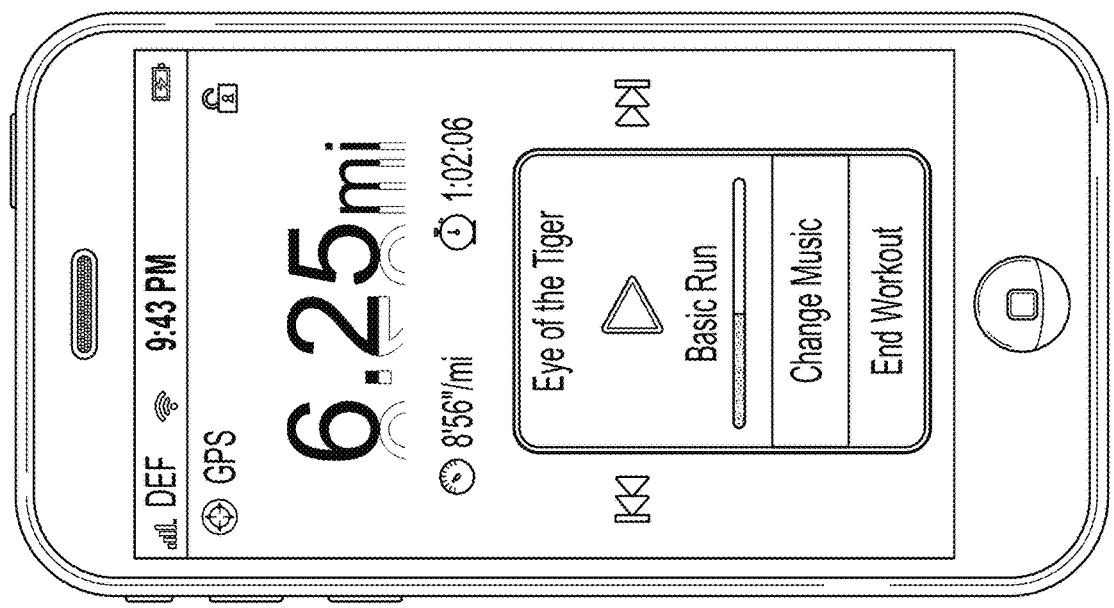

FIGS. 22A-22D illustrate various example interfaces that may be displayed to a user during a user's workout. FIGS. 22A and 22B, for instance, illustrate an in-run interface in a landscape mode while FIGS. 22C and 22D illustrate an in-run interface in a profile mode. In FIGS. 22A and 22C, interface 2200 displays a current workout progress 2203

(e.g., distance, time and pace), the current audio content being played 2205 and the run type 2207 while audio content is paused. Interface 2200 may further include a play option 2209 (e.g., to resume or start playing of audio content). While audio is paused, interface 2200 may provide options 2211 and 2213 to change the music or to end the workout, respectively. 2200 may further provide additional indicators such as a GPS indicator 2215 to identify when GPS information/data is available and a lock indicator 2217 to indicate if the device is locked to input (e.g., to prevent accidental input). In one or more arrangements, a background color or other visual appearance characteristic of one or more visual elements of the interface 2200 may change depending on a current pace, distance, progress toward a goal and the like. In one example, a color or other visual characteristic may change depending on if the user is projected to exceed a goal, if the user is on track to meet the goal and/or if the user is projected to come in short of the goal. For example, a green background may indicate that the user is projected to exceed the goal by a specified amount while yellow may indicate that the user is projected to meet the goal (e.g., reaching the goal but not exceeding the goal by the specified amount). Red may indicate that the user is projected to fall short of the goal.

Interface 2250 in FIGS. 22B and 22D displays progress information while audio content is still playing. Interface 2250 may include information similar to that displayed in interface 2200 of FIGS. 22A and 22C, but, instead of displaying a change music option and an end workout option, interface 2250 may include a powersong option 2251. Powersong option 2251 allows the user to activate a song that he or she may find particularly motivating. Thus, if the user feels that he or she is slowing down or, alternatively, that they have a lot of energy, the user may activate the power song to maximize performance during that segment of the workout. In one or more arrangements, interface 2250 may include an instructional message advising the user on how to lock the interface to prevent accidental input. The message may include, for example, tapping or otherwise interacting with lock indicator 2253.

In some arrangements, no power song may have been selected or be available. Accordingly, the interface might not provide a power song option. FIGS. 23A and 23B illustrate example in-run interfaces displaying workout information without a power song option.

Figure 24B:
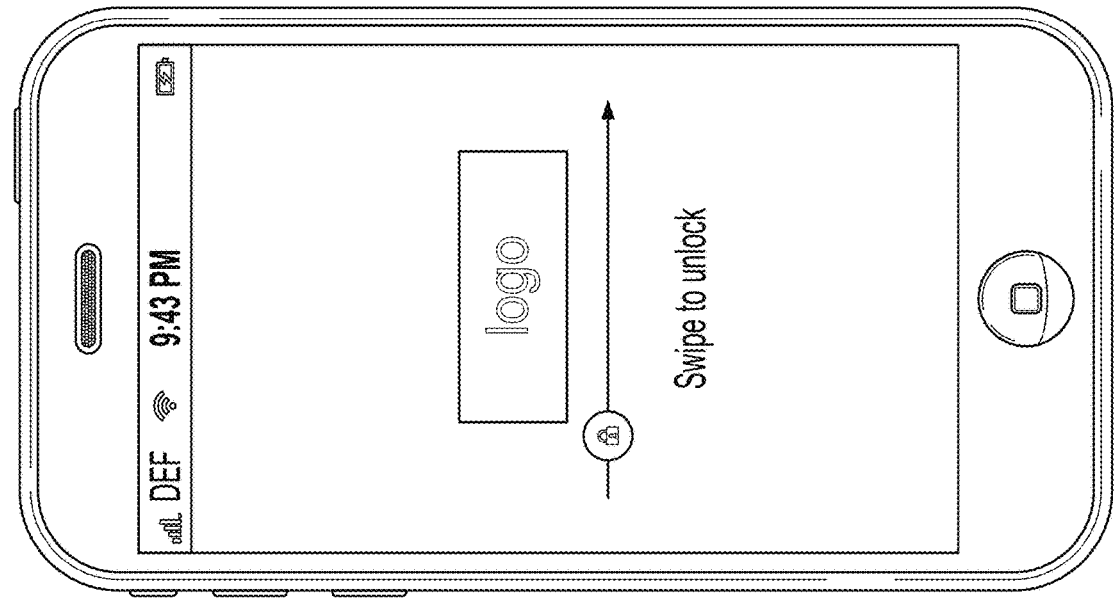
FIGS. 24A-24F illustrate example lock interfaces that may be displayed upon the user locking the interface (e.g., to prevent input) or upon the expiration of a time period during which no user input is detected according to one or more aspects described herein.
Figure 24A:
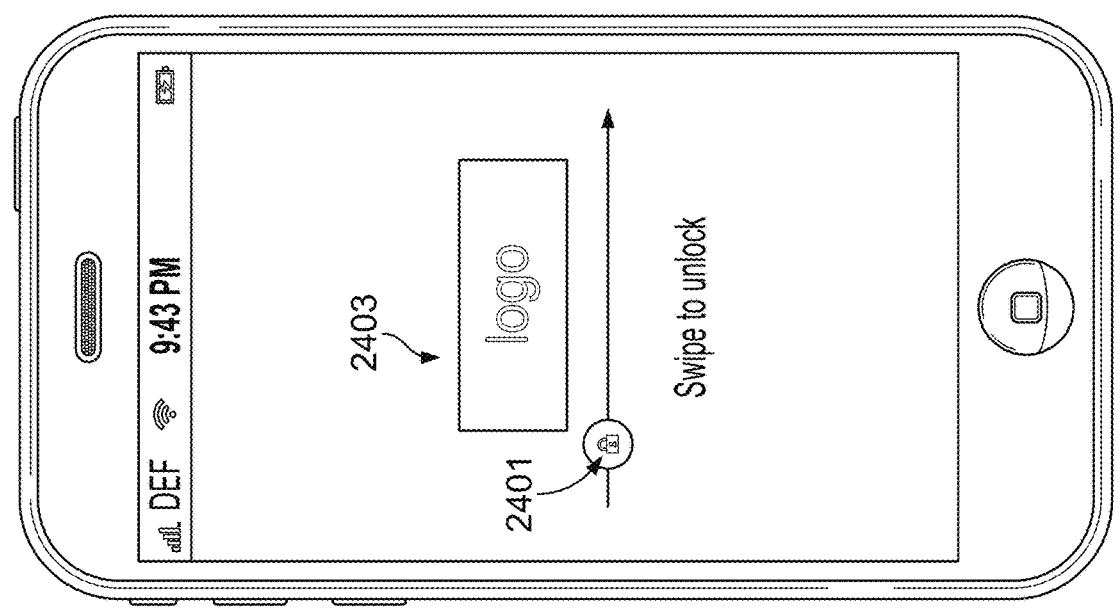
Figure 24D:
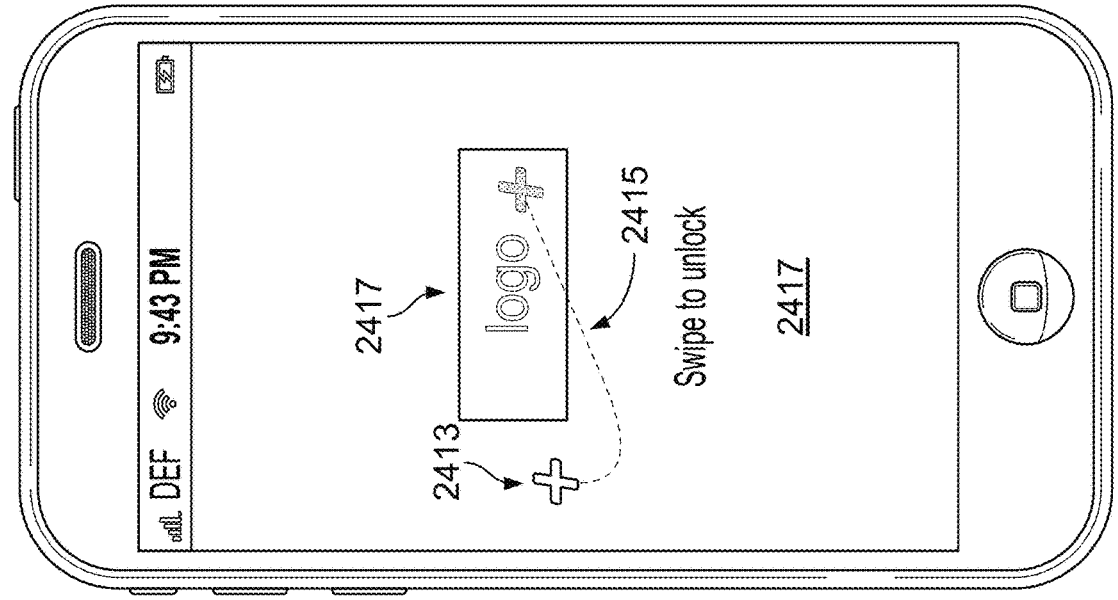
Figure 24C:
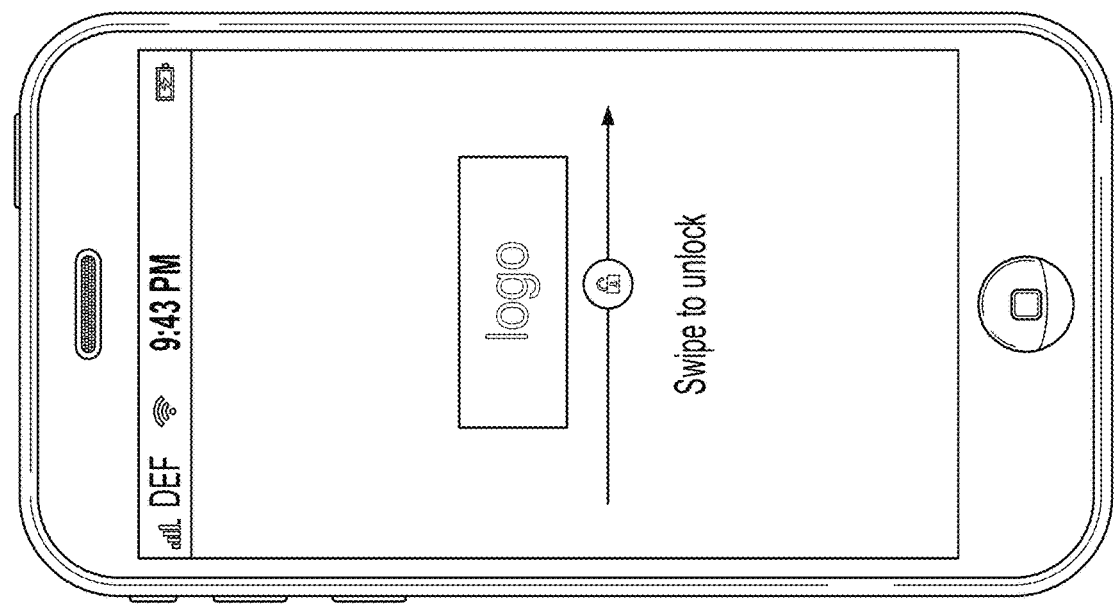
Figure 24F:
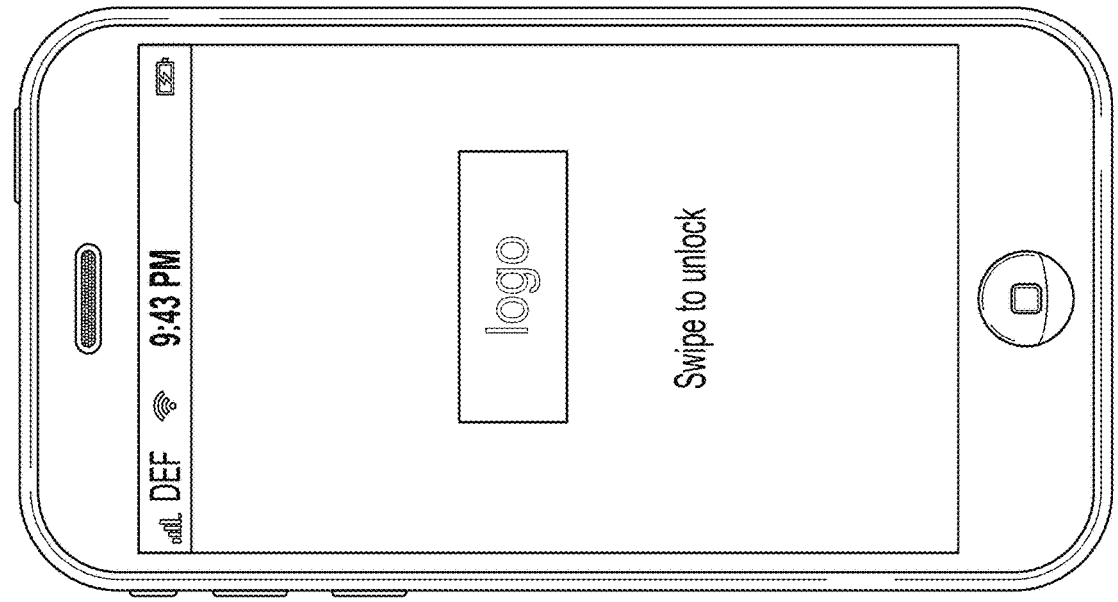
Figure 24E:
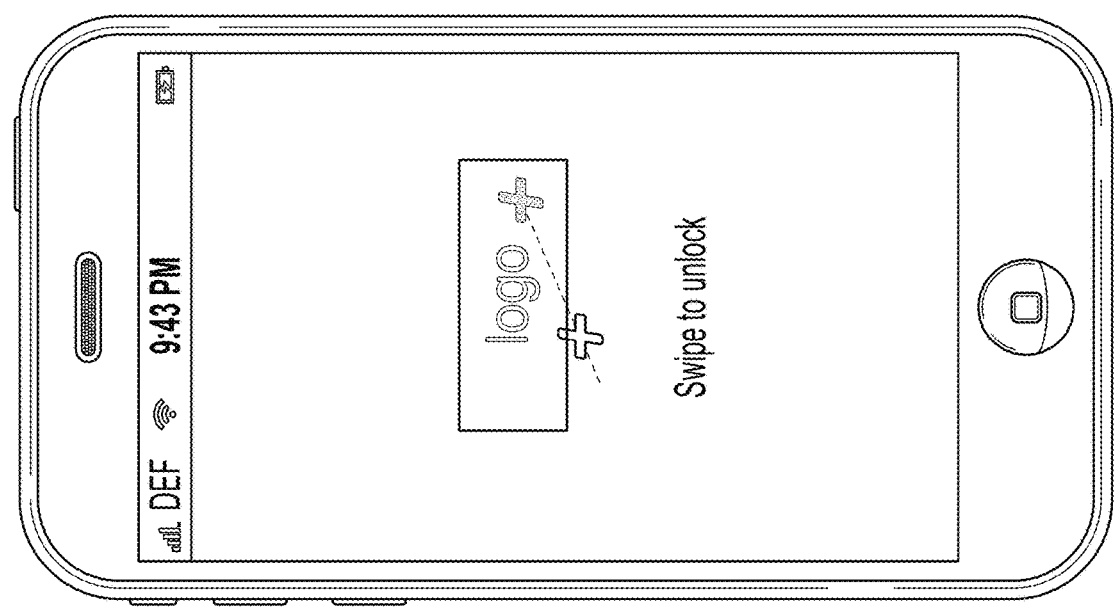

FIG. 24A-24F illustrate example lock interfaces that may be displayed upon the user locking the interface (e.g., to prevent input) or upon the expiration of a time period during which no user input is detected. For example, FIGS. 24A-24C illustrate that a user may unlock the interface by moving a lock symbol 2401 from a left position to a right position. The unlock progress may be indicated by not only the position of symbol 2401 but also by the filling of an outlined image such as image 2403. That is, the device may be unlocked for receiving input upon image 2403 being completely filled. Filling image 2403 may be accomplished by moving symbol 2401 from the left position to a right position. Various different motions, patterns and images may be used for unlocking the device. For example, FIGS. 24D-24F illustrate interface 2410 where the unlock symbol is represented by a plus sign 2413 and where the user must move symbol 2413 along a curved check mark path from 2415. The movement path may correspond to a shape or appearance of the image (e.g., image 2417) or portion thereof.

In some embodiments, the lock icons or images may be predefined and selectable from a menu of lock icons or images. For example, available lock icons and images may be downloaded from an on-line site. Accordingly, a user may customize the lock icon or image used during the workout training application. Additionally, in some examples, the lock icon or image used for the training application may differ from the lock icon or image used when the application is not being used on the device.

Figure 25B:
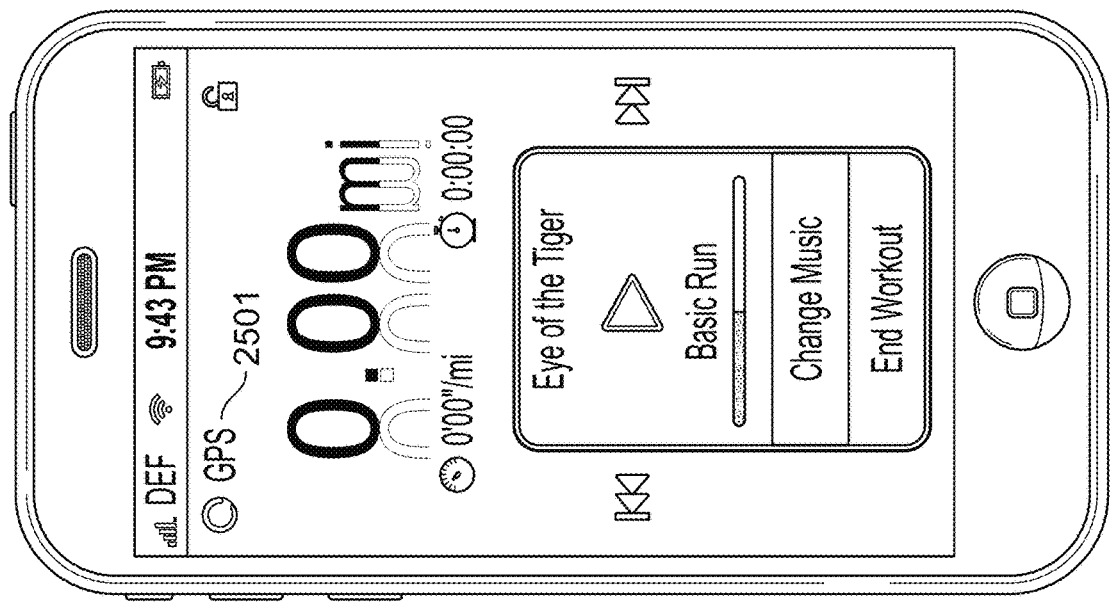
FIGS. 25A-25F illustrate various example user interfaces that may be used to convey a GPS availability and status according to one or more aspects described herein.
Figure 25A:

Figure 25D:
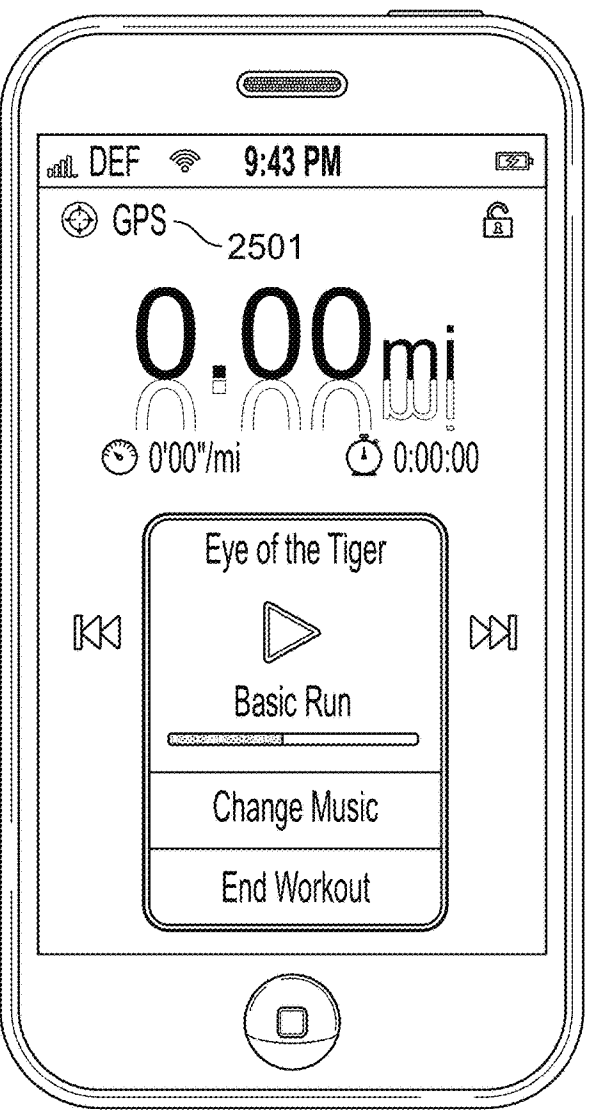
Figure 25C:
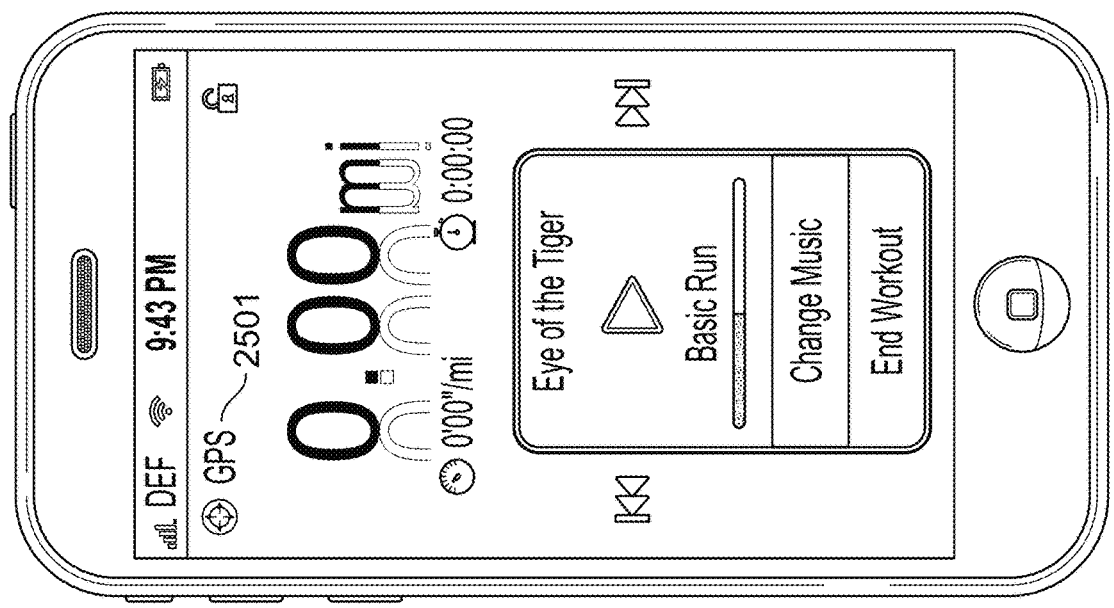

FIGS. 25A-25E illustrate various example user interfaces that may be used to convey a GPS availability and status. For example, FIG. 25A illustrates GPS indicator 2501 in a signal searching mode. FIG. 25B illustrates GPS indicator 2501 if no signal is available or detected. In particular, an outer ring of the GPS indicator 2501 may be displayed in a first state (e.g., as an outline or substantially transparent). FIGS. 25C and 25D illustrates GPS indicator 2501 in second and third states indicating a weak and a strong signal, respectively. The signal strength may be represented by various aspects of indicator 2501 including a transparency level (e.g., more transparent when signal is weaker), a color, a pattern, an animation (e.g., rotating, flashing, fading in and out, etc.) and/or combinations thereof.

In one or more arrangements, if the GPS signal is weak, a message may be displayed notifying the user of the same. For example, interface 2520 of FIG. 25E displays message 2521 that indicates the GPS signal is weak and that the time and distance of the run may still be tracked. For example, instead of using GPS data when it is unavailable, the device may activate and/or begin recording accelerometer data. In one or more arrangements, use of an accelerometer or other sensor (e.g., cellular triangulation) may also be indicated visually in an interface (e.g., using an icon, word, or the like).

Figure 25F:
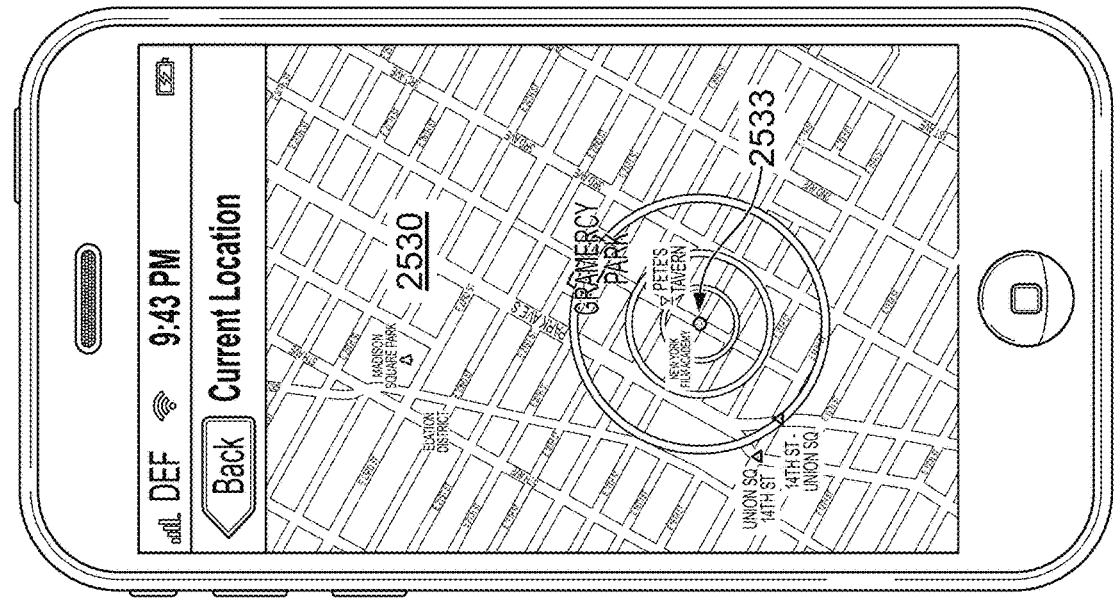
Figure 25E:
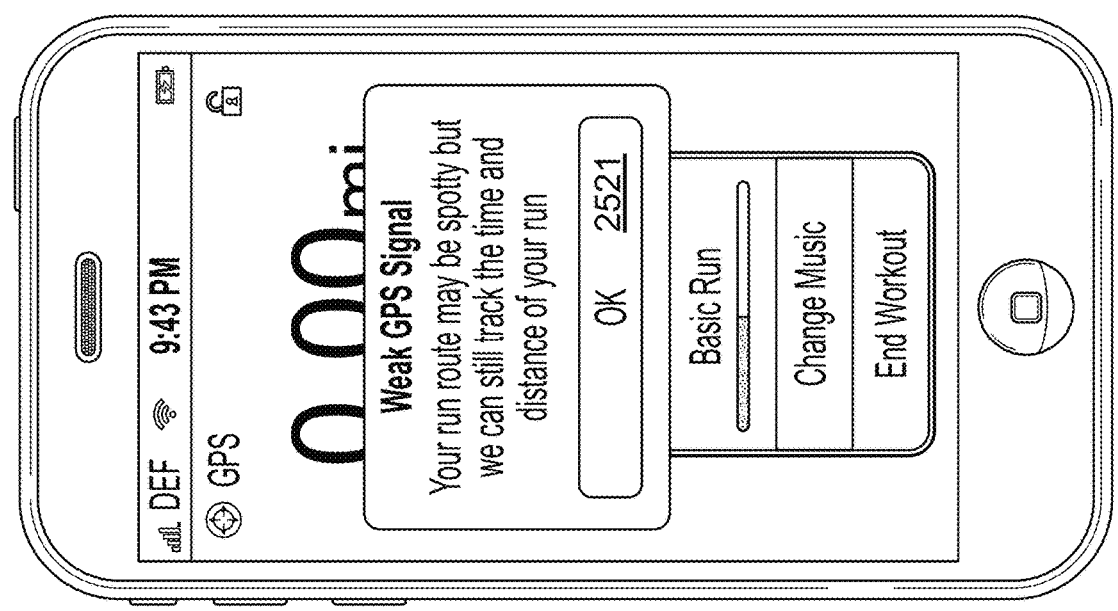

Additionally, a user may select GPS indicator 2501 of FIGS. 25A-25D to view a map identifying the user's current location. Other options or indicators may also be displayed for allowing the user to access the map mode. FIG. 25F illustrates map 2530 with the user's location identified by indicator 2533.

Figure 26B:
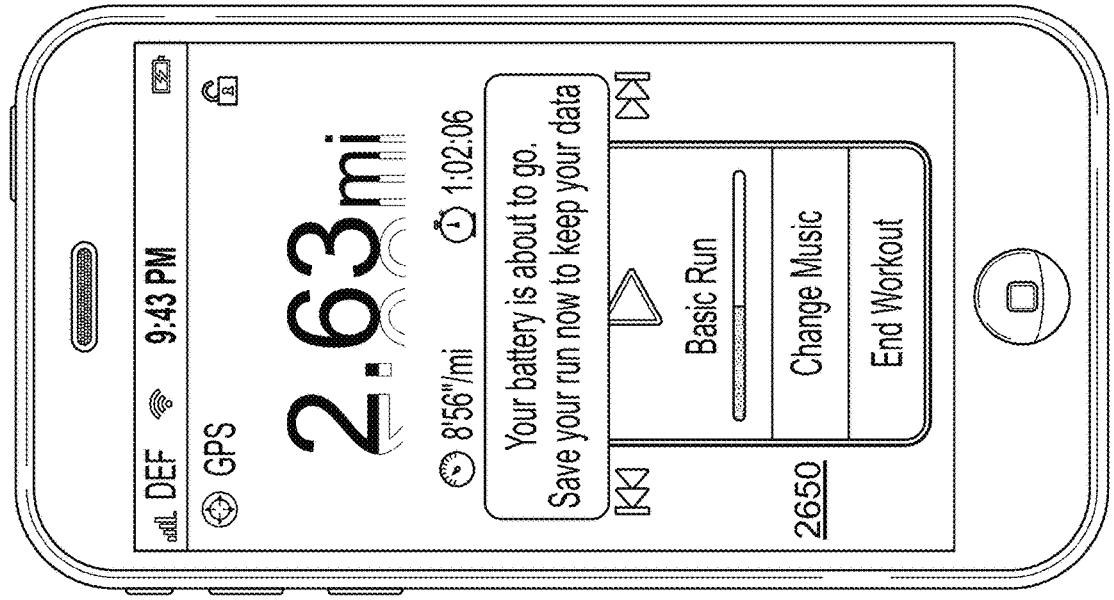
FIGS. 26A and 26B illustrate example alerts that may be provided to the user according to one or more aspects described herein.
Figure 26A:
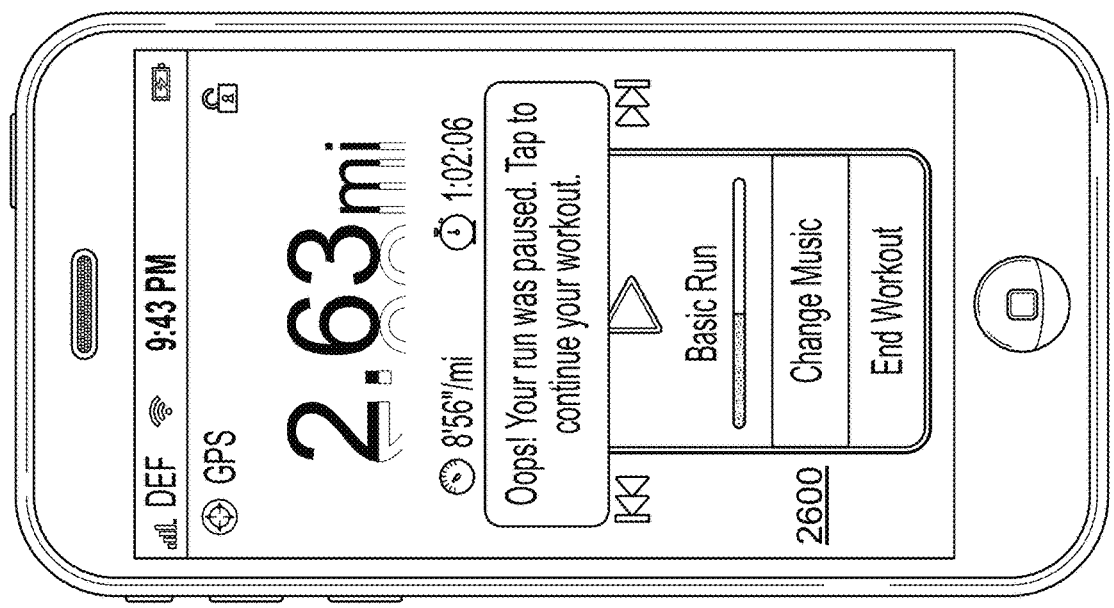

A user may be provided with various alerts during the run upon detection of various events. For example, in interface 2600 of FIG. 26A, the user may be provided with a message indicating that the run was paused. The message may further include instructions on how to resume the workout (e.g., tap to resume). In another example, interface 2650 of FIG. 26B may display a message upon detecting that the battery is about to run out. The message may advise the user to save the workout prior to the battery being depleted. The message may be displayed when the battery is projected to become depleted in a specified amount of time, e.g., 5 minutes, 10 minutes, 15 minutes, 30 seconds, etc.

Figure 27C:
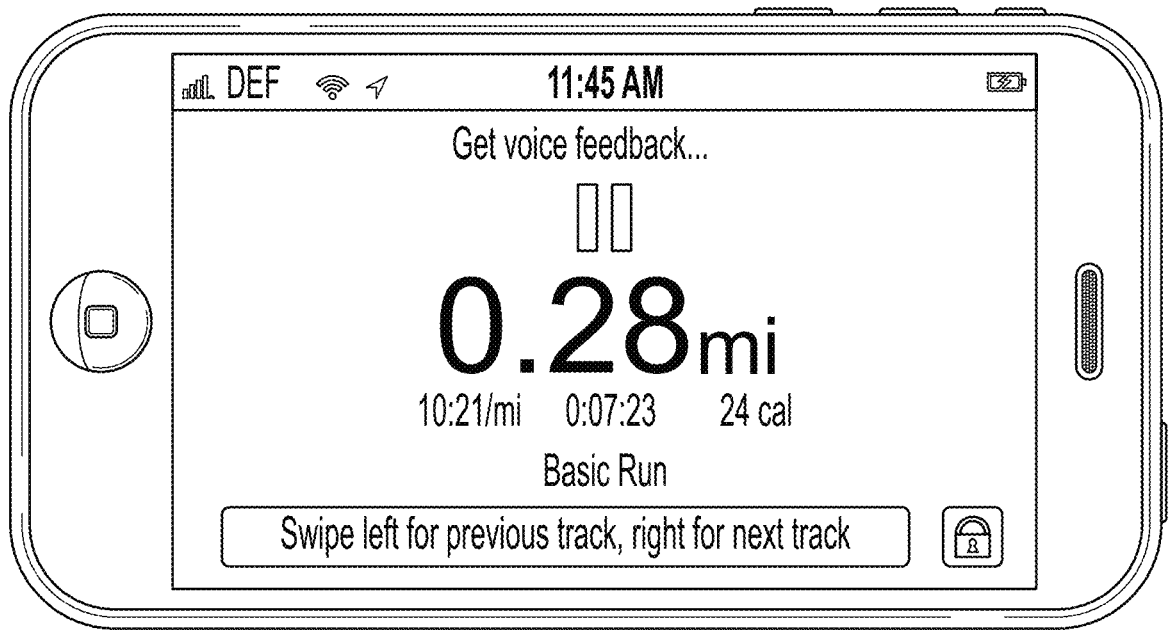
Figure 27D:
Figure 27F:
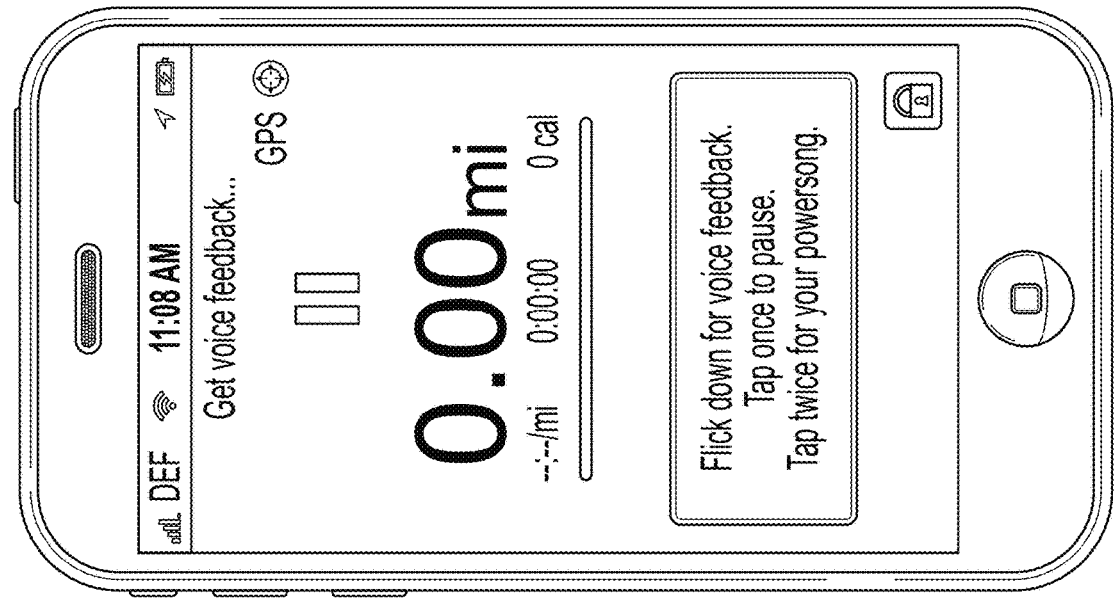
Figure 27E:
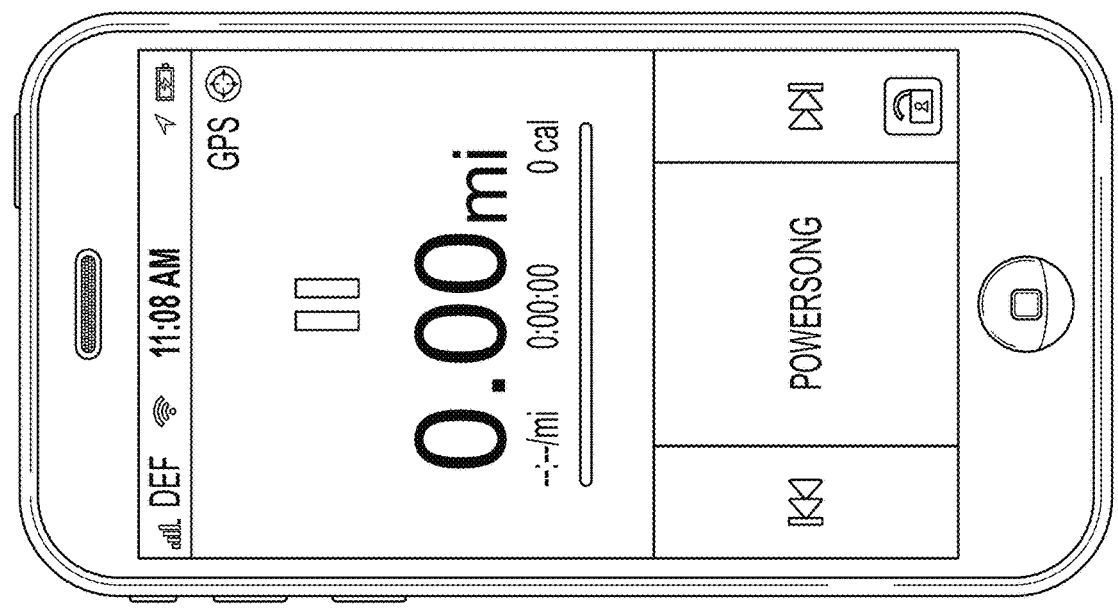
Figure 27H:
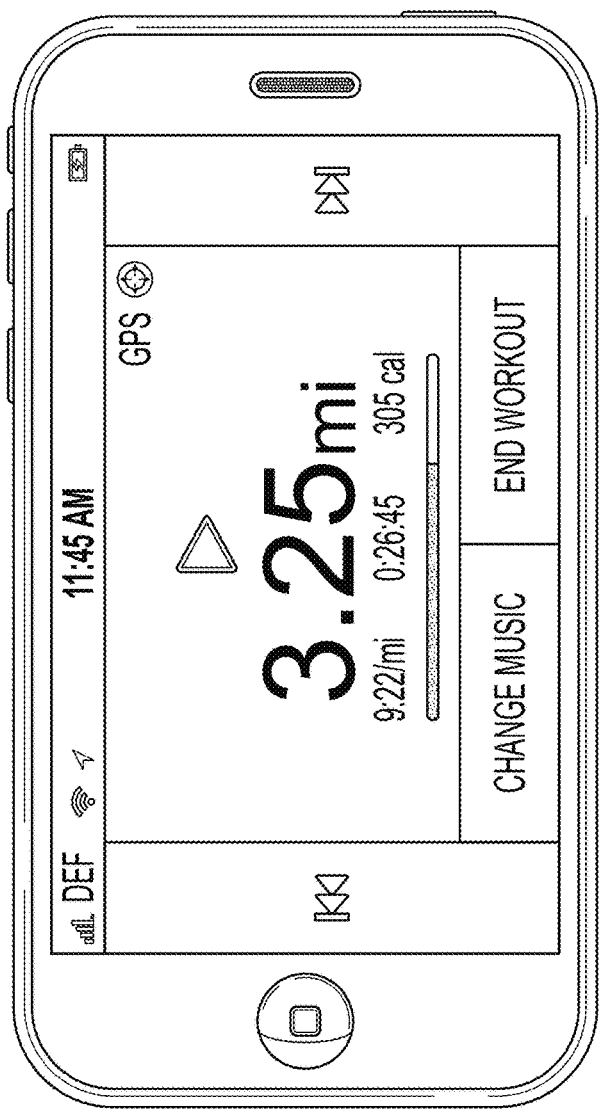

FIGS. 27A-27H illustrate additional or alternative user interfaces that may be displayed while a user is conducting a run. For example, FIG. 27C illustrates an interface displaying a notification message providing instructions for deactivating buttons and activating gesture commands. Gestures may include touch-sensitive motions that correspond to various commands. For example, swiping a user's finger to the right may be used to progress to a previous audio content item and to the left to progress to a next audio content item. In another example, a user may flick or swipe downwards (e.g., in relation to the orientation of the device) to receive voice feedback. Voice feedback may include a vocalization of a current amount of progress (e.g., a distance currently run, an amount of time, a pace, calories burned). Further, tapping once may correspond to pausing the run and/or audio content while tapping twice may automatically activate a power song. Accordingly, the user might not need to view the display to control the device. Additionally, no information including visible options and buttons might need to be displayed for the user to appropriate adjust the functionality and features of the application and device.

Figure 27G:
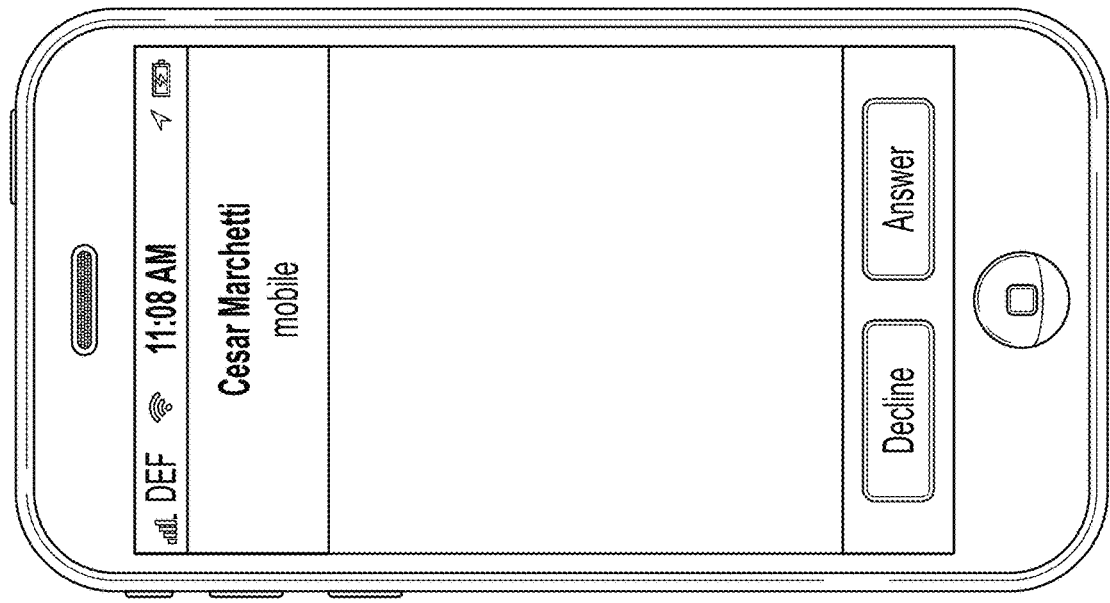

In FIG. 27G, an interface is displayed for when a user receives a voice call during the workout. The interface may be automatically displayed, replacing the in-run workout interface as displayed in FIGS. 27C and 27D. If the user answers the call, the workout and playing of audio content may be automatically paused. Alternatively, if the user declines the call the workout may automatically be continued without interruption (e.g., the interface of FIGS. 27C and 27D may be displayed once more).

In addition to the selected audio content, the fitness monitoring device and application may play other audio content configured to encourage or notify the users of certain events or situations. For example, various sounds such as trumpets, applause, fireworks or other generally encouraging audio may be played when the user reaches certain milestones or goals such as completing each mile, running 1K, setting a new fastest pace for a specified distance and the like. In other examples, the user may be provided with encouraging or instructional messages such as "You are 5 seconds behind target pace. Speed it up" or "You are 20 seconds ahead of target pace. Keep it up." Other messages may include "You're halfway to your goal and you're running [ahead of/behind] target pace" and "You're almost there. I'm wondering if you can run the length of one extra song? Double tap to accept!" In this latter example, the user may be challenged to further improve on the run during the run. The user may accept the challenge, at which time the workout may be automatically extended in accordance with the challenge (e.g., extending the run for 1 more song).

Figure 28B:
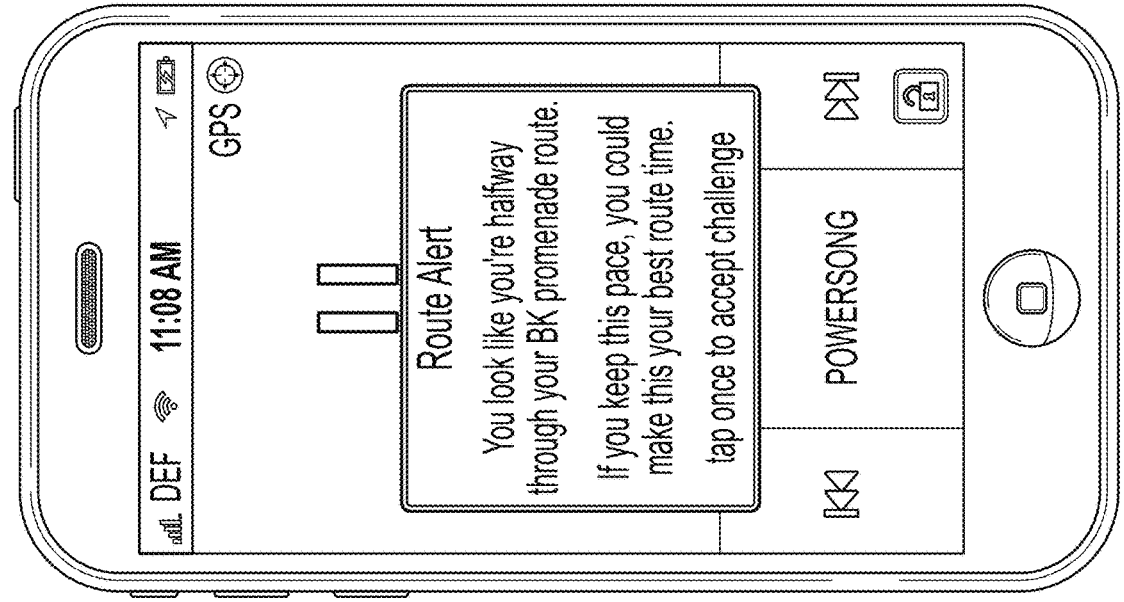
FIGS. 28A and 28B illustrate additional example alerts that may be textual in nature and may be accompanied by corresponding audio messages according to one or more aspects described herein.
Figure 28A:
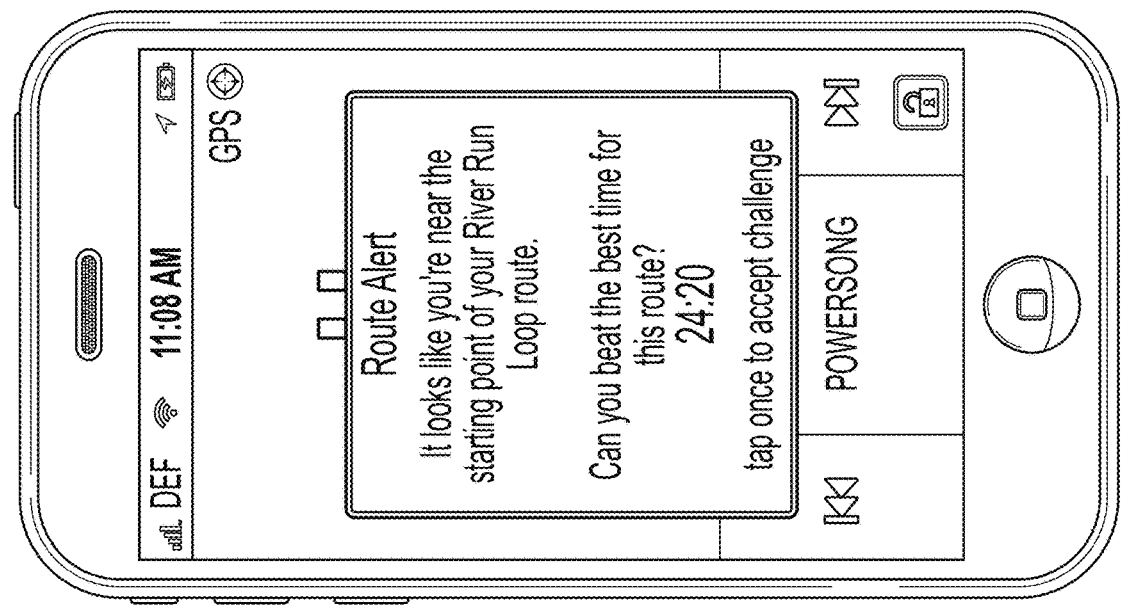

FIGS. 28A and 28B illustrate further alerts that may be textual in nature and may be accompanied by corresponding audio messages. For example, in the interface of FIG. 28A, the user is presented with an alert challenging him or her to beat the best time for a particular route (e.g., if the route was run before). In the interface of FIG. 28B, the user may be provided with a challenge alert to keep up a current pace to achieve a best route time. In each case, various types of gestures or other interactions may be used to accept the challenge. These interactions may include tapping the screen of the device, making a gesture, speaking a voice command, pressing a physical button on the device and the like.

Audio messages may also provide advice or warnings. For example, a message may indicate that there is a hill coming up on the route (e.g., within 0.25 miles, within 0.5 miles, etc.).

Additionally, the device may provide in-run tips to help the user achieve a specified goal. The tips or information may include, for instance, advising the user to start off slow for a predefined amount of time and to accelerate over the course of a second amount of time to a desired or goal pace. As described, the tips and advice may be provided by real-life athletes and/or other fitness celebrities. In some arrangements, the tips and advice may be location-specific. For example, the mobile device may detect other users running on the route based on GPS information and provide an indication of how the user is performing relative to the other users. In other examples, the mobile device may provide information about landmarks, terrain, weather, inclines and the like. In a particular example, a user may be provided advice about a portion of a route a predefined amount of time prior to reaching that portion of the route. The system may calculate an amount of time prior to the user reaching the portion of the route based on a current pace and distance.

In another example or arrangement, location-specific information may be provided to the user during the run. For example, based on a GPS or other location determination system signal, an athletic monitoring device may determine that a landmark or point of interest is about to be passed. The device may thus retrieve audio or video information associated with the landmark or point of interest and provide the information to the user during the run and, in some cases, as the user passes the point of interest. For example, the timing of rendering the audio and video information may be determined based on the user's current detected pace and a distance from the point of interest.

Post-Run

After a user completes his or her run, the user may be presented with a workout summary. Additionally, the device may select, generate and/or display words of encouragement or indications that the user has reached a goal or milestone. For example, a user may receive accolades or motivational messages when the user has recorded his or her longest run (duration or distance) or fastest run (e.g., for a 1K, 10K or other predefined distance). The message may be textual in nature, include audio output, provide haptic feedback and/or combinations thereof. Workout summaries may include different information or options depending on the location of the workout (e.g., indoors or outdoors). For example, a workout summary for an indoor workout may include a calibration function to insure accuracy of the data recorded while an outdoor workout summary might not include the calibration function. The difference in workout summary functionality may be attributable to the accuracy with which a GPS device is able to track distance and/or pace.

Figure 29:
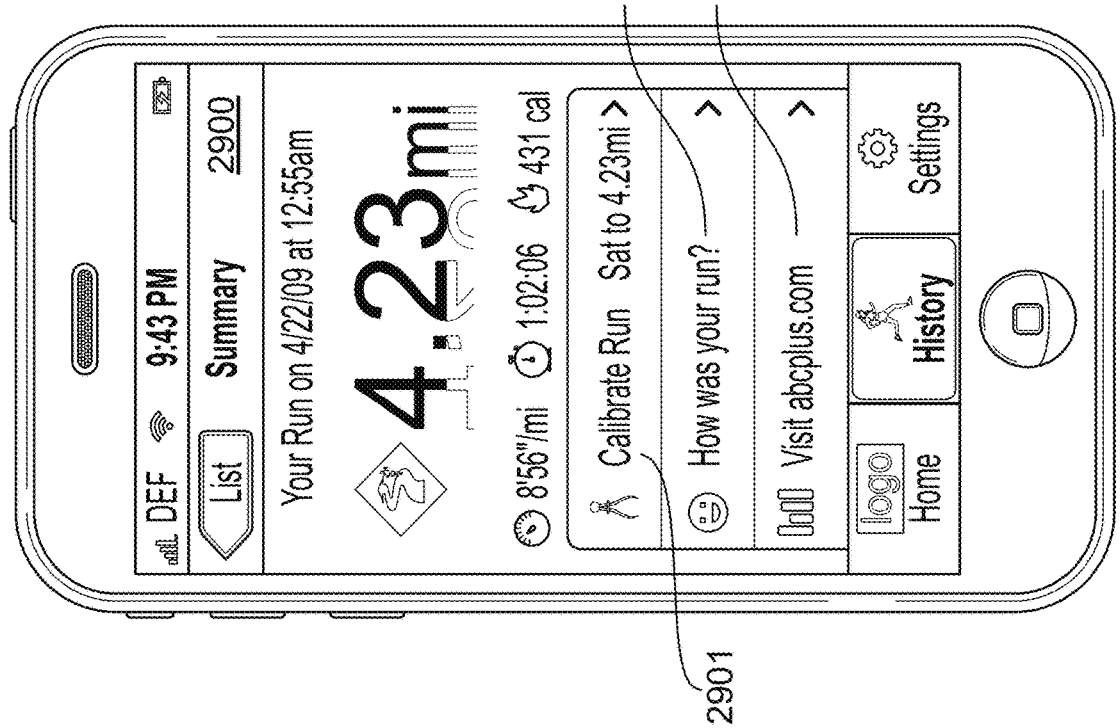
FIG. 29 illustrates an example workout summary for an indoor run according to one or more aspects described herein.

FIG. 29 illustrates a workout summary for an indoor run. In addition to run statistics such as a distance run, pace, time and calories burned, interface 2900 includes a calibrate run option 2901, a mood tagging option 2903 and a service provider site option 2905. Selection of calibrate run option 2901 may allow the user to insure that the recorded statistics of the run is accurate. For example, if the device determines that the user has run 4 miles, but the user actually ran 4.25 miles, the user may adjust the amount through the calibration option 2901.

Figure 30A:
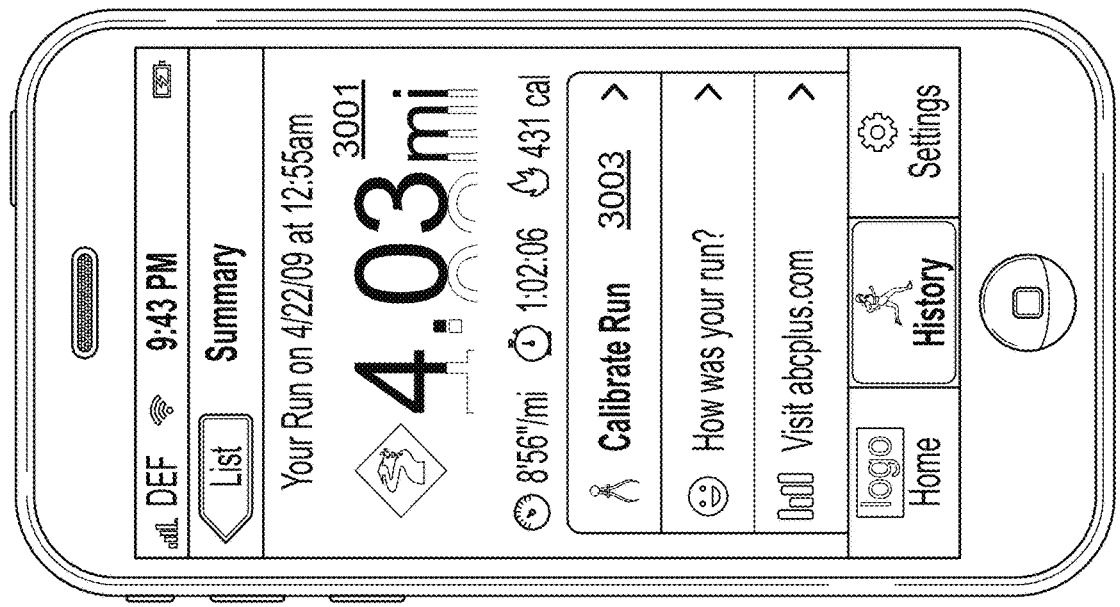
FIGS. 30A-30C illustrate a sequence of example user interfaces in which a user may calibrate the distance run according to one or more aspects described herein.
Figure 30C:
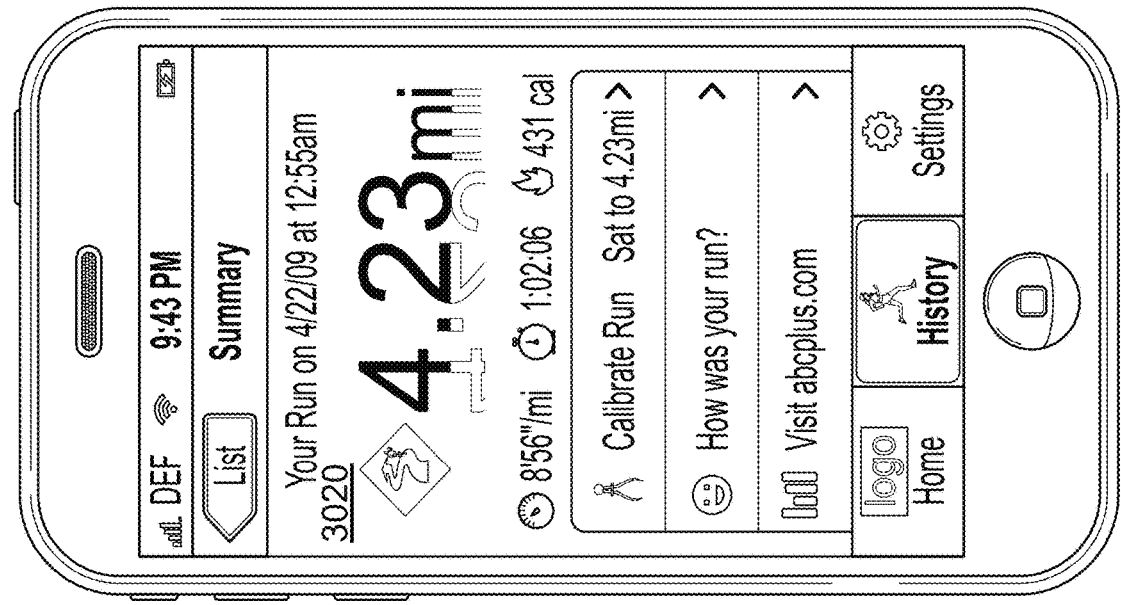
Figure 30B:
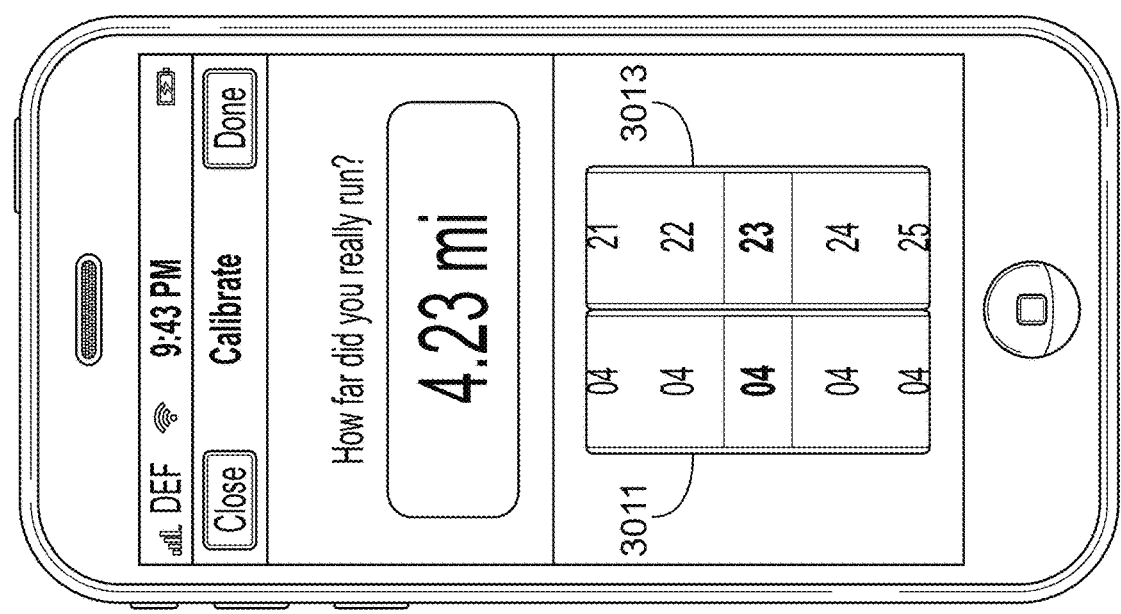

FIGS. 30A-30C illustrate a sequence of user interfaces in which a user may calibrate the distance run. In interface 3001 of FIG. 30A, for example, the workout summary indicates the device detected a total of 4.03 miles run by the user. If the value is not accurate, the user may select calibrate option 3003. FIG. 30B illustrates calibration interface 3010 in which a user may select the number of miles actually run using scroll wheels 3011 and 3013. Once the user has finalized the calibration, the user may return to a workout summary interface such as interface 3020 of FIG. 30C. Interface 3020 may then include the calibrated distance instead of the original distance detected by the device.

Figure 31B:
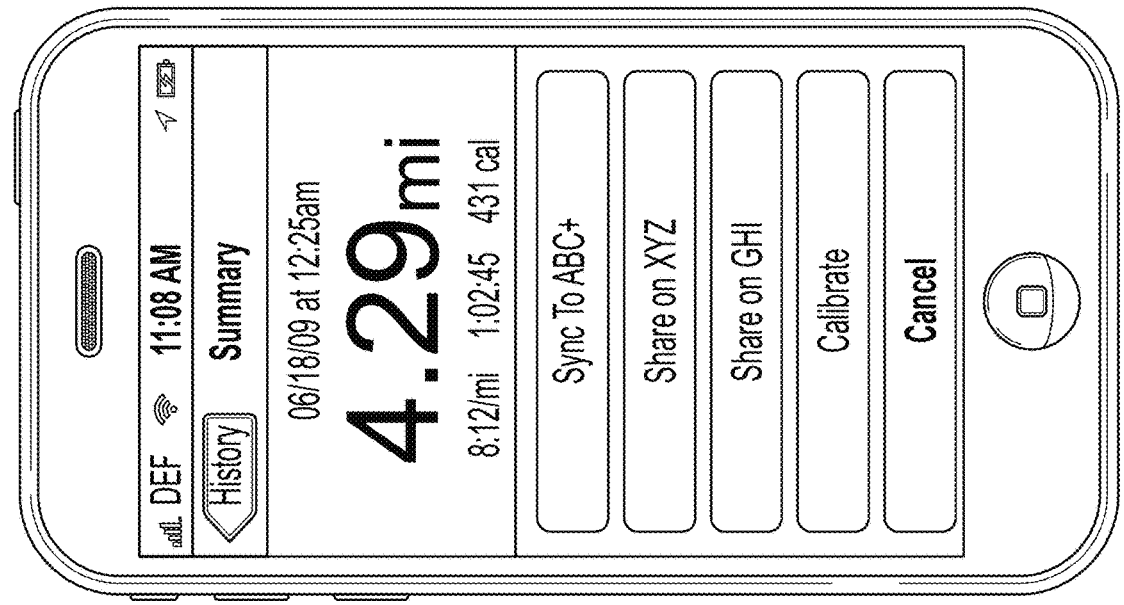
FIGS. 31A-31C illustrate further example interfaces through which the user may calibrate an accelerometer or non-GPS runs according to one or more aspects described herein.
Figure 31A:
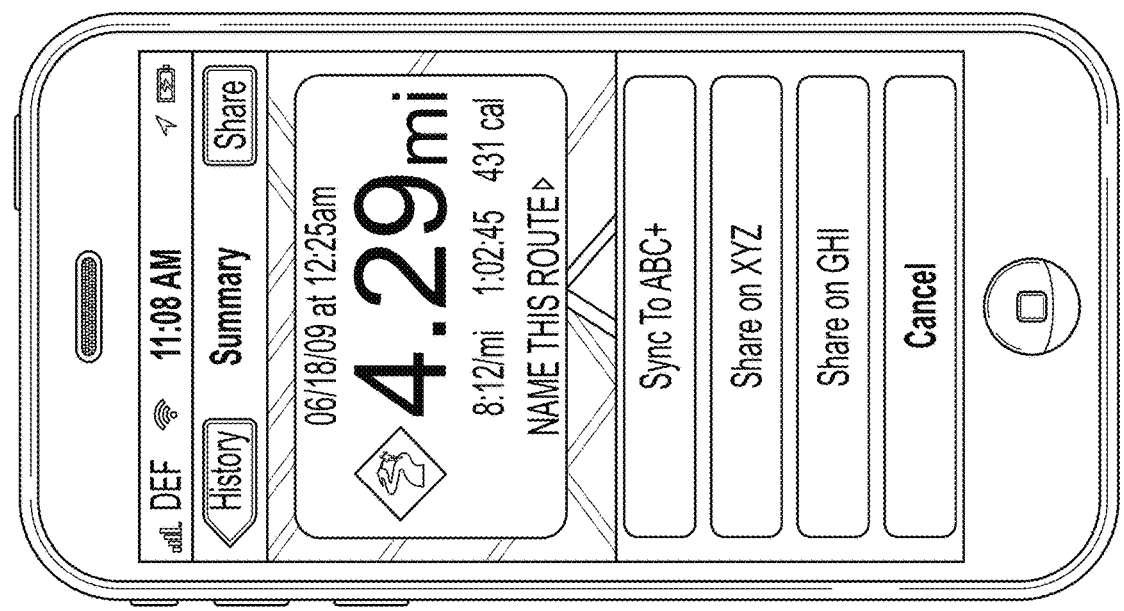
Figure 31C:
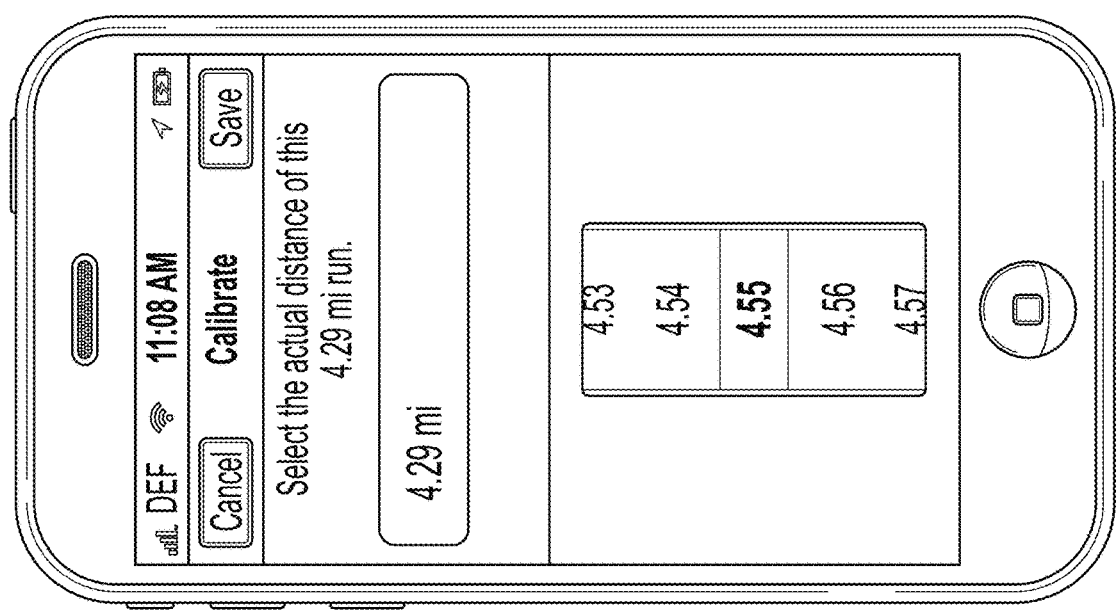

FIGS. 31A-31C illustrate additional example interfaces through which the user may calibrate an accelerometer or non-GPS runs.

FIGS. 32A-32D illustrate example user interfaces through which a user may tag a run based with various types of information and parameters include location-specific attributes. For example, in interface 3201 of FIG. 32B, a user may specify how he or she felt after the run by choosing a mood indicator 3203, weather conditions during run by choosing weather options 3205, a terrain type by selecting a terrain option 3207 and enter notes in notes section 3209.

Weather may be tagged automatically in some instances using GPS functionality. That is, a mobile device may automatically retrieve the weather of a given location detected using a GPS device and tag the workout using the retrieved weather data. Terrain option 3207 may include exercise equipment such as a treadmill, outdoor terrains such as straight road, a dirt path, a winding road and the like. Terrain might also be automatically registered based on the GPS information received. In some instances, the user might not be required to enter any of the tags. While some of the tags may be automatically registered or inputted, the user may be allowed to edit the entries. Thus, the user may tag one, two, or all of the tagging options 3203-3209 as he or she desires.

Figure 32A:
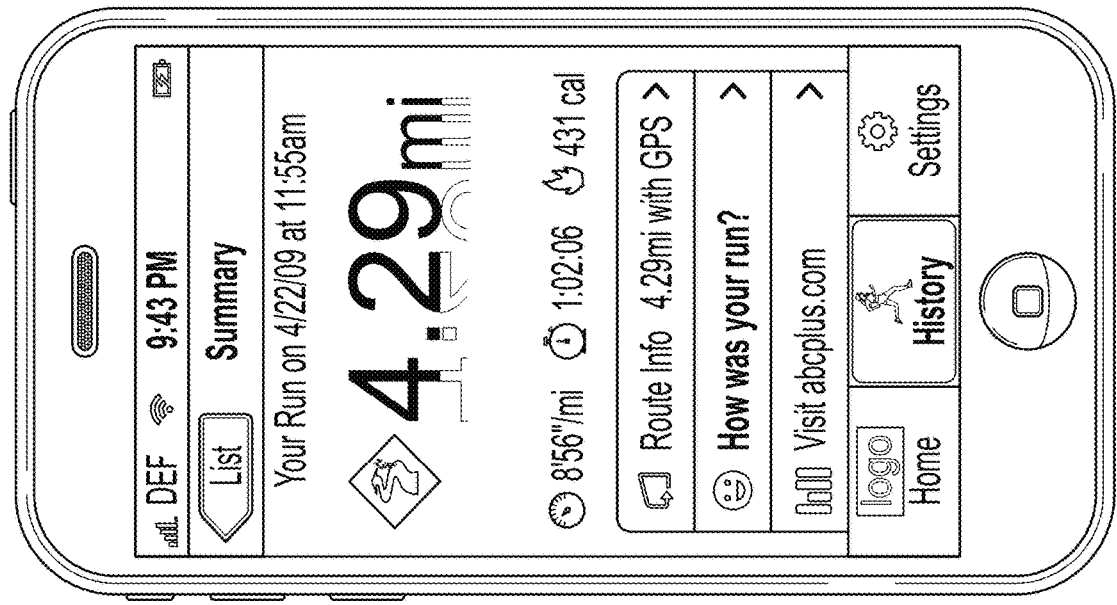
FIGS. 32A-32D illustrate an example series of user interfaces through which a user may tag the run based with various types of information according to one or more aspects described herein.
Figure 32C:
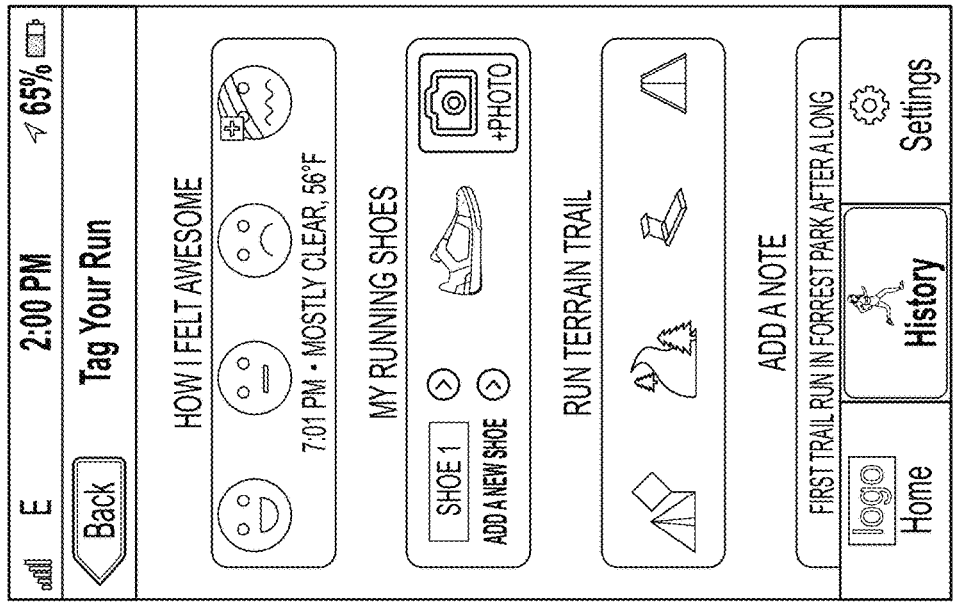
Figure 32B:
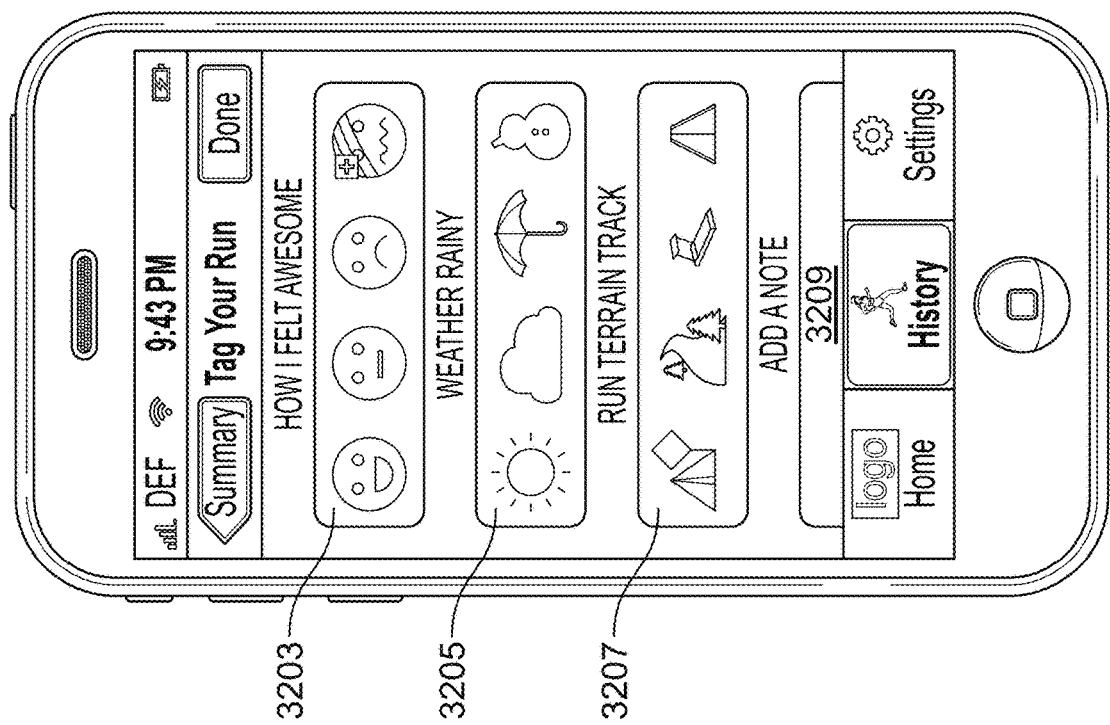

Other tags may also be used and users may define their own customized tags as well. In FIG. 32C, for example, a user may be allowed to select an athletic equipment tag to indicate the type of athletic equipment used or worn during the workout. In a particular example, the user may identify a type of shoe or specific pair of shoes worn during a run. Specific shoes may be defined by the user and stored to the device or a remote system. The tagging of athletic equipment may allow the application, device or remote system to track wear or use (e.g., an amount of athletic activity performed) of the athletic equipment among other information. When the wear reaches a certain threshold (e.g., a number of miles or workouts), the device may alert the user that replacement is recommended. The device may also recommend replacement equipment based on, for example, the user's current type of shoe or other athletic equipment, height, weight, gender, shoe size, gait characteristics and the like. Recommendations may be made at any time and are not limited to replacement conditions. For example, a system may provide recommendations when a new product comes out that matches or is determined to be suitable for the user based on current or past athletic equipment, activities performed, terrain on which the user frequency runs, common weather conditions and the like.

Additionally or alternatively, a user may tag a workout with one or more devices (e.g., sensors, music devices, athletic activity data collection devices, etc.) used during the session. For example, a user may identify that a GPS device was used and/or that a heart rate sensor or an accelerometer was used. In some arrangements, the devices used during the workout may be automatically registered in a tagging menu. The user may then edit the automatically populated devices as desired or necessary.

A monitoring and training application may further provide an ability for the user to tag or otherwise register friends or other individuals associated with a workout session. As such, if a user performed a run with a friend, the user may tag the run with the friend's information. In a particular example, the user may select a username or other identifier associated with the friend in a tagging menu of the application. The username or identifier may correspond to an identifier registered with an athletic tracking and monitoring service, a social networking site, a phone number, a nickname specified in a user's phonebook or the like. Multiple friends or workout partners may be tagged to a single workout session as appropriate. In some arrangements, the device may automatically tag the workout session with known individuals running the same route at the same time. The device might only tag the workout session with individuals that have a confirmed relationship with the user. For example, only individuals that have mutually confirmed a relationship with one another may be tagged in each other's workout sessions.

The use of tags may enable the user to sort by one or more of the tagged parameters. The user may thus limit his or her view of workout history and other workout related information to a desired set based on the one or more filtering parameters such as weather, type of device used, workout partners, equipment used and the like.

Figure 32D:
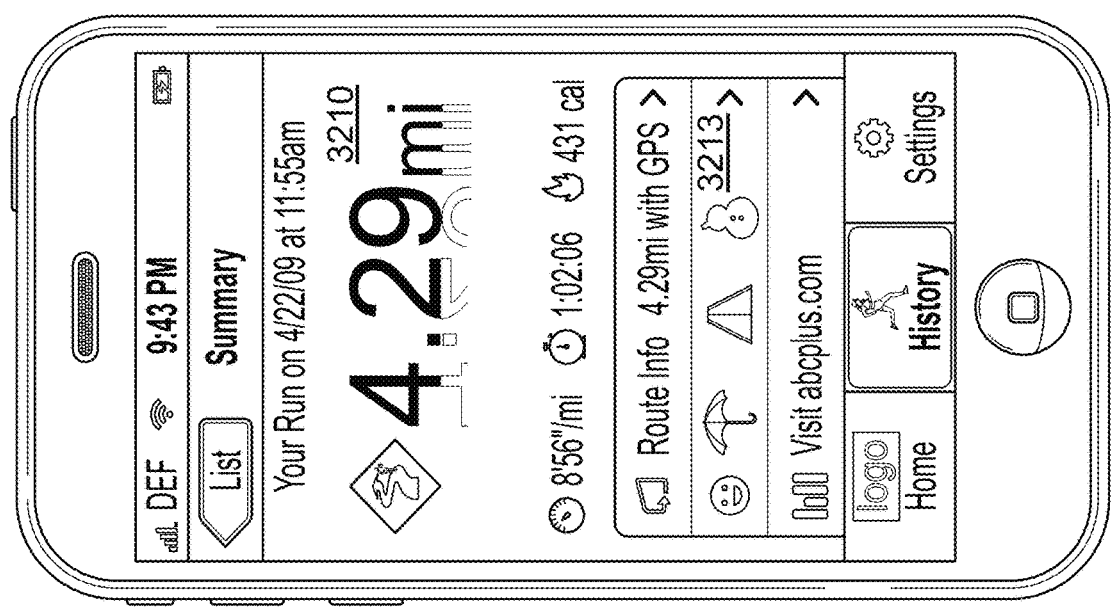

Once the user has completed entering desired tags, the device may return the user to the workout summary interface. FIG. 32D illustrates a summary interface 3210 that displays the tags defined by the user in the workout summary. In particular, the tag icons (e.g., a happy face for a good mood or an umbrella for rainy conditions) may be displayed in the tag option section 3213. The tag icons may replace the text that was previously displayed prior to tagging being completed (e.g., as shown in the interface of FIG. 32A). In one or more arrangements, selecting, hovering over or otherwise interacting with the tagged icons may cause detailed information to be displayed (e.g., in information bubbles).

Figure 33A:
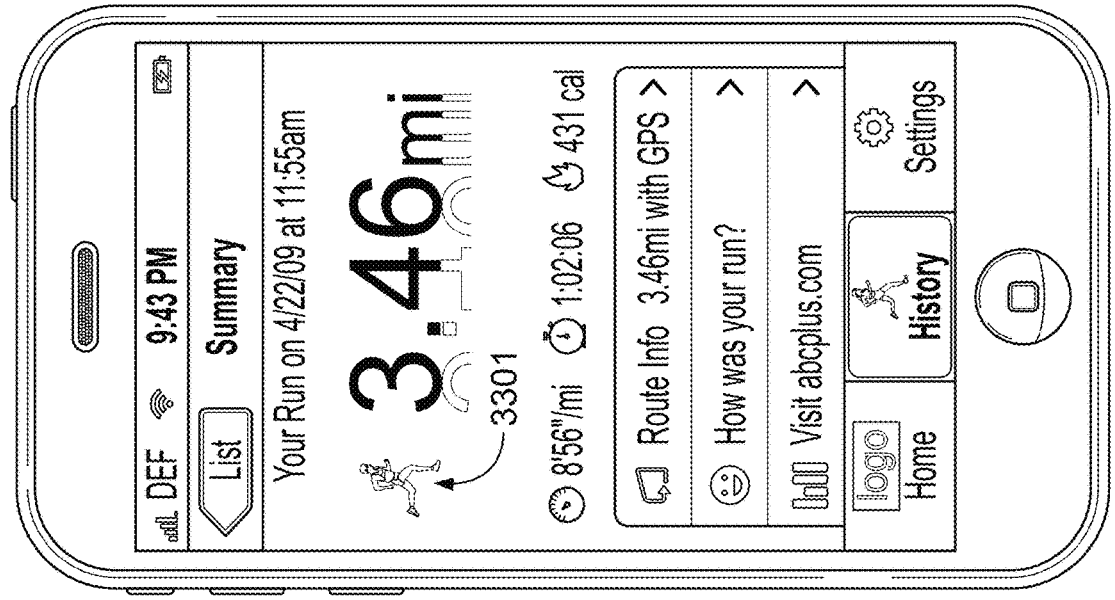
FIGS. 33A-33C illustrate example workout summaries for outdoor runs according to one or more aspects described herein.
Figure 33C:
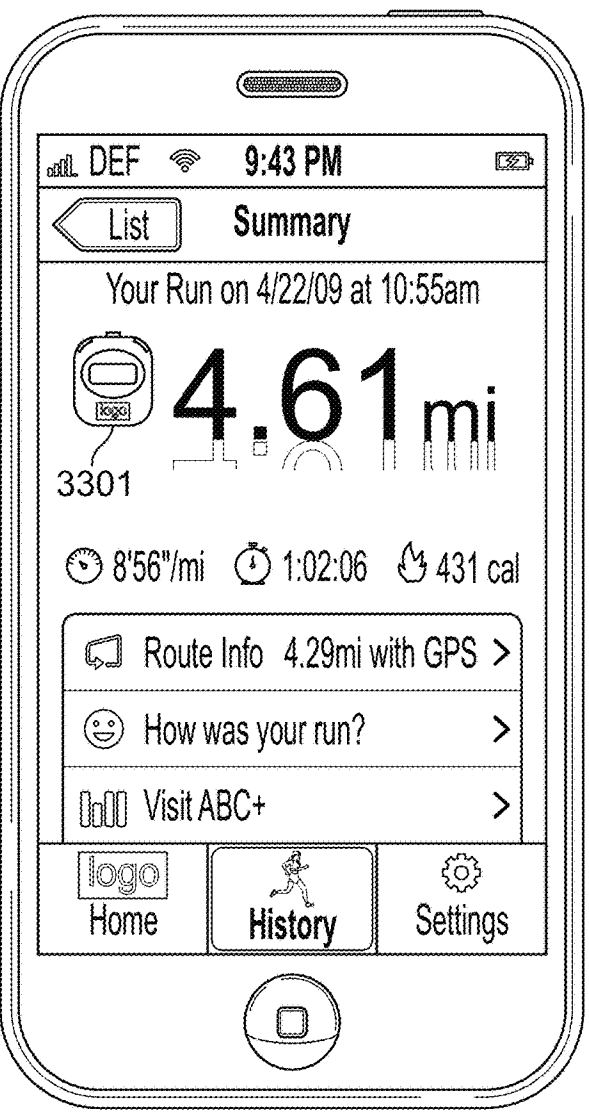
Figure 33B:
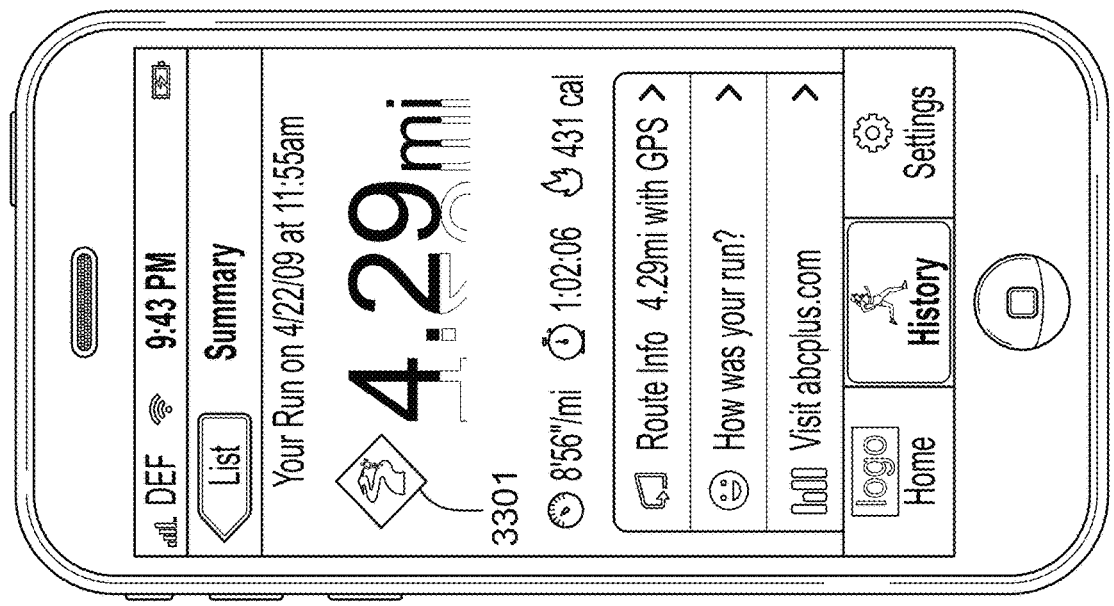

FIGS. 33A-33C illustrate workout summaries for outdoor runs. FIG. 33A illustrates a workout summary for a basic run (e.g., a run without any objectives or goals) while FIG. 33B illustrates a workout summary for a distance run and FIG. 33C illustrates a workout summary for a time run. The run type may be identified by an icon 3301. As noted, an outdoor workout summary might not include a calibrate functionality since the GPS may be considered more reliable and accurate than sensors used to determine an indoor workout (e.g., an accelerometer). Accordingly, each of the interfaces of FIGS. 33A-33C may include a route information option that displays the route taken by the user during the run. For example, upon selection the route information option, the user may be presented with a map with a line identifying the path taken.

Figure 34:
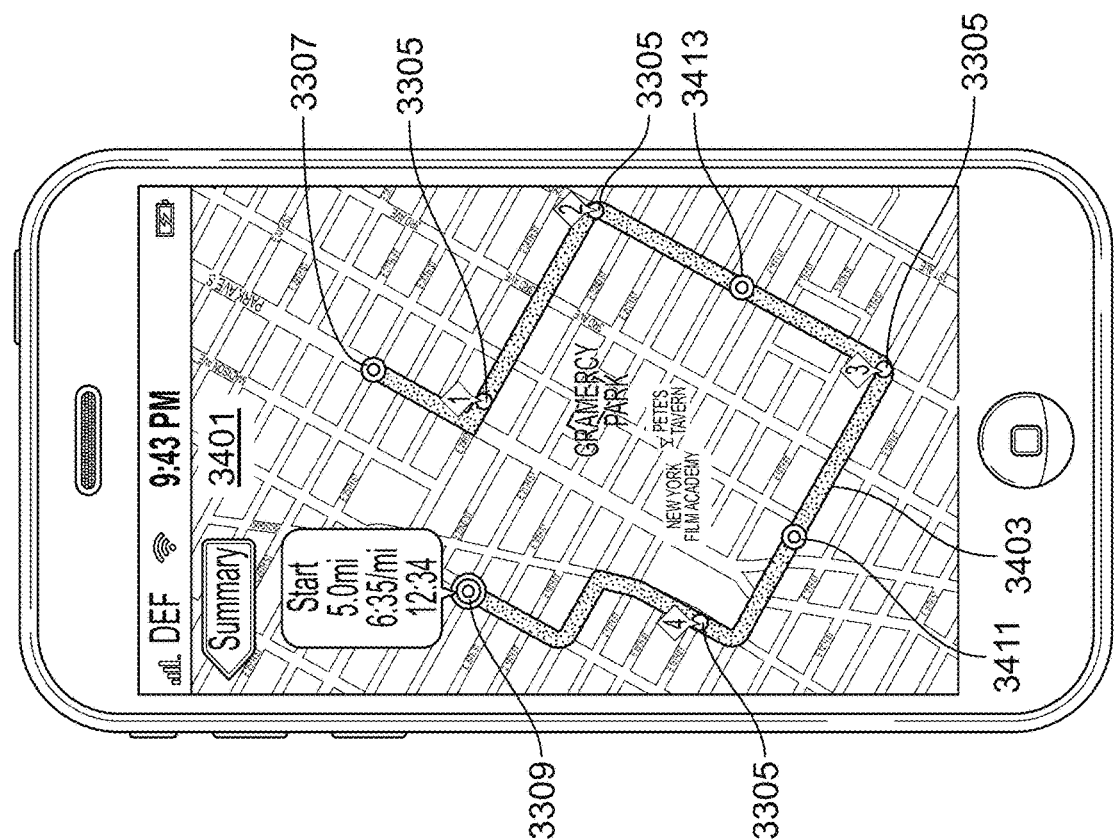
FIG. 34 illustrates an example route information interface according to one or more aspects described herein.

FIG. 34 illustrates a route information interface displaying map 3401 along with a line 3403 representing a user's running path. Mile markers 3405 may also be displayed on line 3403 to identify the various mileage points of the run. Additionally, start and end indicators 3407 and 3409, respectively, may be provided in the interface. Still further, the user's fastest and slowest pace points may be identified by markers 3411 and 3413, respectively. Other information may also be displayed to the user depending on the user's preferences. For example, the user may request that time markers be displayed (e.g., every 5 minutes, every minute, every 10 minutes, every hour). Selecting, hovering over or otherwise interacting with the markers 3405-3413 may provide additional detail information including a song played at the point identified by the marker, a pace, a distance, a time, a user's heart rate and/or other information. Other marks may also be added to map 3401, including markers indicating elevation points. For example, the highest and lowest elevations of a route may be specified on map 3401. In another example, 50 foot changes in elevation may be indicated on map 3401. Elevation markers may also be placed at the points where the user registered the highest and lowest paces.

Alternatively or additionally, users may enter tags based on a GPS-detected location. For example, a user may wish to register a note indicating that he or she felt tired at a certain point along the route. The note may then be automatically registered with a particular GPS coordinates corresponding to the location where the note was entered. Alternatively, the note may be entered after the run and the location manually specified by the user using GPS coordinates. Other information such as location specific descriptions of notable landmarks and the like may also be automatically registered based on the detected GPS location.

Figure 35A:
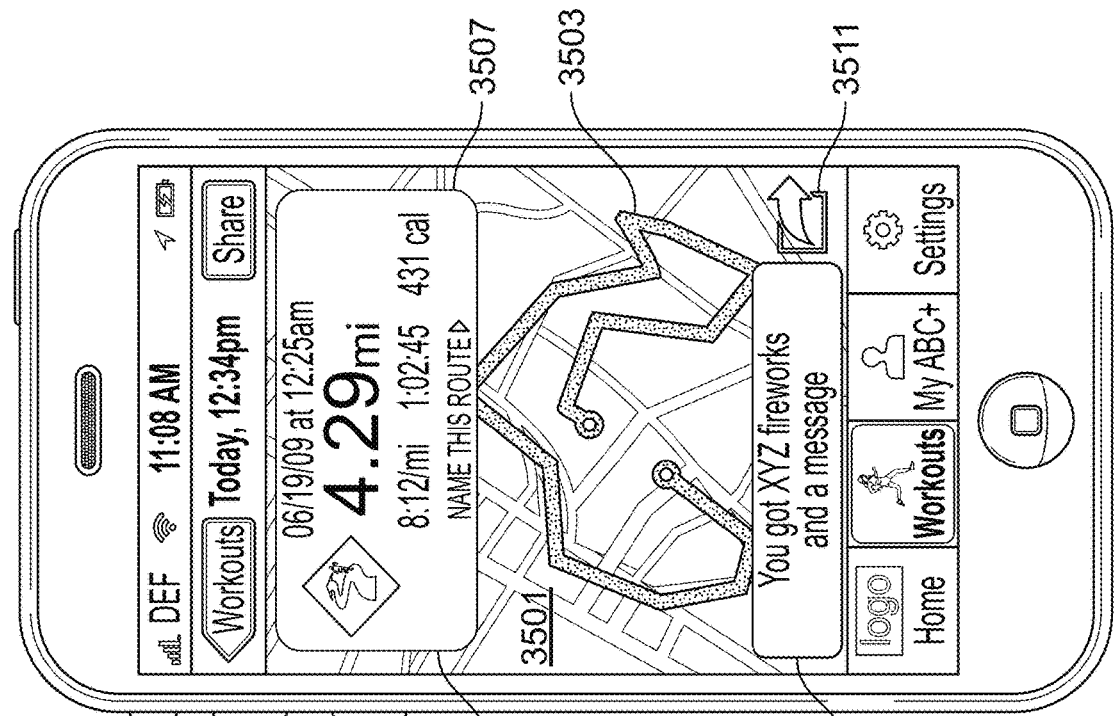
FIGS. 35A-35C illustrate example route summary interfaces in which a map may be displayed according to one or more aspects described herein.
Figure 35C:
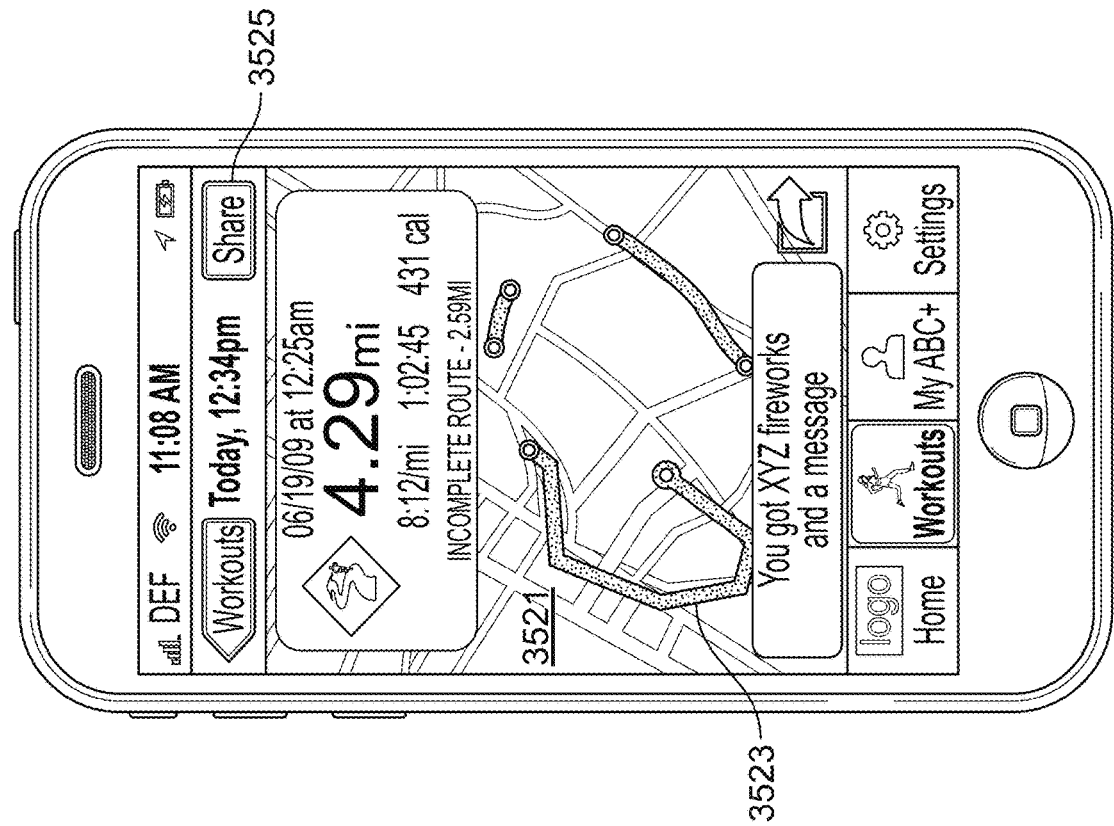
Figure 35B:
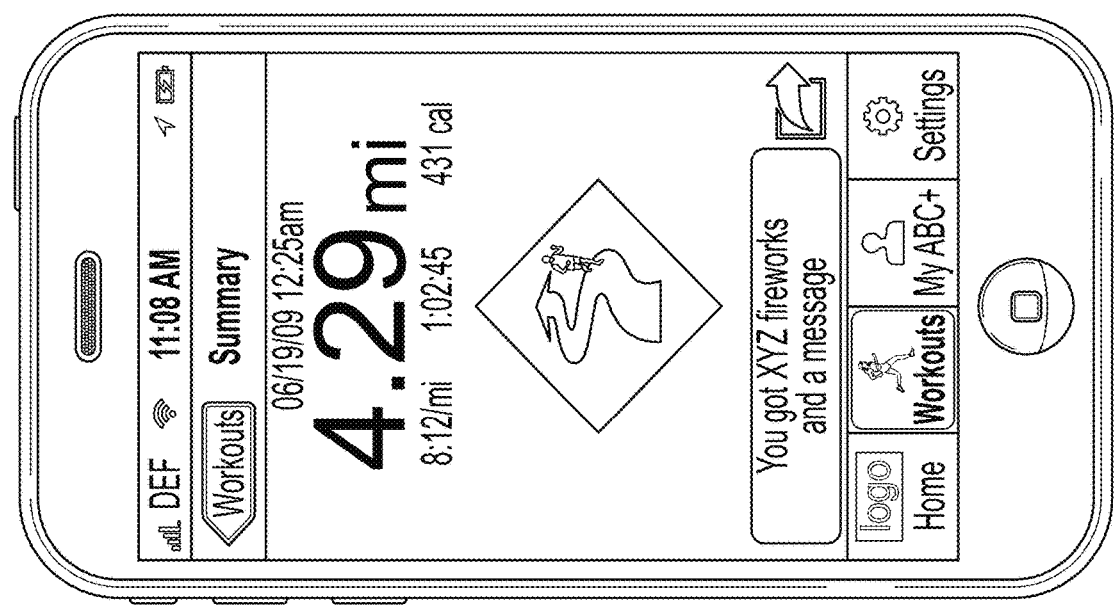

FIGS. 35A-35C illustrate example route summary interfaces in which a map may be displayed if the run was recorded using a GPS or other location determination system while non-GPS recorded runs might not include a map. For example, in FIG. 35A, a map 3501 may be displayed along with a line 3503 representing the route the user took during the run. A summary display 3505 may also be displayed with an option 3507 to name the route. By naming the route the user may be able to more readily identify and select the route for future workouts. According to one or more arrangements, the interface may further include notification 3509 that indicates the user has received messages, accolades or motivational items and an option 3511 to access those messages, accolades and motivational items. In one example, the messages or motivational items may be provided through a social networking site that may be linked to the user's athletic activity monitoring device and/or account.

Figure 36:
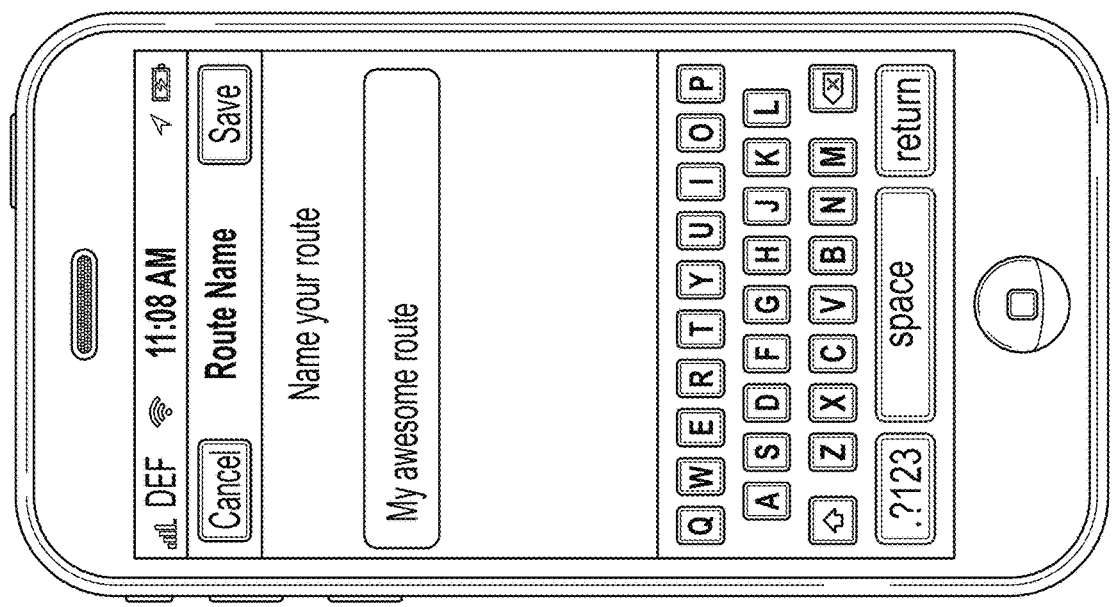
FIG. 36 illustrates an example route naming interface according to one or more aspects described herein.

FIG. 36 illustrates an example route naming interface. In some examples, the route naming interface might only be provided if the user's workout route was recorded using GPS information. Otherwise, there might not be enough information to discern the route being named. Alternatively, users may be able to name all routes. For example, the user may manually identify the route on a map if GPS information was not added. Alternatively or additionally, a user may modify a route automatically detected using GPS as necessary or desired. By naming and storing routes that the user has run, the system may identify, in subsequent workouts, when a route matches a previous stored route. The system may then automatically store the subsequent workout in association with the identified route.

FIG. 35C illustrates a map 3521 including a route summary for a run that was only partially recorded using a GPS device. Accordingly, portions of the route 3523 may be missing due to a lack of GPS data for those portions of the run. Additionally or alternatively, route and workout information may be shared with one or more other users, friends, social network sites and the like. For example, a share option 3525 may be displayed and selected by the user to share the information. Sharing of workout and route information, achievements and the like is discussed in further detail below. In one or more configurations, if GPS data is unavailable, a mobile device may switch to cellular signal triangulation to determine a current position. This information, along with accelerometer data, may provide substitute workout information to fill in any missing GPS information. For example, cellular triangulation may provide location of the runner based on a predefined schedule (e.g., continuous, every 30 seconds, every 5 seconds, every 15 seconds, every minute, aperiodic schedules) while the accelerometer may provide pace and distance information to corroborate the user's location determined using the triangulation data. Portions of a route (e.g., route 3523) that are measured using cellular triangulation and accelerometer systems may be displayed differently (e.g., different color, different pattern) than portions of the route recorded using GPS data.

Figure 37A:
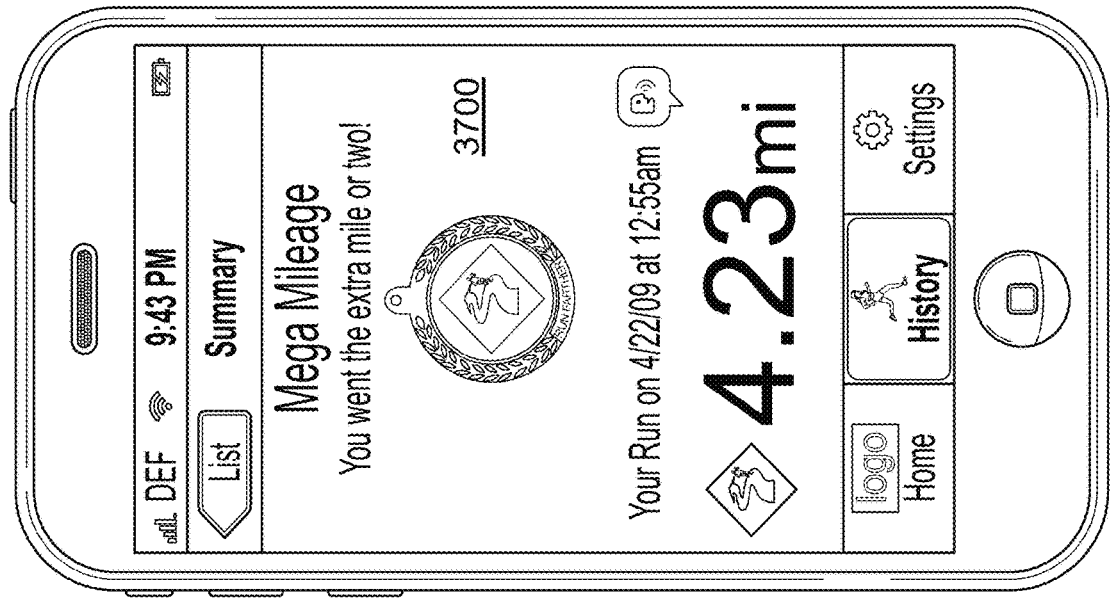
FIG. 37A illustrates an example summary interface displaying a mileage medal for setting a new distance record according to one or more aspects described herein.

When the user completes an improvement run, the user may be presented with additional information in the workout summary. For example, if the user completed the objective set in the improvement run, the user may be provided with a medal or other indicator for the achievement. In FIG. 37A, summary interface 3700 displays a mileage medal for setting a new distance record. The medal may be added as an indicator or tag for the workout entry in a workout history.

Figure 37C:
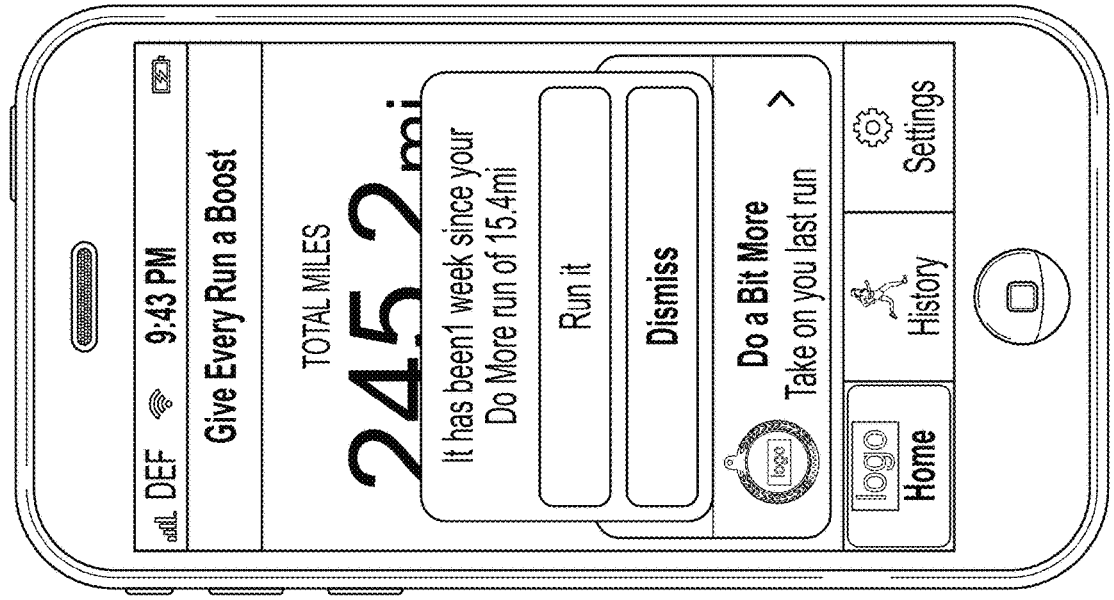
FIG. 37C illustrates an example workout reminder interface according to one or more aspects described herein.
Figure 37B:
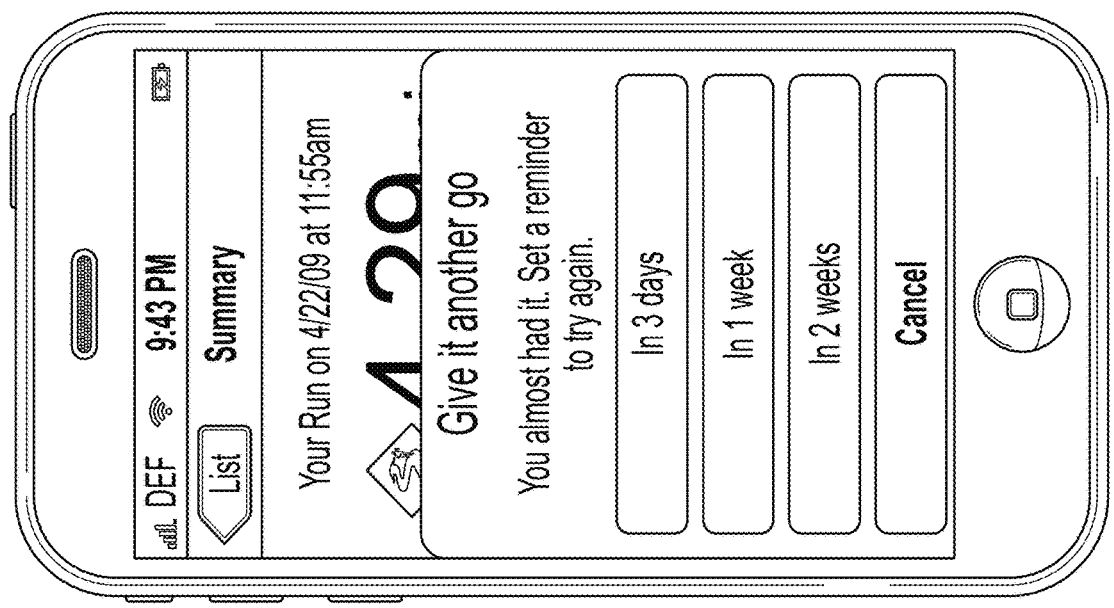
FIG. 37B illustrates an example interface that may be displayed if a user fails to complete an objective or goal according to one or more aspects described herein.

If, however, the user does not reach the goal or objective of the improvement run, the device may display an interface 3710 of FIG. 37B that encourages the user to try the improvement run again (e.g., with the same objective or goal). For example, interface 3710 may provide a selection menu that asks the user to set a time (e.g., in 3 days, in a week in 2 weeks, etc.) to re-try the improvement run.

Reminders may be provided to the user regardless of whether the user completed the improvement run. The reminder may be used to motivate the user to achieve additional improvements or to remind the user to re-try an improvement run that he or she previously attempted but did not complete. FIG. 37C illustrates an example reminder interface. In interface 3720, the user may choose to initiate or schedule a run or to dismiss the reminder.

Figure 38B:
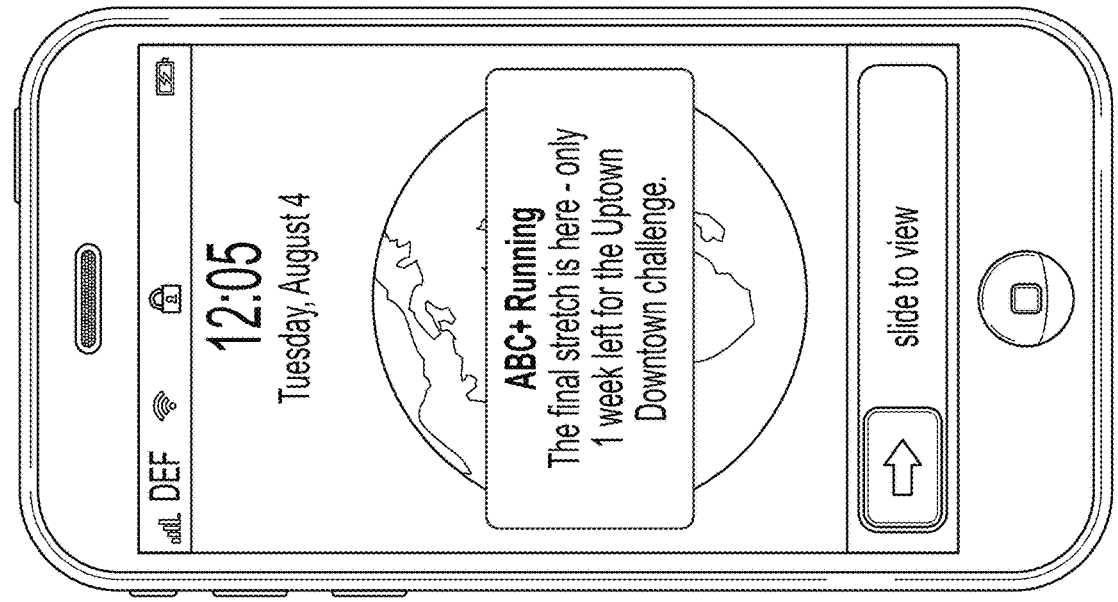
FIGS. 38A and 38B illustrate further example alert and reminder messages that may be displayed to a user according to one or more aspects described herein.
Figure 38A:
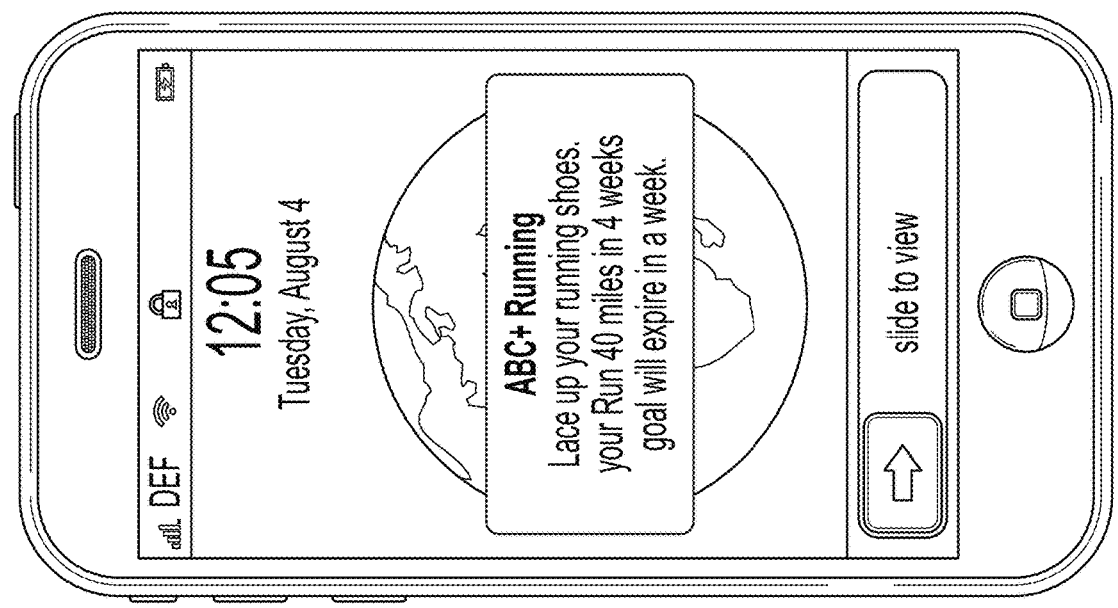

FIGS. 38A-38B illustrate further example alert and reminder messages that may be displayed to a user. The alerts or messages may be triggered and generated by the mobile device or may be received from a remote network server. For example, the mobile device may receive push notifications from a remote fitness monitoring service provider. Notifications may also include messages from other users, friends, system administrators, coaches and the like.

Figure 39B:
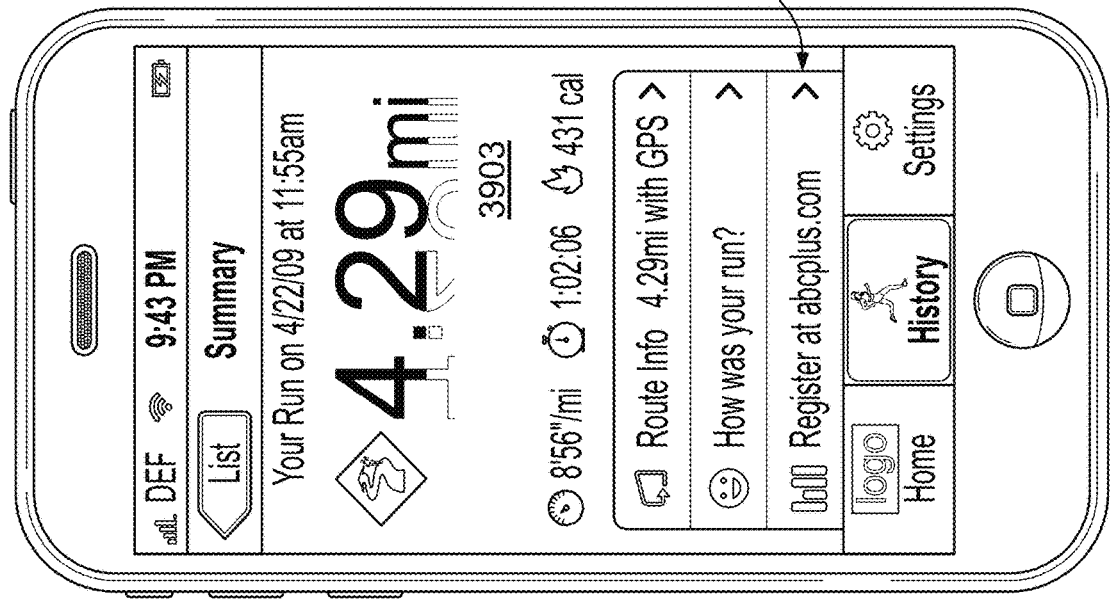
FIG. 39B illustrates an example workout summary interface that includes a registration option according to one or more aspects described herein.
Figure 39A:
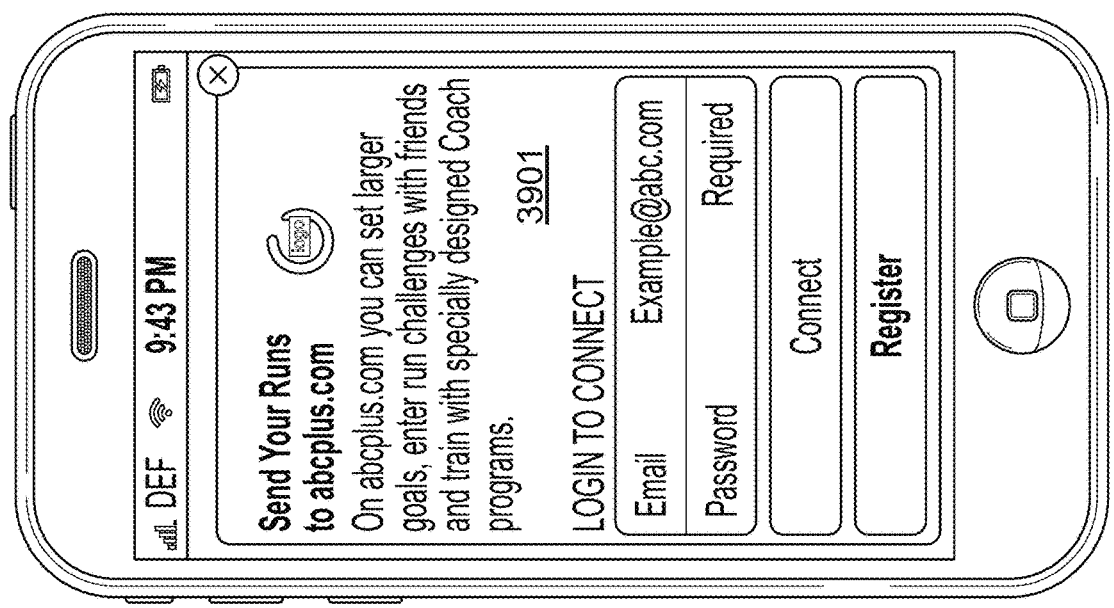
FIG. 39A illustrates an example interface that may be displayed if the user is a member of the service provided by an athletic activity monitoring service provider according to one or more aspects described herein.

As described herein, a user may synchronize workout data with an athletic activity monitoring service provider. If a user has completed his or her first run, the device may display various interfaces in conjunction with the workout summary that allow the user to synchronize his or her data with the service provider. FIG. 39A illustrates an interface 3901 that may be displayed if the user is a member of the service provided by the fitness monitoring service provider. FIG. 39B, on the other hand, illustrates workout summary interface 3903 that includes an option 3905 to register with the service provider.

Figure 40B:
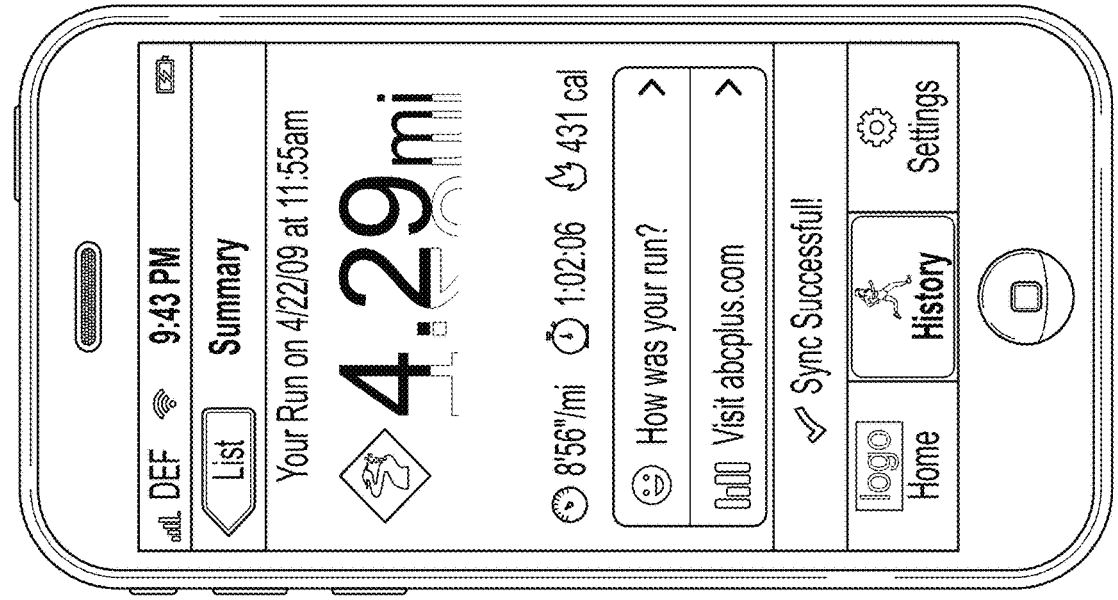
FIGS. 40A-40C illustrate a sequence of example interfaces through which data may be synchronized with a service provider according to one or more aspects described herein.
Figure 40A:
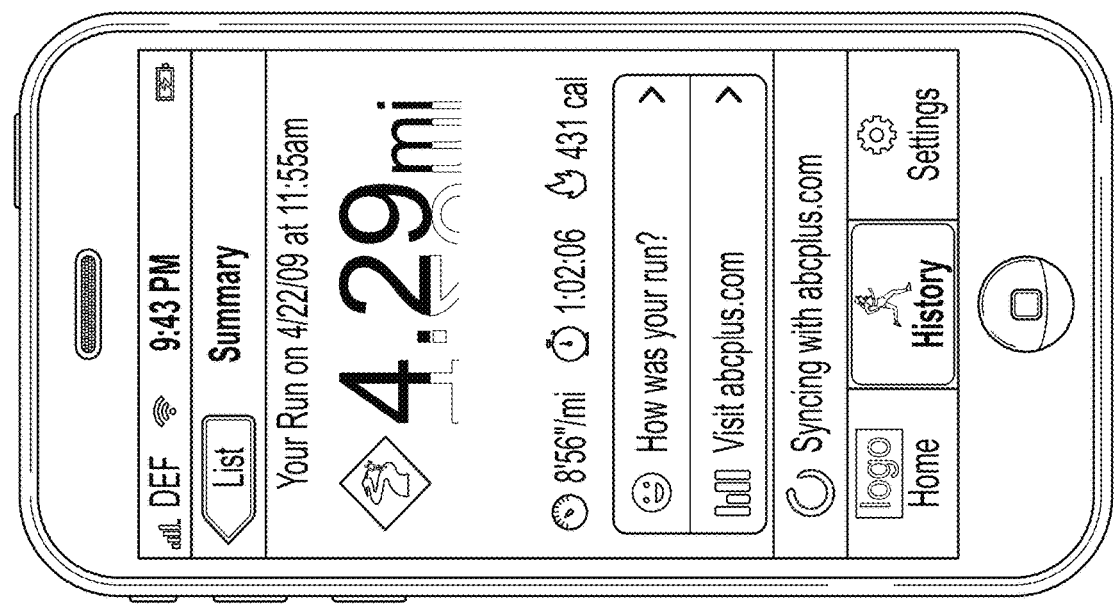
Figure 40C:
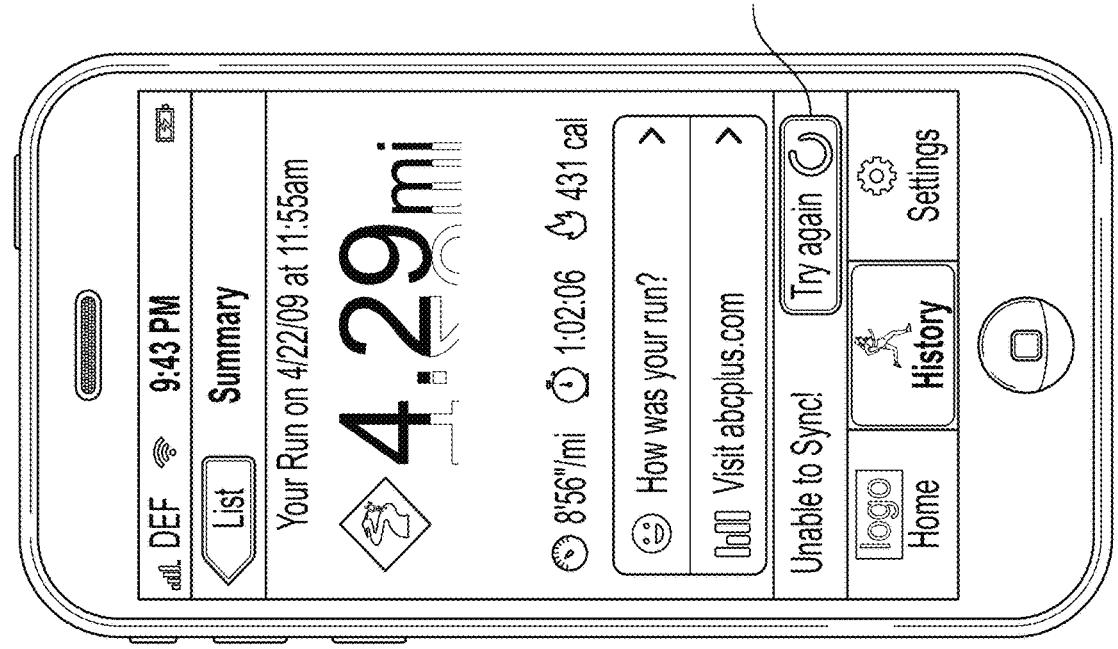

Workout data may be synchronized during a workout summary phase or while viewing a workout history. FIGS. 40A-40C illustrate a sequence of interfaces through which data may be synchronized with the service provider. For example, in the interface of FIG. 40A, the interface may indicate a synchronization in progress message while the interface of FIG. 40B indicates a successful synchronization message. In another example, the interface of FIG. 40C indicates an unsuccessful synchronization message with an option 4001 to reattempt the synchronization.

Figure 41A:
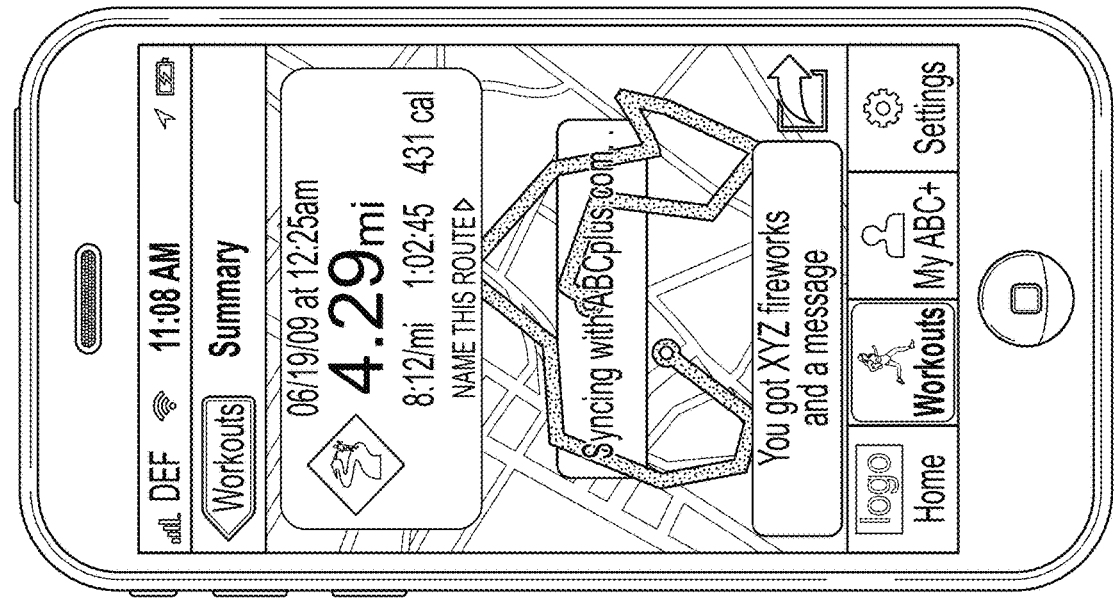
FIGS. 41A-41C illustrate example workout summary interfaces through which synchronization may be conducted according to one or more aspects described herein.
Figure 41C:
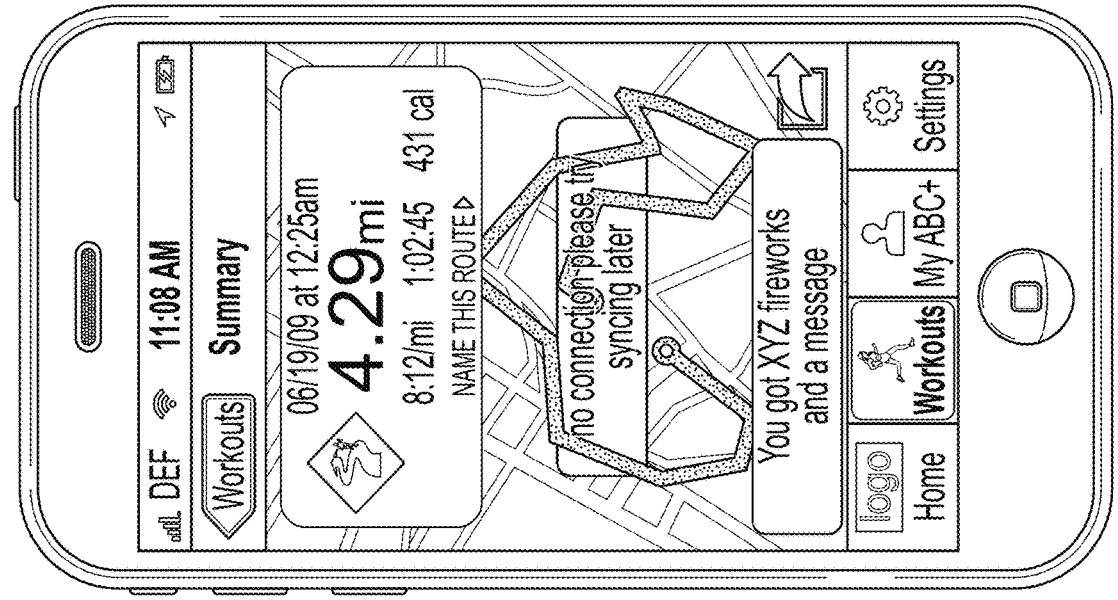
Figure 41B:
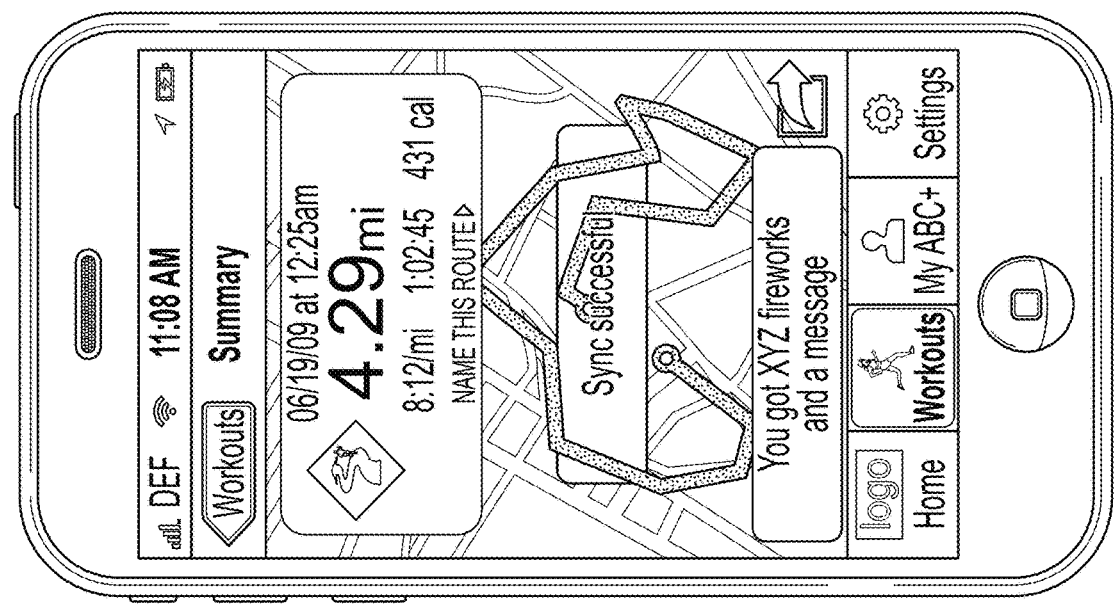

Synchronization may also be performed in a route summary screen such as those illustrated in FIGS. 41A-41C. For example, each of the route summary interfaces may be overlaid with a semi-transparent message that indicates the data is being synched, has been synched or that a connection is not available.

Figure 42B:
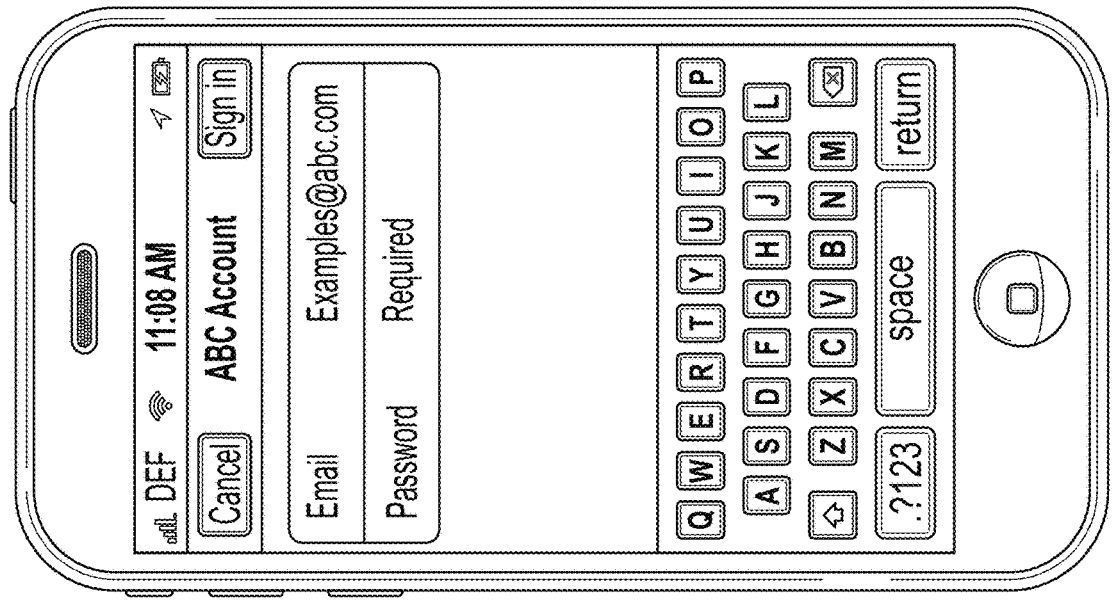
FIGS. 42A-42C illustrate example interfaces through which a user may synchronize athletic activity data by login into or creating a service provider account according to one or more aspects described herein.
Figure 42A:
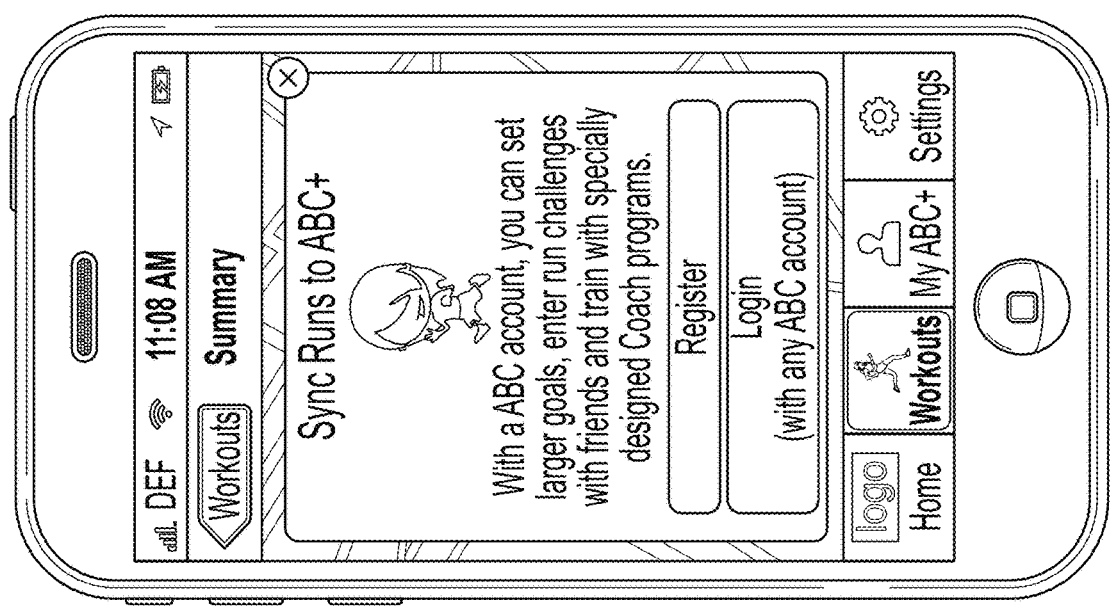
Figure 42C:
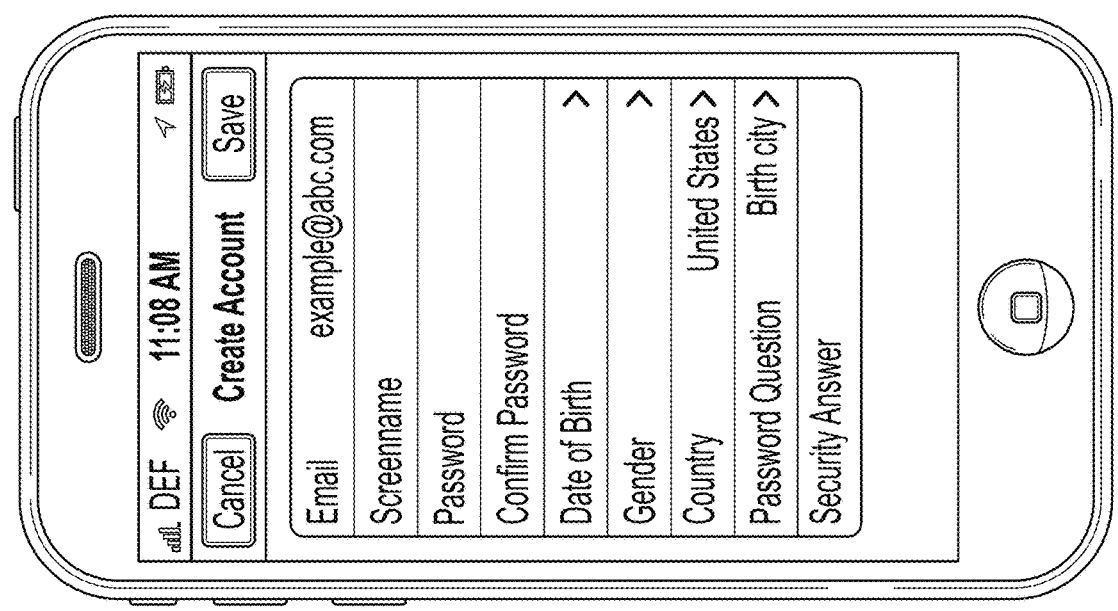

Additionally or alternatively, a synchronization message may include asking the user to register or login as illustrates in FIG. 42A. The user may subsequently login or create an account through interfaces of FIGS. 42B and 42C, respectively.

Figure 43:
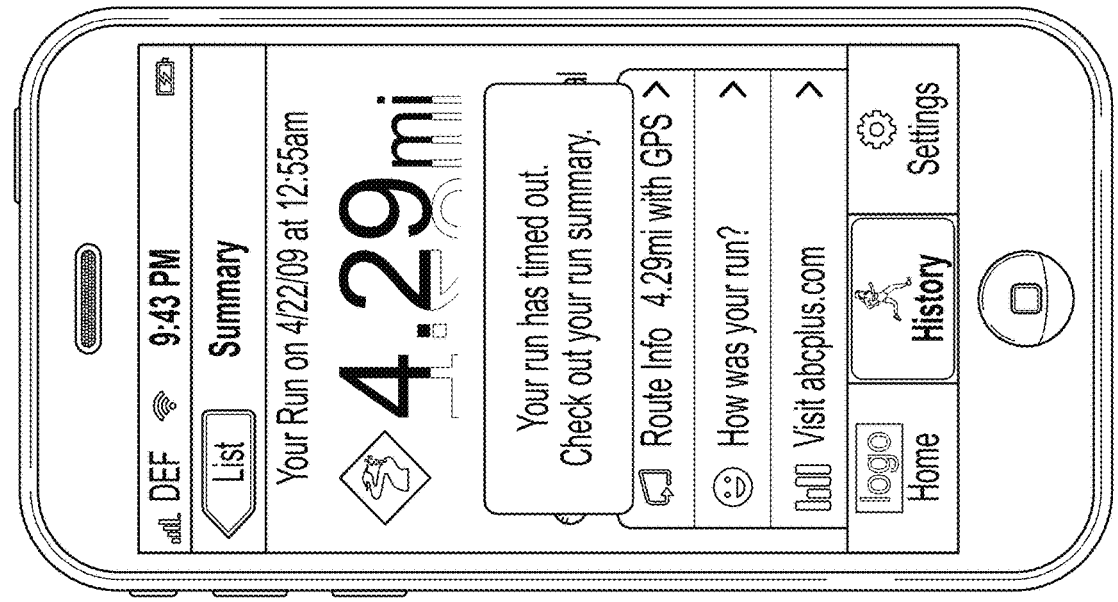
FIG. 43 illustrates an example interface with a message indicating that a workout has timed out according to one or more aspects described herein.

According to one or more aspects, if a run timed out instead of being completed, the user may be provided with an alert message with such a notification. FIG. 43 illustrates an interface with such a message. A run may time out if no athletic activity is detected for a specified amount of time. For example, if a user does not exhibit any athletic activity for 5 continuous minutes, 10 continuous minutes, 30 continuous minutes or the like, the device may automatically end the run and generate a workout summary with an alert message advising of the time out condition. According to one or more aspects, a point at which the run timed out may be displayed on a route map if the run was tracked using GPS or other location determination system. Other location determination systems may include triangulation using cellular signals, Wi-Fi (e.g., the user's location being equated to the location of a Wi-Fi service provider), determining a network service provider location and the like.

Other types of post-run messages may be provided to the user, including coaching. In one or more examples, a post-run message may be generated to challenge the user to exceed one or more metrics of the newly completed run in a subsequent workout session. The messages may also indicate a distance, pace, amount of time required to reach an achievement. Additionally or alternatively, the messages may provide improvement tips generated based on a user's performance in the completed workout. For example, if a user exhibited a significantly slower pace (e.g., 30% below an average pace) during hills, the device may provide a tip for improving performance during inclines. In another example, if a user exhibited a steep decline (e.g., 10%, 20%, 30%, 40%, 50%, 60% or more decline) in pace after the third mile, the device may provide advice for maintaining the pre-fourth mile pace and/or for maintaining a more regular pace throughout the workout.

In addition to visual messages (e.g., text and/or graphic messages), audio messages may also be provided upon completion of a run. For example, the user may be congratulated for completing a longest workout (e.g., either in duration or distance). Other messages may be provided for accepting a mid-run challenge and meeting that challenge. Audio messages may be provided by an automated voice or by a celebrity or friend.

History

Figure 44A:
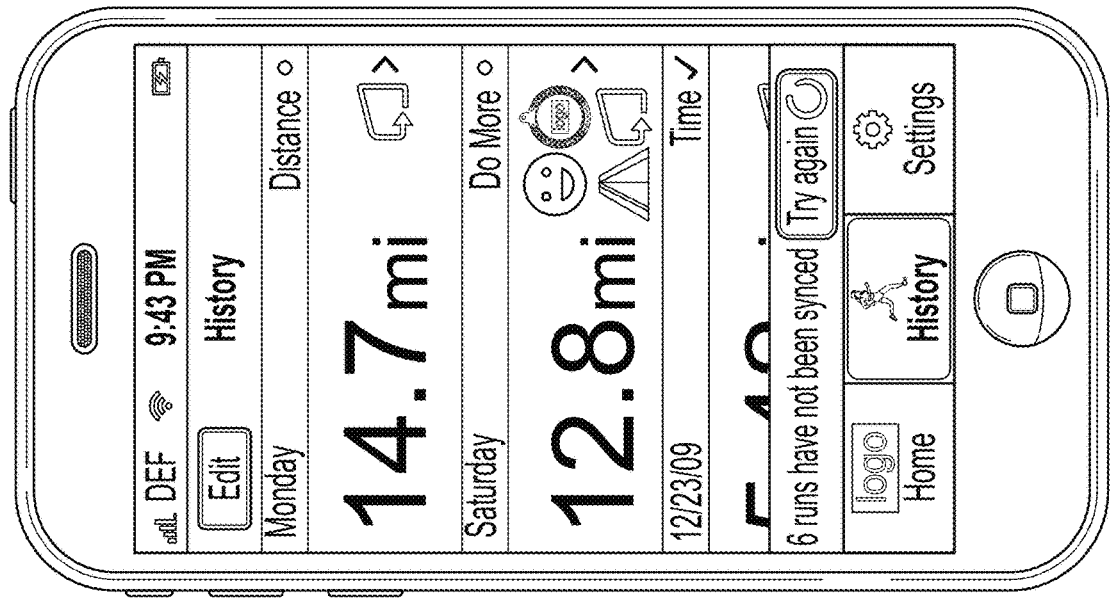
FIGS. 44A-44C illustrate a series of example interfaces in which a synchronization process is performed according to one or more aspects described herein.
Figure 44B:
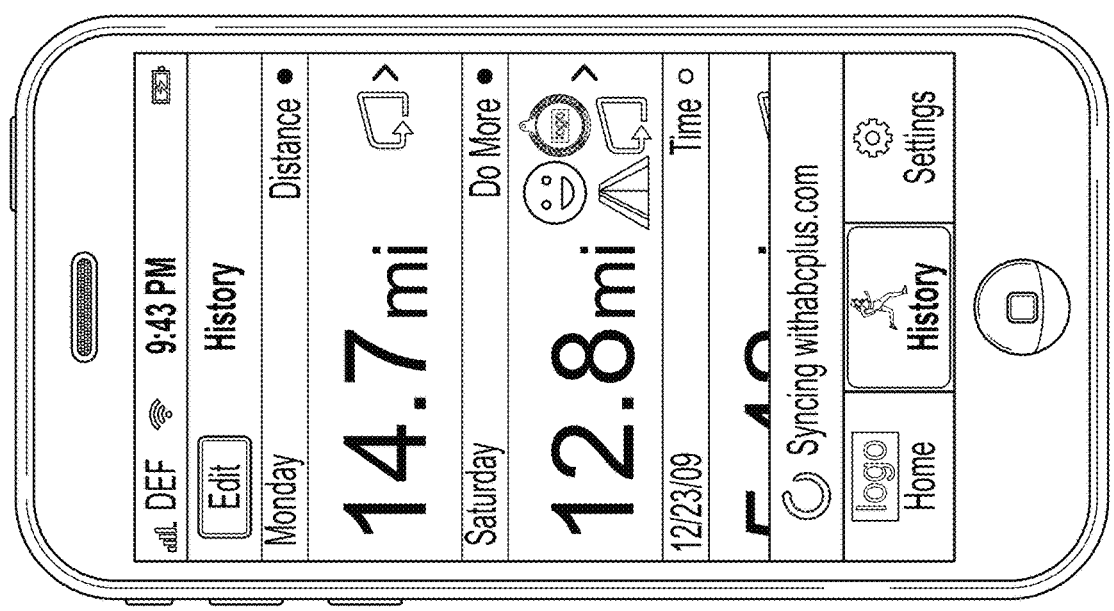
Figure 44C:
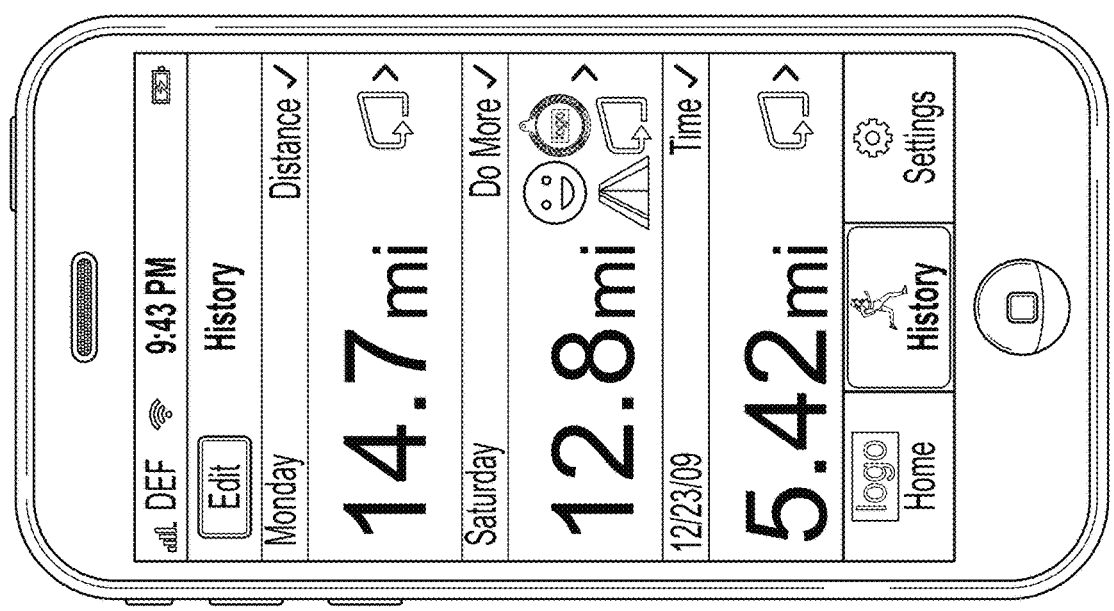

In a history list view, the user may be able to view details and summaries of workouts previously performed and recorded. Additionally or alternatively, the data may be synchronized with a service provider in the history view. FIGS. 44A-44C illustrates a series of interfaces illustrating the synchronization process. Synchronization may be automatic or may be triggered by a user command. If synchronization fails, the synchronization may be re-tried by a user command or automatically based on a predefined retry schedule. Synchronization may be performed each time the history view is loaded or when new workouts have been added since a previous synchronization time. A synchronization history may be stored to facilitate the scheduling of future synchronizations.

Figure 45A:
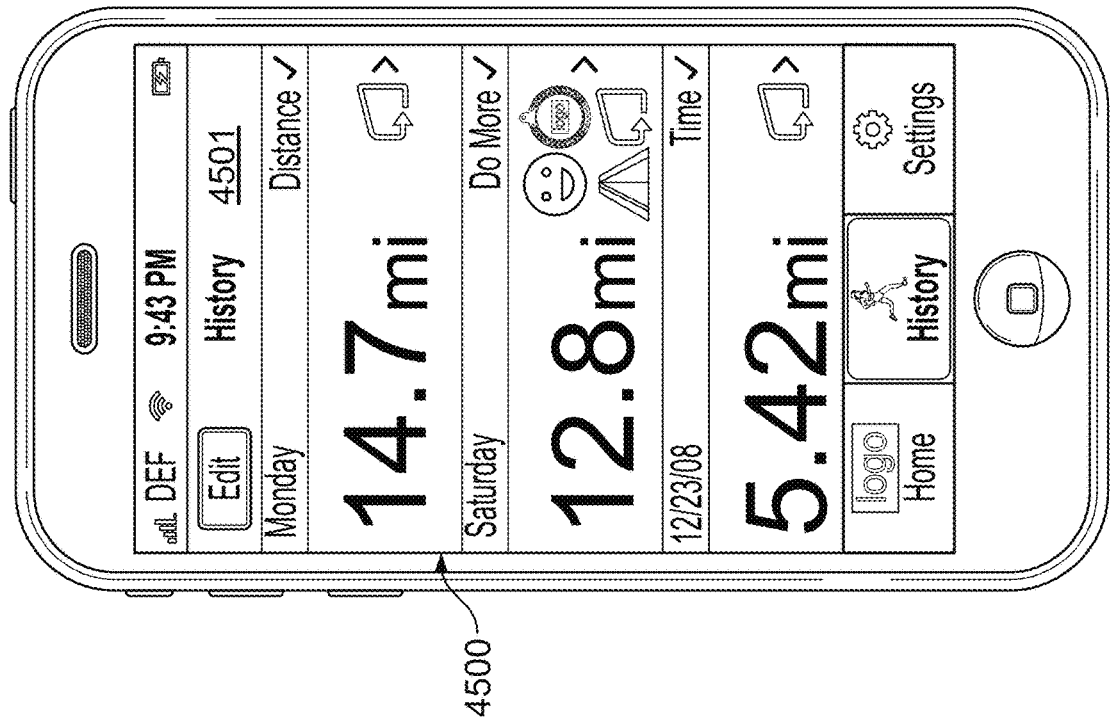
FIGS. 45A and 45B illustrate interfaces through which a user may delete entries from a workout history according to one or more aspects described herein.
Figure 45B:
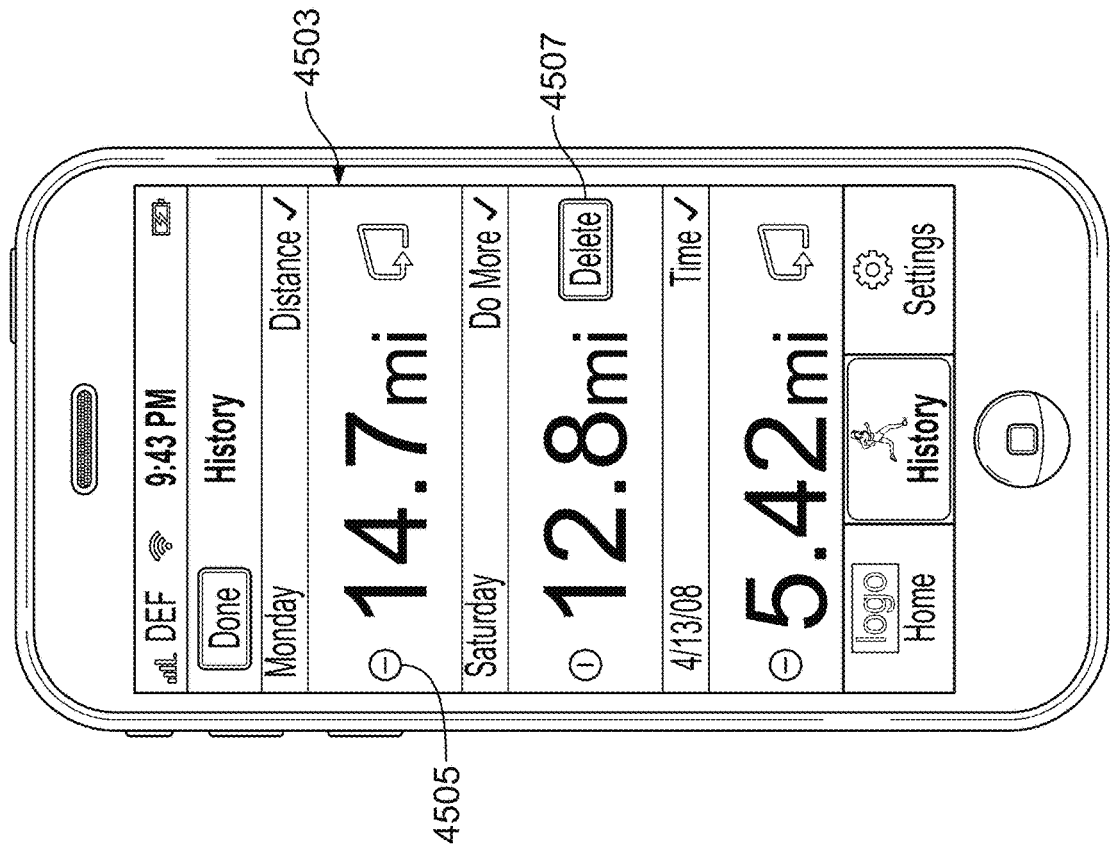

The user may further edit the history list to delete any undesired workout records. For example, in interface 4500 of FIG. 45A, the user may select edit option 01. Upon selecting edit option 4501, interface 4500 may change to provide deletion options. FIG. 45B illustrates a deletion interface 4503 through which a user may delete one or more entries. The user may use options 4505 to select the entries he or she wishes to delete. The user may be required to confirm the deletion by subsequently select a second deletion option 4507. Alternatively, the user may select option 4505 to mark the entries that are to be deleted. Upon selection a complete or confirm option 4509, the marked entries may be automatically deleted. The user may be required to confirm the deletions in either instance.

Figure 46A:
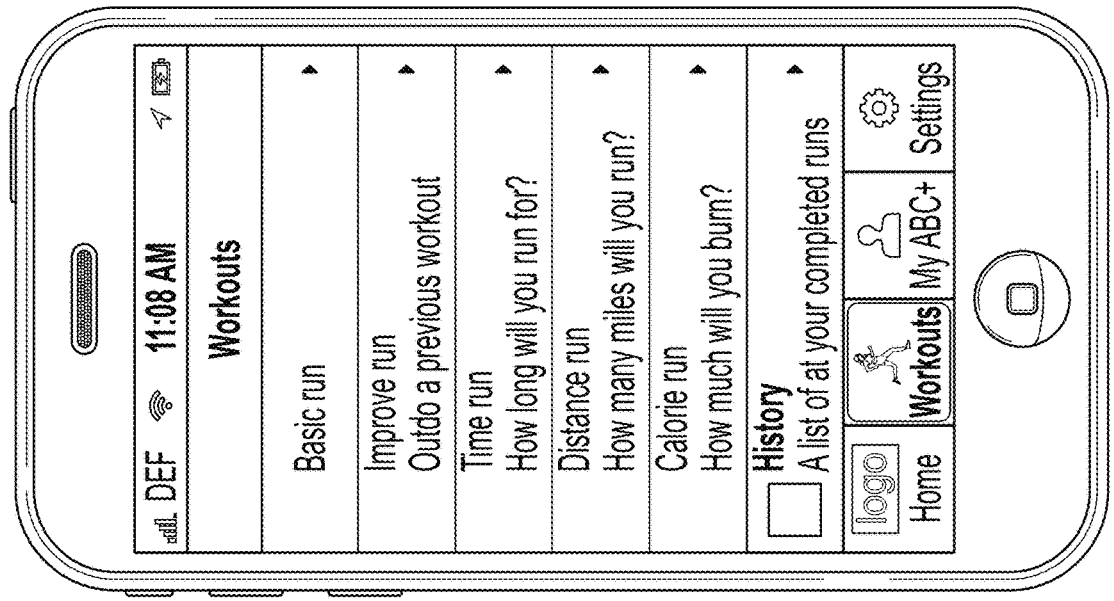
FIGS. 46A-46C illustrate additional example interfaces that may be displayed to convey history information to a user according to one or more aspects described herein.
Figure 46C:
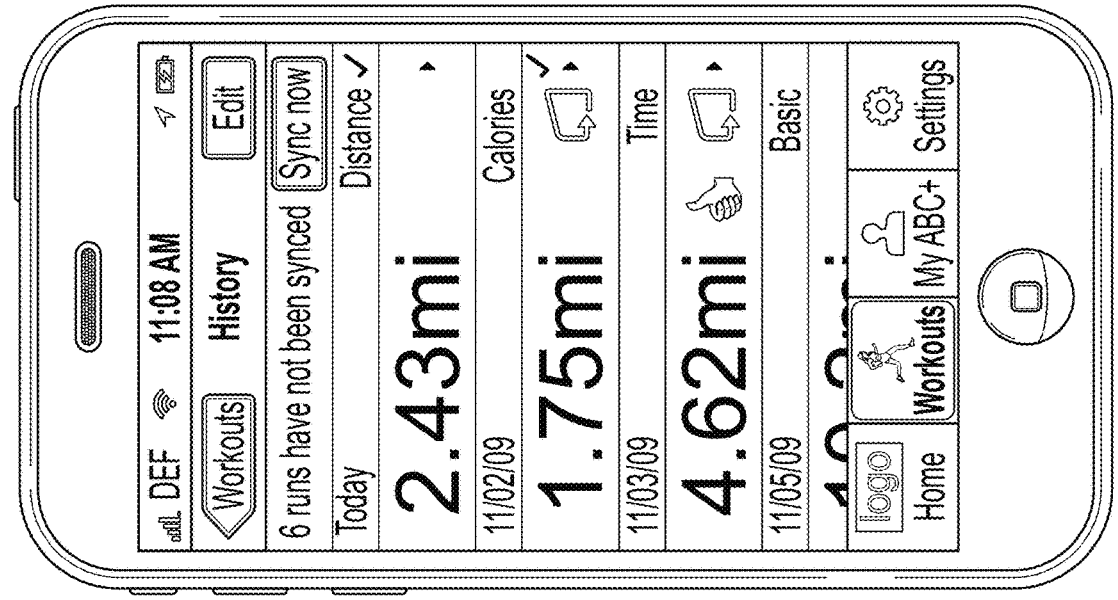
Figure 46B:
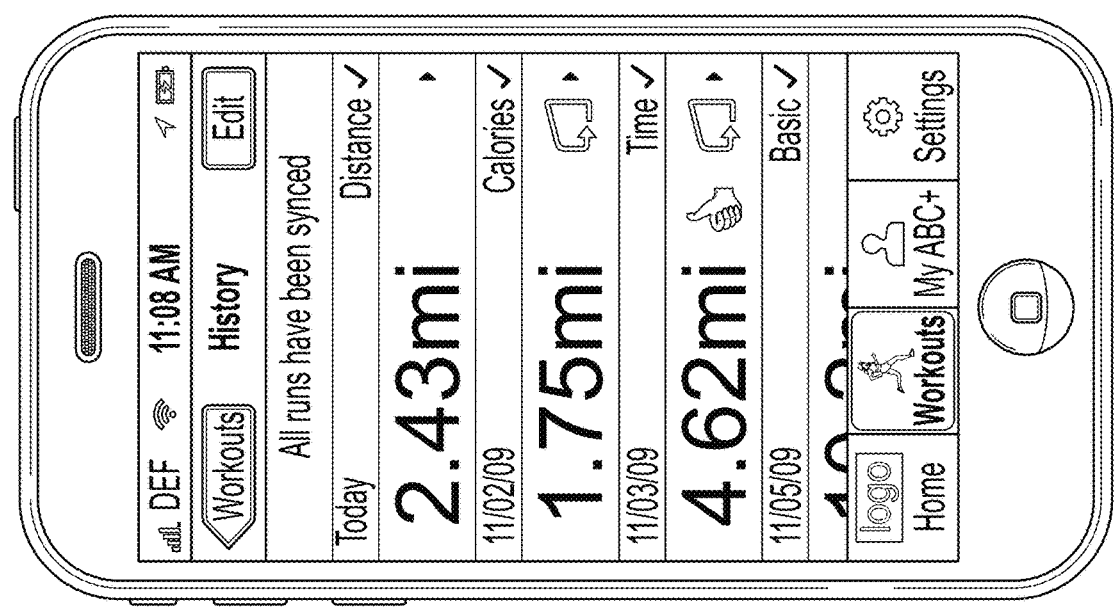

FIGS. 46A-46C illustrate additional example interfaces that may be displayed to convey history information to a user. In FIGS. 46B and 46C, for example, the interfaces may display an indicator or message that identifies whether any run information has not yet been synched with a service provider. If not, the interface may provide a synchronization option to allow the user to synchronize the data immediately (as shown in FIG. 46C). Alternatively or additionally, the user may schedule synchronization for a future date or time.

Settings

Figure 47B:
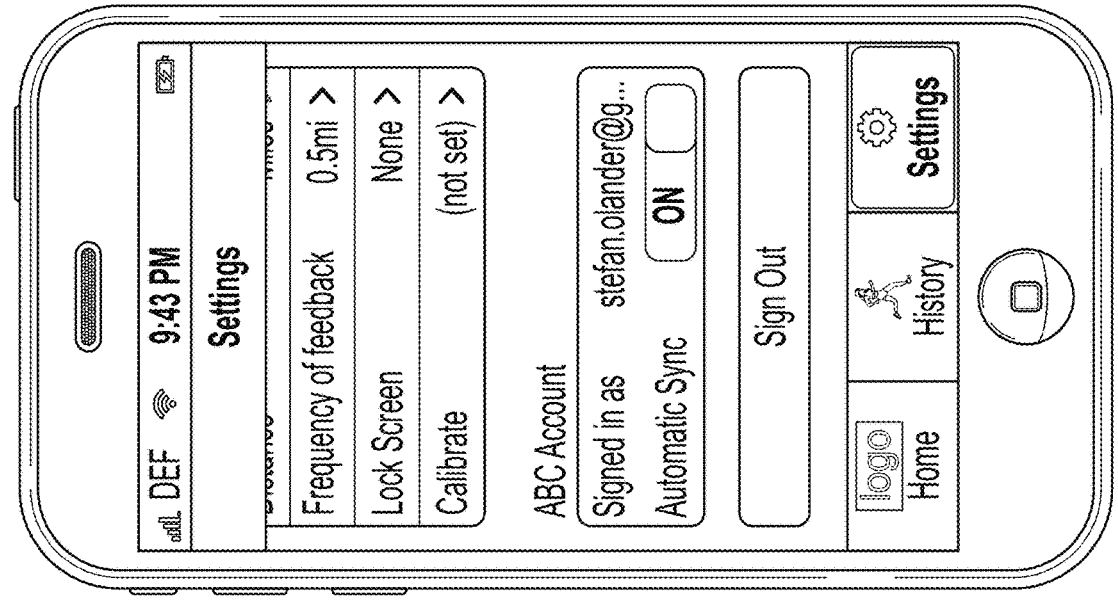
FIGS. 47A and 47B illustrate example portions of various settings interfaces for configuring an athletic activity monitoring device and application according to one or more aspects described herein.
Figure 47A:
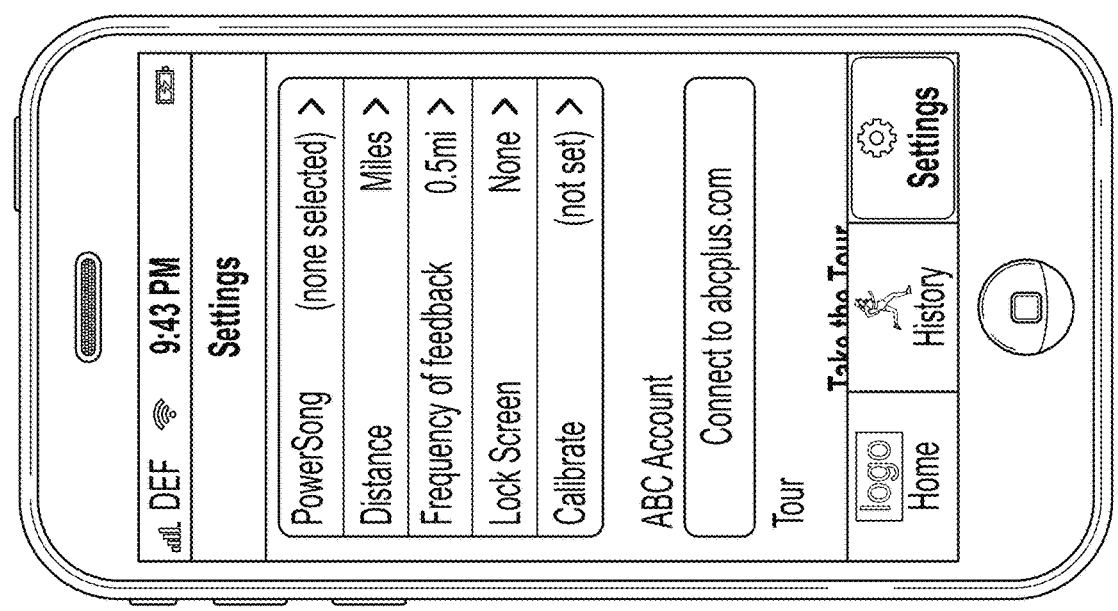
Figure 48B:
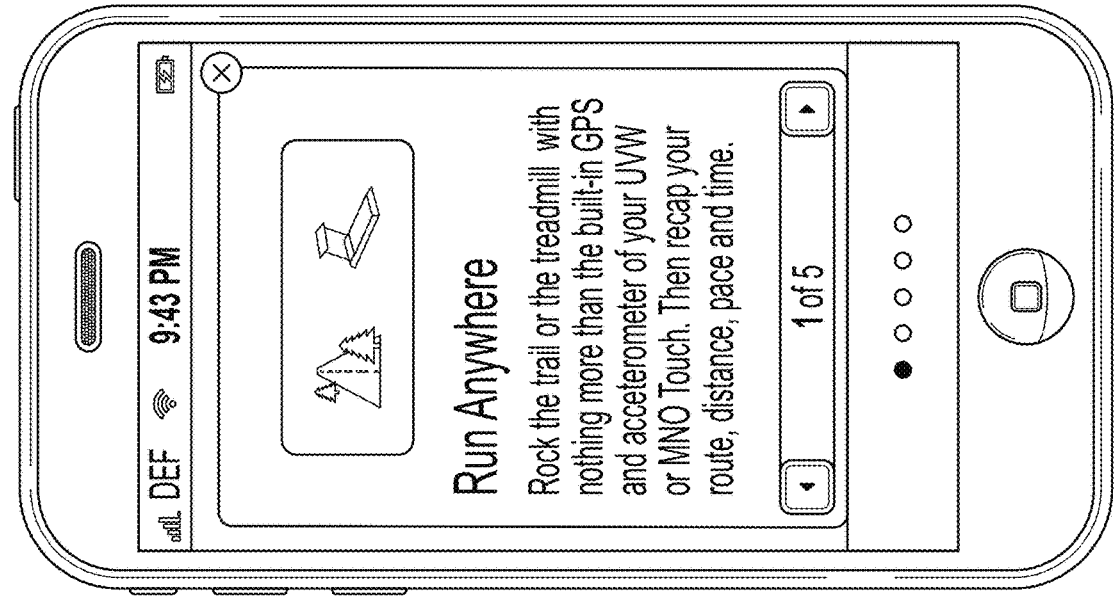
FIGS. 48A-48F illustrate example tour interfaces that provide detailed information describing the available features and functions according to one or more aspects described herein.
Figure 48A:
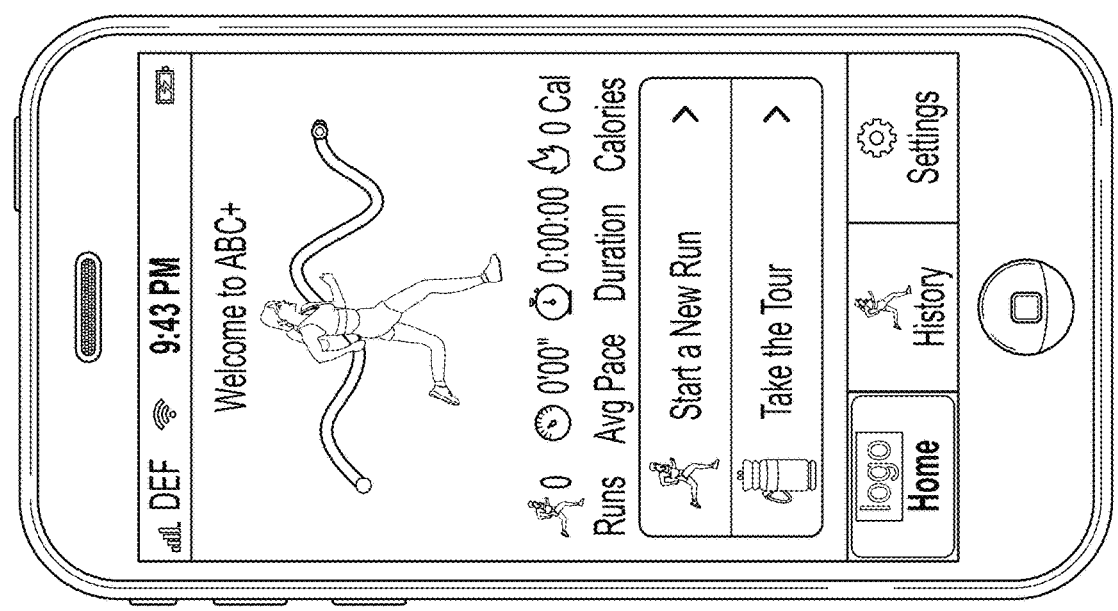
Figure 48D:
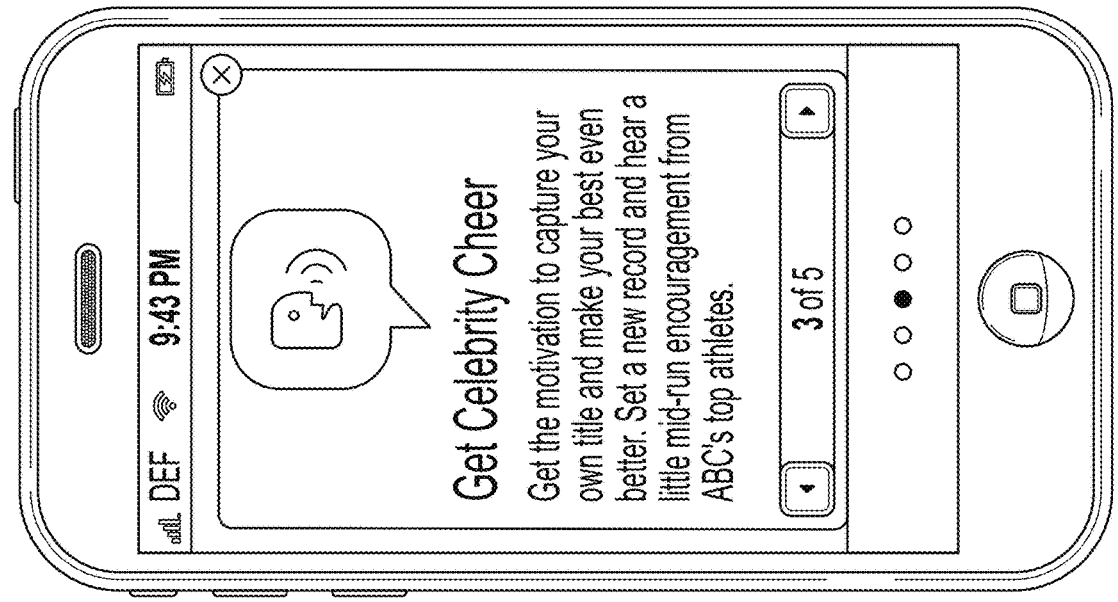
Figure 48C:
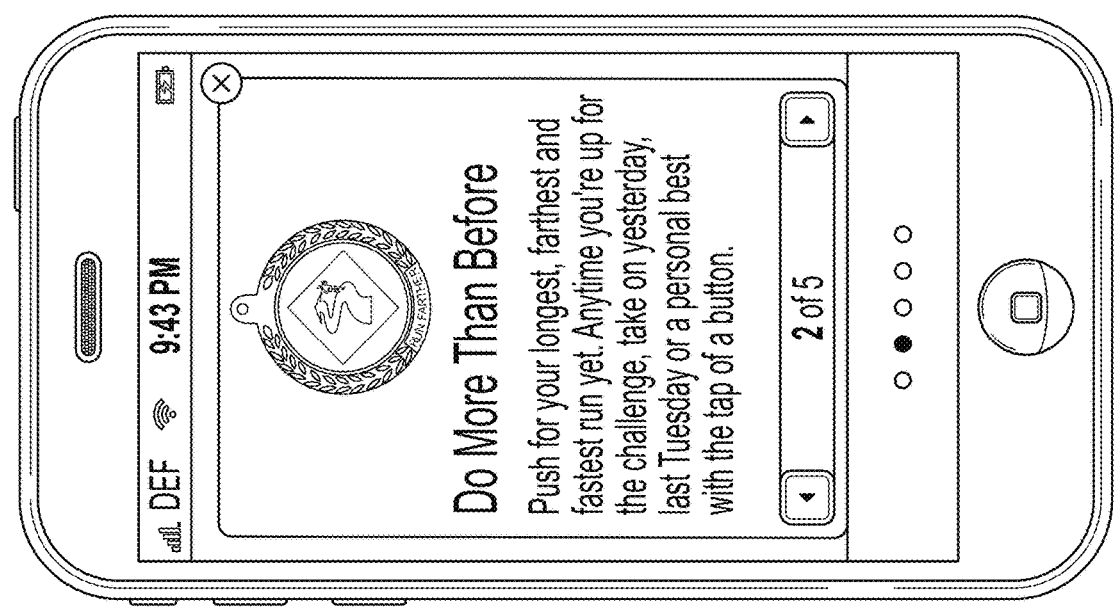
Figure 48F:
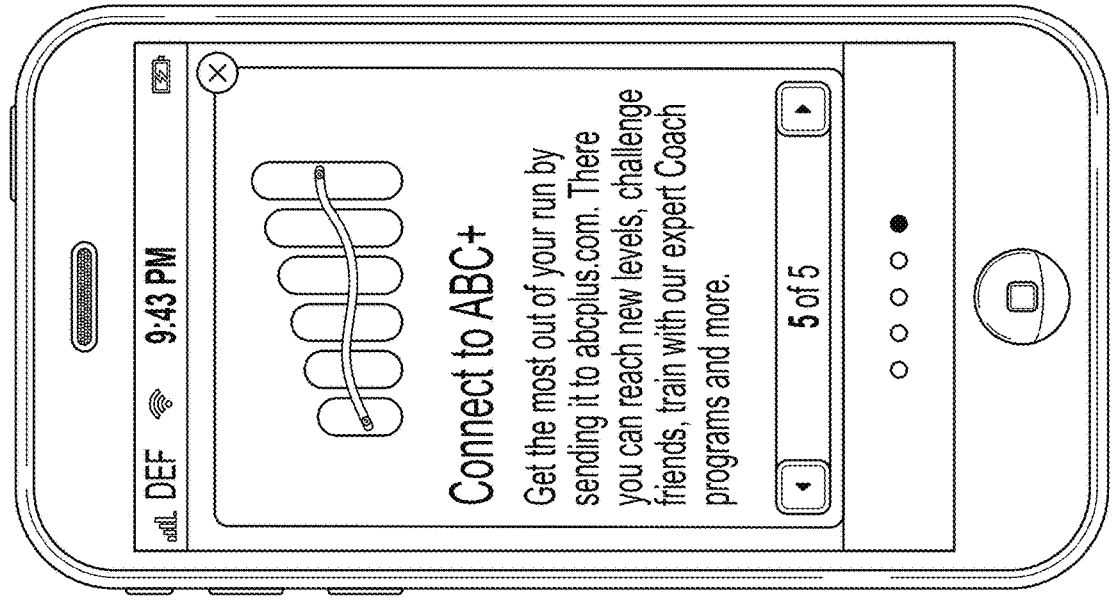
Figure 48E:
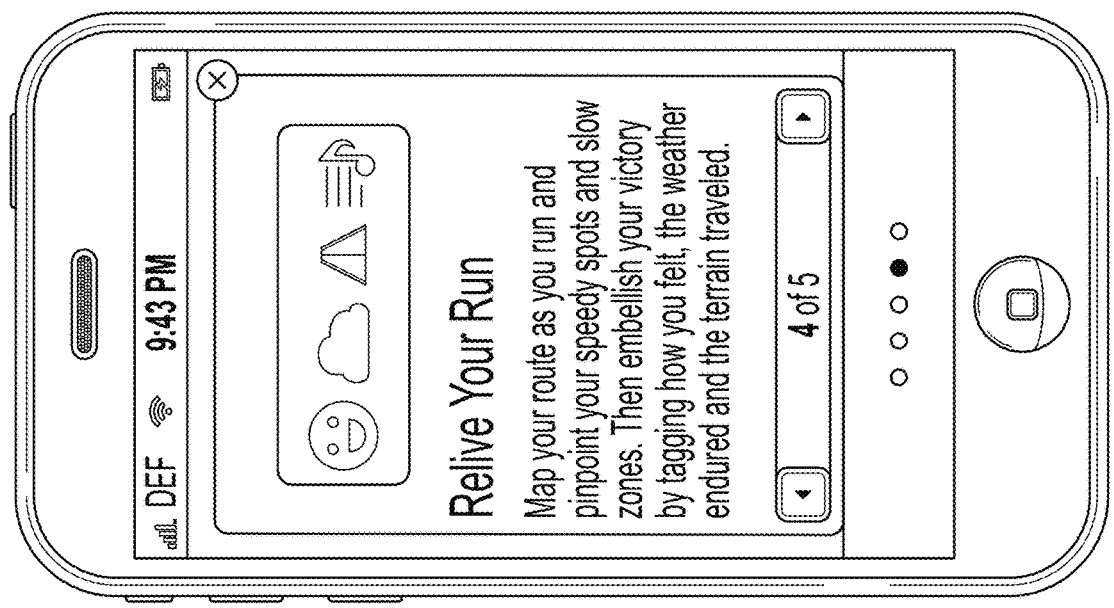
Figure 49B:
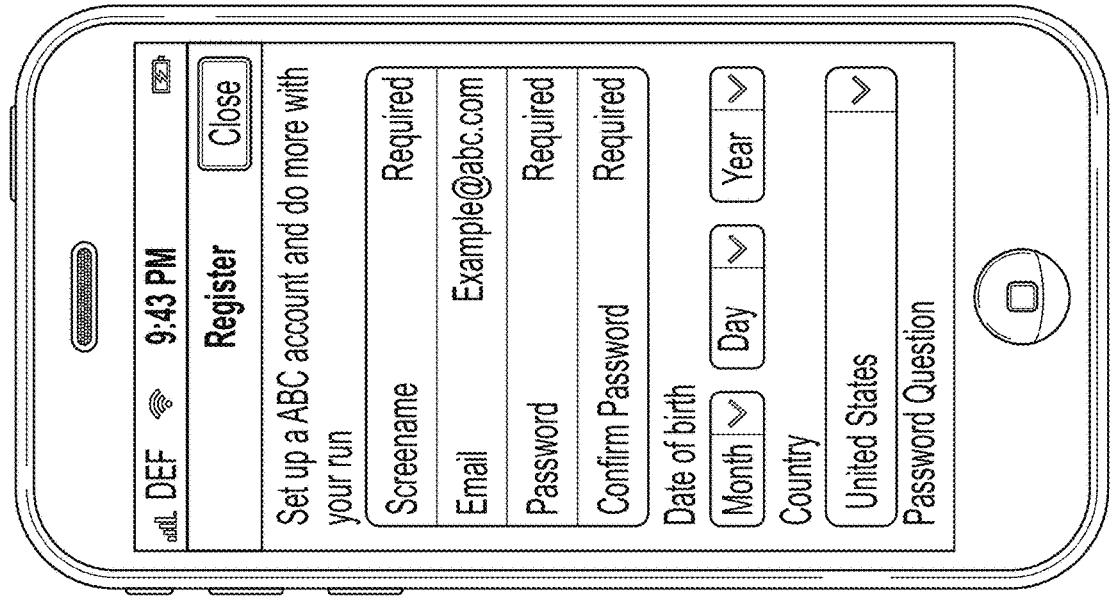
FIGS. 49A-49E illustrate a sequence of example interfaces through which a user may register with a service provider according to one or more aspects described herein.
Figure 49A:
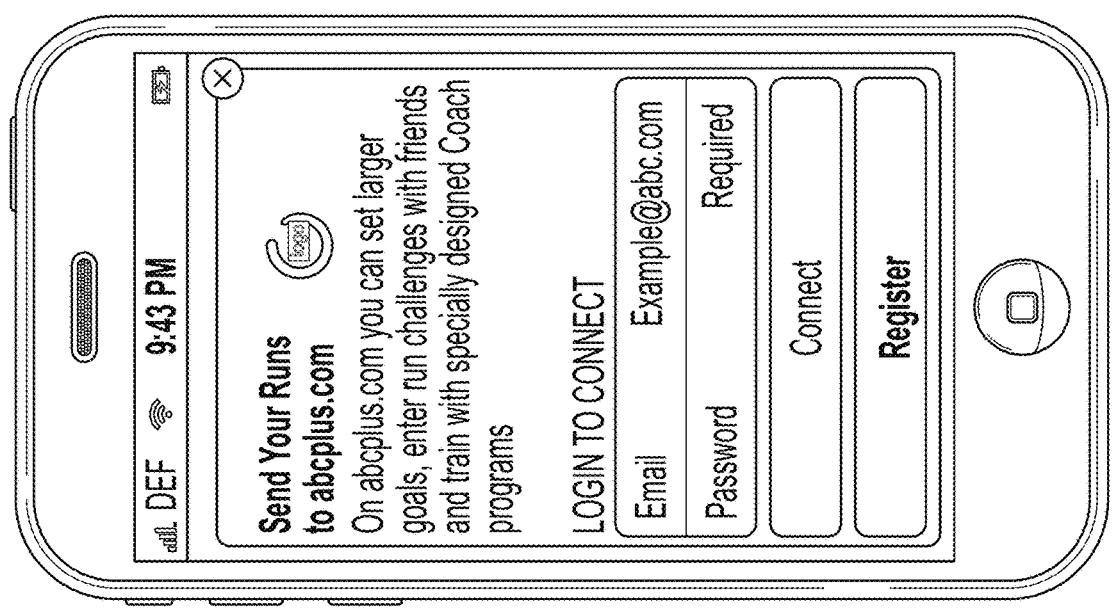
Figure 49D:
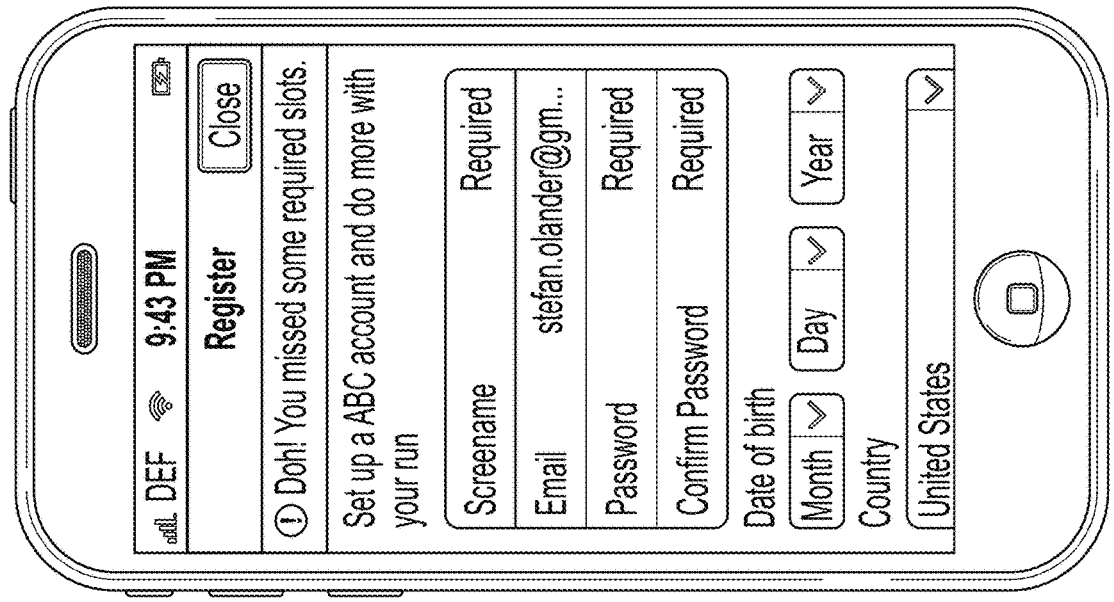
Figure 49C:
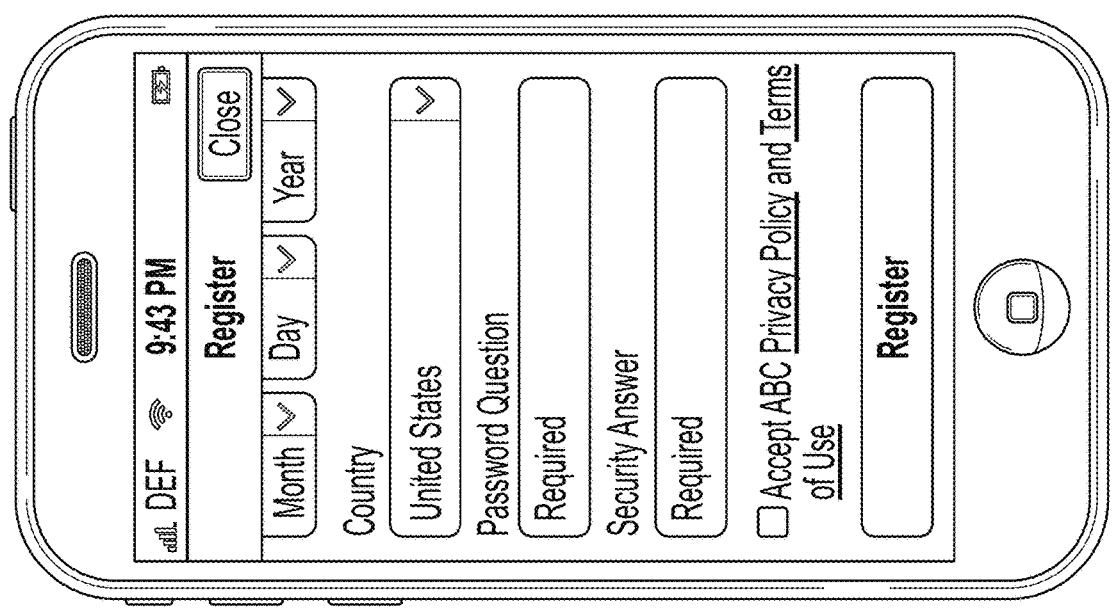

The user may define various settings that may affect the monitoring of a workout, recording of data and synchronization of data. FIGS. 47A and 47B illustrate example portions of various settings interfaces. FIG. 47A includes options allowing the user to define a distance metric (e.g., miles, feet, meters), frequency of feedback, whether the screen should be locked, calibration options and service provider account information (e.g., to allow for data synchronization). In FIG. 47A, the user has not defined or registered with the service provider. Accordingly, a tour option may also be included to allow the user to tour the features or services provided by the service provider upon the user registering.

Selection of the tour option may provide the user with additional information about the fitness monitoring and motivation features and functions of an underlying application and device. For example, FIGS. 48A-48F illustrate tour interfaces that provide detailed information describing the available features and functions.

FIG. 47B illustrates a settings interface portion that may be displayed if the user has provided service provider account information. By defining service provider account information, the user may be provided with a further option to define whether automatically synchronization should be performed. The tour option included in FIG. 47A might not be included in the interface of FIG. 47B. The user may also be provided with an option to sign out of the service provider. By signing out, the interface may change to the interface of FIG. 47A. Alternatively, the service provider account information may be stored and the sign out option replaced with a sign in option.

FIGS. 49A-49E illustrates a sequence of interfaces through which a user may register with a service provider. Some information may be required or optional including a username, an email, password, date of birth and the like.

Figure 50A:
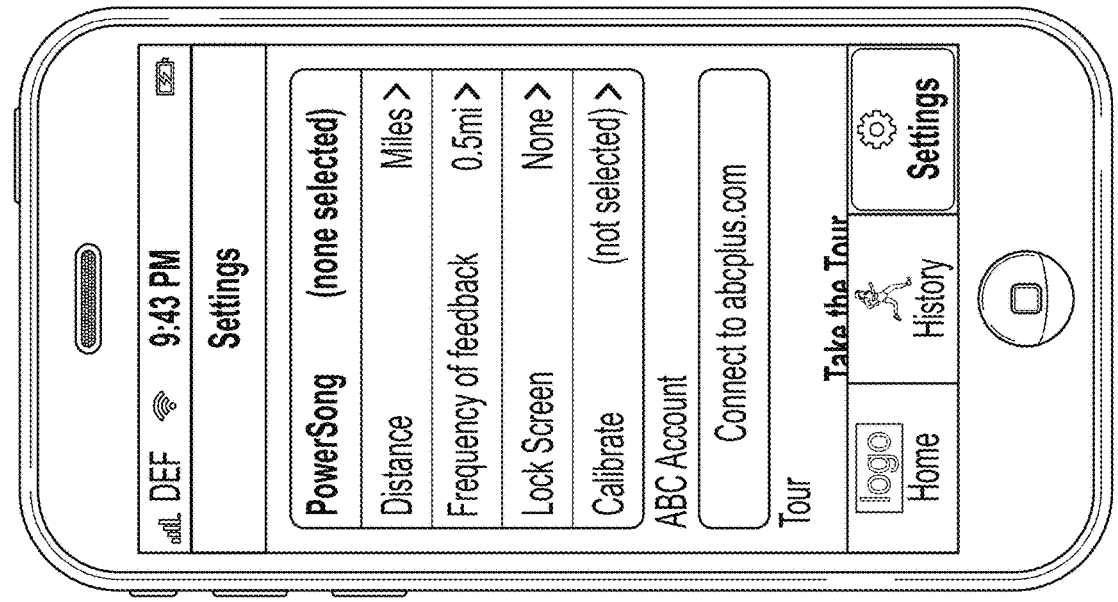
FIGS. 50A and 50B illustrate a sequence of example interfaces where a user may select a power song option and subsequently select a song from a song list according to one or more aspects described herein.
Figure 49E:
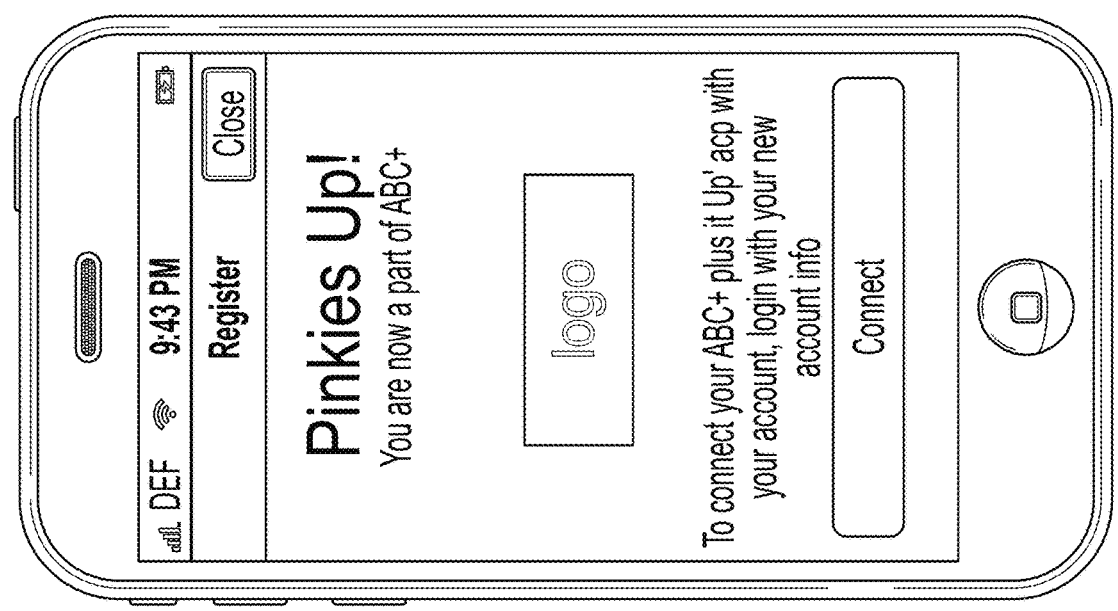
Figure 50B:
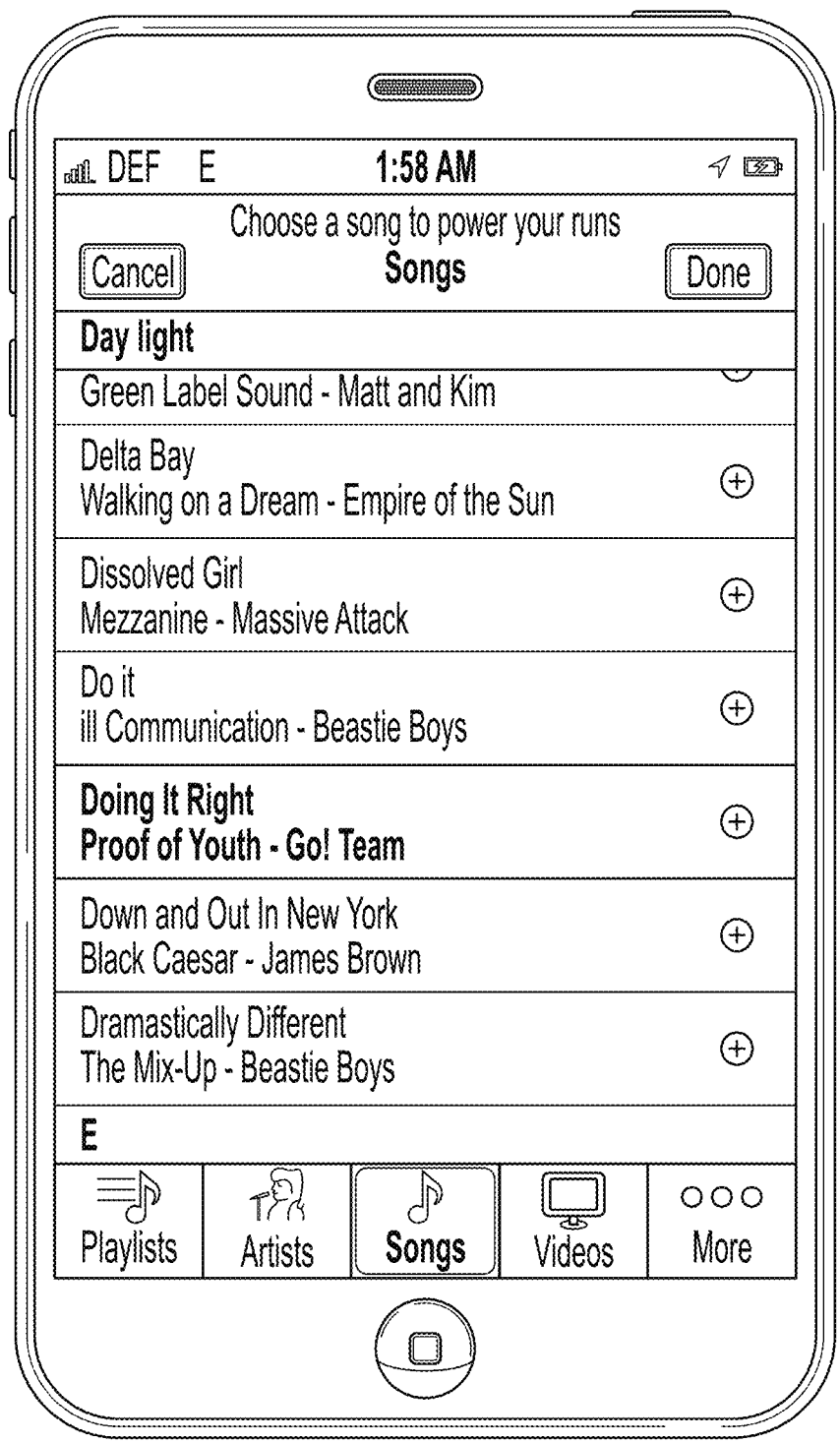

A user may be asked or allowed to choose a power song. A power song may correspond to audio content that the user finds particularly motivating. FIGS. 50A and 50B illustrate a sequence of interfaces where a user initially selects the power song option and subsequently selects a song from a song list. The song list may be a list of songs already owned by the user or may include songs available through an audio content provider. In FIG. 50A, if a power song is not selected, the power song option may indicate as much in a portion of the selection button. In contrast, if a power song is selected, the name of the power song may be displayed in the portion of the selection button.

Figure 51B:
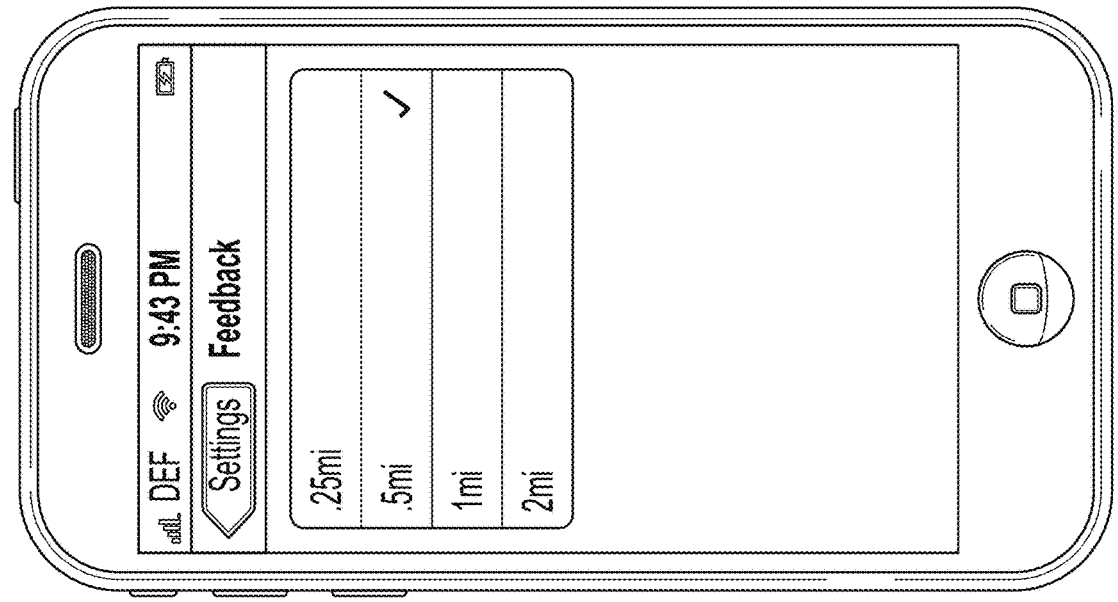
FIGS. 51A-51C illustrate example interfaces that allow the user to set the distance metric, a feedback frequency and a lock screen orientation, respectively, according to one or more aspects described herein.
Figure 51A:
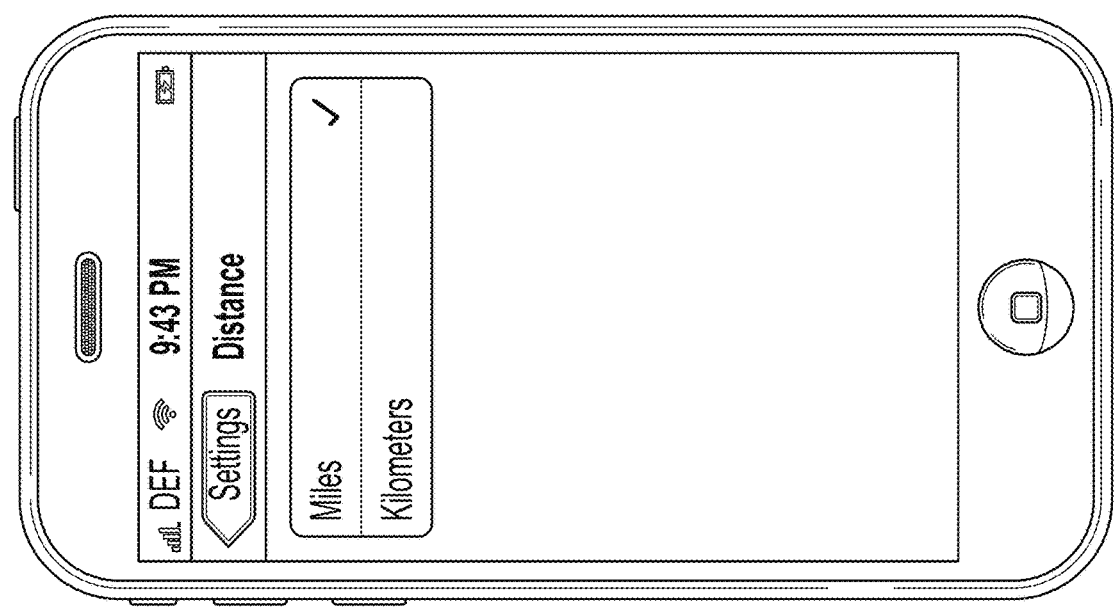
Figure 52A:
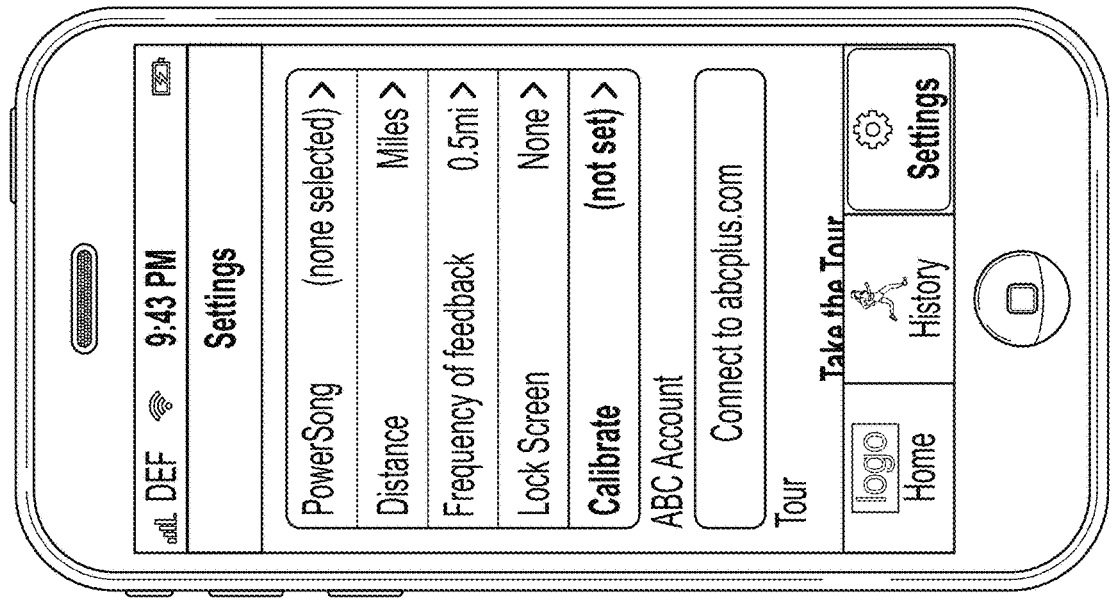
FIGS. 52A-52H illustrate example calibration interfaces for defining various user attributes and preferences that may enable more accurate monitoring and tracking of athletic activity statistics.
Figure 51C:
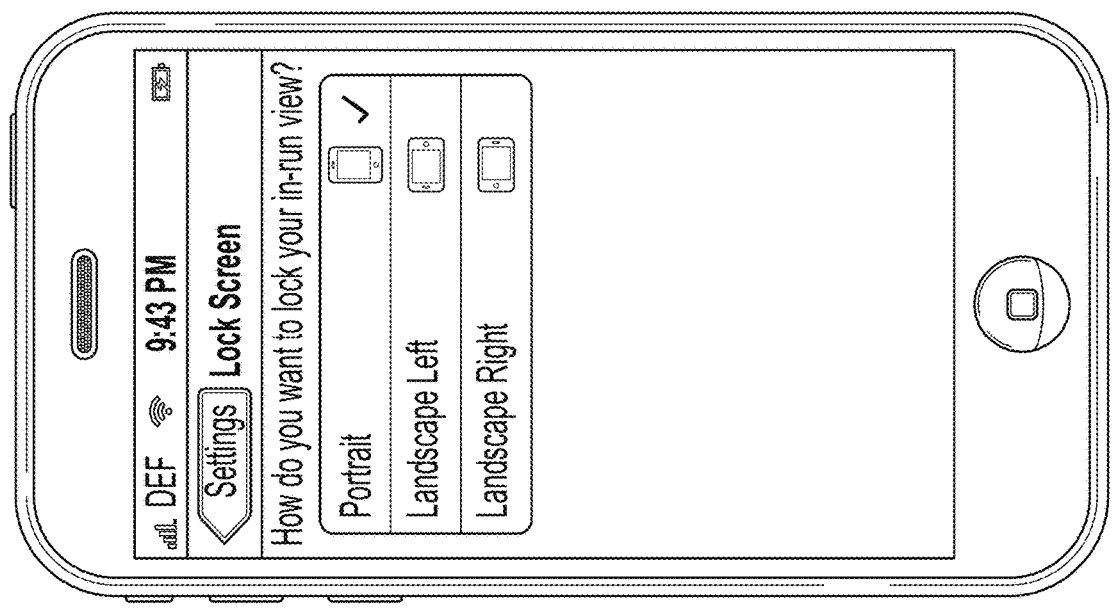
Figure 52C:
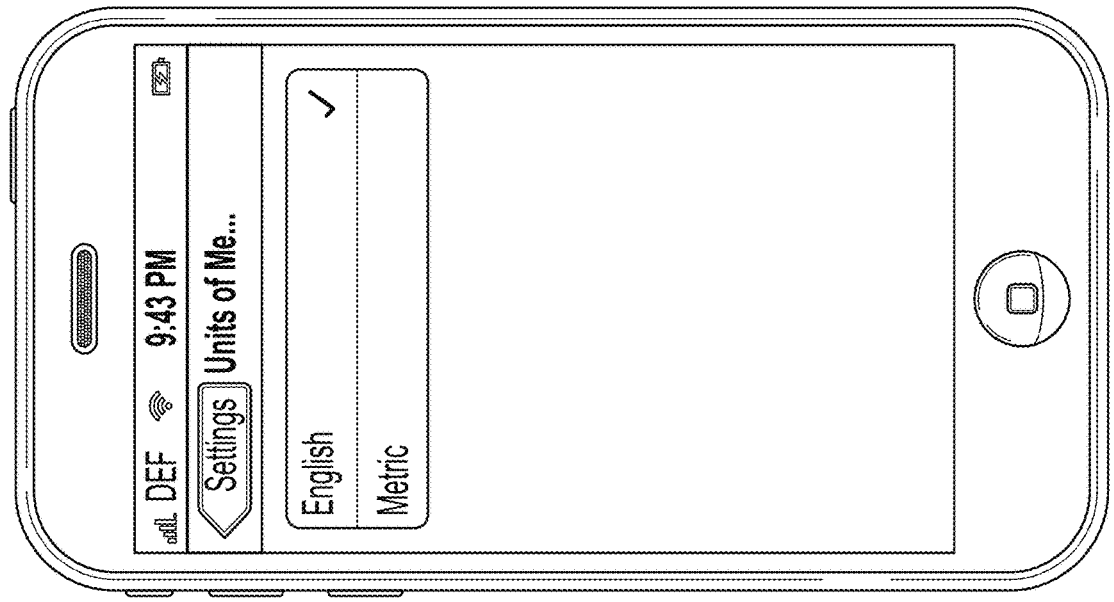
Figure 52B:
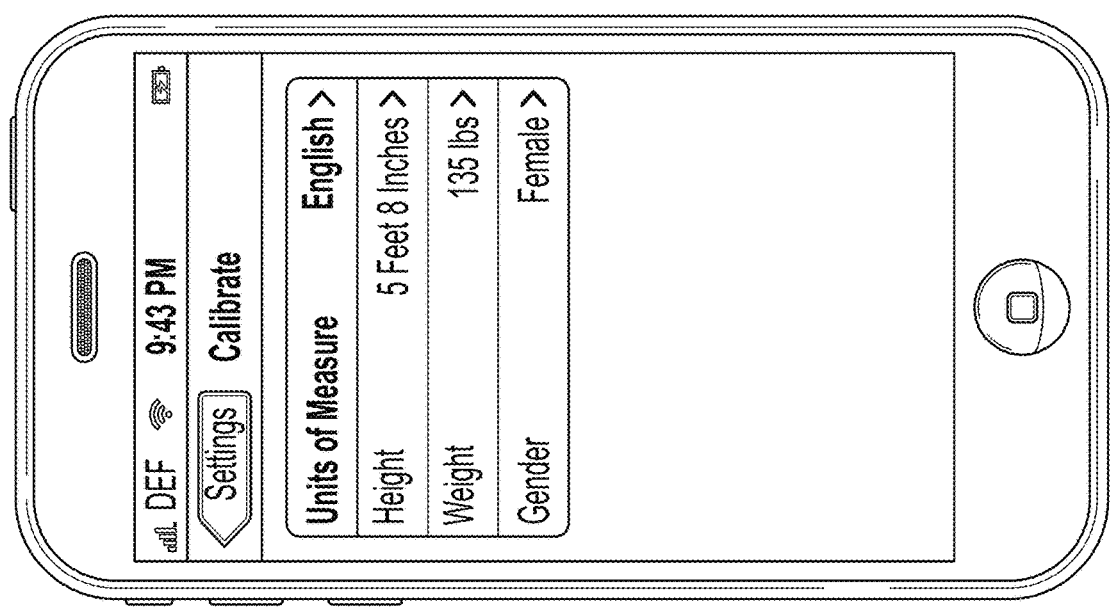
Figure 52E:
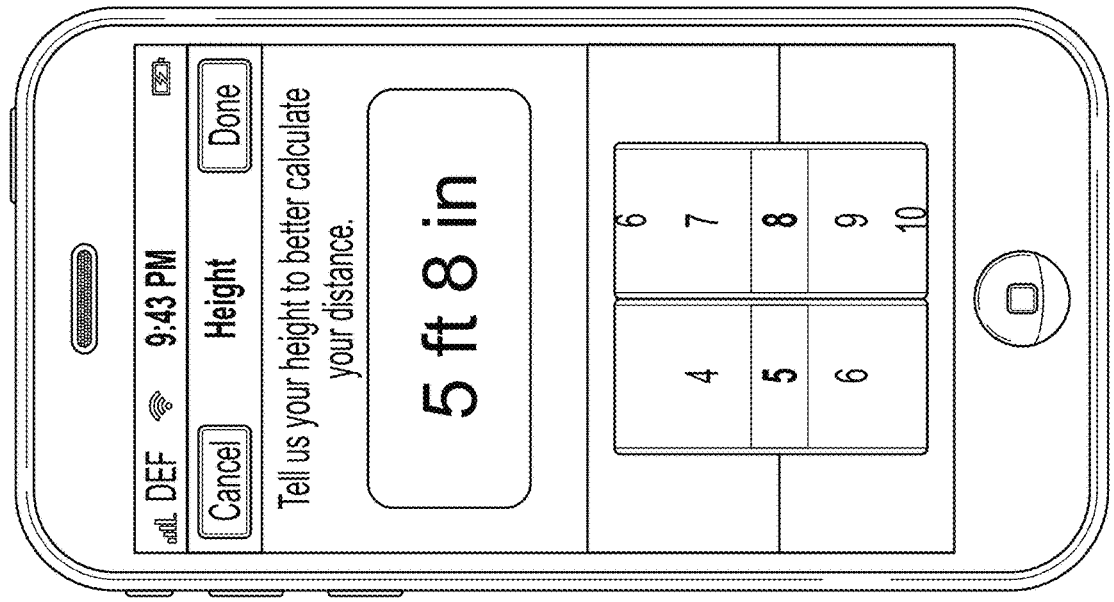
Figure 52D:
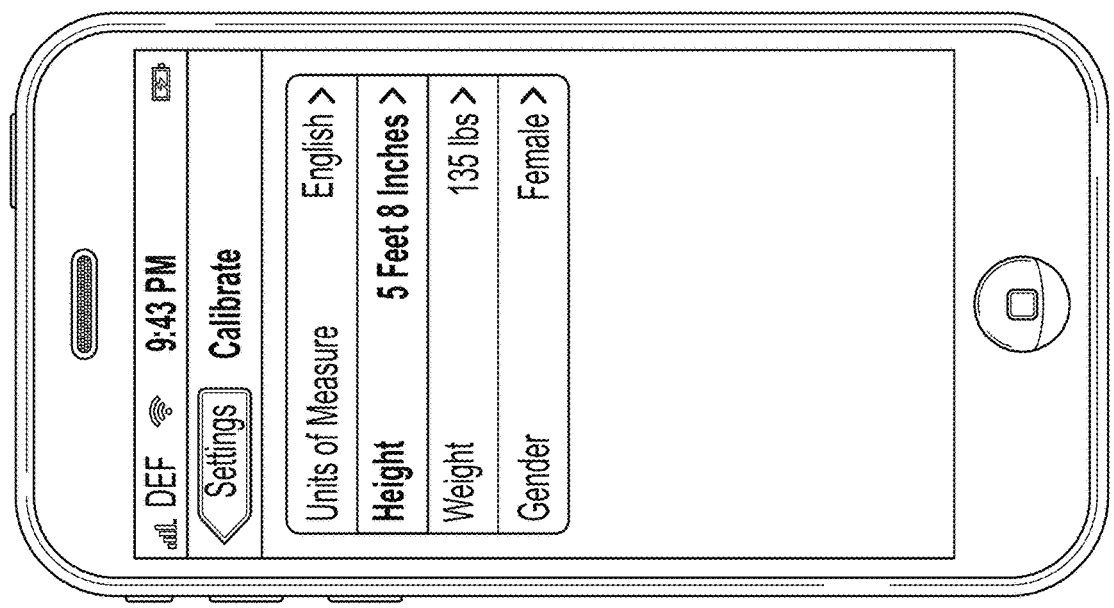
Figure 52G:
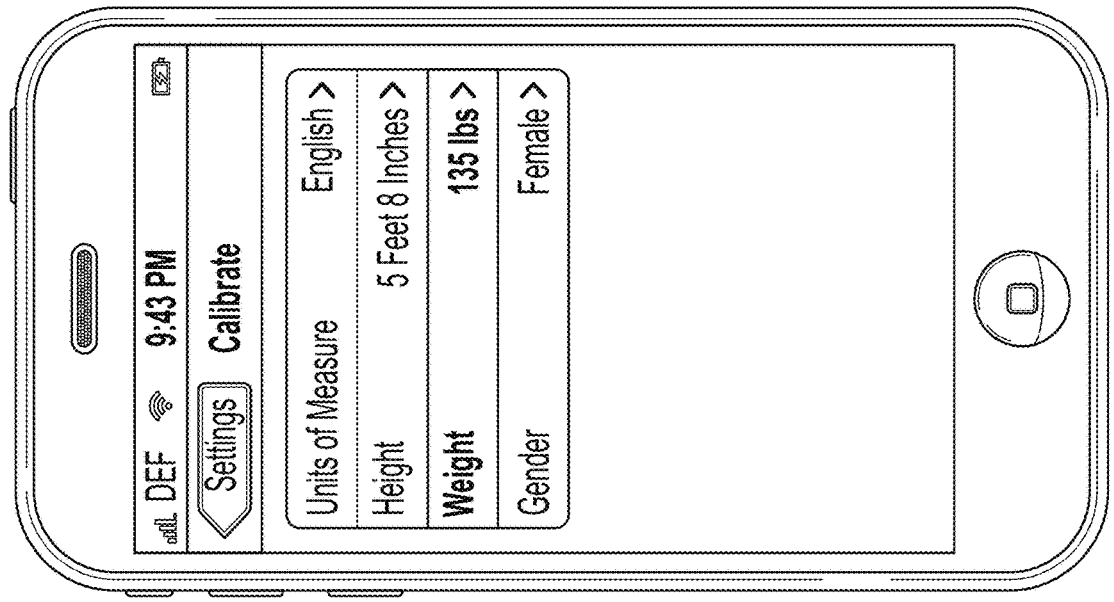
Figure 52F:
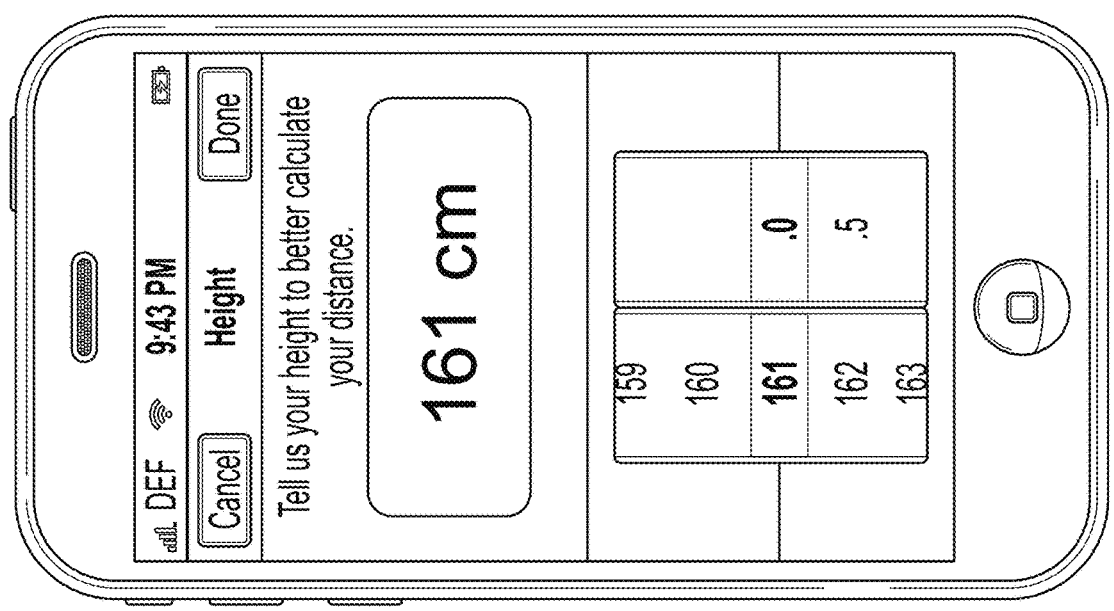

FIGS. 51A-51C illustrate interfaces that allow the user to set the distance metric, a feedback frequency and a lock screen orientation, respectively. For example, FIG. 51A illustrates an interface through which the user may select either miles or kilometers as the unit of measurement. FIG. 51B, on the other hand, allows the user to define how frequently to provide feedback (audio or visual). The frequency may be distance-based or time-based. FIG. 51C illustrates an interface that allows the user to define the orientation in which to lock the interface. For example, the user may select a portrait orientation or a landscape orientation. The selection may be made based on a user preference, an orientation of the device during the run and/or a combination thereof.

FIGS. 52A-52H illustrate calibration interfaces for defining various user attributes and preferences that may enable more accurate monitoring and tracking of athletic activity statistics. Through a calibration menu (e.g., as displayed in FIG. 52B), the user may select the units of measure, a user height, a user weight and the user's gender. The units of measure, for example, may be chosen from options including English and metric. Height and weight may be defined using scroll wheels or other scrolling methods and may allow selection from values of the selected unit of measure. The device may use this data to better determine the results of a user's athletic activity. For example, the accelerometer readings may be translated or converted into calories burned, or distance run using the user's weight, height and gender.

Figure 53A:
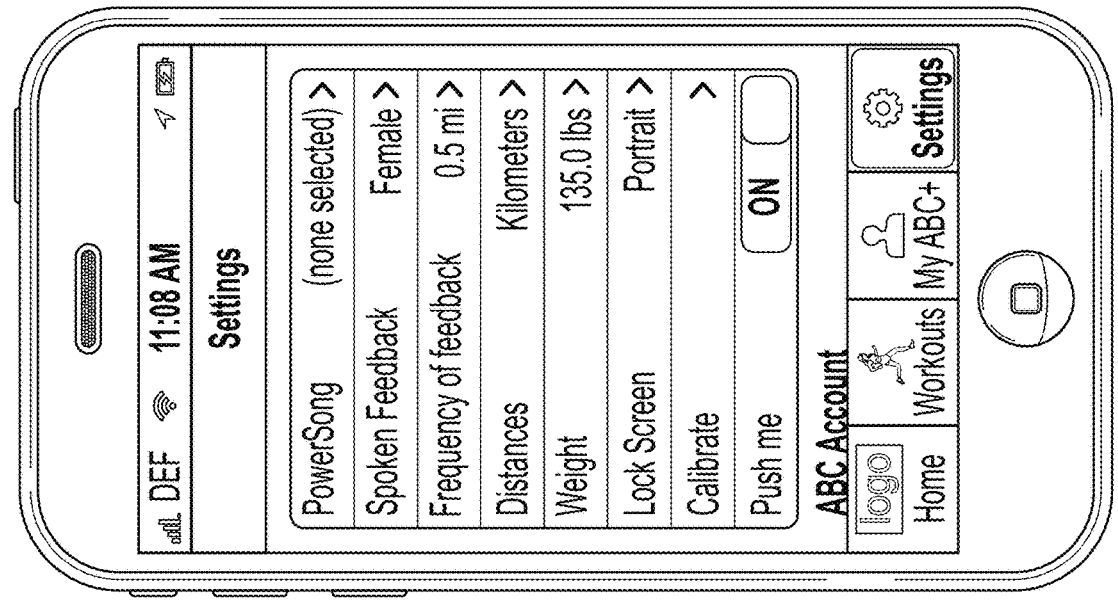
FIGS. 53A-53V illustrate alternative or additional settings interfaces that may be generated and displayed through the mobile fitness monitoring device according to one or more aspects described herein.
Figure 52H:
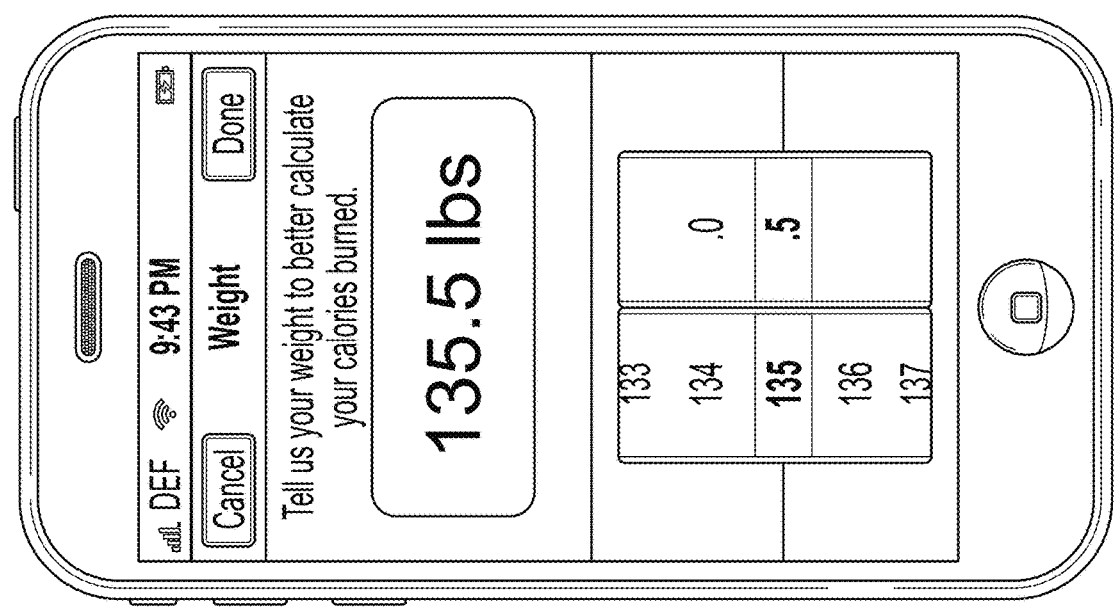
Figure 53C:
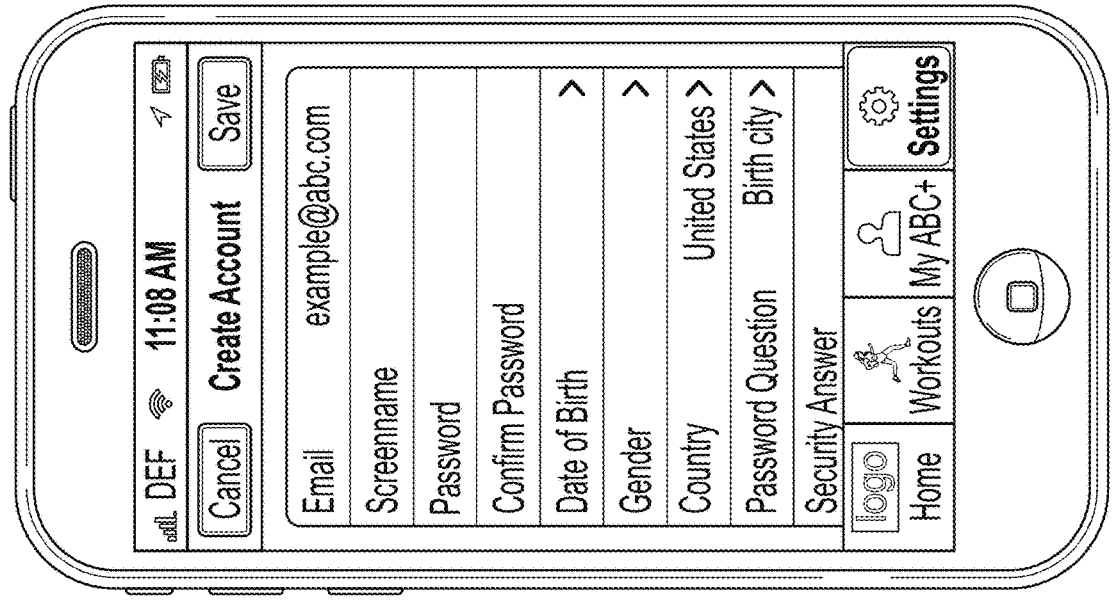
Figure 53B:
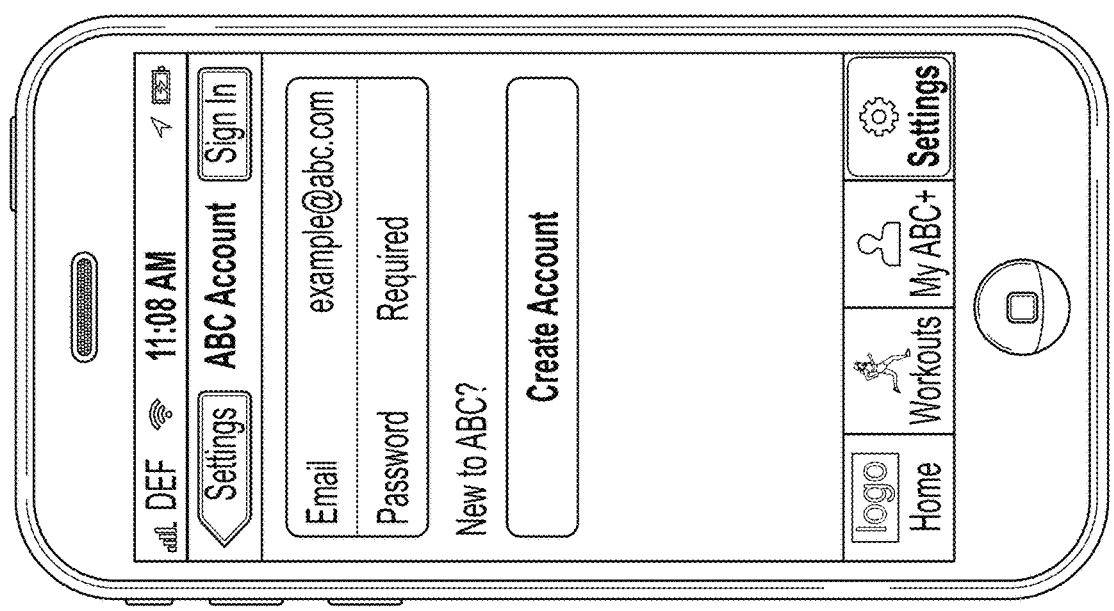
Figure 53E:
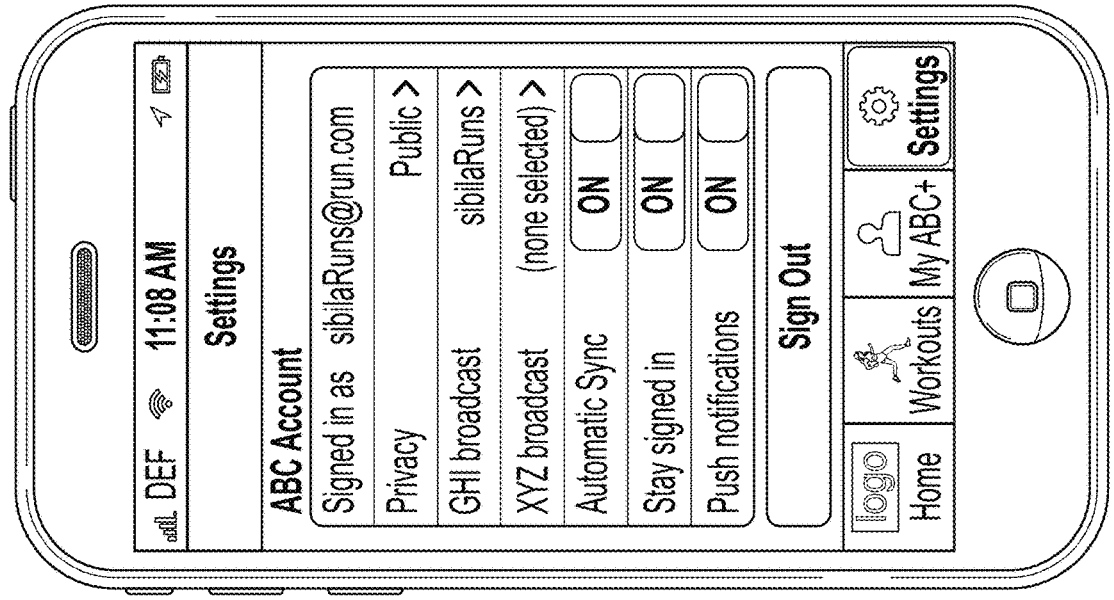
Figure 53D:
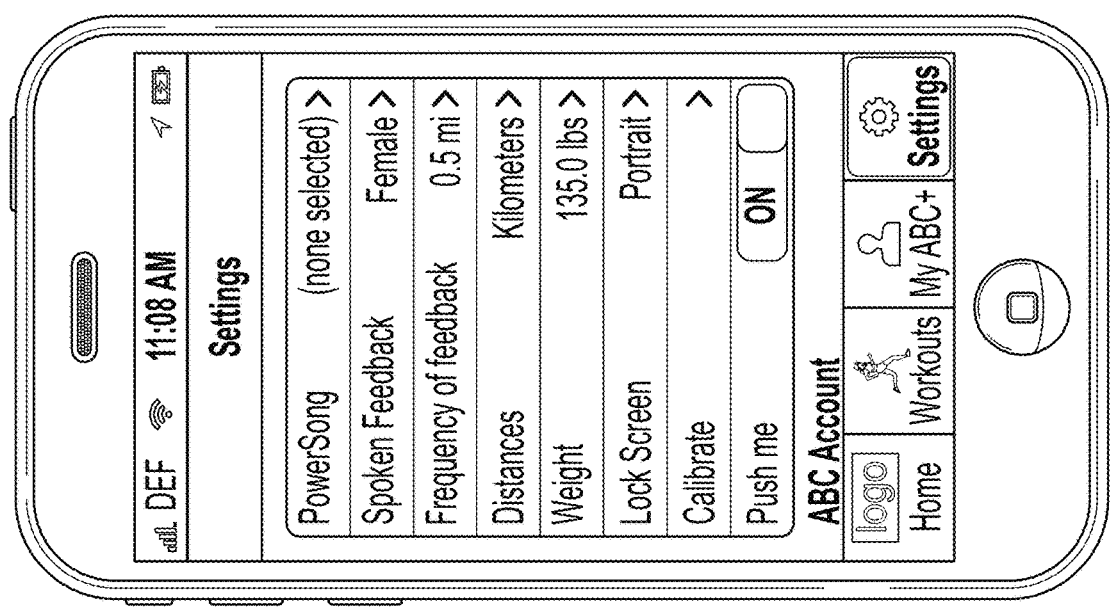
Figure 53F:
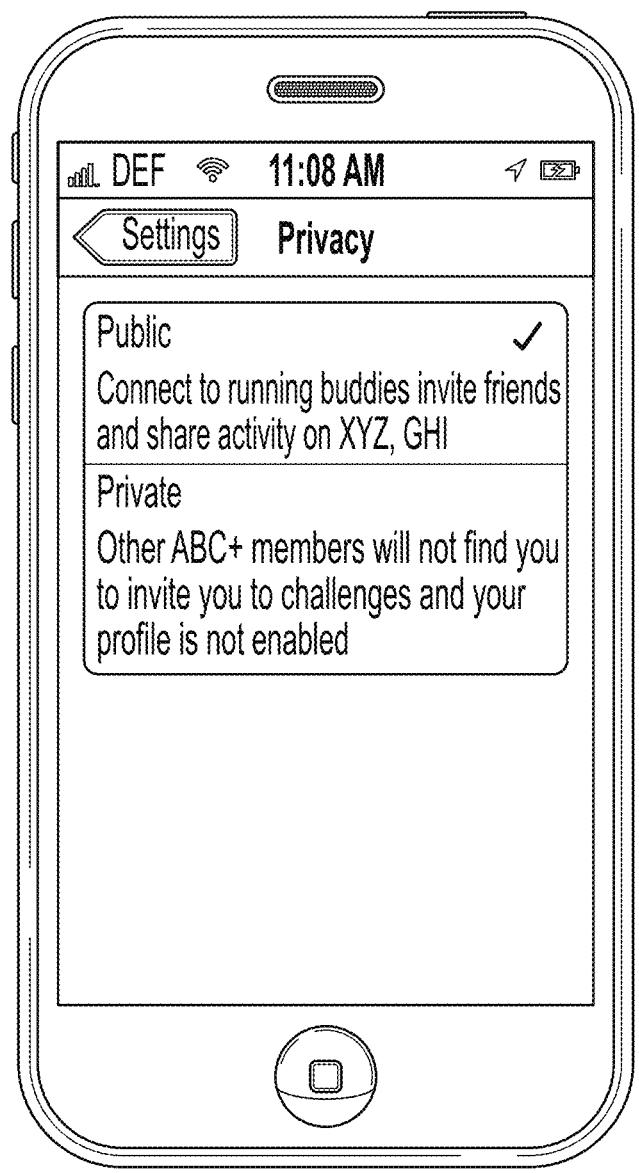
Figure 53G:
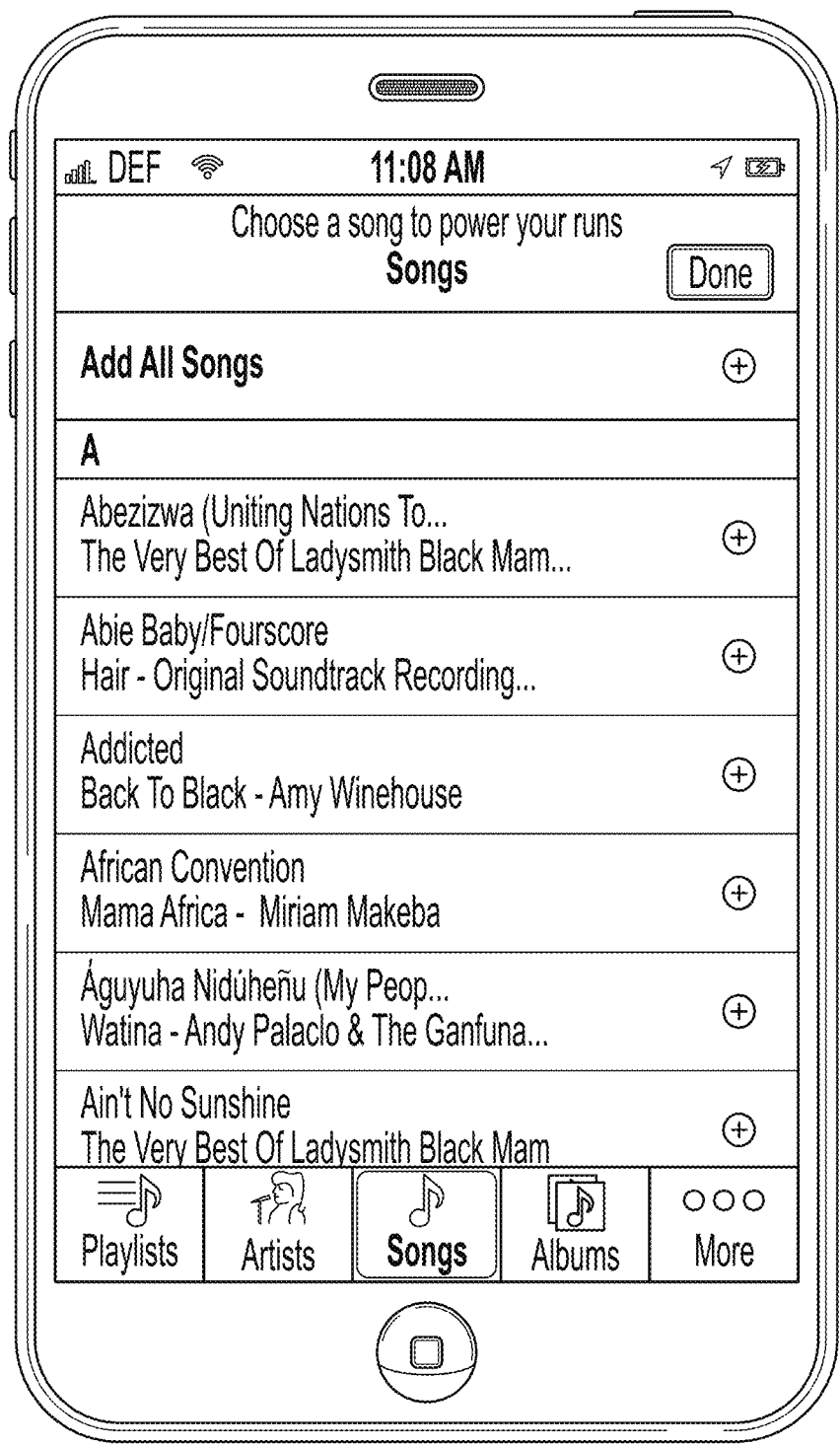
Figure 53I:
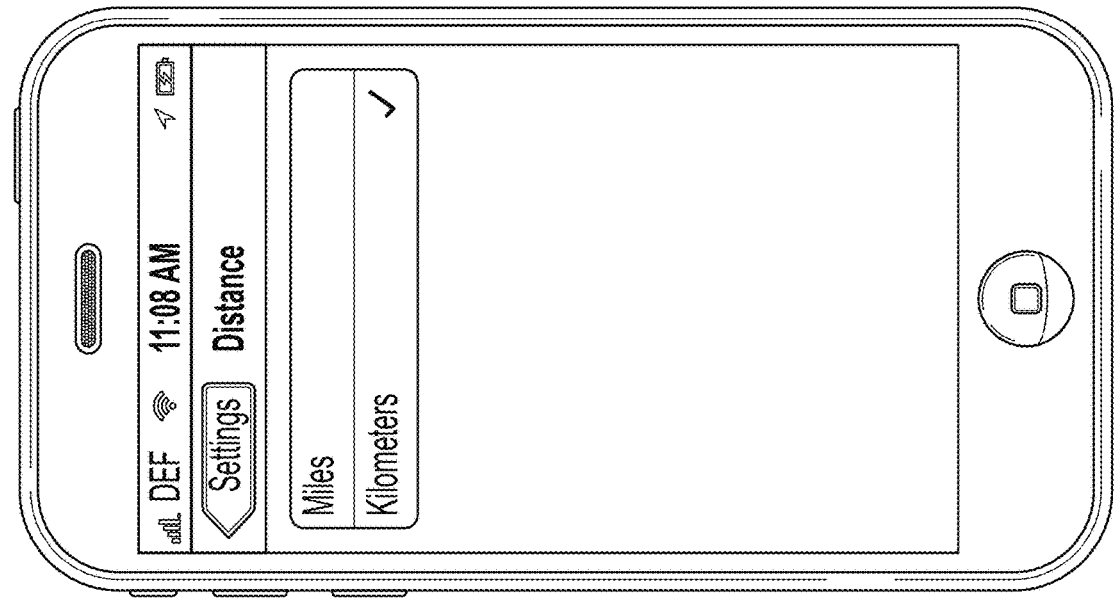
Figure 53H:
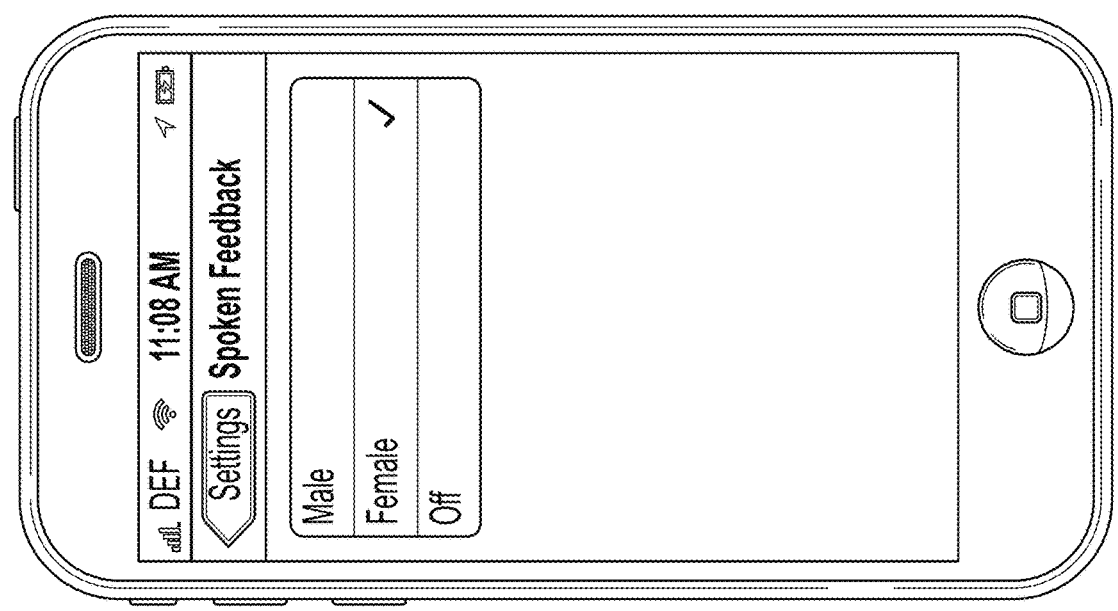
Figure 53K:
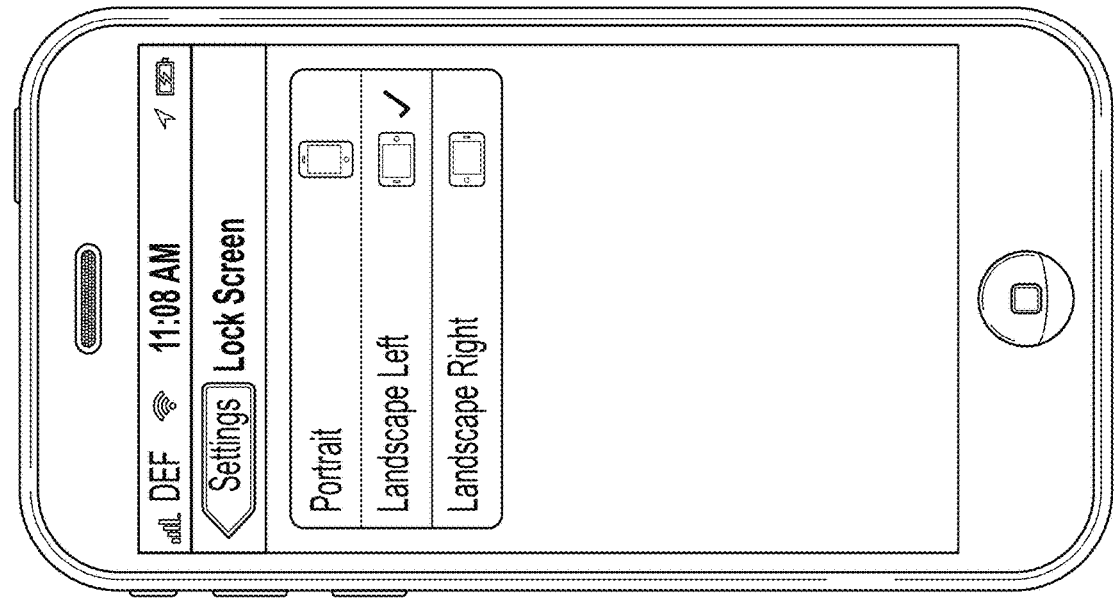
Figure 53J:
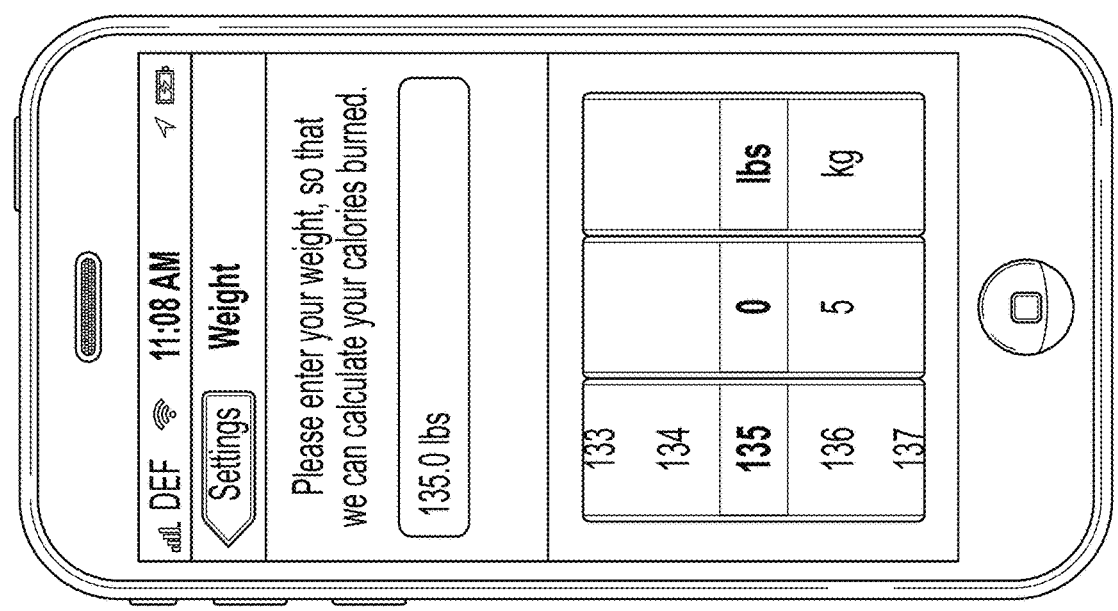
Figure 53M:
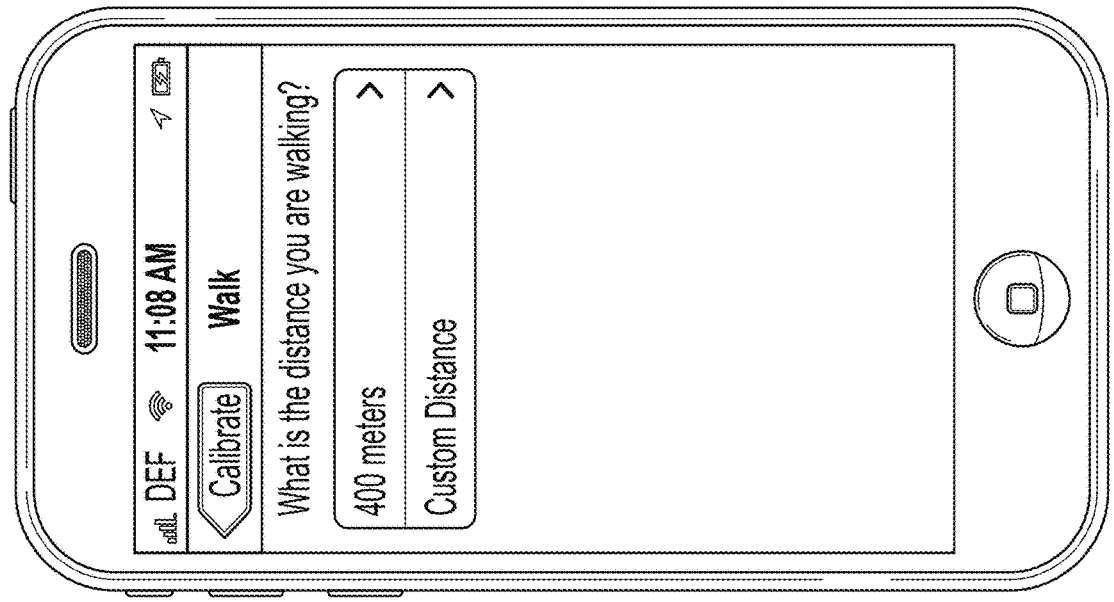
Figure 53L:
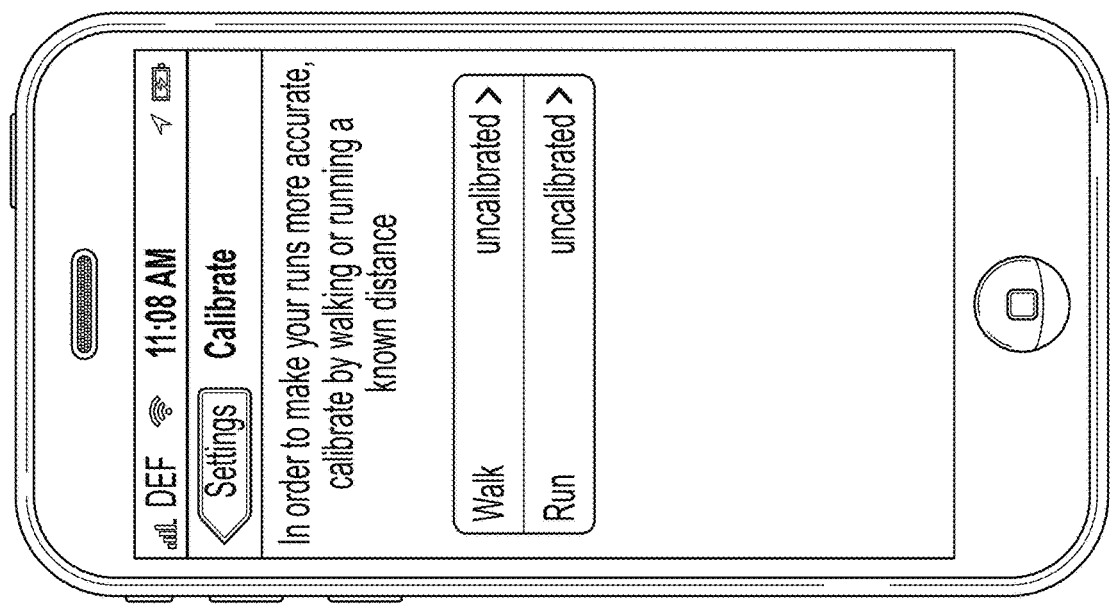
Figure 53N:
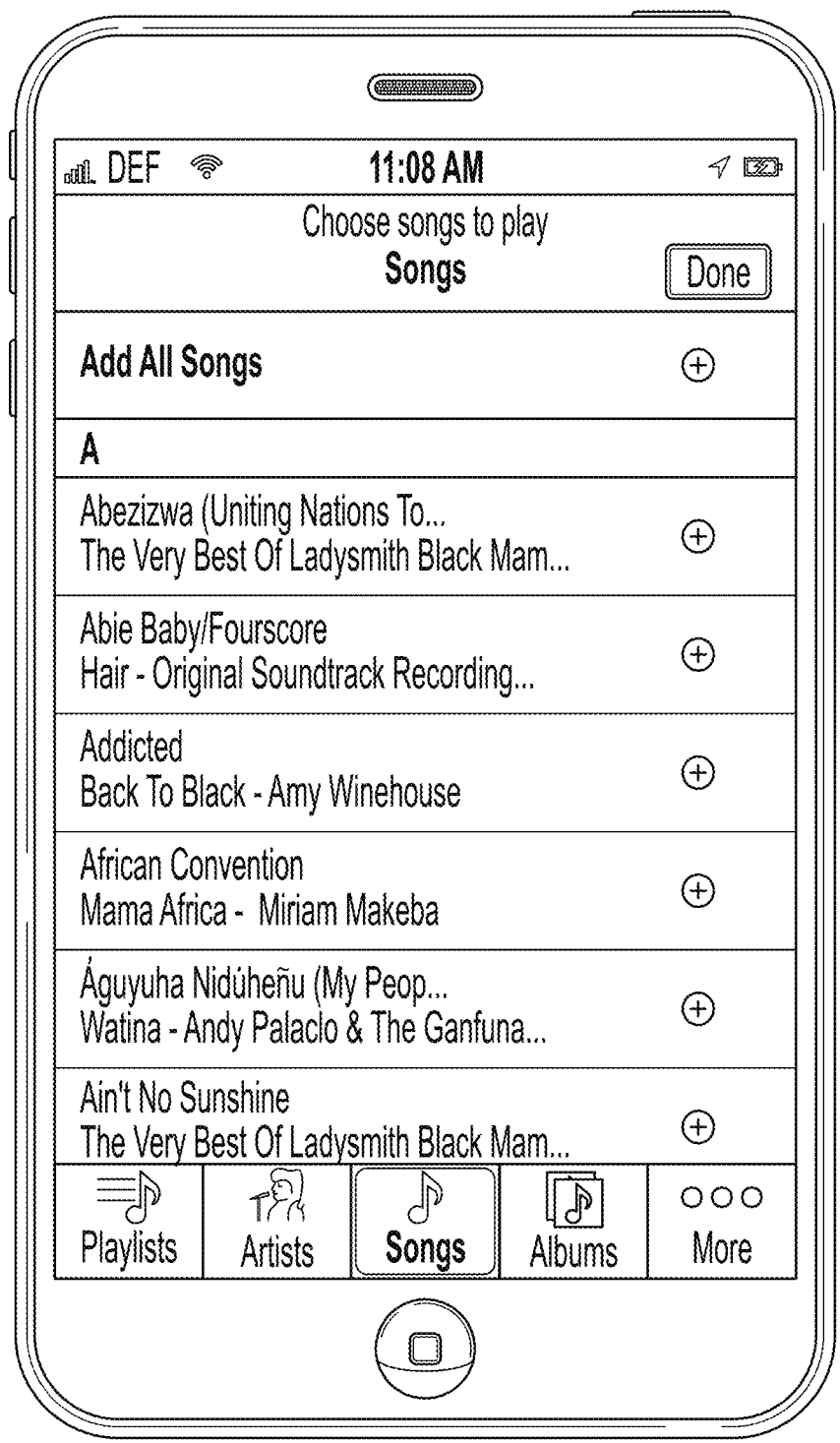
Figure 53P:
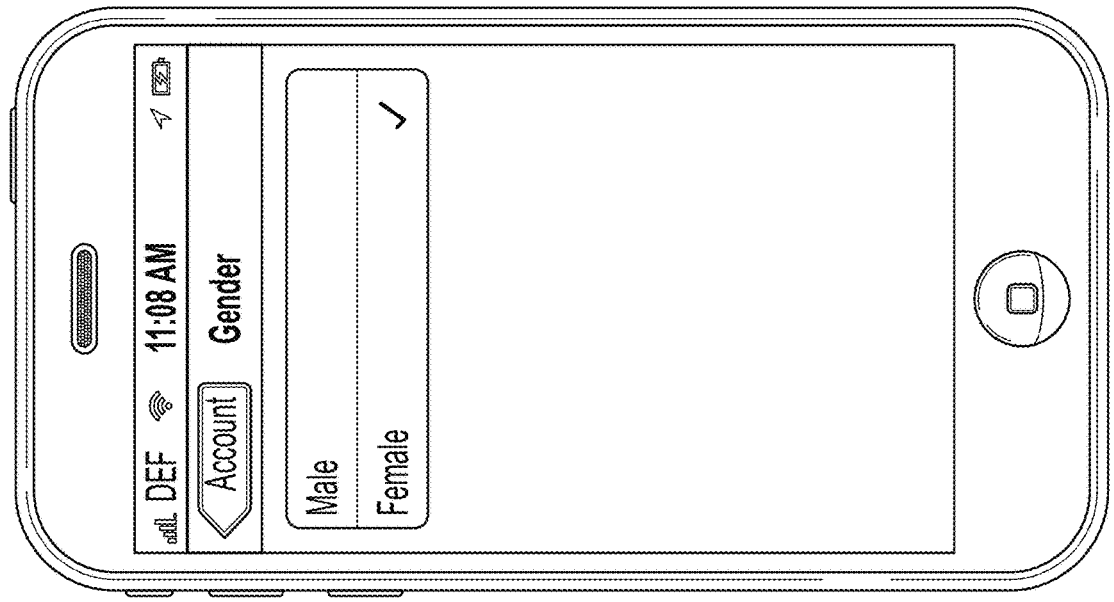
Figure 53O:
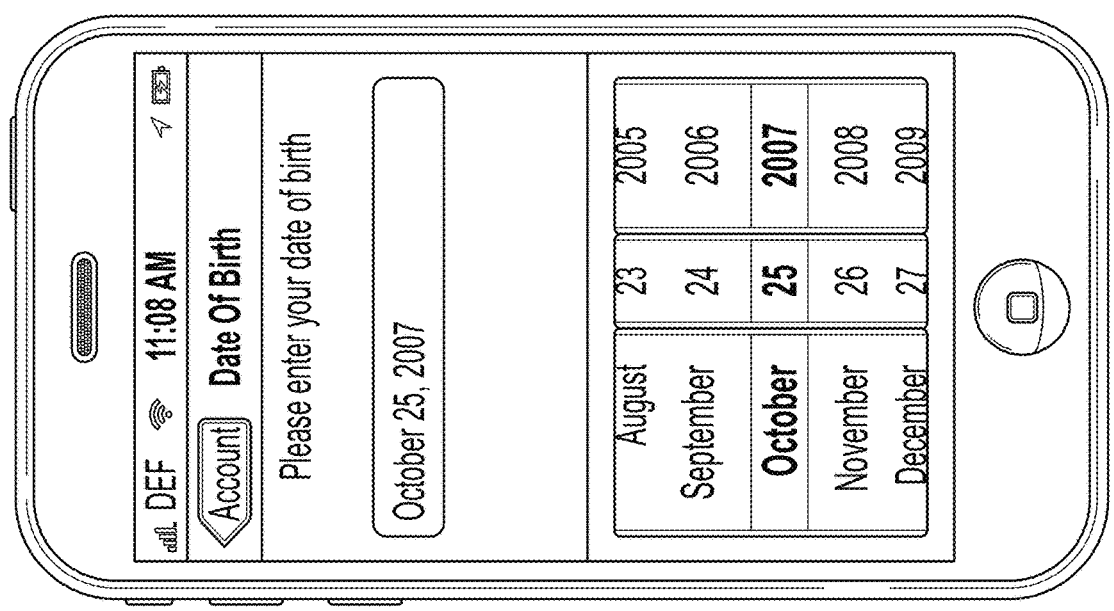
Figure 53R:
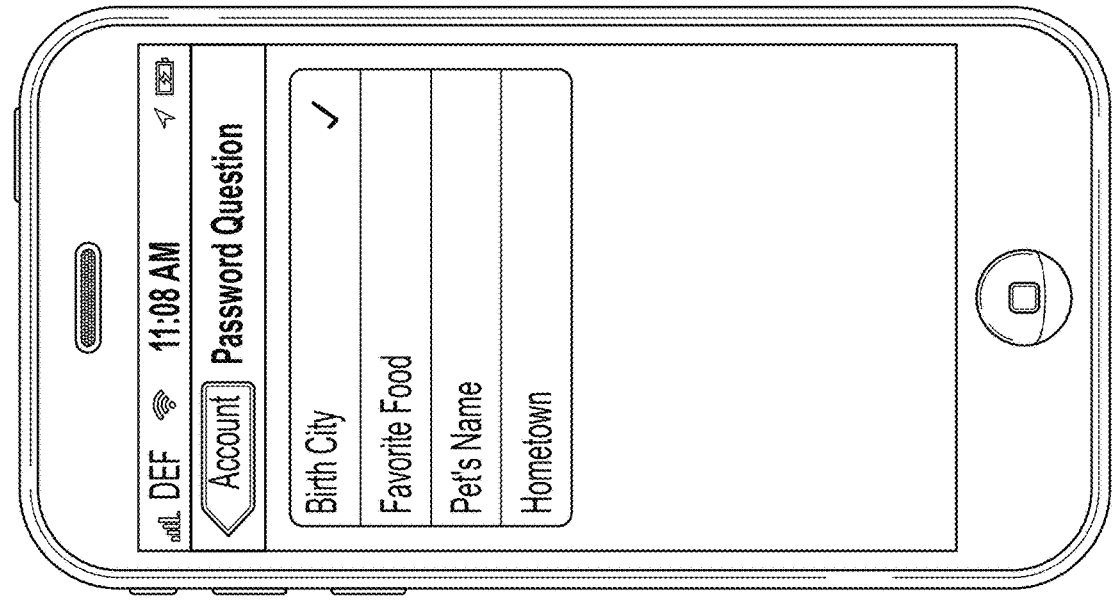
Figure 53Q:
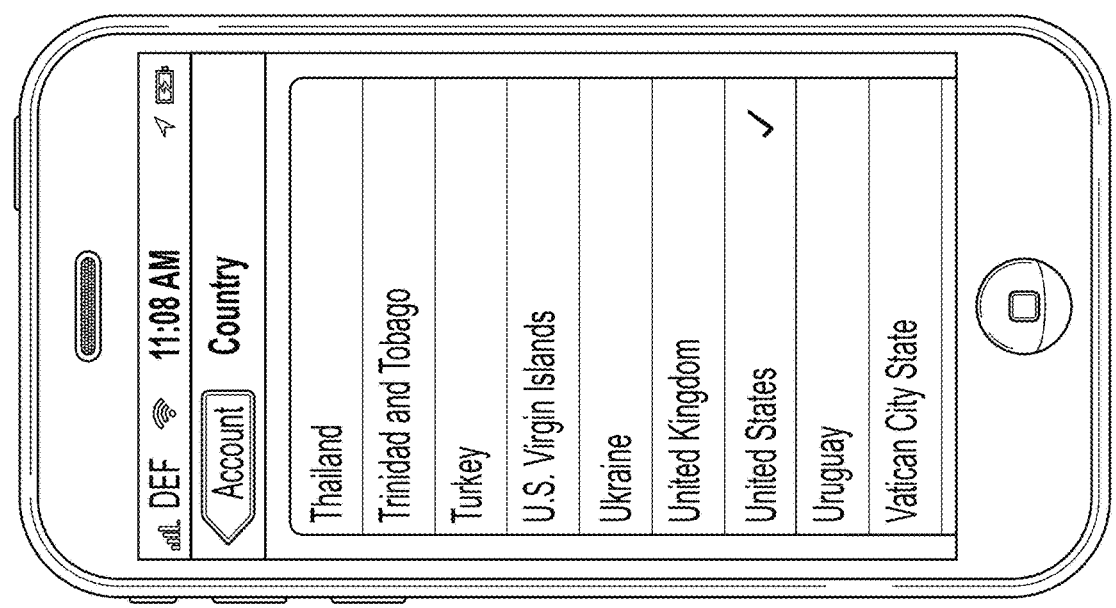
Figure 53T:
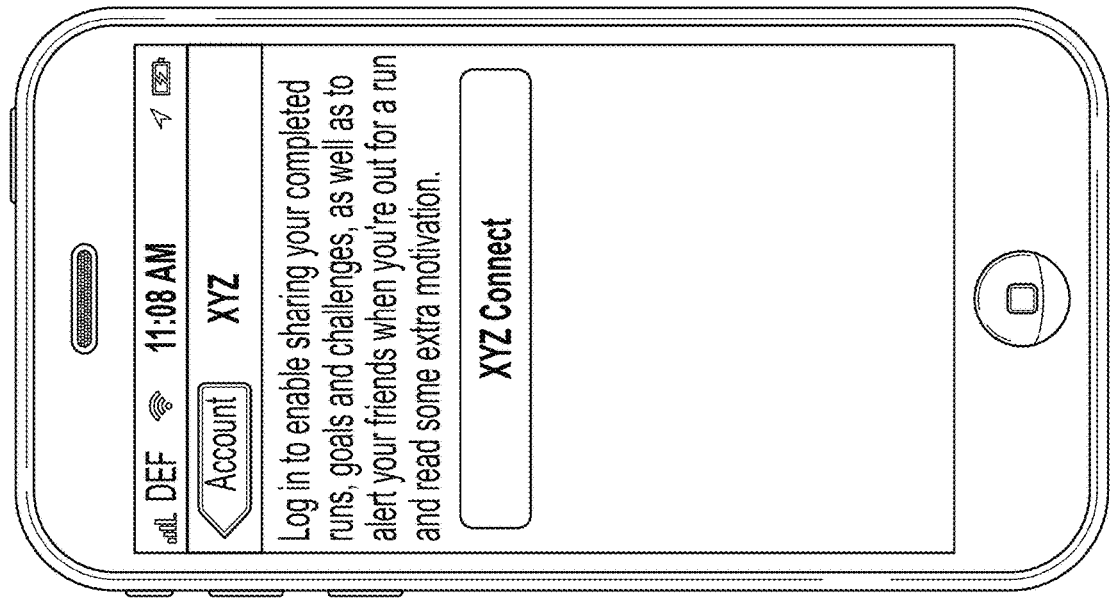
Figure 53S:
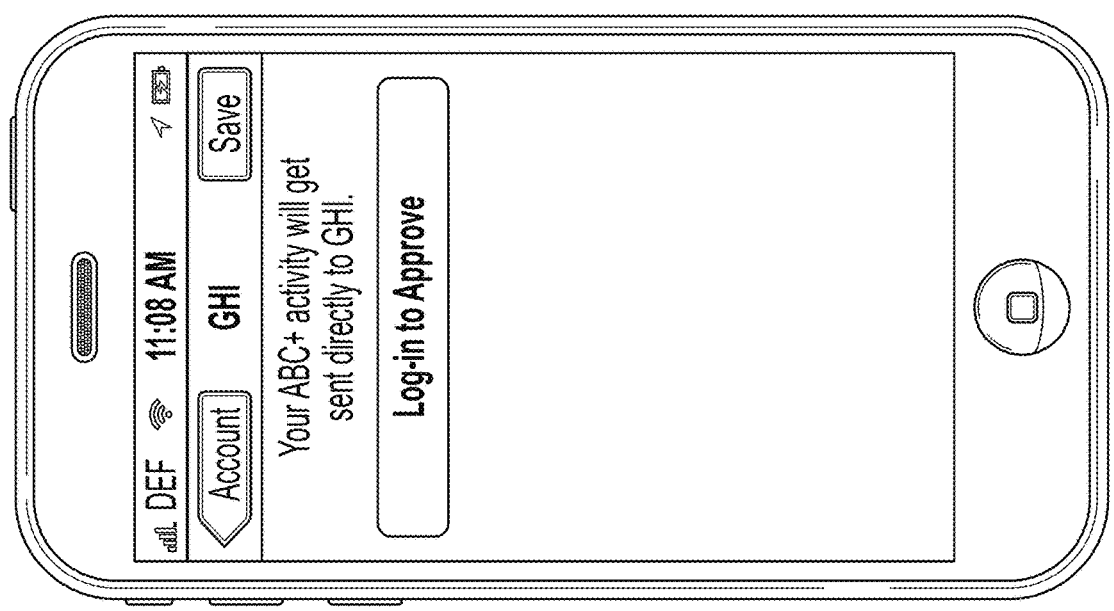
Figure 53V:
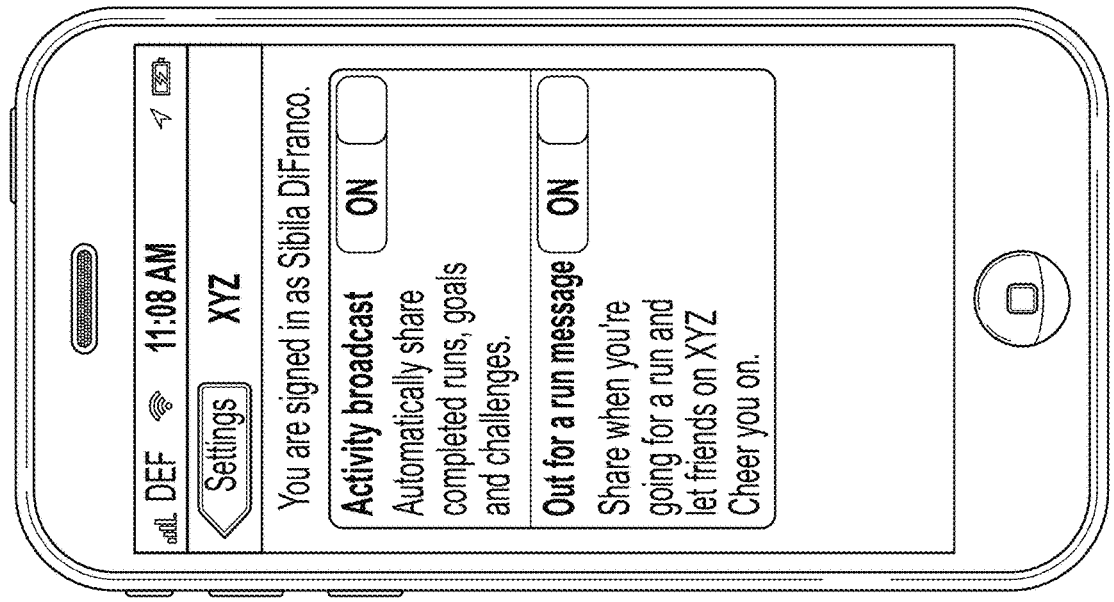
Figure 53U:
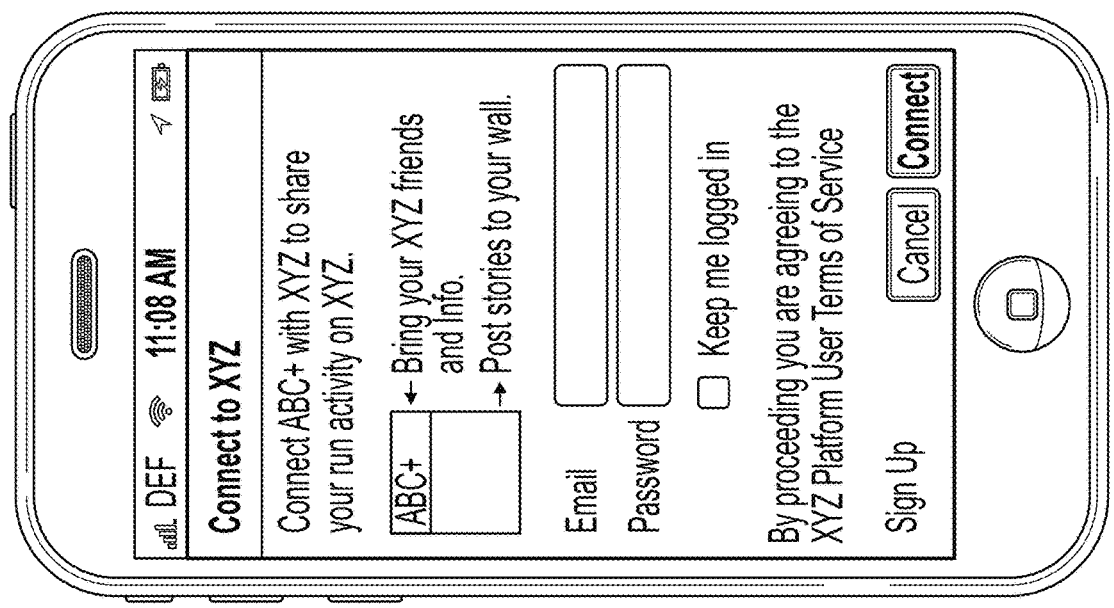

FIGS. 53A-53V illustrate alternative or additional setting interfaces that may be generated and displayed through the mobile fitness monitoring device. The interfaces of FIGS. 53A-53C may, in one or more examples, be configured for beginner users while the interfaces of FIGS. 53D-53F may be configured for more advanced or power users. Advanced or power users may include users that already have registered with a fitness monitoring service provider. Accordingly, FIG. 53E may include additional account and monitoring setting information that might not otherwise be displayed for non-registered users. Additionally, a user may be able to select privacy settings in the interface of FIG. 53F. If a user chooses a private setting, other users might not be able to find the user or view the user's information. If, on the other hand, a public setting is selected, other users may be able to publicly search for the user and view various types of information about the user. The public setting may also allow for sharing information on other sites such as social network sites and news feeds.

In other aspects, a user may define information sharing settings. For example, FIGS. 53S-53V illustrate various setting interfaces that may be used to configure information accounts and sharing settings. FIG. 53S illustrates that workout information may be sent directly to a news feed automatically upon the user logging into the news feed service. The logging into the news feed service may correspond to approval of the automatic sharing feature.

FIG. 53V, on the other hand, may allow the user to set various settings for information sharing on a network site such as a social network site like FACEBOOK. In particular, the user may be able to enable or disable activity broadcasts. Activity broadcasts may include the automatic sharing of completed runs, goals and challenges. Additionally or alternatively, the user may enable or disable a function that notifies other users (e.g., placing a post or status update on the user's network site page) whenever the user is on a run or other workout. This may enable other users to post messages of encouragement and to track the user's progress during the run. Workout data may also be posted to social network sites and social networking feeds mid-run and in real-time. Various other features and functions may also be configured by the user for sharing information.

Workout Sharing

Figure 54B:
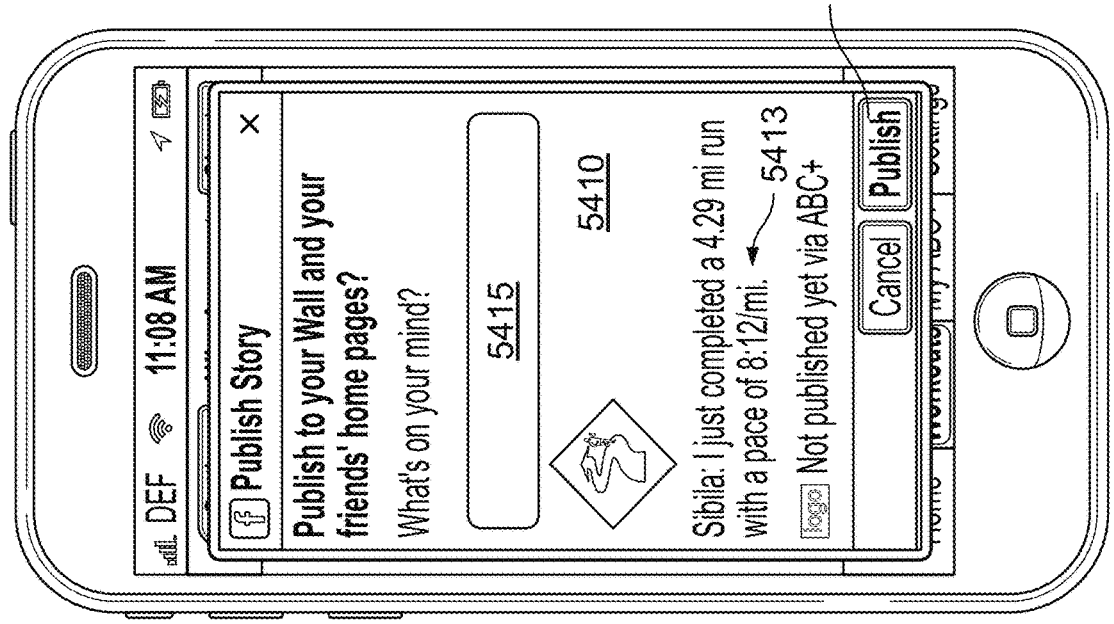
FIGS. 54A-54C illustrate example interfaces through which a user may share workout information on social networking sites and news feeds according to one or more aspects described herein.
Figure 54A:
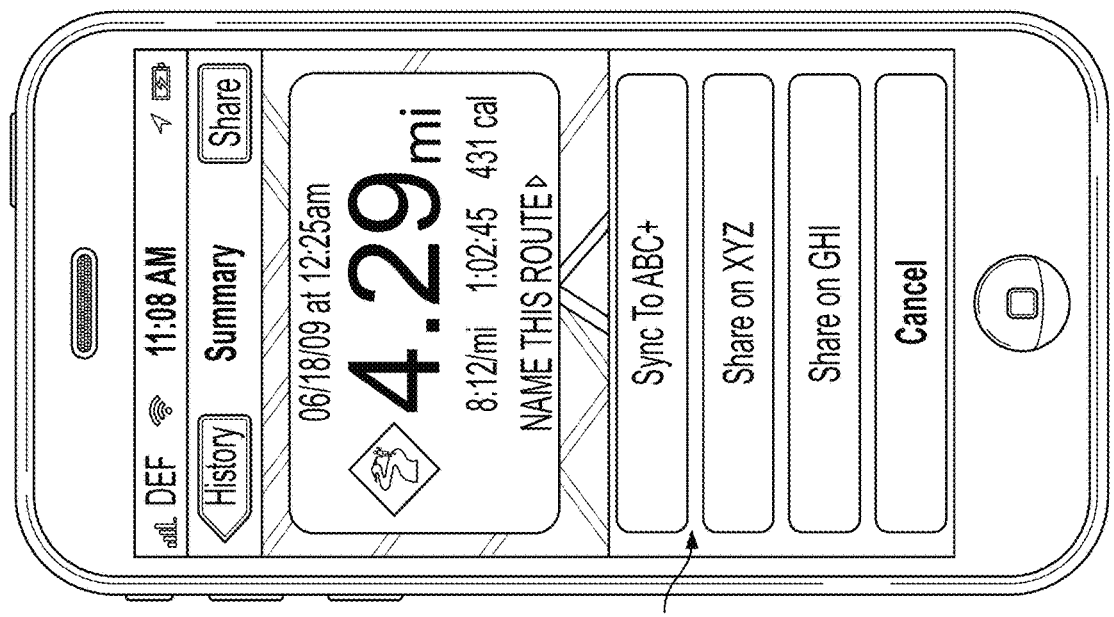
Figure 54C:
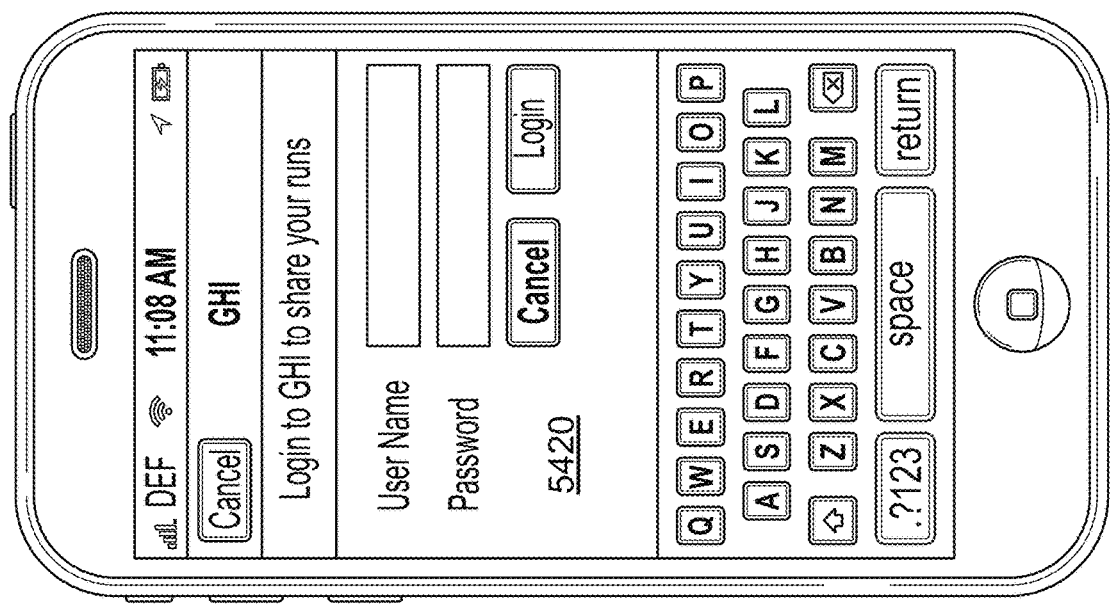

Users may choose to share workout information or portions thereof with one or more other users, friends or through a social networking site. FIGS. 54A-54C illustrate example interfaces through which a user may share workout information on social networking sites and news feeds. In FIG. 54A, the user may be presented with a share menu 5401 that includes multiple sharing outlets including FACEBOOK and TWITTER. Menu 5401 may also include an option to synchronize workout information with a fitness monitoring service provider.

If the user chooses to share workout data through a social network site such as FACEBOOK, an interface such as interface 5410 of FIG. 54B may be displayed. Interface 5410 may include an automatically generated workout update message 5413 and allow the user to include additional information or notes in form 5415. Upon approving the message, the user may publish the data to the social networking site by selecting publish option 5417.

Sharing workout data through a news feed service such as TWITTER may be performed through an interface such as interface 5420 of FIG. 54C. In particular, interface 5420 may require a user's login and password information to automatically access the news feed service. The news feed message may be an automatically generated message that includes workout and/or route information. For example, the message may be automatically generated based on one or more metrics recorded, a type of athletic activity performed and/or a location of the athletic activity performance. The user may be allowed to edit the message and/or create his or her own message.

Figure 83:
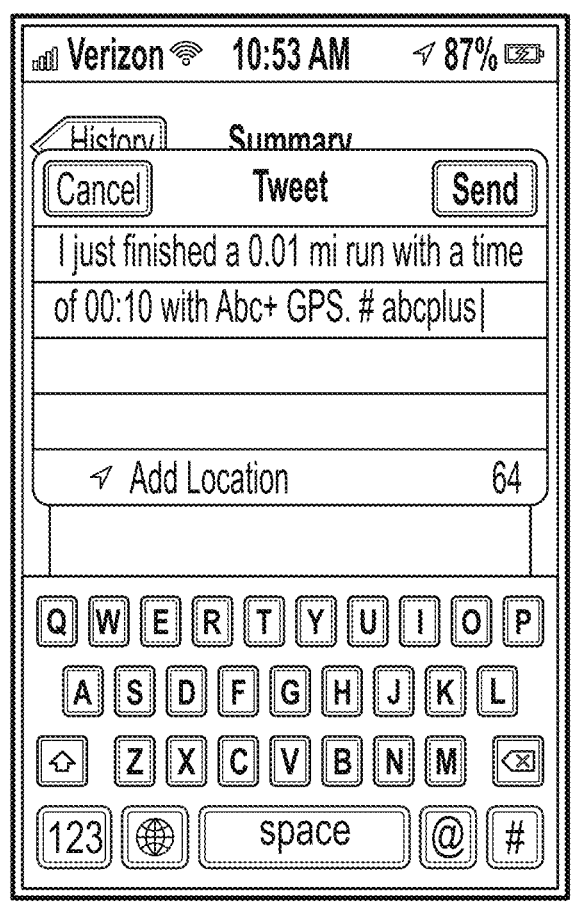
FIG. 83 illustrates an example interface for generating a message for distribution through a social messaging system.

FIG. 83 illustrates an example TWITTER message creation interface.

Figure 55A:
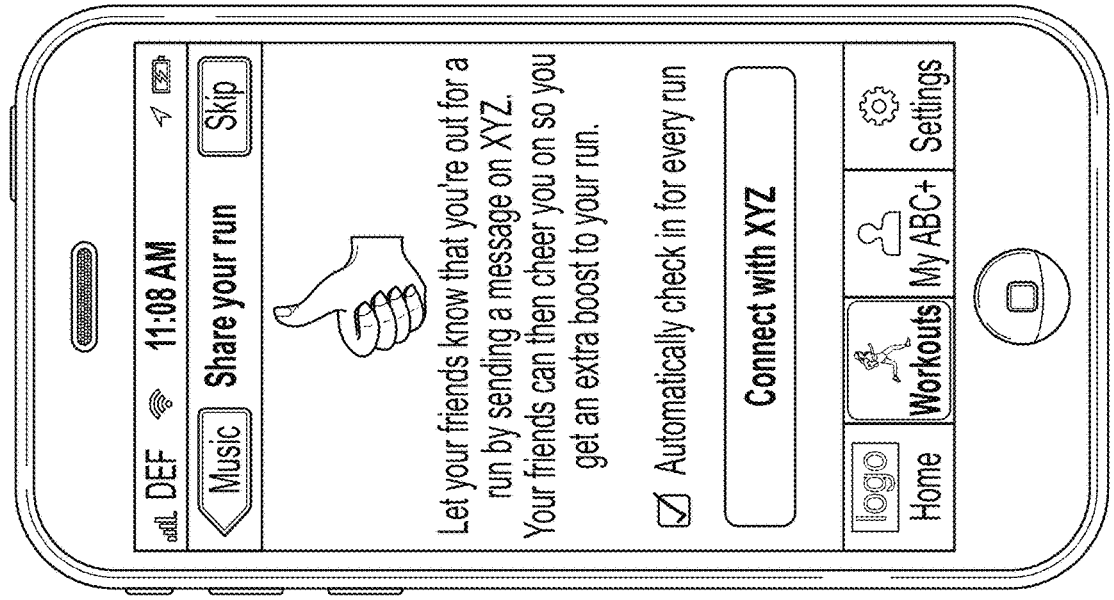
FIGS. 55A and 55B illustrate other example interfaces for sharing workout/run information according to one or more aspects described herein.
Figure 55B:
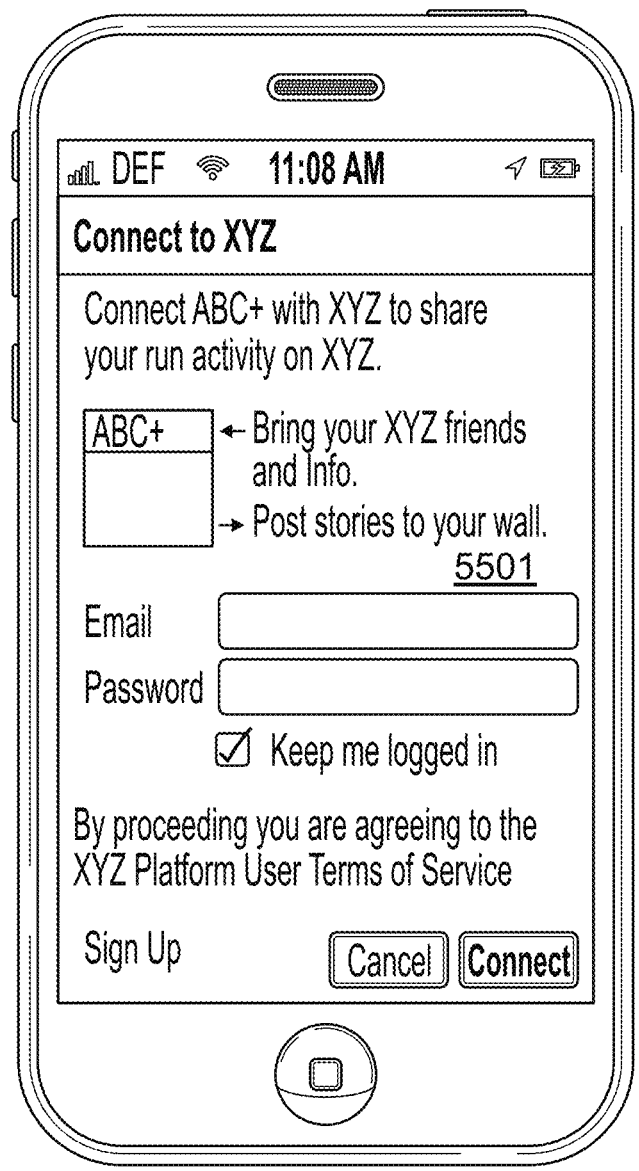

FIGS. 55A and 55B illustrate other example interfaces for sharing workout/run information. Interface 5501 of FIG. 55B, for example, allows the user to enter login information for a social networking site or other information outlet. The login information may be stored and used in association with a fitness monitoring service provider to synchronize and publish data automatically to the information outlet. Once the user is logged in, the system may automatically share new run information through the information outlet. In some arrangements, the information might only be shared in response to receiving a user command or confirmation.

Workout information may be shared through other channels including a fitness monitoring service provider site, a personal homepage and the like. In some arrangements, the user may be able to publish workout information to multiple sites or services simultaneously or non-simultaneously through a single sharing interface.

Figure 56:
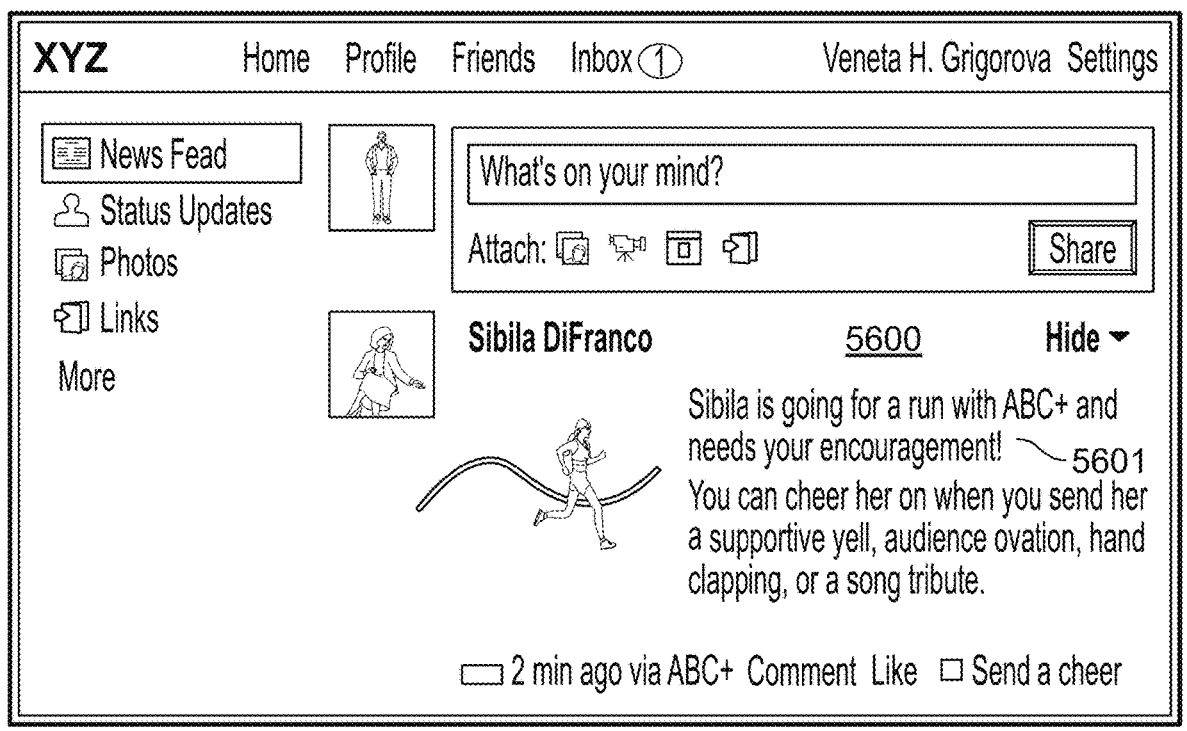
FIG. 56 illustrates an example social networking site interface in which workout information may be posted and conveyed according to one or more aspects described herein.

FIG. 56 illustrates an example social networking site interface in which workout information may be posted and conveyed. Interface 5600 may correspond to a user's personal page and includes a status message 5601 that indicates the user is going for a run and encouraging other users to provide supportive comments.

Figure 57:
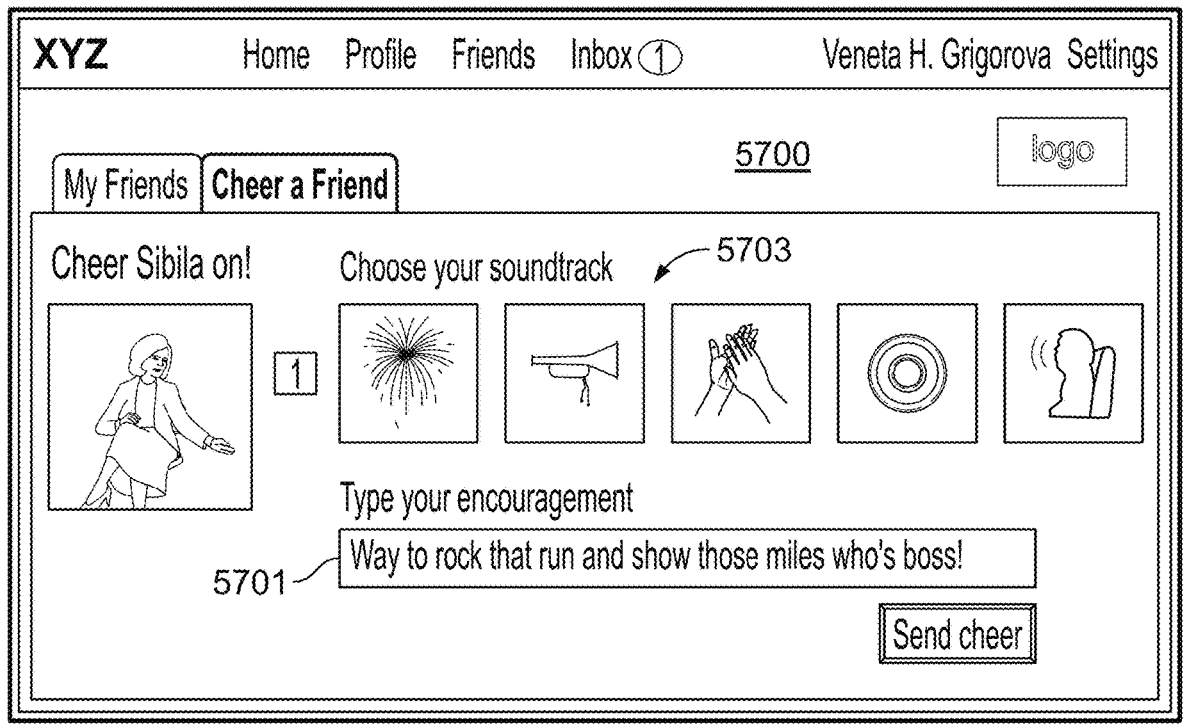
FIG. 57 illustrates an example message entry interface that allows a friend or other user to enter an encouragement message according to one or more aspects described herein.

FIG. 57 illustrates an example message entry interface 5700 that allows a friend or other user to enter an encouragement message in text entry form 5701. The user may also select audio content from a list of predefined sounds 5703.

Figure 58:
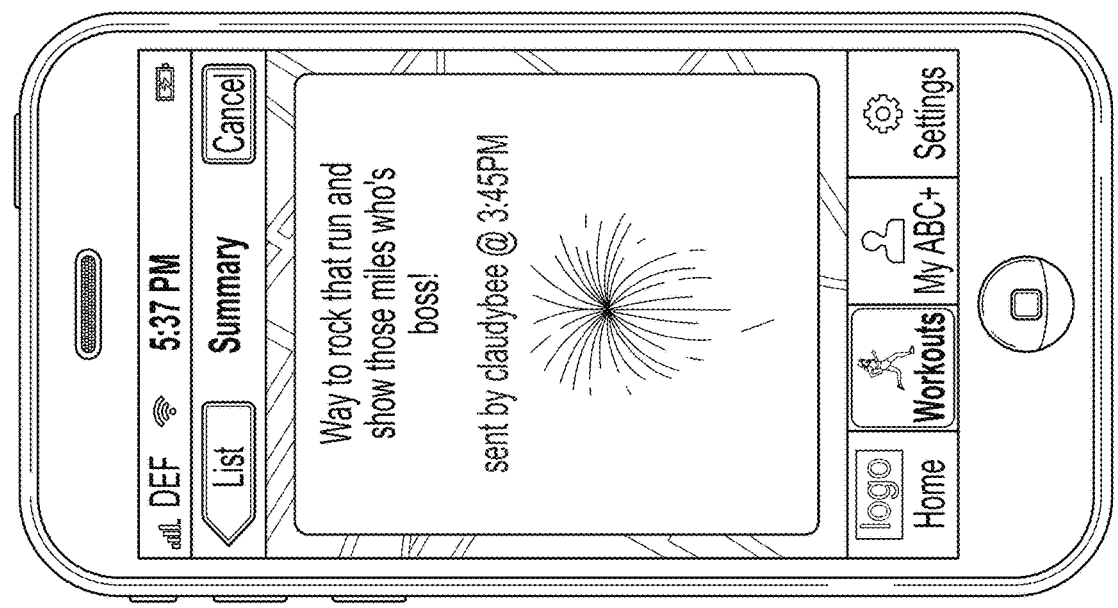
FIG. 58 illustrates an example mobile device interface displaying the message submitted through the interface of FIG. 57.

FIG. 58 illustrates the message submitted through interface 5700 of FIG. 57 and as displayed on a user's mobile device.

Figure 59:
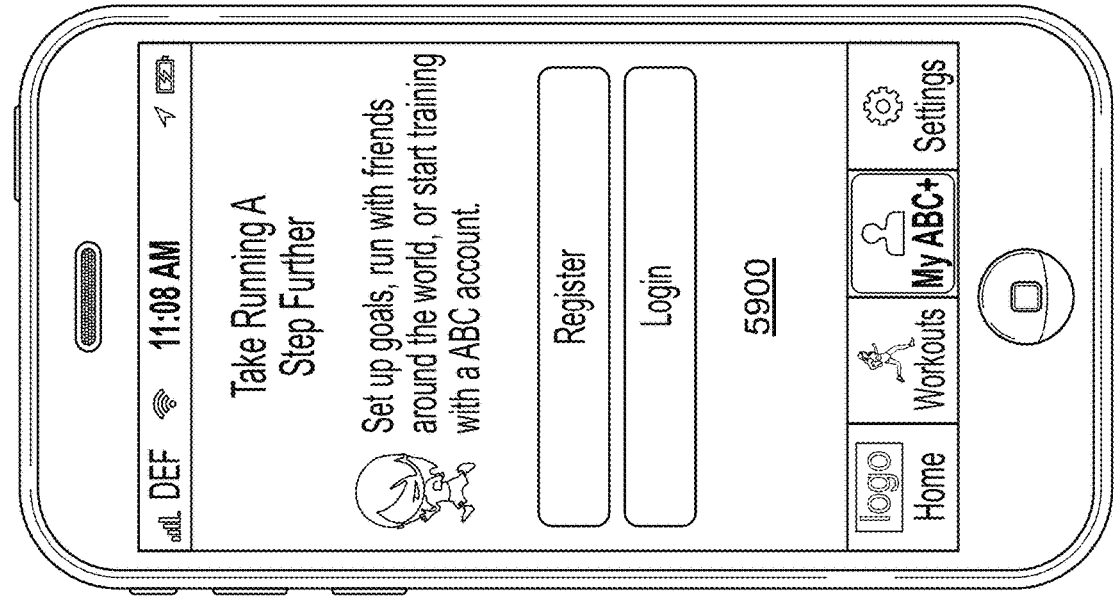
FIG. 59 illustrates a login interface for an athletic activity monitoring service according to one or more aspects described herein.

According to one or more arrangements, a user may further access a remote fitness monitoring service site and receive data through the mobile fitness monitoring device. For example, interfaces may be generated by the mobile monitoring device based on data received from the remote fitness monitoring site through a network. A user may login and/or register with the remote fitness monitoring service through an interface such as interface 5900 of FIG. 59.

Once a user has entered user information and/or login information, the user may navigate through various user interfaces displaying user athletic activity records, achievements, schedules, progress and the like. FIGS. 60A-60D illustrate example interfaces that may be used to navigate and view workout information that may at least partially be received from a remote fitness monitoring site. In FIG. 60A, a user may be informed of a number of runs or workouts that have not yet been synchronized with the remote site. The device may reconcile data between the device and a database of the remote site to identify those workouts or runs that still need to be synchronized. The synchronization message may be displayed as part of a summary of a number of awards and trophies that the user has achieved or earned. Synchronization of the runs may be automatically initiated or initiated through a manual command.

Figure 60B:
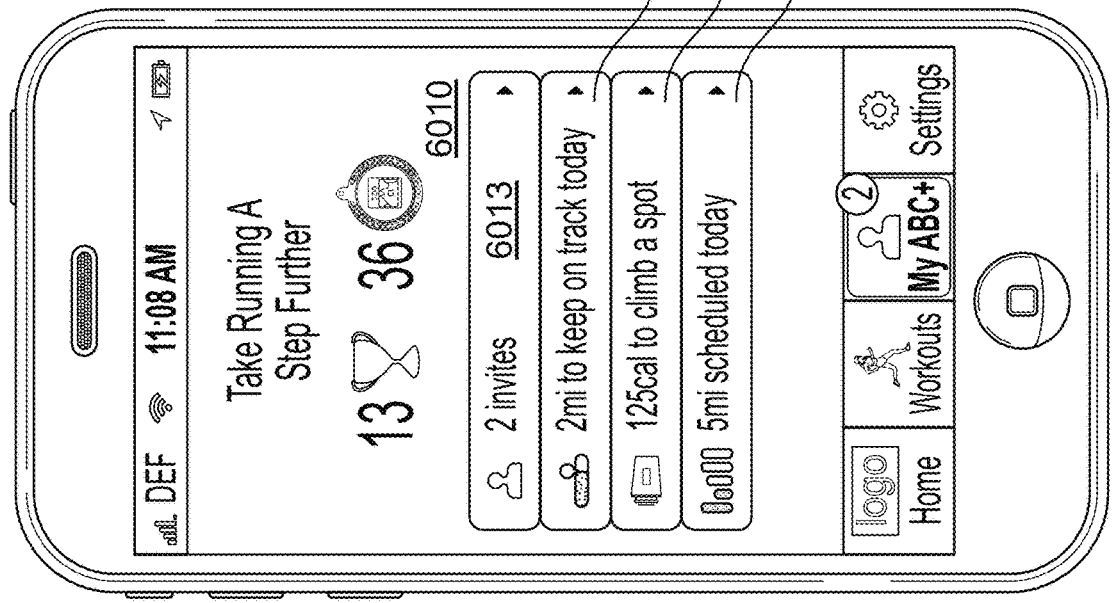
FIGS. 60A-60F illustrate example interfaces that may be used to navigate and view workout information that may at least partially be received from a remote fitness monitoring site according to one or more aspects described herein.
Figure 60A:
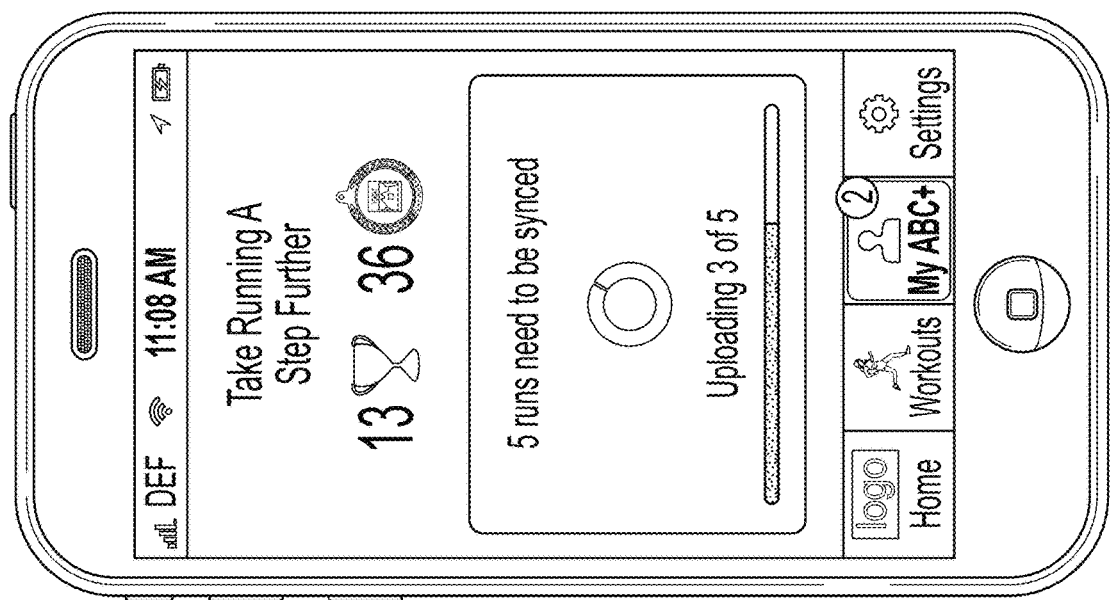

In FIG. 60B, interface 6010 may include a summary of various workout and user data including friend invitations 6013, a daily progress indicator 6015 and goal indicators 6017 and 6019. Friend invitations 6013 may allow for users of the athletic activity monitoring site to interact with one another. Friends may be provided different levels of privileges as opposed to non-friends. For example, friends may be able to view photos, detailed workout information and other personal data about the user while non-friends might only be allowed to view generic profile data such a name, gender and a general activity level. Accordingly, a user may control who is classified as a friend by confirming or accepting friend requests. The daily progress indicator 6015 identifies an amount of additional athletic activity (e.g., a number of miles) that must still be completed to finish a daily goal such as daily goal 6019. In addition to daily goal, goal 6017 may be defined. Goal 6017 may correspond to another achievement that the user wishes to reach. Alternatively or additionally, goal 6017 may correspond to an elevation in predefined fitness levels or increase a user's ranking among multiple fitness users.

Figure 60D:
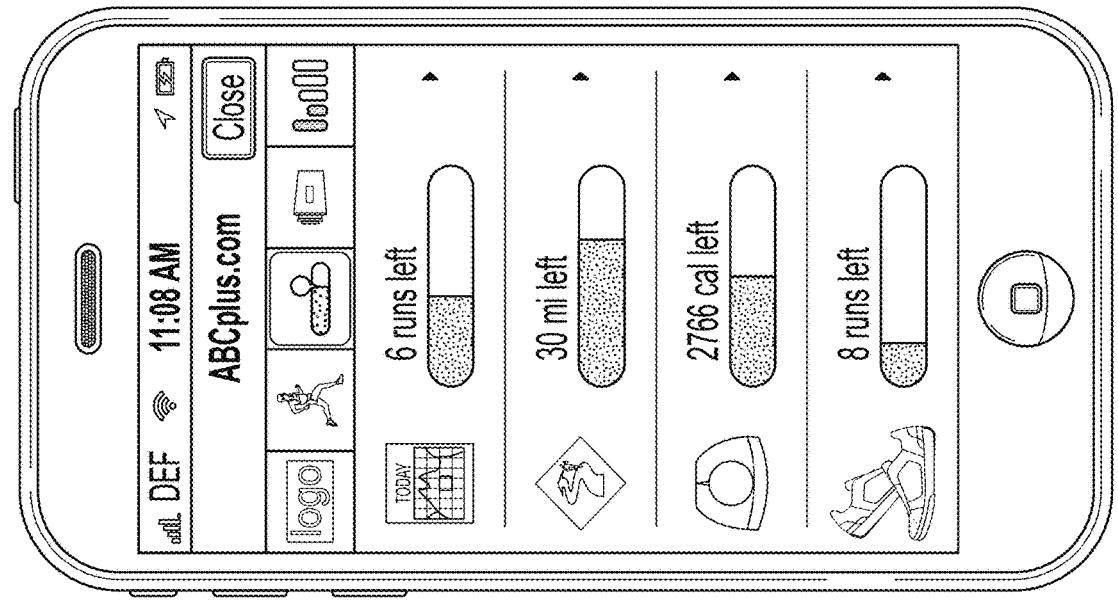
Figure 60C:
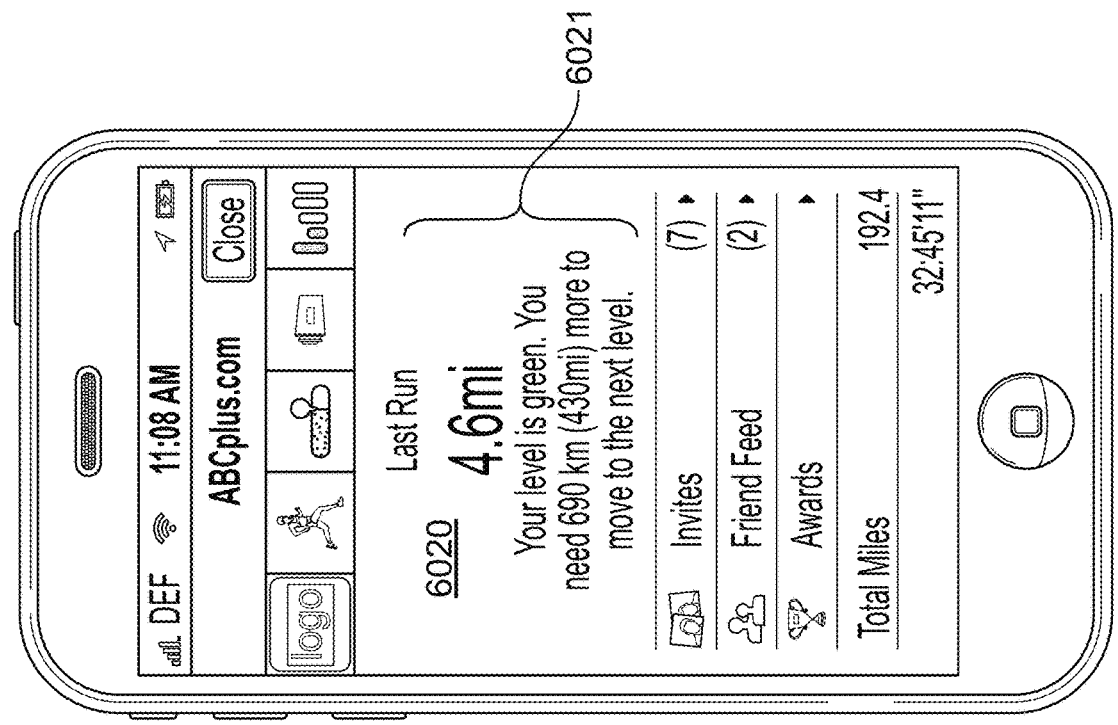

FIG. 60C illustrates an interface 6020 displaying another example workout data summary that may at least partially be received from and/or generated by a remote fitness monitoring service. For example, summary 6021 may include a summary of a last run (e.g., a number of miles run) in addition to a number of friend invites, a number updates in friend feeds and an award viewing option. Additionally or alternatively, summary 6021 may include the total number of miles that have been run and a total amount of time spent performing athletic activity. The friend feed indicator may identify the number of updates that have been posted for the user's friend(s). For example, if a friend has completed a new run and the friend's profile has been updated with that information, the friend feed indicator may reflect that additional update. Feeds may also include manual posts (e.g., user comments or messages) in addition to automatic updates and posts. A user may use the award viewing option to view the accolades, accomplishments, achievements and goals the user has accumulated in his run history. By accessing data from the remote fitness monitoring site, the user may be able to view workout information and history not previously stored on the mobile monitoring device. Accordingly, the user may be able to view a full workout history and not just what is at that time on the mobile device.

Workout sharing may further include sharing a route and/or map of a route that a user is currently using, has completed or has created for future activity. Route or map information may be shared through various outlets including an athletic activity tracking and monitoring service or community and/or a social network or outlet such as FACEBOOK and TWITTER. The activity monitoring application executing on a user's mobile device (e.g., an activity monitoring device) may include settings for synchronizing workout information including the map and/or route information to such services and outlets.

FIG. 77 illustrates an example synchronization setting interface through which a user may configure the application to automatically share certain types of information. Option 7701 specifies whether automatic sharing and synchronization of workouts in general is to be performed while options 7703 and 7705 allow the user to individually configure sharing of specific types of information such as map information and pace data. Other types of information may also be provided with individual sharing controls including date, length of workout, heart rate information, goal information, streak information and the like. In some instances, when the auto share option 7701 is turned off, the information specific options 7703 and 7705 may be turned off automatically as well. Similarly, if the auto share option 7701 is turned on, the information specific sharing options 7703 and 7705 may be turned on automatically in response. By allowing the setting of automatic sharing options, not only might the user be able to share information without having to manually designate every workout, but the user is also able to customize the shared information and features.

The user may further set various conditions and parameters for sharing information. For example, a user may define times during which sharing is allowed and times during which sharing is not allowed or prohibited. In other examples, conditions may include workout metric ranges (e.g., a range of run distances, a range of workout durations, a range of average paces), a frequency of sharing (e.g., only share at most 3 workouts every 7 days), whether the workout was performed alone or with other people, whether a goal was achieved and the like and/or combinations thereof. In a particular example, a workout might only be shared if one or more metrics of the workout exceeds a personal best. Sharing conditions and parameters may be specified for overall sharing, specifically for a group of information types or on a per information type basis or a combination thereof. For example, a first type of information may be associated with a first set of one or more sharing conditions while a second type of activity information may be associated with a second set of one or more sharing conditions. Accordingly, a system may initially determine whether the overall sharing condition has been satisfied and if so, determine whether each information type-specific or information type group-specific condition has been satisfied. If the overall sharing condition is not satisfied, sharing of any of the information types may be prohibited even if the individual information type condition or an information group condition is satisfied.

Figure 78C:
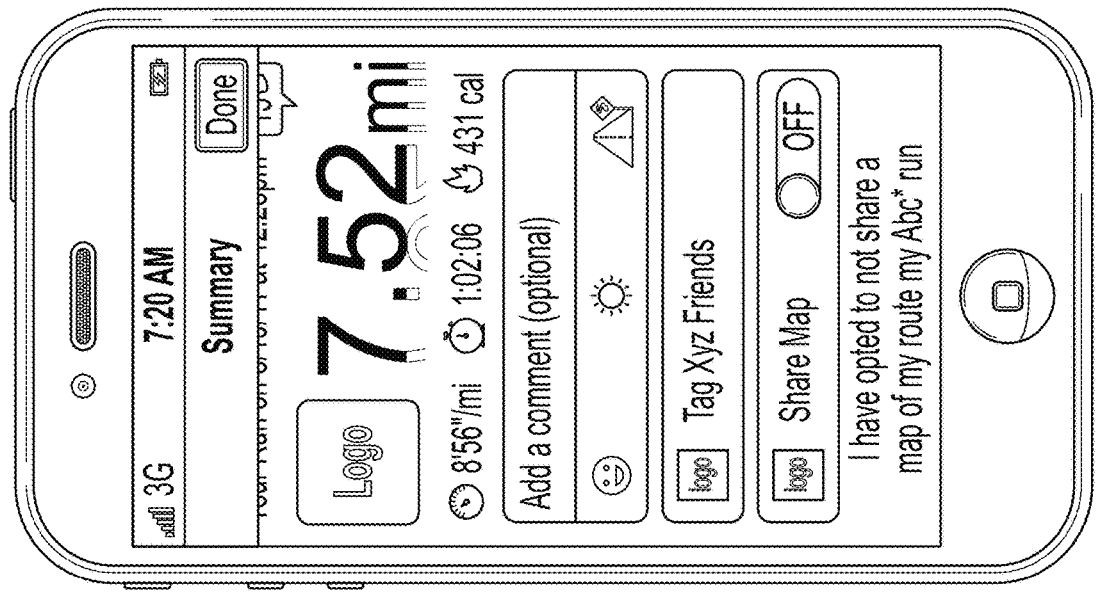
Figure 78B:
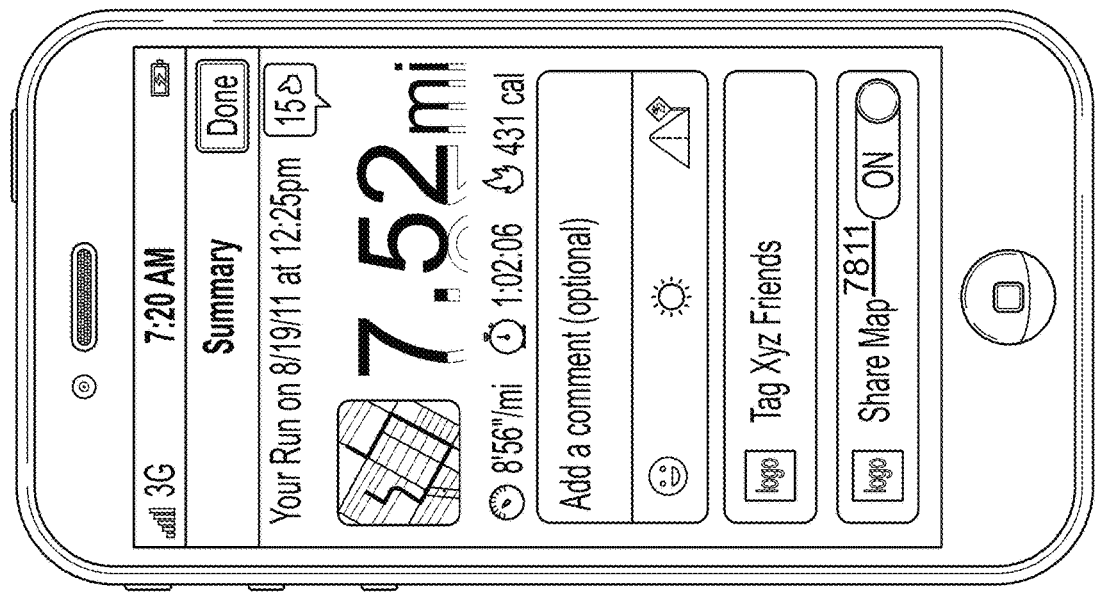

FIGS. 78A-78C illustrate example workout summary interfaces through which a user may input and synchronize workout data and control information that is to be shared. In FIG. 78A, for example, the interface may include summary metrics for the workout in section 7801 and a comment entry field 7803. The user may enter comments or notes about the workout. The comments or notes may also include a message to other users when the summary is posted. The user may further be provided with options for selecting predefined workout attribute tags 7805, including a mood, weather conditions and terrain type as described herein. Alternatively or additionally, the tags 7805 may be automatically populated and user-editable.

Option 7807 provides the user with an option to associate friends or other users within a community or social network with the workout. Tagging a user may include identifying the user as a participant in the workout, causing the workout entry on the community or social network to be inserted into an activity feed or timeline of the tagged user, causing the workout entry to be posted on the other user's activity feed, profile or timeline and the like and/or combinations thereof. According to one aspect, if another user is tagged for a user's workout, the tagged user's workout information for the shared workout may be retrieved. In one example, the tagged user's performance data may be retrieved from the tagged user's account on a social networking system, an athletic activity monitoring system and/or from the tagged user's athletic activity monitoring device. The tagged user's performance data for that shared workout may then be posted in association with (e.g., included as part of) the workout entry for the tagging user. In one example, a workout entry may list performance information for multiple users participating in that workout. Accordingly, a system may identify the tagged user (e.g., an identifier on an activity monitoring site, an identifier on a social network, etc.) and determine whether workout information is available for the workout in which the user was tagged. If so, the workout information of the tagged user may be retrieved and included in a workout entry or post along with the tagging user's performance information for that same workout.

According to other aspects, if multiple users are tagged for a workout, comments or feedback responding to the corresponding workout post or entry on a social network site or community may cause celebratory messages or other types of feedback to all tagged users. Alternatively, the feedback or celebratory messages might only be delivered to the posting user.

When data is synchronized or otherwise transmitted to one or more network sites or systems, a message such as "Sync Complete" may be displayed in information bar 7809. Additionally, information bar 7809 may identify the services, systems, or sites to which the information was transmitted or synchronized. For example, icons, text identifiers, images and the like may be used as identifiers for the synchronized services, systems or sites and be displayed in information bar 7809. The identifiers may also differ in appearance depending on if synchronization was successful for each of the systems or services. In one example, if synchronization with a particular system or service was not successful, that icon, image, text or the like may be displayed in outline form or grayscale instead of in color or filled in. This may allow a user to more easily determine the synchronization status with each of his or her communities/accounts/systems/services etc.

FIG. 78B illustrates an additional synchronization option 7811 that allows a user to toggle whether map/route information is to be shared in a workout posting or entry. If map/route information sharing is activated, a map of an activity route or other information describing the route may be included in a workout summary posting. In one example, the map/route information may correspond to a link to a map or route graphing interface provided by a system different from the social network or other social outlet to which the workout information is being posted (e.g., GOOGLE MAPS, MAP QUEST, etc.). In one example, the link may be generated by the activity monitoring application. If the map/route information sharing is not activated, the map and/or other route information might not be shared in postings. Toggling the map/route information sharing may be performed even after a posting has been submitted and entered on a network site. For example, if a user toggles the map/route information sharing option 7811 after a workout entry has been posted or after workout information has already been transmitted to the network site (e.g., for posting), the application may submit an edited version of the workout entry to replace or modify the previously posted entry or a request to remove the toggled information. In a particular example, the application may request that a map/route link be removed from the post or entry.

FIG. 78C illustrates a workout summary interface in which the map/route information sharing option is toggled off.

Figure 79A:
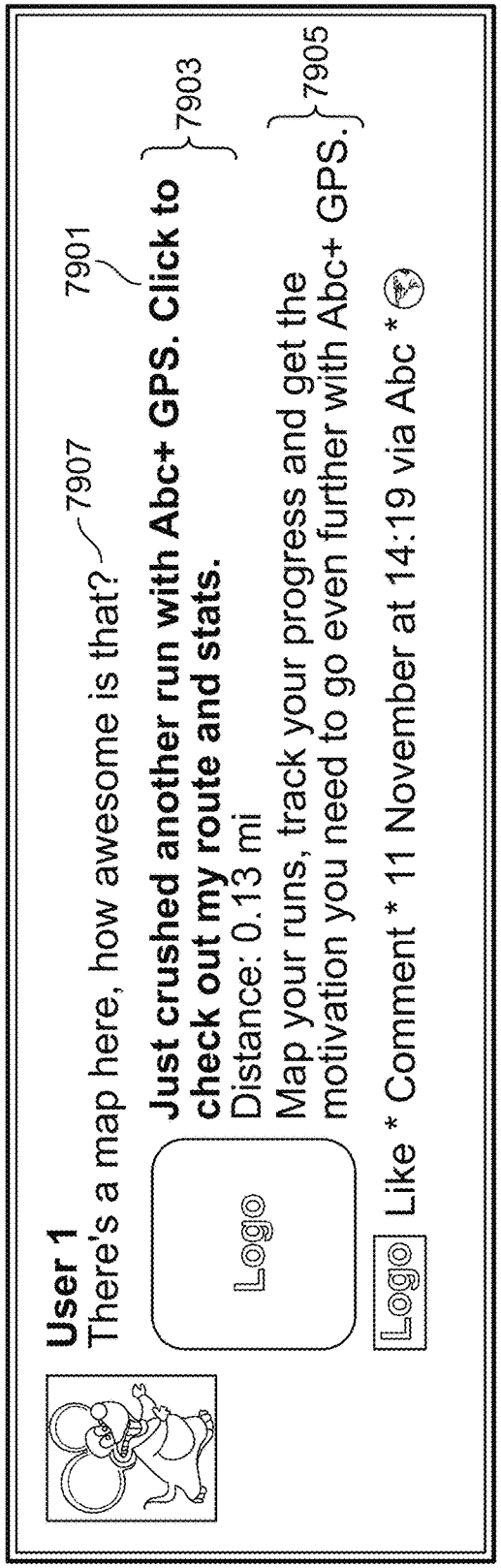
FIGS. 79A and 79B illustrate example workout information entries or posts in a social networking site.
Figure 79B:
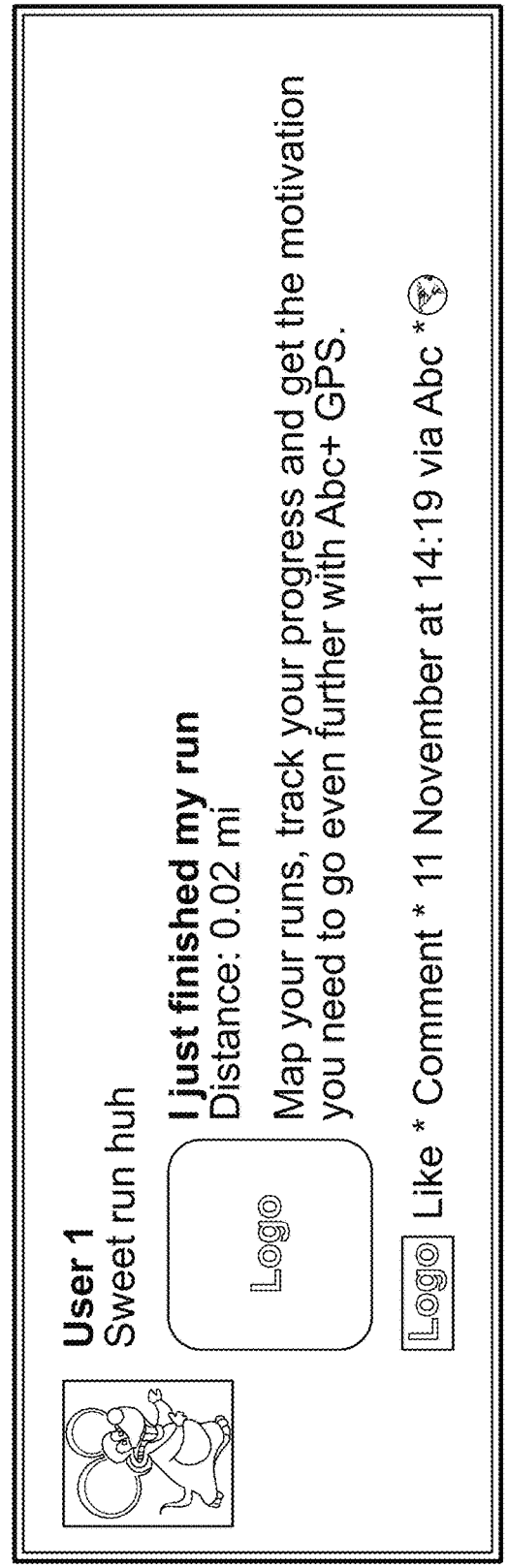

FIGS. 79A and 79B illustrate example workout posts or entries on a network site such as a social network. In FIG. 79A, map/route information is posted to the network site as noted by message 7901 (e.g., indicating "Click to check out my route and stats"). In some arrangements, the posting of map/route information may be specified by an indicator such as an icon, a selectable link, a color, a font size, a particular message and the like and/or combinations thereof. For example, icon 7903 may differ depending on if map/route information is posted and available. In another example, the text "Click to check out my route and stats," may include a link to a mapping interface and/or system different and remote from the network site. Comments entered into a comment field such as field 7803 (FIG. 78A) may be posted as part of the workout entry title 7903 (e.g., "Just crushed another run with Abc+ GPS. Click to check out my route and stats"), as a message 7905 within the entry (e.g., "Map your runs, track your progress and get the motivation you need to go even further with Abc+ GPS") or as user commentary 7907 about, but separate from, the entry. For example, user commentary 7907 may correspond to a subject line describing an entry made on the network site.

FIG. 79B illustrate an example workout entry in which map/route information is not available. For example, the indicator message and/or link "Click to check out my route and stats," is not provided in this example entry.

Figure 80:
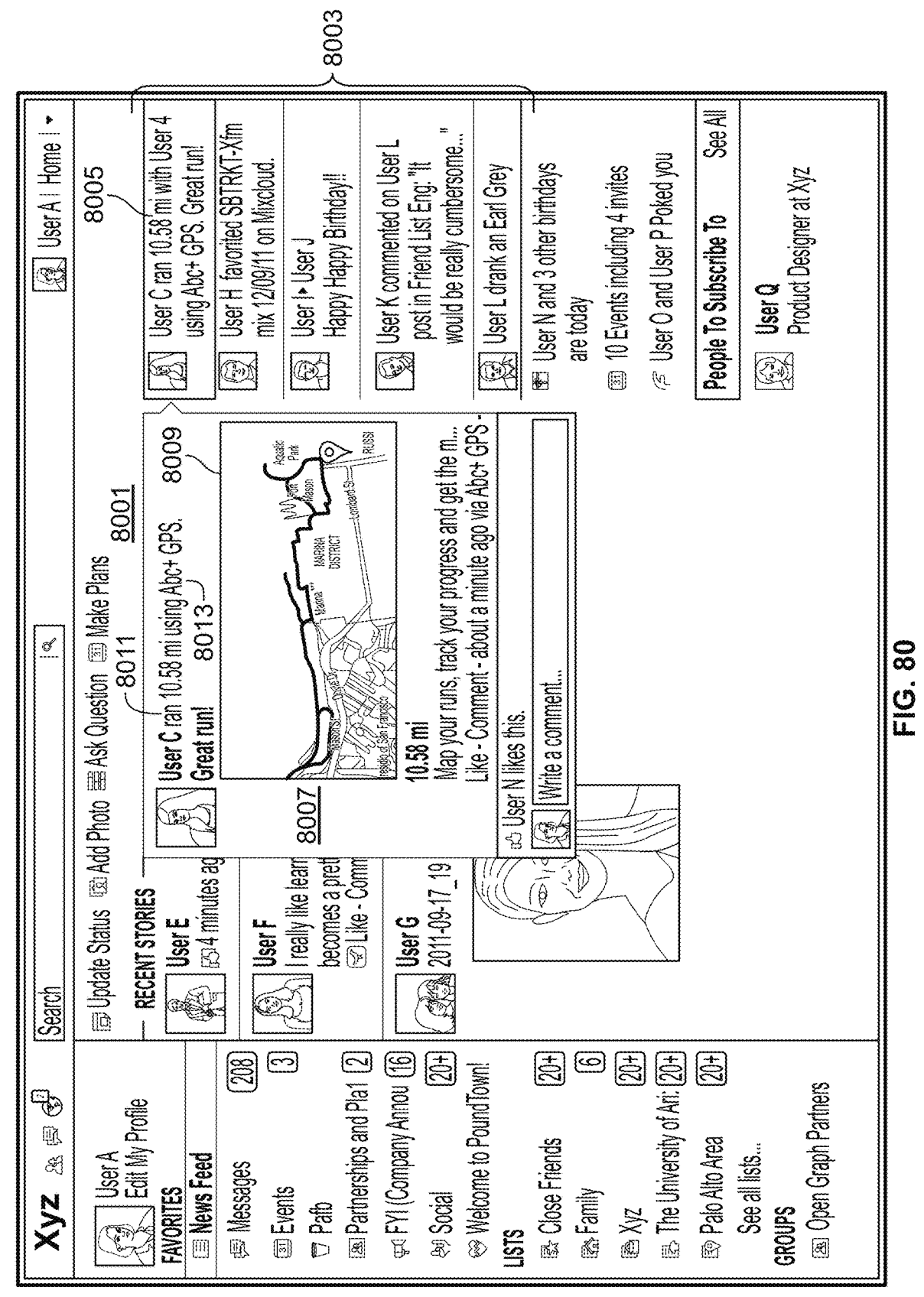

FIG. 80 illustrates another example workout entry for another user. For example, a first user may browse his or her social network page 8001 and be provided with an activity feed 8003 indicating messages, events and activities of other users (such as friends). Entry 8005 in feed 8003 provides a workout entry for another user and upon selection of entry 8005, a pop-up information display 8007 may be presented to display further details. Pop-up display 8007 may include a map of an activity location or route (if such information is shared) as well as other metrics or summary information. Maps may include various information including identification of a route (e.g., latitude and longitude coordinates, cellular triangulation coordinates, etc.), pace information, identification of a goal and the like as described in further detail herein. The map may be interactive such that a user may navigate around the map within window 8009. For example, the user may view geography, streets, topography, landmarks and the like farther to the east, west, north, south, etc. as desired. Window 8009 may also be expandable so that a user may see more geography at the same time. Workout entries may further include a link to other interfaces, pages or sites with different or additional details of the workout.

Entries on a network site or page may be identified by data objects or constructs. These data objects or constructs may be predefined for ease of categorization, analysis and storage. For workout summary entries on a network site, objects such as an action object (e.g., an action performed by a user), and an action monitoring object (e.g., a device or software used to monitor and/or record the action performed) may be predefined as known objects to the social networking site or other network system. In one example, the objects may be defined as part of an application or applet that is configured to execute within the context of the social networking site or other network system by using various APIs and interfaces of the social networking site or system. The application or applet may further be configured to interface with an athletic monitoring site, system or device different form the social networking site to receive activity data and to generate/create workout entries, parse, analyze and/or summarize activity data, generate metrics from the activity data and/or organize the activity data.

The application or applet may further be configured to generate map information including map visuals or images, links to on-line map generation systems/sites based on coordinate information or route data received from the athletic monitoring, system or device. In one example, the application or applet may use a starting coordinate and an ending coordinate with or without one or more intermediate coordinates to generate a map of a route (e.g., interfacing with GOOGLE maps to plot out the route) or using internal mapping capabilities to generate the route map. In other examples, the activity data received from the athletic monitoring site, system or device may include a map image or interactive map object. The activity data may also identify other users who shared in the workout or who have been tagged, as described herein.

When generating a workout entry, the social network system or an application executing thereon may initially determine whether map or route information is available. Availability may be defined by whether such information is included in the activity data received from the activity monitoring site, system or device or may be determined by a response to a request for such information (e.g., sent to the activity monitoring site, system or device). If map/route information is unavailable, the workout entry may be generated with a link to a non-location oriented summary interface such as a performance graph display (e.g., a line graph plotting time vs. pace or time vs. heart rate for a run or other athletic activity) or other textual or image-oriented illustration of the workout. If map/route information is available, the workout entry may be generated with a link to a visual map or visual route depiction in addition to or instead of the non-location oriented summary link. In some arrangements, the system, application or device generating the entry may also determine whether the user's workout information is set to private. If so, a link to a marketing page (e.g., for an athletic activity monitoring service, a device such as the device used to monitor the user's athletic activity) or other public page may be included in the entry instead.

Referring again to FIG. 80, as shown in pop-up information display 8007, a workout entry may define a workout in terms of a run action 8011 and a monitoring device object 8013. These objects may be automatically identified by the social networking site or an application executing thereon. In one example, the application may determine an activity type associated with the activity data received and identify a corresponding action descriptor object. Each action descriptor object may be specific to a single activity type. However, a single activity type may correspond to multiple action descriptor objects. Thus, for a running activity type, the action descriptor "run" may be used while a "walk" action descriptor may be used to describe a walking activity. In other examples, action descriptors may include "lift" for weight lifting, "swam" for swimming, "skied" for skiing and the like. Different action descriptors may also be used depending on a value of a performance metric. For example, if the user's pace was between 4.0 and 6.5 mi/hour, the action descriptor selected may be "jogged," while if the user's pace was above 6.5, the action descriptor selected may be "ran." Thus, the same activity type may have multiple action descriptors.

Additionally, the application or system may automatically identify the activity recording device and/or application and associate a corresponding monitoring device and/or monitoring application descriptor object with a workout entry. Accordingly, if the user used a device having a GPS system, the corresponding descriptor object may be "GPS device."

In another example, if the activity was recorded using a GPS-based application, the corresponding descriptor object may be "GPS application." Device descriptors may be specific to a particular object (brand and model) and/or defined based on capabilities such as based on type of technology included or type of activity configured to be detected. The type of device used including a name or identifier (e.g., serial number, model number, brand name, user specified name of the device, etc.), capability information (e.g., accelerometer, GPS, gyroscope, etc.) and the like and/or combinations thereof. Application descriptors may be similarly specific to a particular type of application, to a category of application capabilities, to a specific application and the like.

Using the above noted information, a social network system or community site (or application executing thereon) may construct an event such as <user> <action> <metric> using <device/application> where <user> identifies the user performing the activity, <action> corresponds to the action descriptor object, <metric> provides a performance value such as miles run, distance swam, weight lifted, etc., and <device/application> corresponds to the monitoring device or application descriptor object. The workout may then be organized, searched, categorized and/or parsed using the above descriptor objects and parameters. For example, all runs may be grouped together or analyzed to determine an average metric such as distance run or average pace by identifying all workout entries with the action descriptor object "ran" or "run." In another example, workout entries using a particular monitoring device or application may be identified and various statistics or workout information may be generated based on the group of workouts corresponding to the particular monitoring device or application.

Figure 81:
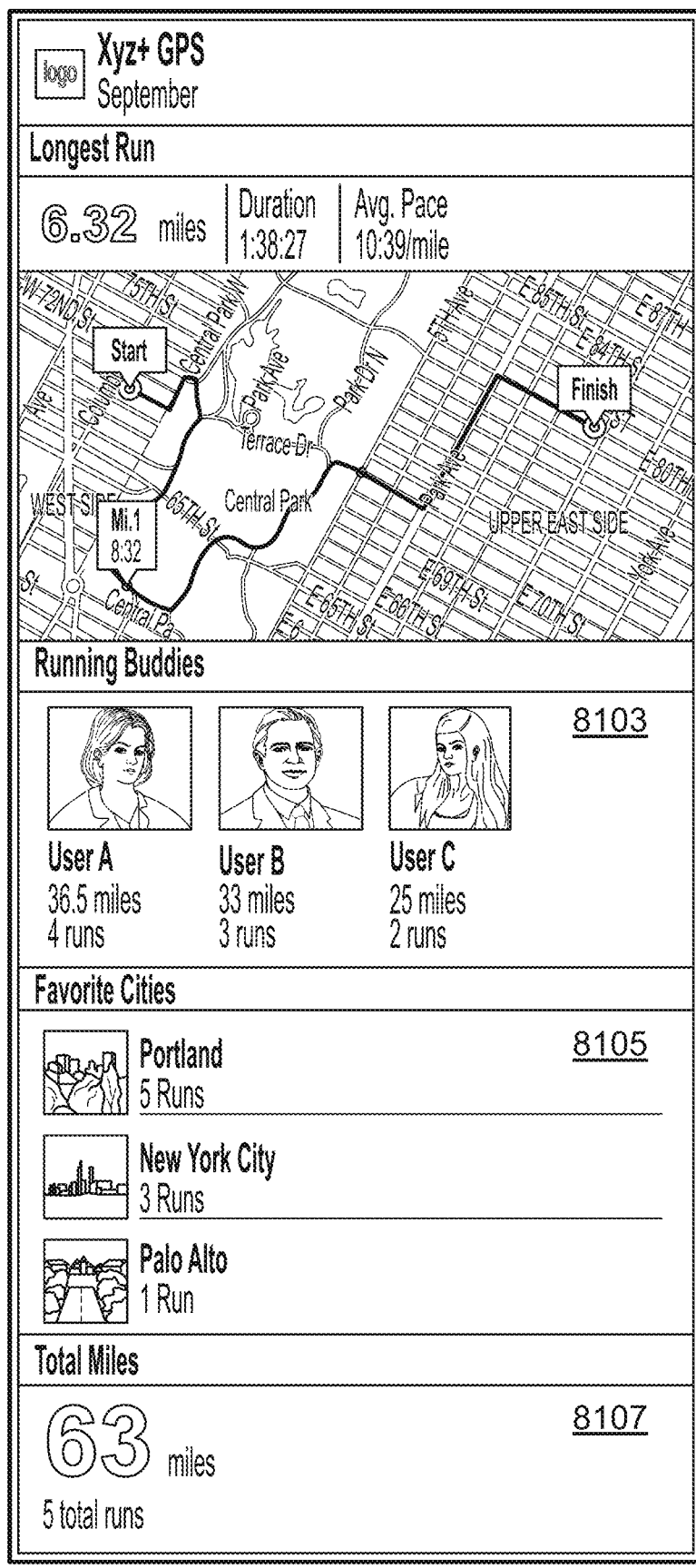
FIG. 81 illustrates an example athletic activity profile page.

FIG. 81 illustrates an example activity summary profile page. The activity summary profile page 8101 may be specific to and/or be provided by an activity monitoring application or applet executing on the social networking site or community server. The profile page may use the predefined descriptor objects in the workout entries to generate summary data including identification of a longest run, longest activity duration, an average page, a most recent run, a shortest run, a fastest run, a fastest pace and the like. In page 8101, a longest run is identified with a duration of that run, an average pace of the run and a map of the route taken. The profile page 8101 may further identify running friends or other users with which the user has performed activity in other user section 8103.

In some arrangements, only a predefined number of users may be displayed in section 8103 and those users may be selected based on a number, duration, distance or other metric of activity performed with the user. For example, section 8103 may be configured to list the top 3 users with whom the profiled user has performed athletic activity based on frequency (e.g., number of activity sessions or number of activity sessions per time period such as week, month, year). In another example, section 8103 may be configured to list the top 5 users with whom the profiled user has performed athletic activity based on total amount of activity performed (e.g., duration, distance, matches, holes of golf etc.). In yet another example, section 8103 may list a top number of users based on the profiled user's average performance with those other users. For example, the top users may be identified as users with whom the profiled user ran the fastest average pace during workouts. In another example, the top users may be identified as users with whom the profiled user ran the farthest per workout.

Page 8101 further includes a list of cities. Other types of locations may be listed such as countries, states, zip codes, area codes, etc. As with section 8103, the location section 8105 may identify the top X number of locations based on an amount of activity performed at those locations, a frequency of workouts at those locations, a user-specified rating of the locations, an average metric of workouts at those locations and the like. Page 8101 may further display a cumulative metric such as distance, duration, points scored, baskets made, goals made, etc., in section 8107. Multiple metrics may be displayed in cumulative fashion. These metrics and/or number of metrics displayed may be user-selected or automatically defined based on an activity or activity type most frequently performed by the user or for which the user has performed the most (in terms of time or distance) activity.

Alternatively or additionally, profile page 8101 may further include top devices based on most use, best performances and the like. The profile page 8101 may be generated based on all or a selected subset of activity data recorded by the user on one or more devices or through an activity monitoring site and might not be limited to workout data provided in posted workout entries. In some arrangements, the data provided in profile page 8101 might only reflect workout data posted in entries on the social network or community site.

Figure 82:
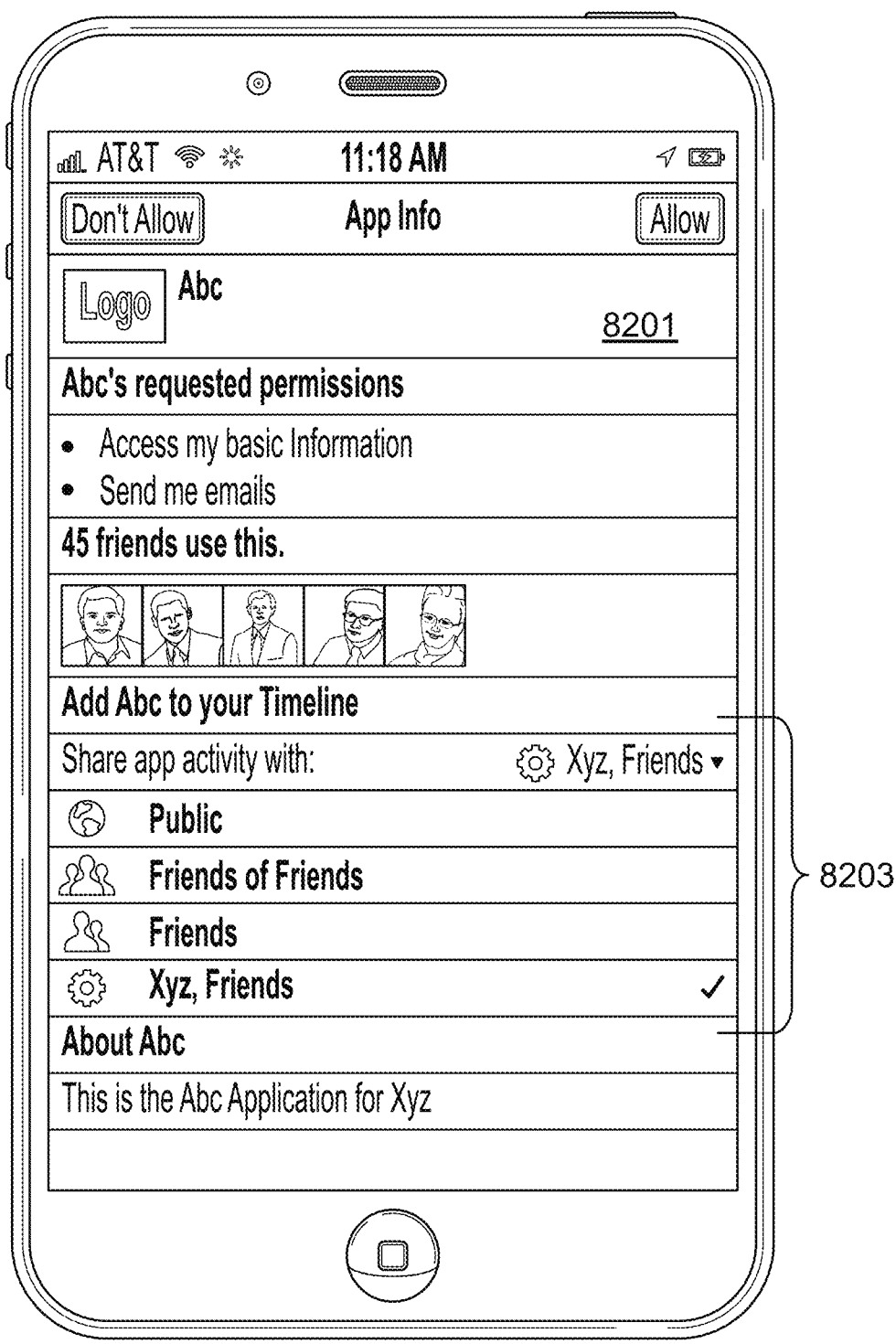
FIG. 82 illustrates an example activity sharing application interface for configuring information sharing options and permissions.

FIG. 82 illustrates an example application configuration interface 8201 that may be used to modify sharing parameters and to confirm sharing permissions. The interface 8201 may identify the permissions or data that will be accessed by the application such as e-mail information access, profile information (age, name, residence, phone number) and the like. The interface 8201 may further identify other users who use the same application. Section 8203 may be included to allow the user to control the entities to which information generated by the application is provided or shared. Several options may be prepopulated in section 8203 including public (e.g., everyone on the social networking site or community system), friends of friends, friends and the social networking system and friends. Sharing information with the social networking system but not the public may allow the social networking system to use the data to determine statistics such as how often the application is used, types of activity users are performing and the like. The social networking system might not publicize the specific data obtained from each user, but may use aggregate information such as the determined statistics for internal or external uses. In some arrangements, section 8203 may include groups or entities defined by the user. For example, a user may define his or her own groups and categorize other users (e.g., friends) in those groups. The user may then select sharing permissions or parameters based on the user-defined groups.

Goals

Figure 61B:
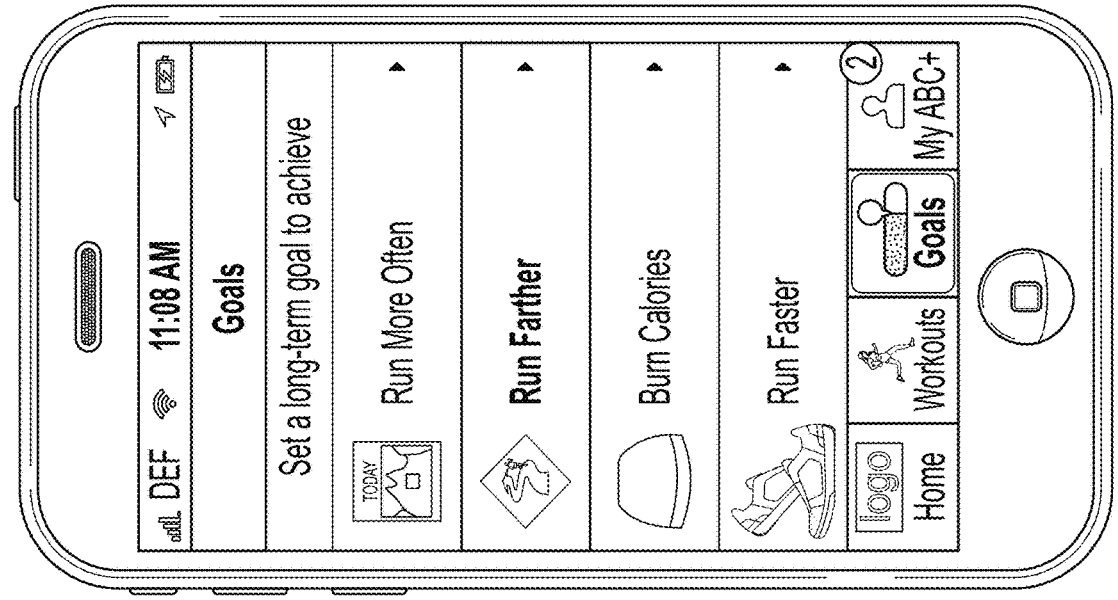
FIGS. 61A-61C illustrate example goal definition interfaces according to one or more aspects described herein.
Figure 61A:
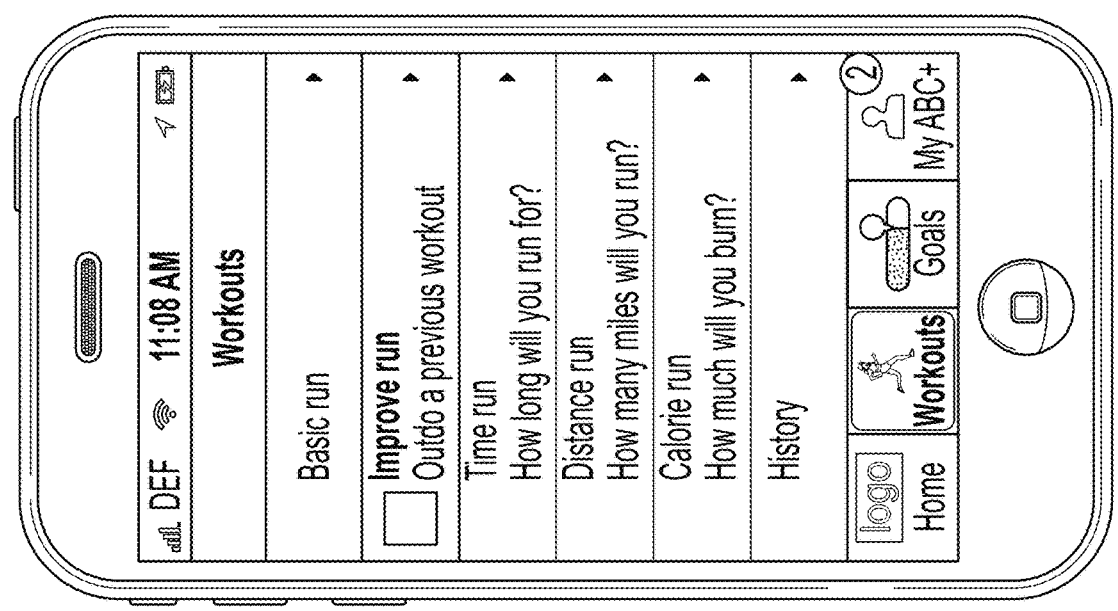
Figure 61C:
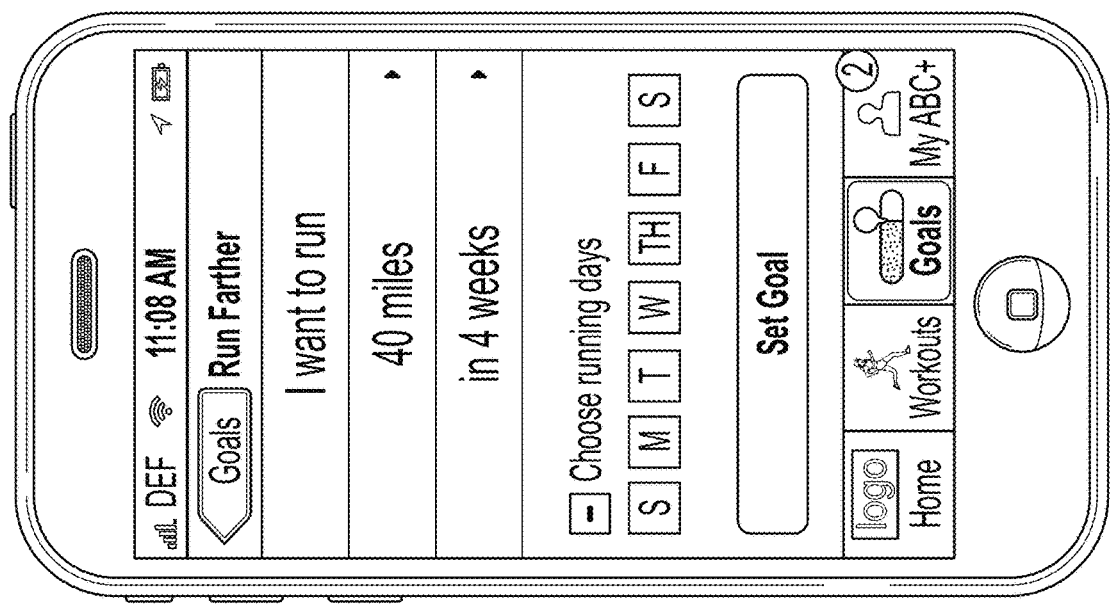

While a user may define an improvement run to set a goal for an immediate run, the user may also be allowed to select a long term goal that may span multiple runs. FIGS. 61A-61C illustrate example goal definition interfaces. In FIGS. 61A and 61B, the user may select an improvement option and subsequently a distance improvement option, respectively. In FIG. 61C, the user may then define the distance improvement goal by selecting an amount of distance the user wishes to run and a time period over which the distance is to be run. The user may also choose which days the user wishes to run in order to achieve the defined goal. Once the various parameters have been selected, the user may set or start the goal. Similar interfaces and options may be defined for other types of goals including time goals, pace goals, calorie goals and the like. The user may also define daily goals. For example, the user may specify how he or she wishes to accomplish the overall goal (e.g., running 40 miles in 4 weeks) on a day to day basis. Accordingly, the user may specify that he or she wishes to run 3 miles on Mondays and 5 miles on Wednesdays. Goals may also be combined. For example, the user may indicate that he or she wishes to run 40 miles in 4 weeks and achieve a pace of 8.5 mi/hour.

Progress towards one or more goals may be tracked in a variety of manners. FIG. 60D, for example, illustrates a goal tracking interface that displays a list of goals and a progress associated therewith. For example, a monthly goal indicates that there are 6 runs left for the month. A distance goal may indicate that there are 30 miles left to be run while a calories goal or objective may indicate that the user still needs to burn 2766 calories to complete the goal.

Figure 60F:
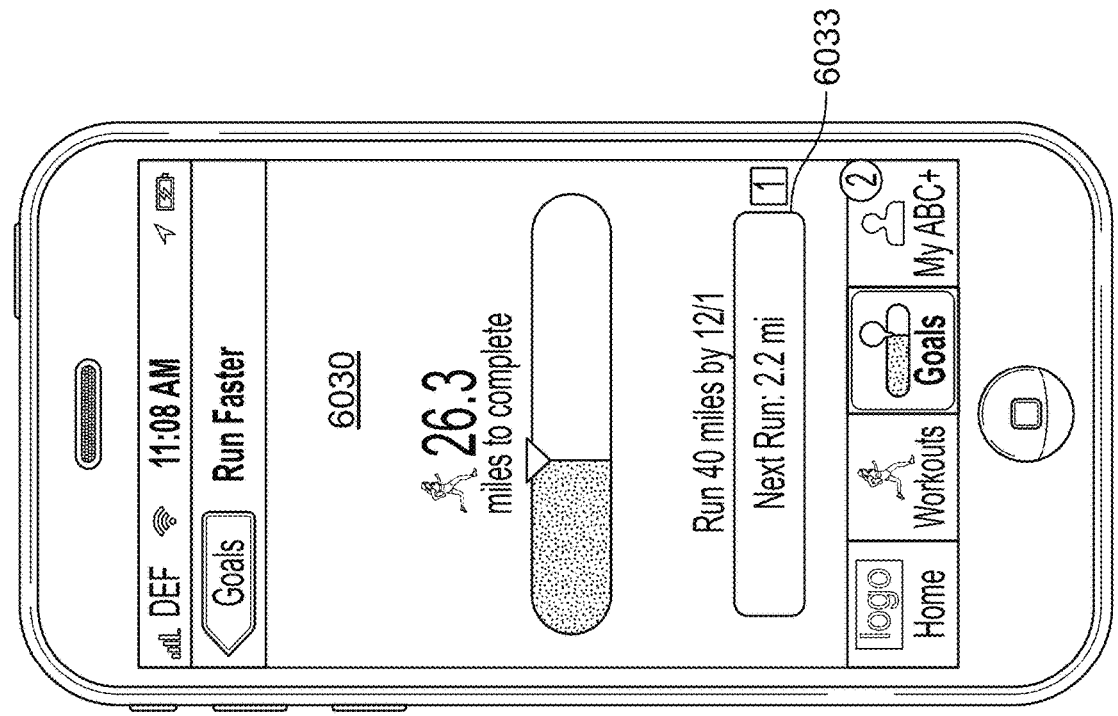
Figure 60E:
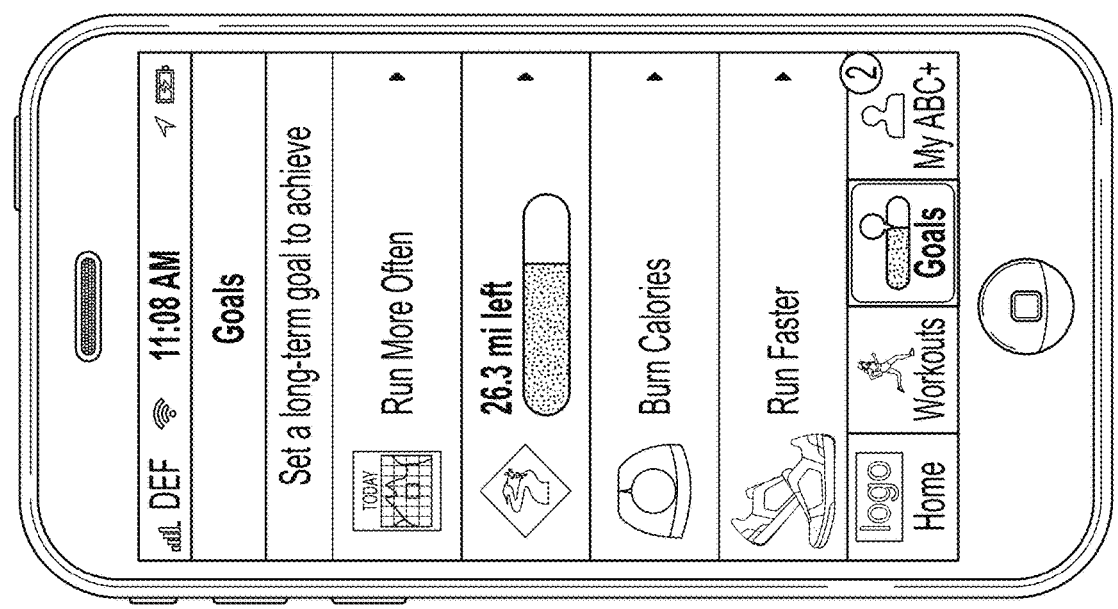

FIGS. 60E and 60F illustrate additional example goal tracking interfaces. For example, in FIG. 60E, a progress bar might not be displayed until the goal type or goal has been selected or the user has placed focus thereon. In FIG. 60F, the interface may display details of the goal and the goal progress. For example, interface 6030 illustrates that the user has 26.3 miles to complete the goal and indicate that the goal is to run 40 miles by December 1. Additionally, the user may be offered an option 6033 to proceed directly to a next workout (e.g., run 2.2 miles).

Figure 62A:
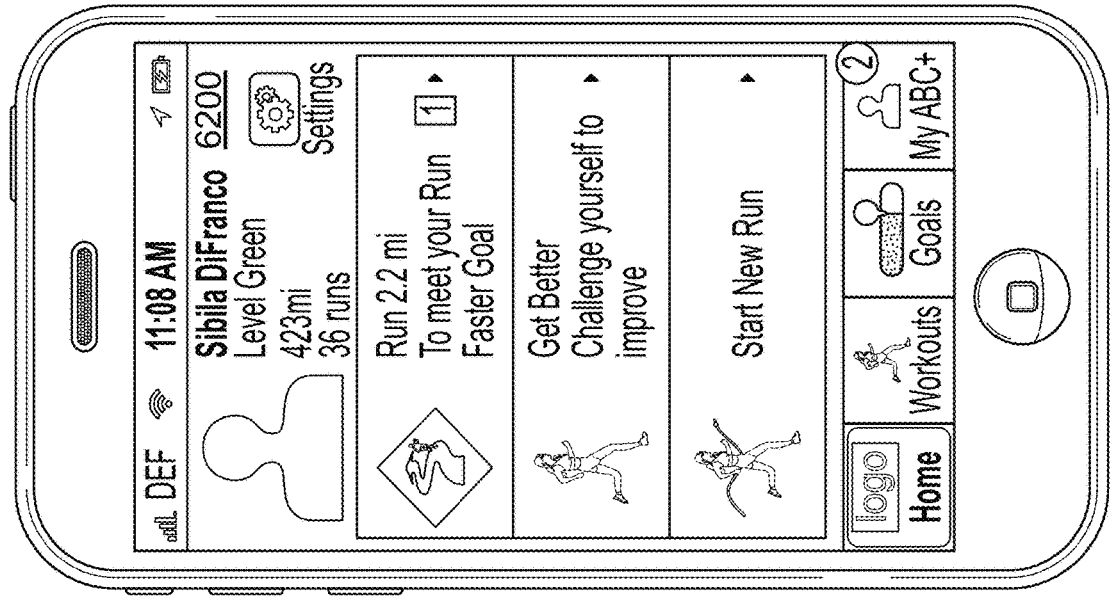
FIGS. 62A and 62B illustrate example interfaces for providing workout and goal reminders according to one or more aspects described herein.
Figure 62B:
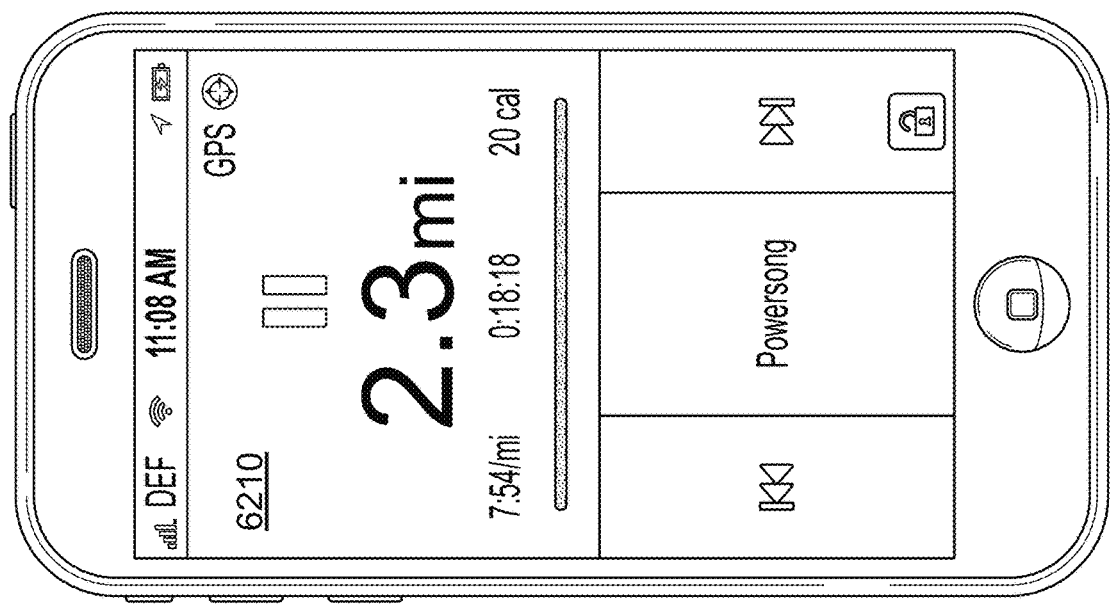

A user may be reminded of goals and workouts for achieving the goal through various interfaces. FIGS. 62A and 62B illustrate example interfaces for providing such reminders. In FIG. 62A, interface 6200 provides a notification that the user must run 2.2 miles to reach his or her predefined goal. In FIG. 62B, interface 6210 may provide various voice notifications during the run. The voice notifications may indicate to the user a progress made toward the goal. For example, the user may be provided with a message that indicates the current portion of the goal has been completed and that progress has been made to the overall goal. The message may, alternatively or additionally, be textual in nature and may further include reminder information such as "Your next run is 3 miles on Saturday" or "You have 5 more runs of 2.2 miles each before completing the goal!"

Motivation—Celebrations & Cheers

When a user completes a goal, reaches a milestone, completes an objective, makes progress or completes an improvement run, a user may be provided with encouraging or celebratory messages. Alternatively or additionally, cheers, words of encouragement and/or other messages may be provided pre- or mid-run. These messages may include audio, video, images, animated images, tactile or haptic feedback (e.g., vibrations) and the like. In one or more arrangements, the celebratory messages may include audio and/or video messages from a celebrity such as a well-known athlete. The user may be allowed to configure when such messages are to be rendered and conveyed to the user. For example, the user might not want celebratory messages during the run and thus, may indicate a preference that all messages be played after a workout or during non-workout times. Accordingly, the user may specify when messages are not to be conveyed as well. Additionally or alternatively, celebratory messages may include sound effects such as a crowd cheering, a bullhorn, cowbell ringing, vuvuzela blasts, fireworks exploding, slot machine jackpot sounds among others.

Figure 63A:
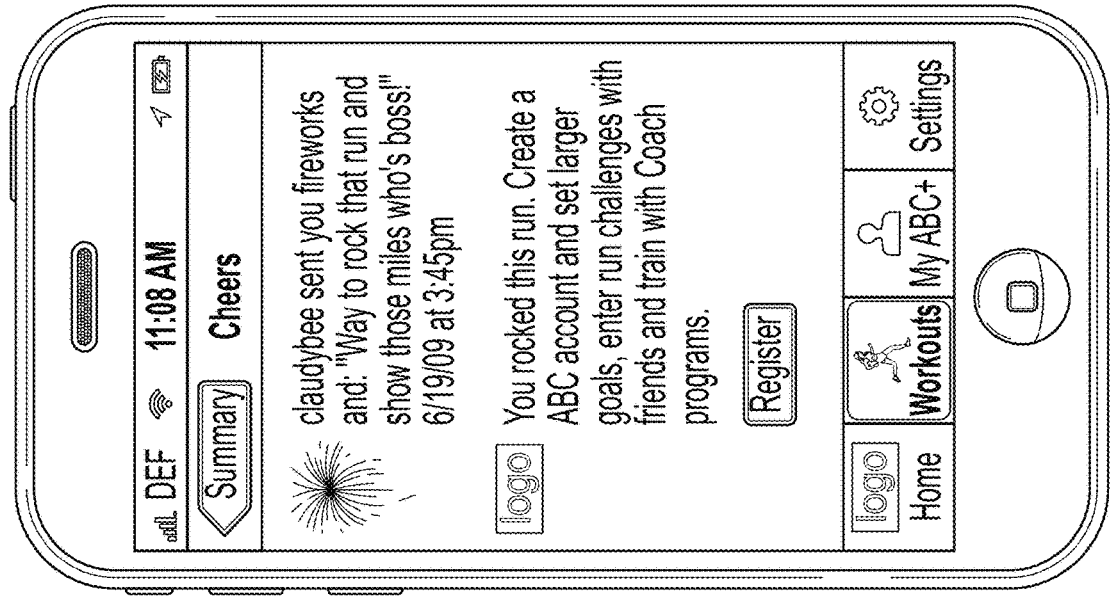
FIGS. 63A-63C illustrate example celebratory interfaces in which one or more congratulatory or motivating messages may be displayed in a list according to one or more aspects described herein.
Figure 63C:
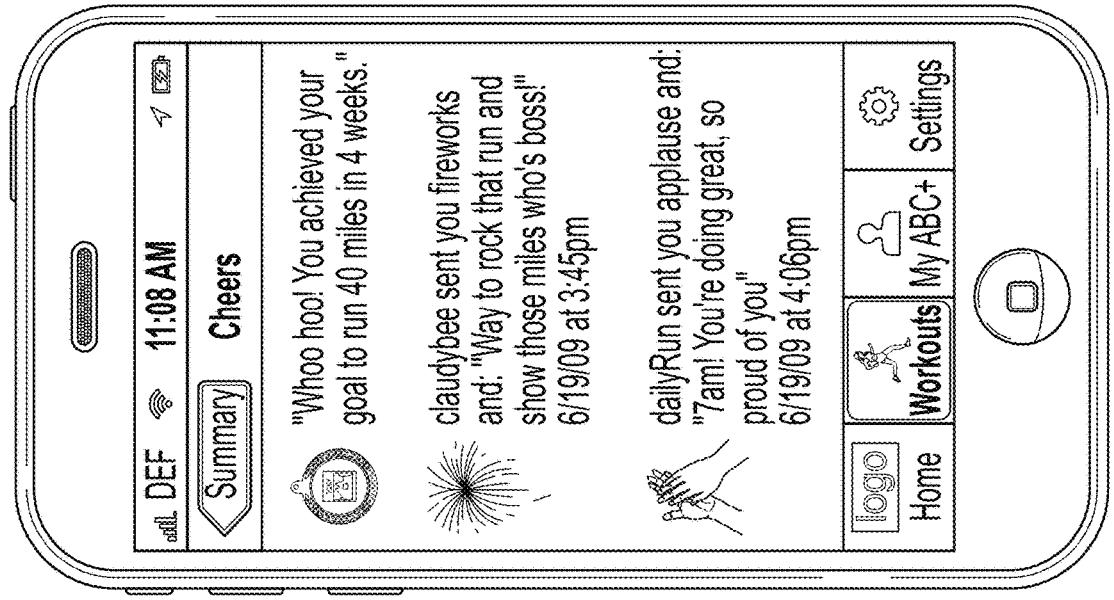
Figure 63B:
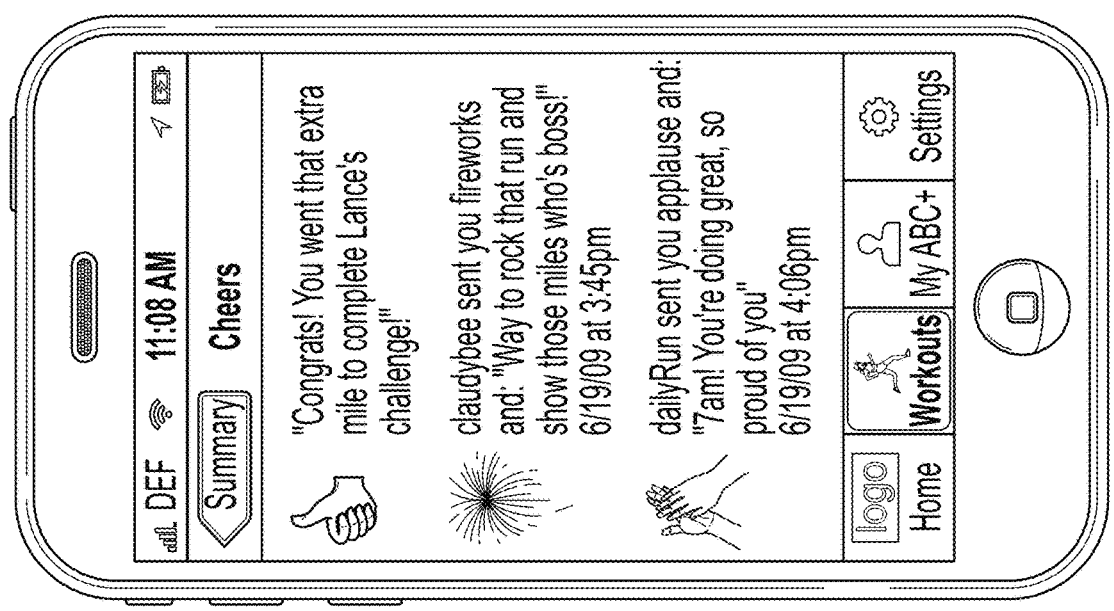
Figure 64B:
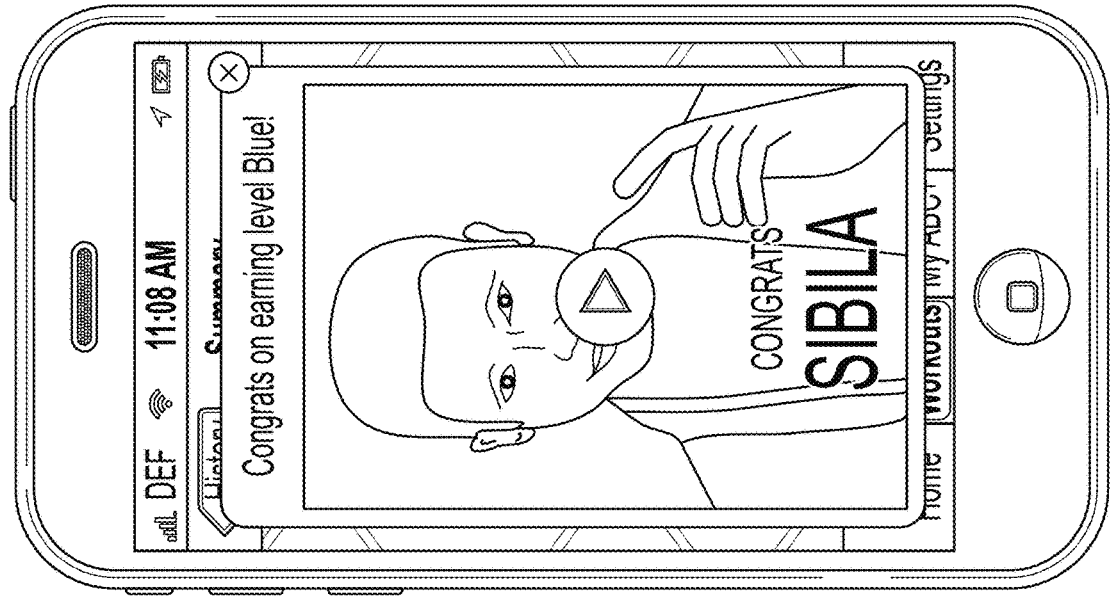
FIGS. 64A-64E illustrate example congratulatory interfaces that include celebrity messages according to one or more aspects described herein.
Figure 64A:
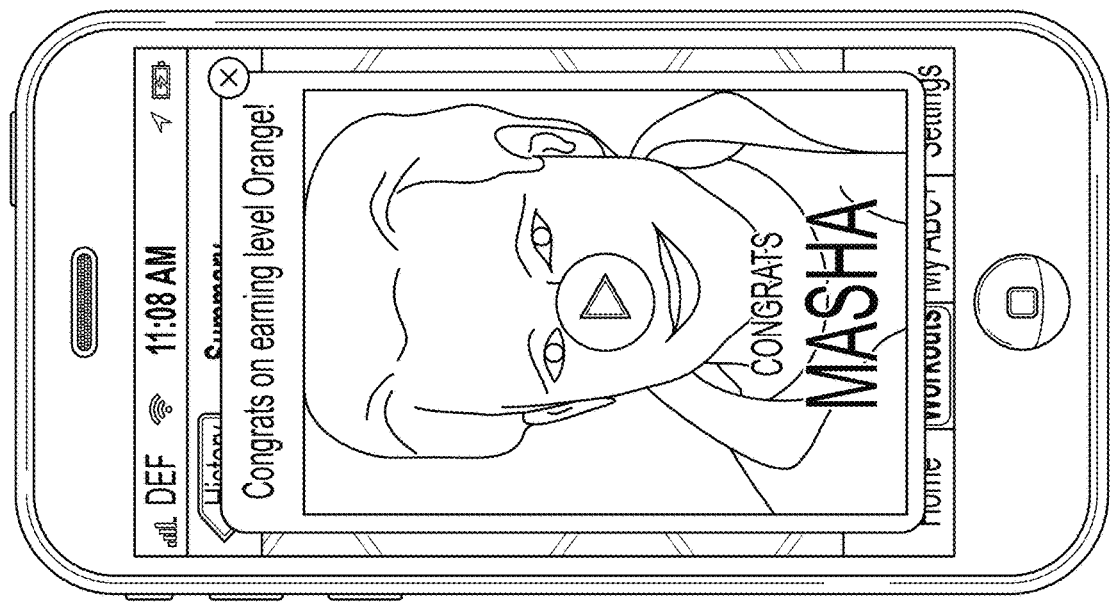
Figure 64D:
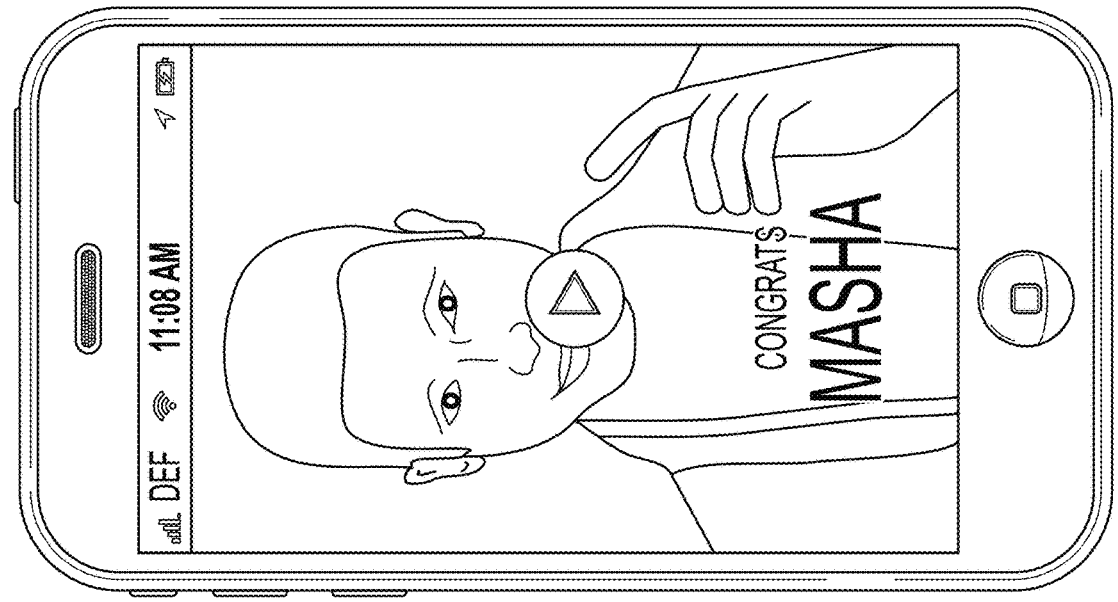
Figure 64C:
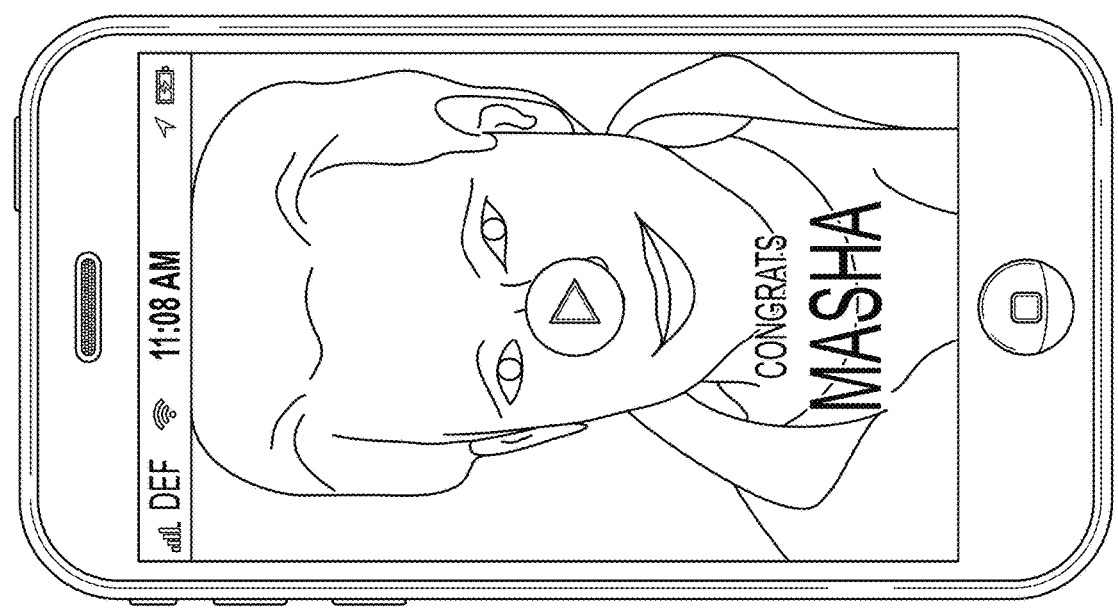

FIGS. 63A-63C illustrate example celebratory interfaces in which one or more congratulatory or motivating messages may be displayed in a list. Some messages may be generated by the mobile device while other messages may be received from other users. In one or more examples, the messages may be converted using text-to-speech systems and played through an audio output device. Alternatively or additionally, other users may send audio and/or video messages. A sender of the message may indicate a triggering event for when the message is to be conveyed to the user. For example, the sender may specify that the message is to be displayed or played to the user when the user reaches a 5 mile mark during a single workout.

In some examples, a user may be congratulated by a celebrity. FIGS. 64A-64E illustrate example congratulatory interfaces that include celebrity messages. The messages may include audio and/or video. The messages may be conveyed for various achievements such as completing an improvement run, reaching a milestone (e.g., 25 miles in a week), setting a fastest pace, fastest distance or fastest time. In one or more arrangements, an achievement may include reaching different fitness levels. For example, running 5 miles or less in a week may be considered to be a first fitness level while running more than 5 miles but less than 10 miles a week may be considered a second fitness level. Additional fitness levels may be defined and various awards or privileges may be associated therewith. For example, the user may receive access to different workouts, receive various awards (e.g., music, products, services), earn recognition through various public channels (e.g., on a fitness monitoring site's main page) and the like.

According to some aspects, a type of celebratory message may be selected for delivery (e.g., transmission, rendering, playback, etc.) to a user based on a number of comments or other interactions received from other users through an on-line community such as a remote social networking site. For example, other users may comment on or indicate that they "like" a workout announcement posted by the user prior to or during a workout session. The other users may also interact with the workout announcement in other ways including forwarding the announcement to others, linking to the announcement from other sites, labeling the announcement with other tags (e.g., emoticons) and the like. An athletic activity monitoring application or service may then determine a number of interactions received through the social networking site in association with the announcement. Different types of celebratory messages (e.g., different sound effects or different categories of messages) may then be selected and triggered depending on the determined number of interactions. For example, louder or more prominent or distinctive sound effects or messages may be selected and triggered as the number of interactions increases. In some arrangements, only positive interactions from other users may be counted. Thus, a "dislike" or expression of disapproval of a user's workout announcement might not count towards an interaction total used to select or trigger celebratory messages.

In some instances, each sound effect or celebratory message may correspond to a range of feedback amounts and/or content of feedback. For example, the first through third comment or other type of feedback may trigger a first message while the fourth through seventh comment may trigger a second message. Different thresholds, triggers and ranges may be set for the different messages. Any number of ranges may be defined as desired. In some arrangements, users providing feedback to a user's workout may select motivational or celebratory content to provide to the user. The system may select one or more of the user-selected content based on popularity. For example, if 6 people selected content A, but 2 people selected content B, content A may be rendered for to the individual performing the workout. In other examples, all of the selected content items may be rendered for the individual.

Other types of messages such as coaching or encouragement may be sent to the user when negative feedback is received. For example, if a user received a "dislike" vote or negative comment on their social networking site in response to a workout post, an athletic performance monitoring device may receive and/or render an encouragement message to motivate the user to improve his or her performance. Similar to the celebratory messages, different types, levels or severities of motivational, coaching or encouragement messages may be provided to the user depending on the number of negative feedback received. Coaching or encouragement messages may include suggested instructions for improving performance.

Figure 65A:
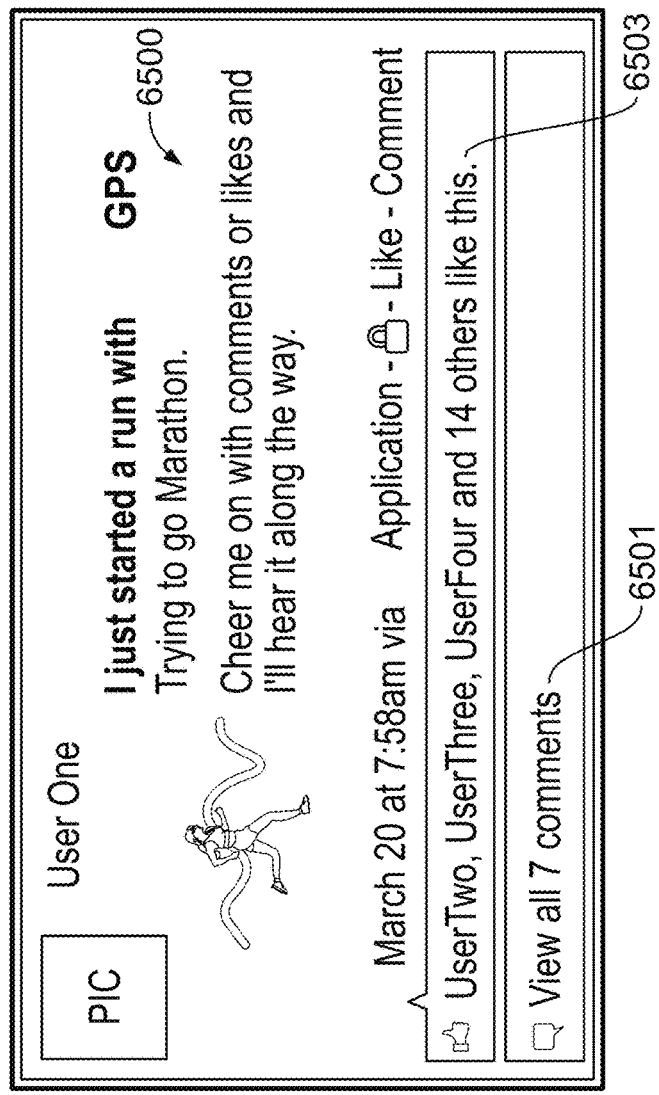
FIGS. 65A-65D illustrate example workout announcements according to one or more aspects described herein.
Figure 64E:
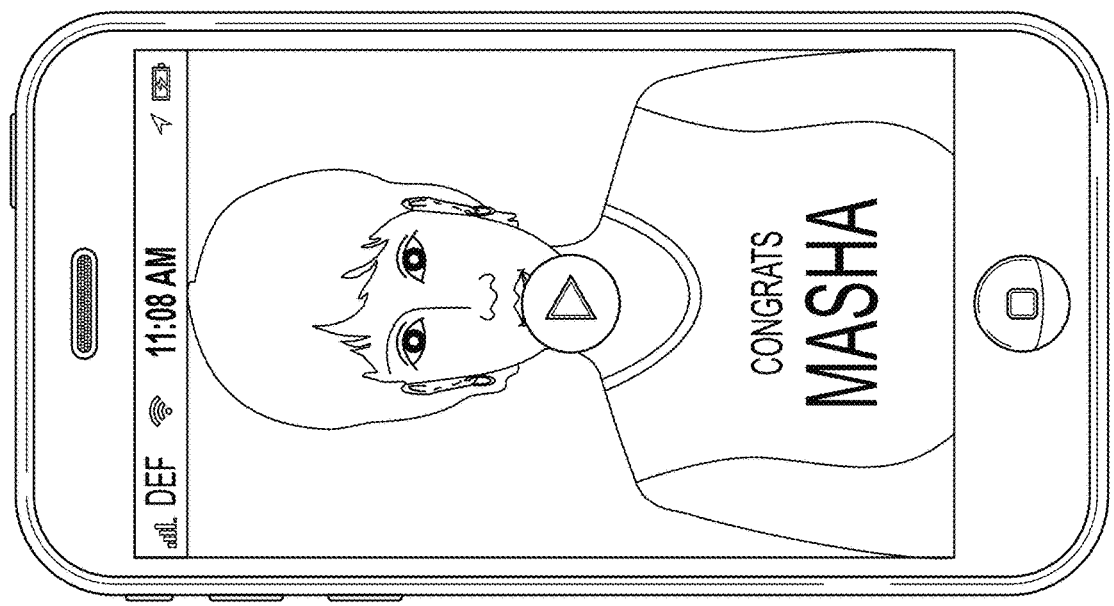

FIG. 65A illustrates an example workout session announcement that may be posted or otherwise provided to an on-line community such as a user's social networking site or conveyed through an on-line community such as a social networking service (e.g., TWITTER) before, during or after a workout. The announcement 6500 may indicate a type of workout that the user is pursuing (e.g., a marathon training run) and a message encouraging other users (e.g., friends and family) to leave comments or indicate approval (or disapproval) of the workout. A number of comments 6501 or indications of approval 6503 may be displayed in conjunction with the announcement as well. In some arrangements, multiple types of feedback and/or feedback from multiple different and/or distinction on-line communities or remote network sites (e.g., social networking services) may be aggregated to determine the amount of feedback received. For example, a number of comments may be added to a number of approval indicators received. In other arrangements, each type of feedback may be counted separately. Additionally or alternatively, only positive feedback or feedback matching one or more predefined rules or parameters (e.g., type of content, words, characters, symbols, etc. used in the feedback, identity of an author/commenter and the like) may be counted towards the amount of feedback. In still other examples, the type of content or message selected for delivery to the user may be based on matching one or more predefined parameters or rules other than or in addition to an amount of feedback. For example, such parameters or rules may include type of content (video, audio, text), words, characters, symbols, etc. used in the feedback, identity of an author/commenter and the like.

Determining an amount of feedback received may include receiving the comments from an on-line community (e.g., social networking site) and counting the amount of feedback received (e.g., a number of comments). In another example, determining the amount of feedback may include receiving an indication of a number of comments or feedback received in response to the posted workout information. In other examples, determining the amount of feedback may be performed by another device. The other device may then provide the determination of the amount of feedback to an athletic monitoring system. The other device may also be configured to select the content (e.g., sound effect, video, text, images, profile picture of one or more people who leave feedback, haptic feedback) to be provided to the user. Providing the determination of the amount of feedback may also be performed from one software or hardware module of a device (e.g., an athletic performance monitoring device) to another software or hardware module of that same device.

Provision of the determination of the amount of feedback may also include storage of the determination of the amount of feedback in memory.

According to some arrangements, the determination of the amount of feedback and the selection of the content may be performed by different devices such as an athletic performance monitoring service and an athletic performance monitoring device. Alternatively, the determination and the content selection may be performed by the same device. In still other arrangements, the determination of the amount of feedback and/or the selection of content may be performed by the on-line community (e.g., the social networking system).

Figure 65B:
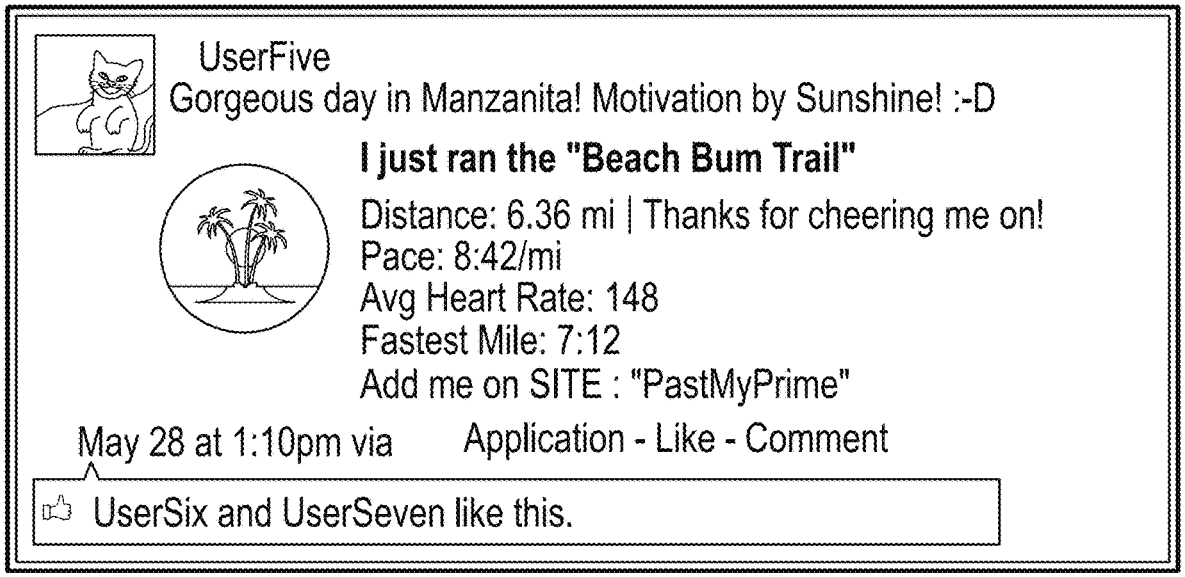
Figure 65C:
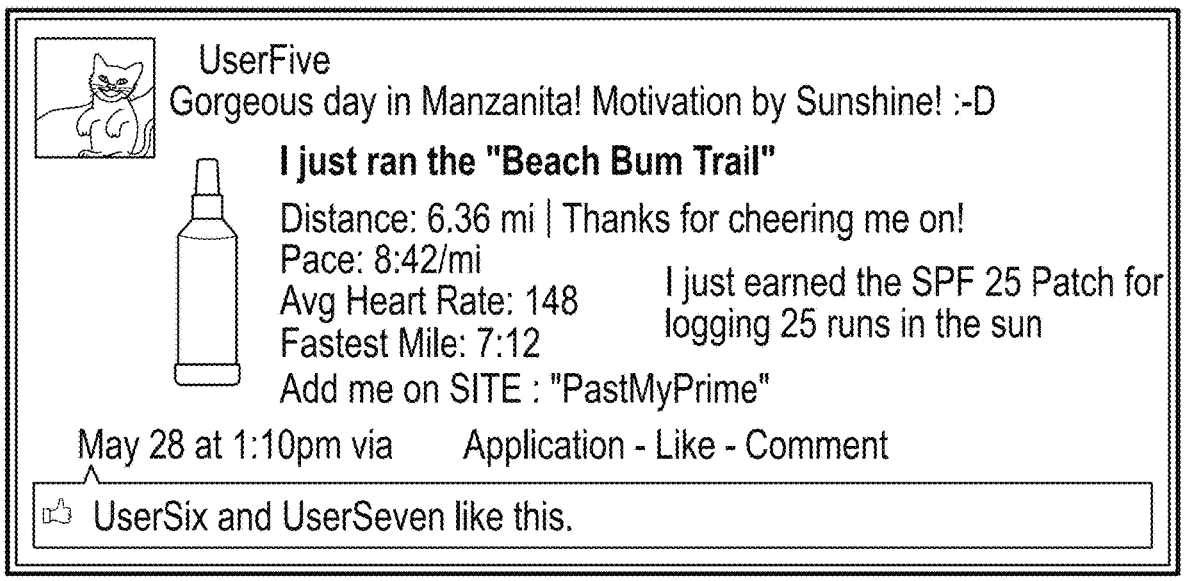

FIGS. 65B and 65C illustrate example workout announcements that may be displayed after a user completes a workout. The workout announcements in these illustrative examples may provide statistics and metrics associated with the completed workout. For example, a distance run, a time run and/or a pace (e.g., an average pace, fastest pace, slowest pace, etc.) may be displayed in the workout announcement. Other users may be allowed to comment on the announcement and celebratory messages may be provided to the user as described above.

Figure 65D:
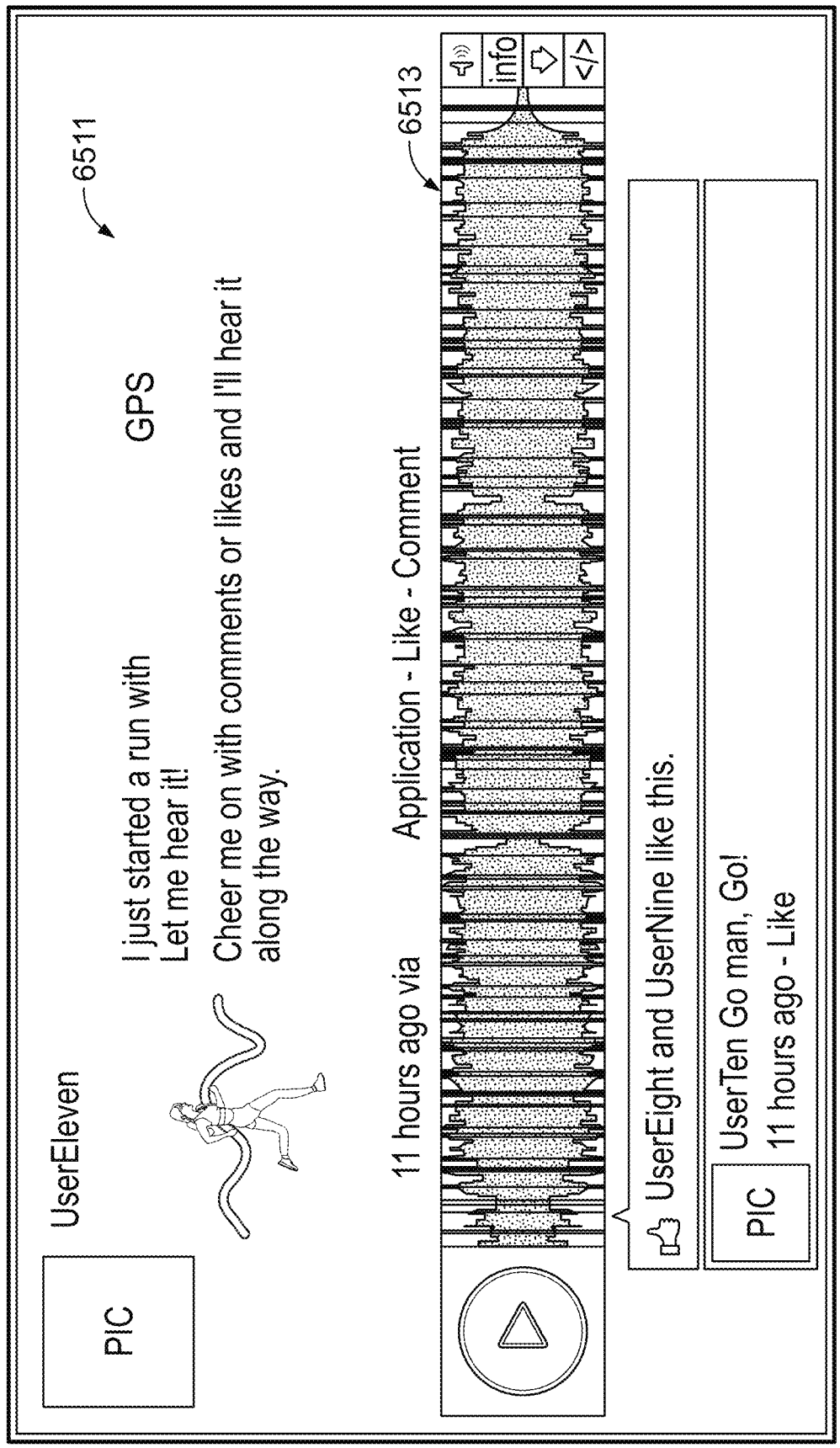

FIG. 65D illustrates another example workout announcement with associated friend or other user feedback. Instead of or in addition to submitting textual comments and/or approval indicators in response to the workout announcement, friends and other users may also record audio and/or video messages to be played to the user. In announcement 6511, for example, a friend has recorded an audio message 6513 in response to the announcement 6511. The audio message 6513 may be immediately played to the user or may be played according to a trigger selected by the creator of audio message 6513 (e.g., completion of the workout, reaching a specified distance, time or pace goal, receiving a certain number of total comments or other type of feedback, etc.). Alternatively or additionally, the user performing the workout may select the triggering event for receiving audio messages left by friends and other individuals.

Sound effects may be used as an efficient way to notify the user that they have received a certain amount of positive feedback without requiring the user to listen to or view a lengthy audio or visual message.

In some embodiments of the invention content or messages are provided to users via a wrist worn device, such as a watch. FIGS. 65E-H illustrate example interfaces associated with a wrist worn device in accordance with one or more aspects of the present disclosure. As illustrated in FIG. 65E, the wrist worn device may include a display (e.g., display 6520) for displaying various content or messages. In some embodiments, the wrist worn device may display a dynamic tile or image that enables a user to quickly launch a software application or applet that permits the wrist worn device to perform various athletic activity tracking and monitoring functions as described in various aspects of the present disclosure. For example, upon receiving input indicating that a user has touched and/or selected icon 6519 in display 6520, the wrist worn device may launch the activity tracking and monitoring software application.

Various images, icons, or tiles may be displayed on the display of the wrist worn device and utilized for launching the software application. For example, a dynamic tile or icon may be displayed on the display of the wrist worn device. In some embodiments, the dynamic tile may display a portion of a leaderboard associated with the user. As discussed in more detail below with respect to FIG. 73, the leaderboards may display athletic activity data for a plurality of users in a manner such that users may compare their individual athletic performances with each other. In other embodiments, the dynamic tile may display information corresponding to the user's current location, the time of day, weather conditions, etc. Various parameters or settings may be provided to the user to adjust or modify the dynamic tile, including options for selecting the type of information displayed in the dynamic tile.

Referring back to FIG. 65E, a portion of an interface displayed on the wrist worn device (e.g., element 6522) may display content or a message to the user, for example, a message indicating that a friend or another user is performing athletic activity performed. In some embodiments, when comments are received from a friend associated with an on-line community (e.g., social networking site), a profile picture of the friend (e.g., image 6523) is displayed on the wrist worn devices. Additional messages and content may also be displayed. The wrist worn device may be connected to headphones via a wired or wireless connection to allow audio content and/or messages to be delivered to a user A wrist worn device may include components that allow the device to communicate with a mobile phone network. In an alternative embodiment, the wrist worn device may include a short range wireless transmitting and receiving component for sending data to and from a mobile terminal, such as a mobile phone. The mobile phone may be configured to communicate with a mobile phone network with conventional components and communication with the wrist worn device with a short range wireless transmitting and receiving component. Bluetooth and Bluetooth low energy are exemplary wireless communication protocol that may be used for communications between the wrist worn device and the mobile terminal. The wrist worn device and mobile terminal may include Bluetooth and/or Bluetooth low energy transmission and reception components.

In some embodiments a wrist worn device may be configured to allow a user to reply to a person who provided content or a message. For example, if the user receives a message or content indicating that the user's friend is performing athletic activity, the user may respond to the friend to provide a motivational message or content to encourage the friend's athletic activity. For example, a user interface element on the display of the wrist worn device (e.g., element 6521) may be configured to transmit a "cheer," words of encouragement, or other motivational message to another user.

Figure 65F:
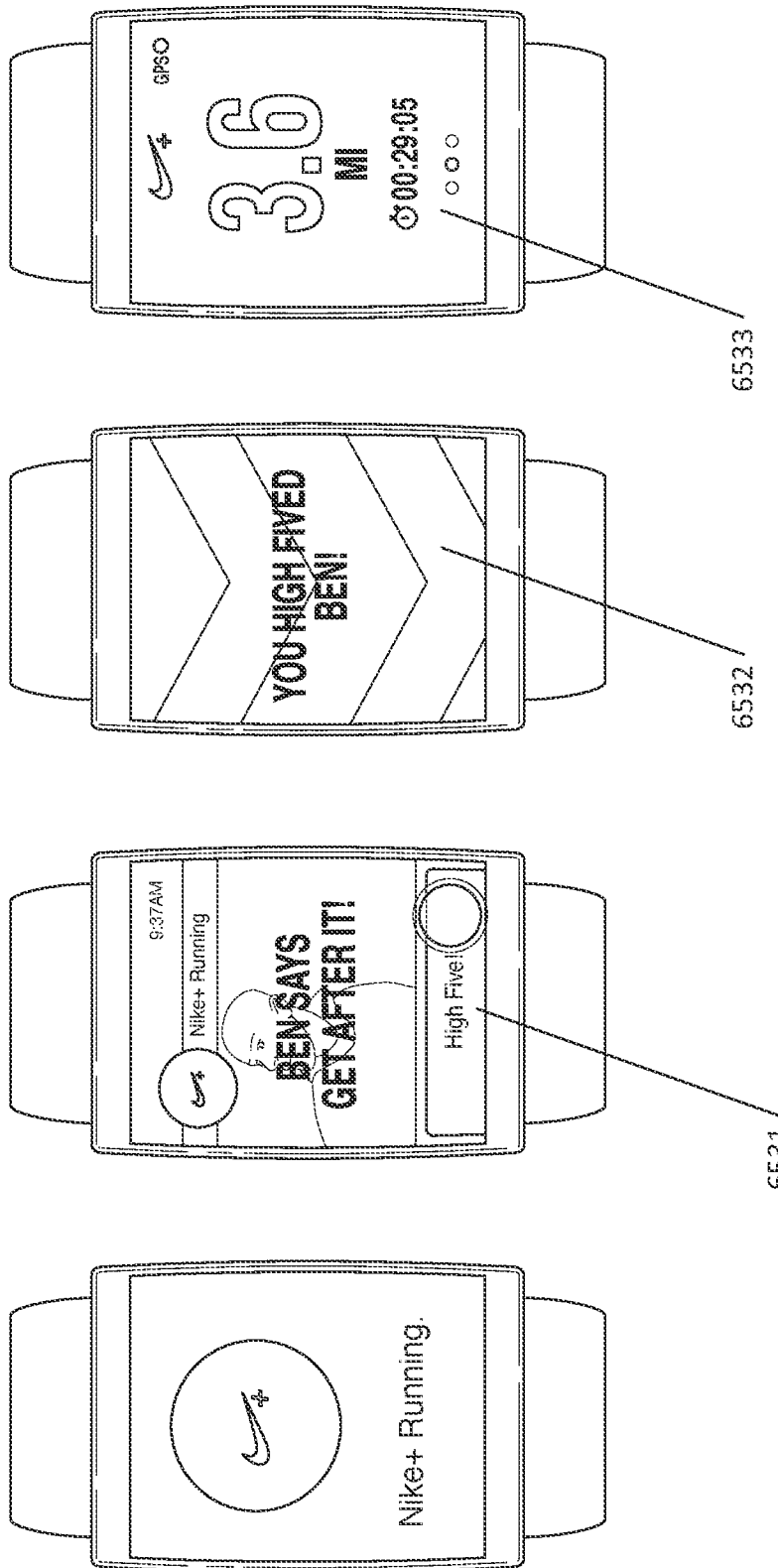

As another example, during a run a user's friend associated with an on-line community (e.g., social networking site) may respond to an announcement posted on the on-line community to provide a message or content to the user. As mentioned above, the message or content may include cheers, words of encouragement and/or other messages. These messages may include audio, video, images, on-line community profile pictures, animated images, tactile or haptic feedback (e.g., vibrations) and the like. The user may see a message or content on a display of the wrist worn device and/or hear the message or content via headphones connected to the wrist worn device or mobile terminal. The wrist worn device may include one or more user interface elements that allow the user to acknowledge the message or content. For example, referring to FIG. 65F, the display of the wrist worn device may include a user interface element (e.g., element 6531) that when selected acknowledges the message or content with a post to the on-line community. For example, as illustrated in FIG. 65F, the user may acknowledge a message or content sent by another user by selecting interface element 6531 to transmit a "high five"

message. In some embodiments, the wrist worn device may display a notification indicating that a message or other content has been transmitted to another user. In other embodiments user interface elements may be configured to acknowledge the message or content by sending a private on-line community message, a text message, an electronic mail message or other types of public and private messages. In one of these embodiments, as illustrated in FIG. 65G, the wrist worn device may display an icon or image associated with each of the users within the on-line community that may receive the transmitted message or content.

Exemplary user interface elements include tradition icons and physical buttons. In other embodiments the wrist worn device may include one or more accelerometers, pressure sensitive switches or other sensing devices configured to sense a user tapping on a display of the wrist worn device. When running a user may receive an encouraging message or content from a friend and tap the display to cause an acknowledgement message or content to be sent to the friend. The acknowledgement message may be sent from the wrist worn device to a mobile phone network or from the wrist worn device to a mobile device, such a mobile phone, and then to the mobile phone network. Of course, in other embodiments acknowledgement messages may be sent via other networks, such as the Internet.

Another option available in accordance with at least some example systems and methods according to certain aspects of the disclosure involves the use of wireless, "hands free," or other non-contacting methods to provide control input to the wrist worn device. For example, a hand or arm mounted accelerometer (e.g., on a wrist-worn device, ring, or the like) may be used to generate and/or transmit an acknowledgement message or content to another user during an athletic performance. By waving a hand or arm (or through some other appropriate action or gesture), output from an arm or hand mounted accelerometer (or other movement sensing or similar device) may be used to generate and/or transmit the acknowledgement message or content Eliminating the need for "hands on" control (e.g., to actuate and/or select a user interface element) can be useful to athletes during athletic performances to avoid diverting their attention and concentration from the performance and to avoid the need to locate and manipulate small controls typically associated with small electronic devices.

As another example, output from the wrist worn device may be used to control a type of acknowledgement message or content that is generated and/or transmitted to other users. In one example, a tap of a user interface element followed by a rotation of the user's wrist in a first direction may cause the wrist worn device (e.g., hand or arm mounted accelerometer) to generate and/or transmit a first type of acknowledgment message (e.g., a text message), while a tap followed by a rotation of the wrist in another direction may cause the wrist worn device to send a second type of acknowledgement message (e.g., an electronic mail message). As will be appreciated, various other types of physical movements or gestures may be performed by the user to generate and/or transmit different types of acknowledgement messages or content in accordance with one or more aspects of the present disclosure.

In one embodiment, the user may transmit content corresponding to an attribute or other type of information in association with one or more parameters or metrics of the user's activity data. By raising an arm and rotating a wrist in a manner that the display of the wrist worn device is facing the user, output from the arm or hand mounted accelerometer (or other movement sensing or similar device) may be used to display an interface providing athletic activity data for the user. For example, referring to FIG. 65F, in response to receiving control input corresponding to a predetermined physical gesture of the user, the wrist worn device may display interface 6533, which depicts athletic activity data associated with an athletic activity performed by the user (e.g., distance traveled, duration of a run, etc.). Upon receiving further control input corresponding to a predetermined gesture or other physical movement (e.g., rotating and/or shaking a wrist), the wrist worn device may display (or scroll through) additional activity data or metrics displayed on interface 6533. As yet another example, the user may transmit one or more metrics associated with the user's athletic activity to another user or group of users by performing one or more additional physical gestures or movements. In another embodiment, the user may transmit a notification to one or more other users when the user reaches certain milestones or activity goals. As will be appreciated, various other types of physical movements or gestures may be performed by the user to access various interfaces and/or perform other interface selections or functions (e.g., ignore an incoming communication, transmit a communication, etc.).

Display of Athletic Activity Data

Athletic activity information and information generated therefrom (e.g., statistics, trends, recommendations, etc.) may be displayed in one or more interfaces as described herein. In one arrangement, a user may access a remote network site that generates and displays athletic activity information for a user registered with an athletic activity monitoring service. In one or more arrangements, the information displays and interfaces may be accessed through the mobile device and/or a fitness monitoring application executing thereon. Alternatively, the user may access the information displays through another computing device. Because in some arrangements, the information displays are generated and provided by a remote fitness monitoring server, the user may access the workout information from a variety of locations and devices without having to synchronize or transfer data to each of those devices or locations.

Figure 66A:
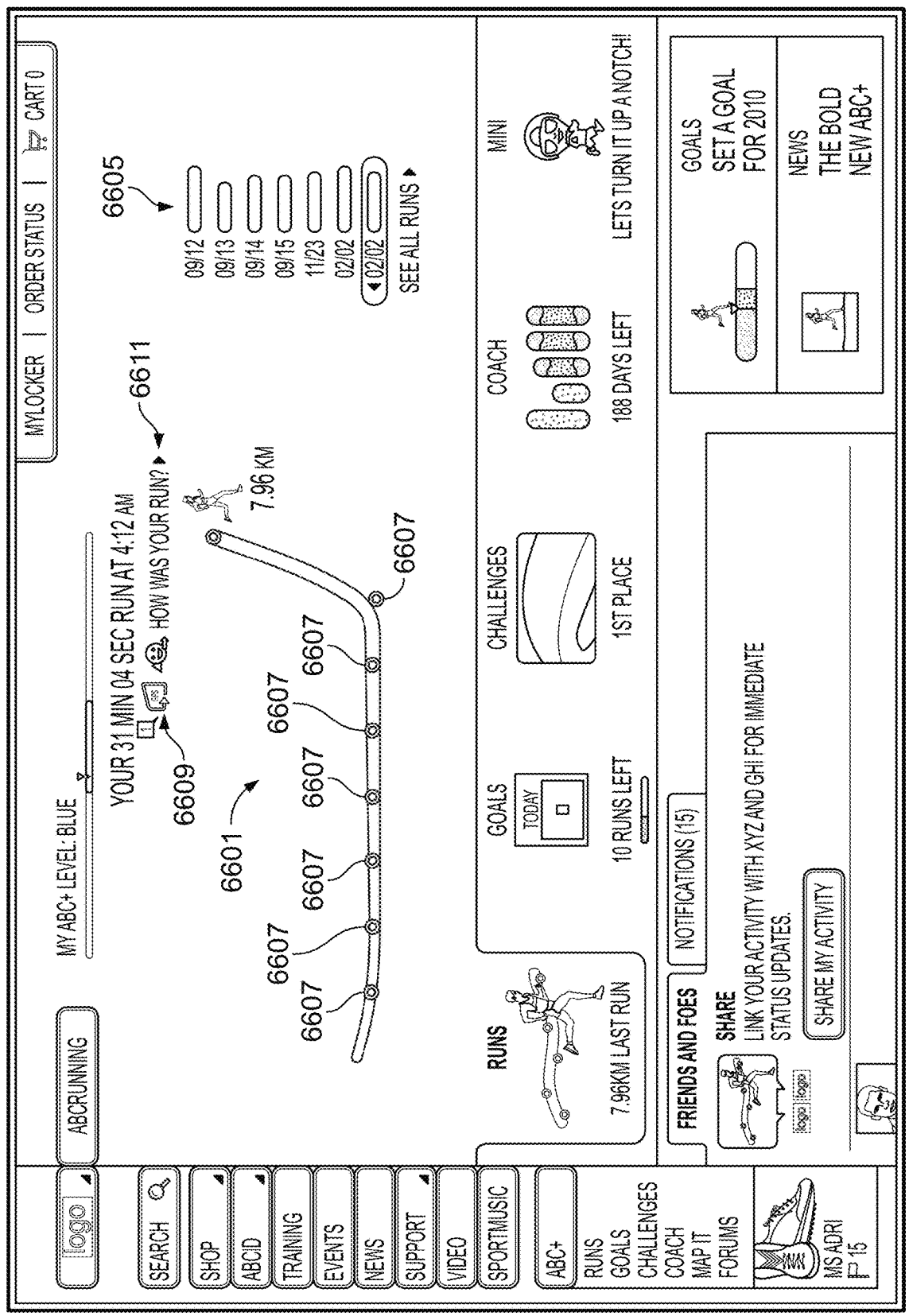
Figure 66B:
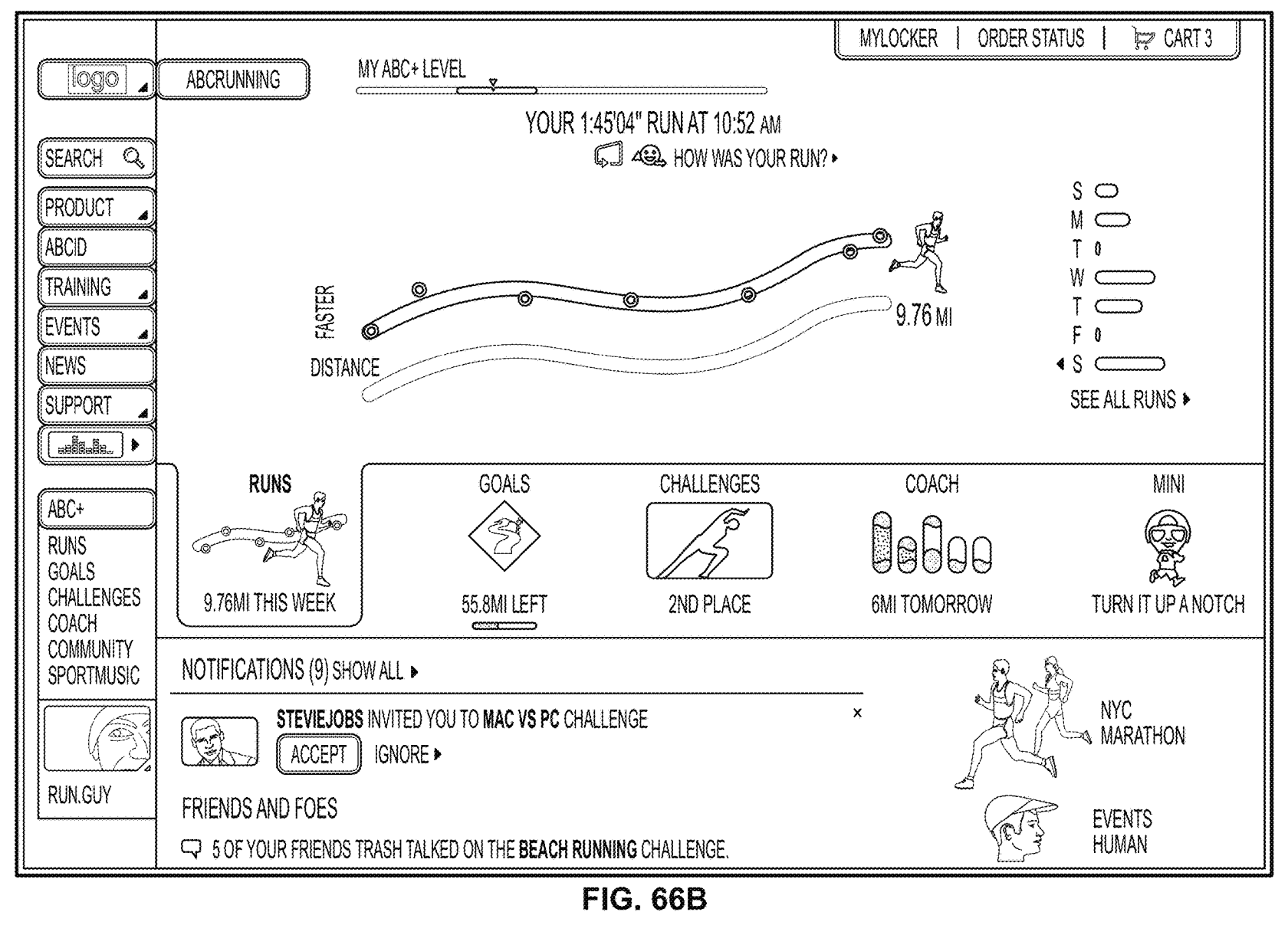

FIGS. 66A and 66B illustrate example interfaces that include a workout review. The workout review may include a graph 6601 of the user's pace over the entire distance run for a selected run. A user may select different runs to view from a workout list such as list 6605. List 6605 may include a predefined number of most recent workouts. Graph 6601 may include indicators or markers 6607 that identify points in the run that correspond to a distance increment such as 1 mile, 1 kilometer, 0.5 miles and the like. The workout review interface may further include workout attribute indicators such as a GPS indicator 6609. GPS indicator 6609 may signify that the workout was recorded with GPS information. Accordingly, a user's route may have been recorded as part of the workout information. Additionally, a user may add further attributes or parameters to the workout. For example, the user may select mood selector option 6611 to enter a mood of the user after the run. The mood may include how the user emotionally and/or physically felt after completing the workout. Other information may also be included in the workout review including news or message feeds, a brief summary of a last run, a goal progress (or an amount left to complete to reach the goal), a challenge progress or position and the like.

Figure 66C:
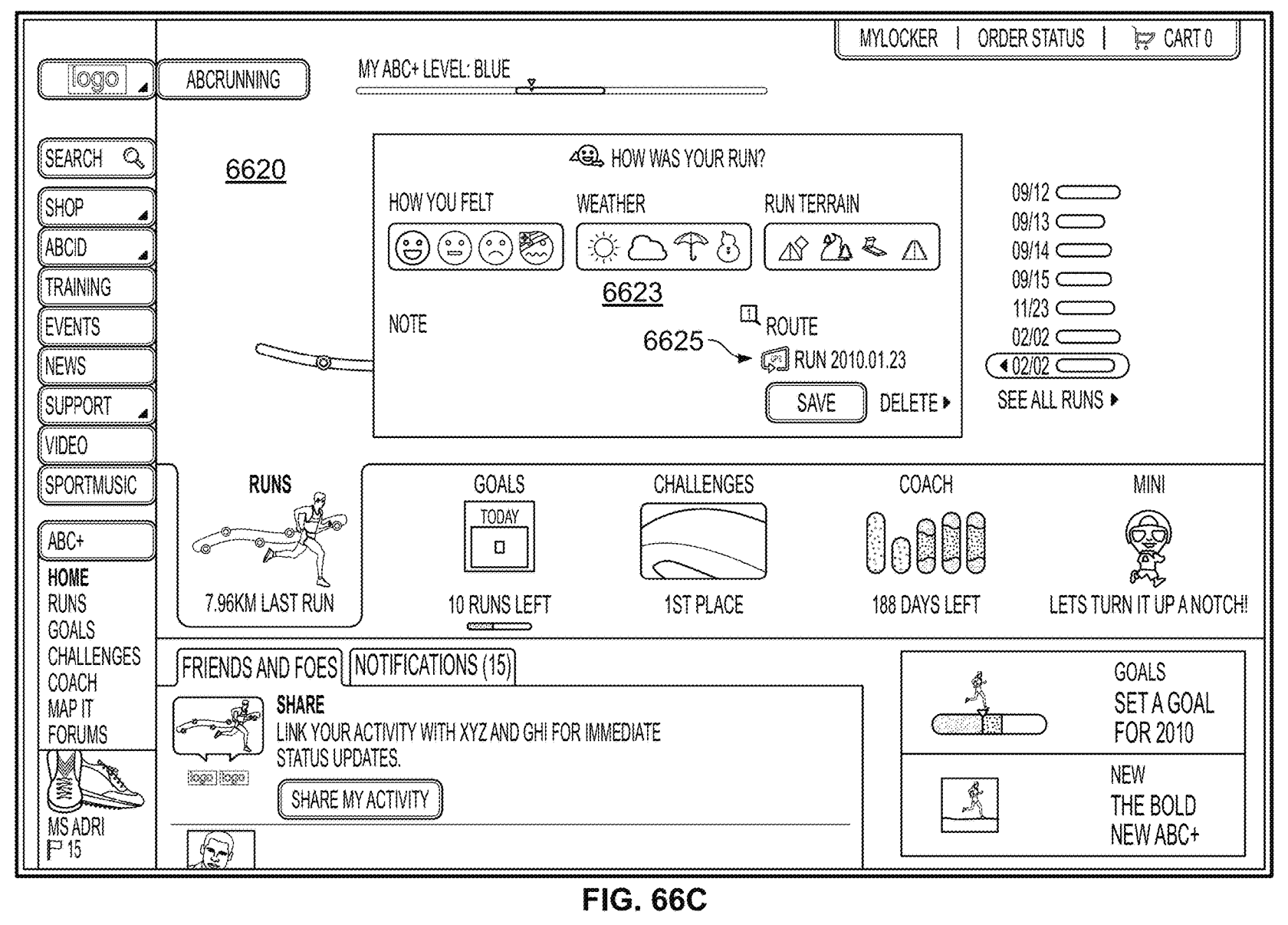
Figure 66D:
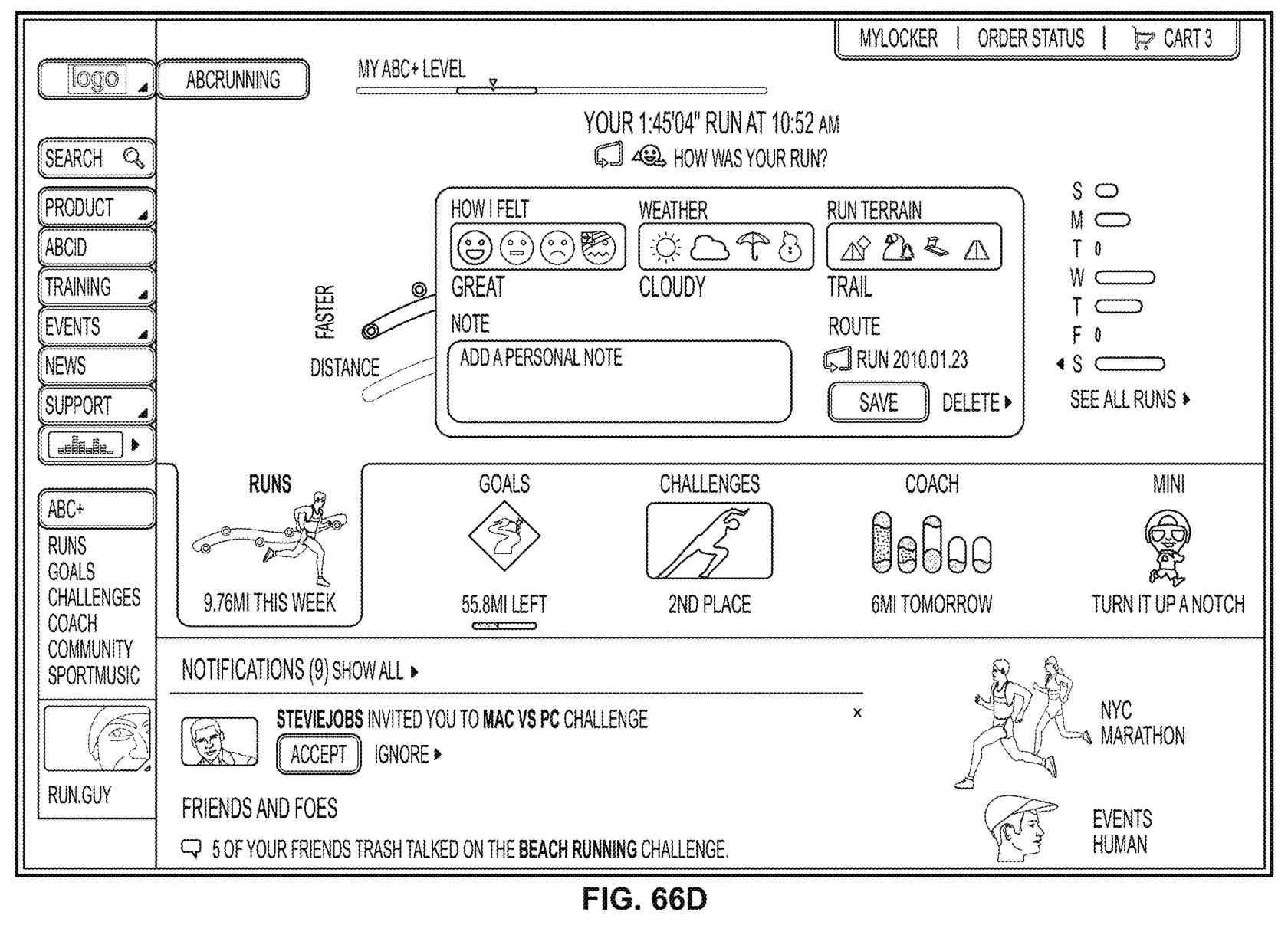

FIGS. 66C and 66D illustrate interfaces for entering attributes of a run or workout. For example, in FIG. 66C, interface 6620 includes an input window 6623 for specifying a user's mood, a weather condition and/or a terrain. Window 6623 may further provide a text entry form configured to receive additional user comments about the workout. In one or more arrangements, window 6623 may display an indicator 6625 if the workout was recorded using location determination systems such as a GPS device.

Figure 66E:
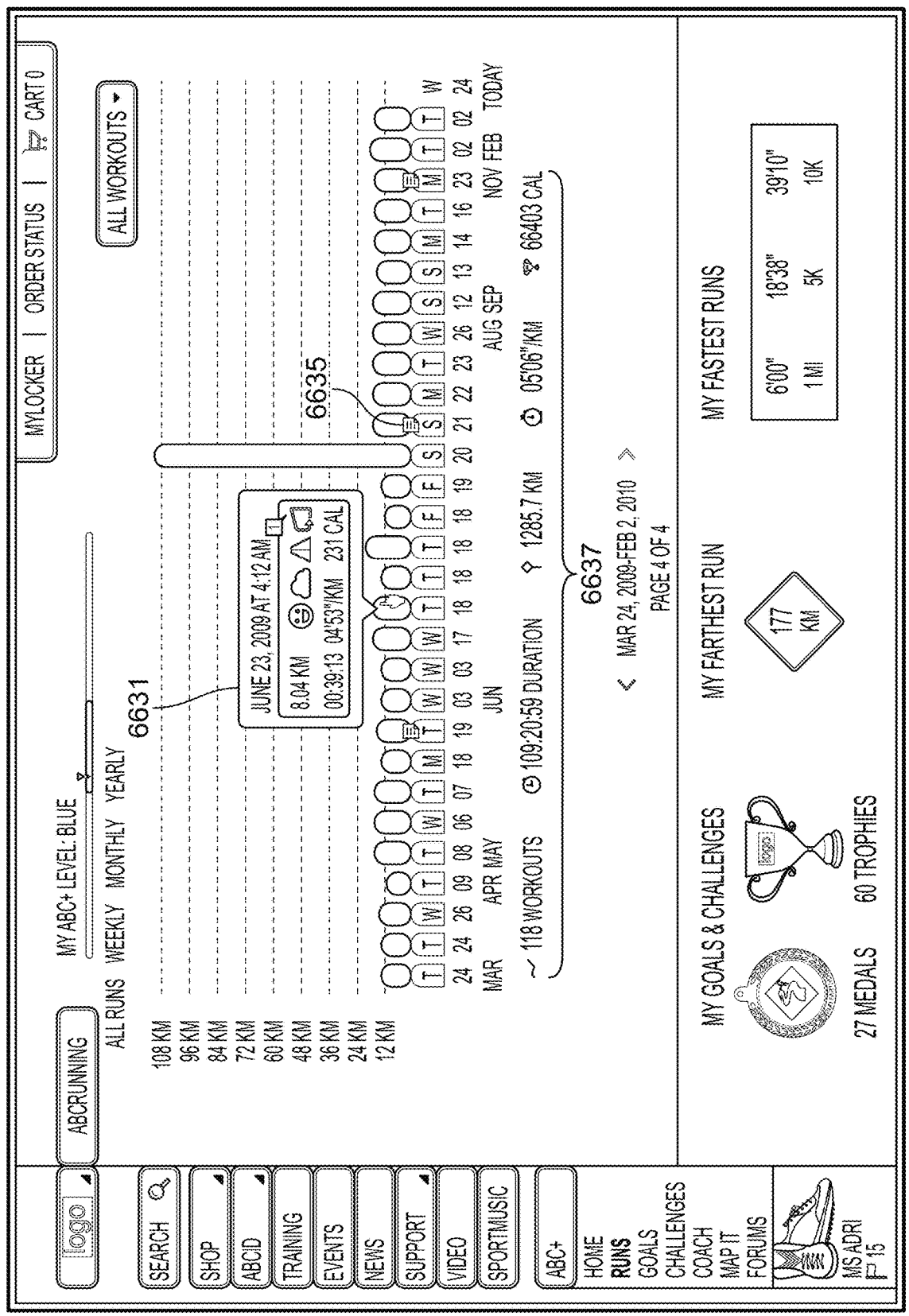
Figure 66F:
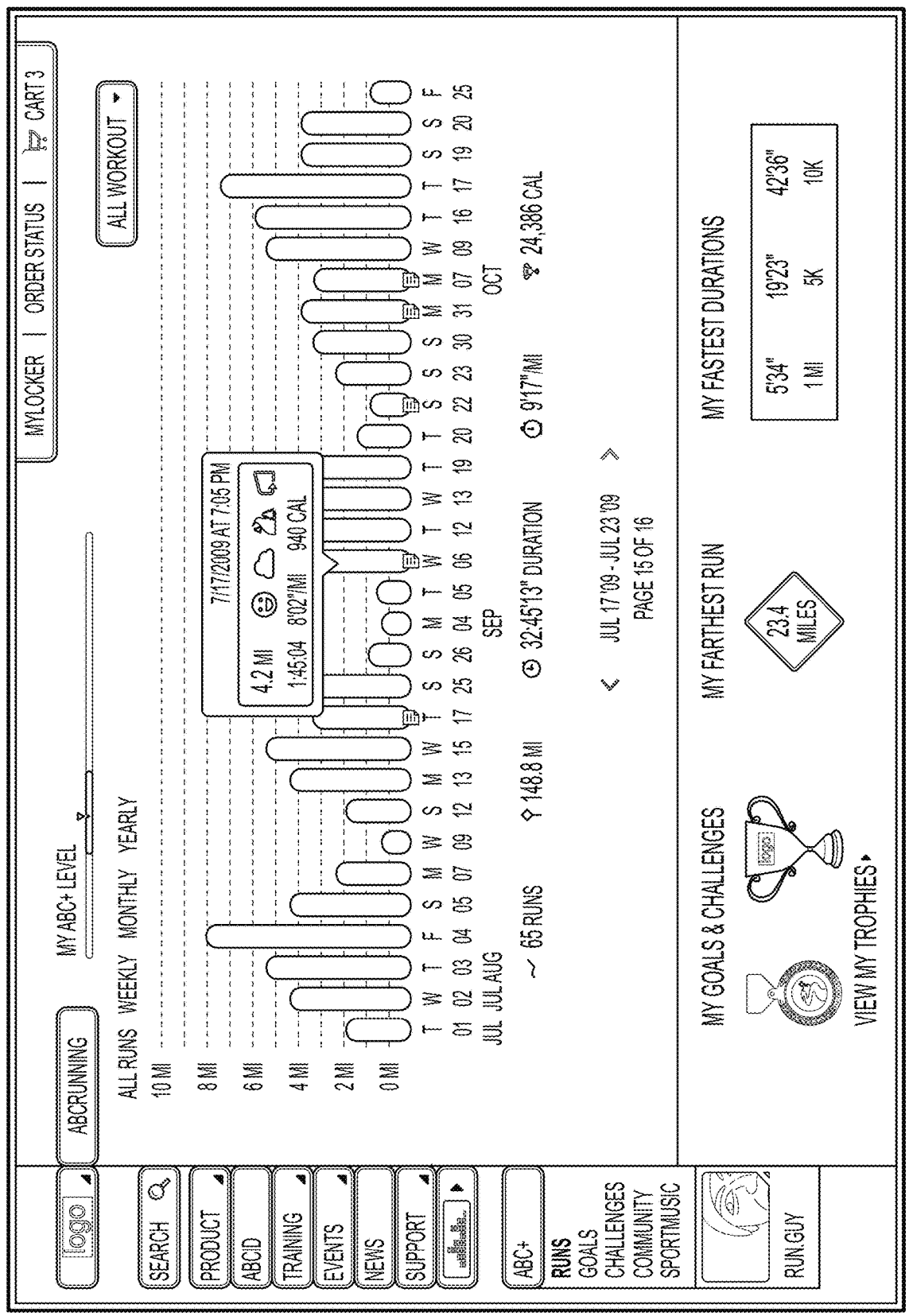

FIGS. 66E and 66F illustrate calendar or timeline views of a workout summary for multiple workouts. Each day may include a bar graph that indicates a distance run on that day (or other time unit such as hour, week, month, etc.). Hovering over or otherwise interacting with each bar graph may cause a detail window such as window 6631 in FIG. 66E to be displayed with additional information about the run. For example, window 6631 may indicate the user's mood after the run, a weather condition, a terrain and whether the workout includes location and route information. If a user has entered a manual or custom note, a note icon 6635 may be displayed in association with bar graphs representing the corresponding workout. Summary data 6637 may also be displayed for indicating a total amount of time, workouts, distance and calories burned for all workouts in the currently displayed timeframe.

Figure 66G:
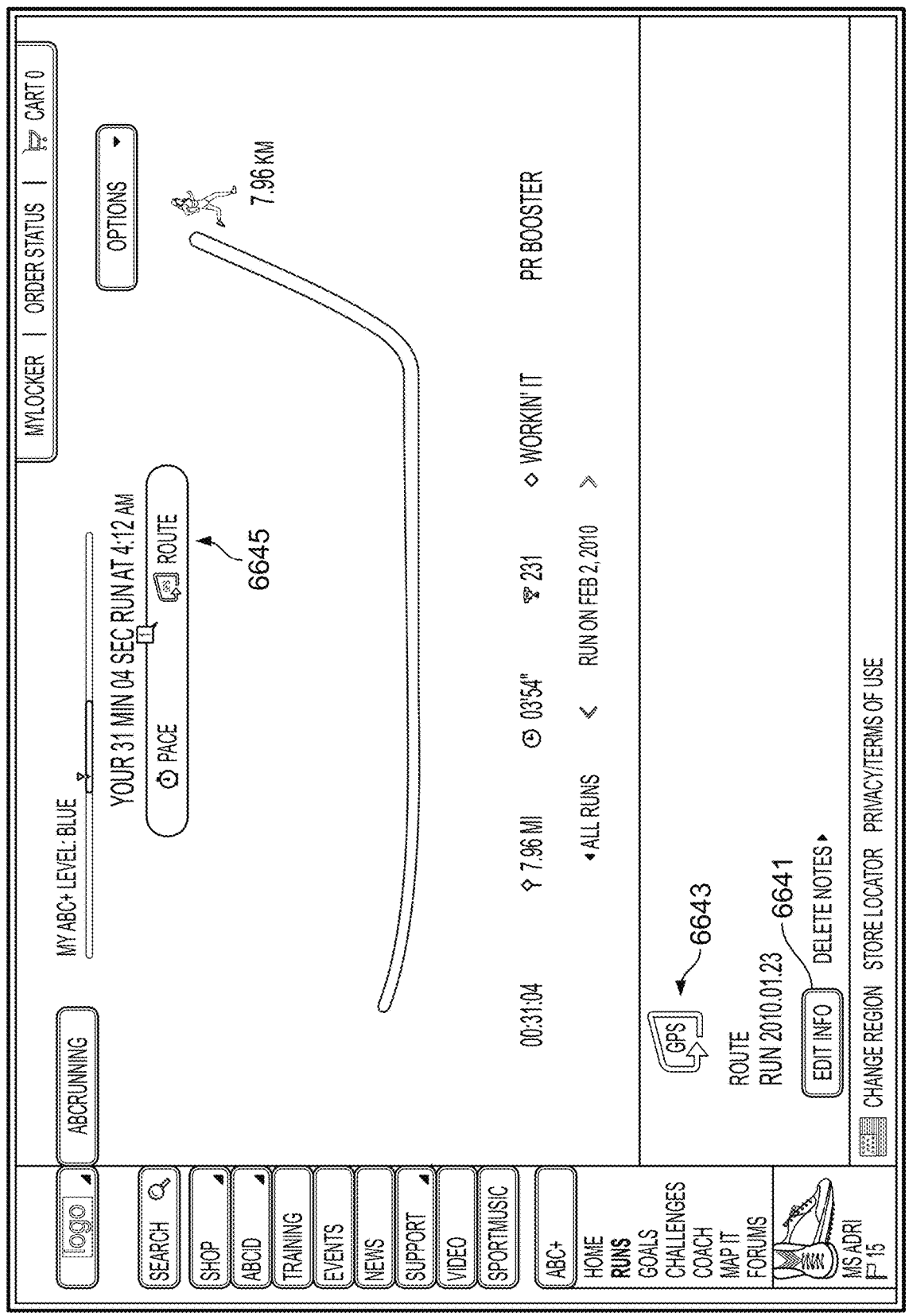
Figure 66H:
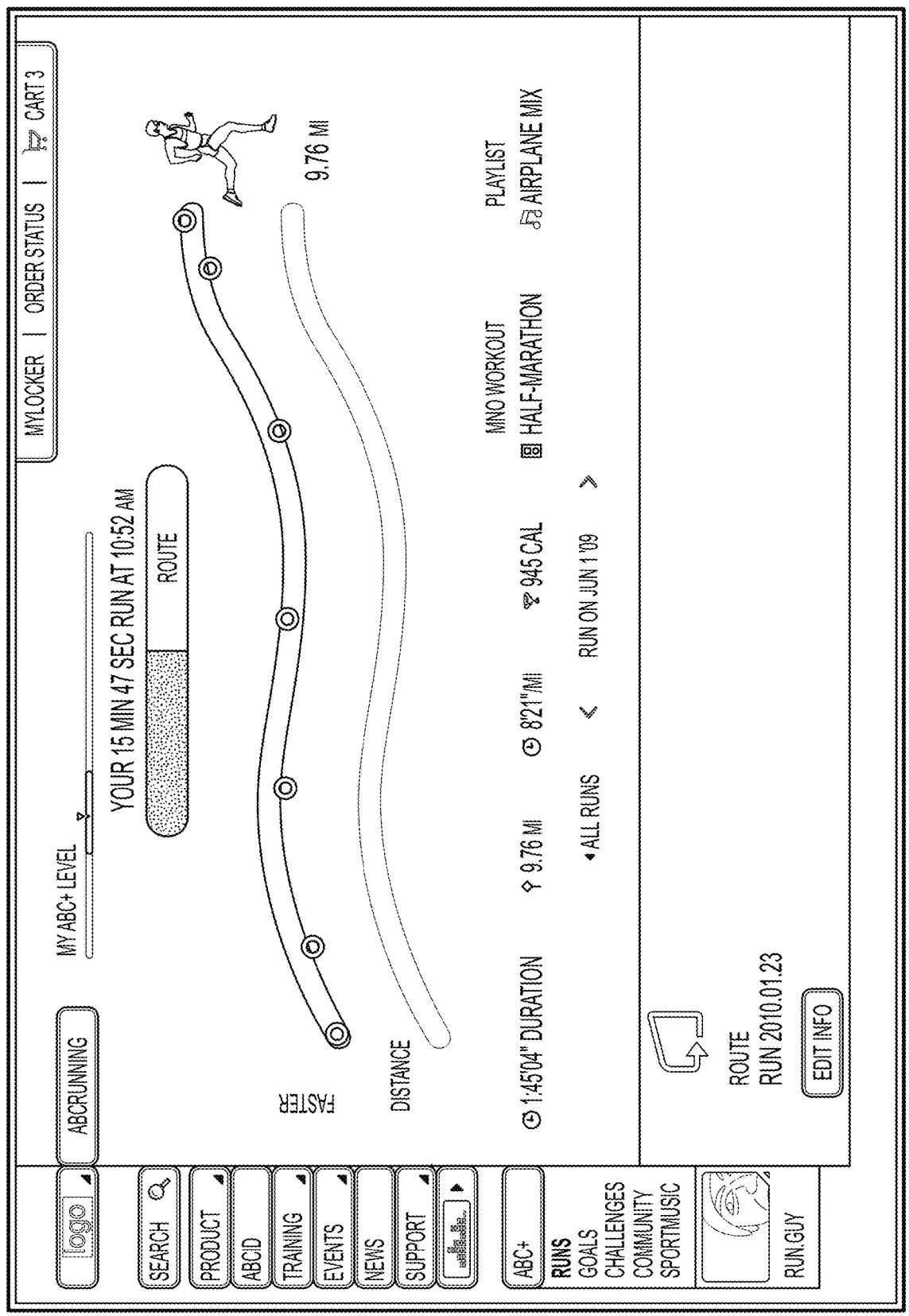

Upon selecting a particular workout to view and/or analyze, the user may be presented with an interface that provides details for the selected workout. FIGS. 66G and 66H illustrate an example run details page that provides a summary of the statistics recorded for the run. In the illustrative example shown in FIG. 66G, the user may be allowed to edit various parameters stored for the workout using edit option 6641. In some arrangements, some parameters might not be changeable such as the distance and time run and/or calories burned. If the run was recorded with a GPS device or other location positioning system, the run details interface may include a GPS indicator 6643. Additionally, the interface may display a route view option 6645 if the run was recorded with location information. Routes and route information is further described in detailed below.

Figure 66I:
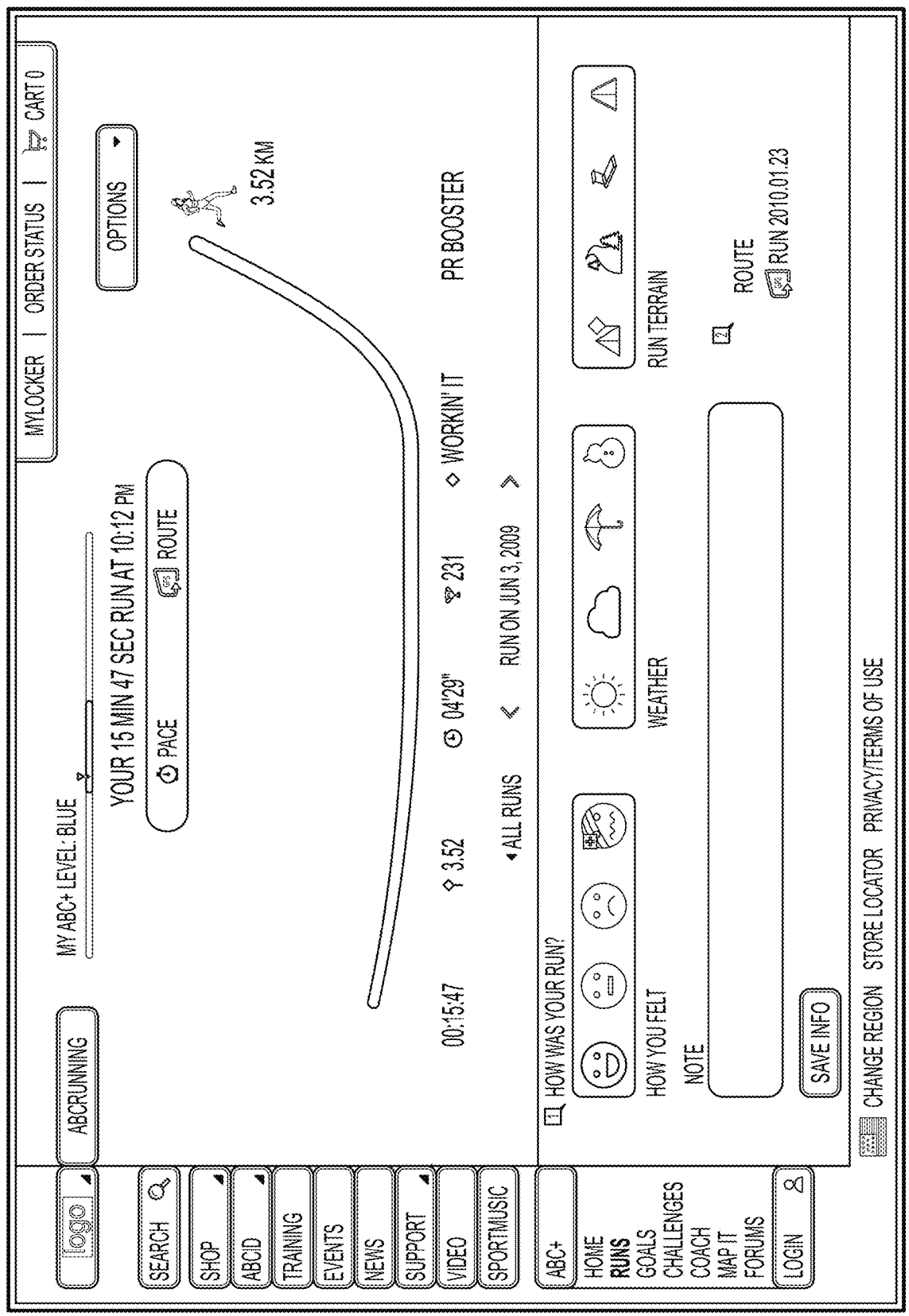
Figure 66J:
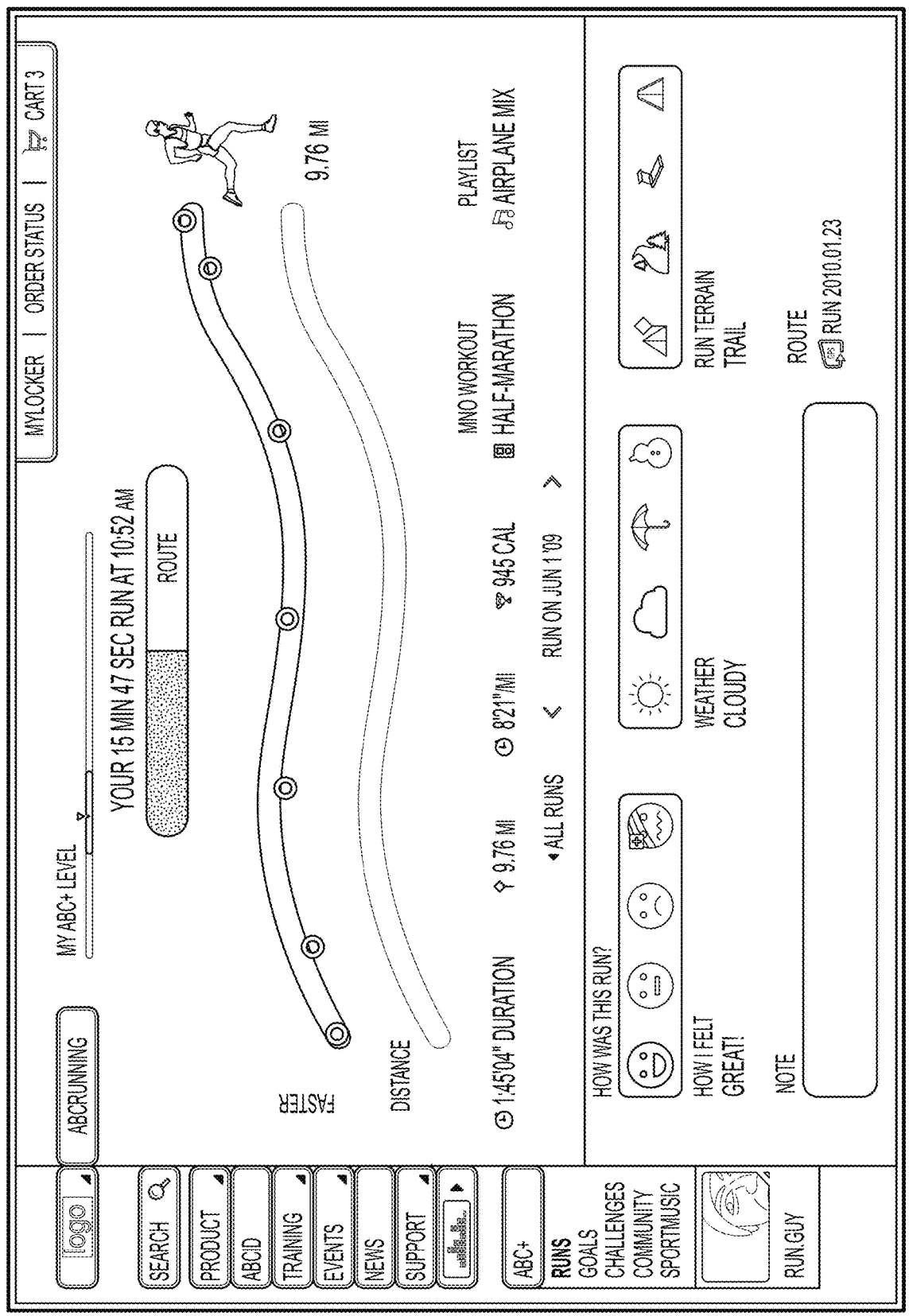

FIGS. 66I and 66J illustrate edit interfaces for modifying one or more parameters of the recorded workout information. For example, the user may be provided with options to modify the user's mood after the run, the weather conditions, the terrain and/or a note. Other parameters may also be modified depending on user preferences, service provider requirements and rules, and the like.

Figure 66K:
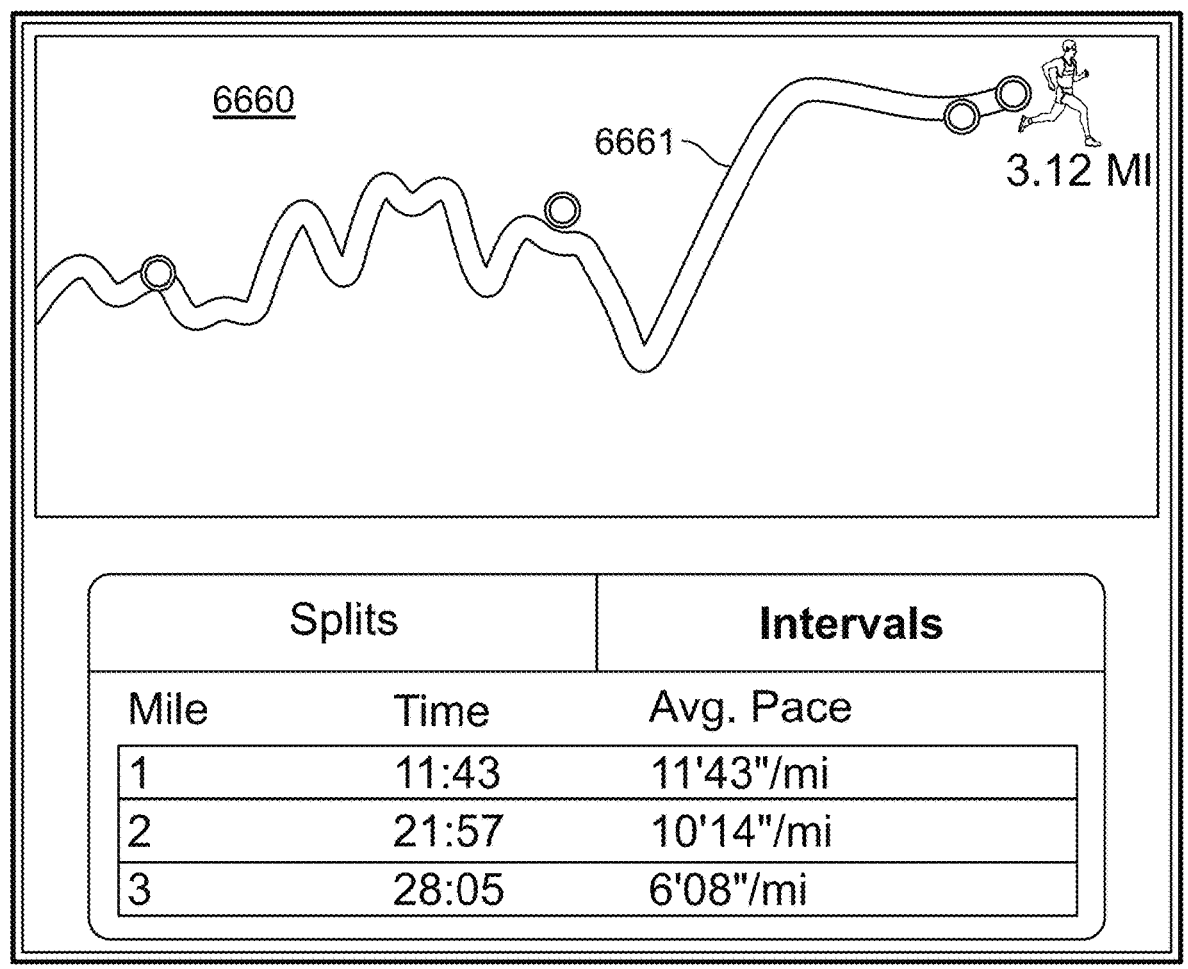

FIG. 66K illustrates an example workout data interface 6660 displaying statistics for a workout session. Interface 6660 may include a run curve 6661 corresponding to time vs. distance, distance vs. pace, time vs. pace and/or various combinations thereof. In some arrangements, the run curve 6661 may include one or more visual characteristics to represent a metric of the workout. For example, different colors may be used to represent the different paces exhibited by the user over the workout. In another example, different patterns or transparencies of the run curve may be used to represent different heart rates. Interface 6660 may further provide additional workout data granularity including split and interval times and paces. In some arrangements, this additional information might only be provided or recorded if a user selected a particular mode for the recordation of the workout or for viewing workout data. In other arrangements, the additional information might be available regardless of a workout recordation mode.

Other types of workout data visualization may include displaying a current run pace curve against or over an average pace curve (e.g., for a set of runs such as all runs or all runs within a specified period of time, all runs for the same route, etc.). Additionally or alternatively, the run curve or other workout data visualization may be displayed with a music playlist that was used during the workout.

Route Tracking, Display and Creation

As described herein, in some arrangements, a user's workout may be recorded with location determination systems. Accordingly, the user's route may be recorded and stored as part of the workout data. Upon retrieval of the workout data, the route may be displayed for the user's review.

FIGS. 67A-67G illustrate a series of route detail interfaces in which route information may be displayed. For example, in interface 6700 of FIG. 67A, the user's route 6701 may be drawn in an animated fashion on a map. Icon 6703 representing the user may be animated and move in accordance with the route of the run. The route may be indicated by preliminary route line 6705 followed by a secondary route line 6707 once icon 6703 has traversed a portion of the route. Icon 6703 may be animated in accordance with a speed of the user along the route. For example, icon 6703 may move slower during portions of route 6701 where the user exhibited a slower pace and faster during portions of route 6701 where the user exhibited a faster pace. The movement animation may be proportional to the user's pace and may be calculated using an algorithm that is based on the user's pace (e.g., mile per hour may be converted to pixels per second). Interface 6700 may further include distance markers 6709 along the route to identify the distance increments (e.g., 1 mile, 1 kilometer, 0.5 mile, etc.). Pace markers 6711 may also be included to indicate the points on the route where the user exhibited the fastest pace and slowest pace. Elevation information may also be provided using elevation markers 6713 to identify the point of higher or highest elevation.

In portion 6715, interface 6700 may include graph 6717 of the user's pace and altitude versus time. Lines 6719 and 6721 may change in appearance (e.g., in animated fashion) as the animation of the user's run using icon 6703 proceeds. For example, portion 6723 of line 6719 may appear bolder indicating that the animation has traversed that portion of the route. Marker 6725 indicates the animations current position in the route. Detailed information relating to that position including distance, time, pace and elevation may be provided as well. A replay option 6727 may be selected to have the animation replayed. A replay may, in one or more arrangements, play the animation at a slower pace as compared to a pace at which the animation is shown on initial load of the run and route details. Legend 6729 may provide explanations for each of markers 6709, 6711 and 6713 as well as corresponding workout data. For example, the pace of the best and worst miles may be displayed while the fastest and slowest pace information may also be provided. Elevation data corresponding to highest elevation marker 6713 may further be displayed. Users may also manually create their own markers to help associate a particular location along the run or workout with a set of performance statistics.

Figure 67A:
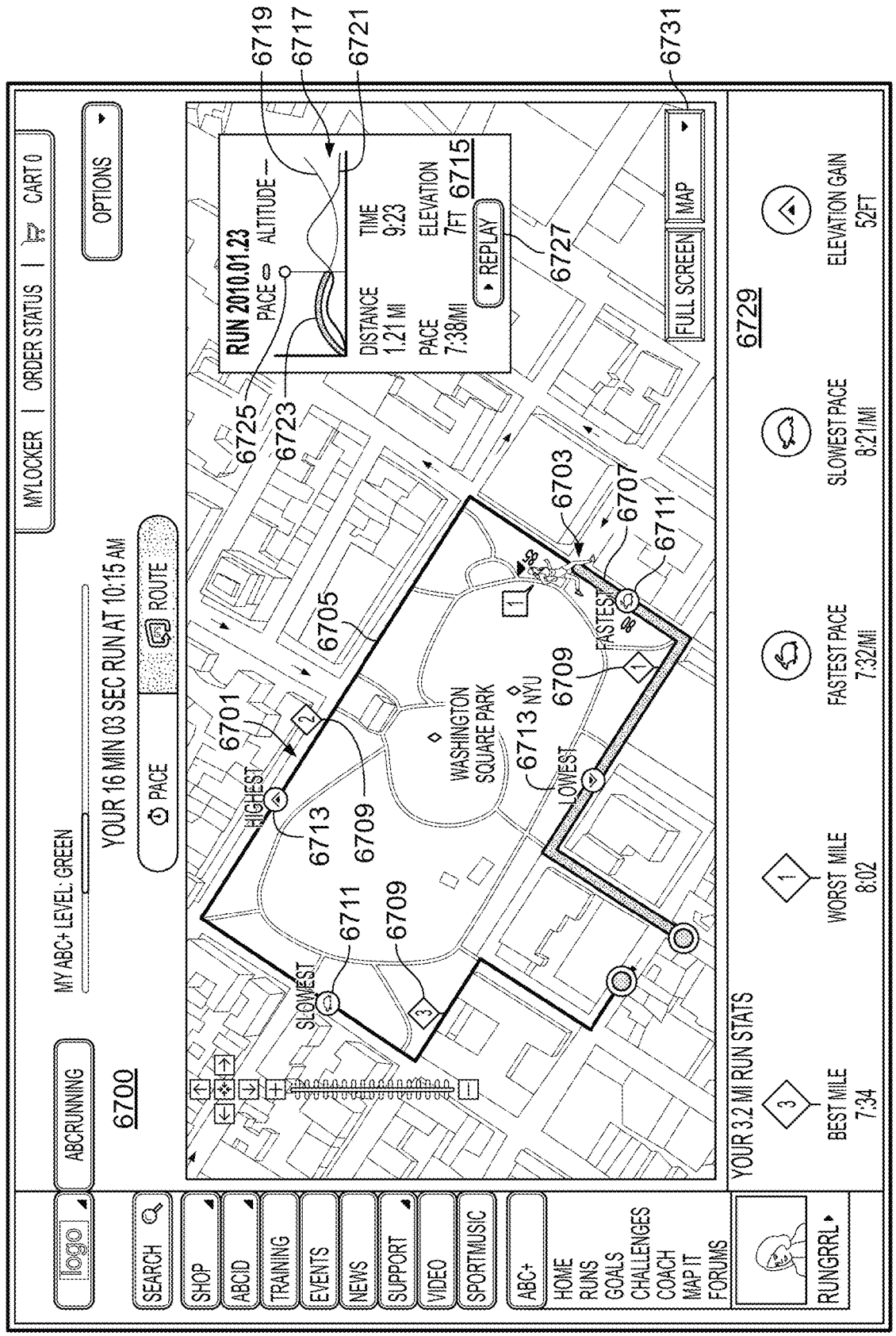
FIGS. 67A-67G illustrate a series of example route detail interfaces in which route information may be displayed according to one or more aspects described herein.
Figure 67B:
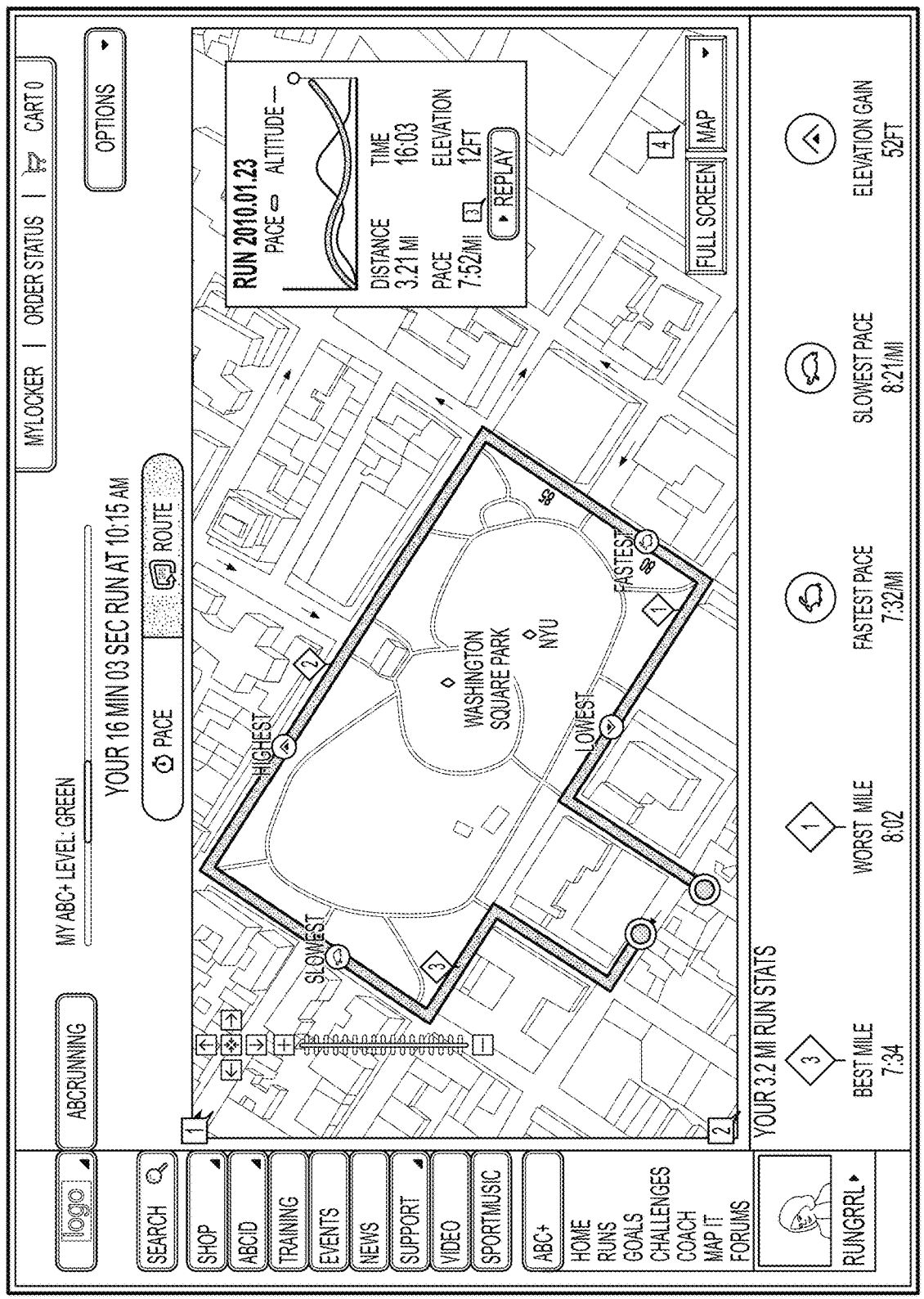
Figure 67C:
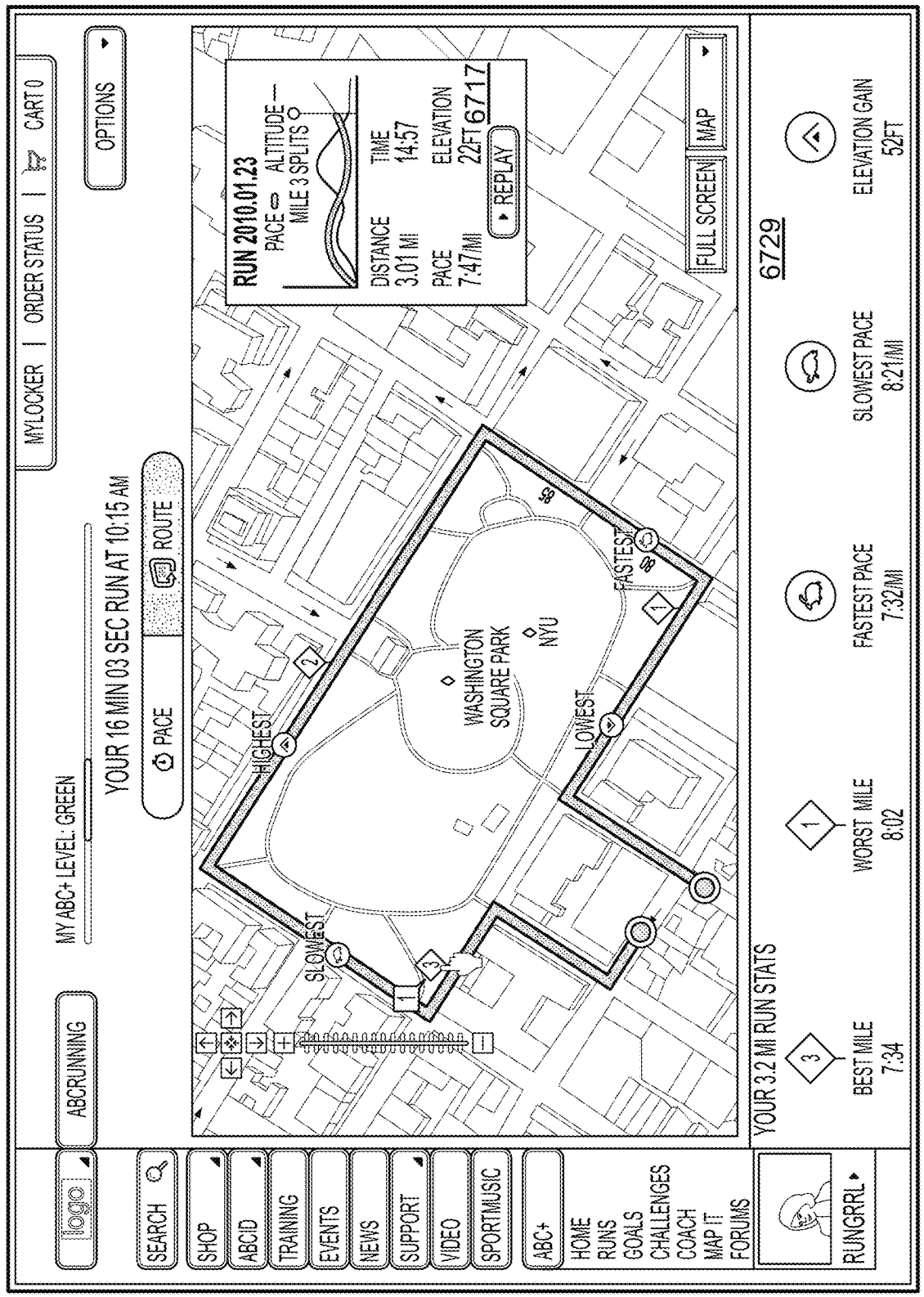
Figure 67D:
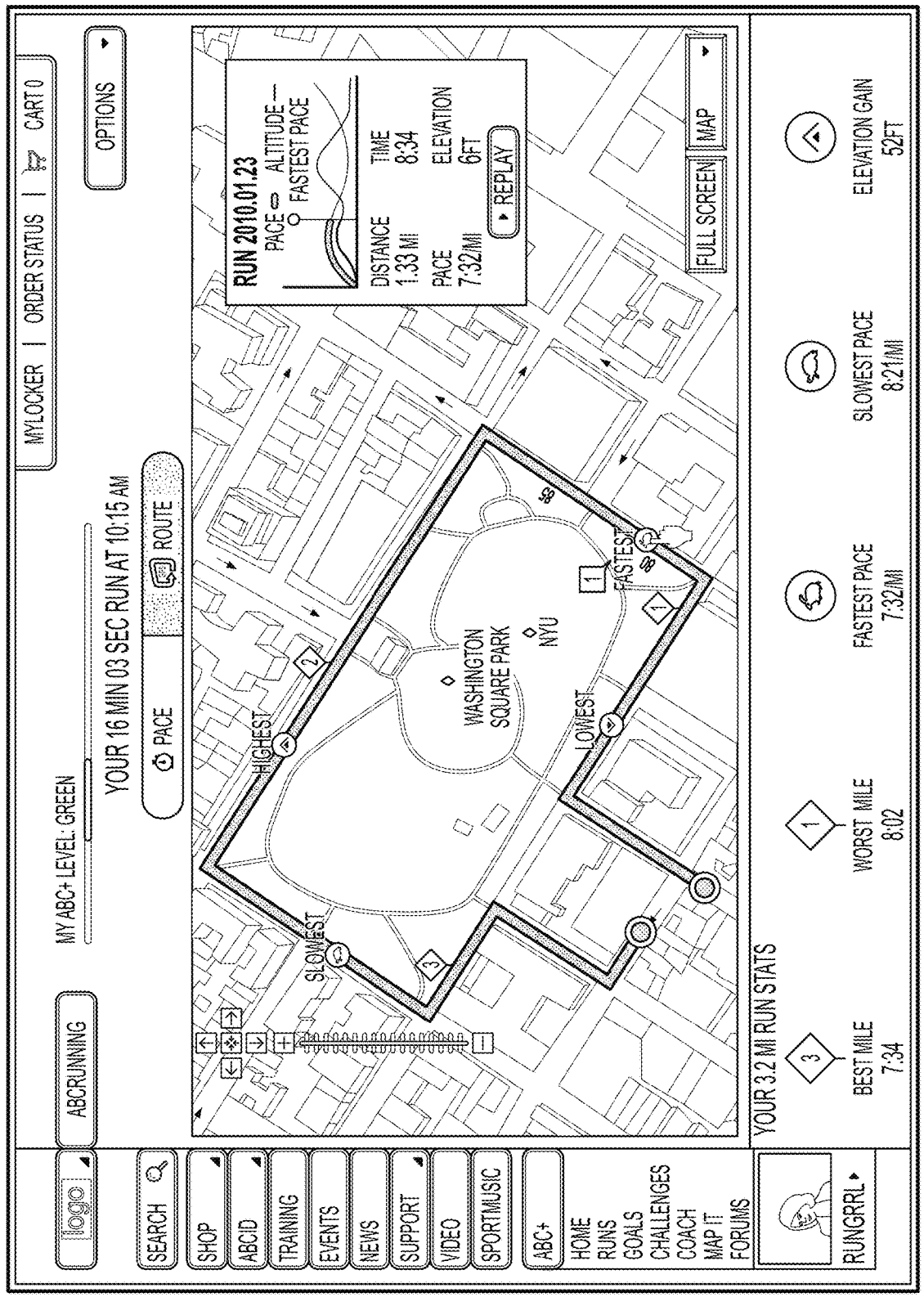
Figure 67E:
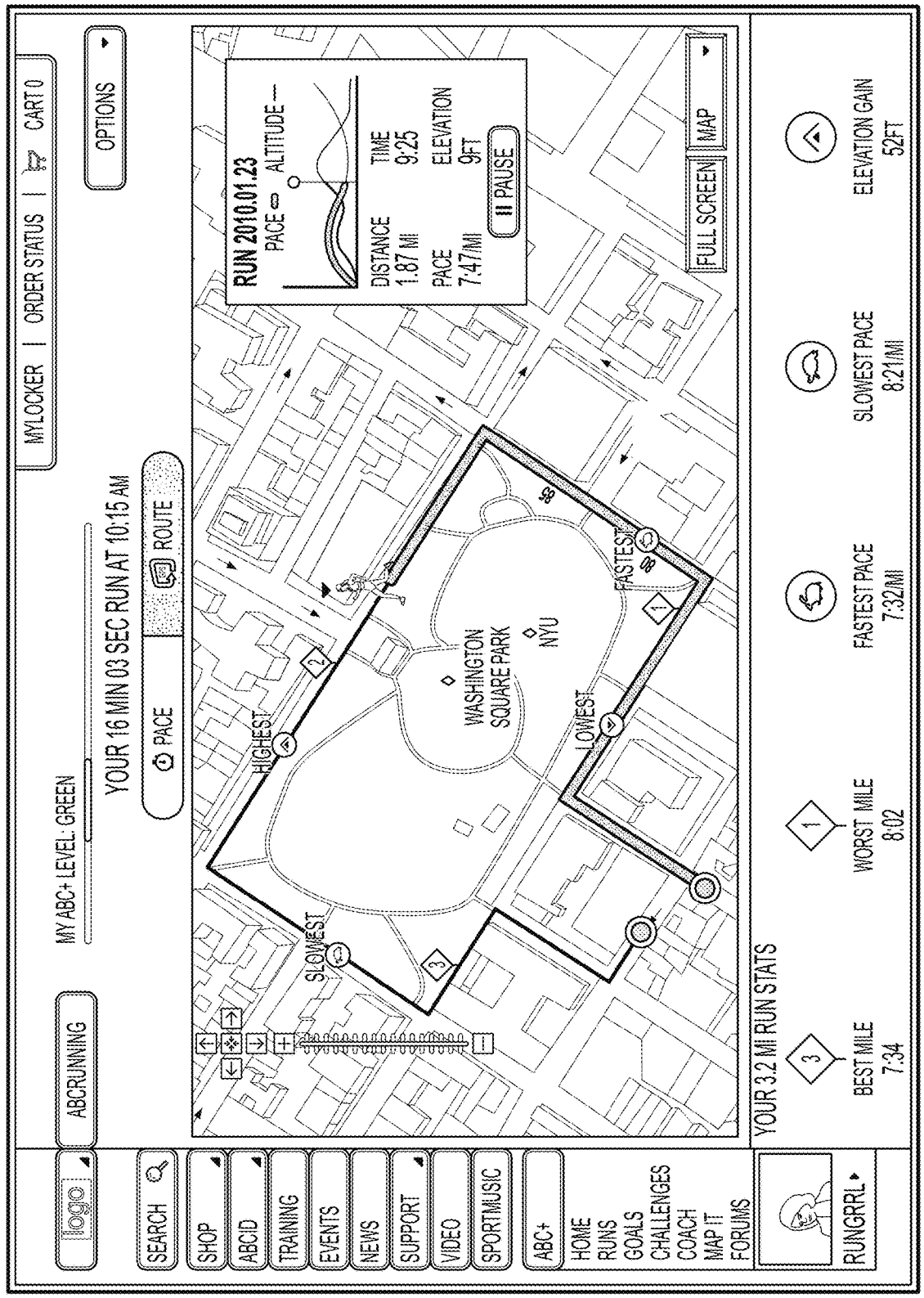

Interacting with one or more of markers 6709, 6711 and 6713 may cause the corresponding workout data to be displayed for that particular point of the user's workout. FIG. 67C illustrates an example interface when a user selects marker 6713. In response to the selection, graph 6717 may be modified accordingly to display the corresponding data. In one or more arrangements, the user's icon (e.g., icon 6703 of FIG. 67A) may be moved immediately to the selected location. Additionally or alternatively, the displayed route may also be modified to reflect the position of the user's icon (e.g., the portion of the route up to the selected point may be changed to reflect traversal). Non-marked portions may also be selectable to view workout data. Legend 6729 may also be updated upon selection of a marker or other point on the route.

Figure 67F:
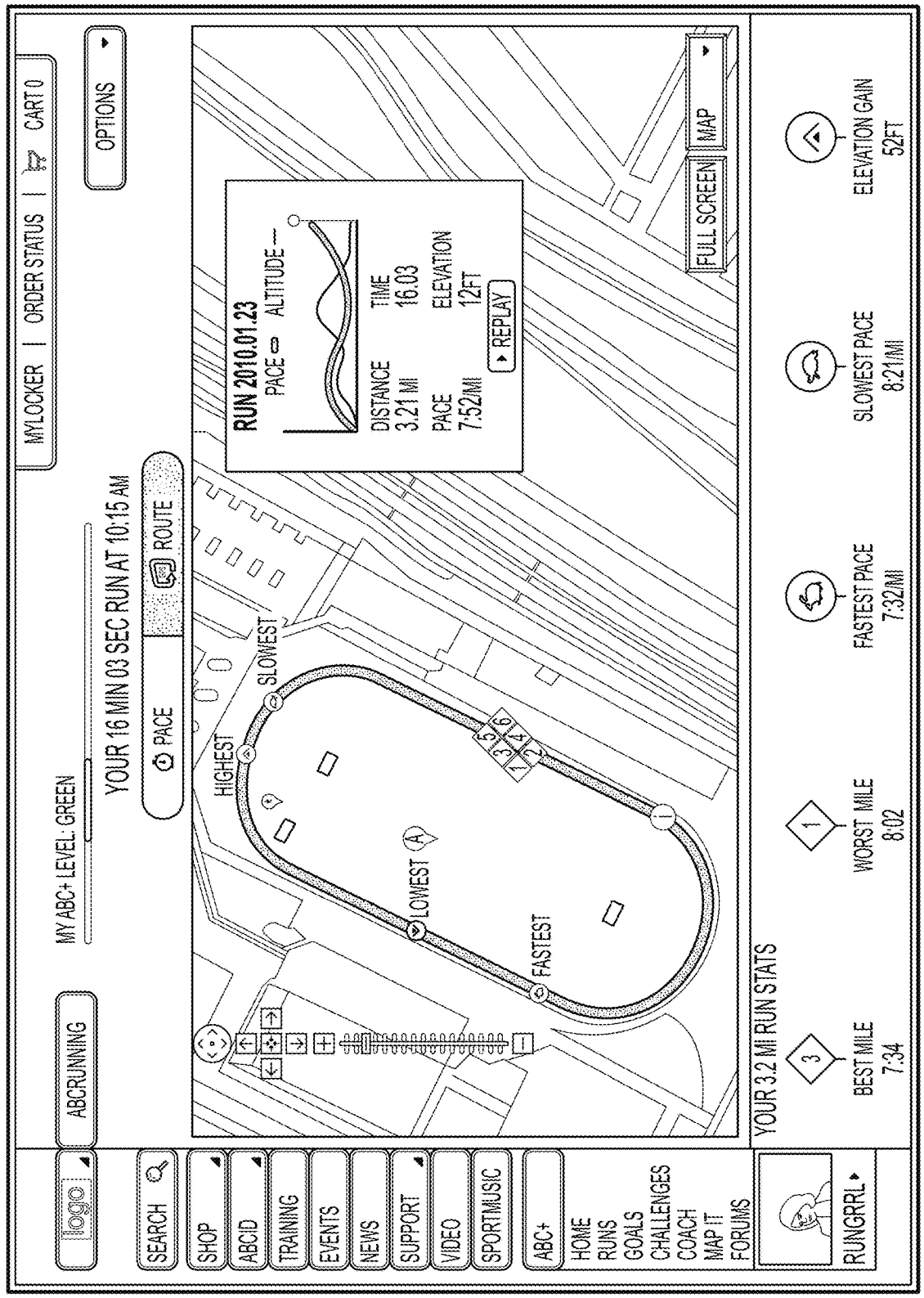

According to one or more additional aspects, map drop-down menu option 6731 (FIG. 67A) may display various options for the underlying map. For example, the user may be able to alter the appearance of the map to display a satellite image, a computer generated representation (as shown in FIG. 67A), a terrain image and/or a hybrid image combining satellite and terrain. FIG. 67F illustrates a route on a map in satellite image mode.

Additionally or alternatively, various types of characteristics of a route or workout may be visually conveyed using visual attributes. For example, a route may include multiple colors indicating different speeds or paces, heart rates and the like exhibited by the user during the run. In a particular example, portions of the route line in which the user exhibited a pace above a first threshold may be displayed in green, while other portions of the route line in which the user exhibited a pace below a second threshold may be displayed in red. Still other portions of the route line in which the user exhibited a pace between the first and second thresholds may be displayed in yellow. Various color gradations and characterizations may be used to represent pace, speed, heart rate, elevation, terrain, weather and the like. Other visual attributes may be used to illustrate the various workout attributes including patterns, transparency, shading, stippling and the like.

Figure 67G:
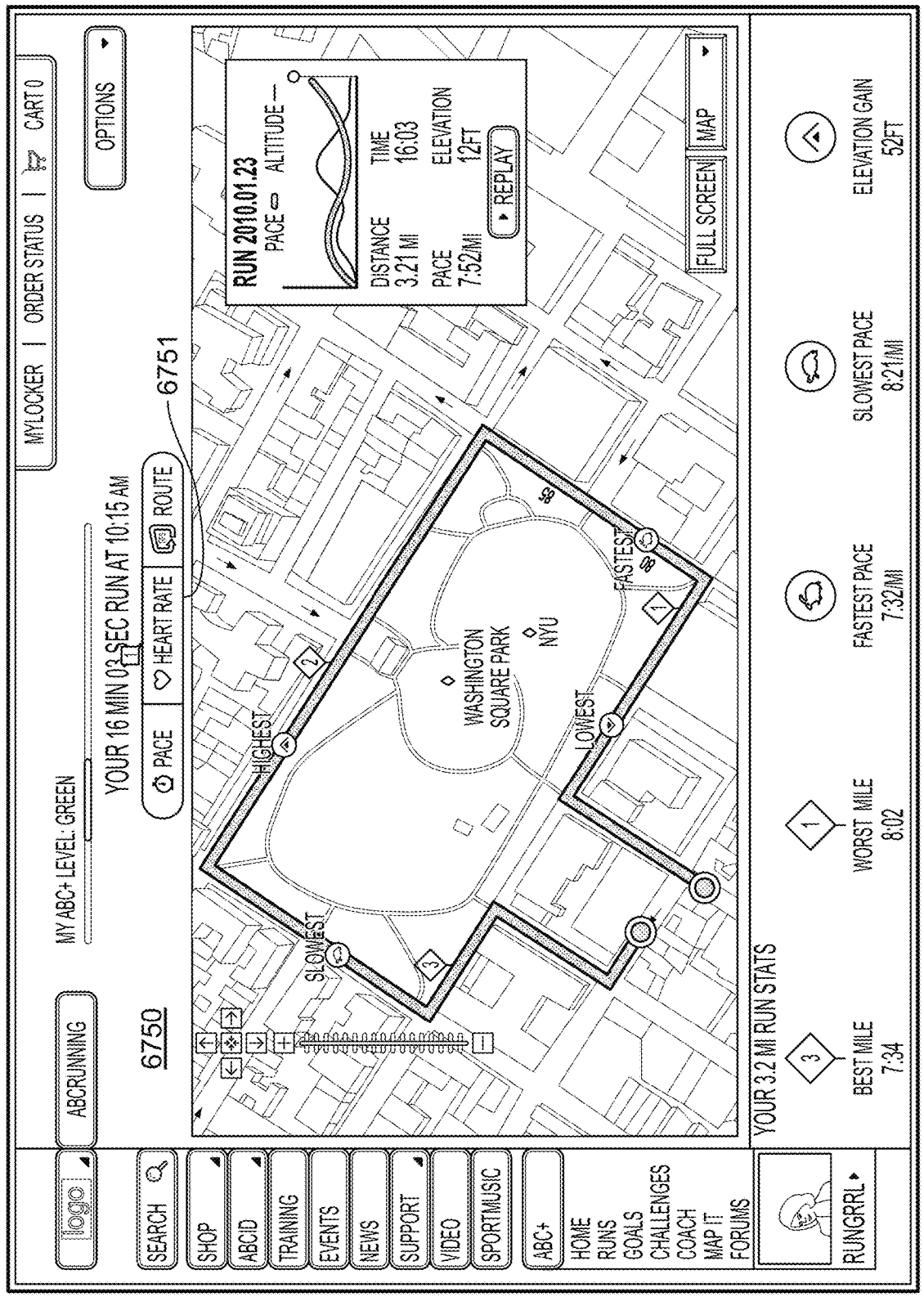

FIG. 67G illustrates a route information interface 6750 in which a heart rate tab 6751 is displayed if heart rate information is available. Selection of heart rate tab 6751 may cause a graph to display heart rate versus time or distance or pace. If heart rate information is available, route information and details may also be supplemented with this data. For example, highest and lowest heart rate markers may be displayed on the route.

Figure 68A:
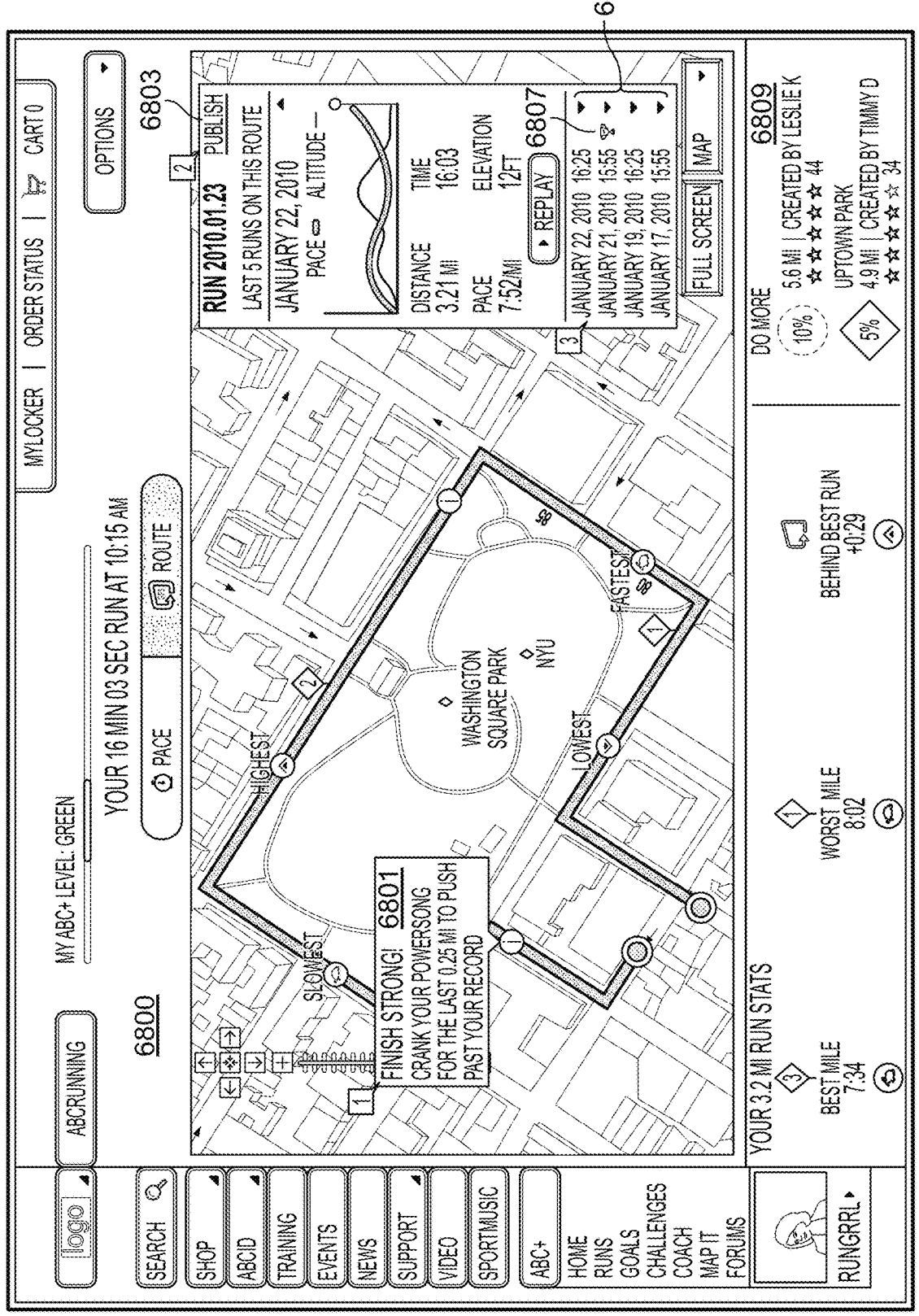
FIG. 68A illustrates another example route detail interface according to one or more aspects described herein.

FIG. 68A illustrates another example route detail interface 6800. Interface 6800 may include additional information such as run insights or suggestions such as suggestion 6801 which recommends playing a power song for a last 0.25 miles to set a new time record for the route. The suggestions may be generated based on various algorithms and parameters and, in one example, may include identifying a portion of the run where the user had the slowest pace and suggesting playing a motivational song to increase that pace. In another example, if a user appears to be exerting significant effort in a first portion of the run/route (e.g., based on heart rate information), the system may suggest that the user run at a slower pace during that first portion so as not to become exhausted for a remaining portion of the route.

Route information may be published in one or more arrangements by selection of publish option 6803. A user may publish information to various outlets including FACEBOOK, TWITTER and/or other social networking sites and news feed services. A menu (not shown) for specifying account information and publication options may be displayed upon selection of publish option 6803.

Interface 6800 may further include a listing 6805 of previous workouts for the same or a similar route. Listing 6805 may include one or more entries and may include a brief summary of workout details including, for example, a run time and whether any achievements were recorded. For example, if the user ran the route in the fastest time on January 21, that entry may include a trophy icon 6807 as an indicator of that achievement or significance. Further, interface 6800 may provide improvement run suggestions in portion 6809. In particular, interface 6800 may display other routes that improve on the current route by a predefined amount of distance. The route suggestions may be generated based on routes the user has run in the past or routes that other users have run.

Figure 68B:
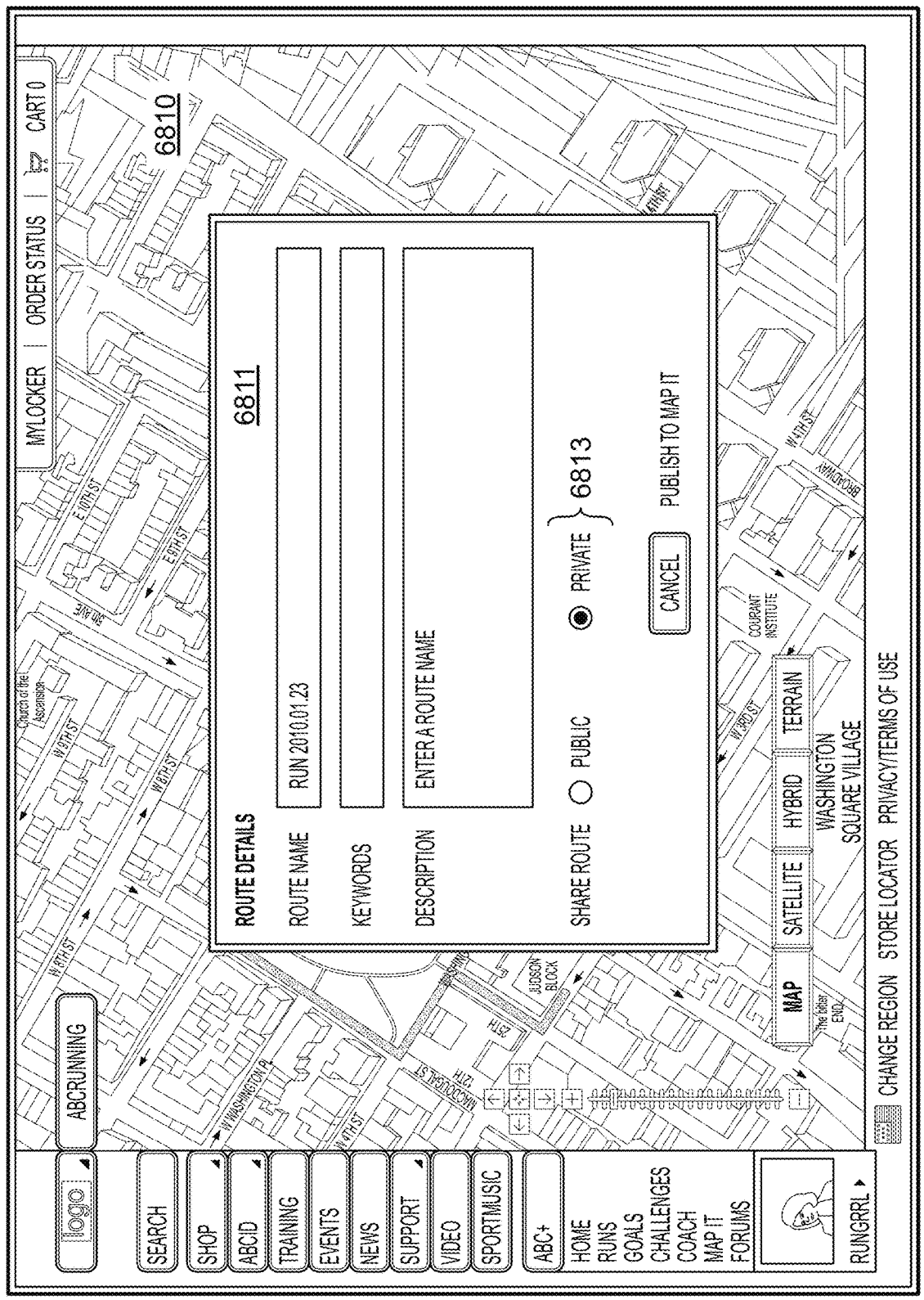
FIG. 68B illustrates an example interface through which a user may save a route and add route details according to one or more aspects described herein.

FIG. 68B illustrates an interface where a user may save a route and add route details. Interface 6810 includes a prompt 6811 in which a route name may be specified in addition to keywords and a description. Keywords may include one or more words that may be used as search terms so that the user or other users may more easily find the route from a database of routes. The description may include a lengthier discussion of the route including scenery, terrain, difficulty, weather, traffic, noise, and the like. The user may further select a privacy of the route using options 6813. For example, by setting the route to private, other users might not be able to find or view the route. Additional privacy parameters and settings may be provided including options for selecting particular individuals or groups of individuals that are permitted to find and/or view the route. Other options may include defining what viewing and access privileges are allowed for each individual or group of individual.

Figure 69A:
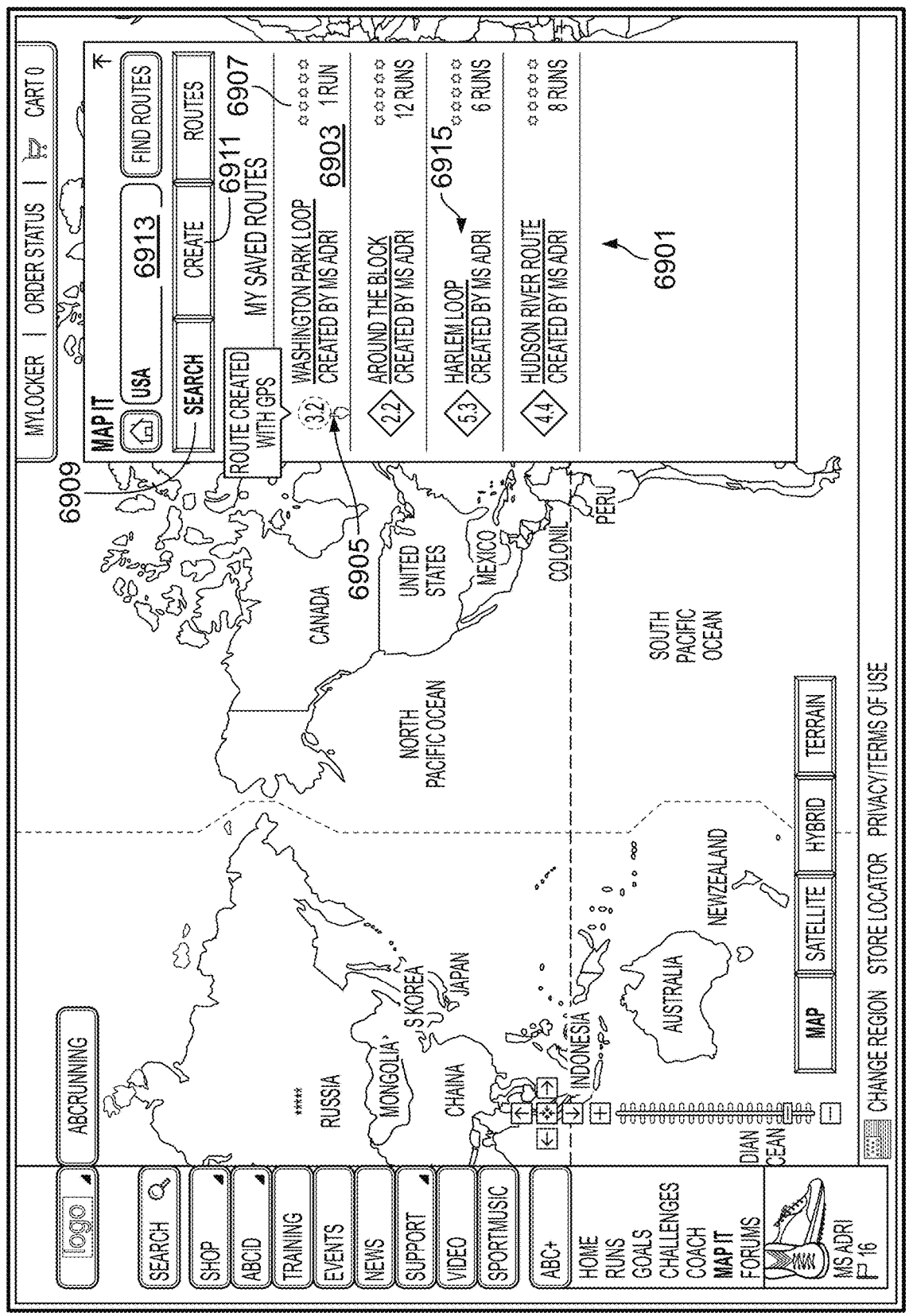
FIG. 69A illustrates an example saved routes interface listing the various routes that a user has run, created and/or saved according to one or more aspects described herein.

FIG. 69A illustrates a saved routes interface listing the various routes that a user has run, created and/or saved. For example, routes list 6901 includes 4 different routes saved by the user. Routes that were created/recorded using GPS such as route 6903 may include one or more indicators or may be displayed in a different manner. For example, the distance indicator 6905 may appear differently than for non-GPS created routes such as route 6915. The saved routes list 6901 may be displayed against a backdrop of a map. The map may include one or more markers identifying the location of the routes and routes in the list 6901 may be numbered or otherwise identified to correspond to the markers. Routes may also be rated by the user or other users that have run the route. The rating may be reflected or indicated by ratings indicator 6907, for example. Other tabs in the interface may include a search tab 6909 and a create tab 6911 for searching a database or list of routes and for creating a route, respectively. Additionally, a quick search bar 6913 may be used for keywords searches while search tab 6909 may provide advanced search options such as distance, terrain, weather and the like.

Figure 69B:
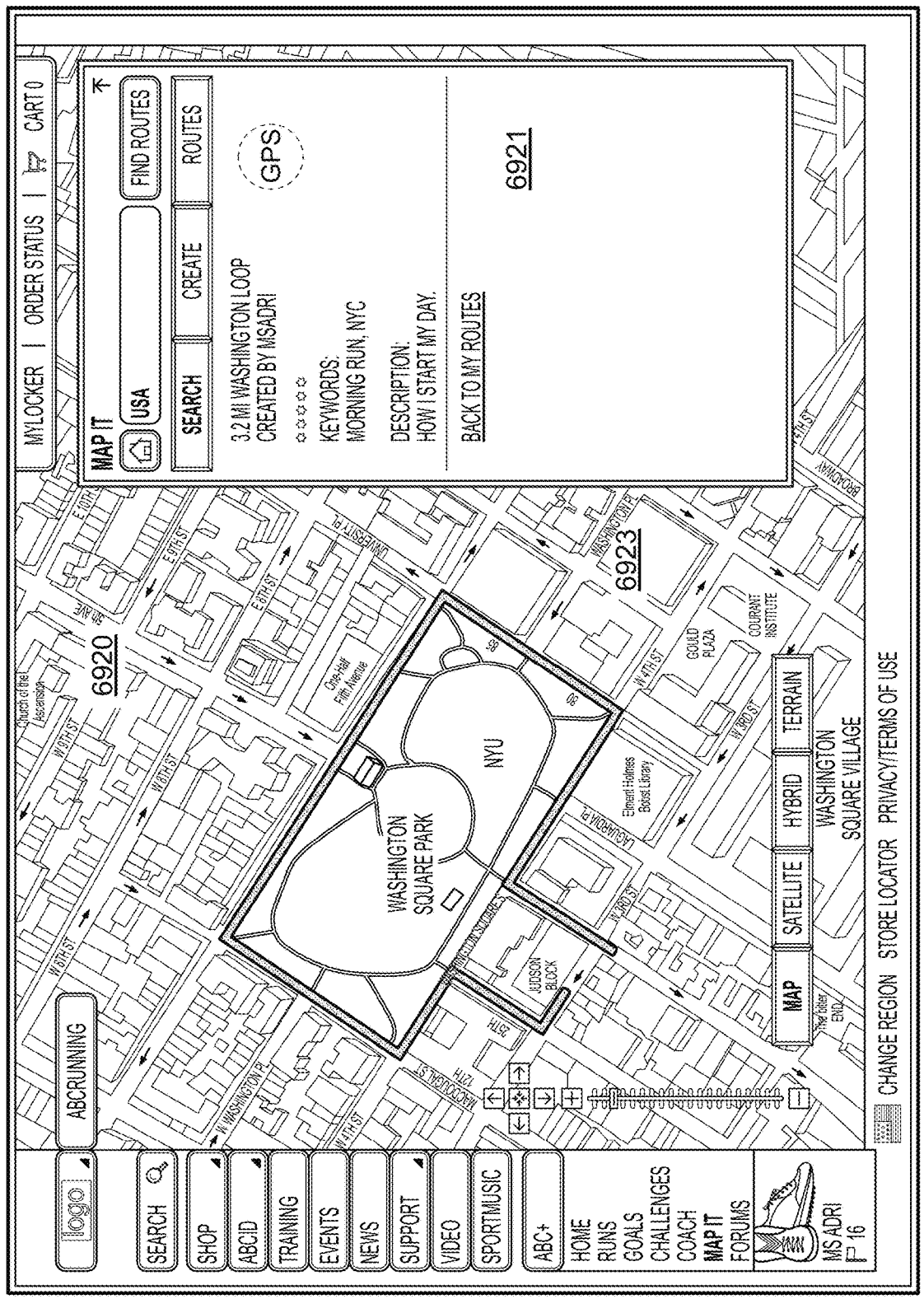
FIG. 69B illustrates an example route interface that may be displayed upon a user selecting a route from a route list according to one or more aspects described herein.

FIG. 69B illustrates a route interface 6920 that may be displayed upon a user selecting a route (e.g., route 6905 of FIG. 69A) from a route list (e.g., route list 6901 of FIG. 69A). Upon selection of a route, route listing 6921 might only display the selected route and provide additional details beyond what was displayed in a route list including multiple routes (e.g., route list 6901 of FIG. 69A). The additional details may include keywords stored in association with the route and a description. The information may further indicate a creator of the route. Underlying map 6923 may also change to display the route at a scale where each portion of the route is discernible. In one example, map 6923 may display an area that is a predefined amount larger than the boundaries of the route. For example, the displayed area of map 6923 may be defined such that the route occupies 60%, 75%, 90% or other percentage of the displayed area.

Figure 70A:
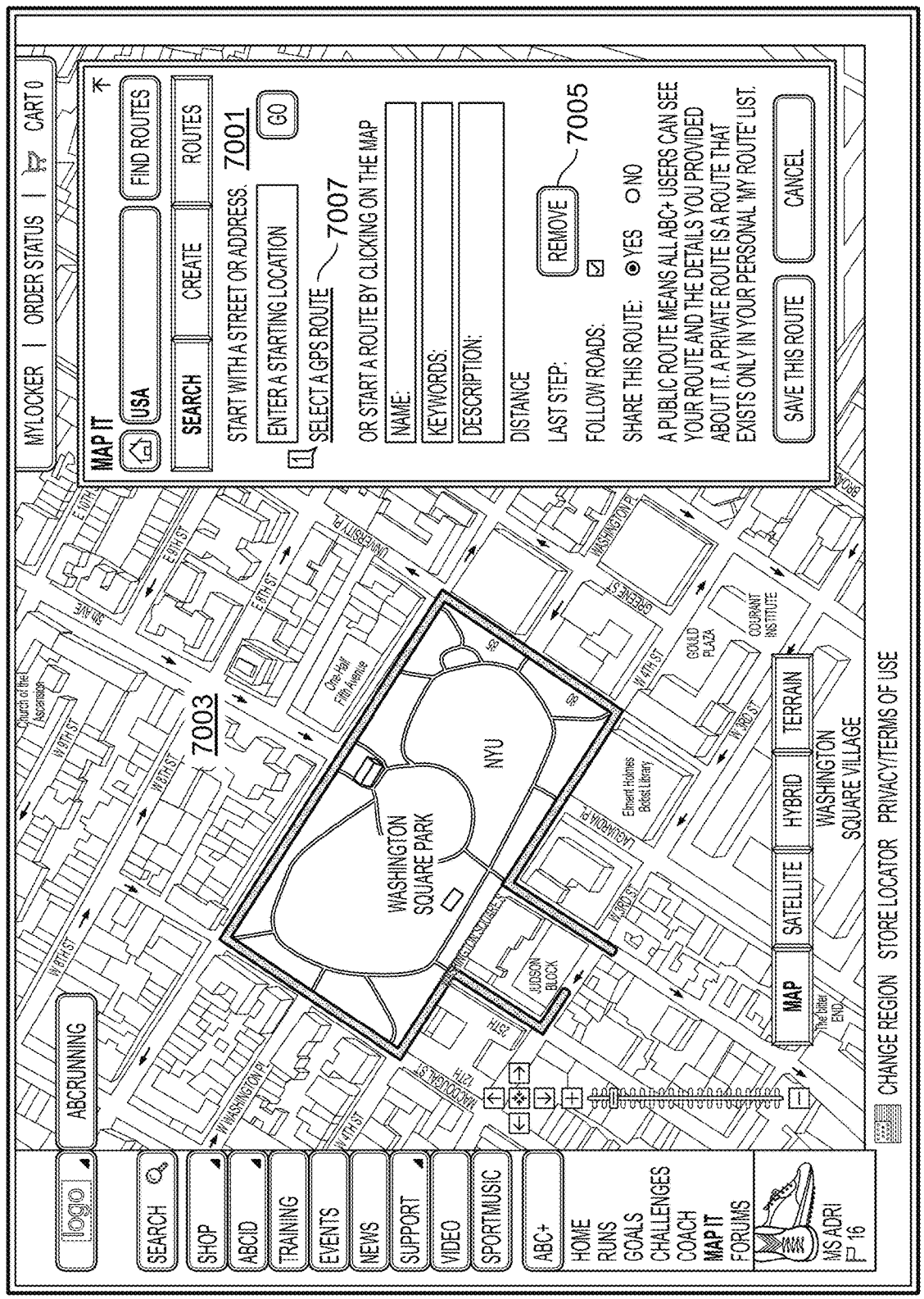
FIG. 70A illustrates an example route creation interface through which a user may define a new route according to one or more aspects described herein.

FIG. 70A illustrates a route creation interface through which a user may define a new route. To create a new route, the user may define a starting location through form 7001. Alternatively, the user may base the route on a recorded GPS route. The user may further specify a name, keywords (e.g., for searching), a description and whether the route is to be shared. Upon selecting a start location, an ending location form (not shown) may be displayed. Starting and ending locations may be selected by interacting with map 7003 or by entering an address. In one or more arrangements, the user may further specify intermediate points that the user wishes to traverse during the run. The user may further specify a distance he or she wishes to run and whether the run should follow roads. Based on these parameters, the system and interface may generate suggested routes and display such routes on map 7003. A user may modify the routes by interacting with the route lines displayed on map 7003, including additional intermediate points, adjusting the distance, modifying the start and end points and the like. The user may further use option 7005 to remove a previous step or steps taken. For example, if the user is creating the route by initially running or walking the route while the creation interface is active and the user makes a mistake in his or her path, the user may pause to remove the last portion of the path.

Figure 70B:
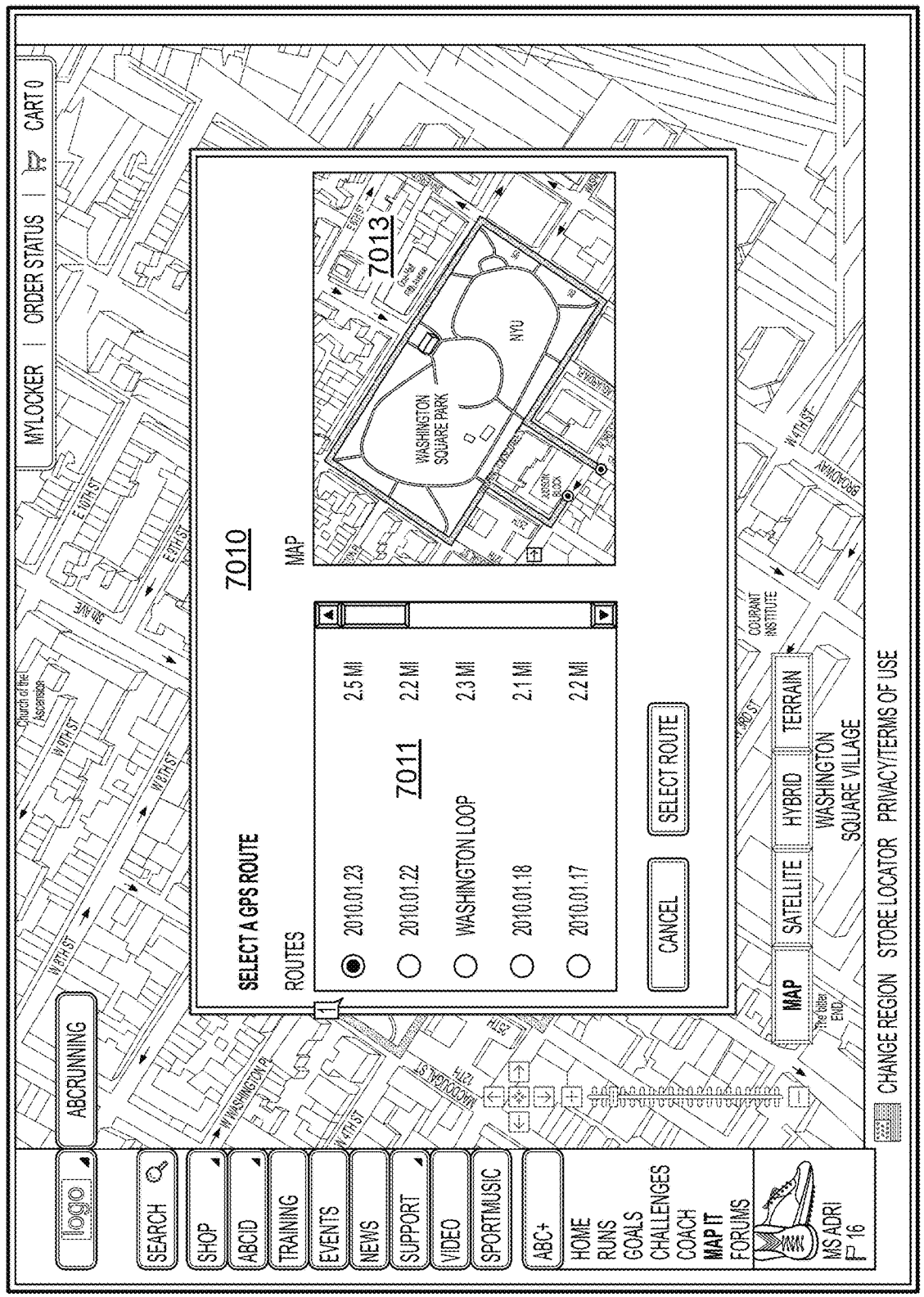
FIG. 70B illustrates an example selection menu where multiple previously recorded routes are displayed according to one or more aspects described herein.

Alternatively, a user may create a route by retrieving a previously recorded GPS route from a database. For example, the user may select option 7007 to retrieve a GPS route. FIG. 70B illustrates selection menu 7010 where multiple previously recorded routes are displayed in list 7011. A mini-map 7013 may be displayed to provide a general overview of the shape and location of the route. List 7011 may be displayed in reverse chronological order, by alphabetical order, by distance or the like.

Figure 70C:
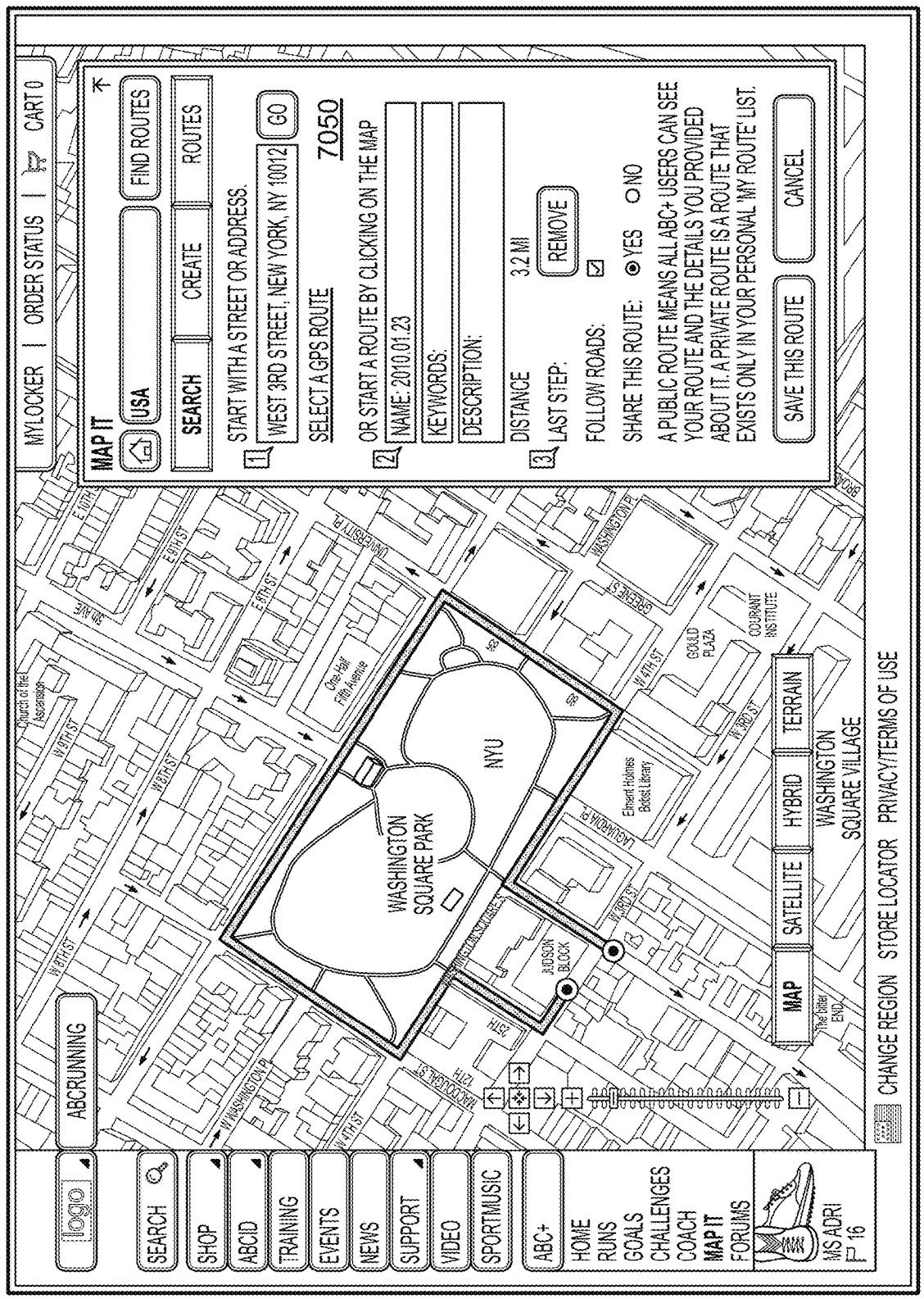
FIG. 70C illustrates another example route creation interface in which one or more fields may be automatically populated according to one or more aspects described herein.

If a user selects a previously recorded GPS route, various fields in a route creation interface may be automatically populated. For example, in FIG. 70C, creation interface 7050 has pre-populated the starting address, distance and the name of the route. If keywords or a description were stored with the selected route, those fields might also be automatically pre-populated. Because the route was generated using a GPS device, the last step and follow roads options may be deactivated. Alternatively, the options may remain active to allow the user to modify the route recorded by the GPS device.

Figure 71A:
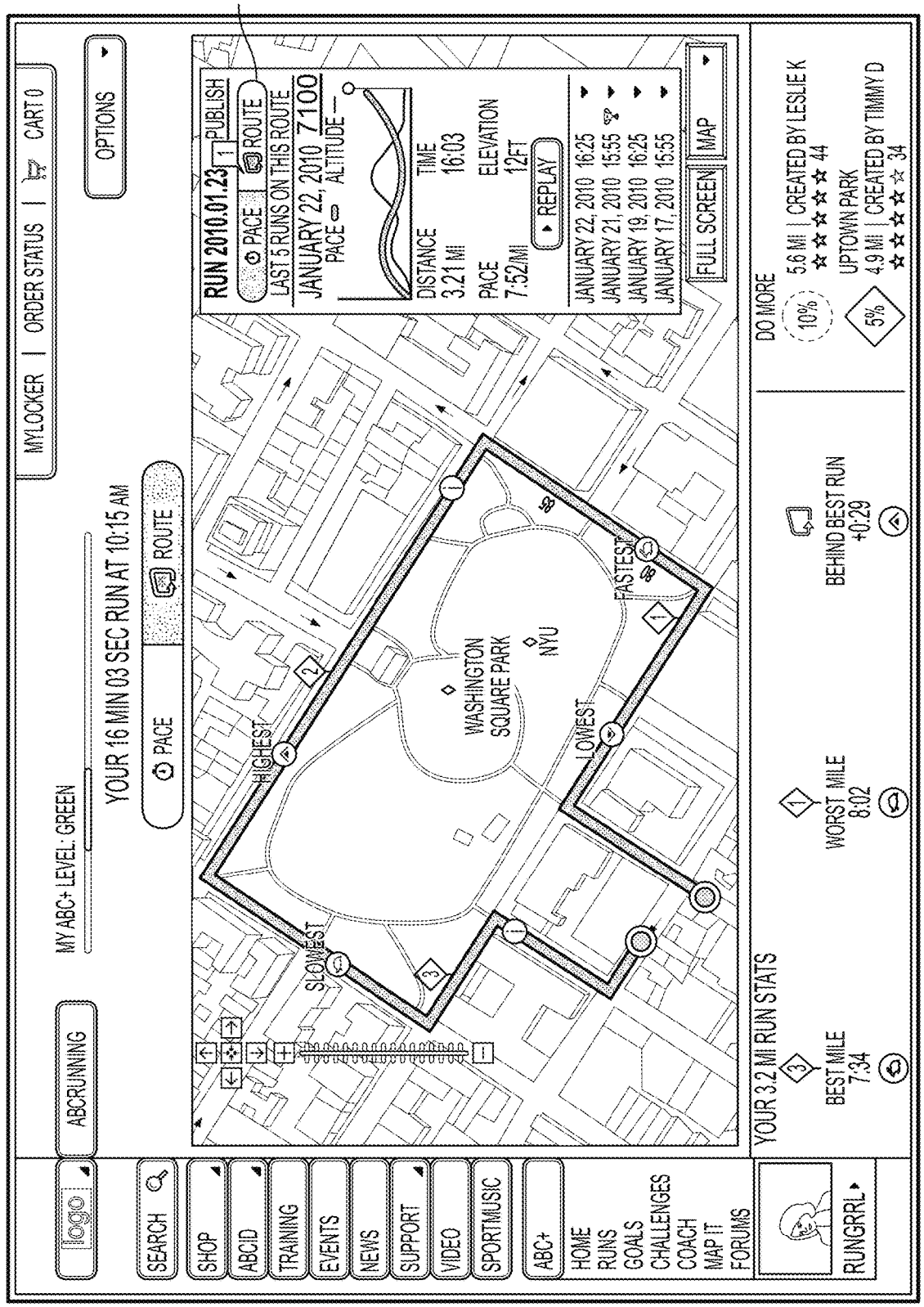
FIGS. 71A and 71B illustrate further example interfaces for viewing route information according to one or more aspects described herein.
Figure 71B:
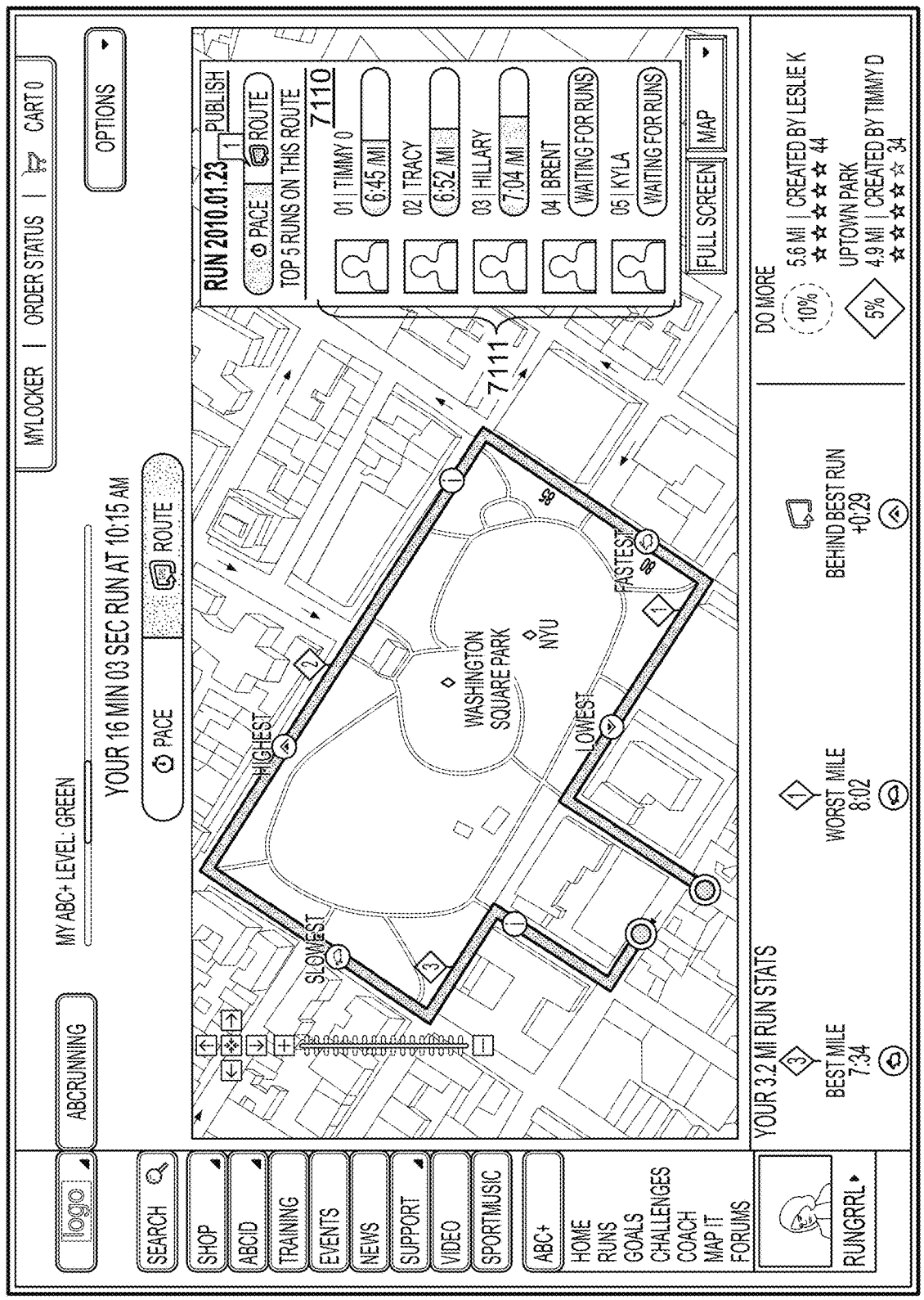
Figure 72A:
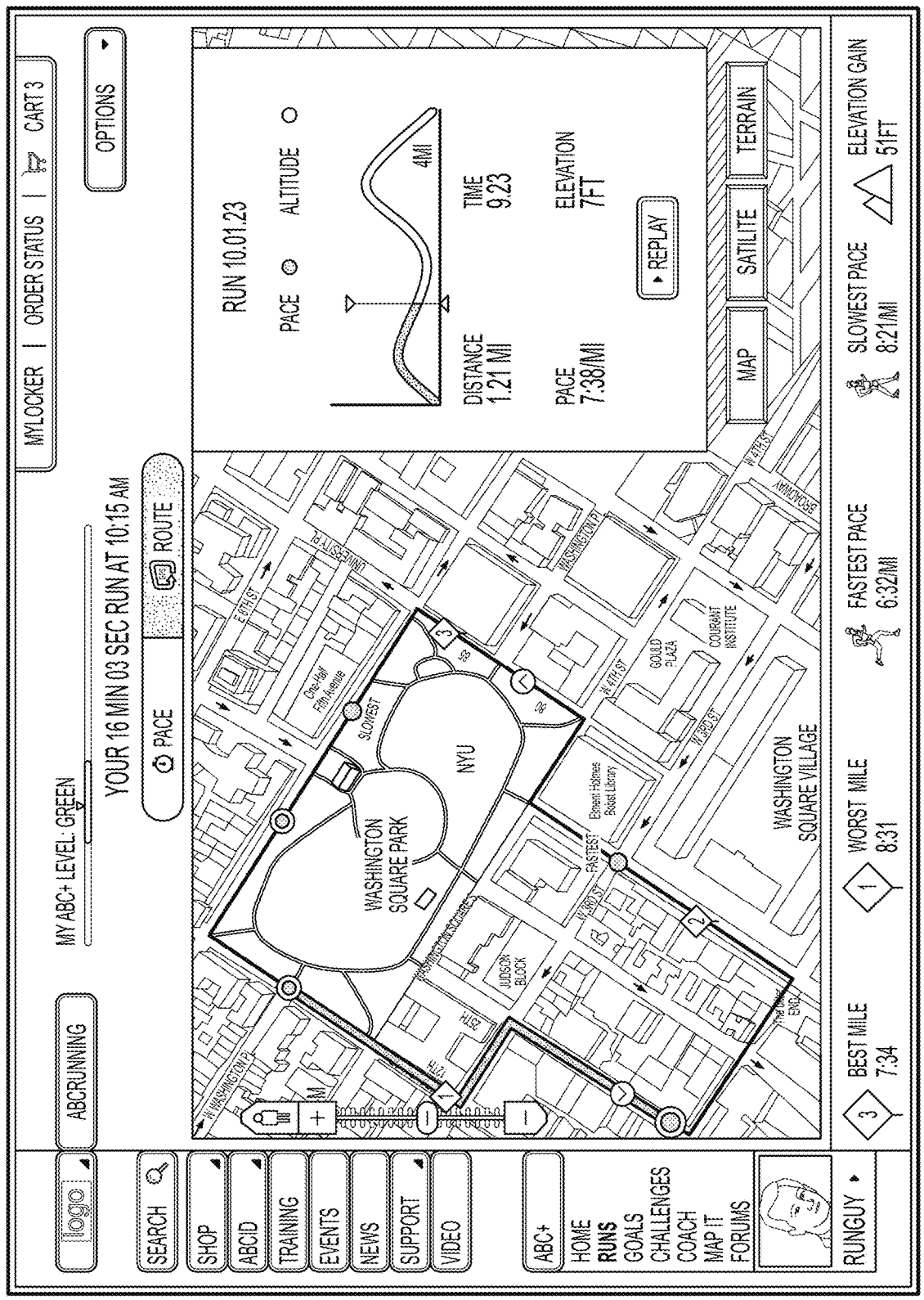
FIGS. 72A-72F illustrate further example route tracking and viewing interfaces according to one or more aspects described herein.
Figure 72B:
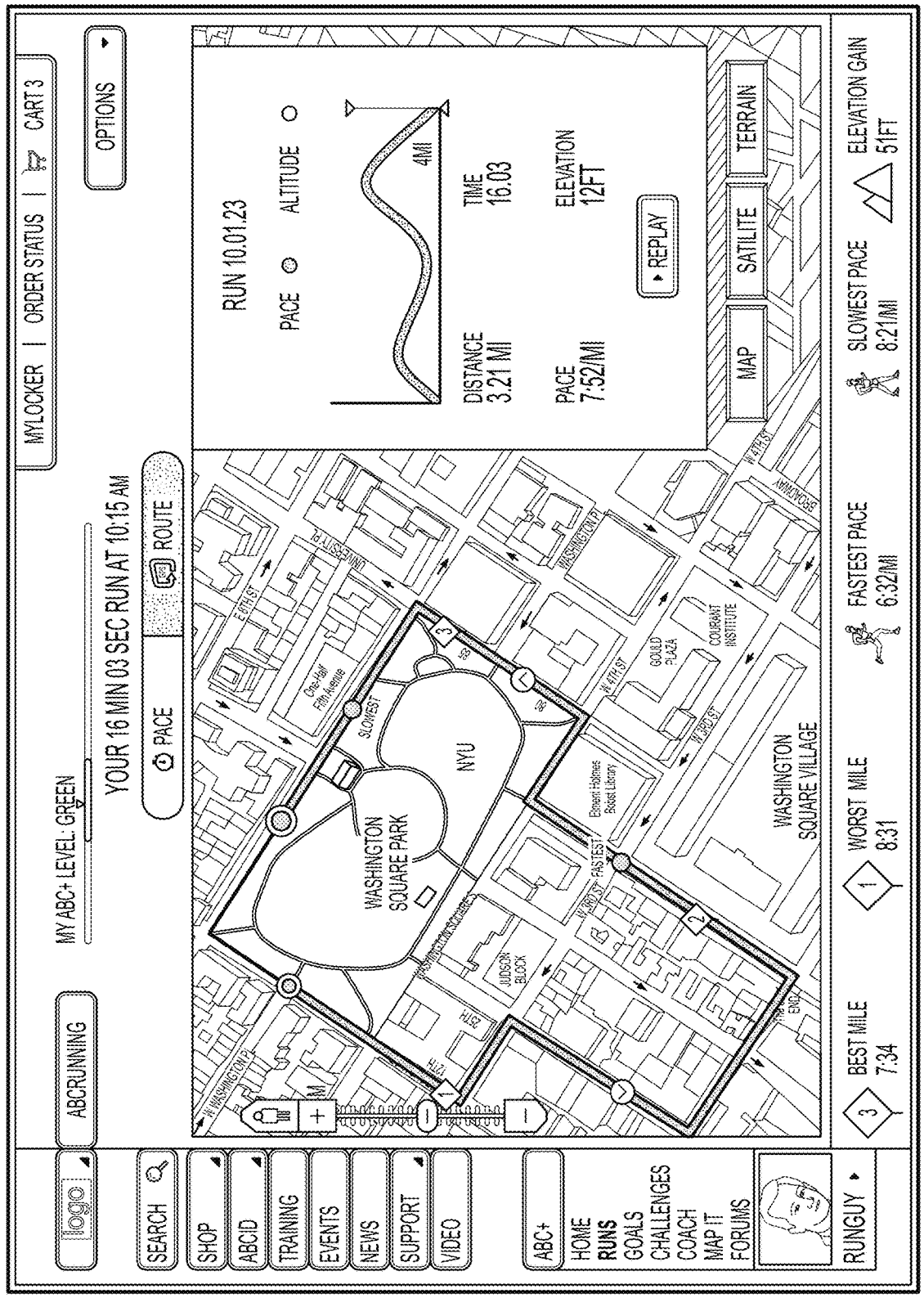
Figure 72C:
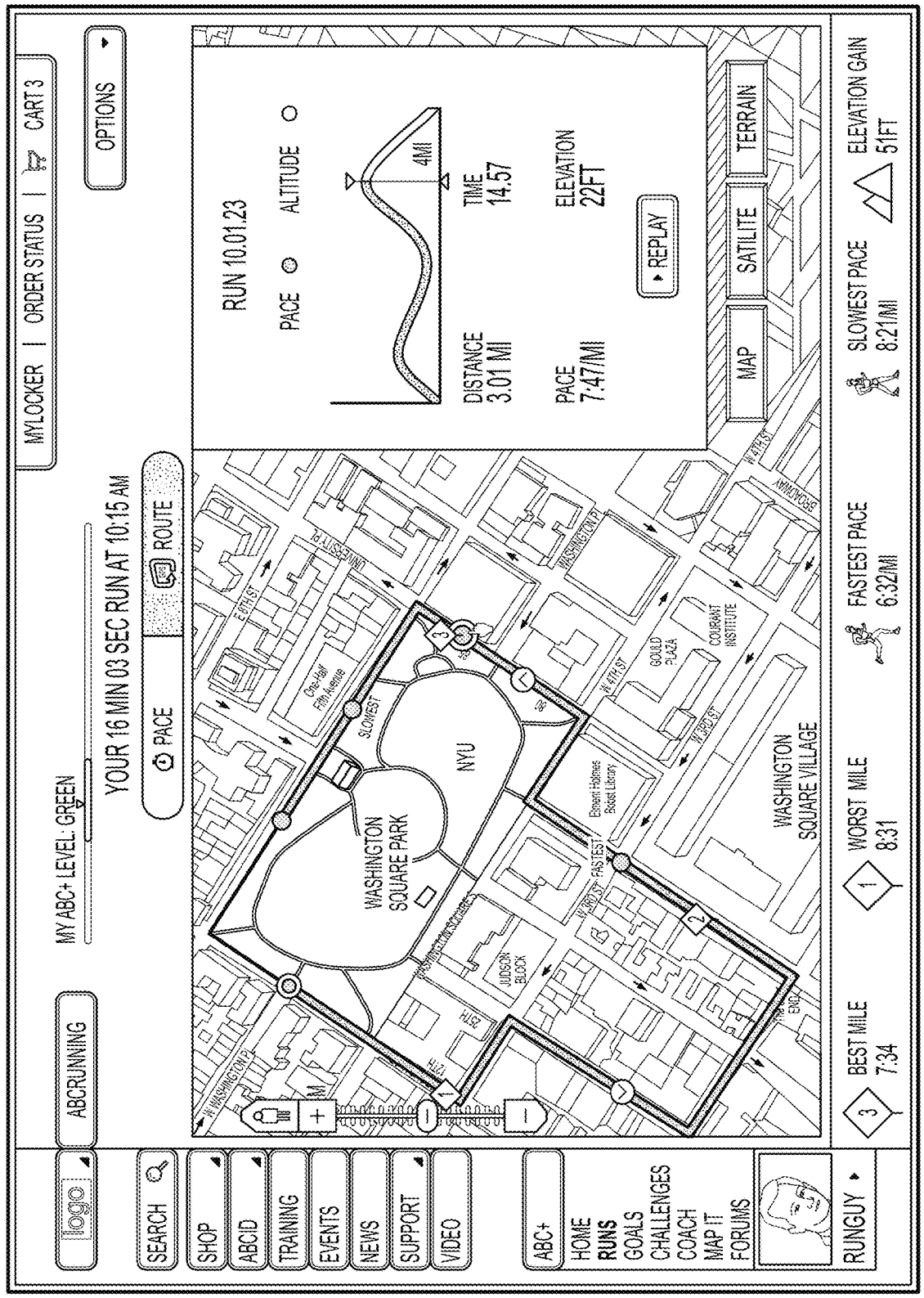
Figure 72D:
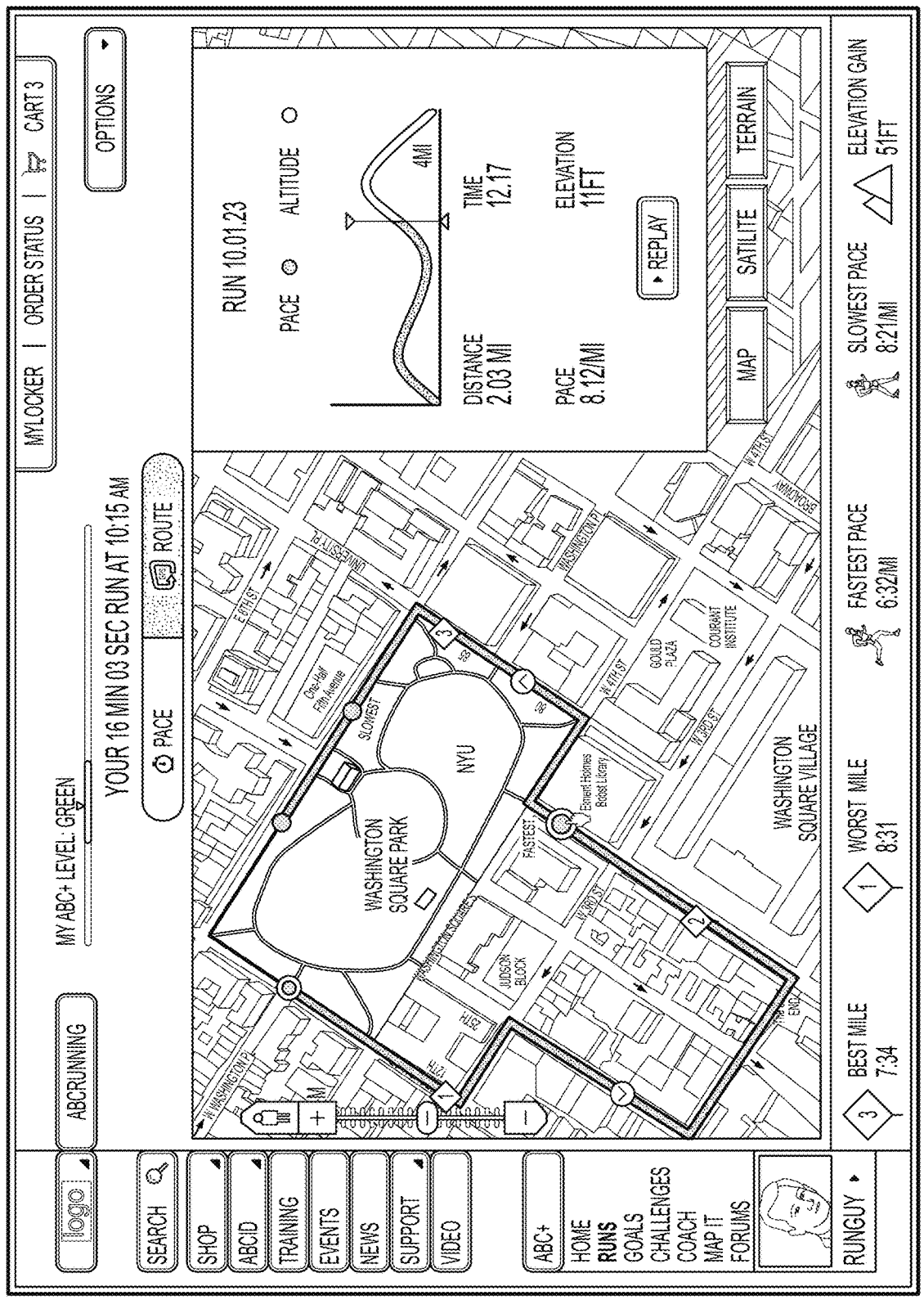
Figure 72E:
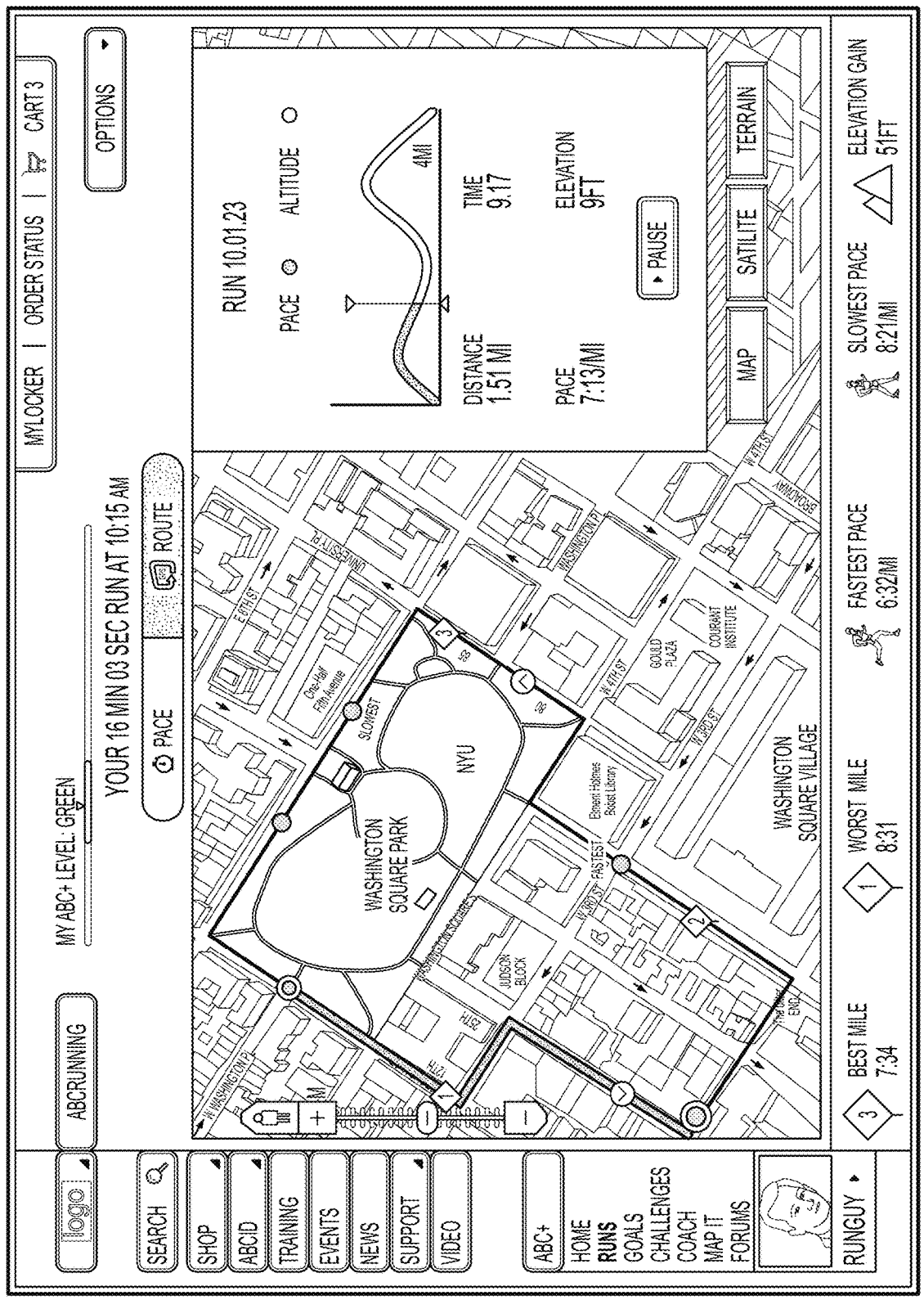
Figure 72F:
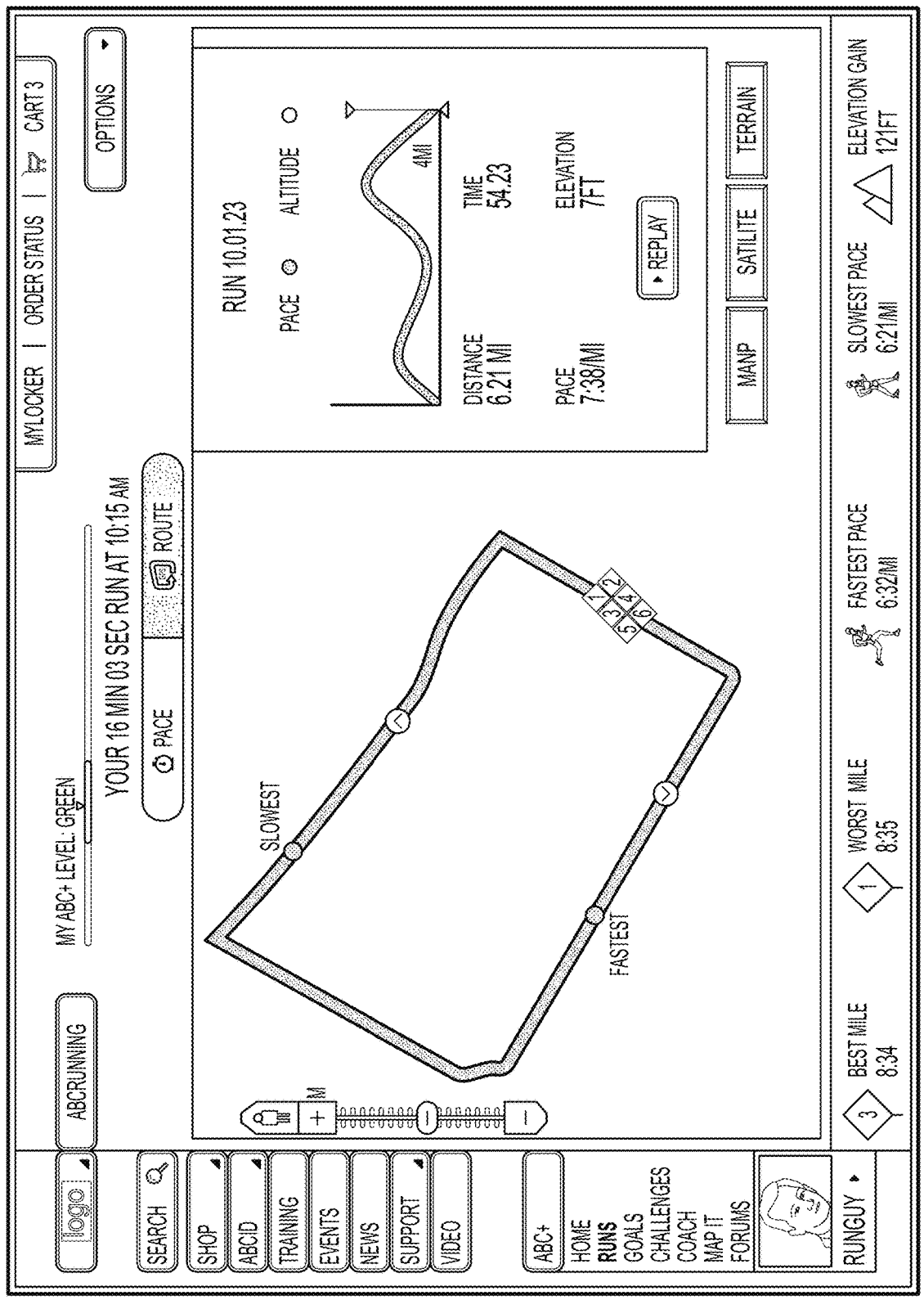

FIGS. 71A and 71B illustrate further example interfaces for viewing route information. In FIG. 71A, route information display 7100 may include a friends tab 7101 that allows the user to view a list of friends that are running or have run the same or a similar route. FIG. 71B illustrates friends list display 7110 in which friends 7111 are displayed in an order indicating a current standing for a challenge associated with the route. For example, a pace challenge may be defined for the route and thus, list display 7110 may list the friends in an order of fastest to slowest pace. Those without pace data may be listed at the bottom in alphabetical order. Friends may also be displayed according to other orders including alphabetical, age, number of times the route has been run by the user, pace and the like.

FIGS. 72A-72F illustrate further example route tracking and viewing interfaces. In one or more arrangements, route tracking may include an option for tagging the route with personal information, automatically determined information and/or user entered information. For example, a user may tag the route with how he or she felt while exercising along the route, a name of the route, a route rating (e.g., how much the user enjoyed the route, scenery rating, noise rating, terrain rating), music suggestions, weather, terrain, landmarks or interesting places along the route and the like. This information may then be shared with other individuals that are seeking a route to use. Different users may tag the route so that the route may be displayed with multiple tags.

By tracking and storing a user's route, an athletic activity monitoring and tracking system may further evaluate the user's performance on that route against other users that have also run the same route. Accordingly, the system may define various achievements based on a user's performance relative to the other users. Examples of achievements include an accolade for running the route the most number of times within a predefined time period, and/or an accolade for running the route the fastest within a predefined time period. The predefined time period may correspond to all-time, a specified number of most recent weeks, months, years, etc., and the like.

Figure 73:
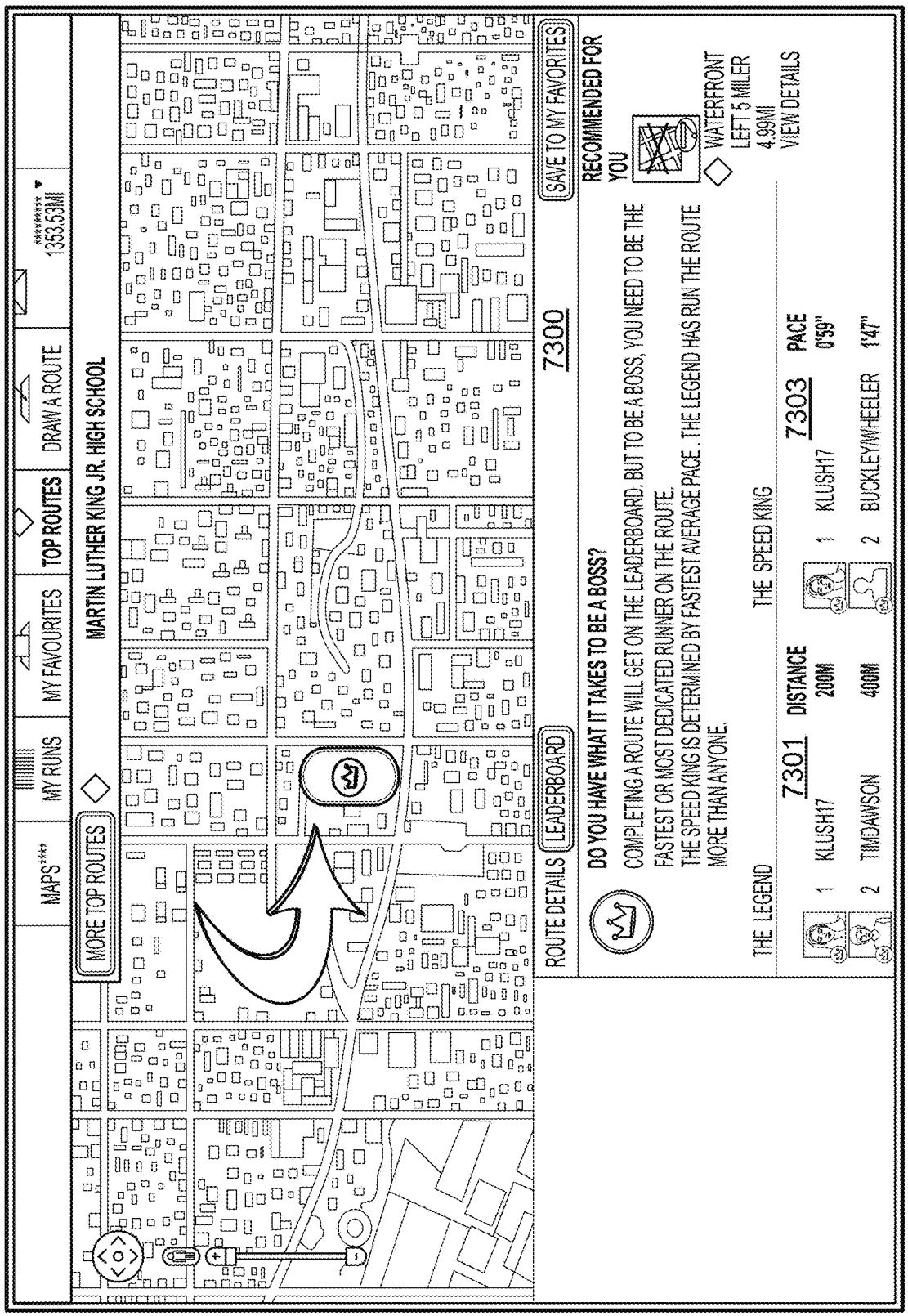
FIG. 73 illustrates an example interface in which route-specific statistics are displayed according to one or more aspects described herein.

FIG. 73 illustrates an example interface 7300 in which route leaderboards 7301 and 7303 are displayed for a particular route. The route may be displayed in map area 7305. Leaderboard 7301 lists users who have run the route according to a number of times the users have run the route. Leaderboard 7303, on the other hand, lists users who have run the route according to fastest pace. In some arrangements, leaderboards 7301 and 7303 might always display the current user and a corresponding number of times run and pace, respectively, to allow the user to compare with the leaders of each leaderboard 7301 and 7303. Upon a user reaching a certain place on the leaderboard, e.g., $1^{st}$, $2^{nd}$, $3^{rd}$, top 10, top 10%, top 20%, etc., a notification may be provided to the user. In one example, the notification may be a push notification delivered to the user's portable device so that the user may be immediately aware of the accomplishment. In other examples, the notification may be delivered through e-mail, text message, multimedia message, voicemail, telephone call and the like.

In some instances, such as that illustrated in FIG. 73, a system might also track various distance runs along a route or a track. For example, leaderboard 7301 illustrates the users who have run the identified distance the most number of times. These types of leaderboards may be used for tracks, for instance, where the tracks provide different distance markers allowing for specific distance runs.

Routes may be displayed or identified on a map to help the user visualize locations where he or she has performed workouts. In addition to identifying the user's workouts, the map may also identify the locations of workouts for other individuals such as friends. In some arrangements the map might only display the current or last recorded workout of the user's friends. In other arrangements, the map might display all recorded workouts of the user's friends over a certain amount of time (e.g., all time, a specified number of months, days, weeks, years, hours and the like). In still other additional or alternative arrangements, the user may specify filters for displaying workouts on the maps. These filters may include parameters such as distance, pace, elevation, incline, weather, geographic region (e.g., state, country, continent, hemisphere, time zone, zip code, etc.). Selecting another user's route location indicator, the user may be able to view the specifics of the route, the other user's workout session on the route and the like.

The use of GPS and other location determination systems provides more granularity and additional functionality for tracking and monitoring athletic performance. In addition, location detection offers users the ability to compare performances with other users and to identify other potential locations where they may run. Various other advantages and features of location determination and route tracking may also be achieved using the aspects described herein.

Live Challenges

Figure 74:
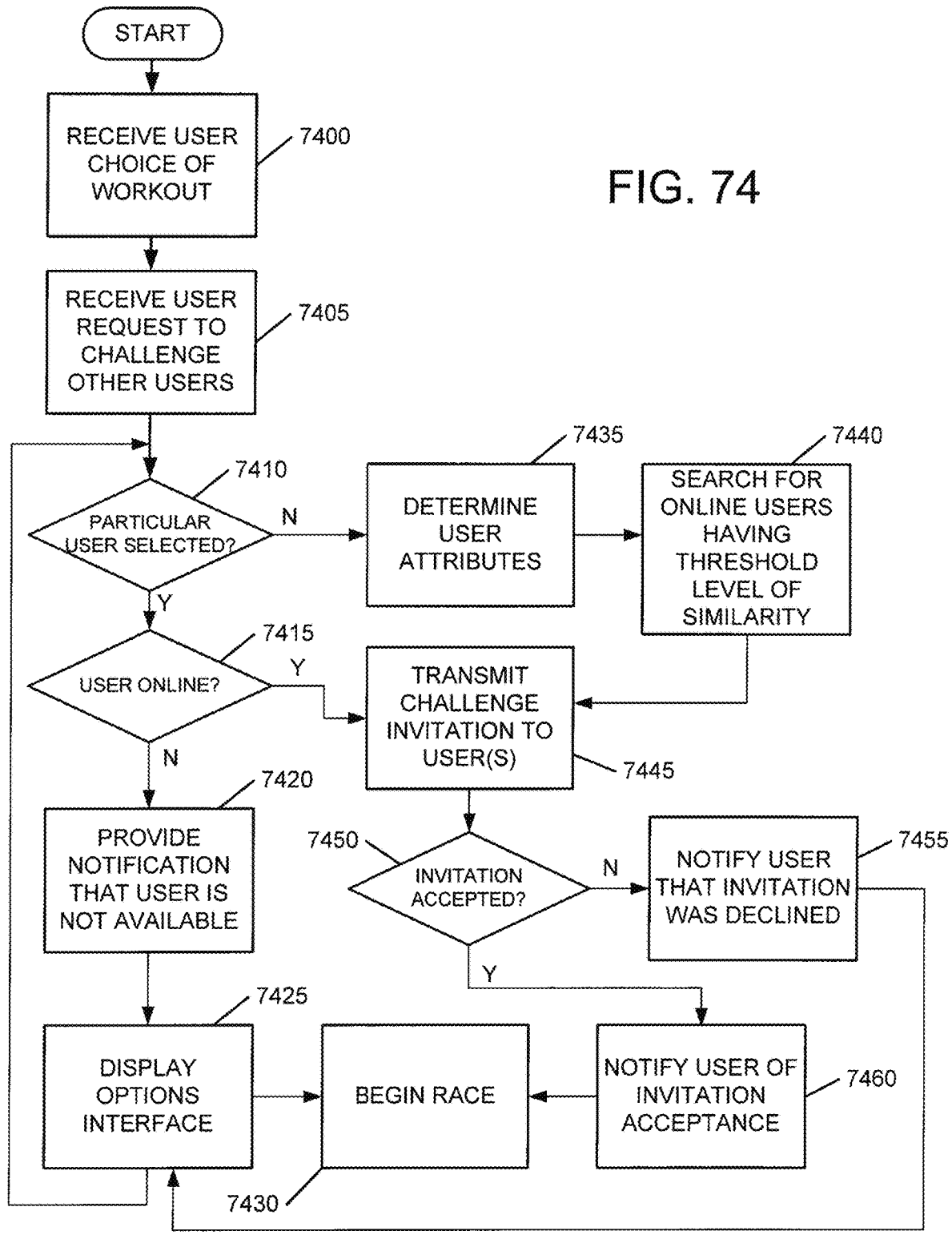
FIG. 74 illustrates an example method for generating and processing a live challenge according to one or more aspects described herein.

According to one or more additional or alternative aspects, a monitoring device and/or service provider may facilitate the matching of a user to a competitor in a live challenge environment. FIG. 74 illustrates an example method for generating and processing a live challenge. For example, in step 7400, a user may choose to a workout such as a 1K run. The workout may be defined and initiated through a device such as a mobile fitness monitoring device. The user may select a predefined run type/configuration or may customize his or her own run. Subsequently, in step 7405, the user may initiate a challenge for the 1K run to one or more other users. In step 7410, a challenge matching system may determine whether the user has specified a particular user to challenge. For example, the user may have selected a friend to challenge. If so, the system may determine if the selected user is currently online with an athletic activity service associated with the matching system in step 7415. For example, if the user is not signed on to the service, the user may be determined to be offline. Alternatively, if the user is online, the user may be deemed to be online. In one or more arrangements, being online may further include an active data communication connection with the user. Thus, if an active data connection is not available with the selected user, the user may be deemed to be offline. If the selected user is determined to be offline, the system may transmit a message indicating that the selected user is not available in step 7420. The system may subsequently display an interface allowing the user to challenge another user or to proceed directly to the run in step 7425. The system may return to step 7410 if the user chooses to challenge another user. Alternatively, the system may proceed to step 7430 where the run may be initiated without the challenge component.

If the user has not selected a particular user to challenge, the system may automatically identify and select one or more users. For example, in step 7435, the system may identify one or more attributes of the present user initiating the run. The attributes may include age, weight, height, fitness level, resting heart rate and the like. In step 7440, the system may search for online users that may have a threshold level of similarity to the present user. The system may subsequently transmit a challenge invitation to each of the matching online users in step 7445. In some arrangements, the matching system may filter out users that are currently performing athletic activity (e.g., as not to interrupt those users). In other arrangements, the matching system may identify users that are within vicinity of the same path or route or a similar route (e.g., of a similar distance). Various other matching parameters and algorithms may be used to find other users to challenge. For example, in some instances, the search scope may be limited to a list of the user's friends rather than all users of the service.

In step 7450, the matching system may determine whether the invited users have accepted the challenge. If not, the system may notify the user that the user's challenge invitation has been declined in step 7455. The system may then display a menu such as that generated and displayed in step 7425. If one or more of the invited users has accepted the challenge, the present user may be notified of the acceptance in step 7460. The workout may then be initiated in step 7430 as a challenge between the accepted participants.

In one or more arrangements, a participant may increase the challenge by selecting an option to increase the goal amount (e.g., distance, calories burned, pace) during the challenge (e.g., mid-run). A notification may then be transmitted to the other participants to ask if they agree to the modification in the challenge. The challenge may then be automatically and immediately modified on the fly if a predefined number of participants agree. For example, the challenge might only be modified if a majority of the participants agree or at least 75% of the participants agree or all participants agree (or some other threshold or rule is met). In other examples, the challenge may be modified for agreeing participants but not participants that do not agree to the modification in the challenge. In such cases, two separate challenges may be created mid-run: one corresponding to the original goal/challenge and another corresponding to the modified goal/challenge. Participants of the modified goal/challenge may also remain participants of the original goal/challenge if the modified goal/challenge is greater than the original.

At the conclusion of the challenge, the users' results may be compared and a winner may be declared. In some arrangements, the service provider may award the winner with an accolade, virtual medal, virtual currency or other prize. Additionally or alternatively, the system may prompt the challenge participants to engage in another run at another scheduled time to further encourage the participants to engage in athletic activity.

Pre-Workout and Post-Workout Challenges

To further motivate users to engage in athletic activity and maintain interest, a training application and device may provide additional challenges pre-workout and/or post-workout. For example, the training application may require a user to complete a pre-workout challenge before being allowed to use the application to define a new run (e.g., time, distance or basic runs) or before being allowed to start a defined workout.

Figure 75:
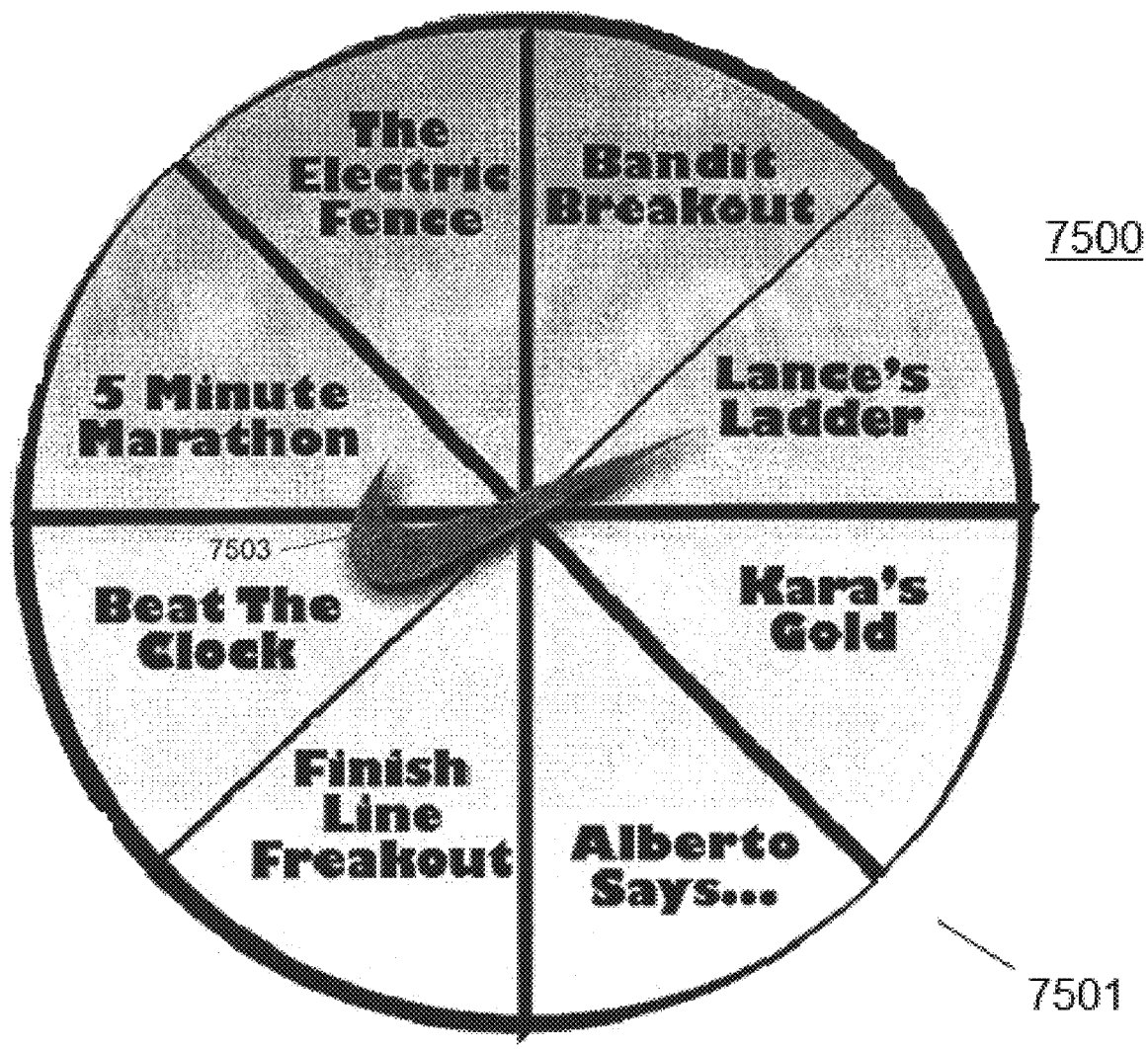
FIGS. 75 and 76 illustrate example interfaces through which a user may select a warm-up or cool-down activity prior to or after a workout session, respectively, according to one or more aspects described herein.

FIG. 75 illustrates an example interface configured to challenge the user to complete a warm-up workout prior to engaging in a workout session. The interface 7500 may comprise an interactive selection mechanism such as a spinnable wheel 7501 populated with multiple predefined warm-up activities. The pre-population of the selection mechanism 7501 with predefined warm-up activities further teaches or advises the user as to appropriate and effective warm-up routines. The user may interact with wheel 7501 (e.g., spin the wheel) by swiping a finger across an interface screen or pressing a "spin" button (not shown). The device may have an algorithm that randomly or pseudo-randomly selects one of the warm-up activities from those populated in wheel 7501. A pointer 7503 may be used to visually illustrate the spinning and to identify the selected warm-up activity. In some arrangements, the device and application may require completion of the selected warm-up activity before allowing the user to initiate a workout session. For example, the application may lock the interface to the warm-up activity until it has been completed. Completion may be detected by the device (e.g., using GPS or accelerometer algorithms) or may be self-reported. In some arrangements, wheel 7501 may be populated with warm-up activities selected from a database of warm-up activities. Accordingly, wheel 7501 may be populated with different warm-up activities at different times (e.g., for different workout sessions).

Figure 76:
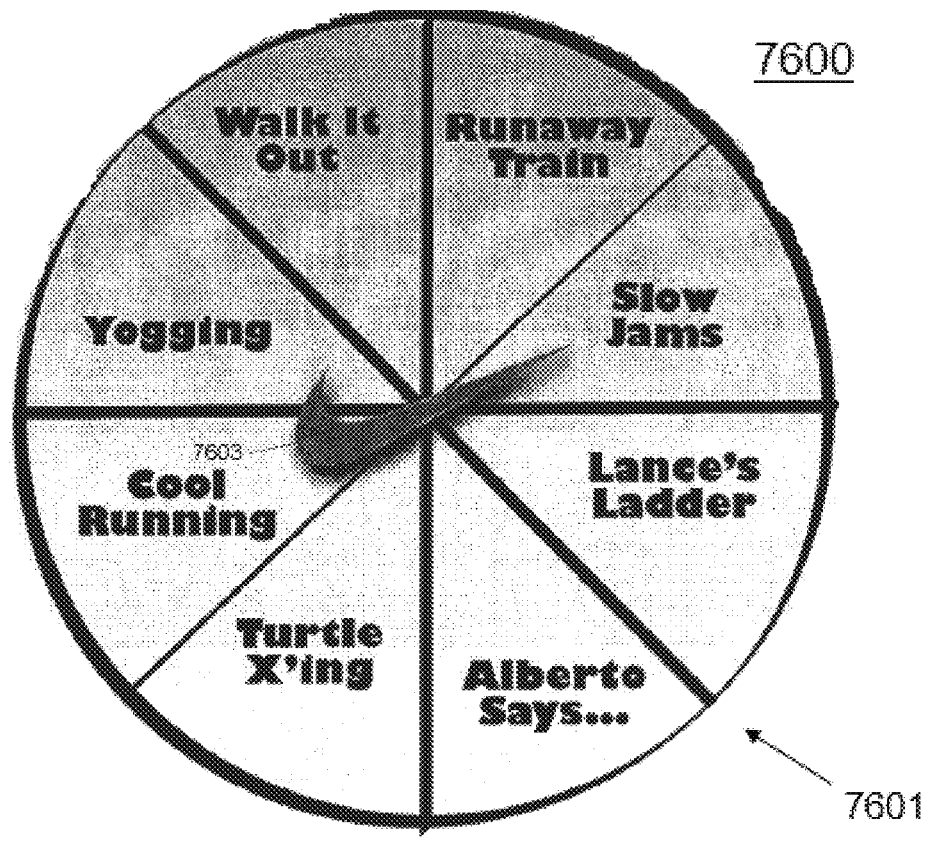

Similar to the pre-workout warm-up activity selection mechanism described in FIG. 75, an athletic training application may further provide a cool down activity selection mechanism. FIG. 76, for example, illustrates a cool down activity selection interface for choosing a cool down activity after completion of a workout. The application may offer this interface to advise users on the importance of cooling down after a workout and effective ways to do so. Selection mechanism 7601 of interface 7600 may operate in similar fashion to the wheel selection mechanism 7501 of FIG. 75. In particular, wheel 7601 may be populated with any number (e.g., 1, 2, 5, 10, 15, 20, etc.) of cool down activities and include a pointer 7603 to illustrate spinning and identify a selected task. In some environments, wheel 7601 may be populated with at least two cool down activities. Cool down tasks may include stretching, walking, slow jogging and the like to help reduce soreness and increase flexibility. In some instances, cool down activities may be required and enforced by not recording or providing credit for the associated workout if the cool down is not performed. For example, workouts may be used to earn a virtual currency or metric. Accordingly, if the user does not perform the cool down, he or she might not earn a corresponding amount of virtual currency or virtual athletic performance metric.

Other selection mechanisms may also be used in addition to or instead of the example wheel selection mechanism of FIGS. 75 and 76. For example, a one-arm bandit selection mechanism may be provided where a user pulls the arm to identify a warm-up or cool down activity that is to be performed. In another example, the application may simulate rolling one or more dice, where each face of the dice lists a different cool down or warm-up activity.

Other Features

Additional features may be included as part of the athletic training application, devices and systems described herein. For example, the athletic training application or system may generate a virtual competitor with which the user may compete during a workout session. The virtual competitor may provide additional motivation for the user. In one example, the user may specify a desired average pace for the virtual competitor and a distance or duration of the intended workout. The application or system may then simulate the progress of the virtual competitor based on the specified average pace and compare the simulated progress of the virtual competitor to the actual progress of the user. The comparison may then be conveyed to the user. In one example, audible messages such as "Speed up! Your competitor is about to overtake you!" or "Keep it up. You are ahead of your competitor," may be provided to the user to provide an indication of relative performance. In other examples, a visual display of the virtual competitor's progress relative to the user's progress may be displayed along a route map. In still other examples, numerical metrics of the virtual competitor's performance may be displayed against the user's performance. Other types of relative performance indicators may be used as well.

CONCLUSION

Providing an activity monitoring system and environment having one or more of the features described herein provides a user with an immersive experience that will encourage and motivate the user to engage in athletic activities and improve his or her fitness. By encouraging the user to exceed previous statistics set in other runs, the user may be motivated by the improvements he or she is able to make. Additionally, users may be able to use a single device for both indoor and outdoor workouts and are thus able to aggregate workout data on a single device. Further, users may be motivated to exercise by being able to issue live challenges to other users. Accordingly, the users may feel as if they are working out with other users even though they are physically running by themselves.

What is claimed is:

1. A method comprising:
    recording, by an athletic activity monitoring device, athletic activity data collected by the athletic activity monitoring device during an athletic activity performed by a user;
    receiving, by the athletic activity monitoring device, a sharing option selection configured to allow the recorded athletic activity data to be shared; and
    transmitting, by the athletic activity monitoring device, to a network page of a social networking site, and in response to receiving the sharing option selection, workout information associated with the recorded athletic activity data, wherein the network page is viewable by one or more other users.

2. The method of claim 1, further comprising tagging a summary of one or more metrics from the recorded athletic activity data with identifiers of one or more other users.

3. The method of claim 1, further comprising providing a message prompt on the network page, the message prompt configured to receive a message to be presented to the one or more other users on the social networking site.

4. The method of claim 1, further comprising:
    receiving a request to deactivate sharing of the workout information; and
    transmitting a modification request to remove the workout information from the social networking site.

5. The method of claim 1, wherein the workout information includes map information identifying a route used by the user to perform the athletic activity.

6. The method of claim 1, wherein the workout information includes map information comprising an image of a map identifying a route used by the user to perform the athletic activity.

7. The method of claim 1, wherein the workout information includes map information comprising a link to a network site displaying a map identifying a location at which the athletic activity was performed by the user.

8. The method of claim 1, wherein the workout information includes map information comprising route information downloadable to an athletic activity monitoring device of another user for use by the other user to perform athletic activity according to a route defined by the route information.

9. The method of claim 1, further comprising generating a social network message on the network page based on a location at which the athletic activity was performed by the user.

10. The method of claim 9, wherein transmitting the workout information comprises modifying the social network message based on a received user edit.

11. A method comprising:
    recording, by an athletic activity monitoring device, athletic activity data collected by the athletic activity monitoring device during an athletic activity performed by a user;
    receiving, by the athletic activity monitoring device, a sharing option selection configured to allow the recorded athletic activity data to be shared; and
    sharing by the athletic activity monitoring device, to an activity feed, and in response to receiving the sharing option selection, workout information associated with the recorded athletic activity data, wherein the activity feed is viewable by one or more other users.

12. The method of claim 11, further comprising tagging a summary of one or more metrics from the recorded athletic activity data with identifiers of one or more other users.

13. The method of claim 11, further comprising providing a message prompt on the activity feed, the message prompt configured to receive a message to be presented to the one or more other users.

14. The method of claim 11, further comprising:
    receiving a request to deactivate sharing of the workout information; and
    transmitting a modification request to remove the workout information from the activity feed.

15. The method of claim 11, wherein the workout information includes map information identifying a route used by the user to perform the athletic activity.

16. A method comprising:
recording, by an athletic activity monitoring device, athletic activity data collected by the athletic activity monitoring device during an athletic activity performed by a user;
receiving, by the athletic activity monitoring device, a sharing option selection configured to allow the recorded athletic activity data to be shared; and
sharing, by the athletic activity monitoring device and to a timeline viewable by one or more other users, workout information associated with the recorded athletic activity data.

17. The method of claim 16, further comprising tagging a summary of one or more metrics from the recorded athletic activity data with identifiers of one or more other users.

18. The method of claim 16, further comprising providing a message prompt on the timeline, the message prompt configured to receive a message to be presented to the one or more other users.

19. The method of claim 16, further comprising:
receiving a request to deactivate sharing of the workout information; and
transmit a modification request to remove the workout information from the timeline.

20. The method of claim 16, wherein the workout information includes map information identifying a route used by the user to perform the athletic activity.

21. A method comprising:
recording, by an athletic activity monitoring device, athletic activity data collected by the athletic activity monitoring device during an athletic activity performed by a user;
receiving, by the athletic activity monitoring device, a sharing option selection configured to allow the recorded athletic activity data to be shared; and
sharing, by the athletic activity monitoring device, to a profile page, and in response to receiving the sharing option selection, workout information associated with the recorded athletic activity data, wherein the profile page is viewable by one or more other users.

22. The method of claim 21, further comprising tagging a summary of one or more metrics from the recorded athletic activity data with identifiers of one or more other users.

23. The method of claim 21, further comprising providing a message prompt on the profile page, the message prompt configured to receive a message to be presented to the one or more other users.

24. The method of claim 21, further comprising:
receiving a request to deactivate sharing of the workout information; and
transmit a modification request to remove the workout information from the profile page.

25. The method of claim 21, wherein the workout information includes map information identifying a route used by the user to perform the athletic activity.

\* \* \* \* \*

UNITED STATES PATENT AND TRADEMARK OFFICE
CERTIFICATE OF CORRECTION

| | |
|---|---|
| PATENT NO. | : 11,783,638 B2 |
| APPLICATION NO. | : 17/746686 |
| DATED | : October 10, 2023 |
| INVENTOR(S) | : Hoffman et al. |

It is certified that error appears in the above-identified patent and that said Letters Patent is hereby corrected as shown below:

In the Claims

Column 70, Claim 11, Line 51:
After "sharing", insert --,--

Signed and Sealed this
Fifth Day of March, 2024

Katherine Kelly Vidal
*Director of the United States Patent and Trademark Office*